US007569681B2

(12) United States Patent
Ting et al.

(10) Patent No.: US 7,569,681 B2
(45) Date of Patent: Aug. 4, 2009

(54) CATERPILLER GENE FAMILY

(75) Inventors: Jenny P.-Y Ting, Chapel Hill, NC (US); Michael W. Linhoff, St. Louis, MO (US); Jonathan A. Harton, Durham, NC (US); Christopher B. Moore, Durham, NC (US)

(73) Assignee: The University of North Carolina at Chapel Hill, Chapel Hill, NC (US)

( * ) Notice: Subject to any disclaimer, the term of this patent is extended or adjusted under 35 U.S.C. 154(b) by 0 days.

(21) Appl. No.: 10/511,989

(22) PCT Filed: Apr. 30, 2003

(86) PCT No.: PCT/US03/13562

§ 371 (c)(1), (2), (4) Date: May 25, 2005

(87) PCT Pub. No.: WO2004/034093

PCT Pub. Date: Apr. 22, 2004

(65) Prior Publication Data

US 2006/0053496 A1 Mar. 9, 2006

Related U.S. Application Data

(60) Provisional application No. 60/376,626, filed on Apr. 30, 2002.

(51) Int. Cl.

| | |
|---|---|
| ***C07H 21/04*** | (2006.01) |
| ***C12N 15/12*** | (2006.01) |
| ***C12N 5/00*** | (2006.01) |
| ***C12Q 1/68*** | (2006.01) |
| ***A01N 63/00*** | (2006.01) |
| ***G01N 33/00*** | (2006.01) |

(52) U.S. Cl. .................. 536/23.5; 435/320.1; 435/325; 435/6; 424/93.1; 800/3

(58) Field of Classification Search ...................... None
See application file for complete search history.

(56) References Cited

U.S. PATENT DOCUMENTS

| | | | | |
|---|---|---|---|---|
| 6,432,442 | B1 | 8/2002 | Buehler et al. | 424/441 |
| 2001/0029033 | A1 | 10/2001 | Shami et al. | 435/69.1 |
| 2003/0027757 | A1 | 2/2003 | Bertin et al. | 514/12 |
| 2004/0253615 | A1 | 12/2004 | Inohara et al. | |

FOREIGN PATENT DOCUMENTS

WO WO 0104307 A1 * 1/2001

OTHER PUBLICATIONS

GenBank Acc. No. AC090160.6, "*Homo sapiens* chromosome 11, clone RP11-431N10, complete sequence," US National Library of Medicine, Aug. 23, 2002, accessed by PTO Jan. 19, 2007 (includes first sheet of AC090160.1, published Feb. 17, 2001).*

GenBank Acc. No. AC004644, "*Homo sapiens* chromosome 16, cosmid clone 367E12 (LANL), complete sequence," US National Library of Medicine, May 1, 1998, accessed by PTO Jan. 19, 2007.*

GenBank Acc. No. AF410477, "*Homo sapiens* cryopyrin (CIAS1) mRNA, complete cds, alternatively spliced," US National Library of Medicine, Nov, 21, 2001, accessed by PTO Jan. 19, 2007.*

Kennell, D.E., "Principles and practices of nucleic acid hybridization," Progr. Nucleic Acid Res. Mol. BIol. 11: 259-301, 1971.*

Ngo et al., "Computational complexity, protein structure prediction, and the Levinthal paradox," in The Protein Folding Problem and Tertiary Structure Prediction, Merz et al. (eds.), Birkhauser Boston: Boston, MA, pp. 433 and 492-495, 1994.*

Rudinger, J., "Characteristics of the amino acids as components of a peptide hormone sequence," in Peptide Hormones, Parsons (ed.), University Park Press: Baltimore, MD, pp. 1-7, 1976.*

Accession No. NT_009325; *Homo sapiens* chromosome 11 genomic contig; Source: *Homo sapiens* (2003).

Accession No. NT_009334; *Homo sapiens* chromosome 11 working draft sequence segment; Source: *Homo sapiens* (Aug. 23, 2001).

Accession No. NT_015360; *Homo sapiens* chromosome 16 working draft sequence segment; Source: *Homo sapiens* (Feb. 6, 2002).

Accession No. NT_024766; *Homo sapiens* chromosome 16 working draft sequence segment; Source: *Homo sapiens* (Feb. 6, 2002).

Aganna, et al. 2002. Association of mutations in the NALP3/CIAS1/PYPAF1 gene with a broad phenotype including recurrent fever, cold sensitivity , sensorineural deafness, and AA amyloidosis. *Arthritis Rheum* 46:2445.

Akira, et al. 2001. Toll-like receptors: critical proteins linking innate and acquired immunity. *Nat Immunol* 2:675.

Alexopoulou, et al. 2001. Recognition of double-stranded RNA and activation of NF-kappaB by Toll-like receptor 3. *Nature* 413:732.

Banerjee, et al. 2001. The leucine-rich repeat domain can determine effective interaction between RPS2 and other host factors in arabidopsis RPS2-mediated disease resistance. *Genetics* 158:439.

Bertin and DiStefano. 2000. The PYRIN domain: a novel motif found in apoptosis and inflammation proteins. *Cell Death Differ*. 7:1273.

Buchanan and Gay. 1996. Structural and functional diversity in the leucine-rich repeat of proteins. *Prog Biophys Mol Biol*. 65:1.

Chen and Goeddel. 2002. TNF-R1 signaling: a beautiful pathway. *Science* 296:1634.

Dodds, et al. 2001. Six Amino Acid Changes Confined to the Leucine-Rich Repeat beta-Strand/beta-Turn Motif Determine the Difference between the P and P2 Rust Resistance Specificities in Flax. *Plant Cell* 13:163.

(Continued)

*Primary Examiner*—Michael Burkhart
(74) *Attorney, Agent, or Firm*—Myers Bigel Sibley & Sajovec, P.A.

(57) ABSTRACT

The present invention relates to a new family of structurally and functionally related nucleic acids and proteins, designed the CATERPILLER family, which is characterized by landmark structural motifs including a nucleotide binding domain and leucine-rich repeat domains.

11 Claims, 68 Drawing Sheets

OTHER PUBLICATIONS

Heery, et al. 1997. a signature motif in transcriptional co-activators mediates binding to nuclear receptors. *Nature* 387:733.

Li and Verma. 2002. NF-kappaB regulation in the immune system. *Nat Rev Immunol* 2:725.

Linhoff, et al. 2001. Two distinct domains within CIITA mediate self-association: involvement of the GTP-binding and leucine-rich repeat domains. *Mol. Cell Biol* 21(9):3001-11.

Samuels, et al. 1998. Familial Mediterranean fever at the millennium. Clinical spectrum, ancient mutations, and a survey of 100 American referrals to the National Institutes of Health. *Medicine* (Baltimore) 77:268.

Steimle, et al. 1993. Complementation cloning of an MHC class II transactivator mutated in hereditary MHC class II deficiency (or bare lymphocyte syndrome). *Cell* 75:135.

Database entry of *Homo sapiens* cryopyrin (CIAS1) mRNA, complete cds, alternatively spliced, Accession No. AF410477.1 <www.ncbi.nlm.nih.gov/entrez/viewer.fcgi?db=nucleotide&val=17026371> (2006).

Database entry of *Homo sapiens* PYRIN-containing APAF1-like protein 1 (PYPAF1) mRNA, complete cds, Accession No. AF420469.1 <www.ncbi.nlm.nih.gov/entrez/viewer.fcgi?db=nucleotide&val=18182338> (2006).

Database entry of *Homo sapiens* NALP3 long isoform (NALP3) mRNA, complete cds, Accession No. AF468522.1 <www.ncbi.nlm.nih.gov/entrez/viewer.fcgi?db=nucleotide&val=18699562> (2006).

Database entry of *Homo sapiens* cryopyrin (CIAS1) mRNA, complete cds, alternatively spliced, Accession No. AF427617.1 <www.ncbi.nlm.nih.gov/entrez/viewer.fcgi?db=nucleotide&val=17026377> (2006).

Database entry of *Homo sapiens* NALP3 short isoform mRNA, complete cds, Accession No. AF418985.2 <www.ncbi.nlm.nih.gov/entrez/viewer.fcgi?db=nucleotide&val=19718650> (2006).

Database entry of *Homo sapiens* cDNA: FLJ23541 fis, clone LNG08276, highly similar to AF054176 *Homosapiens* angiotensin/vasopressin receptor Aii/AVP mRNA, Accession No. AK027194.1 <www.ncbi.nlm.nih.gov/entrez/viewer.fcgi?db=nucleotide&val=10440263> (2006).

Database entry of *Homo sapiens* chromosome 1 clone RP11-433K2, complete sequence, Accession No. AC104335.2 <www.ncbi.nlm.nih.gov/entrez/viewer.fcgi?db=nucleotide&val=22024575> (2006).

Database entry of cold autoinflammatory syndrome 1 [*Homo sapiens*], Accession No. CAI17153.1 <www.ncbi.nlm.nih.gov/entrez/viewer.fcgi?db=protein&val=55961964> (2006).

Database entry of PYRIN-containing APAF1-like protein 1 [*Homo sapiens*], Accession No. AAL65136.1 < www.ncbi.nlm.nih.gov/entrez/viewer.fcgi?db=protein&val=18182339> (2006).

Database entry of NALP3 long isoform [*Homo sapiens*], Accession No. AAL78632.1 <www.ncbi.nlm.nih.gov/entrez/viewer.fcgi?db=protein&val=18699563> (2006.

Database entry of cold autoinflammatory syndrome 1 [*Homo sapiens*], Accession No. CAI17154.1 < www.ncbi.nlm.nih.gov/entrez/viewer.fcgi?db=protein&val=55961965> (2006).

Database entry of cryopyrin [*Homo sapiens*], Accession No. AAL12498.1 <www.ncbi.nlm.nih.gov/entrez/viewer.fcgi?db=protein&val=17927238> (2006).

Database entry of NALP3 intermediate isoform [*Homo sapiens*], Accession No. AAM14669.1 <www.ncbi.nlm.nih.gov/entrez/viewer.fcgi?db=protein&val=20268804> (2006).

Database entry of *Homo sapiens* PYRIN-containing APAF1-like protein 7 mRNA, complete cds, Accession No. AY095146.1 <www.ncbi.nlm.nih.gov/entrez/viewer.fcgi?db=nucleotide&val=21314906> (2006).

Database entry of *Homo sapiens* NACHT, leucine rich repeat and PYD containing 12 (NALP12), transcript variant 2, mRNA, Accession No. NM_144687.1 <www.ncbi.nlm.nih.gov/entrez/viewer.fcgi?db=nucleotide&val=21955153> (2006).

Database entry of *Homo sapiens* NALP12 (NALP12) mRNA, complete cds, Accession No. AY154467.1 <www.ncbi.nlm.nih.gov/entrez/viewer.fcgi?db=nucleotide&val=28436377> (2006).

Database entry of *Homo sapiens* NACHT, leucine rich repeat and PYD containing 12, mRNA (cDNA clone MGC:40117 IMAGE:5212737), complete cds, Accession No. BC028069.1 <www.ncbi.nlm.nih.gov/entrez/viewer.fcgi?db=nucleotide&val=20380399> (2006).

Database entry of *Homo sapiens* cDNA FLJ38141 fis, clone D9OST2002673, weakly similar to *Homo sapiens* caspase recruitment domain protein 7 mRNA, Accession No. AK095460.1 <www.ncbi.nlm.nih.gov/entrez/viewer.fcgi?db=nucleotide&val=21754717> (2006).

Database entry of monarch-1 [*Homo sapiens*], Accession No. AAM75142.1 <www.ncbi.nlm.nih.gov/entrez/viewer.fcgi?db=protein&val=21711821> (2006).

Database entry of PYRIN-containing APAF1-like Protein 7 [*Homo sapiens*], Accession No. AAM18227 <www.ncbi.nlm.nih.gov/entrez/viewer.fcgi?db=protein&val=21314907> (2006).

Database entry of monarch-1 splice form II [*Homo sapiens*], Accession No. AAM75143.1 <www.ncbi.nlm.nih.gov/entrez/viewer.fcgi?db=protein&val=21711823> (2006).

Database entry of monarch-1 splice form III [*Homo sapiens*], Accession No. AM75144.1 <www.ncbi.nlm.nih.gov/entrez/viewer.fcgi?db=protein&val=21711825> (2006).

Database entry of monarch-1 splice form IV [*Homo sapiens*], Accession No. AAM75145.1 <www.ncbi.nlm.nih.gov/entrez/viewer.fcgi?db=protein&val=21711827> (2006).

Database entry of *Mus musculus* similar to PYRIN-containing APAF1-like protein 7; (LOC245127), mRNA, Accession No. XM_142563.2 <www.ncbi.nlm.nih.gov/entrez/viewer.fcgi?db=nucleotide&val=23604080> (2006).

Accession No. AF389420, *Homo sapiens* NOD27 (NOD27) mRNA, complete cds; Source: *Homo sapiens* (Jun. 4, 2001).

Accession No. AF231021; *Homo sapiens* Leucine-Rich-Repeat Protein RNO2 mRNA, complete cds; Source: *Homo sapiens*; (2001).

Accession No. NM_033297; *Homo sapiens* Neuronal Apoptosis Inhibitor Protein 12 (NALP12), mRNA; Source: *Homo sapiens* (2003).

Accession No. AF526389; *Homo sapiens* cryopyrin (CIAS1) gene, intron 6; Source: *Homo sapiens* (Jul. 2, 2002).

Accession No. AK025131; *Homo sapiens* cDNA: FLJ21478 fis, clone COL05012; Source: *Homo sapiens* (Aug. 29, 2000).

Accession No. AK025212; *Homo sapiens* cDNA: FLJ21559 fis, clone COL06406; Source: *Homo sapiens*.

Accession No. AK025362; *Homo sapiens* cDNA: FLJ21709 fis, clone COL10077; Source: *Homo sapiens* (Aug. 29, 2000).

Accession No. AK027416; *Homo sapiens* cDNA FLJ14510 fis, clone NT2RM1000623, weakly similar to Ribonuclease Inhibitor; Source: *Homo sapiens* (May 10, 2001).

Accession No. AK074109; *Homo sapiens* mRNA for FLJ00180 protein; Source: *Homo sapiens* (Jan. 21, 2002).

Accession No. AK074133; *Homo sapiens* mRNA for FLJ00206 protein, Source: *Homo sapiens* (Jan. 21, 2002).

Accession No. AK074182; *Homo sapiens* mRNA for FLJ00255 protein, Source: *Homo sapiens* (Jan. 21, 2002).

Accession No. AK090431; *Homo sapiens* mRNA for FLJ00348 protein; Source: *Homo sapiens* (Jul. 4, 2002).

Accession No. AK090439; *Homo sapiens* mRNA for FLJ00359 protein; Source: *Homo sapiens* (Jul. 4, 2002).

Accession No. AK090476; *Homo sapiens* mRNA for FLJ00398 protein; Source: *Homo sapiens* (Jul. 4, 2002).

Accession No. AK097030; *Homo sapiens* cDNA FLJ39711 fis, clone SMINT2013032; Source: *Homo sapiens* (Jul. 4, 2002).

Accession No. AY051112; *Homo sapiens* cryopyrin (CIAS1) gene, exon 1; Source: *Homo sapiens* (Aug. 15, 2001).

Accession No. AY051113; *Homo sapiens* cryopyrin (CIAS1) gene, exon 2; Source: *Homo sapiens* (Aug. 15, 2001).

Accession No. AY051114; *Homo sapiens* cryopyrin (CIAS1) gene, exon 3; Source: *Homo sapiens* (Aug. 15, 2001).

Accession No. AY051115; *Homo sapiens* cryopyrin (CIAS1) gene, exon 3; Source: *Homo sapiens* (Aug. 15, 2001).

Accession No. AY051116; *Homo sapiens* cryopyrin (CIAS1) gene, exons 7 and 8; Source: *Homo sapiens* (Aug. 15, 2001).

Accession No. AY051117; *Homo sapiens* cryopyrin (CIAS1) gene, exon 9 and complete cds, alternatively spliced; Source: *Homo sapiens* (Aug. 15, 2001).

Accession No. AY056059; *Homo sapiens* cryopyrin (CIAS1) gene, exon 4; Source: *Homo sapiens* (Aug. 15, 2001).
Accession No. AY056060; *Homo sapiens* cryopyrin (CIAS1) gene, exon 6; Source: *Homo sapiens* (Aug. 15, 2001).
Accession No. AY092033; *Homo sapiens* NALP3 intermediate isoform (NALP3) mRNA, complete cds; Source: *Homo sapiens* (Mar. 27, 2002).
Accession No. AY116204; *Homo sapiens* monarch-1 mRNA, complete cds; alternatively spliced; Source: *Homo sapiens* (May 29, 2002).
Accession No. AY116205; Accession No. AY116207; *Homo sapiens* monarch-1 splice form II mRNA, complete cds; alternatively spliced; Source: *Homo sapiens* (May 29, 2002).
Accession No. AY116206; *Homo sapiens* monarch-1 splice form III mRNA, complete cds; alternatively spliced; Source: *Homo sapiens* (May 29, 2002).
Accession No. AY116207; *Homo sapiens* monarch-1 splice form IV mRNA, complete cds; alternatively spliced; Source: *Homo sapiens* (May 29, 2002).
Accession No. AY154469; *Homo sapiens* NALP14 (NALP14) mRNA, complete cds; Source: *Homo sapiens* (Sep. 25, 2002).
Accession No. BC013199; *Homo sapiens* NOD9 protein, mRNA (cDNA clone Image:4387619), partial cds; Source: *Homo sapiens* (Aug. 27, 2001).
Accession No. NM_004895 *Homo sapiens* cold auto inflammatory syndrome 1 (CIAS1), transcript variant 1, mRNA; Source: *Homo sapiens* (2004).
Accession No. NM_024618; *Homo sapiens* NOD9 protein (NOD9), transcript variant 1, mRNA; Source: *Homo sapiens* (2003).
Accession No. NM_145827; *Mus musculus* cold auto inflammatory syndrome 1 homolog (human) (Cias1), mRNA; Source: *Mus musculus* (2003).
Accession No. NM_170722; *Homo sapiens* NOD9 protein (NOD9), transcript variant 2, mRNA; Source: *Homo sapiens* (2003).
Beg, et al. 1993. Tumor necrosis factor and interleukin-1 lead to phosphorylation and loss of I kappa B alpha: a mechanism for NF-kappa B activation. *Mol Cell Biol* 13:3301.
Bertin, et al. 1999. Human CARD4 protein is a novel CED-4/Apaf-1 cell death family member that activates NF-kappaB. *J Biol Chem* 274:12955.
Beutler, B. 2001. Autoimmunity and apoptosis: the Crohn's connection. *Immunity* 15:5.
Bouchier-Hayes, et al. 2001. Cardinal, a novel caspase recruitment domain protein, is an inhibitor of multiple NF-kappa B activation pathways. *J Biol Chem* 276:44069.
Brown, et al. 1998. The MHC class II transactivator (CIITA) requires conserved leucine charged domains for interactions with the conserved W box promoter element. *Nucleic.Acids.Res*. 26:4128.
Cressman, et al. 1999. A defect in the nuclear translocation of CIITA causes a form of type II bare lymphocyte syndrome. *Immunity*. 10:163.
Dangl and Jones. 2001. Plant pathogens and integrated defence responses to infection. *Nature* 411:826.
Dode, et al. 2002. New Mutations of CIAS1 That Are Responsible for Muckle-Wells Syndrome and Familial Cold Urticaria: A Novel Mutation Underlies Both Syndromes. *Am J Hum Genet* 70: 1498.
Dowds, et al. 2003. Regulation of cryopyrin/Pypaf1 signaling by pyrin, the familial Mediterranean fever gene product. *Biochem. Biophys. Res. Commun*. 302(3):575-80.
Feldmann, et al. 2002. Chronic infantile neurological cutaneous and articular syndrome is caused by mutations in CIAS1, a gene highly expressed in polymorphonuclear cells and chondrocytes. *Am J Hum Genet* 71:198.
Fiorentino, et al. 2002. A novel PAAD-containing protein that modulates NF-kappa B induction by cytokines tumor necrosis factor-alpha and interleukin-I beta. *J Biol Chem* 277:35333.
Fontes, et al. 1999. Interactions between the class II transactivator and CREB binding protein increase transcription of major histocompatibility complex class II genes. *Mol.Cell Biol*. 19:941.
Fukui et al. "Haematopoietic Cell-Specific CDM Family Protein DOCK2 is Essential for Lymphocyte Migration" *Nature* 412:826-831 (2001).
Hake, et al, 2000. CIITA leucine-rich repeats control nuclear localization, In vivo recruitment to the major histocompatibility complex (MHC) class II enhanceosome, and MHC class II gene transactivation [In Process Citation]. *Mol.Cell.Biol* 20(20):7716-25.
Harton and Ting. 2000. Class II transactivator: mastering the art of major histocompatibility complex expression. *Mol.Cell Biol* 20(17):6185-94.
Harton, et al. 1999. GTP binding by class II transactivator: role in nuclear import. *Science* 285:1402.
Harton, et al. 2002. Leucine-rich repeats of the class II transactivator control its rate of nuclear accumulation. *Hum Immunol*. 63(7):588-601.
Hemmi, et al. 2000. A Toll-like receptor recognizes bacterial DNA. *Nature* 408:740.
Hlaing, et al. 2001. Molecular cloning and characterization of DEFCAP-L and -S, two isoforms of a novel member of the mammalian Ced-4 family of apoptosis proteins. *J.Biol.Chem*. 276(12):9230-8.
Hoffman, et al. 2001. Mutation of a new gene encoding a putative pyrin-like protein causes familial cold autoinflammatory syndrome and Muckle-Wells syndrome. *Nat. Genet*. 29:301.
Holt, et al. 2003. Resistance gene signaling in plants—complex similarities to animal innate immunity. *Curr Opin Immunol* 15:20.
Hugot, et al. 2001. Association of NOD2 leucine-rich repeat variants with susceptibility to Crohn's disease. *Nature* 411:599.
Inohara, et al. 1999. Nod1, an Apaf-1-like activator of caspase-9 and nuclear factor- kappaB. *Journal of Biological Chemistry* 274:14560.
Inohara, et al. 2000. An induced proximity model for NF-kappa B activation in the Nod1/RICK and RIP signaling pathways. *J Biol Chem* 275:27823.
Inohara, et al. Human nod1 confers responsiveness to bacterial lipopolysaccharides. *J.Biol.Chem*. 276(4):2551-4.
International Search Report for International Patent Application No. PCT/US03/13562 mailed on Oct. 1, 2004.
Kaisho and Akira. 2000. Critical roles of Toll-like receptors in host defense. *Crit Rev Immunol* 20:393.
Koonin and Aravind. 2000. The NACHT family—a new group of predicted NTPases implicated in apoptosis and MHC transcription activation. *Trends.Biochem.Sci*. 25(5):223-4.
Kretsovali, et al. 1998. Involvement of CREB binding protein in expression of major histocompatibility complex class II genes via interaction with the class II transactivator. *Mol.Cell Biol*. 18:6777.
Kretsovali, et al. 2001. Self-association of CIITA correlates with its intracellular localization and transactivaiton. *J.Biol.Chem*. 276(34):32191-7.
MacKeigan, et al. 2000. MEK inhibition enhances paclitaxel-induced tumor apoptosis. *J Biol Chem* 275:38953.
Manji, et al. 2002. PYPAF1, a PYRIN-containing Apaf1-like protein that assembles with ASC and regulates activation of NF-kappa B. *J Biol Chem* 277:11570.
Martinon, et al. 2002. The inflammasome: a molecular platform triggering activation of inflammatory caspases and processing of proIL-beta. *Mol Cell* 10:417.
Masternak, et al. 2000. CIITA is a transcriptional coactivator that is recruited to MHC Class II promoters by multiple synergistic interactions with an enhanceosome complex. *Genes and Development* 14:1156.
Miceli-Richard, et al. 2001. CARD15 mutations in Blau syndrome. *Nat Genet* 29:19.
Nelson, L. M. 2001. Autoimmune ovarian failure: comparing the mouse model and the human disease. *J Soc Gynecol Investig* 8:S55.
Nickerson, et al. 2001. Dendritic cell-specific MHC class II transactivator contains a caspase recruitment domain that confers potent transactivation activity. *J Biol Chem* 276:19089.
Ogura, et al. 2001. A frameshift mutation in NOD2 associated with susceptibility to Crohn's disease. *Nature* 411(6837):603-606.
Ogura, et al. 2001. Nod2, a Nod1/Apaf-1 family member that is restricted to monocytes and activates NF-kappaB. *J Biol Chem* 276:4812.
Pan, et al. 2000. Divergent evolution of plant NBS-LRR resistance gene homologues in dicot and cereal genomes. *J Mol Evol* 50:203.

Phillips et al. "Expression of RNO-2 Inhibits Growth and Induces Differentiation and Apoptosis in leukemia Cells" *Blood* 98(11): 192b (2001) (Abstract).
Poltorak, et al. 1998. Defective LPS signaling in C3H/HeJ and C57BL/10ScCr mice: mutations in Tlr4 gene. *Science* 282:2085-2088.
Reith and Mach. 2001. The bare lymphocyte syndrome and the regulation of MHC expression. *Annu Rev Immunol* 19:331.
Riley, et al. 1995, Activation of class II MHC genes requires both the X box region and the class II transactivator (CIITA). *Immunity* 2:533.
Schuster and Nelson. 2000. Toll receptors: an expanding role in our understanding of human disease. *J.Leukoc.Biol.* 67(6):767-73.
Schwandner, et al. 1999. Peptidoglycan- and lipoteichoic acid-induced cell activation is mediated by toll-like receptor 2. *J Biol Chem* 274:17406.
Shami et al. "Identification and Characterization of a Novel Gene that is Upregulated in Leukaemia Cells by Nitric Oxide" *British Journal of Haematology* 112(1):138-147 (2001).
Sisk, et al. 2000. MHC class II transactivator inhibits IL-4 gene transcription by competing with NF-AT to bind the coactivator CREB binding protein (CBP)/p300. *J.Immunol.* 165(5):2511-7.
Sisk, et al. 2001. Self-association of CIITA and its transactivation potential. *Mol Cell Biol* 21:4919.
Spilianakis, et al. 2000. Acetylation by PCAF enhances CIITA nuclear accumulation and transactivation of major histocompatibility complex class II genes. *Mol.Cell.Biol.* 20(22):8489-98.
Srinivasula et al. "The PYRIN-CARD Protein ASC is an Activating Adaptor for Capase-1" *The Journal of Biological Chemistry* 277(24):21119-21122 (2002).
Stehlik, et al. 2002. The PAAD/PYRIN-family protein ASC is a dual regulator of a conserved step in nuclear factor kappaB activation pathways. *J Exp Med* 196:1605.
Suzuki, et al. 2002. IRAK-4 as the central TIR signaling mediator in innate immunity. *Trends Immunol* 23:50.
Tong, et al. 2000. Mater encodes a maternal protein in mice with a leucine-rich repeat domain homologous to porcine ribonuclease inhibitor. *Mamm Genome* 11:281.
Tong, et al. 2000. Mater, a maternal effect gene required for early embryonic development in mice. *Nat Genet* 26:267.
Torchia, et al. 1997. The transcriptional co-activator p/CIP binds CBP and mediates nuclear-receptor function. *Nature* 387:677.
Towey and Kelly, 2002. Nuclear localisation of CIITA is controlled by a carboxy terminal leucine-rich repeat region. *Mol Immunol* 38:627.
Traut, T. W. 1994. The functions and consensus motifs of nine types of peptide segments that form different types of nucleotide-binding sites. *Eur J Biochem* 222:9.
Tschopp et al. "NALPS: A Novel Protein Family Involved in Inflammation" *Nature Reviews* 4(2): 95-104 (2003).
Van Der Hoorn, et al. 2001. Identification of distinct specificity determinants in resistance protein cf-4 allows construction of a cf-9 mutant that confers recognition of avirulence protein avr4. *Plant Cell* 13:273.
Wang, et al. 2002. PYPAF7, a novel PYRIN-containing Apaf1-like protein that regulates activation of NF-kappa B and caspase-1-dependent cytokine processing. *J. Biol. Chem.* 277(33):29874-80.
Williams et al. "Cutting Edge: Monarch-1: A Pyrin/Nucleotide-Binding Domain/Leucine-Rich Repeat Protein that Controls Classical and nonclassical MHC Class I Genes" *The Journal of Immunology* 170: 5354-5358 (2003).
Wong, et al. 2002. Regulation and specificity of MHC2TA promoter usage in human primary T lymphocytes and cell line. *J Immunol* 169:3112.
Yao and Cooper. 1995. Requirement for phosphatidylinositol-3 kinase in the prevention of apoptosis by nerve growth factor. *Science* 267:2003.
Zhang, et al. 1999. Bacterial lipopolysaccharide activates nuclear factor-kappaB through interleukin-1 signaling mediators in cultured human dermal endothelial cells and mononuclear phagocytes. *J Biol Chem* 274:7611.
Zhou and Glimcher. 1995. Human MHC class II gene transcription directed by the carboxyl terminus of CIITA, one of the defective genes in type II MHC combined immune deficiency. *Immunity* . 2:545.
Zhu, et al. 2000. Transcriptional scaffold: CIITA interacts with NF-Y, RFX, and CREB to cause stereospecific regulation of the class II major histocompatibility complex promoter. *Mol.Cell Biol* 20(16):6051-61.
Moore et al. "NLRX1 is a Regulator of Mitochondrial Antiviral Immunity" *Nature* 451:573-579 (2008).

* cited by examiner

MOTIF I

```
-TVVL-G-AGhGKTTLAbbhhL-WA-G-Lr (SEQ ID NO:150)
* *** *  * *** **  *   *
```

MOTIF II

```
F-rhFrh-CbEh------Sh-aLl---rP (SEQ ID NO:151)
    *              * *** *
```

MOTIF III

```
-lh--PaRLLFlhDGFDEL (SEQ ID NO:152)
***      **********
```

MOTIF IV

```
LL-SLLbK-LLPEASLLlTpRP-Ah (SEQ ID NO:153)
 *  **    *  * *******
```

MOTIF V

```
L--hL---b-h-h-GFSE-abb--YF--r-a (SEQ ID NO:154)
```

MOTIF VI[1]

```
A-bsh--hb-N--Lr-hC-VP-hCWhVCp-Lb-Qha-G (SEQ ID NO:155)
             *      * ** ***
```

MOTIF VII

```
T-T-hr--rh---h (SEQ ID NO:156)
```

MOTIF VIII[2]

```
Lb-LC-LAAEGhW----hF--aDL---GL----h--FL---hh (SEQ ID NO:157)
                                         **
```

MOTIF IX[3]

```
Y-FhHLphQEF-AAhrYhL (SEQ ID NO:158)
     * * *** *
```

MOTIF X

```
FLFGLL-(-)n-b-LE--Fs--hS--hb (SEQ ID NO:159)
```

MOTIF XI

```
haLF-Clra-QE-aFh---h-----h-h (SEQ ID NO:160)
```

MOTIF XII

```
ahhV-pFCLbbC--h--L-L (SEQ ID NO:161)
```

*FIG. 2B*

MOTIF I

| | | * *** * * *** ** * * |
|---|---|---|
| 1.1 | MELLFDPDDEHSEPV | HTVVFQGAAGIGKTILARKMMLDWASGTLYQ |
| 19.3 | IETLFEPDEERPEPP | RTVVMQGAAGIGKSMLAHKVMLDWADGKLFQ |
| 19.1 | EYKELNDAYTAAARR | HTVVLEGPDGIGKTTLLRKVMLDWAEGNLWK |
| 12 | --------------- | ------------------------------- |
| DEFCAP | IRDLFGPGLDTQEP- | RIVILQGAAGIGKSTLARQVKEAWGRGQLYG |
| 11.2 | LEHLFDVDVKTGAQP | QIVVLQGAAGVGKTTLVRKAMLDWAEGSLYQ |
| 19.5 | LDRLFAPKETGKQP- | RTVIIQGPQGIGKTTLLMKLMMAWSDNKIFR |
| 19.7 | LQRLLDPNRTRAQA- | QTIVLVGRAGVGKTTLAMRAMLHWANGVLFQ |
| 19.2 | LPCLLLPKRPQGRQP | KTVAIQGAPGIGKTILAKKVMFEWARNKFYA |
| 11.1 | VEALFDSGEKPSLAP | SLVVLQGSAGTGKTTLARKMVLDWATGTLYP |
| Nalp2/19.4 | LIPFSNPRVLPGPFS | YTVVLYGPAGLGKTTLAQKLMLDWAEDNLIH |
| 19.8 | TLAGAFDSDRWGFRP | RTVVLHGKSGIGKSALARRIVLCWAQGGLYQ |
| 11.4 | TFNRLFRRDEEGRRP | LTVVLQGPAGIGKTMAAKKILYDWAAGKLYQ |
| 19.6 | LQLAYDSTSYYSANN | LNVFLMGERASGKTIVINLAVLRWIKGEMWQ |
| X | --------------- | --VVLQACAGTGKTAVVHKFMFDWAAGTVTP |
| 11.3 | LSQLFNPDACGRRV- | QTVVLYGTVGTGKSTLVRKMVLDWCYGRLPA |
| CIITA | EVLLAAKEHRRPRET | RVIAVLGKAGQGKSYWAGAVSRAWACGRLPQ |
| 16.1 | VSISDLFNTRVNKGP | RVTVLLGKAGMGKTTLAHRLCQKWAEGHLNC |
| 16.2 | LDRLFLPLSRVSVPP | RVSITIGVAGMGKTTLVRHFVRLWAHGQVGK |
| Nod2 | LEELFSTPGHLNDDA | DTVLVVGEAGSGKSTLLQRLHLLWAAGQDFQ |
| Nod1 | ACLLDHTTGILNEQG | ETIFILGDAGVGKSMLLQRLQSLWATGRLDA |
| Ipaf | RVEQLTLNGLLQALQ | SPCIIEGESGKGKSTLLQRIAMLWGSGKCKA |
| NAIP | VQEPLVLPEVFGNLN | SVMCVEGEAGSGKTVLLKKIAFLWASGCCPL |

MOTIF II

| | * * *** * | |
|---|---|---|
| 1.1 | -DRFDYLFYIHCREVS---LVTQRSLGDLIMSCCP | ----DPNPPIH |
| 19.3 | -GRFDYLFYINCREMNQ--SATECSMQDLIFSCWP | ----EPSAPLQ |
| 19.1 | -DRFTFVFFLNVCEMN---GIAETSLLELLSRDWP | ----ESSEKIE |
| 12 | ----------------------------------- | ----------- |
| DEFCAP | -DRFQHVFYFSCRELA---QSKVVSLAELIGKDGT | ----ATPAPIR |
| 11.2 | -QRFKYVFYLNGREIN---QLKERSFAQLISKDWP | ----STEGPIE |
| 19.5 | -DRFLYTFYFCCRELR---ELPPTSLADLISREWP | ----DPAAPIT |
| 19.7 | -QRFSYVFYLSCHKIR---YMKETTFAELISLDWP | ----DFDAPIE |
| 19.2 | -HKRWCAFYFHCQEVN---QTTDQSFSELIEQKWP | ----GSQDLVS |
| 11.1 | -GRFDYVFYVSCKEVV---LLLESKLEQLLFWCCG | ----DNQAPVT |
| Nalp2/19.4 | -K-FKYAFYLSCRELS---RLGPCSFAELVFRDWP | ----ELQDDIP |
| 19.8 | -GMFSYVFFLPVREMQ---RKKESSVTEFISREWP | ----DSQAPVT |
| 11.4 | -GQVDFAFFMPCGELLE--RPGTRSLADLILDQCP | ----DRGAPVP |
| 19.6 | -NMISYVVHLTSHEIN---QMTNSSLAELIAKDWP | ----DGQAPIA |
| X | -GRCDYLIYVNCIEIS---HIANLSSADLILTLFK | -----INGPIL |
| 11.3 | ---FELLIPFSCEDLSS-LGPAPASLCQLVAQRYT | ----PLKEVLP |
| CIITA | ---YDFVFSVPCHCLNR--PGDAYGLQDLLFSLGP | QPLVAADEVFS |
| 16.1 | -FQALFLFEFRQLNLIT--RFLTPSELLFDLYLSP | ES--DHDTVFQ |
| 16.2 | -D-FSLVLPLTFRDLN---THEKLCADRLICSVFP | -----HVGEPS |
| Nod2 | -E-FLFVFPFSCRQLQC--MAKPLSVRTLLFEHCC | WPDVGQEDIFQ |
| Nod1 | -G-VKFFFHFRCRMFSCFKESDRLCLQDLLFKHYC | YPERDPEEVFA |
| Ipaf | LTKFKFVFFLRLSRAQG--GLFETLCDQLLDIPGT | ---IRKQTFMA |
| NAIP | LNRFQLVFYLSLSSTRPDEGLASIICDQLLEKEGS | ---VTEMCMRN |

*FIG. 3A*

| | MOTIF III | |
|---|---|---|
| | *** ********** | |
| 1.1 | KIVRKPSRILFLMDGFDELQ | GAFDEHI----GPLCTDWQKAERGD |
| 19.3 | ELIRVPERLLFIIDGFDELK | PSFHDPQ----GPWCLCWEEKRPTE |
| 19.1 | DIFSQPERILFIMDGFEQLK | FNLQLK-----ADLSDDWRQRQPMP |
| 12 | HFFPQPEQILFIMDGFEQLK | FDLELK-----ADLCDDWRQQQPTQ |
| DEFCAP | QILSRPERLLFILDGVDEPG | WVLQEPS----SELCLHWSQPQPAD |
| 11.2 | EIMYQPSSLLFIIDSFDELN | FAFEEPE----FALCEDWTQEHPVS |
| 19.5 | EIVSQPERLLFVIDSFEELQ | GGLNEPD----SDLCGDLMEKRPVQ |
| 19.7 | EFMSQPEKLLFIIDGFEEII | ISESRSESLDDGSPCTDWYQELPVT |
| 19.2 | KIMSKPDQLLLLLDGFEELT | STLIDR----LEDLSEDWRQKLPGS |
| 11.1 | EILRQPERLLFILDGFDELQ | RPFEEK---------LKKRGLSPKE |
| Nalp2/19.4 | HILAQARKILFVIDGFDELG | AAPGALI----EDICGDWEKKKPVP |
| 19.8 | EIMSRPERLLFIIDGFDDLG | SVLNNDT-----KLCKDWAEKQPPF |
| 11.4 | QMLAQPQRLLFILDGADELP | ALGGPE-----AAPCTDPFEAASGA |
| 19.6 | DILSDPKKLLFILEDLDNIR | FELNVN----ESALCSNSTQKVPIP |
| X | DTILIYPKILLILDRFPELQ | DPVGDQE----EDLSVHPQERRPVE |
| 11.3 | LMAAAGSHLLFVLHGLEHLN | LDFRLAG----TGLCSDPEEPQEPA |
| CIITA | HILKRPDRVLLILDAFEELE | AQDGFLH----STCGPAPAEPCSLR |
| 16.1 | YLEKNADQVLLIFDGLDEAL | QPMGPDg-------------PGPVL |
| 16.2 | LAVAVPARALLILDGLDECR | TPLDFSN----TVACTDPKKEIPVD |
| Nod2 | LLLDHPDRVLLTFDGFDEFK | FRFTDR-----ERHCS-PTDPTSVQ |
| Nod1 | FLLRFPHVALFTFDGLDELH | SDLDLSR----VPDSSCPWEPAHPL |
| Ipaf | MLLKLRQRVLFLLDGYNEFK | PQNC--------------------- |
| NAIP | IIQQLKNQVLFLLDDYKEIC | SIPQ--------------------- |

| | MOTIF IV | MOTIF V |
|---|---|---|
| | * ** * * ******* | |
| 1.1 | ILLSSLIRKKLLPEASLLITTRPVALEK | LQHLLDHPRHVEILGFS |
| 19.3 | LLLNSLIRKKLLPELSLLITTRPTALEK | LHRLLEHPRHVEILGFS |
| 19.1 | IILSSLLQKKMLPESSLLIALGKLAMQK | HYFMLRHPKLIKLLGFS |
| 12 | IILSSLLQKKMIPESSLLIALGKVGMQK | NYFMLXHPKLIKLPGFT |
| DEFCAP | ALLGSLLGKTILPEASFLITARTTALQN | LIPSLEQARWVEVLGFS |
| 11.2 | FLMSSLLRKVMLPEASLLVTTRLTTSKR | LKQLLKNHHYVELLGMS |
| 19.5 | VLLSSLLRKKMLPEASLLIAIKPVCPKE | LRDQVTISEIYQPRGFN |
| 19.7 | KILHSLLKKELVPLATLLITIKTWFVRD | LKASLVNPCFVQITGFT |
| 19.2 | VLLSSLLSKTMLPEATLLIMIRFTSWQT | CKPLLKCPSLVTLPGFN |
| 11.1 | SLLHLLIRRHTLPTCSLLITTRPLALRN | LEPLLKQARHVHILGFS |
| Nalp2/19.4 | VLLGSLLNRVMLPKAALLVTTRPRALRD | LRILAEEPIYIRVEGFL |
| 19.8 | TLIRSLLRKVLLPESFLIVTVRDVGTEK | LKSEVVSPRYLLVRGIS |
| 11.4 | RVLGGLLSKALLPTALLLVTTRAAAPGR | LQGRLCSPQCAEVRGFS |
| 19.6 | VLLVSLLKRKMAPGCWFLISSRPTRGNN | VKTFLKEVDCCTTLQLS |
| X | SLLCSFVRKKLFPESSLLITARPTAMKK | LHSLLKQPIQAEILWFT |
| 11.3 | AIIVNLLRKYMLPQASILVTTRPSAIGR | IPSKY-VGRYGEICGFS |
| CIITA | GLLAGLFQKKLLRGCTLLLTARPRG-RL | VQSLSKADALFELSGFS |
| 16.1 | TLFSHLCNGTLLPGCRVMATSRPGK--L | PACLPAEAAMVHMLGFD |
| 16.2 | HLITNIIRGNLFPEVSIWITSRPSASGQ | IPGGL-VDRMTEIRGFN |
| Nod2 | TLLFNLLQGNLLKNARKVVTSRPAAVSA | FLRKY-IRTEFNLKGFS |
| Nod1 | VLLANLLSGKLLKGASKLLTARTGIEVP | RQFLR---KKVLLRGFS |
| Ipaf | PEIEALIKENHRFKNMVIVTTTTECLRH | IRQFGALTAEVGDMTED |
| NAIP | -VIGKLIQKNHLSRTCLLIAVRTNRARD | IRRYLETILEIKAFPFY |

*FIG. 3B*

| | MOTIF V | | MOTIF VI1 |
|---|---|---|---|
| 1.1 | EAKRKE-YFFKYFSDE | ------------------A | QARAAFSLI |
| 19.3 | EAERKE-YFYKYFHNA | ------------------E | QAGQVFNYV |
| 19.1 | ESEKKS-YFSYFFGEK | ------------------S | KALKVFNFV |
| 12 | ELERKL-YFSYFFSEK | ------------------N | KALKAFHFV |
| DEFCAP | ESSRKE-YFYRYFTDE | ------------------R | QAIRAFRLV |
| 11.2 | EDAREE-YIYQFFEDK | ------------------R | WAMKVFSSL |
| 19.5 | ESDRLV-YFCCFFKDP | ------------------K | RAMEAFNLV |
| 19.7 | GDDLRV-YFMRHFDDS | ------------------S | EVEKILQQL |
| 19.2 | TMEKIK-YFQMYFGHT | ------------------E | EGDQVLSFA |
| 11.1 | EEERAR-YFSSYFTDE | ------------------K | QADRAFDIV |
| Nalp2/19.4 | EEDRRA-YFLRHFGDE | ------------------D | QAMRAFELM |
| 19.8 | GEQRIHLLLERGIGE- | ------------------H | QKTQGLRAI |
| 11.4 | DKDKKK-YFYKFFRDE | ------------------R | RAERAYRFV |
| 19.6 | NGKREI-YFNSFFKDR | ------------------Q | RASAALQLV |
| X | DTEKRA-YLLSQFSGA | ------------------N | TTMKVFYDL |
| 11.3 | DTNLQKLYFQLRLNQP | YCGYAVGGSGVSATPAQRDH | LVQMLSRNL |
| CIITA | MEQAQA-YVMRYFESS | ---------------GMTE | HQDRALTLL |
| 16.1 | GPRVEE-YVNHFFSAQ | ------------------P | SREGALVEL |
| 16.2 | EEEIKVC-LEQMFPED | -----------------QA | LLGWMLSQV |
| Nod2 | EQGIEL-YLRKRHHEP | ------------------G | VADRLIRLL |
| Nod1 | PSHLRA-YARRMFPER | ------------------A | LQDRLLSQL |
| Ipaf | SAQALIREVLIKELA- | ------------------- | --EGLLLQI |
| NAIP | NTVCILRKLFSHNMT- | ------------------- | RLRKFMVYF |

MOTIF VI1

| | * * ** *** | |
|---|---|---|
| 1.1 | QENEVLFTMCFIPLVCWIVCTGLKQQMESGK | SLAQTSK---- |
| 19.3 | RDNEPLFTMCFVPLVCWVVCTCLQQQLEGGG | LLRQTSR---- |
| 19.1 | RDNGPLFILCHNPFTCWLVCTCVKQRLERGE | DLEINSQ---- |
| 12 | RDTGQRFILCHNPFICWLVCTCMKWQLERGE | DLEINSQNTFI |
| DEFCAP | KSNKELWALCLVPWVSWLACTCLMQQMKRKE | KLTLTSK---- |
| 11.2 | KSNEMLFSMCQVPLVCWAACTCLKQQMEKGG | DVTLTCQ---- |
| 19.5 | RESEQLFSICQIPLLCWILCTSLKQEMQKGK | DLALTCQ---- |
| 19.7 | RKNETLFHSCSAPMVCWTVCSCLKQPKVRYY | DLQSITQ---- |
| 19.2 | MENTILFSMCRVPVVCWMVCSGLKQQMERGN | NLTQSCP---- |
| 11.1 | QKNDILYKACQVPGICWVVCSWLQGQMERGK | VVLETPR---- |
| Nalp2/19.4 | RSNAALFQLGSAPAVCWIVCTTLKLQMEKGE | DPVPTCL---- |
| 19.8 | MNNRELLDQCQVPAVGSLICVALQLQDVVGE | SVAPFNQ---- |
| 11.4 | KENETLFALCFVPFVCWIVCTVLRQQLELGR | DLSRTSK---- |
| 19.6 | HEDEILVGLCRVAILCWITCTVLKRQMDKGR | DFQLCCQ---- |
| X | XENEDLDIMSSLPIVSWMICNVLQSQGDGDR | TLLRSLQ---- |
| 11.3 | EGHHQIAAACFLPSYCWLVCATLHFLHAPTP | AGQ-------- |
| CIITA | RDRPLLLSHSHSPTLCRAVCQLSEALLELGE | DAKLPS----- |
| 16.1 | QTNGRLRSLCAVPALCQVACLCLHHLLPDHA | PGQSVALLP-- |
| 16.2 | QADRALYLMCTVPAFCRLTGMALGHLWRSRT | GPQDAELWPPR |
| Nod2 | QETSALHGLCHLPVFSWMVSKCHQELLLQEG | GSPK------- |
| Nod1 | EANPNLCSLCSVPLFCWIIFRCFQHFRAAFE | GSPQLPDC-TM |
| Ipaf | QKSRCLRNLMKTPLFVVITCAIQMGESEFHS | HTQTTLF---- |
| NAIP | GKNQSLQKIQKTPLFVAAICAHWFQYPFDPS | FDDVAVF---- |

*FIG. 3C*

| | MOTIF VII | | MOTIF VIII² |
|---|---|---|---|
| 1.1 | TSTAVYVFFLSSLLQ | PRGGSQEH-----------GLCA- | HLWGLC |
| 19.3 | TTTAVYMLYLLSLMQ | PKPGAPRL-----------QPPP- | NQRGLC |
| 19.1 | NTTYLYASFLTTVFK | AGSQSFPPK----------VNRA- | RLKSLC |
| 12 | HLLKMNASFLTNVFK | AGSQSFPPK----------VNRA- | RLKSLC |
| DEFCAP | TTTTLCLHYLAQALQ | AQPLGP------------------ | QLRDLC |
| 11.2 | TTTALFTCYISSLFT | PVDGGSPSL----------PNQA- | QLRRLC |
| 19.5 | STTSVYSSFVFNLFT | PEGAEGPTP----------QTQH- | QLKALC |
| 19.7 | TTTSLYAYFFSNLFS | TAEVDLADD----------SWPG- | QWRALC |
| 19.2 | NATSVFVRYISSLFP | TRAENFSRK----------IHQA- | QLEGLC |
| 11.1 | NSTDIFMAYVSTFLP | PDDDGGCSE----------LSRHR | VLRSLC |
| Nalp2/19.4 | TRTGLFLRFLCSRFP | QGAQLRG----------------- | ALRTLS |
| 19.8 | TLTGLHAAFVFHQLT | PRGVVRRCLN---------LEERV | VLKRFC |
| 11.4 | TTTSVYLLFITSVLS | SAPVADGPR----------LQG-- | DLRNLC |
| 19.6 | TPTDLHAHFLADALT | SEAGLTANQY---------HLG-- | LLKRLC |
| X | TMTDVYLFYFSKCLK | TLTGISVWE------------GQS | CLWGLC |
| 11.3 | TLTSIYTSFLRLNFS | GETLDSTDPSNL-------SLMAY | AARTMG |
| CIITA | TLTGLYVGLLGRAAL | DSPPG------------------- | ALAELA |
| 16.1 | NMTQLYMQMVLALSP | PGHLPTS----------------- | SLLDLG |
| 16.2 | TLCELYSWYFRMALS | GEGQEKGKAS--PRIEQVAHGGRK | MVGTLG |
| Nod2 | TTTDMYLLILQHFLL | HATPPDSASQ--GLGPSLLRGRLP | TLLHLG |
| Nod1 | TLTDVFLLVTEVHLN | RMQPSSLVQRNTRSPVETLHAGRD | TLCSLG |
| Ipaf | ---------HTFYDL | LIQKNKHKHKG-----VAASDFIR | SLDHCG |
| NAIP | ---------KSYMER | LSLRNK----------ATAEILKA | TVSSCG |

MOTIF VIII²

**

| | | |
|---|---|---|
| 1.1 | SLAADGIWNQKILFEESDLRNHGLQKA-DVSAFLRMNLFQK | EVD-- |
| 19.3 | SLAADGLWNQKILFEEQDLRKHGLDGE-DVSAFLNMNIFQK | DIN-- |
| 19.1 | ALAAEGIWTYTFVFSHGDLRRNGLSES-EGVMWVGMRLLQR | R---- |
| 12 | ALAAEGIWTHAFVF---DLWRNGLSES-EGLMWVGMKLLQR | X---- |
| DEFCAP | SLAAEGIWQKKTLFSPDDLRKHGLDGA-IISTFLKMGILQE | HP--- |
| 11.2 | QVAAKGIWTMTYVFYRENLRRLGLTQS-DVSSFMDSNIIQK | DAE-- |
| 19.5 | SLAAEGMWTDTFEFCEDDLRRNGVVDA-DIPALLGTKILLK | YGE-- |
| 19.7 | SLAIEGLWSMNFTFNKEDTEIEGLEVP-FIDSLYEFNILQK | IND-- |
| 19.2 | HLAADSMWHRKWVLGKEDLEEAKLDQT-GVTAFLGMSILRR | IAG-- |
| 11.1 | SLAAEGIQHQRFLFEEAELRKHNLDGP-RLAAFLSSNDYQL | GLA-- |
| Nalp2/19.4 | LLAAQGLWAQTSVLHREDLERLGVQES-DLRLFLDGDILRQ | DRV-- |
| 19.8 | RMAVEGVWNRKSVFDGDDLMVQGLGES-ELRALFHMNILLP | DSH-- |
| 11.4 | RLAREGVLGRRAQFAEKELEQLELRGSKVQTLFLSKKELPG | VLE-- |
| 19.6 | LLAAGGLFLSTLNFSGEDLRCVGFTEA-DVSVLQAANILLP | SNT-- |
| X | RLAAEGLQNHQVLFAVSDLRRHGIGVCDTNCTFLSRFLKKA | EG--- |
| 11.3 | KLAYEGVSSRKTYFSEEDVCGCLEAGIRTEEEFQLLHIFRR | DALRF |
| CIITA | KLAWELGRRHQSTLQEDQFPSADVRTWAMAK-----GLVQH | PPR-- |
| 16.1 | EVALRGLETGKVIFYAKDIAPPLIAFGATHSLLTSFCVCTG | PG--- |
| 16.2 | RLAFHGLLKKKYVFYEQDMKAFGVDLALLQGAPCSCFLQRE | ETL-- |
| Nod2 | RLALWGLGMCCYVFSAQQLQAAQVSPDDISLGFLVRAKGVV | PG--- |
| Nod1 | QVAHRGMEKSLFVFTQEEVQASGLQERDMQLGFLRALPELG | PGG-- |
| Ipaf | DLALEGVFSHKFDFELQDVSSVNEDVLLTTGLLC------- | ----- |
| NAIP | ELALKGFFSCCFEFNDDDLAEAGVDEDEDLTMCL------- | ----- |

*FIG. 3D*

MOTIF IX[3]

| | | * * *** * | |
|---|---|---|---|
| 1.1 | ---------CEK | FYSFIHMTFQEFFAAMYYLLE | EEKEGRTNV--- |
| 19.3 | ---------CER | YYSFIHLSFQEFFAAMYYILD | EGEGGAG----- |
| 19.1 | ----------GD | CFAFMHLCIQEFCAAMFYLLK | RPKDDPN----- |
| 12 | ----------GE | CFTFIHVCIQEFCATMFYLLK | RPKDDPN----- |
| DEFCAP | ---------IPL | SYSFIHLCFQEFFAAMSYVLE | DEKGRGKHS--- |
| 11.2 | ---------YEN | CYVFTHLHVQEFFAAMFYMLK | GSWEAGNP---- |
| 19.5 | ---------RES | SYVFLHVCIQEFCAALFYLLK | GSWEAGNP---- |
| 19.7 | ---------CGG | CTTFTHLSFQEFFAAMSFVLE | EPREFPP-H--- |
| 19.2 | ---------EED | HYVFTLVTFQEFFAALFYVLC | FPQRLKN----- |
| 11.1 | ---------IKK | FYSFRHISFQDFFHAMSYLVK | EDQSRLG----- |
| Nalp2/19.4 | ---------SKG | CYSFIHLSFQQFLTALFYTLE | KEEEEDRD---- |
| 19.8 | ---------CEE | YYTFFHLSLQDFCAALYYVLE | GLEIEPALC--- |
| 11.4 | ---------TEV | TYQFIDQSFQEFLAALSYLLE | DGGVPRT----- |
| 19.6 | ---------HKD | RYKFIHLNVQEFCTAIAFLMA | VPNYLIP----- |
| X | ---------AVS | VYTFLHFSFQEFLTAVFHALK | NDNSWMF----- |
| 11.3 | FLAPCVEPGRAG | TFVFTVPAMQEYLAALYIVLG | LRKTTLQ----- |
| CIITA | --------AAES | ELAFPSFLLQCFLGALWLALS | GEIKDKE----- |
| 16.1 | --------HQQT | GYAFTHLSLQEFLAALHLMAS | PKVNKDT----- |
| 16.2 | --------ASSV | AYCFTHLSLQEFVAAAYYYGA | SRRAIFDLFTES |
| Nod2 | ---------STA | PLEFLHITFQCFFAAFYLALS | ADVPPALLRHLF |
| Nod1 | ---------DQQ | SYEFFHLTLQAFFTAFFLVLD | DRVGTQELLRFF |
| | | | |
| Ipaf | ---KYTAQRFKP | KYKFFHKSFQEYTAGRRLSSL | L |
| NAIP | -MSKFTAQRLRP | FYRFLSPAFQEFLAGMRLIEL | L |

| | |
|---|---|
| 1.1 | -------------PGSRLKLPSRDVTVLLENYGKFEK-GYLIFVV |
| 19.3 | --------------------PDQDVTRLLTEYAFSER-SFLALTS |
| 19.1 | -------------P------AIGSITQLVRASVVQPQ-TLLTQVG |
| 12 | -------------P------TIGSITQLVRASVAQPQ-THSTQVG |
| DEFCAP | -------------N------CIIDLEKTLEAYGIHG--LFGASTT |
| 11.2 | -------------S----CQPFEDLKSLLQSTSYKD--PHLTQMK |
| 19.5 | --------------------AVRCVQELLVANFEKARRAHWIFLG |
| 19.7 | -------------S------TKPQEMKMLLQHVLLDKEAYWTPVV |
| 19.2 | ------------------FHVLSHVNIQRLIASPRGSKSYLSHMG |
| 11.1 | -------------K-----ESRREVQRLLEVKEQEGN-DEMTLTM |
| Nalp2/19.4 | ----------------GHTWDIGDVQKLLSGVERLRN-PDLIQAG |
| 19.8 | -------------P------LYVEKTKRSMELKQAGFHIHSLWMK |
| 11.4 | --------------------AAGGVGTLLRGDAQPHS--HLVLTT |
| 19.6 | ----------------------S---GSREYKEKREQYSDFNQVF |
| X | --------------------FYQAEKMWQEMFQQYG-KGFSSLMI |
| 11.3 | --KVGKEVAELVGRVGEDVSLVLGIMAKLLPLRALPLLFNLIKVV |
| CIITA | ----------------------LPQYLALTPRKKRPYDNWLEGVP |
| 16.1 | -------------------LTQYVTLHSRWVQRTKARLGLSDHLP |
| 16.2 | -------G------VSWPRLGFLTHFRSAAQRAMQAEDGRLDVFL |
| Nod2 | NCGRPGNSPMARLLPTMCIQASEGKDSSVAALLQKAEPHNLQITA |
| Nod1 | QEWMPPAGAATTSCYPPFLPFQCLQGSGPAREDLFKNKDHFQFTN |
| | |
| Ipaf | (SEQ ID NO:183) |
| NAIP | (SEQ ID NO:184) |

FIG. 3E

| | MOTIF X | | MOTIF X | |
|---|---|---|---|---|
| 1.1 | RFLFGLVN | QERT-------- | SYLEKKLSCMISQQIRL | ELLKWIE |
| 19.3 | RFLFGLLN | EETR-------- | SHLEKSLCWKVSPHIKM | DLLQWIQ |
| 19.1 | IFMFGIST | EEIV-------- | SMLETSFGFPLSKDLKQ | EITQCLE |
| 12 | VFVFGIST | EEII-------- | SLLETSFGFPLLKDLKK | EITQCLK |
| DEFCAP | RFLLGLLS | DEGE-------- | REMENIFHCRLSQ--GR | NLMQWVP |
| 11.2 | CFLFGLLN | EDRV-------- | KQLERTFNCKMSLKIKS | KLLQCME |
| 19.5 | CFLTGLLN | KKEQ-------- | EKLDAFFGFQLSQEIKQ | QIHQCLK |
| 19.7 | LFFFGLLN | KNIA-------- | RELEDTLHCKISPRVME | ELLKWGE |
| 19.2 | LFLFGFLN | EACA-------- | SAVEQSFQCKVSFGNKR | KLLKVIP |
| 11.1 | QFLLDISK | KDSF-------- | SNLELKFCFRISPCLAQ | DLKHFKE |
| Nalp2/19.4 | YYSFGLAN | EKRA-------- | KELEATFGCRMSPDIKQ | ELLRCDI |
| 19.8 | RFLFGLVS | EDVR-------- | RPLEVLLGCPVPLGVKQ | KLLHWVS |
| 11.4 | RFLFGLLS | AERM-------- | RDIERHFGCMVSERVKQ | EALRWVQ |
| 19.6 | TFIFGLLN | ANRR-------- | KILETSFGYQLPMVDSF | KWYSVGY |
| X | XFLFGLLH | KGKG-------- | KAVETTFGRKVSPGLQE | ELLKWTE |
| 11.3 | PRVFGRMV | GKSR-------- | RAVLAQLGCPIKNLDAL | ENAQAIK |
| CIITA | RFLAGLIF | QPPA-------- | RCLGALLGPSAAASVDR | KQKVLAR |
| 16.1 | TFLAGLAS | CTCR-------- | -PFLSHLAQGNEDCVGA | KQAAVVQ |
| 16.2 | RFLSGLLS | PRVN-------A | LLAGSLLAQGEHQAYRT | QVAELLQ |
| Nod2 | AFLAGLLS | REHWG------- | LLAECQTSEKALLRRQA | CARWCLA |
| Nod1 | LFLCGLLS | KAKQKLL----R | HLVPAAALRRKRKALWA | HLFSSLR |

| | |
|---|---|
| 1.1 | VKAK------------------------AKKLHDQPS |
| 19.3 | SKAQ------------------------SDGSTLQQG |
| 19.1 | SLSQ------------------------CEADREAIA |
| 12 | SLSQ------------------------XEADREVIG |
| DEFCAP | SLQ----------------------------LLLQPH |
| 11.2 | VLGN------------------------SDYSPSQLG |
| 19.5 | SLGE------------------------RGNPQGQVD |
| 19.7 | ELGK------------------------AESASLQFH |
| 19.2 | LLHK------------------------CDPPSPGSG |
| 11.1 | QMES------------------------MKHNRTWDL |
| Nalp2/19.4 | SCKG--------------------------GHSTVTD |
| 19.8 | LLGQ------------------------QPNATTPGD |
| 11.4 | GQGQGCPGVAPEVTEGAKGLEDTEEPEEEEEGEEPNY |
| 19.6 | MKHLD-----------------------RDPEKLTH |
| X | REIK------------------------DKSSRLQIE |
| 11.3 | KKLG----------------------KLGRQVLPPSE |
| CIITA | YLKR-----------------------LQPGTLRARQ |
| 16.1 | VLKK-----------------------LATRKLTGPK |
| 16.2 | GCLR-------------------------PDAAVCAR |
| Nod2 | RSLR-----------KHFHSIPPAAPGEAKSVHAMPG |
| Nod1 | GYLKSLPR---------------VQVESFNQVQAMPT |

FIG. 3F

MOTIF XI

| | | |
|---|---|---|
| 1.1 | QLELFYCLYEMQEEDFVQRAMDYFPKIEIN- | -L--STR |
| 19.3 | SLEFFSCLYEIQEEEFIQQALSHFQVIVVSN | -I--ASK |
| 19.1 | FQELFIGLFETQEKEFVTKVMNFFEEVFIY- | -I--GNI |
| 12 | FQELFHDLFATQEKEFVTEVINFFEEVFIC- | -T--GNI |
| DEFCAP | SLESLHCLYETRNKTFLTQVMAHFEEMGMC- | -V--ETD |
| 11.2 | FLELFHCLYETQDKAFISQAMRCFPKVAIN- | -I--CEK |
| 19.5 | SLAIFYCLFEMQDPAFVKQAVNLLQEANFH- | -I--IDN |
| 19.7 | ILRLFHCLHESQEEDFTKKMLGRIFEVDLN- | -I--LED |
| 19.2 | VPQLFYCLHEIREEAFVSQALNDYHKVVLR- | -I--GNN |
| 11.1 | EFSLYEAKIKNLVKGIQMNNVSFKIKHSNEK | -K--SQS |
| Nalp2/19.4 | LQELLGCLYESQEEELVKEVMAQFKEISLH- | ----LNA |
| 19.8 | TLDAFHCLFETQDKEFVRLALNSFQEVWLP- | -I--NQN |
| 11.4 | PLELLYCLYETQEDAFVRQALCRFPELALQR | -V-RFCR |
| 19.6 | HMPLFYCLYENREEEFVKTIVDALMEVTVYL | -Q---SD |
| X | PVDLFHCLYEIQEEEYAKRIIDDLQSIILLQ | PT--YTK |
| 11.3 | LLDHLFFHYEFQNQRFSAEVLSSLRQLNLAG | -V-RMTP |
| CIITA | LLELLHCAHEAEEAGIWQHVVQELPGRLSFL | G-TRLTP |
| 16.1 | VVELCHCVDETQEPELASLTAQSLPYQLPFH | N-FPLTC |
| 16.2 | AINVLHCLHELQHTELARSVEEAMESGALAR | LTGPAHR |
| Nod2 | FIWLIRSLYEMQEERLARKAARGLNVGHLKL | TFCSVGP |
| Nod1 | FIWMLRCIYETQSQKVGQLAARGICANYLKL | TYCNACS |

MOTIF XII

| | | |
|---|---|---|
| 1.1 | MDHMVSSFCIENCHRVESLSLGF | (SEQ ID NO:162) |
| 19.3 | MEHMVSSFCLKRCRSAQVLHLYG | (SEQ ID NO:163) |
| 19.1 | EHLVIASFCLKHCQHLTTLRMCV | (SEQ ID NO:164) |
| 12 | EHLVVSSFCRKHCQNLTTLRMCV | (SEQ ID NO:165) |
| DEFCAP | MELLVCTFCIKFSRHVKKLQLIE | (SEQ ID NO:166) |
| 11.2 | IHLLVSSFCLKHCRCLRTIRLSV | (SEQ ID NO:167) |
| 19.5 | VDLVVSAYCLKYCSSLRKLCFSV | (SEQ ID NO:168) |
| 19.7 | EELQASSFCLKHCKRLNKLRLSV | (SEQ ID NO:169) |
| 19.2 | KEVQVSAFCLKRCQYLHEVELT- | (SEQ ID NO:170) |
| 11.1 | QNLFSVKSSLSHGPKEEQKCPSV | (SEQ ID NO:171) |
| Nalp2/19.4 | VDVVPSSFCVKHCRNLQKMSLQV | (SEQ ID NO:172) |
| 19.8 | LDLIASSFCLQHCPYLRKIRVDV | (SEQ ID NO:173) |
| 11.4 | MDVAVLSYCVRCCPAGQALRLIS | (SEQ ID NO:174) |
| 19.6 | KDMMVSLYCLDYCCHLRTLKLSV | (SEQ ID NO:175) |
| X | MDILVMSFCVKSSHSHLSVSLKC | (SEQ ID NO:176) |
| 11.3 | VKCTVVAAVLGSGRHALDEVNLA | (SEQ ID NO:177) |
| CIITA | PDAHVLGKALEAAGQDFSLDLRS | (SEQ ID NO:178) |
| 16.1 | TDLATLTNILEHREAPIHLDFDG | (SEQ ID NO:179) |
| 16.2 | AALAYLLQVSDACAQEANLSLSL | (SEQ ID NO:180) |
| Nod2 | TECAALAFVLQHLRRPVALQLDY | (SEQ ID NO:181) |
| Nod1 | ADCSALSFVLHHFPKRLALDLDN | (SEQ ID NO:182) |

*FIG. 3G*

1 ATTGGTGAGTGGGGCAGGGCAGGAGGGAACTGAAGAGTGAGAAAGCATTA
51 TTTCAGCAAAAGGTCTTTCCTCCCTTGCTCACTCCTCCAACCACTGGCTC
101 AGCCTCTCCGCCCGCTGCCTGTGAATGATGCAATGGAAGGTGTGCTGGGG
151 TCGCCCTGTGTCCCGTGCATAGGAGCATCTCAGCCTCCAGGTCCTCTCCT
201 TTGGGGCTTACGGCACCCCCATGCTACGAACCGCAGGCAGGGACGGCCTC
251 TGTCGCCTGTCCACCTACTTGGAAGAACTCGAGGCTGTGGAACTGAAGAA
301 GTTCAAGTTATACCTGGGGACCGCGACAGAGCTGGGAGAAGGCAAGATCC
351 CCTGGGGAAGCATGGAGAAGGCCGGTCCCCTGGAAATGGCCCAGCTGCTC
401 ATCACCCACTTCGGGCCAGAGGAGGCCTGGAGGTTGGCTCTCAGCACCTT
451 TGAGCGGATAAACAGGAAGGACCTGTGGGAGAGAGGACAGAGAGAGGACC
501 TGGTGAGGGATACCCCACCTGGTGGCCCGTCCTCACTTGGGAACCAGTCA
551 ACATGCCTTCTGGAAGTCTCTCTTGTCACTCCAAGAAAAGATCCCCAGGA
601 AACCTACAGGGACTATGTCCGCAGGAAATTCCGGCTCATGGAAGACCGCA
651 ATGCGCGCCTAGGGGAATGTGTCAACCTCAGCCACCGGTACACCCGGCTC
701 CTGCTGGTGAAGGAGCACTCAAACCCCATGCAGGTCCAGCAGCAGCTTCT
751 GGACACAGGCCGGGGACACGCGAGGACCGTGGGACACCAGGCTAGCCCCA
801 TCAAGATAGAGACCCTCTTTGAGCCAGACGAGGAGCGCCCCGAGCCACCG
851 CGCACCGTGGTCATGCAAGGCGCGGCAGGGATAGGCAAGTCCATGCTGGC
901 ACACAAGGTGATGCTGGACTGGGCGGACGGGAAGCTCTTCCAAGGCAGAT
951 TTGATTATCTCTTCTACATCAACTGCAGGGAGATGAACCAGAGTGCCACG
1001 GAATGCAGCATGCAAGACCTCATCTTCAGCTGCTGGCCTGAGCCCAGCGC
1051 GCCTCTCCAGGAGCTCATCCGAGTTCCCGAGCGCCTCCTTTTCATCATCG
1101 ACGGCTTCGATGAGCTCAAGCCTTCTTTCCACGATCCTCAGGGACCCTGG
1151 TGCCTCTGCTGGGAGGAGAAACGGCCCACGGAGCTGCTTCTTAACAGCTT
1201 AATTCGGAAGAAGCTGCTCCCTGAGCTATCTTTGCTCATCACCACACGGC
1251 CCACGGCTTTGGAGAAGCTCCACCGTCTGCTGGAGCACCCCAGGCATGTG
1301 GAGATCCTGGGCTTCTCTGAGGCAGAAAGGAAGGAATACTTCTACAAGTA
1351 TTTCCACAATGCAGAGCAGGCGGGCCAAGTCTTCAATTACGTGAGGGACA
1401 ACGAGCCTCTCTTCACCATGTGCTTCGTCCCCCTGGTGTGCTGGGTGGTG
1451 TGTACCTGCCTCCAGCAGCAGCTGGAGGGTGGGGGGCTGTTGAGACAGAC
1501 GTCCAGGACCACCACTGCAGTGTACATGCTCTACCTGCTGAGTCTGATGC
1551 AACCCAAGCCGGGGGCCCCGCGCCTCCAGCCCCCACCCAACCAGAGAGGG
1601 TTGTGCTCCTTGGCGGCAGATGGGCTCTGGAATCAGAAAATCCTATTTGA
1651 GGAGCAGGACCTCCGGAAGCACGGCCTAGACGGGGAAGACGTCTCTGCCT
1701 TCCTCAACATGAACATCTTCCAGAAGGACATCAACTGTGAGAGGTACTAC
1751 AGCTTCATCCACTTGAGTTTCCAGGAATTCTTTGCAGCTATGTACTATAT
1801 CCTGGACGAGGGGGAGGGCGGGGCAGGCCCAGACCAGGACGTGACCAGGC
1851 TGTTGACCGAGTACGCGTTTTCTGAAAGGAGCTTCCTGGCACTCACCAGC
1901 CGCTTCCTGTTTGGACTCCTGAACGAGGAGACCAGGAGCCACCTGGAGAA
1951 GAGTCTCTGCTGGAAGGTCTCGCCGCACATCAAGATGGACCTGTTGCAGT
2001 GGATCCAAAGCAAAGCTCAGAGCGACGGCTCCACCCTGCAGCAGGGCTCC
2051 TTGGAGTTCTTCAGCTGCTTGTACGAGATCCAGGAGGAGGAGTTTATCCA
2101 GCAGGCCCTGAGCCACTTCCAGGTGATCGTGGTCAGCAACATTGCCTCCA
2151 AGATGGAGCACATGGTCTCCTCGTTCTGTCTGAAGCGCTGCAGGAGCGCC
2201 CAGGTGCTGCACTTGTATGGCGCCACCTACAGCGCGGACGGGGAAGACCG
2251 CGCGAGGTGCTCCGCAGGAGCGCACACGCTGTTGGTGCAGCTCAGACCAG
2301 AGAGGACCGTTCTGCTGGACGCCTACAGTGAACATCTGGCAGCGGCCCTG
2351 TGCACCAATCCAAACCTGATAGAGCTGTCTCTGTACCGAAATGCCCTGGG
2401 CAGCCGGGGGGTGAAGCTGCTCTGTCAAGGACTCAGACACCCCAACTGCA
2451 AACTTCAGAACCTGAGGCTGAAGAGGTGCCGCATCTCCAGCTCAGCCTGC
2501 GAGGACCTCTCTGCAGCTCTCATAGCCAATAAGAATTTGACAAGGATGGA

FIG. 6A

2551 TCTCAGTGGCAACGGCGTTGGATTCCCAGGCATGATGCTGCTTTGCGAGG
2601 GCCTGCGGCATCCCCAGTGCAGGCTGCAGATGATTCAGTTGAGGAAGTGT
2651 CAGCTGGAGTCCGGGGCTTGTCAGGAGATGGCTTCTGTGCTCGGCACCAA
2701 CCCACATCTGGTTGAGTTGGACCTGACAGGAAATGCACTGGAGGATTTGG
2751 GCCTGAGGTTACTATGCCAGGGACTGAGGCACCCAGTCTGCAGACTACGG
2801 ACTTTGTGGCTGAAGATCTGCCGCCTCACTGCTGCTGCCTGTGACGAGCT
2851 GGCCTCAACTCTCAGTGTGAACCAGAGCCTGAGAGAGCTGGACCTGAGCC
2901 TGAATGAGCTGGGGGACCTCGGGGTGCTGCTGCTGTGTGAGGGCCTCAGG
2951 CATCCCACGTGCAAGCTCCAGACCCTGCGGTTGGGCATCTGCCGGCTGGG
3001 CTCTGCCGCCTGTGAGGGTCTTTCTGTGGTGCTCCAGGCCAACCACAACC
3051 TCCGGGAGCTGGACTTGAGTTTCAACGACCTGGGAGACTGGGGCCTGTGG
3101 TTGCTGGCTGAGGGGCTGCAACATCCCGCCTGCAGACTCCAGAAACTGTG
3151 GCTGGATAGCTGTGGCCTCACAGCCAAGGCTTGTGAGAATCTTTACTTCA
3201 CCCTGGGGATCAACCAGACCTTGACCGACCTTTACCTGACCAACAACGCC
3251 CTAGGGGACACAGGTGTCCGACTGCTTTGCAAGCGGCTGAGCCATCCTGG
3301 CTGCAAACTCCGAGTCCTCTGGTTATTTGGGATGGACCTGAATAAAATGA
3351 CCCACAGTAGGTTGGCAGCGCTTCGAGTAACAAAACCTTATTTGGACATT
3401 GGCTGCTGAATGGTCCTATCTGCTGGCTCTCCCCTGAGATCTGGACAGAG
3451 GAAGATGGGAGGGTGCTCATCACCCCCCCAGCATAATGATCAGCCTCCTT
3501 CCTAGAGACAGACTCATGCAGATTGAGATCAAAAGTCCCTCTGCTTGGGA
3551 TCAAATTAATGTTTGACAGAGCTGGCCAGGCGTGGTGGCTCATGTATGTA
3601 ATCCTAGCACTTCGAGAGGCCGAGGCAGGTGGATCACGAGGTCAGGAGTT
3651 TGAGATTAGCCTGGCCAAGATGGTGAAACCCTGTCTCTACTAAAAATAAA
3701 AAAAAATTAGCCAGGAAAAAAAAAAAAAAAAA (SEQ ID NO:1)

*FIG. 6B*

1 MLRTAGRDGLCRLSTYLEELEAVELKKFKLYLGTATELGEGKIPWGSMEK
51 AGPLEMAQLLITHFGPEEAWRLALSTFERINRKDLWERGQREDLVRDTPP
101 GGPSSLGNQSTCLLEVSLVTPRKDPQETYRDYVRRKFRLMEDRNARLGEC
151 VNLSHRYTRLLLVKEHSNPMQVQQQLLDTGRGHARTVGHQASPIKIETLF
201 EPDEERPEPPRTVVMQGAAGIGKSMLAHKVMLDWADGKLFQGRFDYLFYI
251 NCREMNQSATECSMQDLIFSCWPEPSAPLQELIRVPERLLFIIDGFDELK
301 PSFHDPQGPWCLCWEEKRPTELLLNSLIRKKLLPELSLLITTRPTALEKL
351 HRLLEHPRHVEILGFSEAERKEYFYKYFHNAEQAGQVFNYVRDNEPLFTM
401 CFVPLVCWVVCTCLQQQLEGGGLLRQTSRTTTAVYMLYLLSLMQPKPGAP
451 RLQPPPNQRGLCSLAADGLWNQKILFEEQDLRKHGLDGEDVSAFLNMNIF
501 QKDINCERYYSFIHLSFQEFFAAMYYILDEGEGGAGPDQDVTRLLTEYAF
551 SERSFLALTSRFLFGLLNEETRSHLEKSLCWKVSPHIKMDLLQWIQSKAQ
601 SDGSTLQQGSLEFFSCLYEIQEEEFIQQALSHFQVIVVSNIASKMEHMVS
651 SFCLKRCRSAQVLHLYGATYSADGEDRARCSAGAHTLLVQLRPERTVLLD
701 AYSEHLAAALCTNPNLIELSLYRNALGSRGVKLLCQGLRHPNCKLQNLRL
751 KRCRISSSACEDLSAALIANKNLTRMDLSGNGVGFPGMMLLCEGLRHPQC
801 RLQMIQLRKCQLESGACQEMASVLGTNPHLVELDLTGNALEDLGLRLLCQ
851 GLRHPVCRLRTLWLKICRLTAAACDELASTLSVNQSLRELDLSLNELGDL
901 GVLLLCEGLRHPTCKLQTLRLGICRLGSAACEGLSVVLQANHNLRELDLS
951 FNDLGDWGLWLLAEGLQHPACRLQKLWLDSCGLTAKACENLYFTLGINQT
1001 LTDLYLTNNALGDTGVRLLCKRLSHPGCKLRVLWLFGMDLNKMTHSRLAA
1051 LRVTKPYLDIGC (SEQ ID NO:2)

*FIG. 6C*

1 ATTGGTGAGTGGGGCAGGGCAGGAGGGAACTGAAGAGTGAGAAAGCATTA
51 TTTCAGCAAAAGGTCTTTCCTCCCTTGCTCACTCCTCCAACCACTGGCTC
101 AGCCTCTCCGCCCGCTGCCTGTGAATGATGCAATGGAAGGTGTGCTGGGG
151 TCGCCCTGTGTCCCGTGCATAGGAGCATCTCAGCCTCCAGGTCCTCTCCT
201 TTGGGGCTTACGGCACCCCCATGCTACGAACCGCAGGCAGGGACGGCCTC
251 TGTCGCCTGTCCACCTACTTGGAAGAACTCGAGGCTGTGGAACTGAAGAA
301 GTTCAAGTTATACCTGGGGACCGCGACAGAGCTGGGAGAAGGCAAGATCC
351 CCTGGGGAAGCATGGAGAAGGCCGGTCCCCTGGAAATGGCCCAGCTGCTC
401 ATCACCCACTTCGGGCCAGAGGAGGCCTGGAGGTTGGCTCTCAGCACCTT
451 TGAGCGGATAAACAGGAAGGACCTGTGGGAGAGAGGACAGAGAGAGGACC
501 TGGTGAGGGATACCCCACCTGGTGGCCCGTCCTCACTTGGGAACCAGTCA
551 ACATGCCTTCTGGAAGTCTCTCTTGTCACTCCAAGAAAAGATCCCCAGGA
601 AACCTACAGGGACTATGTCCGCAGGAAATTCCGGCTCATGGAAGACCGCA
651 ATGCGCGCCTAGGGGAATGTGTCAACCTCAGCCACCGGTACACCCGGCTC
701 CTGCTGGTGAAGGAGCACTCAAACCCCATGCAGGTCCAGCAGCAGCTTCT
751 GGACACAGGCCGGGGACACGCGAGGACCGTGGGACACCAGGCTAGCCCCA
801 TCAAGATAGAGACCCTCTTTGAGCCAGACGAGGAGCGCCCCGAGCCACCG
851 CGCACCGTGGTCATGCAAGGCGCGGCAGGGATAGGCAAGTCCATGCTGGC
901 ACACAAGGTGATGCTGGACTGGGCGGACGGGAAGCTCTTCCAAGGCAGAT
951 TTGATTATCTCTTCTACATCAACTGCAGGGAGATGAACCAGAGTGCCACG
1001 GAATGCAGCATGCAAGACCTCATCTTCAGCTGCTGGCCTGAGCCCAGCGC
1051 GCCTCTCCAGGAGCTCATCCGAGTTCCCGAGCGCCTCCTTTTCATCATCG
1101 ACGGCTTCGATGAGCTCAAGCCTTCTTTCCACGATCCTCAGGGACCCTGG
1151 TGCCTCTGCTGGGAGGAGAAACGGCCCACGGAGCTGCTTCTTAACAGCTT
1201 AATTCGGAAGAAGCTGCTCCCTGAGCTATCTTTGCTCATCACCACACGGC
1251 CCACGGCTTTGGAGAAGCTCCACCGTCTGCTGGAGCACCCCAGGCATGTG
1301 GAGATCCTGGGCTTCTCTGAGGCAGAAAGGAAGGAATACTTCTACAAGTA
1351 TTTCCACAATGCAGAGCAGGCGGGCCAAGTCTTCAATTACGTGAGGGACA
1401 ACGAGCCTCTCTTCACCATGTGCTTCGTCCCCCTGGTGTGCTGGGTGGTG
1451 TGTACCTGCCTCCAGCAGCAGCTGGAGGGTGGGGGGCTGTTGAGACAGAC
1501 GTCCAGGACCACCACTGCAGTGTACATGCTCTACCTGCTGAGTCTGATGC
1551 AACCCAAGCCGGGGGCCCCGCGCCTCCAGCCCCCACCCAACCAGAGAGGG
1601 TTGTGCTCCTTGGCGGCAGATGGGCTCTGGAATCAGAAAATCCTATTTGA
1651 GGAGCAGGACCTCCGGAAGCACGGCCTAGACGGGGAAGACGTCTCTGCCT
1701 TCCTCAACATGAACATCTTCCAGAAGGACATCAACTGTGAGAGGTACTAC
1751 AGCTTCATCCACTTGAGTTTCCAGGAATTCTTTGCAGCTATGTACTATAT
1801 CCTGGACGAGGGGGAGGGCGGGGCAGGCCCAGACCAGGACGTGACCAGGC
1851 TGTTGACCGAGTACGCGTTTTCTGAAAGGAGCTTCCTGGCACTCACCAGC
1901 CGCTTCCTGTTTGGACTCCTGAACGAGGAGACCAGGAGCCACCTGGAGAA
1951 GAGTCTCTGCTGGAAGGTCTCGCCGCACATCAAGATGGACCTGTTGCAGT
2001 GGATCCAAAGCAAAGCTCAGAGCGACGGCTCCACCCTGCAGCAGGGCTCC
2051 TTGGAGTTCTTCAGCTGCTTGTACGAGATCCAGGAGGAGGAGTTTATCCA
2101 GCAGGCCCTGAGCCACTTCCAGGTGATCGTGGTCAGCAACATTGCCTCCA
2151 AGATGGAGCACATGGTCTCCTCGTTCTGTCTGAAGCGCTGCAGGAGCGCC
2201 CAGGTGCTGCACTTGTATGGCGCCACCTACAGCGCGGACGGGGAAGACCG
2251 CGCGAGGTGCTCCGCAGGAGCGCACACGCTGTTGGTGCAGCTCAGACCAG
2301 AGAGGACCGTTCTGCTGGACGCCTACAGTGAACATCTGGCAGCGGCCCTG
2351 TGCACCAATCCAAACCTGATAGAGCTGTCTCTGTACCGAAATGCCCTGGG
2401 CAGCCGGGGGGTGAAGCTGCTCTGTCAAGGACTCAGACACCCCAACTGCA
2451 AACTTCAGAACCTGAGGCTGAAGAGGTGCCGCATCTCCAGCTCAGCCTGC
2501 GAGGACCTCTCTGCAGCTCTCATAGCCAATAAGAATTTGACAAGGATGGA

*FIG. 6D*

2551 TCTCAGTGGCAACGGCGTTGGATTCCCAGGCATGATGCTGCTTTGCGAGG
2601 GCCTGCGGCATCCCCAGTGCAGGCTGCAGATGATTCAGTTGAGGAAGTGT
2651 CAGCTGGAGTCCGGGGCTTGTCAGGAGATGGCTTCTGTGCTCGGCACCAA
2701 CCCACATCTGGTTGAGTTGGACCTGACAGGAAATGCACTGGAGGATTTGG
2751 GCCTGAGGTTACTATGCCAGGGACTGAGGCACCCAGTCTGCAGACTACGG
2801 ACTTTGTGGCTGAAGATCTGCCGCCTCACTGCTGCTGCCTGTGACGAGCT
2851 GGCCTCAACTCTCAGTGTGAACCAGAGCCTGAGAGAGCTGGACCTGAGCC
2901 TGAATGAGCTGGGGGACCTCGGGGTGCTGCTGCTGTGTGAGGGCCTCAGG
2951 CATCCCACGTGCAAGCTCCAGACCCTGCGGTTGGGCATCTGCCGGCTGGG
3001 CTCTGCCGCCTGTGAGGGTCTTTCTGTGGTGCTCCAGGCCAACCACAACC
3051 TCCGGGAGCTGGACTTGAGTTTCAACGACCTGGGAGACTGGGGCCTGTGG
3101 TTGCTGGCTGAGGGGCTGCAACATCCCGCCTGCAGACTCCAGAAACTGTG
3151 GTGGTTATTTGGGATGGACCTGAATAAAATGACCCACAGTAGGTTGGCAG
3201 CGCTTCGAGTAACAAAACCTTATTTGGACATTGGCTGCTGAATGGTCCTA
3251 TCTGCTGGCTCTCCCCTGAGATCTGGACAGAGGAAGATGGAGGGTGCTC
3301 ATCACCCCCCCAGCATAATGATCAGCCTCCTTCCTAGAGACAGACTCATG
3351 CAGATTGAGATCAAAAGTCCCTCTGCTTGGGATCAAATTAATGTTTGACA
3401 GAGCTGGCCAGGCGTGGTGGCTCATGTATGTAATCCTAGCACTTCGAGAG
3451 GCCGAGGCAGGTGGATCACGAGGTCAGGAGTTTGAGATTAGCCTGGCCAA
3501 GATGGTGAAACCCTGTCTCTACTAAAAATAAAAAAAAATTAGCCAGGAAA
3551 AAAAAAAAAAAAA (SEQ ID NO:3)

*FIG. 6E*

1 MLRTAGRDGLCRLSTYLEELEAVELKKFKLYLGTATELGEGKIPWGSMEK
51 AGPLEMAQLLITHFGPEEAWRLALSTFERINRKDLWERGQREDLVRDTPP
101 GGPSSLGNQSTCLLEVSLVTPRKDPQETYRDYVRRKFRLMEDRNARLGEC
151 VNLSHRYTRLLLVKEHSNPMQVQQQLLDTGRGHARTVGHQASPIKIETLF
201 EPDEERPEPPRTVVMQGAAGIGKSMLAHKVMLDWADGKLFQGRFDYLFYI
251 NCREMNQSATECSMQDLIFSCWPEPSAPLQELIRVPERLLFIIDGFDELK
301 PSFHDPQGPWCLCWEEKRPTELLLNSLIRKKLLPELSLLITTRPTALEKL
351 HRLLEHPRHVEILGFSEAERKEYFYKYFHNAEQAGQVFNYVRDNEPLFTM
401 CFVPLVCWVVCTCLQQQLEGGGLLRQTSRTTTAVYMLYLLSLMQPKPGAP
451 RLQPPPNQRGLCSLAADGLWNQKILFEEQDLRKHGLDGEDVSAFLNMNIF
501 QKDINCERYYSFIHLSFQEFFAAMYYILDEGEGGAGPDQDVTRLLTEYAF
551 SERSFLALTSRFLFGLLNEETRSHLEKSLCWKVSPHIKMDLLQWIQSKAQ
601 SDGSTLQQGSLEFFSCLYEIQEEEFIQQALSHFQVIVVSNIASKMEHMVS
651 SFCLKRCRSAQVLHLYGATYSADGEDRARCSAGAHTLLVQLRPERTVLLD
701 AYSEHLAAALCTNPNLIELSLYRNALGSRGVKLLCQGLRHPNCKLQNLRL
751 KRCRISSSACEDLSAALIANKNLTRMDLSGNGVGFPGMMLLCEGLRHPQC
801 RLQMIQLRKCQLESGACQEMASVLGTNPHLVELDLTGNALEDLGLRLLCQ
851 GLRHPVCRLRTLWLKICRLTAAACDELASTLSVNQSLRELDLSLNELGDL
901 GVLLLCEGLRHPTCKLQTLRLGICRLGSAACEGLSVVLQANHNLRELDLS
951 FNDLGDWGLWLLAEGLQHPACRLQKLWWLFGMDLNKMTHSRLAALRVTKP
1001 YLDIGC (SEQ ID NO:4)

*FIG. 6F*

```
   1 ATTGGTGAGTGGGGCAGGGCAGGAGGGAACTGAAGAGTGAGAAAGCATTA
  51 TTTCAGCAAAAGGTCTTTCCTCCCTTGCTCACTCCTCCAACCACTGGCTC
 101 AGCCTCTCCGCCCGCTGCCTGTGAATGATGCAATGGAAGGTGTGCTGGGG
 151 TCGCCCTGTGTCCCGTGCATAGGAGCATCTCAGCCTCCAGGTCCTCTCCT
 201 TTGGGGCTTACGGCACCCCCATGCTACGAACCGCAGGCAGGGACGGCCTC
 251 TGTCGCCTGTCCACCTACTTGGAAGAACTCGAGGCTGTGGAACTGAAGAA
 301 GTTCAAGTTATACCTGGGGACCGCGACAGAGCTGGGAGAAGGCAAGATCC
 351 CCTGGGGAAGCATGGAGAAGGCCGGTCCCCTGGAAATGGCCCAGCTGCTC
 401 ATCACCCACTTCGGGCCAGAGGAGGCCTGGAGGTTGGCTCTCAGCACCTT
 451 TGAGCGGATAAACAGGAAGGACCTGTGGGAGAGAGGACAGAGAGAGGACC
 501 TGGTGAGGGATACCCCACCTGGTGGCCCGTCCTCACTTGGGAACCAGTCA
 551 ACATGCCTTCTGGAAGTCTCTCTTGTCACTCCAAGAAAAGATCCCCAGGA
 601 AACCTACAGGGACTATGTCCGCAGGAAATTCCGGCTCATGGAAGACCGCA
 651 ATGCGCGCCTAGGGGAATGTGTCAACCTCAGCCACCGGTACACCCGGCTC
 701 CTGCTGGTGAAGGAGCACTCAAACCCCATGCAGGTCCAGCAGCAGCTTCT
 751 GGACACAGGCCGGGGACACGCGAGGACCGTGGGACACCAGGCTAGCCCCA
 801 TCAAGATAGAGACCCTCTTTGAGCCAGACGAGGAGCGCCCCGAGCCACCG
 851 CGCACCGTGGTCATGCAAGGCGCGGCAGGGATAGGCAAGTCCATGCTGGC
 901 ACACAAGGTGATGCTGGACTGGGCGGACGGGAAGCTCTTCCAAGGCAGAT
 951 TTGATTATCTCTTCTACATCAACTGCAGGGAGATGAACCAGAGTGCCACG
1001 GAATGCAGCATGCAAGACCTCATCTTCAGCTGCTGGCCTGAGCCCAGCGC
1051 GCCTCTCCAGGAGCTCATCCGAGTTCCCGAGCGCCTCCTTTTCATCATCG
1101 ACGGCTTCGATGAGCTCAAGCCTTCTTTCCACGATCCTCAGGGACCCTGG
1151 TGCCTCTGCTGGGAGGAGAAACGGCCCACGGAGCTGCTTCTTAACAGCTT
1201 AATTCGGAAGAAGCTGCTCCCTGAGCTATCTTTGCTCATCACCACACGGC
1251 CCACGGCTTTGGAGAAGCTCCACCGTCTGCTGGAGCACCCCAGGCATGTG
1301 GAGATCCTGGGCTTCTCTGAGGCAGAAAGGAAGGAATACTTCTACAAGTA
1351 TTTCCACAATGCAGAGCAGGCGGGCCAAGTCTTCAATTACGTGAGGGACA
1401 ACGAGCCTCTCTTCACCATGTGCTTCGTCCCCCTGGTGTGCTGGGTGGTG
1451 TGTACCTGCCTCCAGCAGCAGCTGGAGGGTGGGGGCTGTTGAGACAGAC
1501 GTCCAGGACCACCACTGCAGTGTACATGCTCTACCTGCTGAGTCTGATGC
1551 AACCCAAGCCGGGGGCCCCGCGCCTCCAGCCCCCACCCAACCAGAGAGGG
1601 TTGTGCTCCTTGGCGGCAGATGGGCTCTGGAATCAGAAAATCCTATTTGA
1651 GGAGCAGGACCTCCGGAAGCACGGCCTAGACGGGGAAGACGTCTCTGCCT
1701 TCCTCAACATGAACATCTTCCAGAAGGACATCAACTGTGAGAGGTACTAC
1751 AGCTTCATCCACTTGAGTTTCCAGGAATTCTTTGCAGCTATGTACTATAT
1801 CCTGGACGAGGGGGAGGGCGGGGCAGGCCCAGACCAGGACGTGACCAGGC
1851 TGTTGACCGAGTACGCGTTTTCTGAAAGGAGCTTCCTGGCACTCACCAGC
1901 CGCTTCCTGTTTGGACTCCTGAACGAGGAGACCAGGAGCCACCTGGAGAA
1951 GAGTCTCTGCTGGAAGGTCTCGCCGCACATCAAGATGGACCTGTTGCAGT
2001 GGATCCAAAGCAAAGCTCAGAGCGACGGCTCCACCCTGCAGCAGGGCTCC
2051 TTGGAGTTCTTCAGCTGCTTGTACGAGATCCAGGAGGAGGAGTTTATCCA
2101 GCAGGCCCTGAGCCACTTCCAGGTGATCGTGGTCAGCAACATTGCCTCCA
2151 AGATGGAGCACATGGTCTCCTCGTTCTGTCTGAAGCGCTGCAGGAGCGCC
2201 CAGGTGCTGCACTTGTATGGCGCCACCTACAGCGCGGACGGGGAAGACCG
2251 CGCGAGGTGCTCCGCAGGAGCGCACACGCTGTTGGTGCAGCTCAGACCAG
2301 AGAGGACCGTTCTGCTGGACGCCTACAGTGAACATCTGGCAGCGGCCCTG
2351 TGCACCAATCCAAACCTGATAGAGCTGTCTCTGTACCGAAATGCCCTGGG
2401 CAGCCGGGGGGTGAAGCTGCTCTGTCAAGGACTCAGACACCCCAACTGCA
2451 AACTTCAGAACCTGAGGCTGAAGAGGTGCCGCATCTCCAGCTCAGCCTGC
2501 GAGGACCTCTCTGCAGCTCTCATAGCCAATAAGAATTTGACAAGGATGGA
```

*FIG. 6G*

2551 TCTCAGTGGCAACGGCGTTGGATTCCCAGGCATGATGCTGCTTTGCGAGG
2601 GCCTGCGGCATCCCCAGTGCAGGCTGCAGATGATTCAGTTGAGGAAGTGT
2651 CAGCTGGAGTCCGGGGCTTGTCAGGAGATGGCTTCTGTGCTCGGCACCAA
2701 CCCACATCTGGTTGAGTTGGACCTGACAGGAAATGCACTGGAGGATTTGG
2751 GCCTGAGGTTACTATGCCAGGGACTGAGGCACCCAGTCTGCAGACTACGG
2801 ACTTTGTGGCTGTGGCTGGATAGCTGTGGCCTCACAGCCAAGGCTTGTGA
2851 GAATCTTTACTTCACCCTGGGGATCAACCAGACCTTGACCGACCTTTACC
2901 TGACCAACAACGCCCTAGGGGACACAGGTGTCCGACTGCTTTGCAAGCGG
2951 CTGAGCCATCCTGGCTGCAAACTCCGAGTCCTCTGGTTATTTGGGATGGA
3001 CCTGAATAAAATGACCCACAGTAGGTTGGCAGCGCTTCGAGTAACAAAAC
3051 CTTATTTGGACATTGGCTGCTGAATGGTCCTATCTGCTGGCTCTCCCCTG
3101 AGATCTGGACAGAGGAAGATGGGAGGGTGCTCATCACCCCCCCAGCATAA
3151 TGATCAGCCTCCTTCCTAGAGACAGACTCATGCAGATTGAGATCAAAAGT
3201 CCCTCTGCTTGGGATCAAATTAATGTTTGACAGAGCTGGCCAGGCGTGGT
3251 GGCTCATGTATGTAATCCTAGCACTTCGAGAGGCCGAGGCAGGTGGATCA
3301 CGAGGTCAGGAGTTTGAGATTAGCCTGGCCAAGATGGTGAAACCCTGTCT
3351 CTACTAAAAATAAAAAAAAATTAGCCAGGAAAAAAAAAAAAAAAA
(SEQ ID NO:5)

FIG. 6H

1 MLRTAGRDGLCRLSTYLEELEAVELKKFKLYLGTATELGEGKIPWGSMEK
51 AGPLEMAQLLITHFGPEEAWRLALSTFERINRKDLWERGQREDLVRDTPP
101 GGPSSLGNQSTCLLEVSLVTPRKDPQETYRDYVRRKFRLMEDRNARLGEC
151 VNLSHRYTRLLLVKEHSNPMQVQQQLLDTGRGHARTVGHQASPIKIETLF
201 EPDEERPEPPRTVVMQGAAGIGKSMLAHKVMLDWADGKLFQGRFDYLFYI
251 NCREMNQSATECSMQDLIFSCWPEPSAPLQELIRVPERLLFIIDGFDELK
301 PSFHDPQGPWCLCWEEKRPTELLLNSLIRKKLLPELSLLITTRPTALEKL
351 HRLLEHPRHVEILGFSEAERKEYFYKYFHNAEQAGQVFNYVRDNEPLFTM
401 CFVPLVCWVVCTCLQQQLEGGGLLRQTSRTTTAVYMLYLLSLMQPKPGAP
451 RLQPPPNQRGLCSLAADGLWNQKILFEEQDLRKHGLDGEDVSAFLNMNIF
501 QKDINCERYYSFIHLSFQEFFAAMYYILDEGEGGAGPDQDVTRLLTEYAF
551 SERSFLALTSRFLFGLLNEETRSHLEKSLCWKVSPHIKMDLLQWIQSKAQ
601 SDGSTLQQGSLEFFSCLYEIQEEEFIQQALSHFQVIVVSNIASKMEHMVS
651 SFCLKRCRSAQVLHLYGATYSADGEDRARCSAGAHTLLVQLRPERTVLLD
701 AYSEHLAAALCTNPNLIELSLYRNALGSRGVKLLCQGLRHPNCKLQNLRL
751 KRCRISSSACEDLSAALIANKNLTRMDLSGNGVGFPGMMLLCEGLRHPQC
801 RLQMIQLRKCQLESGACQEMASVLGTNPHLVELDLTGNALEDLGLRLLCQ
851 GLRHPVCRLRTLWLWLDSCGLTAKACENLYFTLGINQTLTDLYLTNNALG
901 DTGVRLLCKRLSHPGCKLRVLWLFGMDLNKMTHSRLAALRVTKPYLDIGC
(SEQ ID NO:6)

FIG. 6I

```
   1 ATTGGTGAGTGGGGCAGGGCAGGAGGGAACTGAAGAGTGAGAAAGCATTA
  51 TTTCAGCAAAAGGTCTTTCCTCCCTTGCTCACTCCTCCAACCACTGGCTC
 101 AGCCTCTCCGCCCGCTGCCTGTGAATGATGCAATGGAAGGTGTGCTGGGG
 151 TCGCCCTGTGTCCCGTGCATAGGAGCATCTCAGCCTCCAGGTCCTCTCCT
 201 TTGGGGCTTACGGCACCCCCATGCTACGAACCGCAGGCAGGGACGGCCTC
 251 TGTCGCCTGTCCACCTACTTGGAAGAACTCGAGGCTGTGGAACTGAAGAA
 301 GTTCAAGTTATACCTGGGGACCGCGACAGAGCTGGGAGAAGGCAAGATCC
 351 CCTGGGGAAGCATGGAGAAGGCCGGTCCCCTGGAAATGGCCCAGCTGCTC
 401 ATCACCCACTTCGGGCCAGAGGAGGCCTGGAGGTTGGCTCTCAGCACCTT
 451 TGAGCGGATAAACAGGAAGGACCTGTGGGAGAGAGGACAGAGAGAGGACC
 501 TGGTGAGGGATACCCCACCTGGTGGCCCGTCCTCACTTGGGAACCAGTCA
 551 ACATGCCTTCTGGAAGTCTCTCTTGTCACTCCAAGAAAAGATCCCCAGGA
 601 AACCTACAGGGACTATGTCCGCAGGAAATTCCGGCTCATGGAAGACCGCA
 651 ATGCGCGCCTAGGGGAATGTGTCAACCTCAGCCACCGGTACACCCGGCTC
 701 CTGCTGGTGAAGGAGCACTCAAACCCCATGCAGGTCCAGCAGCAGCTTCT
 751 GGACACAGGCCGGGGACACGCGAGGACCGTGGGACACCAGGCTAGCCCCA
 801 TCAAGATAGAGACCCTCTTTGAGCCAGACGAGGAGCGCCCCGAGCCACCG
 851 CGCACCGTGGTCATGCAAGGCGCGGCAGGGATAGGCAAGTCCATGCTGGC
 901 ACACAAGGTGATGCTGGACTGGGCGGACGGGAAGCTCTTCCAAGGCAGAT
 951 TTGATTATCTCTTCTACATCAACTGCAGGGAGATGAACCAGAGTGCCACG
1001 GAATGCAGCATGCAAGACCTCATCTTCAGCTGCTGGCCTGAGCCCAGCGC
1051 GCCTCTCCAGGAGCTCATCCGAGTTCCCGAGCGCCTCCTTTTCATCATCG
1101 ACGGCTTCGATGAGCTCAAGCCTTCTTTCCACGATCCTCAGGGACCCTGG
1151 TGCCTCTGCTGGGAGGAGAAACGGCCCACGGAGCTGCTTCTTAACAGCTT
1201 AATTCGGAAGAAGCTGCTCCCTGAGCTATCTTTGCTCATCACCACACGGC
1251 CCACGGCTTTGGAGAAGCTCCACCGTCTGCTGGAGCACCCCAGGCATGTG
1301 GAGATCCTGGGCTTCTCTGAGGCAGAAAGGAAGGAATACTTCTACAAGTA
1351 TTTCCACAATGCAGAGCAGGCGGGCCAAGTCTTCAATTACGTGAGGGACA
1401 ACGAGCCTCTCTTCACCATGTGCTTCGTCCCCCTGGTGTGCTGGGTGGTG
1451 TGTACCTGCCTCCAGCAGCAGCTGGAGGGTGGGGGCTGTTGAGACAGAC
1501 GTCCAGGACCACCACTGCAGTGTACATGCTCTACCTGCTGAGTCTGATGC
1551 AACCCAAGCCGGGGGCCCCGCGCCTCCAGCCCCCACCCAACCAGAGAGGG
1601 TTGTGCTCCTTGGCGGCAGATGGGCTCTGGAATCAGAAAATCCTATTTGA
1651 GGAGCAGGACCTCCGGAAGCACGGCCTAGACGGGGAAGACGTCTCTGCCT
1701 TCCTCAACATGAACATCTTCCAGAAGGACATCAACTGTGAGAGGTACTAC
1751 AGCTTCATCCACTTGAGTTTCCAGGAATTCTTTGCAGCTATGTACTATAT
1801 CCTGGACGAGGGGGAGGGCGGGGCAGGCCCAGACCAGGACGTGACCAGGC
1851 TGTTGACCGAGTACGCGTTTTCTGAAAGGAGCTTCCTGGCACTCACCAGC
1901 CGCTTCCTGTTTGGACTCCTGAACGAGGAGACCAGGAGCCACCTGGAGAA
1951 GAGTCTCTGCTGGAAGGTCTCGCCGCACATCAAGATGGACCTGTTGCAGT
2001 GGATCCAAAGCAAAGCTCAGAGCGACGGCTCCACCCTGCAGCAGGGCTCC
2051 TTGGAGTTCTTCAGCTGCTTGTACGAGATCCAGGAGGAGGAGTTTATCCA
2101 GCAGGCCCTGAGCCACTTCCAGGTGATCGTGGTCAGCAACATTGCCTCCA
2151 AGATGGAGCACATGGTCTCCTCGTTCTGTCTGAAGCGCTGCAGGAGCGCC
2201 CAGGTGCTGCACTTGTATGGCGCCACCTACAGCGCGGACGGGGAAGACCG
2251 CGCGAGGTGCTCCGCAGGAGCGCACACGCTGTTGGTGCAGCTCAGACCAG
2301 AGAGGACCGTTCTGCTGGACGCCTACAGTGAACATCTGGCAGCGGCCCTG
2351 TGCACCAATCCAAACCTGATAGAGCTGTCTCTGTACCGAAATGCCCTGGG
2401 CAGCCGGGGGGTGAAGCTGCTCTGTCAAGGACTCAGACACCCCAACTGCA
2451 AACTTCAGAACCTGAGGCTGAAGAGGTGCCGCATCTCCAGCTCAGCCTGC
2501 GAGGACCTCTCTGCAGCTCTCATAGCCAATAAGAATTTGACAAGGATGGA
```

FIG. 6J

2551 TCTCAGTGGCAACGGCGTTGGATTCCCAGGCATGATGCTGCTTTGCGAGG
2601 GCCTGCGGCATCCCCAGTGCAGGCTGCAGATGATTCAGTTGAGGAAGTGT
2651 CAGCTGGAGTCCGGGGCTTGTCAGGAGATGGCTTCTGTGCTCGGCACCAA
2701 CCCACATCTGGTTGAGTTGGACCTGACAGGAAATGCACTGGAGGATTTGG
2751 GCCTGAGGTTACTATGCCAGGGACTGAGGCACCCAGTCTGCAGACTACGG
2801 ACTTTGTGGTGGTTATTTGGGATGGACCTGAATAAAATGACCCACAGTAG
2851 GTTGGCAGCGCTTCGAGTAACAAAACCTTATTTGGACATTGGCTGCTGAA
2901 TGGTCCTATCTGCTGGCTCTCCCCTGAGATCTGGACAGAGGAAGATGGGA
2951 GGGTGCTCATCACCCCCCCAGCATAATGATCAGCCTCCTTCCTAGAGACA
3001 GACTCATGCAGATTGAGATCAAAAGTCCCTCTGCTTGGGATCAAATTAAT
3051 GTTTGACAGAGCTGGCCAGGCGTGGTGGCTCATGTATGTAATCCTAGCAC
3101 TTCGAGAGGCCGAGGCAGGTGGATCACGAGGTCAGGAGTTTGAGATTAGC
3151 CTGGCCAAGATGGTGAAACCCTGTCTCTACTAAAAATAAAAAAAAATTAG
3201 CCAGGAAAAAAAAAAAAAAAAA (SEQ ID NO:7)

FIG. 6K

1 MLRTAGRDGLCRLSTYLEELEAVELKKFKLYLGTATELGEGKIPWGSMEK
51 AGPLEMAQLLITHFGPEEAWRLALSTFERINRKDLWERGQREDLVRDTPP
101 GGPSSLGNQSTCLLEVSLVTPRKDPQETYRDYVRRKFRLMEDRNARLGEC
151 VNLSHRYTRLLLVKEHSNPMQVQQQLLDTGRGHARTVGHQASPIKIETLF
201 EPDEERPEPPRTVVMQGAAGIGKSMLAHKVMLDWADGKLFQGRFDYLFYI
251 NCREMNQSATECSMQDLIFSCWPEPSAPLQELIRVPERLLFIIDGFDELK
301 PSFHDPQGPWCLCWEEKRPTELLLNSLIRKKLLPELSLLITTRPTALEKL
351 HRLLEHPRHVEILGFSEAERKEYFYKYFHNAEQAGQVFNYVRDNEPLFTM
401 CFVPLVCWVVCTCLQQQLEGGGLLRQTSRTTTAVYMLYLLSLMQPKPGAP
451 RLQPPPNQRGLCSLAADGLWNQKILFEEQDLRKHGLDGEDVSAFLNMNIF
501 QKDINCERYYSFIHLSFQEFFAAMYYILDEGEGGAGPDQDVTRLLTEYAF
551 SERSFLALTSRFLFGLLNEETRSHLEKSLCWKVSPHIKMDLLQWIQSKAQ
601 SDGSTLQQGSLEFFSCLYEIQEEEFIQQALSHFQVIVVSNIASKMEHMVS
651 SFCLKRCRSAQVLHLYGATYSADGEDRARCSAGAHTLLVQLRPERTVLLD
701 AYSEHLAAALCTNPNLIELSLYRNALGSRGVKLLCQGLRHPNCKLQNLRL
751 KRCRISSSACEDLSAALIANKNLTRMDLSGNGVGFPGMMLLCEGLRHPQC
801 RLQMIQLRKCQLESGACQEMASVLGTNPHLVELDLTGNALEDLGLRLLCQ
851 GLRHPVCRLRTLWWLFGMDLNKMTHSRLAALRVTKPYLDIGC
(SEQ ID NO:8)

FIG. 6L

```
   1 ATGTTGCCGTCTACAGCCAGGGATGGCCTCTATCGACTGTCTACCTACCT
  51 GGAAGAACTCGAGGCTGGGGAACTGAAGAAATTCAAATTATTCCTGGGGA
 101 TTGCAGAGGACCTGAGCCAGGACAAAATTCCCTGGGGACGAATGGAGAAG
 151 GCTGGTCCTCTGGAAATGGCTCAGCTGATGGTGGCCCACATGGGGACAAG
 201 GGAGGCTTGGCTTCTGGCTCTCAGCACCTTTCAGAGGATTCACAGGAAGG
 251 ACCTGTGGGAGCGAGGACAGGGAGAAGACCTGGTGAGGGGTAAGGAGGGC
 301 AAGGGAGATCTACAGACAACCTACAAAGACTATGTCCGAAGGAAATTCCA
 351 GCTAATGGAAGACCGCAATGCACGATTAGGCGAATGTGTGAACCTGAGCA
 401 ATCGTTACACTCGGCTTCTCCTAGTAAAAGAACACTCAAATCCTATCTGG
 451 ACACAGCAGAAATTTGTAGATGTAGAGTGGGAACGCTCCAGAACCAGGCG
 501 TCACCAGACTAGTCCTATCCAAATGGAGACCCTCTTTGAGCCAGACGAAG
 551 AACGCCCCGAGCCACCACACACAGTGGTATTACAAGGGGCAGCGGGGATG
 601 GGGAAGTCCATGCTGGCCCACAAAGTGATGTTGGACTGGGCCGATGGGAG
 651 GCTCTTCCAAGGCCGGTTTGATTATGTCTTCTATATCAGCTGCAGGGAGT
 701 TGAATAGAAGCCACACCCAGTGCAGTGTACAAGACCTCATCTCCAGCTGC
 751 TGGCCGGAGCGTGGTATATCCCTCGAAGACCTCATGCAGGCTCCTGACCG
 801 TCTCCTATTCATCATTGATGGCTTCGATAAACTCCATCCTTCTTTCCATG
 851 ATGCTCAGGGTCCCTGGTGCCTCTGCTGGGAGGAGAAACAACCTACTGAA
 901 GTCCTCCTCGGAAGTCTGATTCGGAGGTTGCTTCTGCCCCAGGTCTCTCT
 951 GCTCATCACCACACGACCCTGTGCACTGGAGAAGCTGCACGGCTTGCTAG
1001 AACACCCCAGGCACGTGGAGATCCTGGGCTTCTCCGAGGAAGCTAGGAAG
1051 GAATATTTCTACAGATATTTCCACAACACTGGACAAGCAAGCCGGGTGTT
1101 AAGCTTCTTGATGGACTATGAGCCCCTCTTTACCATGTGTTTTGTTCCCA
1151 TGGTGTCCTGGGTGGTCTGCACCTGCCTAAAGCAGCAGCTGGAAAGTGGG
1201 GAGCTTTTAAGACAAACACCTAGGACCACCACAGCTGTTTATATGTTCTA
1251 CCTTCTGAGCCTGATGCAGCCCAAGCCAGGGACTCCAACCTTCAAAGTCC
1301 CAGCCAACCAGAGAGGCCTGGTCTCTCTGGCTGCAGAGGGCCTCTGGAAT
1351 CAGAAGATTCTATTTGATGAACAGGATCTTGGGAAACACGGCCTAGATGG
1401 AGCAGATGTGTCCACTTTCCTCAACGTGAACATATTCCAGAAGGGTATCA
1451 AATGTGAGAAATTCTACAGCTTCATCCACCTGAGTTTCCAGGAATTCTTC
1501 GCAGCCATGTACTGTGCACTGAATGGCAGAGAGGCGGTGAGGAGAGCGCT
1551 GGCTGAGTATGGTTTTTCGGAAAGGAACTTCTTGGCCCTCACGGTCCACT
1601 TTCTGTTTGGCCTCCTCAACGAAGAGATGAGATGCTACCTTGAGAGGAAT
1651 CTCGGCTGGAGCATCTCCCCTCAGGTGAAGGAGGAAGTGTTGGCATGGAT
1701 CCAAAACAAGGCTGGGAGTGAAGGCTCCACCCTGCAGCATGGCTCCCTGG
1751 AGCTACTCAGCTGCTTGTATGAGGTCCAGGAGGAGGACTTCATCCAGCAG
1801 GCCCTGAGCCACTTTCAAGTGGTTGTAGTCAGAAGCATCTCAACAAAGAT
1851 GGAGCACATGGTCTGCTCGTTTTGTGCGAGGTATTGCAGAAGTACAGAAG
1901 TGCTTCACTTGCATGGGAGTGCTTATAGTACAGGCATGGAGGACGACCCA
1951 CCAGAACCTTCAGGAGTCCAGACTCAGTCCACATACTTACAGGAAAGGAA
2001 CATGCTGCCTGATGTCTACAGTGCATACCTTTCAGCAGCTGTCTGTACCA
2051 ACTCCAACCTGATCGAGCTGGCCTTATACCGAAATGCCTTGGGCAGCCAG
2101 GGTGTAAGGCTGCTCTGTCAAGGCCTCCGACATGCCAGCTGCAAGCTGCA
2151 GAACCTGAGGCTGAAGAGGTGTCAGATCTCCGGATCAGCCTGCCAGGACC
2201 TCGCAGCCGCTGTCATCGCCAACAGGAATTTAATCAGGCTGGACCTCAGT
2251 GACAACAGCATTGGGGTGCCAGGCCTGGAGCTGCTCTGTGAGGGGCTGCA
2301 GCACCCCAGGTGTAGGCTGCAGATGATCCAGCTGAGGAAGTGTCTGTTGG
2351 AGGCTGCAGCTGGCCGATCCCTGGCTTCTGTTCTCAGCAACAACTCATAT
2401 CTGGTAGAACTGGATCTGACAGGAAACCCCTTGGAAGATTCGGGGCTGAA
2451 GTTACTGTGTCAAGGGCTAAGGCACCCTGTCTGCAGGCTGCGTACCCTGT
2501 GGCTGAAGATCTGCCACCTTGGACAAGCTTCCTGCGAAGATCTGGCCTCT
```

*FIG. 18A*

2551 ACTCTCAAAATGAACCAGAGCCTGCTGGAGCTGGACCTGGGTCTGAATGA
2601 TCTTGGAGATTCTGGGGTGCTTCTGCTGTGTGAAGGCCTCAGTCATCCAG
2651 ATTGCAAACTCCAGACCCTTCGGTTGGGCATTTGCCGACTGGGCTCAGTC
2701 GCGTGTGTGGGGATCGCCAGTGTGCTCCAGGTCAACACATGCCTCCAAGA
2751 GCTGGACCTGAGCTTCAATGACTTGGGAGACAGGGGCCTGCAGCTGCTGG
2801 GGGAAGGCCTGAGGCACCAGACCTGCAGACTCCAGAAGCTGTGGCTGGAC
2851 AACTGCGGACTCACCTCCAAAGCATGTGAGGACCTTTCTTCTATCCTGGG
2901 AATCAGCCAGACCCTGCATGAGCTTTATTTGACCAATAATGCTCTGGGGG
2951 ACACAGGTGTCTGTCTGCTGTGCAAGAGGCTGAGGCATCCAGGCTGCAAG
3001 CTTCGAGTCCTGTGGCTGTTTGGGATGGACCTGAATAAAAAGACTCACAG
3051 GAGGATGGCAGCACTTCGAGTCACAAAACCGTACCTGGATATTGGGTGTT
3101 GA (SEQ ID NO:9)

FIG. 18B

1 MLPSTARDGLYRLSTYLEELEAGELKKFKLFLGIAEDLSQDKIPWGRMEK
51 AGPLEMAQLMVAHMGTREAWLLALSTFQRIHRKDLWERGQGEDLVRGKEG
101 KGDLQTTYKDYVRRKFQLMEDRNARLGECVNLSNRYTRLLLVKEHSNPIW
151 TQQKFVDVEWERSRTRRHQTSPIQMETLFEPDEERPEPPHTVVLQGAAGM
201 GKSMLAHKVMLDWADGRLFQGRFDYVFYISCRELNRSHTQCSVQDLISSC
251 WPERGISLEDLMQAPDRLLFIIDGFDKLHPSFHDAQGPWCLCWEEKQPTE
301 VLLGSLIRRLLLPQVSLLITTRPCALEKLHGLLEHPRHVEILGFSEEARK
351 EYFYRYFHNTGQASRVLSFLMDYEPLFTMCFVPMVSWVVCTCLKQQLESG
401 ELLRQTPRTTTAVYMFYLLSLMQPKPGTPTFKVPANQRGLVSLAAEGLWN
451 QKILFDEQDLGKHGLDGADVSTFLNVNIFQKGIKCEKFYSFIHLSFQEFF
501 AAMYCALNGREAVRRALAEYGFSERNFLALTVHFLFGLLNEEMRCYLERN
551 LGWSISPQVKEEVLAWIQNKAGSEGSTLQHGSLELLSCLYEVQEEDFIQQ
601 ALSHFQVVVVRSISTKMEHMVCSFCARYCRSTEVLHLHGSAYSTGMEDDP
651 PEPSGVQTQSTYLQERNMLPDVYSAYLSAAVCTNSNLIELALYRNALGSQ
701 GVRLLCQGLRHASCKLQNLRLKRCQISGSACQDLAAAVIANRNLIRLDLS
751 DNSIGVPGLELLCEGLQHPRCRLQMIQLRKCLLEAAAGRSLASVLSNNSY
801 LVELDLTGNPLEDSGLKLLCQGLRHPVCRLRTLWLKICHLGQASCEDLAS
851 TLKMNQSLLELDLGLNDLGDSGVLLLCEGLSHPDCKLQTLRLGICRLGSV
901 ACVGIASVLQVNTCLQELDLSFNDLGDRGLQLLGEGLRHQTCRLQKLWLD
951 NCGLTSKACEDLSSILGISQTLHELYLTNNALGDTGVCLLCKRLRHPGCK
1001 LRVLWLFGMDLNKKTHRRMAALRVTKPYLDIGC (SEQ ID NO:10)

FIG. 18C

1 ATGGCAGATTCATCATCATCTTCTTTCTTTCCTGATTTTGGGCTGCTATT
51 GTATTTGGAGGAGCTAAACAAAGAGGAATTAAATACATTCAAGTTATTCC
101 TAAAGGAGACCATGGAACCTGAGCATGGCCTGACACCCTGGAATGAAGTG
151 AAGAAGGCCAGGCGGGAGGACCTGGCCAATTTGATGAAGAAATATTATCC
201 AGGAGAGAAAGCCTGGAGTGTGTCTCTCAAAATCTTTGGCAAGATGAACC
251 TGAAGGATCTGTGTGAGAGAGCGAAAGAAGAGATCAACTGGTCGGCCCAG
301 ACTATAGGACCAGATGATGCCAAGGCTGGAGAGACACAAGAAGATCAGGA
351 GGCAGTGCTGGGTGATGGAACAGAATACAGAAATAGAATAAAGGAAAAAT
401 TTTGCATCACTTGGGACAAGAAGTCTTTGGCTGGAAAGCCTGAAGATTTC
451 CATCATGGAATTGCAGAGAAAGATAGAAAACTGTTGGAACACTTGTTCGA
501 TGTGGATGTCAAAACCGGTGCACAGCCACAGATCGTGGTGCTTCAGGGAG
551 CTGCTGGAGTTGGGAAAACAACCTTGGTGAGAAAGGCAATGTTAGATTGG
601 GCAGAGGGCAGTCTCTACCAGCAGAGGTTTAAGTATGTTTTTTATCTCAA
651 TGGGAGAGAAATTAACCAGCTGAAAGAGAGAAGCTTTGCTCAATTGATAT
701 CAAAGGACTGGCCCAGCACAGAAGGCCCCATTGAAGAAATCATGTACCAG
751 CCAAGTAGCCTCTTGTTTATTATTGACAGTTTCGATGAACTGAACTTTGC
801 CTTTGAAGAACCTGAGTTTGCACTGTGCGAAGACTGGACCCAAGAACACC
851 CAGTGTCCTTCCTCATGAGTAGTTTGCTGAGGAAAGTGATGCTCCCTGAG
901 GCATCCTTATTGGTGACAACAAGACTCACAACTTCTAAGAGACTAAAGCA
951 GTTGTTGAAGAATCACCATTATGTAGAGCTACTAGGAATGTCTGAGGATG
1001 CAAGAGAGGAGTATATTTACCAGTTTTTTGAAGATAAGAGGTGGGCCATG
1051 AAAGTATTCAGTTCACTAAAAAGCAATGAGATGCTGTTTAGCATGTGCCA
1101 AGTCCCCCTAGTGTGCTGGGCCGCTTGTACTTGTCTGAAGCAGCAAATGG
1151 AGAAGGGTGGTGATGTCACATTGACCTGCCAAACAACCACAGCTCTGTTT
1201 ACCTGCTATATTTCTAGCTTGTTCACACCAGTAGATGGAGGCTCTCCTAG
1251 TCTACCCAACCAAGCCCAGCTGAGAAGACTGTGCCAAGTCGCTGCCAAAG
1301 GAATATGGACTATGACTTACGTGTTTTACAGAGAAAATCTCAGAAGGCTT
1351 GGGTTAACTCAATCTGATGTCTCTAGTTTTATGGACAGCAATATTATTCA
1401 GAAGGACGCAGAGTATGAAAACTGCTATGTGTTCACCCACCTTCATGTTC
1451 AGGAGTTTTTTGCAGCTATGTTCTATATGTTGAAAGGCAGTTGGGAAGCT
1501 GGGAACCCTTCCTGCCAGCCTTTTGAAGATTTGAAGTCATTACTTCAAAG
1551 CACAAGTTATAAAGACCCCCATTTGACACAGATGAAGTGCTTTTTGTTTG
1601 GCCTTTTGAATGAAGATCGAGTAAAACAACTGGAGAGGACTTTTAACTGT
1651 AAAATGTCACTGAAGATAAAATCAAAGTTACTTCAGTGTATGGAAGTATT
1701 AGGAAACAGTGACTATTCTCCATCACAGCTGGGATTTCTGGAGTTGTTTC
1751 ACTGTCTGTATGAGACTCAAGATAAAGCGTTTATAAGCCAGGCAATGAGA
1801 TGTTTCCCAAAGGTTGCCATTAATATTTGTGAGAAAATACATTTGCTTGT
1851 ATCTTCTTTCTGCCTTAAGCACTGCCGGTGTTTGCGGACCATCAGGCTGT
1901 CTGTAACTGTGGTATTTGAGAAGAAGATATTAAAAACAAGCCTCCCAACT
1951 AACACTTGGTTGAAATTTATCACTTTCCCTGATGGTTGTCAGGATATCTC
2001 TACTTCTTTGATTCATAACAAGAATCTGATGCATCTTGACCTAAAAGGGA
2051 GTGATATAGGGGATAATGGAGTAAAGTCATTGTGTGAGGCCTTGAAACAC
2101 CCAGAGTGTAAACTACAGACTCTCAGGCTGGAATCTTGCAACCTAACTGT
2151 ATTTGTTGTCTAAATATATCTAATGCTCTCATCAGAAGCCAGAGCCTGA
2201 TATTTCTGAATCTGTCAACCAATAATCTGTTGGATGATGGAGTGCAGCTT
2251 TTGTGTGAGGCCTTAAGACATCCAAAGTGTTATCTAGAGAGACTGTCCTT
2301 AGAAAGCTGTGGTCTCACAGAGGCTGGCTGTGAGTATCTTTCTTTGGCTC
2351 TCATCAGCAATAAAAGACTGACACATTTGTGCTTGGCAGACAATGTCTTG
2401 GGTGATGGTGGAGTAAAGCTTATGAGTGATGCCCTGCAACATGCACAATG
2451 TACTCTGAAGAGCCTTGTGCTGAGGCGTTGCCATTTCACTTCACTTAGCA

FIG. 21A

2501 GTGAATATCTGTCAACTTCTCTTCTACACAACAAGAGCCTGACGCATCTG
2551 GATCTAGGATCAAACTGGCTACAAGACAATGGAGTGAAGCTTCTGTGTGA
2601 TGTCTTTCGGCATCCAAGCTGTAATCTTCAGGACTTGGAATTGATGGGCT
2651 GTGTTCTCACTAATGCATGTTGTCTGGATCTGGCTTCTGTTATTTTGAAT
2701 AACCCAAACCTGAGGAGCCTGGACCTTGGGAACAACGATTTGCAGGATGA
2751 TGGAGTGAAAATTCTGTGTGATGCTTTGAGATATCCAAACTGTAACATTC
2801 AGAGGCTCGGGTTGGAATACTGTGGTTTGACATCTCTCTGCTGTCAAGAT
2851 CTCTCCTCTGCTCTTATCTGCAACAAAAGACTGATAAAAATGAATCTGAC
2901 ACAGAATACCTTAGGATATGAAGGAATTGTGAAGTTATATAAAGTCTTGA
2951 AGTCTCCTAAGTGTAAACTACAAGTTCTAGGACAACAGGATTTCCAAGCT
3001 GCCCAAGGAAAACTCCAACAAAGAGCTGGCTCTGGATGA
(SEQ ID NO:11)

FIG. 21B

1 MADSSSSSFFPDFGLLLYLEELNKEELNTFKLFLKETMEPEHGLTPWNEV
51 KKARREDLANLMKKYYPGEKAWSVSLKIFGKMNLKDLCERAKEEINWSAQ
101 TIGPDDAKAGETQEDQEAVLGDGTEYRNRIKEKFCITWDKKSLAGKPEDF
151 HHGIAEKDRKLLEHLFDVDVKTGAQPQIVVLQGAAGVGKTTLVRKAMLDW
201 AEGSLYQQRFKYVFYLNGREINQLKERSFAQLISKDWPSTEGPIEEIMYQ
251 PSSLLFIIDSFDELNFAFEEPEFALCEDWTQEHPVSFLMSSLLRKVMLPE
301 ASLLVTTRLTTSKRLKQLLKNHHYVELLGMSEDAREEYIYQFFEDKRWAM
351 KVFSSLKSNEMLFSMCQVPLVCWAACTCLKQQMEKGGDVTLTCQTTTALF
401 TCYISSLFTPVDGGSPSLPNQAQLRRLCQVAAKGIWTMTYVFYRENLRRL
451 GLTQSDVSSFMDSNIIQKDAEYENCYVFTHLHVQEFFAAMFYMLKGSWEA
501 GNPSCQPFEDLKSLLQSTSYKDPHLTQMKCFLFGLLNEDRVKQLERTFNC
551 KMSLKIKSKLLQCMEVLGNSDYSPSQLGFLELFHCLYETQDKAFISQAMR
601 CFPKVAINICEKIHLLVSSFCLKHCRCLRTIRLSVTVVFEKKILKTSLPT
651 NTWLKFITFPDGCQDISTSLIHNKNLMHLDLKGSDIGDNGVKSLCEALKH
701 PECKLQTLRLESCNLTVFCCLNISNALIRSQSLIFLNLSTNNLLDDGVQL
751 LCEALRHPKCYLERLSLESCGLTEAGCEYLSLALISNKRLTHLCLADNVL
801 GDGGVKLMSDALQHAQCTLKSLVLRRCHFTSLSSEYLSTSLLHNKSLTHL
851 DLGSNWLQDNGVKLLCDVFRHPSCNLQDLELMGCVLTNACCLDLASVILN
901 NPNLRSLDLGNNDLQDDGVKILCDALRYPNCNIQRLGLEYCGLTSLCCQD
951 LSSALICNKRLIKMNLTQNTLGYEGIVKLYKVLKSPKCKLQVLGQQDFQA
1001 AQGKLQQRAGSG (SEQ ID NO:12)

FIG. 21C

1 ATGGCAGATTCATCATCATCTTCTTTCTTTCCTGATTTTGGGCTGCTATT
51 GTATTTGGAGGAGCTAAACAAAGAGGAATTAAATACATTCAAGTTATTCC
101 TAAAGGAGACCATGGAACCTGAGCATGGCCTGACACCCTGGAATGAAGTG
151 AAGAAGGCCAGGCGGGAGGACCTGGCCAATTTGATGAAGAAATATTATCC
201 AGGAGAGAAAGCCTGGAGTGTGTCTCTCAAAATCTTTGGCAAGATGAACC
251 TGAAGGATCTGTGTGAGAGAGCGAAAGAAGAGATCAACTGGTCGGCCCAG
301 ACTATAGGACCAGATGATGCCAAGGCTGGAGAGACACAAGAAGATCAGGA
351 GGCAGTGCTGGGTGATGGAACAGAATACAGAAATAGAATAAAGGAAAAAT
401 TTTGCATCACTTGGGACAAGAAGTCTTTGGCTGGAAAGCCTGAAGATTTC
451 CATCATGGAATTGCAGAGAAAGATAGAAAACTGTTGGAACACTTGTTCGA
501 TGTGGATGTCAAAACCGGTGCACAGCCACAGATCGTGGTGCTTCAGGGAG
551 CTGCTGGAGTTGGGAAAACAACCTTGGTGAGAAAGGCAATGTTAGATTGG
601 GCAGAGGGCAGTCTCTACCAGCAGAGGTTTAAGTATGTTTTTTATCTCAA
651 TGGGAGAGAAATTAACCAGCTGAAAGAGAGAAGCTTTGCTCAATTGATAT
701 CAAAGGACTGGCCCAACACAAAAGCCCCCATTGAAGAAATCATGTACCAG
751 CCAAGTAGCCTCTTGTTTATTATAGACAGTTTCGATGAACTGAACTTTGC
801 CTTTGAAGAACCTGAGTTTGCACTGTGCGAAGACTGGACCCAAGACAACC
851 CAGTGTCCTTCCTCATGAGTAGTTTGCTGAGGAAAGTGATGCTCCCTGAG
901 GCATCCTTATTGGTGACAACAAGACTCACAACTTCTAAGAGACTAAAGCA
951 GTTGTTGAAGAATCACCATTATGTAGAGCTACTAGGAATGTCTGAGGATG
1001 CAAGAGAGGAGTATATTTACCAGTTTTTTGAAGATAAGAGGTGGGCCATG
1051 AAAGTATTCAGTTCACTAAAAAGCAATGAGATGCTGTTTAGCATGTGCCA
1101 AGTCCCCCTAGTGTGCTGGGCCGCTTGTACTTGTCTGAAGCAGCAAATGG
1151 AGAAGGGTGGTGATGTCACATTGACCTGCCAAACAACCACAGCTCTGTTT
1201 ACCTGCTATATTTCTAGCTTGTTCACACCAGTAGATGGAGGCTCTCCTAG
1251 TCTACCCAACCAAGCCCAGCTGAGAAGACTGTGCCAAGTCGCTGCCAAAG
1301 GAATATGGACTATGACTTACGTGTTTTACAGAGAAAATCTCAGAAGGCTT
1351 GGGTTAACTCAATCTGATGTCTCTAGTTTTATGGACAGCAATATTATTCA
1401 GAAGGACGCAGAGTATGAAAACTGCTATGTGTTCACCCACCTTCATGTTC
1451 AGGAGTTTTTTGCAGCTATGTTCTATATGTTGAAGGGCAGTTGGGAAGCT
1501 GGGAACCCTTCCTGCCAGCCTTTTGAAGATTTGAAGTCATTACTTCAAAG
1551 CACAAGTTATAAAGACCCCCATTTGACACAGATGAAGTGCTTTTTGTTTG
1601 GCCTTTTGAATGAAGATCGAGTAAAACAACTGGAGAGGACTTTTAACTGT
1651 AAAATGTCACTGAAGATAAAATCAAAGTTACTTCAGTGTATGGAAGTATT
1701 AGGAAACAGTGACTATTCTCCATCACAGCTGGGATTTCTGGAGTTGTTTC
1751 ACTGTCTGTATGAGACTCAAGATAAAGCGTTTATAAGCCAGGCAATGAGA
1801 TGTTTCCCAAAGGTTGCCATTAATATTTGTGAGAAAATACATTGGCTTGT
1851 ATCTTCTTTCTGCCTTAAGCACTGCCGATGTTTGCAGACCATCAGGCTGT
1901 CTGTAACTGTGCTATTTGAGAAGAAGACATTAAAAACAAGCCTCCCAACT
1951 AACACTTGGGATGGTGATCGCATTACTCACTGTTGGAAAGATCTCTGTTC
2001 TGTGCTTCATACAAATGAACACTTGAGAGAATTGGACCTGTACCATAGCA
2051 ACCTTGATAAATCAGCAATGAATATCCTGCATCATGAACTAAGCCACCCA
2101 AACTGTAAACTACAAAAACTACTGTTGAAATTTATCACTTTCCCTGATGG
2151 TTGTCAGGATATCTCTACTTCTTTGATTCATAACAAGAATCTGATGCATC
2201 TTGACCTAAAAGGGAGTGATATAGGGGATAATGGAGTAAAGTCATTGTGT
2251 GAGGCCTTGAAACACCCAGAGTGTAAACTACAGACTCTCAGCTTAGAAAG

*FIG. 21D*

2301 CTGTGGTCTCACAGAGGCTGGCTGTGAGTATCTTTCTTTGGCTCTCATCA
2351 GCAATAAAAGACTGACACATTTGTGCTTGGCAGACAATGTCTTGGGTGAT
2401 GGTGGAGTAAAGCTTATGAGTGATGCCCTGCAACATGCACAATGTACTCT
2451 GAAGAGCCTTGTGCTGAGGCGTTGCCATTTCACTTCACTTAGCAGTGAAT
2501 ATCTGTCAACTTCTCTTCTACACAACAAGAGCCTGACGCATCTGGATCTA
2551 GGATCAAACTGGCTACAAGACAATGGAGTGAAGCTTCTGTGTGATGTCTT
2601 TCGGCATCCAAGCTGTAATCTTCAGGACTTGGAATTGATGGGCTGTGTTC
2651 TCACTAATGCATGTTGTCTGGATCTGGCTTCTGTTATTTTGAATAACCCA
2701 AACCTGAGGAGCCTGGACCTTGGGAACAACGATTTGCAGGATGATGGAGT
2751 GAAAATTCTGTGTGATGCTTTGAGATATCCAAACTGTAACATTCAGAGGC
2801 TCGGGTGA (SEQ ID NO:13)

*FIG. 21E*

1 MADSSSSSFFPDFGLLLYLEELNKEELNTFKLFLKETMEPEHGLTPWNEV
51 KKARREDLANLMKKYYPGEKAWSVSLKIFGKMNLKDLCERAKEEINWSAQ
101 TIGPDDAKAGETQEDQEAVLGDGTEYRNRIKEKFCITWDKKSLAGKPEDF
151 HHGIAEKDRKLLEHLFDVDVKTGAQPQIVVLQGAAGVGKTTLVRKAMLDW
201 AEGSLYQQRFKYVFYLNGREINQLKERSFAQLISKDWPNTKAPIEEIMYQ
251 PSSLLFIIDSFDELNFAFEEPEFALCEDWTQDNPVSFLMSSLLRKVMLPE
301 ASLLVTTRLTTSKRLKQLLKNHHYVELLGMSEDAREEYIYQFFEDKRWAM
351 KVFSSLKSNEMLFSMCQVPLVCWAACTCLKQQMEKGGDVTLTCQTTTALF
401 TCYISSLFTPVDGGSPSLPNQAQLRRLCQVAAKGIWTMTYVFYRENLRRL
451 GLTQSDVSSFMDSNIIQKDAEYENCYVFTHLHVQEFFAAMFYMLKGSWEA
501 GNPSCQPFEDLKSLLQSTSYKDPHLTQMKCFLFGLLNEDRVKQLERTFNC
551 KMSLKIKSKLLQCMEVLGNSDYSPSQLGFLELFHCLYETQDKAFISQAMR
601 CFPKVAINICEKIHWLVSSFCLKHCRCLQTIRLSVTVLFEKKTLKTSLPT
651 NTWDGDRITHCWKDLCSVLHTNEHLRELDLYHSNLDKSAMNILHHELSHP
701 NCKLQKLLLKFITFPDGCQDISTSLIHNKNLMHLDLKGSDIGDNGVKSLC
751 EALKHPECKLQTLSLESCGLTEAGCEYLSLALISNKRLTHLCLADNVLGD
801 GGVKLMSDALQHAQCTLKSLVLRRCHFTSLSSEYLSTSLLHNKSLTHLDL
851 GSNWLQDNGVKLLCDVFRHPSCNLQDLELMGCVLTNACCLDLASVILNNP
901 NLRSLDLGNNDLQDDGVKILCDALRYPNCNIQRLG (SEQ ID NO:14)

*FIG. 21F*

```
   1 AAGCTATACAGCGGCACCGCCGGAACCTGGCTGAGTGGTTCAGCCGGCTG
  51 CCCAGGGAGGAGCGCCAGTTTGGCCCAACCTTTGCCCTAGACACGGTCCA
 101 CGTTGACCCTGTGATCCGCGAGAGTACCCCTGATGAGCTACTTCGCCCAC
 151 CCGCGGAGCTGGCCTTGGAGCATCAGCCACCCCAGGCCGGGCTCCCCCCA
 201 CTGGCCTTGTCTCAGCTCTTTAACCCGGATGCCTGTGGGCGCCGGGTGCA
 251 GACAGTGGTGCTGTATGGGACAGTGGGCACAGGCAAGAGCACGCTGGTGC
 301 GCAAGATGGTTCTGGACTGGTGTTATGGGCGGCTGCCGGCCTTCGAGCTG
 351 CTCATCCCCTTCTCCTGTGAGGACCTGTCATCCCTGGGCCCTGCCCCAGC
 401 CTCCCTGTGCCAACTTGTGGCCCAGCGCTACACGCCCCTGAAGGAGGTTC
 451 TGCCCCTGATGGCTGCTGCTGGGTCCCACCTCCTCTTTGTGCTCCATGGC
 501 TTAGAGCATCTCAACCTCGACTTCCGGCTGGCAGGCACGGGACTTTGTAG
 551 TGACCCGGAGGAACCGCAGGAACCAGCTGCTATCATCGTCAACCTGCTGC
 601 GCAAATACATGCTGCCTCAGGCCAGCATTCTGGTGACCACTCGGCCCTCT
 651 GCCATTGGCCGTATCCCCAGCAAGTACGTGGGCCGCTATGGTGAGATCTG
 701 CGGTTTCTCTGATACCAACCTGCAGAAGCTCTACTTCCAGCTCCGCCTCA
 751 ACCAGCCGTACTGCGGGTATGCCGTTGGCGGTTCAGGTGTCTCTGCCACA
 801 CCAGCTCAGCGTGACCACCTGGTGCAGATGCTCTCCCGGAACCTGGAGGG
 851 GCACCACCAGATAGCCGCTGCCTGCTTCCTGCCGTCCTATTGCTGGCTCG
 901 TTTGTGCCACCTTGCACTTCCTGCATGCCCCCACGCCTGCTGGGCAGACC
 951 CTTACAAGCATCTATACCAGCTTCCTGCGCCTCAACTTCAGCGGGGAAAC
1001 CCTGGACAGCACTGACCCCTCCAATTTGTCCCTGATGGCCTATGCAGCCC
1051 GAACCATGGGCAAGTTGGCCTATGAGGGGGTGTCCTCCCGCAAGACCTAC
1101 TTCTCTGAAGAGGATGTCTGTGGCTGCCTGGAGGCTGGCATCAGGACGGA
1151 GGAGGAGTTTCAGCTGCTGCACATCTTCCGTCGGGATGCCCTGAGGTTTT
1201 TCCTGGCCCCATGTGTGGAGCCAGGGCGTGCAGGCACCTTCGTGTTCACC
1251 GTGCCCGCCATGCAGGAATACCTGGCTGCCCTCTACATTGTGCTGGGTTT
1301 GCGCAAGACGACCCTGCAAAAGGTGGGCAAGGAAGTGGCTGAGCTCGTGG
1351 GCCGTGTTGGGGAGGACGTCAGCCTGGTACTGGGCATCATGGCCAAGCTG
1401 CTGCCTCTGCGGGCTCTGCCTCTGCTCTTCAACCTGATCAAGGTGGTTCC
1451 ACGAGTGTTTGGGCGCATGGTGGGTAAAAGCCGGGAGGCGGTGGCTCAGG
1501 CCATGGTGCTGGAGATGTTTCGAGAGGAGGACTACTACAACGATGATGTT
1551 CTGGACCAGATGGGCGCCAGTATCCTGGGCGTGGAGGGCCCCCGGCGCCA
1601 CCCAGATGAGCCCCCTGAGGATGAAGTCTTCGAGCTCTTCCCCATGTTCA
1651 TGGGGGGGCTTCTCTCTGCCCACAACCGAGCTGTGCTAGCTCAGCTTGGC
1701 TGCCCCATCAAGAACCTGGATGCCCTGGAGAATGCCCAGGCCATCAAGAA
1751 GAAGCTGGGCAAGCTGGGCCGGCAGGTGCTGCCCCCATCAGAGCTCCTTG
1801 ACCACCTCTTCTTCCACTATGAGTTCCAGAACCAGCGCTTCTCCGCTGAG
1851 GTGCTCAGCTCCCTGCGTCAGCTCAACCTGGCAGGTGTGCGCATGACACC
1901 AGTCAAGTGCACAGTGGTGGCAGCTGTGCTGGGCAGCGGAAGGCATGCCC
1951 TGGATGAGGTGAACTTGGCCTCCTGCCAGCTAGATCCTGCTGGGCTGCGC
2001 ACACTCCTGCCTGTCTTCCTGCGTGCCCGGAAGCTGGGCTTGCAACTCAA
2051 CAGCCTGGGCCCTGAGGCCTGCAAGGACCTCCGAGACCTGTTGCTGCATG
2101 ACCAGTGCCAAATTACCACACTGCGGCTGTCCAACAACCCGCTGACGGCG
2151 GCAGGCCTGGAGCTGCTGGCTGCCCAGCTGGACCGCAACCGGCAGCTGCA
2201 GGAGCTGAACGTGGCGTACAACGGTGCTGGTGACACAGCGGCCCTGGCCC
2251 TGGCCAGAGCTGCCCGGGAGCACCCTTCCCTGGAACTGCTACAAGCTCTA
2301 CTGAATGGCATCGACTTTCTCTCTCCTGCCAGCCTCTACTTCAATGAGCT
2351 GAGCTCAGAGGGCCGCCAGGTCTTGCGAGACTTGGGGGGTGCTGCTGAAG
2401 GTGGTGCCCGGGTGGTGGTGTCACTGACAGAGGGGACGGCGGTGTCAGAA
2451 TACTGGTCAGTGATCCTCAGTGAAGTCCAGCGGAACCTCAATAGCTGGGA
2501 TCGGGCCCGGGTTCAGCGACACCTTGAGCTCCTACTGCGGGATCTGGAAG
2551 ATAGCCGGGGTGCCACCCTTAATCCTTGGCGCAAGGCCCAGCTGCTGCGA
2601 GTGGAGGGCGAG (SEQ ID NO:15)
```

*FIG. 25A*

```
1   AIQRHRRNLAEWFSRLPREERQFGPTFALDTVHVDPVIRESTPDELLRPP
51  AELALEHQPPQAGLPPLALSQLFNPDACGRRVQTVVLYGTVGTGKSTLVR
101 KMVLDWCYGRLPAFELLIPFSCEDLSSLGPAPASLCQLVAQRYTPLKEVL
151 PLMAAAGSHLLFVLHGLEHLNLDFRLAGTGLCSDPEEPQEPAAIIVNLLR
201 KYMLPQASILVTTRPSAIGRIPSKYVGRYGEICGFSDTNLQKLYFQLRLN
251 QPYCGYAVGGSGVSATPAQRDHLVQMLSRNLEGHHQIAAACFLPSYCWLV
301 CATLHFLHAPTPAGQTLTSIYTSFLRLNFSGETLDSTDPSNLSLMAYAAR
351 TMGKLAYEGVSSRKTYFSEEDVCGCLEAGIRTEEEFQLLHIFRRDALRFF
401 LAPCVEPGRAGTFVFTVPAMQEYLAALYIVLGLRKTTLQKVGKEVAELVG
451 RVGEDVSLVLGIMAKLLPLRALPLLFNLIKVVPRVFGRMVGKSREAVAQA
501 MVLEMFREEDYYNDDVLDQMGASILGVEGPRRHPDEPPEDEVFELFPMFM
551 GGLLSAHNRAVLAQLGCPIKNLDALENAQAIKKKLGKLGRQVLPPSELLD
601 HLFFHYEFQNQRFSAEVLSSLRQLNLAGVRMTPVKCTVVAAVLGSGRHAL
651 DEVNLASCQLDPAGLRTLLPVFLRARKLGLQLNSLGPEACKDLRDLLLHD
701 QCQITTLRLSNNPLTAAGLELLAAQLDRNRQLQELNVAYNGAGDTAALAL
751 ARAAREHPSLELLQALLNGIDFLSPASLYFNELSSEGRQVLRDLGGAAEG
801 GARVVVSLTEGTAVSEYWSVILSEVQRNLNSWDRARVQRHLELLLRDLED
851 SRGATLNPWRKAQLLRVEGE (SEQ ID NO:16)
```

*FIG. 25B*

```
1    ATGAGGTGGGGCCACCATTTGCCCAGGGCCTCTTGGGGCTCTGGTTTTAG
51   AAGAGCACTCCAGCGACCAGATGATCGTATCCCCTTCCTGATCCACTGGA
101  GTTGGCCCCTTCAAGGGGAGCGTCCCTTTGGGCCCCCTAGGGCCTTTATA
151  CGCCACCACGGAAGCTCGGTAGATAGCGCTCCCCCATCCGGGAGGCATGG
201  ACGGCTGTTCCCCAGCGCCTCTGCAACTGAAGCTATACAGCGGCACCGCC
251  GGAACCTGGCTGAGTGGTTCAGCCGGCTGCCCAGGGAGGAGCGCCAGTTT
301  GGCCCAACCTTTGCCCTAGACACGGTCCACGTTGACCCTGTGATCCGCGA
351  GAGTACCCCTGATGAGCTACTTCGCCCACCCGCGGAGCTGGCCCTGGAGC
401  ATCAGCCACCCCAGGCCGGGCTCCCCCCACTGGCCTTGTCTCAGCTCTTT
451  AACCCGGATGCCTGTGGGCGCCGGGTGCAGACAGTGGTGCTGTATGGGAC
501  AGTGGGCACAGGCAAGAGCACGCTGGTGCGCAAGATGGTTCTGGACTGGT
551  GTTATGGGCGGCTGCCGGCCTTCGAGCTGCTCATCCCCTTCTCCTGTGAG
601  GACCTGTCATCCCTGGGCCCTGCCCCAGCCTCCCTGTGCCAACTTGTGGC
651  CCAGCGCTACACGCCCCTGAAGGAGGTTCTGCCCCTGATGGCTGCTGCTG
701  GGTCCCACCTCCTCTTTGTGCTCCATGGCTTAGAGCATCTCAACCTCGAC
751  TTCCGGCTGGCAGGCACGGGACTTTGTAGTGACCCGGAGGAACCGCAGGA
801  ACCAGCTGCTATCATCGTCAACCTGCTGCGCAAATACATGCTGCCTCAGG
851  CCAGCATTCTGGTGACCACTCGGCCCTCTGCCATTGGCCGTATCCCCAGC
901  AAGTACGTGGGCCGCTATGGTGAGATCTGCGGTTTCTCTGATACCAACCT
951  GCAGAAGCTCTACTTCCAGCTCCGCCTCAACCAGCCGTACTGCGGGTATG
1001 CCGTTGGCGGTTCAGGTGTCTCTGCCACACCAGCTCAGCGTGACCACCTG
1051 GTGCAGATGCTCTCCCGGAACCTGGAGGGGCACCACCAGATAGCCGCTGC
1101 CTGCTTCCTGCCGTCCTATTGCTGGCTCGTTTGTGCCACCTTGCACTTCC
1151 TGCATGCCCCCACGCCTGCTGGGCAGACCCTTACAAGCATCTATACCAGC
1201 TTCCTGCGCCTCAACTTCAGCGGGGAAACCCTGGACAGCACTGACCCCTC
1251 CAATTTGTCCCTGATGGCCTATGCAGCCCGAACCATGGGCAAGTTGGCCT
1301 ATGAGGGGGTGTCCTCCCGCAAGACCTACTTCTCTGAAGAGGATGTCTGT
1351 GGCTGCCTGGAGGCTGGCATCAGGACGGAGGAGGAGTTTCAGCTGCTGCA
```

*FIG. 25C*

1451 CATCTTCCGTCGGGATGCCCTGAGGTTTTCCTGGCCCCATGTGTGGAGC
1501 CAGGGCGTGCAGGCACCTTCGTGTTCACCGTGCCCGCCATGCAGGAATAC
1551 CTGGCTGCCCTCTACATTGTGCTGGGTTTGCGCAAGACGACCCTGCAAAA
1601 GGTGGGCAAGGAAGTGGCTGAGCTCGTGGGCCGTGTTGGGGAGGACGTCA
1651 GCCTGGTACTGGGCATCATGGCCAAGCTGCTGCCTCTGCGGGCTCTGCCT
1701 CTGCTCTTCAACCTGATCAAGGTGGTTCCACGAGTGTTTGGGCGCATGGT
1751 GGGTAAAAGCCGGGAGGCGGTGACTCAGGCCATGGTGCTGGAGATGTTTC
1801 GAGAGGAGGACTACTACAACGATGATGTTCTGGACCAGATGGGCGCCAGT
1851 ATCCTGGGCGTGGAGGGCCCCCGGCGCCACCCAGATGAGCCCCCTGAGGA
1901 TGAAGTCTTCGAGCTCTTCCCCATGTTCATGGGGGGGCTTCTCTCTGCCC
1951 ACAACCGAGCTGTGCTAGCTCAGCTTGGCTGCCCCATCAAGAACCTGGAT
2001 GCCCTGGAGAATGCCCAGGCCATCAAGAAGAAGCTGGGCAAGCTGGGCCG
2051 GCAGGTGCTGCCCCCATCAGAGCTCCTTGACCACCTCTTCTTCCACTATG
2101 AGTTCCAGAACCAGCGCTTCTCCGCTGAGGTGCTCAGCTCCCTGCGTCAG
2151 CTCAACCTGGCAGGTGTGCGCATGACACCAGTCAAGTGCACAGTGGTGGC
2201 AGCTGTGCTGGGCAGCGGAAGGCATGCCCTGGATGAGGTGAACTTGGCCT
2251 CCTGCCAGCTAGATCCTGCTGGGCTGCGCACACTCCTGCCTGTCTTCCTG
2301 CGTGCCCGGAAGCTGGGCTTGCAACTCAACAGCCTGGGCCCTGAGGCCTG
2351 CAAGGACCTCCGAGACCTGTTGCTGCATGACCAGTGCCAAATTACCACAC
2401 TGCGGCTGTCCAACAACCCGCTGACGGAGGCAGGTGTTGCCGTGCTAATG
2451 GAGGGGCTGGCAGGAAACACCTCAGTGACGCACCTGTCCCTGCTGCACAC
2501 GGGCCTTGGGGACGAAGGCCTGGAGCTGCTGGCTGCCCAGCTGGACCGCA
2551 ACCGGCAGCTGCAGGAGCTGAACGTGGCGTACAACGGTGCTGGTGACACA
2601 GCGGCCCTGGCCCTGGCCAGAGCTGCCCGGGAGCACCCTTCCCTGGAACT
2651 GCTACACCTCTACTTCAATGAGCTGAGCTCAGAGGGCCGCCAGGTCTTGC
2701 GAGACTTGGGGGGTGCTGCTGAAGGTGGTGCCCGGGTGGTGGTGTCACTG
2751 ACAGAGGGGACGGCGGTGTCAGAATACTGGTCAGTGATCCTCAGTGAAGT
2801 CCAGCGGAACCTCAATAGCTGGGATCGGGCCCGGGTTCAGCGACACCTTG
2851 AGCTCCTACTGCGGGATCTGGAAGATAGCCGGGGTGCCACCCTTAATCCT
2901 TGACGCAAGGCCCAGCTGCTGCGAGTGGAGGGCGAGGTCAGGGCCCTCCT
2951 GGAGCAGCTGGGAAGCTCTGGAAGCTGAGACACTGGCGGCAGGCACCTAG
3001 CTATGTGACCACTGGCCCTAAACCTTTTCCCTCTGTGGCCTCCTGGCTTG
3051 CACTGCTCCCTCTAGAA (SEQ ID NO:17)

*FIG. 25D*

1 MRWGHHLPRASWGSGFRRALQRPDDRIPFLIHWSWPLQGERPFGPPRAFI
51 RHHGSSVDSAPPSGRHGRLFPSASATEAIQRHRRNLAEWFSRLPREERQF
101 GPTFALDTVHVDPVIRESTPDELLRPPAELALEHQPPQAGLPPLALSQLF
151 NPDACGRRVQTVVLYGTVGTGKSTLVRKMVLDWCYGRLPAFELLIPFSCE
201 DLSSLGPAPASLCQLVAQRYTPLKEVLPLMAAAGSHLLFVLHGLEHLNLD
251 FRLAGTGLCSDPEEPQEPAAIIVNLLRKYMLPQASILVTTRPSAIGRIPS
301 KYVGRYGEICGFSDTNLQKLYFQLRLNQPYCGYAVGGSGVSATPAQRDHL
351 VQMLSRNLEGHHQIAAACFLPSYCWLVCATLHFLHAPTPAGQTLTSIYTS
401 FLRLNFSGETLDSTDPSNLSLMAYAARTMGKLAYEGVSSRKTYFSEEDVC
451 GCLEAGIRTEEEFQLLHIFRRDALRFFLAPCVEPGRAGTFVFTVPAMQEY
501 LAALYIVLGLRKTTLQKVGKEVAELVGRVGEDVSLVLGIMAKLLPLRALP
551 LLFNLIKVVPRVFGRMVGKSREAVTQAMVLEMFREEDYYNDDVLDQMGAS
601 ILGVEGPRRHPDEPPEDEVFELFPMFMGGLLSAHNRAVLAQLGCPIKNLD
651 ALENAQAIKKKLGKLGRQVLPPSELLDHLFFHYEFQNQRFSAEVLSSLRQ
701 LNLAGVRMTPVKCTVVAAVLGSGRHALDEVNLASCQLDPAGLRTLLPVFL
751 RARKLGLQLNSLGPEACKDLRDLLLHDQCQITTLRLSNNPLTEAGVAVLM
801 EGLAGNTSVTHLSLLHTGLGDEGLELLAAQLDRNRQLQELNVAYNGAGDT
851 AALALARAAREHPSLELLHLYFNELSSEGRQVLRDLGGAAEGGARVVVSL
901 TEGTAVSEYWSVILSEVQRNLNSWDRARVQRHLELLLRDLEDSRGATLNP
(SEQ ID NO:18)

*FIG. 25E*

```
   1 ATGAGATGGGGCCACCATTTGCCCAGGGCCTCTTGGGGCTCTGGTTTTAG
  51 AAGAGCACTCCAGCGACCAGATGATCGTATCCCCTTCCTGATCCACTGGA
 101 GTTGGCCCCTTCAAGGGGAGCGTCCCTTTGGGCCCCCTAGGGCCTTTATA
 151 CGCCACCACGGAAGCTCGGTAGATAGCGCTCCCCCATCCGGGAGGCATGG
 201 ACGGCTGTTCCCCAGCGCCTCTGCAACTGAAGCTATACAGCGGCACCGCC
 251 GGAACCTGGCTGAGTGGTTCAGCCGGCTGCCCAGGGAGGAGCGCCAGTTT
 301 GGCCCAACCTTTGCCCTAGACACGGTCCACGTTGACCCTGTGATCCGCGA
 351 GAGTACCCCTGATGAGCTACTTCGCCCACCCGCGGAGCTGGCCCTGGAGC
 401 ATCAGCCACCCCAGGCCGGGCTCCCCCCACTGGCCTTGTCTCAGCTCTTT
 451 AACCCGGATGCCTGTGGGCGCCGGGTGCAGACAGTGGTGCTGTATGGGAC
 501 AGTGGGCACAGGCAAGAGCACGCTGGTGCGCAAGATGGTTCTGGACTGGT
 551 GTTATGGGCGGCTGCCGGCCTTCGAGCTGCTCATCCCCTTCTCCTGTGAG
 601 GACCTGTCATCCCTGGGCCCTGCCCCAGCCTCCCTGTGCCAACTTGTGGC
 651 CCAGCGCTACACGCCCCTGAAGGAGGTTCTGCCCCTGATGGCTGCTGCTG
 701 GGTCCCACCTCCTCTTTGTGCTCCATGGCTTAGAGCATCTCAACCTCGAC
 751 TTCCGGCTGGCAGGCACGGGACTTTGTAGTGACCCGGAGGAACCGCAGGA
 801 ACCAGCTGCTATCATCGTCAACCTGCTGCGCAAATACATGCTGCCTCAGG
 851 CCAGCATTCTGGTGACCACTCGGCCCTCTGCCATTGGCCGTATCCCCAGC
 901 AAGTACGTGGGCCGCTATGGTGAGATCTGCGGTTTCTCTGATACCAACCT
 951 GCAGAAGCTCTACTTCCAGCTCCGCCTCAACCAGCCGTACTGCGGGTATG
1001 CCGTTGGCGGTTCAGGTGTCTCTGCCACACCAGCTCAGCGTGACCACCTG
1051 GTGCAGATGCTCTCCCGGAACCTGGAGGGGCACCACCAGATAGCCGCTGC
1101 CTGCTTCCTGCCGTCCTATTGCTGGCTCGTTTGTGCCACCTTGCACTTCC
1151 TGCATGCCCCCACGCCTGCTGGGCAGACCCTTACAAGCATCTATACCAGC
1201 TTCCTGCGCCTCAACTTCAGCGGGGAAACCCTGGACAGCACTGACCCCTC
1251 CAATTTGTCCCTGATGGCCTATGCAGCCCGAACCATGGGCAAGTTGGCCT
1301 ATGAGGGGGTGTCCTCCCGCAAGACCTACTTCTCTGAAGAGGATGTCTGT
1351 GGCTGCCTGGAGGCTGGCATCAGGACGGAGGAGGAGTTTCAGCTGCTGCA
1401 CATCTTCCGTCGGGATGCCCTGAGGTTTTTCCTGGCCCCATGTGTGGAGC
1451 CAGGGCGTGCAGGCACCTTCGTGTTCACCGTGCCCGCCATGCAGGAATAC
1501 CTGGCTGCCCTCTACATTGTGCTGGGTTTGCGCAAGACGACCCTGCAAAA
1551 GGTGGGCAAGGAAGTGGCTGAGCTCGTGGGCCGTGTTGGGGAGGACGTCA
1601 GCCTGGTACTGGGCATCATGGCCAAGCTGCTGCCTCTGCGGGCTCTGCCT
1651 CTGCTCTTCAACCTGATCAAGGTGGTTCCACGAGTGTTTGGGCGCATGGT
1701 GGGTAAAAGCCGGGAGGCGGTGACTCAGGCCATGGTGCTGGAGATGTTTC
1751 GAGAGGAGGACTACTACAACGATGATGTTCTGGACCAGATGGGCGCCAGT
1801 ATCCTGGGCGTGGAGGGCCCCCGGCGCCACCCAGATGAGCCCCCTGAGGA
1851 TGAAGTCTTCGAGCTCTTCCCCATGTTCATGGGGGGGCTTCTCTCTGCCC
1901 ACAACCGAGCTGTGCTAGCTCAGCTTGGCTGCCCCATCAAGAACCTGGAT
1951 GCCCTGGAGAATGCCCAGGCCATCAAGAAGAAGCTGGGCAAGCTGGGCCG
2001 GCAGGTGCTGCCCCCATCAGAGCTCCTTGACCACCTCTTCTTCCACTATG
2051 AGTTCCAGAACCAGCGCTTCTCCGCTGAGGTGCTCAGCTCCCTGCGTCAG
2101 CTCAACCTGGCAGGTGTGCGCATGACACCAGTCAAGTGCACAGTGGTGGC
2151 AGCTGTGCTGGGCAGCGGAAGGCATGCCCTGGATGAGGTGAACTTGGCCT
2201 CCTGCCAGCTAGATCCTGCTGGGCTGCGCACACTCCTGCCTGTCTTCCTG
2251 CGTGCCCGGAAGCTGGGCTTGCAACTCAACAGCCTGGGCCCTGAGGCCTG
2301 CAAGGACCTCCGAGACCTGTTGCTGCATGACCAGTGCCAAATTACCACAC
2351 TGCGGCTGTCCAACAACCCGCTGACGGAGGCAGGTGTTGCCGTGCTAATG
2401 GAGGGGCTGGCAGGAAACACCTCAGTGACGCACCTGTCCCTGCTGCACAC
2451 GGGCCTTGGGGACGAAGGCCTGGAGCTGCTGGCTGCCCAGCTGGACCGCA
2501 ACCGGCAGCTGCAGGAGCTGAACGTGGCGTACAACGGTGCTGGTGACACA
2551 GCGGCCCTGGCCCTGGCCAGAGCTGCCCGGGAGCACCCTTCCCTGGAACT
2601 GCTACAGGGTGTCGCCATCCAGATGTGTTGGAAGCTTCCCCTCCTGCCTT
2651 ATGCTCACCTGTGGACACCGAGGATGCCCTCACATTGGTGCTTTCTCCTC
2701 ATCCTCATGCCCCCTTTGCCACAATGGTATGATGGCTTGGTAGCCCCTCG
2751 AGGCAGATGCACCTGACTTGCTGCTATTAAAAAGCCGTGTGCCTTCTACC
     (SEQ ID NO:19)
```

*FIG. 25F*

```
  1 MRWGHHLPRASWGSGFRRALQRPDDRIPFLIHWSWPLQGERPFGPPRAFI
 51 RHHGSSVDSAPPSGRHGRLFPSASATEAIQRHRRNLAEWFSRLPREERQF
101 GPTFALDTVHVDPVIRESTPDELLRPPAELALEHQPPQAGLPPLALSQLF
151 NPDACGRRVQTVVLYGTVGTGKSTLVRKMVLDWCYGRLPAFELLIPFSCE
201 DLSSLGPAPASLCQLVAQRYTPLKEVLPLMAAAGSHLLFVLHGLEHLNLD
251 FRLAGTGLCSDPEEPQEPAAIIVNLLRKYMLPQASILVTTRPSAIGRIPS
301 KYVGRYGEICGFSDTNLQKLYFQLRLNQPYCGYAVGGSGVSATPAQRDHL
351 VQMLSRNLEGHHQIAAACFLPSYCWLVCATLHFLHAPTPAGQTLTSIYTS
401 FLRLNFSGETLDSTDPSNLSLMAYAARTMGKLAYEGVSSRKTYFSEEDVC
451 GCLEAGIRTEEEFQLLHIFRRDALRFFLAPCVEPGRAGTFVFTVPAMQEY
501 LAALYIVLGLRKTTLQKVGKEVAELVGRVGEDVSLVLGIMAKLLPLRALP
551 LLFNLIKVVPRVFGRMVGKSREAVTQAMVLEMFREEDYYNDDVLDQMGAS
601 ILGVEGPRRHPDEPPEDEVFELFPMFMGGLLSAHNRAVLAQLGCPIKNLD
651 ALENAQAIKKKLGKLGRQVLPPSELLDHLFFHYEFQNQRFSAEVLSSLRQ
701 LNLAGVRMTPVKCTVVAAVLGSGRHALDEVNLASCQLDPAGLRTLLPVFL
751 RARKLGLQLNSLGPEACKDLRDLLLHDQCQITTLRLSNNPLTEAGVAVLM
801 EGLAGNTSVTHLSLLHTGLGDEGLELLAAQLDRNRQLQELNVAYNGAGDT
851 AALALARAAREHPSLELLQGVAIQMCWKLPLLPYAHLWTPRMPSHWCFLL
901 ILMPPLPQWYDGLVAPRGRCT(SEQ ID NO:20)
```

*FIG. 25G*

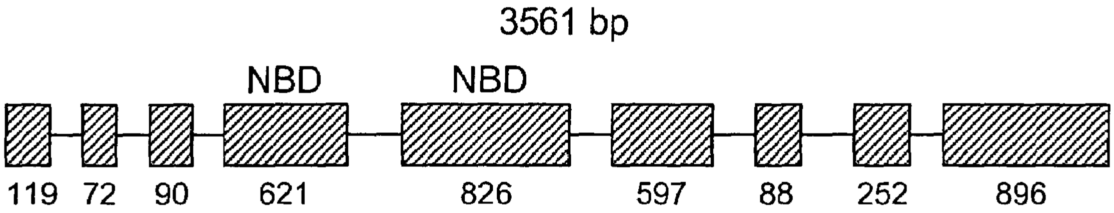

*FIG. 26*

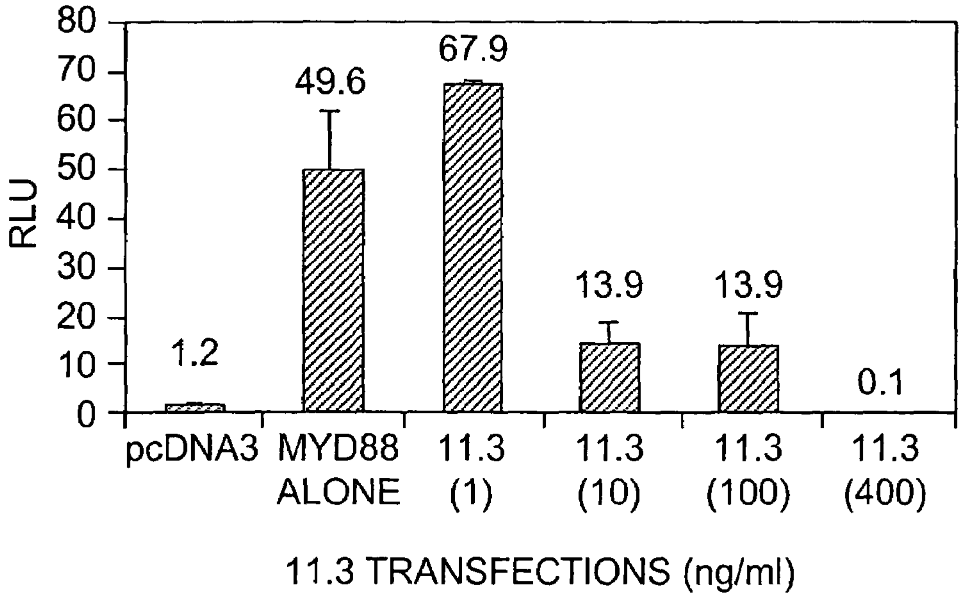

*FIG. 27*

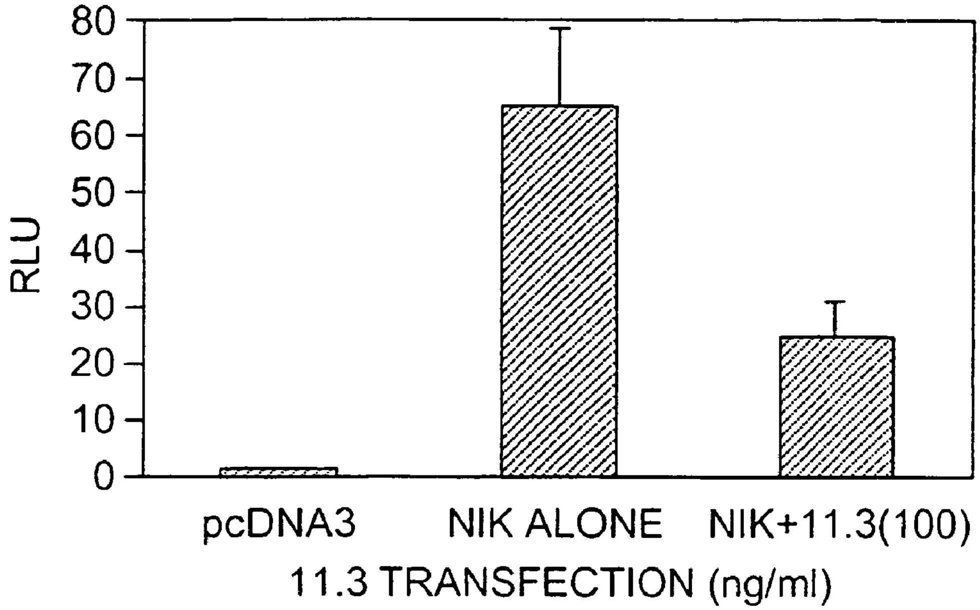

*FIG. 28*

1 ATGCTGCAGAATTTTAAGTACCCAAAGTTTCTCAACAAGTTGATTTTCAA
51 GCAAGCTCACCGGTTCCCCAGCTCATCTTCCTTCCAGTTCCCCTGTCCCC
101 CAGCTCAACTGCCTGCCCTCAGTTCACCTGTCCCCCAGTTCATCTTCCTC
151 CTAGCTCCCCTGTCCCCTAGCTCACCTGTGCCCCAGCTCCCCTGTCCCCC
201 AGGCTGGCTCCTCATGGACCCCGTTGGCCTCCAGCTCGGCAACAAGAACC
251 TGTGGAGCTGTCTTGTGAGGCTGCTCACCAAAGACCCAGAATGGCTGAAC
301 GCCAAGATGAAGTTCTTCCTCCCCAACACGGACCTGGATTCCAGGAACGA
351 GACCTTGGACCCTGAACAGAGAGTCATCCTGCAACTCAACAAGCTGCATG
401 TCCAGGGTTCGGACACCTGGCAGTCTTTCATTCATTGTGTGTGCATGCAG
451 CTGGAGGTGCCTCTGGACCTGGAGGTGCTGCTGCTGAGTACTTTTGGCTA
501 TGATGATGGGTTCACCAGCCAGCTGGGAGCTGAGGGGAAAAGCCAACCTG
551 AATCTCAGCTCCACCATGGCCTGAAGCGCCCACATCAGAGCTGTGGGTCC
601 TCACCCCGCCGGAAGCAGTGCAAGAAGCAGCAGCTAGAGTTGGCCAAGAA
651 GTACCTGCAGCTCCTGCGGACCTCTGCCCAGCAGCGCTACAGGAGCCAAA
701 TCCCTGGGTCAGGGCAGCCCCACGCCTTCCACCAGGTCTATGTCCCTCCA
751 ATCCTGCGCCGGGCCACAGCATCCTTAGACACTCCGGAGGGGGCCATTAT
801 GGGGGACGTCAAGGTGGAAGATGGTGCTGACGTGAGCATCTCGGACCTCT

*FIG. 29A*

851 TCAACACCAGGGTTAACAAGGGCCCGAGGGTGACCGTGCTTTTGGGGAAG
901 GCTGGCATGGGCAAGACCACGCTGGCCCACCGGCTCTGCCAGAAGTGGGC
951 AGAGGGCCATCTGAACTGTTTCCAGGCCCTGTTCCTTTTGAATTCCGCC
1001 AGCTCAACTTGATCACGAGGTTCCTGACACCGTCCGAGCTCCTTTTTGAT
1051 CTGTACCTGAGCCCTGAATCGGACCACGACACTGTCTTCCAGTACCTGGA
1101 GAAGAACGCTGACCAAGTCCTGCTGATCTTTGATGGGCTAGATGAGGCCC
1151 TCCAGCCTATGGGTCCTGATGGCCCAGGCCCAGTCCTCACCCTTTTCTCC
1201 CATCTCTGCAATGGGACCCTCCTGCCTGGCTGCCGGGCAGCCATGGTCCA
1251 CATGTTGGGCTTTGATGGCCACGGGTGGAAGAATATGTGAATCACTTCT
1301 TCAGCGCCCAGCCATCGCGGGAGGGGGCCCTGGTGGAGTTACAGACAAAT
1351 GGACGTCTCCGAAGCCTGTGTGCGGTGCCCGCACTGTGCCAAGTCGCCTG
1401 TCTCTGCCTCCACCATCTGCTTCCTGACCACGCCCCAGGCCAGTCTGTGG
1451 CCCTCCTGCCCAACATGACTCAGCTCTATATGCAGATGGTGCTCGCCCTC
1501 AGCCCCCCTGGGCACTTGCCCACCTCGTCCCTACTGGACCTGGGGGAGGT
1551 GGCCCTGAGGGGCCCTGGAGACAGGGAAGGCCCTGGGCACCAGCAGACAG
1601 GCTATGCTTTCACCCACCTCAGCCTGCAGGAGTTTCTTGCTGCCCTGCAC
1651 CTGATGGCCAGCCCCAAGGTGAACAAAGACACACTTACCCAGTATGTTAC
1701 CCTCCATTCCCGCTGGGTACAGCGGACCAAAGCTAGACTGGGCCTCTCAG
1751 ACCACCTCCCCACCTTCCTGGCGGGCCTGGCATCCTGCACCTGCCGCCCC
1801 TTCCTTAGCCACCTGGCGCAGGGCAATGAGGACTGTGTGGGTGCCAAGCA
1851 GGCTGCTGTAGTGCAGGTGTTGAAGAAGTTGGCCACCCGCAAGCTCACAG
1901 GGCCAAAGGTTGTAGAGCTGTGTCACTGTGTGGATGAGACACAGGAGCCT
1951 GAGCTGGCCAGTCTCACCGCACAAAGCCTCCCCTATCAACTGCCCTTCCA
2001 CAATTTCCCACTGACCTGCACCGACCTGGCCACCCTGACCAACATCCTAG
2051 AGCACAGGGAGGCCCCCATCCACCTGGATTTTGATGGCTGTCCCCTGGAG
2101 CCCCACTGCCCTGAGGCTCTGGTAGGCTGTGGGCAGATAGAGAATCTCAG
2151 CTTTAAGAGCAGGAAGTGTGGGGATGCCTTTGCAGAAGCCCTCTCCAGGA
2201 GCTTGCCGACAATGGGGAGGCTGCAGATGCTGGGGTTAGCAGGAAGTAAA
2251 ATCACTGCCCGAGGCATCAGCCACCTGGTGAAAGCTTTGCCTCTCTGTCC
2301 ACAGCTGAAAGAAGTCAGTTTTCGGGACAACCAGCTCAGTGACCAGGTGG
2351 TGCTGAACATTGTGGAGGTTCTCCCTCACCTACCACGGCTCCGGAAGCTT
2401 GACCTCTCAGGGAACCAGCTGGAAGATGAAGGCTGTCGGCTGATGGCAGA
2451 GGCTGCATCCCAGCTGCACATCGCCAGGAAGCTGGACCTCAGTAACAACG
2501 GGCTTTCTGTGGCCGGGGTGCATTGTGTGCTGAGGGCCGTGAGTGCGTGC
2551 TGGACCCTGGCAGAGCTGCACATCAGGCTGACACATTGTGGCCTCCAAGA
2601 AAAGCACCTAGAGCAGCTCTGCAAGGCTCTGGGAGGAAGCTGCCACCTCG
2651 GTCACCTCCACCTCGACTTCTCAGGCAATGCTCTGGGGGATGAAGGTGCA
2701 GCCCGGCTGGCTCAGCTGCTCCCAGGGCTGGGAGCTCTGCAGTCCTTGAA
2751 CCTCAGTGAGAACGGTTTGTCCCTGGATGCCGTGTTGGGTTTGGTTCGGT
2801 GCTTCTCCACTCTGCAGTGGCTCTTCCGCTTGGACATCAGCCTCAGTGAG
2851 TGTCCTCTGGAGCCCCCAAGCCTCACCCGCCTCTGTGCCACTCTGAAGGA
2901 CTGCCCGGGACCCCTGGAACTGCAATTGTCCTGTGAGTTCCTGAGTGACC
2951 AGAGCCTGGAGACTCTACTGGACTGCTTACCTCAACTCCCTCAGCTGAGC
3001 CTGCTGCAGCTGAGCCAGACGGGACTGTCCCCGAAAAGCCCCTTCCTGCT
3051 GGCCAACACCTTAAGCCTGTGTCCACGGGTTAAAAAGGTGGATCTCAGGT
3101 TCACAGGCTGCAGCCTCAGCCAGGAGCACGTAGAGTCACTCTGCTGGTTG
3151 CTGAGCAAGTGTAAAGACCTCAGCCAGGTGGATCTCTCAGCAAACCTGCT
3201 GGGCGACAGCGGACTCAGATGCCTTCTGGAATGTCTGCCGCAGGTGCCCA
3251 TCTCCGGTTTGCTTGAGAGCTTGGTCACGGCCTGTGGGACTGTGTCGCCG
3301 ATCGCGCCCGGCAACCCCCAATGGCCACCGAAGTGTGCCATCCGCGTGCG
3351 ATGGGGGACACCGTGCTGCGGGCTGTCGTTCAGGACATCTTATGTGGGGT
3401 ATTGCGGCGCCAATACCCGGTCACCCCTATTGCAGGGGGGGATATGGCAT
3451 TCTCCTCTATGTGG (SEQ ID NO:21)

*FIG. 29B*

1 MLQNFKYPKFLNKLIFKQAHRFPSSSSFQFPCPPAQLPALSSPVPQFIFL
51 LAPLSPSSPVPQLPCPPGWLLMDPVGLQLGNKNLWSCLVRLLTKDPEWLN
101 AKMKFFLPNTDLDSRNETLDPEQRVILQLNKLHVQGSDTWQSFIHCVCMQ
151 LEVPLDLEVLLLSTFGYDDGFTSQLGAEGKSQPESQLHHGLKRPHQSCGS
201 SPRRKQCKKQQLELAKKYLQLLRTSAQQRYRSQIPGSGQPHAFHQVYVPP
251 ILRRATASLDTPEGAIMGDVKVEDGADVSISDLFNTRVNKGPRVTVLLGK
301 AGMGKTTLAHRLCQKWAEGHLNCFQALFLFEFRQLNLITRFLTPSELLFD
351 LYLSPESDHDTVFQYLEKNADQVLLIFDGLDEALQPMGPDGPGPVLTLFS
401 HLCNGTLLPGCRAAMVHMLGFDGPRVEEYVNHFFSAQPSREGALVELQTN
451 GRLRSLCAVPALCQVACLCLHHLLPDHAPGQSVALLPNMTQLYMQMVLAL
501 SPPGHLPTSSLLDLGEVALRGPGDREGPGHQQTGYAFTHLSLQEFLAALH
551 LMASPKVNKDTLTQYVTLHSRWVQRTKARLGLSDHLPTFLAGLASCTCRP
601 FLSHLAQGNEDCVGAKQAAVVQVLKKLATRKLTGPKVVELCHCVDETQEP
651 ELASLTAQSLPYQLPFHNFPLTCTDLATLTNILEHREAPIHLDFDGCPLE
701 PHCPEALVGCGQIENLSFKSRKCGDAFAEALSRSLPTMGRLQMLGLAGSK
751 ITARGISHLVKALPLCPQLKEVSFRDNQLSDQVVLNIVEVLPHLPRLRKL
801 DLSGNQLEDEGCRLMAEAASQLHIARKLDLSNNGLSVAGVHCVLRAVSAC
851 WTLAELHIRLTHCGLQEKHLEQLCKALGGSCHLGHLHLDFSGNALGDEGA
901 ARLAQLLPGLGALQSLNLSENGLSLDAVLGLVRCFSTLQWLFRLDISLSE
951 CPLEPPSLTRLCATLKDCPGPLELQLSCEFLSDQSLETLLDCLPQLPQLS
1001 LLQLSQTGLSPKSPFLLANTLSLCPRVKKVDLRFTGCSLSQEHVESLCWL
1051 LSKCKDLSQVDLSANLLGDSGLRCLLECLPQVPISGLLESLVTACGTVSP
1101 IAPGNPQWPPKCAIRVRWGTPCCGLSFRTSYVGYCGANTRSPLLQGGIWH
1151 SPLC (SEQ ID NO:22)

*FIG. 29C*

1 GGCCCAGTCCTCACCCTTTTCTCCCATCTCTGCAATGGGACCCTCCTGCC
51 TGGCTGCCGGGTGATGGCTACCTCCCGTCCAGGGAAGCTGCCTGCCTGCC
101 TGCCTGCAGAGGCAGCCATGGTCCACATGTTGGGCTTTGATGGGCCACGG
151 GTGGAAGAATATGTGAATCACTTCTTCAGCGCCCAGCCATCGCGGGAGGG
201 GGCCCTGGTGGAGTTACAGACAAATGGACGTCTCCGAAGCCTGTGTGCGG
251 TGCCCGCACTGTGCCAAGTCGCCTGTCTCTGCCTCCACCATCTGCTTCCT
301 GACCACGCCCCAGGCCAGTCTGTGGCCCTCCTGCCCAACATGACTCAGCT
351 CTATATGCAGATGGTGCTCGCCCTCAGCCCCCCTGGGCACTTGCTCACCT
401 CGTCCCTACTGGACCTGGGGGAGGTGGCCCTGAGGGGCCTGGAGACAGGG
451 AAGGTTATCTTCTATGCAAAAGATATTGCTCCACCCTTGATAGCTTTTGG
501 GGCCACTCACAGCCTGCTGACTTCCTTCTGCGTCCGCACAGGCCCTGGGC
551 ACCAGCAGACAGGCTATGCTTTCACCCACCTCAGCCTGCAGGAGTTTCTT
601 GCTGCCCTGCACCTGATGGCCAGCCCCAAGGTGAACAAAGACACACTTAC
651 CCAGTATGTTACCCTCCATTCCCGCTGGGTACAGCGGACCAAAGCTAGAC
701 TGGGCCTCTCAGACCACCTCCCCACCTTCCTGGCGGGCCTGGCATCCTGC
751 ACCTGCCGCCCCTTCCTTAGCCACCTGGCGCAGGGCAATGAGGACTGTGT
801 GGGTGCCAAGCAGGCTGCTGTAGTGCAGGTGTTGAAGAAGTTGGCCACCC
851 GCAAGCTCACAGGGCCAAAGGTTGTAGAGCTGTGTCACTGTGTGGATGAG
901 ACACAGGAGCCTGAGCTGGCCAGTCTCACCGCACAAAGCCTCCCCTATCA
951 ACTGCCCTTCCACAATTTCCCACTGACCTGCACCGACCTGGCCACCCTGA
1001 CCAACATCCTAGAGCACAGGGAGGCCCCCATCCACCTGGATTTTGATGGC
1051 TGTCCCCTGGAGCCCCACTGCCCTGAGGCTCTGGTAGGCTGTGGGCAGAT
1101 AGAGAATCTCAGCTTTAAGAGCAGGAAGTGTGGGGATGCCTTTGCAGAAG
1151 CCCTCTCCAGGAGCTTGCCGACAATGGGGAGGCTGCAGATGCTGGGGTTA

*FIG. 29D*

1201 GCAGGAAGTAAAATCACTGCCCGAGGCATCAGCCACCTGGTGAAAGCTTT
1251 GCCTCTCTGTCCACAGCTGAAAGAAGTCAGTTTTCGGGACAACCAGCTCA
1301 GTGACCAGGTGGTGCTGAACATTGTGGAGGTTCTCCCTCACCTACCACGG
1351 CTCCGGAAGCTTGACCTGAGCAGCAACAGCATCTGCGTGTCAACCCTACT
1401 CTGCTTGGCAAGGGTGGCAGTCACGTGTCCTACCGTCAGGATGCTTCAGG
1451 CCAGGGAGCGGACCATCATCTTCCTTCTTTCCCCGCCCACAGAGACAACT
1501 GCAGAGCTACAAAGAGCTCCAGACCTGCAGGAAAGTGACGGCCAGAGGAA
1551 AGGGGCTCAGAGCAGAAGCTTGACGCTCAGGCTGCAGAAGTGTCAGCTCC
1601 AGGTCCACGATGCGGAGGCCCTCATAGCCCTGCTCCAGGAAGGCCCTCAC
1651 CTGGAGGAAGTGGACCTCTCAGGGAACCAGCTGGAAGATGAAGGCTGTCG
1701 GCTGATGGCAGAGGCTGCATCCCAGCTGCACATCGCCAGGAAGCTGGACC
1751 TCAGCGACAACGGGCTTTCTGTGGCCGGGGTGCATTGTGTGCTGAGGGCC
1801 GTGAGTGCGTGCTGGACCCTGGCAGAGCTGCACATCAGCCTGCAGCACAA
1851 AACTGTGATCTTCATGTTTGCCCAGGAGCCAGAGGAGCAGAAGGGGCCCC
1901 AGGAGAGGGCTGCATTTCTTGACAGCCTCATGCTCCAGATGCCCTCTGAG
1951 CTGCCTCTGAGCTCCCGAAGGATGAGGCTGACACATTGTGGCCTCCAAGA
2001 AAAGCACCTAGAGCAGCTCTGCAAGGCTCTGGGAGGAAGCTGCCACCTCG
2051 GTCACCTCCACCTCGACTTCTCAGGCAATGCTCTGGGGGATGAAGGTGCA
2101 GCCCGGCTGGCTCAGCTGCTCCCAGGGCTGGGAGCTCTGCAGTCCTTGAA
2151 CCTCAGTGAGAACGGTTTGTCCCTGGATGCCGTGTTGGGCTTGGTTCGGT
2201 GCTTCTCCACTCTGCAGTGGCTCTTCCGCTTGGACATCAGCTTTGAAAGC
2251 CAACACATCCTCCTGAGAGGGGACAAGACAAGCAGCCTCAGTGAGTGTCC
2301 TCTGGAGCCCCCAAGCCTCACCCGCCTCTGTGCCACTCTGAAGGACTGCC
2351 CGGGACCCCTGGAACTGCAATTGTCCTGTGAGTTCCTGAGTGACCAGAGC
2401 CTGGAGACTCTACTGGACTGCTTACCTCAACTCCCTCAGCTGAGCCTGCT
2451 GCAGCTGAGCCAGACGGGACTGTCCCCGAAAAGCCCCTTCCTGCTGGCCA
2501 ACACCTTAAGCCTGTGTCCACGGGTTAAAAAGGTGGATCTCAGGTCCCTG
2551 CACCATGCAACTTTGCACTTCAGATCCAACGAGGAGGAGGAAGGCGTGTG
2601 CTGTGGCAGGTTCACAGGCTGCAGCCTCAGCCAGGAGCACGTAGAGTCAC
2651 TCTGCTGGTTGCTGAGCAAGTGTAAAGACCTCAGCCAGGTGGATCTGAGT
2701 CACAACAGCATTTCTCAGGAAAGTGCCCTGTACCTGCTGGAGACACTGCC
2751 CTCCTGCCCACGTGTCCGGGAGGCCTCAGTGAACCTGGGCTCTGAGCAGA
2801 GCTTCCGGATTCACTTCTCCAGAGAGGACCAGGCTGGGAAGACACTCAGG
2851 CTAAGTGAGTGCAGCTTCCGGCCAGAGCACGTGTCCAGGCTGGCCACCGG
2901 CTTGAGCAAGTCCCTGCAGCTGACGGAGCTCACGCTGACCCAGTGCTGCC
2951 TGGGCCAGAAGCAGCTGGCCATCCTCCTGAGCTTGGTGGGGCGACCCGCA
3001 GGGCTGTTCAGCCTCAGGGTGCAGGAGCCGTGGGCGGACAGAGCCAGGGT
3051 TCTCTCCCTGTTAGAAGTCTGCGCCCAGGCCTCAGGCAGTGTCACTGAAA
3101 TCAGCATCTCCGAGACCCAGCAGCAGCTCTGTGTCCAGCTGGAATTTCCT
3151 CGCCAGGAAGAGAATCCAGAAGCTGTGGCACTCAGGTTGGCTCACTGTGA
3201 CCTTGGAGCCCACCACAGCCTTCTTGTCGGGCAGCTGATGGAGACATGTG
3251 CCAGGCTGCAGCAGCTCAGCTTGTCTCAGGTTAACCTCTGTGAGGACGAT
3301 GATGCCAGTTCCCTGCTGCTGCAGAGCCTCCTGCTGTCCCTCTCTGAGCT
3351 GAAGACATTTCGGCTGACCTCCAGCTGTGTGAGCACCGAGGGCCTCGCCC
3401 ACCTGGCATCTGGTCTGGGCCACTGCCACCACTTGGAGGAGCTGGACTTG
3451 TCTAACAATCAATTTGATGAGGAGGGCACCAAGGCGCTGATGAGGGCCCT
3501 TGAGGGGAAATGGATGCTAAAGAGGCTGGACCTCAGTCACCTTCTGCTGA
3551 ACAGCTCCACCTTGGCCTTGCTTACTCACAGACTAAGCCAGATGACCTGC
3601 CTGCAGAGCCTCAGACTGAACAGGAACAGTATCGGTGATGTCGGTTGCTG
3651 CCACCTTTCTGAGGCTCTCAGGGCTGCCACCAGCCTAGAGGAGCTGGACT
3701 TGAGCCACAACCAGATTGGAGACGCTGGTGTCCAGCACTTAGCTACCATC

*FIG. 29E*

3751 CTGCCTGGGCTGCCAGAGCTCAGGAAGATAGACCTCTCAGGGAATAGCAT
3801 CAGCTCAGCCGGGGGAGTGCAGTTGGCAGAGTCTCTCGTTCTTTGCAGGC
3851 GCCTGGAGGAGTTGATGCTTGGCTGCAATGCCCTGGGGGATCCCACAGCC
3901 CTGGGGCTGGCTCAGGAGCTGCCCCAGCACCTGAGGGTCCTACACCTACC
3951 ATTCAGCCATCTGGGCCCAGGTGGGGCCCTGAGCCTGGCCCAGGCCCTGG
4001 ATGGATCCCCCCATTTGGAAGAGATCAGCTTGGCGGAAAACAACCTGGCT
4051 GGAGGGGTCCTGCGTTTCTGTATGGAGCTCCCGCTGCTCAGACAGATAGA
4101 CCTGGTTTCCTGTAAGATTGACAACCAGACTGCCAAGCTCCTCACCTCCA
4151 GCTTCACGAGCTGCCCTGCCCTGGAAGTAATCTTGCTGTCCTGGAATCTC
4201 CTCGGGGATGAGGCAGCTGCCGAGCTGGCCCAGGTGCTGCCGAAGATGGG
4251 CCGGCTGAAGAGAGTGGACCTGGAGAAGAATCAGATCACAGCTTTGGGGG
4301 CCTGGCTCCTGGCTGAAGGACTGGCCCAGGGGTCTAGCATCCAAGTCATC
4351 CGCCTCTGGAATAACCCCATTCCCTGCGACATGGCCCAGCACCTGAAGAG
4401 CCAGGAGCCCAGGCTGGACTTTGCCTTCTTTGACAACCAGCCCCAGGCCC
4551 CTTGGGGTACTTGA (SEQ ID NO:23)

FIG. 29F

1 GPVLTLFSHLCNGTLLPGCRVMATSRPGKLPACLPAEAAMVHMLGFDGPR
51 VEEYVNHFFSAQPSREGALVELQTNGRLRSLCAVPALCQVACLCLHHLLP
101 DHAPGQSVALLPNMTQLYMQMVLALSPPGHLLTSSLLDLGEVALRGLETG
151 KVIFYAKDIAPPLIAFGATHSLLTSFRVCTGPGHQQTGYAFTHLSLQEFL
201 AALHLMASPKVNKDTLTQYVTLHSRWVQRTKARLGLSDHLPTFLAGLASC
251 TCRPFLSHLAQGNEDCVGAKQAAVVQVLKKLATRKLTGPKVVELCHCVDE
301 TQEPELASLTAQSLPYQLPFHNFPLTCTDLATLTNILEHREAPIHLDFDG
351 CPLEPHCPEALVGCGQIENLSFKSRKCGDAFAEALSRSLPTMGRLQMLGL
401 AGSKITARGISHLVKALPLCPQLKEVSFRDNQLSDQVVLNIVEVLPHLPR
451 LRKLDLSSNSICVSTLLCLARVAVTCPTVRMLQARERTIIFLLSPPTETT
501 AELQRAPDLQESDGQRKGAQSRSLTLRLQKCQLQVHDAEALIALLQEGPH
551 LEEVDLSGNQLEDEGCRLMAEAASQLHIARKLDLSDNGLSVAGVHCVLRA
601 VSACWTLAELHISLQHKTVIFMFAQEPEEQKGPQERAAFLDSLMLQMPSE
651 LPLSSRRMRLTHCGLQEKHLEQLCKALGGSCHLGHLHLDFSGNALGDEGA
701 ARLAQLLPGLGALQSLNLSENGLSLDAVLGLVRCFSTLQWLFRLDISFES
751 QHILLRGDKTSSLSECPLEPPSLTRLCATLKDCPGPLELQLSCEFLSDQS
801 LETLLDCLPQLPQLSLLQLSQTGLSPKSPFLLANTLSLCPRVKKVDLRSL
851 HHATLHFRSNEEEEGVCCGRFTGCSLSQEHVESLCWLLSKCKDLSQVDLS
901 HNSISQESALYLLETLPSCPRVREASVNLGSEQSFRIHFSREDQAGKTLR
951 LSECSFRPEHVSRLATGLSKSLQLTELTLTQCCLGQKQLAILLSLVGRPA
1001 GLFSLRVQEPWADRARVLSLLEVCAQASGSVTEISISETQQQLCVQLEFP
1051 RQEENPEAVALRLAHCDLGAHHSLLVGQLMETCARLQQLSLSQVNLCEDD
1101 DASSLLLQSLLLSLSELKTFRLTSSCVSTEGLAHLASGLGHCHHLEELDL
1151 SNNQFDEEGTKALMRALEGKWMLKRLDLSHLLLNSSTLALLTHRLSQMTC
1201 LQSLRLNRNSIGDVGCCHLSEALRAATSLEELDLSHNQIGDAGVQHLATI
1251 LPGLPELRKIDLSGNSISSAGGVQLAESLVLCRRLEELMLGCNALGDPTA
1301 LGLAQELPQHLRVLHLPFSHLGPGGALSLAQALDGSPHLEEISLAENNLA
1351 GGVLRFCMELPLLRQIDLVSCKIDNQTAKLLTSSFTSCPALEVILLSWNL
1401 LGDEAAAELAQVLPKMGRLKRVDLEKNQITALGAWLLAEGLAQGSSIQVI
1451 RLWNNPIPCDMAQHLKSQEPRLDFAFFDNQPQAPWGT
(SEQ ID NO:24)

FIG. 29G

```
   1 ATGGACCCCGTTGGCCTCCAGCTCGGCAACAAGAACCTGTGGAGCTGTCTTGTGAGGCTG
   1  M  D  P  V  G  L  Q  L  G  N  K  N  L  W  S  C  L  V  R  L
  61 CTCACCAAAGACCCAGAATGGCTGAACGCCAAGATGAAGTTCTTCCTCCCCAACACGGAC
  21  L  T  K  D  P  E  W  L  N  A  K  M  K  F  F  L  P  N  T  D
 121 CTGGATTCCAGGAACGAGACCTTGGACCCTGAACAGAGAGTCATCCTGCAACTCAACAAG
  41  L  D  S  R  N  E  T  L  D  P  E  Q  R  V  I  L  Q  L  N  K
 181 CTGCATGTCCAGGGTTCGGACACCTGGCAGTCTTTCATTCATTGCGTGTGCATGCAGCTG
  61  L  H  V  Q  G  S  D  T  W  Q  S  F  I  H  C  V  C  M  Q  L
 241 GAGGTGCCTCTGGACCTGGAGGTGCTTCTGCTAAGTACTTTTGGCTATGATGATGGGTTC
  81  E  V  P  L  D  L  E  V  L  L  L  S  T  F  G  Y  D  D  G  F
 301 ACCAGCCAGCTGGGAGCTGAGGGGAAAAGCCAACCTGAATCTCAGCTCCACCATGGCCTG
 101  T  S  Q  L  G  A  E  G  K  S  Q  P  E  S  Q  L  H  H  G  L
 361 AAGCGCCCACATCAGAGCTGTGGGTCCTCACCCCGCCGGAAGCAGTGCAAGAAGCAGCAG
 121  K  R  P  H  Q  S  C  G  S  S  P  R  R  K  Q  C  K  K  Q  Q
 421 CTAGAGTTGGCCAAGAAGTACCTGCAGCTCCTGCGGACCTCTGCCCAGCAGCGCTACAGG
 141  L  E  L  A  K  K  Y  L  Q  L  L  R  T  S  A  Q  Q  R  Y  R
 481 AGCCAAATCCCTGGGTCAGGGCAGCCCCACGCCTTCCACCAGGTCTATGTCCCTCCAATC
 161  S  Q  I  P  G  S  G  Q  P  H  A  F  H  Q  V  Y  V  P  P  I
 541 CTGCGCCGGGCCACAGCATCCTTAGACACTCCGGAGGGGGCCATTATGGGGGACGTCAAG
 181  L  R  R  A  T  A  S  L  D  T  P  E  G  A  I  M  G  D  V  K
 601 GTGGAAGATGGTGCTGACGTGAGCATCTCGGACCTCTTCAACACCAGGGTTAACAAGGGC
 201  V  E  D  G  A  D  V  S  I  S  D  L  F  N  T  R  V  N  K  G
 661 CCGAGGGTGACCGTGCTTTTGGGGAAGGCTGGCATGGGCAAGACCACGCTGGCCCACCGG
 221  P  R  V  T  V  L  L  G  K  A  G  M  G  K  T  T  L  A  H  R
 721 CTCTGCCAGAAGTGGGCAGAGGGCCATCTGAACTGTTTCCAGGCCCTGTTCCTTTTTGAA
 241  L  C  Q  K  W  A  E  G  H  L  N  C  F  Q  A  L  F  L  F  E
 781 TTCCGCCAGCTCAACTTGATCACGAGGTTCCTGACACCGTCCGAGCTCCTTTTTGATCTG
 261  F  R  Q  L  N  L  I  T  R  F  L  T  P  S  E  L  L  F  D  L
 841 TACCTGAGCCCTGAATCGGACCACGACACTGTCTTCCAGTACCTGGAGAAGAACGCTGAC
 281  Y  L  S  P  E  S  D  H  D  T  V  F  Q  Y  L  E  K  N  A  D
 901 CAAGTCCTGCTGATCTTTGATGGGCTAGATGAGGCCCTCCAGCCTATGGGTCCTGATGGC
 301  Q  V  L  L  I  F  D  G  L  D  E  A  L  Q  P  M  G  P  D  G
 961 CCAGGCCCAGTCCTCACCCTTTTCTCCCATCTCTGCAATGGGACCCTCCTGCCTGGCTGC
 321  P  G  P  V  L  T  L  F  S  H  L  C  N  G  T  L  L  P  G  C
1021 CGGGTGATGGCTACCTCCCGTCCAGGGAAGCTGCCTGCCTGCCTGCCTGCAGAGGCAGCC
 341  R  V  M  A  T  S  R  P  G  K  L  P  A  C  L  P  A  E  A  A
1081 ATGGTCCACATGTTGGGCTTTGATGGGCCACGGGTGGAAGAATATGTGAATCACTTCTTC
 361  M  V  H  M  L  G  F  D  G  P  R  V  E  E  Y  V  N  H  F  F
1141 AGCGCCCAGCCATCGCGGGAGGGGGCCCTGGTGGAGTTACAGACAAATGGACGTCTCCGA
 381  S  A  Q  P  S  R  E  G  A  L  V  E  L  Q  T  N  G  R  L  R
1201 AGCCTGTGTGCGGTGCCCGCACTGTGCCAAGTCGCCTGTCTCTGCCTCCACCATCTGCTT
 401  S  L  C  A  V  P  A  L  C  Q  V  A  C  L  C  L  H  H  L  L
1261 CCTGACCACGCCCCAGGCCAGTCTGTGGCCCTCCTGCCCAACATGACTCAGCTCTATATG
 421  P  D  H  A  P  G  Q  S  V  A  L  L  P  N  M  T  Q  L  Y  M
1321 CAGATGGTGCTCGCCCTCAGCCCCCCTGGGCACTTGCCCACCTCGTCCCTACTGGACCTG
 441  Q  M  V  L  A  L  S  P  P  G  H  L  P  T  S  S  L  L  D  L
1381 GGGGAGGTGGCCCTGAGGGGCCTGGAGACAGGGAAGGTTATCTTCTATGCAAAAGATATT
 461  G  E  V  A  L  R  G  L  E  T  G  K  V  I  F  Y  A  K  D  I
1441 GCTCCACCCTTGATAGCTTTTGGGGCCACTCACAGCCTGCTGACTTCCTTCTGCGTCTGC
 481  A  P  P  L  I  A  F  G  A  T  H  S  L  L  T  S  F  C  V  C
1501 ACAGGCCCTGGGCACCAGCAGACAGGCTATGCTTTCACCCACCTCAGCCTGCAGGAGTTT
 501  T  G  P  G  H  Q  Q  T  G  Y  A  F  T  H  L  S  L  Q  E  F
1561 CTTGCTGCCCTGCACCTGATGGCCAGCCCCAAGGTGAACAAAGACACACTTACCCAGTAT
 521  L  A  A  L  H  L  M  A  S  P  K  V  N  K  D  T  L  T  Q  Y
```

*FIG. 30A*

```
1621 GTTACCCTCCATTCCCGCTGGGTACAGCGGACCAAAGCTAGACTGGGCCTCTCAGACCAC
 541 V   T   L   H   S   R   W   V   Q   R   T   K   A   R   L   G   L   S   D   H
1681 CTCCCCACCTTCCTGGCGGGCCTGGCATCCTGCACCTGCCGCCCCTTCCTTAGCCACCTG
 561 L   P   T   F   L   A   G   L   A   S   C   T   C   R   P   F   L   S   H   L
1741 GCGCAGGGCAATGAGGACTGTGTGGGTGCCAAGCAGGCTGCTGTAGTGCAGGTGTTGAAG
 581 A   Q   G   N   E   D   C   V   G   A   K   Q   A   A   V   V   Q   V   L   K
1801 AAGTTGGCCACCCGCAAGCTCACAGGGCCAAAGGTTGTAGAGCTGTGTCACTGTGTGGAT
 601 K   L   A   T   R   K   L   T   G   P   K   V   V   E   L   C   H   C   V   D
1861 GAGACACAGGAGCCTGAGCTGGCCAGTCTCACCGCACAAAGCCTCCCCTATCAACTGCCC
 621 E   T   Q   E   P   E   L   A   S   L   T   A   Q   S   L   P   Y   Q   L   P
1921 TTCCACAATTTCCCACTGACCTGCACCGACCTGGCCACCCTGACCAACATCCTAGAGCAC
 641 F   H   N   F   P   L   T   C   T   D   L   A   T   L   T   N   I   L   E   H
1981 AGGGAGGCCCCCATCCACCTGGATTTTGATGGCTGTCCCCTGGAGCCCCACTGCCCTGAG
 681 R   E   A   P   I   H   L   D   F   D   G   C   P   L   E   P   H   C   P   E
2041 GCTCTGGTAGGCTGTGGGCAGATAGAGAATCTCAGCTTTAAGAGCAGGAAGTGTGGGGAT
 701 A   L   V   G   C   G   Q   I   E   N   L   S   F   K   S   R   K   C   G   D
2101 GCCTTTGCAGAAGCCCTCTCCAGGAGCTTGCCGACAATGGGGAGGCTGCAGATGCTGGGG
 721 A   F   A   E   A   L   S   R   S   L   P   T   M   G   R   L   Q   M   L   G
2161 TTAGCAGGAAGTAAAATCACTGCCCGAGGCATCAGCCACCTGGTGAAAGCTTTGCCTCTC
 741 L   A   G   S   K   I   T   A   R   G   I   S   H   L   V   K   A   L   P   L
2221 TGTCCACAGCTGAAAGAAGTCAGTTTTCGGGACAACCAGCTCAGTGACCAGGTGGTGCTG
 761 C   P   Q   L   K   E   V   S   F   R   D   N   Q   L   S   D   Q   V   V   L
2281 AACATTGTGGAGGTTCTCCCTCACCTACCACGGCTCCGGAAGCTTGACCTGAGCAGCAAC
 781 N   I   V   E   V   L   P   H   L   P   R   L   R   K   L   D   L   S   S   N
2341 AGCATCTGCGTGTCAACCCTACTCTGCTTGGCAAGGGTGGCAGTCACGTGTCCTACCGTC
 801 S   I   C   V   S   T   L   L   C   L   A   R   V   A   V   T   C   P   T   V
2401 AGGATGCTTCAGGCCAGGGAGCGGACCATCATCTTCCTTCTTTCCCCGCCCACAGAGACA
 821 R   M   L   Q   A   R   E   R   T   I   I   F   L   L   S   P   P   T   E   T
2461 ACTGCAGAGCTACAAAGAGCTCCAGACCTGCAGGAAAGTGACGGCCAGAGGAAAGGGGCT
 841 T   A   E   L   Q   R   A   P   D   L   Q   E   S   D   G   Q   R   K   G   A
2521 CAGAGCAGAAGCTTGACGCTCAGGCTGCAGAAGTGTCAGCTCCAGGTCCACGATGCGGAG
 861 Q   S   R   S   L   T   L   R   L   Q   K   C   Q   L   Q   V   H   D   A   E
2581 GCCCTCATAGCCCTGCTCCAGGAAGGCCCTCACCTGGAGGAAGTGGACCTCTCAGGGAAC
 881 A   L   I   A   L   L   Q   E   G   P   H   L   E   E   V   D   L   S   G   N
2641 CAGCTGGAAGATGAAGGCTGTCGGCTGATGGCAGAGGCTGCATCCCAGCTGCACATCGCC
 901 Q   L   E   D   E   G   C   R   L   M   A   E   A   A   S   Q   L   H   I   A
2701 AGGAAGCTGGACCTCAGCGACAACGGGCTTTCTGTGGCCGGGGTGCATTGTGTGCTGAGG
 921 R   K   L   D   L   S   D   N   G   L   S   V   A   G   V   H   C   V   L   R
2761 GCCGTGAGTGCGTGCTGGACCCTGGCAGAGCTGCACATCAGCCTGCAGCACAAAACTGTG
 941 A   V   S   A   C   W   T   L   A   E   L   H   I   S   L   Q   H   K   T   V
2821 ATCTTCATGTTTGCCCAGGAGCCAGAGGAGCAGAAGGGGCCCCAGGAGAGGGCTGCATTT
 961 I   F   M   F   A   Q   E   P   E   E   Q   K   G   P   Q   E   R   A   A   F
2881 CTTGACAGCCTCATGCTCCAGATGCCCTCTGAGCTGCCTCTGAGCTCCCGAAGGATGAGG
 981 L   D   S   L   M   L   Q   M   P   S   E   L   P   L   S   S   R   R   M   R
2941 CTGACACATTGTGGCCTCCAAGAAAAGCACCTAGAGCAGCTCTGCAAGGCTCTGGGAGGA
1001 L   T   H   C   G   L   Q   E   K   H   L   E   Q   L   C   K   A   L   G   G
3001 AGCTGCCACCTCGGTCACCTCCACCTCGACTTCTCAGGCAATGCTCTGGGGGATGAAGGT
1021 S   C   H   L   G   H   L   H   L   D   F   S   G   N   A   L   G   D   E   G
3061 GCAGCCCGGCTGGCTCAGCTGCTCCCAGGGCTGGGAGCTCTGCAGTCCTTGAACCTCAGT
1041 A   A   R   L   A   Q   L   L   P   G   L   G   A   L   Q   S   L   N   L   S
3121 GAGAACGGTTTGTCCCTGGATGCCGTGTTGGGCTTGGTTCGGTGCTTCTCCACTCTGCAG
1061 E   N   G   L   S   L   D   A   V   L   G   L   V   R   C   F   S   T   L   Q
3181 TGGCTCTTCCGCTTGGACATCAGCTTTGAAAGCCAACACATCCTCCTGAGAGGGGACAAG
1081 W   L   F   R   L   D   I   S   F   E   S   Q   H   I   L   L   R   G   D   K
```

FIG. 30B

```
3241 ACAAGCAGGGATATGTGGGCCACTGGATCTTTGCCAGACTTCCCAGCTGCAGCCAAGTTC
2001  T  S  R  D  M  W  A  T  G  S  L  P  D  F  P  A  A  K  F
3301 TTAGGGTTCCGTCAGCGCTGCATCCCCAGGAGCCTCTGCCTCAGTGAGTGTCCTCTGGAG
2021  L  G  F  R  Q  R  C  I  P  R  S  L  C  L  S  E  C  P  L  E
3361 CCCCCAAGCCTCACCCGCCTCTGTGCCACTCTGAAGGACTGCCCGGGACCCCTGGAACTG
2041  P  P  S  L  T  R  L  C  A  T  L  K  D  C  P  G  P  L  E  L
3421 CAATTGTCCTGTGAGTTCCTGAGTGACCAGAGCCTGGAGACTCTACTGGACTGCTTACCT
2061  Q  L  S  C  E  F  L  S  D  Q  S  L  E  T  L  L  D  C  L  P
3481 CAACTCCCTCAGCTGAGCCTGCTGCAGCTGAGCCAGACGGGACTGTCCCCGAAAAGCCCC
2081  Q  L  P  Q  L  S  L  L  Q  L  S  Q  T  G  L  S  P  K  S  P
3541 TTCCTGCTGGCCAACACCTTAAGCCTGTGTCCACGGGTTAAAAAGGTGGATCTCAGGTCC
2101  F  L  L  A  N  T  L  S  L  C  P  R  V  K  K  V  D  L  R  S
3601 CTGCACCATGCAACTTTGCACTTCAGATCCAACGAGGAGGAGGAAGGCGTGTGCTGTGGC
2121  L  H  H  A  T  L  H  F  R  S  N  E  E  E  E  G  V  C  C  G
3661 AGGTTCACAGGCTGCAGCCTCAGCCAGGAGCACGTAGAGTCACTCTGCTGGTTGCTGAGC
2141  R  F  T  G  C  S  L  S  Q  E  H  V  E  S  L  C  W  L  L  S
3721 AAGTGTAAAGACCTCAGCCAGGTGGATCTCTCAGCAAACCTGCTGGGCGACAGCGGACTC
2161  K  C  K  D  L  S  Q  V  D  L  S  A  N  L  L  G  D  S  G  L
3781 AGATGCCTTCTGGAATGTCTGCCGCAGGTGCCCATCTCCGGTTTGCTTGATCTGAGTCAC
2181  R  C  L  L  E  C  L  P  Q  V  P  I  S  G  L  L  D  L  S  H
3841 AACAGCATTTCTCAGGAAAGTGCCCTGTACCTGCTGGAGACACTGCCCTCCTGCCCACGT
2201  N  S  I  S  Q  E  S  A  L  Y  L  L  E  T  L  P  S  C  P  R
3901 GTCCGGGAGGCCTCAGTGAACCTGGGCTCTGAGCAGAGCTTCCGGATTCACTTCTCCAGA
2221  V  R  E  A  S  V  N  L  G  S  E  Q  S  F  R  I  H  F  S  R
3961 GAGGACCAGGCTGGGAAGACACTCAGGCTAAGTGAGTGCAGCTTCCGGCCAGAGCACGTG
2241  E  D  Q  A  G  K  T  L  R  L  S  E  C  S  F  R  P  E  H  V
4021 TCCAGGCTGGCCACCGGCTTGAGCAAGTCCCTGCAGCTGACGGAGCTCACGCTGACCCAG
2261  S  R  L  A  T  G  L  S  K  S  L  Q  L  T  E  L  T  L  T  Q
4081 TGCTGCCTGGGCCAGAAGCAGCTGGCCATCCTCCTGAGCTTGGTGGGGCGACCCGCAGGG
2281  C  C  L  G  Q  K  Q  L  A  I  L  L  S  L  V  G  R  P  A  G
4141 CTGTTCAGCCTCAGGGTGCAGGAGCCGTGGGCGGACAGAGCCAGGGTTCTCTCCCTGTTA
2301  L  F  S  L  R  V  Q  E  P  W  A  D  R  A  R  V  L  S  L  L
4201 GAAGTCTGCGCCCAGGCCTCAGGCAGTGTCACTGAAATCAGCATCTCCGAGACCCAGCAG
2321  E  V  C  A  Q  A  S  G  S  V  T  E  I  S  I  S  E  T  Q  Q
4261 CAGCTCTGTGTCCAGCTGGAATTTCCTCGCCAGGAAGAGAATCCAGAAGCTGTGGCACTC
2341  Q  L  C  V  Q  L  E  F  P  R  Q  E  E  N  P  E  A  V  A  L
4321 AGGTTGGCTCACTGTGACCTTGGAGCCCACCACAGCCTTCTTGTCGGGCAGCTGATGGAG
2361  R  L  A  H  C  D  L  G  A  H  H  S  L  L  V  G  Q  L  M  E
4381 ACATGTGCCAGGCTGCAGCAGCTCAGCTTGTCTCAGGTTAACCTCTGTGAGGACGATGAT
2381  T  C  A  R  L  Q  Q  L  S  L  S  Q  V  N  L  C  E  D  D  D
4441 GCCAGTTCCCTGCTGCTGCAGAGCCTCCTGCTGTCCCTCTCTGAGCTGAAGACATTTCGG
2401  A  S  S  L  L  L  Q  S  L  L  L  S  L  S  E  L  K  T  F  R
4501 CTGACCTCCAGCTGTGTGAGCACCGAGGGCCTCGCCCACCTGGCATCTGGTCTGGGCCAC
2421  L  T  S  S  C  V  S  T  E  G  L  A  H  L  A  S  G  L  G  H
4561 TGCCACCACTTGGAGGAGCTGGACTTGTCTAACAATCAATTTGATGAGGAGGGCACCAAG
2441  C  H  H  L  E  E  L  D  L  S  N  N  Q  F  D  E  E  G  T  K
4621 GCGCTGATGAGGGCCCTTGAGGGGAAATGGATGCTAAAGAGGCTGGACCTCAGTCACCTT
2461  A  L  M  R  A  L  E  G  K  W  M  L  K  R  L  D  L  S  H  L
4681 CTGCTGAACAGCTCCACCTTGGCCTTGCTTACTCACAGACTAAGCCAGATGACCTGCCTG
2481  L  L  N  S  S  T  L  A  L  L  T  H  R  L  S  Q  M  T  C  L
4741 CAGAGCCTCAGACTGAACAGGAACAGTATCGGTGATGTCGGTTGCTGCCACCTTTCTGAG
2501  Q  S  L  R  L  N  R  N  S  I  G  D  V  G  C  C  H  L  S  E
4801 GCTCTCAGGGCTGCCACCAGCCTAGAGGAGCTGGACTTGAGCCACAACCAGATTGGAGAC
2521  A  L  R  A  A  T  S  L  E  E  L  D  L  S  H  N  Q  I  G  D
```

FIG. 30C

```
4861 GCTGGTGTCCAGCACTTAGCTACCATCCTGCCTGGGCTGCCAGAGCTCAGGAAGATAGAC
2541  A  G  V  Q  H  L  A  T  I  L  P  G  L  P  E  L  R  K  I  D
4921 CTCTCAGGGAATAGCATCAGCTCAGCCGGGGGAGTGCAGTTGGCAGAGTCTCTCGTTCTT
2561  L  S  G  N  S  I  S  S  A  G  G  V  Q  L  A  E  S  L  V  L
4981 TGCAGGCGCCTGGAGGAGTTGATGCTTGGCTGCAATGCCCTGGGGGATCCCACAGCCCTG
2581  C  R  R  L  E  E  L  M  L  G  C  N  A  L  G  D  P  T  A  L
5041 GGGCTGGCTCAGGAGCTGCCCCAGCACCTGAGGGTCCTACACCTACCATTCAGCCATCTG
2601  G  L  A  Q  E  L  P  Q  H  L  R  V  L  H  L  P  F  S  H  L
5101 GGCCCAGGTGGGGCCCTGAGCCTGGCCCAGGCCCTGGATGGATCCCCCCATTTGGAAGAG
2621  G  P  G  G  A  L  S  L  A  Q  A  L  D  G  S  P  H  L  E  E
5161 ATCAGCTTGGCGGAAAACAACCTGGCTGGAGGGGTCCTGCGTTTCTGTATGGAGCTCCCG
2641  I  S  L  A  E  N  N  L  A  G  G  V  L  R  F  C  M  E  L  P
5221 CTGCTCAGACAGATAGACCTGGTTTCCTGTAAGATTGACAACCAGACTGCCAAGCTCCTC
2661  L  L  R  Q  I  D  L  V  S  C  K  I  D  N  Q  T  A  K  L  L
5281 ACCTCCAGCTTCACGAGCTGCCCTGCCCTGGAAGTAATCTTGCTGTCCTGGAATCTCCTC
2681  T  S  S  F  T  S  C  P  A  L  E  V  I  L  L  S  W  N  L  L
5341 GGGGATGAGGCAGCTGCCGAGCTGGCCCAGGTGCTGCCGAAGATGGGCCGGCTGAAGAGA
2701  G  D  E  A  A  A  E  L  A  Q  V  L  P  K  M  G  R  L  K  R
5401 GTGGACCTGGAGAAGAATCAGATCACAGCTTTGGGGGCCTGGCTCCTGGCTGAAGGACTG
2721  V  D  L  E  K  N  Q  I  T  A  L  G  A  W  L  L  A  E  G  L
5464 GCCCAGGGGTCTAGCATCCAAGTCATCCGCCTCTGGAATAACCCCATTCCCTGCGACATG
2741  A  Q  G  S  S  I  Q  V  I  R  L  W  N  N  P  I  P  C  D  M
5521 GCCCAGCACCTGAAGAGCCAGGAGCCCAGGCTGGACTTTGCCTTCTTTGACAACCAGCCC
2761  A  Q  H  L  K  S  Q  E  P  R  L  D  F  A  F  F  D  N  Q  P
5581 CAGGCCCCTTGGGGTACTTGA   (SEQ ID NO:185)
2781  Q  A  P  W  G  T  -    (SEQ ID NO:186)
```

*FIG. 30D*

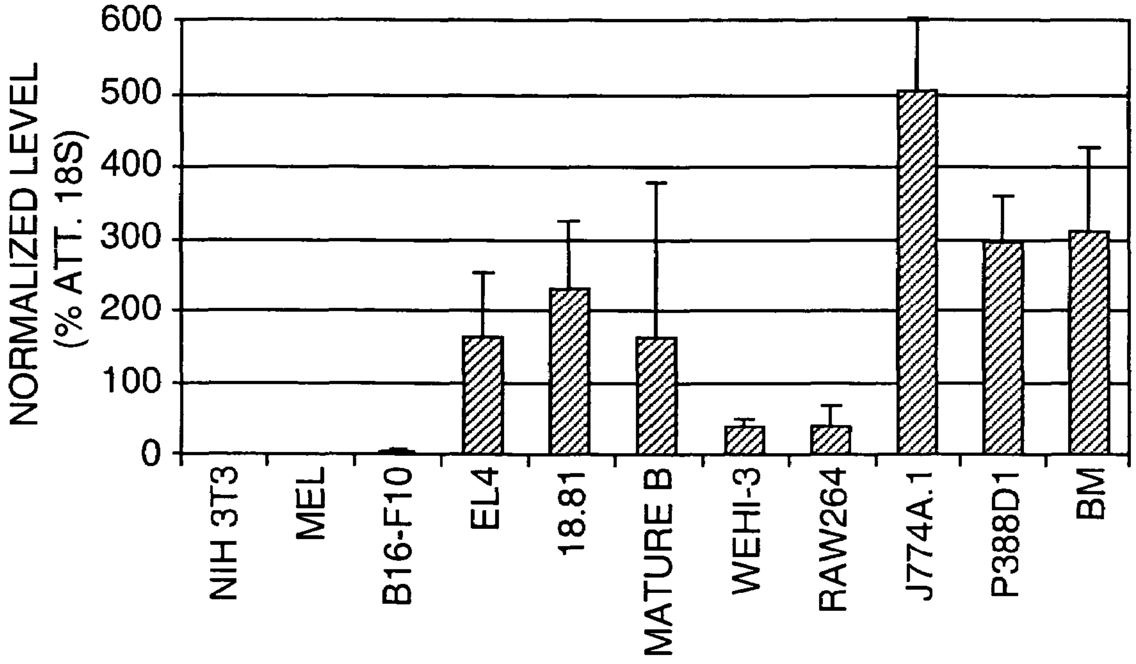

*FIG. 31A*

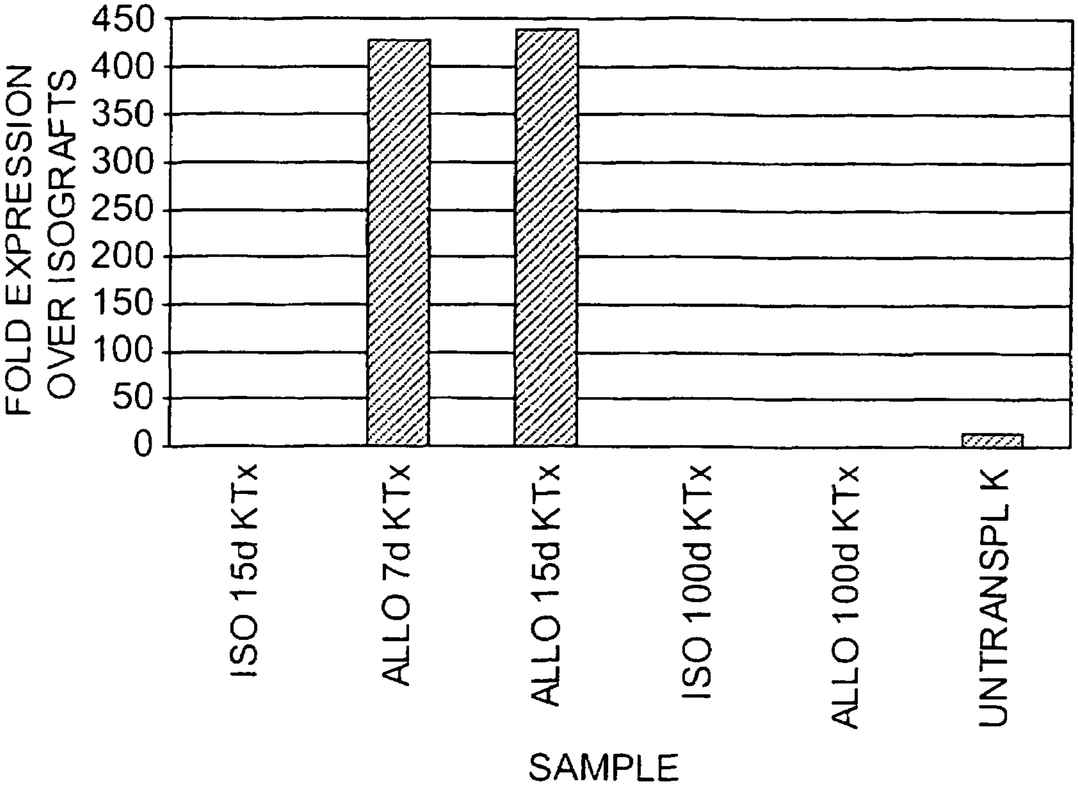

*FIG. 33B*

```
   1 ATGAGGAAGCAAGAGGTGCGGACGGGCAGGGAGGCCGGCCAGGGCCACGG
  51 TACGGGCTCCCCAGCCGAGCAGGTGAAAGCCCTCATGGATCTGCTGGCTG
 101 GGAAGGGCAGTCAAGGCTCCCAGGCCCCGCAGGCCCTGGATAGGACACCG
 151 GATGCCCCGCTGGGGCCCTGCAGCAATGACTCAAGGATACAGAGGCACCG
 201 CAAGGCCCTGCTGAGCAAGGTGGAGGTGGCCCGGAGCTGGGCGGACCCT
 251 GGCACAGGCTGGCCTCCCTCCTGCTGGTGGAGGGCCTGACGGACCTGCAG
 301 CTGAGGGAACACGACTTCACACAGGTGGAGGCCACCCGCGGGGGCGGGCA
 351 CCCCGCCAGGACCGTCGCCCTGGACCGGCTCTTCCTGCCTCTCTCCCGGG
 401 TGTCTGTCCCACCCCGGGTCTCCATCACTATCGGGGTGGCCGGCATGGGC
 451 AAGACCACCCTGGTGAGGCACTTCGTCCGCCTCTGGGCCCATGGGCAGGT
 501 CGGCAAGGACTTCTCGCTGGTGCTGCCTCTGACCTTCCGGGATCTCAACA
 551 CCCACGAGAAGCTGTGTGCCGACCGACTCATCTGCTCGGTCTTCCCGCAC
 601 GTCGGGGAGCCCAGCCTGGCGGTGGCAGTCCCAGCCAGGGCCCTCCTGAT
 651 CCTGGACGGCTTGGATGAGTGCAGGACGCCTCTGGACTTCTCCAACACCG
 701 TGGCCTGCACGGACCCAAAGAAGGAGATCCCGGTGGACCACCTGATCACC
 751 AACATCATCCGTGGCAACCTCTTTCCGGAAGTTTCCATCTGGATCACCTC
 801 CCGTCCCAGTGCATCTGGCCAGATCCCAGGGGGCCTGGTGGACCGGATGA
 851 CGGAGATCCGGGGCTTTAACGAGGAGGAGATCAAGGTGTGTTTGGAGCAG
 901 ATGTTCCCCGAGGACCAGGCCCTTCTGGGCTGGATGCTGAGCCAAGTGCA
 951 GGCTGACAGGGCCCTGTACCTGATGTGCACCGTCCCAGCCTTCTGCAGGC
1001 TCACGGGGATGGCGCTAGGCCACCTGTGGCGCAGCAGGACGGGGCCCCAG
1051 GATGCAGAGCTGTGGCCCCCGAGGACCCTGTGCGAGCTCTACTCATGGTA
1101 CTTTAGGATGGCCCTCAGCGGGGAGGGGCAGGAGAAGGGCAAGGCAAGCC
```

*FIG. 34A*

1151 CTCGCATCGAGCAGGTGGCCCATGGTGGCCGCAAGATGGTGGGGACATTG
1201 GGCCGTCTGGCCTTCCATGGGCTGCTCAAGAAGAAATACGTGTTTTACGA
1251 GCAAGACATGAAGGCGTTTGGTGTAGACCTCGCTCTGCTGCAGGGCGCCC
1301 CGTGCAGCTGCTTCCTGCAGAGAGAGGAGACGTTGGCATCGTCAGTGGCC
1351 TACTGCTTCACCCACCTGTCCCTGCAGGAGTTTGTGGCAGCCGCGTATTA
1401 CTATGGCGCATCCAGGAGGGCCATCTTCGACCTCTTCACTGAGAGCGGCG
1451 TATCCTGGCCCAGGCTGGGCTTCCTCACGCATTTCAGGAGCGCAGCCCAG
1501 CGGGCCATGCAGGCAGAGGACGGGAGGCTGGACGTGTTCCTGCGCTTCCT
1551 CTCCGGCCTCTTGTCTCCGAGGGTCAATGCCCTCCTGGCCGGCTCCCTGC
1601 TGGCCCAAGGCGAGCACCAGGCCTACCGGACCCAGGTGGCTGAGCTCCTG
1651 CAGGGCTGCCTGCGCCCCGATGCCGCAGTCTGTGCACGGGCCATCAACGT
1701 GTTGCACTGCCTGCATGAGCTGCAGCACACCGAGCTGGCCCGCAGCGTGG
1751 AGGAGGCCATGGAGAGCGGGGCCCTGGCCAGGCTGACTGGTCCCGCGCAC
1801 CGCGCTGCCCTGGCCTACCTCCTGCAGGTGTCCGACGCCTGTGCCCAGGA
1851 GGCCAACCTGTCCCTGAGCCTCAGCCAGGGCGTCCTTCAGAGCCTGCTGC
1901 CCCAGCTGCTCTACTGCCGGAAGCTCAGGCTGCGTTACTTCAGTCTCTCC
1951 CGTCGCCTGGTCATCTTCTCCCTGTGTCTGTCTCCACATGGTGCTGTCCT
2001 CTCTTTTTTTTTGAGATGGAGTCTTGCTCTGTCGCCCAGGCTGGAATACA
2051 GTGGCGCGATCTCAGCTCACTGCAAACGCTGCCTCCTGGGTTCAAGCGAT
2101 TCTCCTGCCTCAGCCTCCCTAGTAGCTGGGATTACAGGTGCCCGCCATCA
2151 TGCCTGGCTAATTTTTGTGTTTTTAGTAGAGACGGGGTTTCACCATGTTG
2201 GCCAGGCTGCTCTCAAACTCCTGACCTCAG (SEQ ID NO:25)

*FIG. 34B*

1 MRKQEVRTGREAGQGHGTGSPAEQVKALMDLLAGKGSQGSQAPQALDRTP
51 DAPLGPCSNDSRIQRHRKALLSKVGGGPELGGPWHRLASLLLVEGLTDLQ
101 LREHDFTQVEATRGGGHPARTVALDRLFLPLSRVSVPPRVSITIGVAGMG
151 KTTLVRHFVRLWAHGQVGKDFSLVLPLTFRDLNTHEKLCADRLICSVFPH
201 VGEPSLAVAVPARALLILDGLDECRTPLDFSNTVACTDPKKEIPVDHLIT
251 NIIRGNLFPEVSIWITSRPSASGQIPGGLVDRMTEIRGFNEEEIKVCLEQ
301 MFPEDQALLGWMLSQVQADRALYLMCTVPAFCRLTGMALGHLWRSRTGPQ
351 DAELWPPRTLCELYSWYFRMALSGEGQEKGKASPRIEQVAHGGRKMVGTL
401 GRLAFHGLLKKKYVFYEQDMKAFGVDLALLQGAPCSCFLQREETLASSVA
451 YCFTHLSLQEFVAAAYYYGASRRAIFDLFTESGVSWPRLGFLTHFRSAAQ
501 RAMQAEDGRLDVFLRFLSGLLSPRVNALLAGSLLAQGEHQAYRTQVAELL
551 QGCLRPDAAVCARAINVLHCLHELQHTELARSVEEAMESGALARLTGPAH
601 RAALAYLLQVSDACAQEANLSLSLSQGVLQSLLPQLLYCRKLRLRYFSLS
651 RRLVIFSLCLSPHGAVLSFFLRWSLALSPRLEYSGAISAHCKRCLLGSSD
701 SPASASLVAGITGARHHAWLIFVFLVETGFHHVGQAALKLLTS
(SEQ ID NO:26)

*FIG. 34C*

```
   1 ATTCCCAGGGCATCTACCACCACGCAGCTGGAGCAGGGCTGAGCCCAGGA
  51 GCATGGAGATGGACGCCCCCAGGCCCCCCAGTCTTGCTGTCCCTGGAGCA
 101 GCATCGAGGCCCGGGAGAACTGTGGACAACGGAAGGCTGAGCCCCATCCA
 151 TTGAGTTCCTGGGGCCCCACTGGAGGGGCTGCTGTGGCCAGGGTGCACGG
 201 TCACAAATGAAGACACCAAGGCGCAGAGAGGTGACTCAGCCTGCCCTCAG
 251 TCACCTATCTGCTCCTGGAGGTGATCCCCGACTCCATGAGGAAGCAAGAG
 301 GTGCGGACGGGCAGGGAGGCCGGCCAGGGCCACGGTACGGGCTCCCCAGC
 351 CGAGCAGGTGAAAGCCCTCATGGATCTGCTGGCTGGGAAGGGCAGTCAAG
 401 GCTCCCAGGCCCCGCAGGCCCTGGATAGGACACCGGATGCCCCGCTGGGG
 451 CCCTGCAGCAATGACTCAAGGATACAGAGGCACCGCAAGGCCCTGCTGAG
 501 CAAGGTGGGAGGTGGCCCGGAGCTGGGCGGACCCTGGCACAGGCTGGCCT
 551 CCCTCCTGCTGGTGGAGGGCCTGACGGACCTGCAGCTGAGGGAACACGAC
 601 TTCACACAGGTGGAGGCCACCCGCGGGGGCGGGCACCCCGCCAGGACCGT
 651 CGCCCTGGACCGGCTCTTCCTGCCTCTCTCCCGGGTGTCTGTCCCACCCC
 701 GGGTCTCCATCACTATCGGGGTGGCCGGCATGGGCAAGACCACCCTGGTG
 751 AGGCACTTCGTCCGCCTCTGGGCCCATGGGCAGGTCGGCAAGGACTTCTC
 801 GCTGGTGCTGCCTCTGACCTTCCGGGATCTCAACACCCACGAGAAGCTGT
 851 GTGCCGACCGACTCATCTGCTCGGTCTTCCCGCACGTCGGGGAGCCCAGC
 901 CTGGCGGTGGCAGTCCCAGCCAGGGCCCTCCTGATCCTGGACGGCTTGGA
 951 TGAGTGCAGGACGCCTCTGGACTTCTCCAACACCGTGGCCTGCACGGACC
1001 CAAAGAAGGAGATCCCGGTGGACCACCTGATCACCAACATCATCCGTGGC
1051 AACCTCTTTCCGGAAGTTTCCATCTGGATCACCTCCCGTCCCAGTGCATC
1101 TGGCCAGATCCCAGGGGGCCTGGTGGACCGGATGACGGAGATCCGGGGCT
1151 TTAACGAGGAGGAGATCAAGGTGTGTTTGGAGCAGATGTTCCCCGAGGAC
1201 CAGGCCCTTCTGGGCTGGATGCTGAGCCAAGTGCAGGCTGACAGGGCCCT
1251 GTACCTGATGTGCACCGTCCCAGCCTTCTGCAGGCTCACGGGGATGGCGC
1301 TAGGCCACCTGTGGCGCAGCAGGACGGGGCCCCAGGATGCAGAGCTGTGG
1351 CCCCCGAGGACCCTGTGCGAGCTCTACTCATGGTACTTTAGGATGGCCCT
1401 CAGCGGGGAGGGGCAGGAGAAGGGCAAGGCAAGCCCTCGCATCGAGCAGG
1451 TGGCCCATGGTGGCCGCAAGATGGTGGGGACATTGGGCCGTCTGGCCTTC
1501 CATGGGCTGCTCAAGAAGAAATACGTGTTTTACGAGCAAGACATGAAGGC
1551 GTTTGGTGTAGACCTCGCTCTGCTGCAGGGCGCCCCGTGCAGCTGCTTCC
1601 TGCAGAGAGAGGAGACGTTGGCATCGTCAGTGGCCTACTGCTTCACCCAC
1651 CTGTCCCTGCAGGAGTTTGTGGCAGCCGCGTATTACTATGGCGCATCCAG
1701 GAGGGCCATCTTCGACCTCTTCACTGAGAGCGGCGTATCCTGGCCCAGGC
1751 TGGGCTTCCTCACGCATTTCAGGAGCGCAGCCCAGCGGGCCATGCAGGCA
1801 GAGGACGGGAGGCTGGACGTGTTCCTGCGCTTCCTCTCCGGCCTCTTGTC
1851 TCCGAGGGTCAATGCCCTCCTGGCCGGCTCCCTGCTGGCCCAAGGCGAGC
1901 ACCAGGCCTACCGGACCCAGGTGGCTGAGCTCCTGCAGGGCTGCCTGCGC
1951 CCCGATGCCGCAGTCTGTGCACGGGCCATCAACGTGTTGCACTGCCTGCA
2001 TGAGCTGCAGCACACCGAGCTGGCCCGCAGCGTGGAGGAGGCCATGGAGA
2051 GCGGGGCCCTGGCCAGGCTGACCGGTCCCGCGCACCGCGCTGCCCTGGCC
2101 TACCTCCTGCAGGTGTCCGACGCCTGTGCCCAGGAGGCCAACCTGTCCCT
2151 GAGCCTCAGCCAGGGCGTCCTTCAGAGCCTGCTGCCCCAGCTGCTCTACT
2201 GCCGGAAGCTCAGGCTGGACACCAACCAGTTCCAGGACCCCGTGATGGAG
2251 CTGCTGGGCAGCGTGCTGAGTGGGAAGGACTGTCGCATTCAGAAGATCAG
2301 CTTGGCGGAGAACCAGATCAGTAACAAAGGGGCCAAAGCTCTGGCCAGAT
2351 CCCTCTTGGTCAACAGAAGTCTGACCTCTCTGGACCTCCGCGGTAACTCC
2401 ATTGGACCACAAGGGGCCAAGGCGCTGGCAGACGCTTTGAAGATCAACCG
2451 CACCCTGACCTCCCTGAGCCTCCAGGGCAACACCGTTAGGGATGATGGTG
2501 CCAGGTCCATGGCTGAGGCCTTGGCCTCCAACCGGACCCTCTCCATGCTG
```

*FIG. 34D*

2801 CACCTGCAGAAGAACAGCATCGGGCCCATGGGAGCCCAGCGGATGGCAGA
2851 TGCCTTGAAGCAGAACAGGAGTCTGAAAGAGCTCATGTTCTCCAGTAATA
2901 GTATTGGTGATGGAGGTGCCAAGGCCCTGGCTGAGGCCCTGAAGGTGAAC
2951 CAGGGCCTGGAGAGCCTGGACCTGCAGAGCAATTCCATCAGTGACGCAGG
3001 AGTGGCAGCACTGATGGGGGCCCTCTGCACCAACCAGACCCTCCTCAGCC
3051 TCAGCCTTCGAGAAAACTCCATCAGTCCCGAGGGAGCCCAGGCCATCGCT
3151 CATGCCCTCTGCGCCAACAGCACCCTGAAGAACCTGGACCTGACAGCCAA
3201 CCTCCTCCACGACCAGGGTGCCCGGGCCATCGCAGTGGCAGTGAGAGAAA
3251 ACCGCACCCTCACCTCCCTTCACCTGCAGTGGAACTTCATCCAGGCCGGC
3301 GCTGCCCAGGCCCTGGGACAAGCACTACAGCTCAACAGGAGCCTCACCAG
3351 CTTAGATTTACAGGAGAACGCCATCGGGGATGACGGAGCGTGTGCGGTGG
3401 CCCGTGCACTGAAGGTCAACACAGCCCTCACTGCTCTCTATCTCCAGGTG
3451 GCCTCAATTGGTGCTTCAGGCGCCCAGGTGCTAGGGGAAGCCTTGGCTGT
3501 GAACAGAACCTTGGAGATTCTCGACTTAAGAGGAAATGCCATTGGGGTGG
3551 CTGGAGCCAAAGCCCTGGCAAATGCTCTGAAGGTAAACTCAAGTCTCCGG
3601 AGACTCAATCTTCAAGAGAATTCTCTGGGGATGGACGGGGCGATATGCAT
3651 TGCCACAGCACTGTCTGGAAACCACAGGCTCCAGCATATCAATCTCCAGG
3701 GAAACCACATTGGGGACTCCGGGGCCAGGATGATCTCAGAGGCCATCAAG
3751 ACAAATGCTCCCACGTGCACTGTTGAAATGTGATCCTGG
(SEQ ID NO:27)

*FIG. 34E*

1 MRKQEVRTGREAGQGHGTGSPAEQVKALMDLLAGKGSQGSQAPQALDRTP
51 DAPLGPCSNDSRIQRHRKALLSKVGGGPELGGPWHRLASLLLVEGLTDLQ
101 LREHDFTQVEATRGGGHPARTVALDRLFLPLSRVSVPPRVSITIGVAGMG
151 KTTLVRHFVRLWAHGQVGKDFSLVLPLTFRDLNTHEKLCADRLICSVFPH
201 VGEPSLAVAVPARALLILDGLDECRTPLDFSNTVACTDPKKEIPVDHLIT
251 NIIRGNLFPEVSIWITSRPSASGQIPGGLVDRMTEIRGFNEEEIKVCLEQ
301 MFPEDQALLGWMLSQVQADRALYLMCTVPAFCRLTGMALGHLWRSRTGPQ
351 DAELWPPRTLCELYSWYFRMALSGEGQEKGKASPRIEQVAHGGRKMVGTL
401 GRLAFHGLLKKKYVFYEQDMKAFGVDLALLQGAPCSCFLQREETLASSVA
451 YCFTHLSLQEFVAAAYYYGASRRAIFDLFTESGVSWPRLGFLTHFRSAAQ
501 RAMQAEDGRLDVFLRFLSGLLSPRVNALLAGSLLAQGEHQAYRTQVAELL
551 QGCLRPDAAVCARAINVLHCLHELQHTELARSVEEAMESGALARLTGPAH
601 RAALAYLLQVSDACAQEANLSLSLSQGVLQSLLPQLLYCRKLRLDTNQFQ
651 DPVMELLGSVLSGKDCRIQKISLAENQISNKGAKALARSLLVNRSLTSLD
701 LRGNSIGPQGAKALADALKINRTLTSLSLQGNTVRDDGARSMAEALASNR
751 TLSMLHLQKNSIGPMGAQRMADALKQNRSLKELMFSSNSIGDGGAKALAE
801 ALKVNQGLESLDLQSNSISDAGVAALMGALCTNQTLLSLSLRENSISPEG
851 AQAIAHALCANSTLKNLDLTANLLHDQGARAIAVAVRENRTLTSLHLQWN
901 FIQAGAAQALGQALQLNRSLTSLDLQENAIGDDGACAVARALKVNTALTA
951 LYLQVASIGASGAQVLGEALAVNRTLEILDLRGNAIGVAGAKALANALKV
1001 NSSLRRLNLQENSLGMDGAICIATALSGNHRLQHINLQGNHIGDSGARMI
1051 SEAIKTNAPTCTVEM (SEQ ID NO:28)

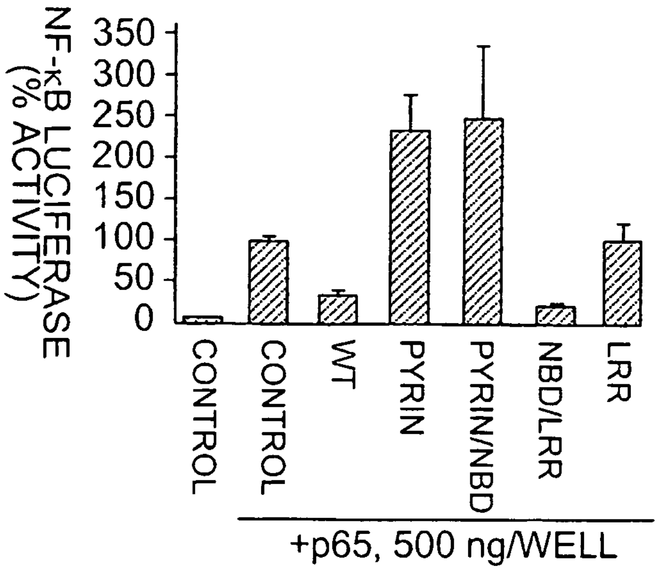

1 ATGGCAAGCACCCGCTGCAAGCTGGCCAGGTACCTGGAGGACCTGGAGGA
51 TGTGGACTTGAAGAAATTTAAGATGCACTTAGAGGACTATCCTCCCCAGA
101 AGGGCTGCATCCCCCTCCCGAGGGGTCAGACAGAGAAGGCAGACCATGTG
151 GATCTAGCCACGCTAATGATCGACTTCAATGGGGAGGAGAAGGCGTGGGC
201 CATGGCCGTGTGGATCTTCGCTGCGATCAACAGGAGAGACCTTTATGAGA
251 AAGCAAAAAGAGATGAGCCGAAGTGGGGTTAG (SEQ ID NO:29)

FIG. 42A

1 MASTRCKLARYLEDLEDVDLKKFKMHLEDYPPQKGCIPLPRGQTEKADHV
51 DLATLMIDFNGEEKAWAMAVWIFAAINRRDLYEKAKRDEPKWG
(SEQ ID NO:30)

FIG. 42B

1 ATGGCAAGCACCCGCTGCAAGCTGGCCAGGTACCTGGAGGACCTGGAGGA
51 TGTGGACTTGAAGAAATTTAAGATGCACTTAGAGGACTATCCTCCCCAGA
101 AGGGCTGCATCCCCCTCCCGAGGGGTCAGACAGAGAAGGCAGACCATGTG
151 GATCTAGCCACGCTAATGATCGACTTCAATGGGGAGGAGAAGGCGTGGGC
201 CATGGCCGTGTGGATCTTCGCTGCGATCAACAGGAGAGACCTTTATGAGA
251 AAGCAAAAAGAGATGAGCCGAAGTGGGGTTCAGATAATGCACGTGTTTCG
301 AATCCCACTGTGATATGCCAGGAAGACAGCATTGAAGAGGAGTGGATGGG
351 TTTACTGGAGTACCTTTCGAGAATCTCTATTTGTAAAATGAAGAAAGATT
401 ACCGTAAGAAGTACAGAAAGTACGTGAGAAGCAGATTCCAGTGCATTGAA
451 GACAGGAATGCCCGTCTGGGTGAGAGTGTGAGCCTCAACAAACGCTACAC
501 ACGACTGCGTCTCATCAAGGAGCACCGGAGCCAGCAGGAGAGGGAGCAGG
551 AGCTTCTGGCCATCGGCAAGACCAAGACGTGTGAGAGCCCCGTGAGTCCC
601 ATTAAGATGGAGTTGCTGTTTGACCCCGATGATGAGCATTCTGAGCCTGT
651 GCACACCGTGGTGTTCCAGGGGGCGGCAGGGATTGGGAAAACAATCCTGG
701 CCAGGAAGATGATGTTGGACTGGGCGTCGGGGACACTCTACCAAGACAGG
751 TTTGACTATCTGTTCTATATCCACTGTCGGGAGGTGAGCCTTGTGACACA
801 GAGGAGCCTGGGGGACCTGATCATGAGCTGCTGCCCCGACCCAAACCCAC
851 CCATCCACAAGATCGTGAGAAAACCCTCCAGAATCCTCTTCCTCATGGAC
901 GGCTTCGATGAGCTGCAAGGTGCCTTTGACGAGCACATAGGACCGCTCTG
951 CACTGACTGGCAGAAGGCCGAGCGGGGAGACATTCTCCTGAGCAGCCTCA
1001 TCAGAAAGAAGCTGCTTCCCGAGGCCTCTCTGCTCATCACCACGAGACCT

FIG. 42C

1051 GTGGCCCTGGAGAAACTGCAGCACTTGCTGGACCATCCTCGGCATGTGGA
1101 GATCCTGGGTTTCTCCGAGGCCAAAAGGAAAGAGTACTTCTTCAAGTACT
1151 TCTCTGATGAGGCCCAAGCCAGGGCAGCCTTCAGTCTGATTCAGGAGAAC
1201 GAGGTCCTCTTCACCATGTGCTTCATCCCCCTGGTCTGCTGGATCGTGTG
1251 CACTGGACTGAAACAGCAGATGGAGAGTGGCAAGAGCCTTGCCCAGACAT
1301 CCAAGACCACCACCGCGGTGTACGTCTTCTTCCTTTCCAGTTTGCTGCAG
1351 CCCCGGGGAGGGAGCCAGGAGCACGGCCTCTGCGCCCACCTCTGGGGGCT
1401 CTGCTCTTTGGCTGCAGATGGAATCTGGAACCAGAAAATCCTGTTTGAGG
1451 AGTCCGACCTCAGGAATCATGGACTGCAGAAGGCGGATGTGTCTGCTTTC
1501 CTGAGGATGAACCTGTTCCAAAAGGAAGTGGACTGCGAGAAGTTCTACAG
1551 CTTCATCCACATGACTTTCCAGGAGTTCTTTGCCGCCATGTACTACCTGC
1601 TGGAAGAGGAAAAGGAAGGAAGGACGAACGTTCCAGGGAGTCGTTTGAAG
1651 CTTCCCAGCCGAGACGTGACAGTCCTTCTGGAAAACTATGGCAAATTCGA
1701 AAAGGGGTATTTGATTTTTGTTGTACGTTTCCTCTTTGGCCTGGTAAACC
1751 AGGAGAGGACCTCCTACTTGGAGAAGAAATTAAGTTGCAAGATCTCTCAG
1801 CAAATCAGGCTGGAGCTGCTGAAATGGATTGAAGTGAAAGCCAAAGCTAA
1851 AAAGCTGCAGATCCAGCCCAGCCAGCTGGAATTGTTCTACTGTTTGTACG
1901 AGATGCAGGAGGAGGACTTCGTGCAAAGGGCCATGGACTATTTCCCCAAG
1951 ATTGAGATCAATCTCTCCACCAGAATGGACCACATGGTTTCTTCCTTTTG
2001 CATTGAGAACTGTCATCGGGTGGAGTCACTGTCCCTGGGGTTTCTCCATA
2051 ACATGCCCAAGGAGGAAGAGGAGGAGGAAAAGGAAGGCCGACACCTTGAT
2101 ATGGTGCAGTGTGTCCTCCCAAGCTCCTCTCATGCTGCCTGTTCTCATGG
2151 ATAG (SEQ ID NO:31

*FIG. 42D*

1 MASTRCKLARYLEDLEDVDLKKFKMHLEDYPPQKGCIPLPRGQTEKADHV
51 DLATLMIDFNGEEKAWAMAVWIFAAINRRDLYEKAKRDEPKWGSDNARVS
101 NPTVICQEDSIEEEWMGLLEYLSRISICKMKKDYRKKYRKYVRSRFQCIE
151 DRNARLGESVSLNKRYTRLRLIKEHRSQQEREQELLAIGKTKTCESPVSP
201 IKMELLFDPDDEHSEPVHTVVFQGAAGIGKTILARKMMLDWASGTLYQDR
251 FDYLFYIHCREVSLVTQRSLGDLIMSCCPDPNPPIHKIVRKPSRILFLMD
301 GFDELQGAFDEHIGPLCTDWQKAERGDILLSSLIRKKLLPEASLLITTRP
351 VALEKLQHLLDHPRHVEILGFSEAKRKEYFFKYFSDEAQARAAFSLIQEN
401 EVLFTMCFIPLVCWIVCTGLKQQMESGKSLAQTSKTTTAVYVFFLSSLLQ
451 PRGGSQEHGLCAHLWGLCSLAADGIWNQKILFEESDLRNHGLQKADVSAF
501 LRMNLFQKEVDCEKFYSFIHMTFQEFFAAMYYLLEEEKEGRTNVPGSRLK
551 LPSRDVTVLLENYGKFEKGYLIFVVRFLFGLVNQERTSYLEKKLSCKISQ
601 QIRLELLKWIEVKAKAKKLQIQPSQLELFYCLYEMQEEDFVQRAMDYFPK
651 IEINLSTRMDHMVSSFCIENCHRVESLSLGFLHNMPKEEEEEEKEGRHLD
701 MVQCVLPSSSHAACSHG (SEQ ID NO:32)

*FIG. 42E*

1 ATGGCAAGCACCCGCTGCAAGCTGGCCAGGTACCCCACTGTGATATGCCA
51 GGAAGACAGCATTGAAGAGGAGTGGATGGGTTTACTGGAGTACCTTTCGA
101 GAATCTCTATTTGTAAAATGAAGAAAGATTACCGTAAGAAGTACAGAAAG
151 TACGTGAGAAGCAGATTCCAGTGCATTGAAGACAGGAATGCCCGTCTGGG
201 TGAGAGTGTGAGCCTCAACAAACGCTACACACGACTGCGTCTCATCAAGG
251 AGCACCGGAGCCAGCAGGAGAGGGAGCAGGAGCTTCTGGCCATCGGCAAG
301 ACCAAGACGTGTGAGAGCCCCGTGAGTCCCATTAAGATGGAGTTGCTGTT
351 TGACCCCGATGATGAGCATTCTGAGCCTGTGCACACCGTGGTGTTCCAGG
401 GGGCGGCAGGGATTGGAAAAACAATCCTGGCCAGGAAGATGATGTTGGAC

*FIG. 42F*

451 TGGGCGTCGGGGACACTCTACCAAGACAGGTTTGACTATCTGTTCTATAT
501 CCACTGTCGGGAGGTGAGCCTTGTGACACAGAGGAGCCTGGGGACCTGA
551 TCATGAGCTGCTGCCCCGACCCAAACCCACCCATCCACAAGATCGTGAGA
601 AAACCCTCCAGAATCCTCTTCCTCATGGACGGCTTCGATGAGCTGCAAGG
651 TGCCTTTGACGAGCACATAGGACCGCTCTGCACTGACTGGCAGAAGGCCG
701 AGCGGGGAGACATTCTCCTGAGCAGCCTCATCAGAAAGAAGCTGCTTCCC
751 GAGGCCTCTCTGCTCATCACCACGAGACCTGTGGCCCTGGAGAAACTGCA
801 GCACTTGCTGGACCATCCTCGGCATGTGGAGATCCTGGGTTTCTCCGAGG
851 CCAAAAGGAAAGAGTACTTCTTCAAGTACTTCTCTGATGAGGCCCAAGCC
901 AGGGCAGCCTTCAGTCTGATTCAGGAGAACGAGGTCCTCTTCACCATGTG
951 CTTCATCCCCCTGGTCTGCTGGATCGTGTGCACTGGACTGAAACAGCAGA
1001 TGGAGAGTGGCAAGAGCCTTGCCCAGACATCCAAGACCACCACCGCGGTG
1051 TACGTCTTCTTCCTTTCCAGTTTGCTGCAGCCCCGGGGAGGGAGCCAGGA
1101 GCACGGCCTCTGCGCCCACCTCTGGGGGCTCTGCTCTTTGGCTGCAGATG
1151 GAATCTGGAACCAGAAAATCCTGTTTGAGGAGTCCGACCTCAGGAATCAT
1201 GGACTGCAGAAGGCGGATGTGTCTGCTTTCCTGAGGATGAACCTGTTCCA
1251 AAAGGAAGTGGACTGCGAGAAGTTCTACAGCTTCATCCACATGACTTTCC
1301 AGGAGTTCTTTGCCGCCATGTACTACCTGCTGGAAGAGGAAAAGGAAGGA
1351 AGGACGAACGTTCCAGGGAGTCGTTTGAAGCTTCCCAGCCGAGACGTGAC
1401 AGTCCTTCTGGAAAACTATGGCAAATTCGAAAAGGGGTATTTGATTTTTG
1451 TTGTACGTTTCCTCTTTGGCCTGGTAAACCAGGAGAGGACCTCCTACTTG
1501 GAGAAGAAATTAAGTTGCAAGATCTCTCAGCAAATCAGGCTGGAGCTGCT
1551 GAAATGGATTGAAGTGAAAGCCAAAGCTAAAAAGCTGCAGATCCAGCCCA
1601 GCCAGCTGGAATTGTTCTACTGTTTGTACGAGATGCAGGAGGAGGACTTC
1651 GTGCAAAGGGCCATGGACTATTTCCCCAAGATTGAGATCAATCTCTCCAC
1701 CAGAATGGACCACATGGTTTCTTCCTTTTGCATTGAGAACTGTCATCGGG
1751 TGGAGTCACTGTCCCTGGGGTTTCTCCATAACATGCCCAAGGAGGAAGAG
1801 GAGGAGGAAAAGGAAGGCCGACACCTTGATATGGTGCAGTGTGTCCTCCC
1851 AAGCTCCTCTCATGCTGCCTGTTCTCATGGATTGGTGAACAGCCACCTCA
1901 CTTCCAGTTTTTGCCGGGGCCTCTTTTCAGTTCTGAGCACCAGCCAGAGT
1951 CTAACTGAATTGGACCTCAGTGACAATTCTCTGGGGGACCCAGGGATGAG
2001 AGTGTTGTGTGAAACGCTCCAGCATCCTGGCTGTAACATTCGGAGATTGT
2051 GGTTGGGGCGCTGTGGCCTCTCGCATGAGTGCTGCTTCGACATCTCCTTG
2101 GTCCTCAGCAGCAACCAGAAGCTGGTGGAGCTGGACCTGAGTGACAACGC
2151 CCTCGGTGACTTCGGAATCAGACTTCTGTGTGTGGGACTGAAGCACCTGT
2201 TGTGCAATCTGAAGAAGCTCTGGTTGGTCAGCTGCTGCCTCACATCAGCA
2251 TGTTGTCAGGATCTTGCATCAGTATTGAGCACCAGCCATTCCCTGACCAG
2301 ACTCTATGTGGGGGAGAATGCCTTGGGAGACTCAGGAGTCGCAATTTTAT
2351 GTGAAAAAGCCAAGAATCCACAGTGTAACCTGCAGAAACTGGGGTTGGTG
2401 AATTCTGGCCTTACGTCAGTCTGTTGTTCAGCTTTGTCCTCGGTACTCAG
2451 CACTAATCAGAATCTCACGCACCTTTACCTGCGAGGCAACACTCTCGGAG
2501 ACAAGGGGATCAAACTACTCTGTGAGGGACTCTTGCACCCCGACTGCAAG
2551 CTTCAGGTGTTGGAATTAGACAACTGCAACCTCACGTCACACTGCTGCTG
2601 GGATCTTTCCACACTTCTGACCTCCAGCCAGAGCCTGCGAAAGCTGAGCC
2651 TGGGCAACAATGACCTGGGCGACCTGGGGGTCATGATGTTCTGTGAAGTG
2701 CTGAAACAGCAGAGCTGCCTCCTGCAGAACCTGGGGTTGTCTGAAATGTA
2751 TTTCAATTATGAGACAAAAAGTGCGTTAGAAACACTTCAAGAAGAAAAGC
2801 CTGAGCTGACCGTCGTCTTTGAGCCTTCTTGGTAG
(SEQ ID NO:33)

*FIG. 42G*

```
  1 MASTRCKLARYPTVICQEDSIEEEWMGLLEYLSRISICKMKKDYRKKYRK
 51 YVRSRFQCIEDRNARLGESVSLNKRYTRLRLIKEHRSQQEREQELLAIGK
101 TKTCESPVSPIKMELLFDPDDEHSEPVHTVVFQGAAGIGKTILARKMMLD
151 WASGTLYQDRFDYLFYIHCREVSLVTQRSLGDLIMSCCPDPNPPIHKIVR
201 KPSRILFLMDGFDELQGAFDEHIGPLCTDWQKAERGDILLSSLIRKKLLP
251 EASLLITTRPVALEKLQHLLDHPRHVEILGFSEAKRKEYFFKYFSDEAQA
301 RAAFSLIQENEVLFTMCFIPLVCWIVCTGLKQQMESGKSLAQTSKTTTAV
351 YVFFLSSLLQPRGGSQEHGLCAHLWGLCSLAADGIWNQKILFEESDLRNH
401 GLQKADVSAFLRMNLFQKEVDCEKFYSFIHMTFQEFFAAMYYLLEEEKEG
451 RTNVPGSRLKLPSRDVTVLLENYGKFEKGYLIFVVRFLFGLVNQERTSYL
501 EKKLSCKISQQIRLELLKWIEVKAKAKKLQIQPSQLELFYCLYEMQEEDF
551 VQRAMDYFPKIEINLSTRMDHMVSSFCIENCHRVESLSLGFLHNMPKEEE
601 EEEKEGRHLDMVQCVLPSSSHAACSHGLVNSHLTSSFCRGLFSVLSTSQS
651 LTELDLSDNSLGDPGMRVLCETLQHPGCNIRRLWLGRCGLSHECCFDISL
701 VLSSNQKLVELDLSDNALGDFGIRLLCVGLKHLLCNLKKLWLVSCCLTSA
751 CCQDLASVLSTSHSLTRLYVGENALGDSGVAILCEKAKNPQCNLQKLGLV
801 NSGLTSVCCSALSSVLSTNQNLTHLYLRGNTLGDKGIKLLCEGLLHPDCK
851 LQVLELDNCNLTSHCCWDLSTLLTSSQSLRKLSLGNNDLGDLGVMMFCEV
901 LKQQSCLLQNLGLSEMYFNYETKSALETLQEEKPELTVVFEPSW
    (SEQ ID NO:34)
```

FIG. 42H

```
  1 ATGGCAAGCACCCGCTGCAAGCTGGCCAGGTACCATGGATTGGTGAACAG
 51 CCACCTCACTTCCAGTTTTTGCCGGGGCCTCTTTTCAGTTCTGAGCACCA
101 GCCAGAGTCTAACTGAATTGGACCTCAGTGACAATTCTCTGGGGGACCCA
151 GGGATGAGAGTGTTGTGTGAAACGCTCCAGCATCCTGGCTGTAACATTCG
201 GAGATTGTGGTTGGGGCGCTGTGGCCTCTCGCATGAGTGCTGCTTCGACA
251 TCTCCTTGGTCCTCAGCAGCAACCAGAAGCTGGTGGAGCTGGACCTGAGT
301 GACAACGCCCTCGGTGACTTCGGAATCAGACTTCTGTGTGTGGGACTGAA
351 GCACCTGTTGTGCAATCTGAAGAAGCTCTGGTTGGTCAGCTGCTGCCTCA
401 CATCAGCATGTTGTCAGGATCTTGCATCAGTATTGAGCACCAGCCATTCC
451 CTGACCAGACTCTATGTGGGGGAGAATGCCTTGGGAGACTCAGGAGTCGC
501 AATTTTATGTGAAAAAGCCAAGAATCCACAGTGTAACCTGCAGAAACTGG
551 GGTTGGTGAATTCTGGCCTTACGTCAGTCTGTTGTTCAGCTTTGTCCTCG
601 GTACTCAGCACTAATCAGAATCTCACGCACCTTTACCTGCGAGGCAACAC
651 TCTCGGAGACAAGGGGATCAAACTACTCTGTGAGGGACTCTTGCACCCCG
701 ACTGCAAGCTTCAGGTGTTGGAATTAGACAACTGCAACCTCACGTCACAC
751 TGCTGCTGGGATCTTTCCACACTTCTGACCTCCAGCCAGAGCCTGCGAAA
801 GCTGAGCCTGGGCAACAATGACCTGGGCGACCTGGGGGTCATGATGTTCT
851 GTGAAGTGCTGAAACAGCAGAGCTGCCTCCTGCAGAACCTGGGGTTGTCT
901 GAAATGTATTTCAATTATGAGACAAAAAGTGCGTTAGAAACACTTCAAGA
951 AGAAAAGCCTGAGCTGACCGTCGTCTTTGAGCCTTCTTGGTAG
    (SEQ ID NO:35)
```

FIG. 42I

```
  1 MASTRCKLARYHGLVNSHLTSSFCRGLFSVLSTSQSLTELDLSDNSLGDP
 51 GMRVLCETLQHPGCNIRRLWLGRCGLSHECCFDISLVLSSNQKLVELDLS
101 DNALGDFGIRLLCVGLKHLLCNLKKLWLVSCCLTSACCQDLASVLSTSHS
151 LTRLYVGENALGDSGVAILCEKAKNPQCNLQKLGLVNSGLTSVCCSALSS
201 VLSTNQNLTHLYLRGNTLGDKGIKLLCEGLLHPDCKLQVLELDNCNLTSH
251 CCWDLSTLLTSSQSLRKLSLGNNDLGDLGVMMFCEVLKQQSCLLQNLGLS
301 EMYFNYETKSALETLQEEKPELTVVFEPSW (SEQ ID NO:36)
```

FIG. 42J

```
   1 ATGGCAAGCACCCGCTGCAAGCTGGCCAGGTACCTGGAGGACCTGGAGGA
  51 TGTGGACTTGAAGAAATTTAAGATGCACTTAGAGGACTATCCTCCCCAGA
 101 AGGGCTGCATCCCCCTCCCGAGGGGTCAGACAGAGAAGGCAGACCATGTG
 151 GATCTAGCCACGCTAATGATCGACTTCAATGGGGAGGAGAAGGCGTGGGC
 201 CATGGCCGTGTGGATCTTCGCTGCGATCAACAGGAGAGACCTTTATGAGA
 251 AAGCAAAAAGAGATGAGCCGAAGTGGGGTTCAGATAATGCACGTGTTTCG
 301 AATCCCACTGTGATATGCCAGGAAGACAGCATTGAAGAGGAGTGGATGGG
 351 TTTACTGGAGTACCTTTCGAGAATCTCTATTTGTAAAATGAAGAAAGATT
 401 ACCGTAAGAAGTACAGAAAGTACGTGAGAAGCAGATTCCAGTGCATTGAA
 451 GACAGGAATGCCCGTCTGGGTGAGAGTGTGAGCCTCAACAAACGCTACAC
 501 ACGACTGCGTCTCATCAAGGAGCACCGGAGCCAGCAGGAGAGGGAGCAGG
 551 AGCTTCTGGCCATCGGCAAGACCAAGACGTGTGAGAGCCCCGTGAGTCCC
 601 ATTAAGATGGAGTTGCTGTTTGACCCCGATGATGAGCATTCTGAGCCTGT
 651 GCACACCGTGGTGTTCCAGGGGGCGGCAGGGATTGGGAAAACAATCCTGG
 701 CCAGGAAGATGATGTTGGACTGGGCGTCGGGGACACTCTACCAAGACAGG
 751 TTTGACTATCTGTTCTATATCCACTGTCGGGAGGTGAGCCTTGTGACACA
 801 GAGGAGCCTGGGGGACCTGATCATGAGCTGCTGCCCCGACCCAAACCCAC
 851 CCATCCACAAGATCGTGAGAAAACCCTCCAGAATCCTCTTCCTCATGGAC
 901 GGCTTCGATGAGCTGCAAGGTGCCTTTGACGAGCACATAGGACCGCTCTG
 951 CACTGACTGGCAGAAGGCCGAGCGGGGAGACATTCTCCTGAGCAGCCTCA
1001 TCAGAAAGAAGCTGCTTCCCGAGGCCTCTCTGCTCATCACCACGAGACCT
1051 GTGGCCCTGGAGAAACTGCAGCACTTGCTGGACCATCCTCGGCATGTGGA
1101 GATCCTGGGTTTCTCCGAGGCCAAAAGGAAAGAGTACTTCTTCAAGTACT
1151 TCTCTGATGAGGCCCAAGCCAGGGCAGCCTTCAGTCTGATTCAGGAGAAC
1201 GAGGTCCTCTTCACCATGTGCTTCATCCCCCTGGTCTGCTGGATCGTGTG
1251 CACTGGACTGAAACAGCAGATGGAGAGTGGCAAGAGCCTTGCCCAGACAT
1301 CCAAGACCACCACCGCGGTGTACGTCTTCTTCCTTTCCAGTTTGCTGCAG
1351 CCCCGGGGAGGGAGCCAGGAGCACGGCCTCTGCGCCCACCTCTGGGGGCT
1401 CTGCTCTTTGGCTGCAGATGGAATCTGGAACCAGAAAATCCTGTTTGAGG
1451 AGTCCGACCTCAGGAATCATGGACTGCAGAAGGCGGATGTGTCTGCTTTC
1501 CTGAGGATGAACCTGTTCCAAAAGGAAGTGGACTGCGAGAAGTTCTACAG
1551 CTTCATCCACATGACTTTCCAGGAGTTCTTTGCCGCCATGTACTACCTGC
1601 TGGAAGAGGAAAAGGAAGGAAGGACGAACGTTCCAGGGAGTCGTTTGAAG
1651 CTTCCCAGCCGAGACGTGACAGTCCTTCTGGAAAACTATGGCAAATTCGA
1701 AAAGGGGTATTTGATTTTTGTTGTACGTTTCCTCTTTGGCCTGGTAAACC
1751 AGGAGAGGACCTCCTACTTGGAGAAGAAATTAAGTTGCAAGATCTCTCAG
1801 CAAATCAGGCTGGAGCTGCTGAAATGGATTGAAGTGAAAGCCAAAGCTAA
1851 AAAGCTGCAGATCCAGCCCAGCCAGCTGGAATTGTTCTACTGTTTGTACG
1901 AGATGCAGGAGGAGGACTTCGTGCAAAGGGCCATGGACTATTTCCCCAAG
1951 ATTGAGATCAATCTCTCCACCAGAATGGACCACATGGTTTCTTCCTTTTG
2001 CATTGAGAACTGTCATCGGGTGGAGTCACTGTCCCTGGGGTTTCTCCATA
2051 ACATGCCCAAGGAGGAAGAGGAGGAGGAAAAGGAAGGCCGACACCTTGAT
2101 ATGGTGCAGTGTGTCCTCCCAAGCTCCTCTCATGCTGCCTGTTCTCATGG
2151 GTTGGGGCGCTGTGGCCTCTCGCATGAGTGCTGCTTCGACATCTCCTTGG
2201 TCCTCAGCAGCAACCAGAAGCTGGTGGAGCTGGACCTGAGTGACAACGCC
2251 CTCGGTGACTTCGGAATCAGACTTCTGTGTGTGGGACTGAAGCACCTGTT
2301 GTGCAATCTGAAGAAGCTCTGGTTGGTCAGCTGCTGCCTCACATCAGCAT
2351 GTTGTCAGGATCTTGCATCAGTATTGAGCACCAGCCATTCCCTGACCAGA
2401 CTCTATGTGGGGGAGAATGCCTTGGGAGACTCAGGAGTCGCAATTTTATG
2451 TGAAAAAGCCAAGAATCCACAGTGTAACCTGCAGAAACTGGGGTTGGTGA
2501 ATTCTGGCCTTACGTCAGTCTGTTGTTCAGCTTTGTCCTCGGTACTCAGC
```

FIG. 42K

2551 ACTAATCAGAATCTCACGCACCTTTACCTGCGAGGCAACACTCTCGGAGA
2601 CAAGGGGATCAAACTACTCTGTGAGGGACTCTTGCACCCCGACTGCAAGC
2651 TTCAGGTGTTGGAATTAGACAACTGCAACCTCACGTCACACTGCTGCTGG
2701 GATCTTTCCACACTTCTGACCTCCAGCCAGAGCCTGCGAAAGCTGAGCCT
2751 GGGCAACAATGACCTGGGCGACCTGGGGGTCATGATGTTCTGTGAAGTGC
2801 TGAAACAGCAGAGCTGCCTCCTGCAGAACCTGGGGTTGTCTGAAATGTAT
2851 TTCAATTATGAGACAAAAAGTGCGTTAGAAACACTTCAAGAAGAAAAGCC
2901 TGAGCTGACCGTCGTCTTTGAGCCTTCTTGGTAG
(SEQ ID NO:148)

FIG. 42L

1 MASTRCKLARYLEDLEDVDLKKFKMHLEDYPPQKGCIPLPRGQTEKADHV
51 DLATLMIDFNGEEKAWAMAVWIFAAINRRDLYEKAKRDEPKWGSDNARVS
101 NPTVICQEDSIEEEWMGLLEYLSRISICKMKKDYRKKYRKYVRSRFQCIE
151 DRNARLGESVSLNKRYTRLRLIKEHRSQQEREQELLAIGKTKTCESPVSP
201 IKMELLFDPDDEHSEPVHTVVFQGAAGIGKTILARKMMLDWASGTLYQDR
251 FDYLFYIHCREVSLVTQRSLGDLIMSCCPDPNPPIHKIVRKPSRILFLMD
301 GFDELQGAFDEHIGPLCTDWQKAERGDILLSSLIRKKLLPEASLLITTRP
351 VALEKLQHLLDHPRHVEILGFSEAKRKEYFFKYFSDEAQARAAFSLIQEN
401 EVLFTMCFIPLVCWIVCTGLKQQMESGKSLAQTSKTTTAVYVFFLSSLLQ
451 PRGGSQEHGLCAHLWGLCSLAADGIWNQKILFEESDLRNHGLQKADVSAF
501 LRMNLFQKEVDCEKFYSFIHMTFQEFFAAMYYLLEEEKEGRTNVPGSRLK
551 LPSRDVTVLLENYGKFEKGYLIFVVRFLFGLVNQERTSYLEKKLSCKISQ
601 QIRLELLKWIEVKAKAKKLQIQPSQLELFYCLYEMQEEDFVQRAMDYFPK
651 IEINLSTRMDHMVSSFCIENCHRVESLSLGFLHNMPKEEEEEEKEGRHLD
701 MVQCVLPSSSHAACSHGLGRCGLSHECCFDISLVLSSNQKLVELDLSDNA
751 LGDFGIRLLCVGLKHLLCNLKKLWLVSCCLTSACCQDLASVLSTSHSLTR
801 LYVGENALGDSGVAILCEKAKNPQCNLQKLGLVNSGLTSVCCSALSSVLS
851 TNQNLTHLYLRGNTLGDKGIKLLCEGLLHPDCKLQVLELDNCNLTSHCCW
901 DLSTLLTSSQSLRKLSLGNNDLGDLGVMMFCEVLKQQSCLLQNLGLSEMY
951 FNYETKSALETLQEEKPELTVVFEPSW (SEQ ID NO:149)

FIG. 42M

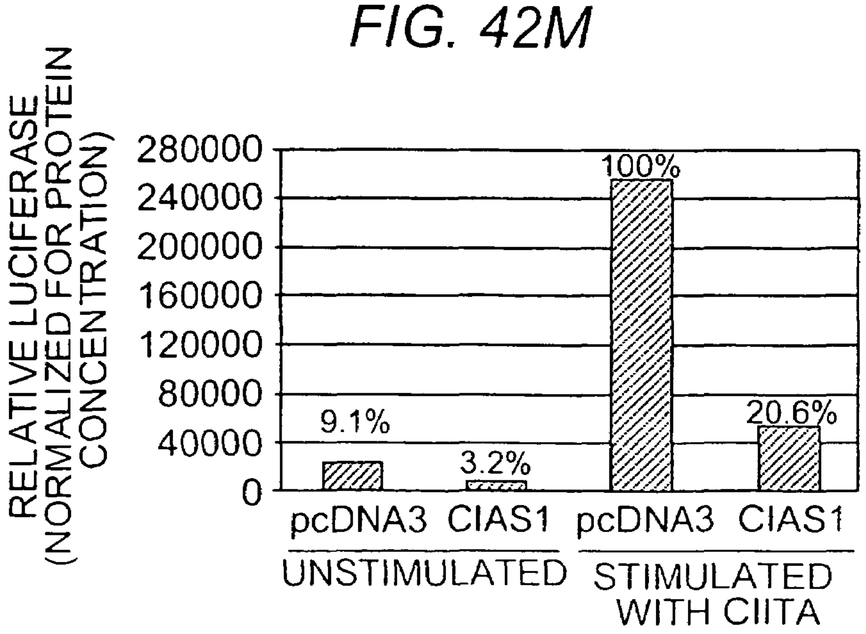

FIG. 43

SEQUENCE LISTING

<160> NUMBER OF SEQ ID NOS: 186

<210> SEQ ID NO 1
<211> LENGTH: 3731
<212> TYPE: DNA
<213> ORGANISM: Homo sapiens

<400> SEQUENCE: 1

```
attggtgagt ggggcagggc aggagggaac tgaagagtga gaaagcatta tttcagcaaa      60
aggtctttcc tcccttgctc actcctccaa ccactggctc agcctctccg cccgctgcct     120
gtgaatgatg caatggaagg tgtgctgggg tcgccctgtg tcccgtgcat aggagcatct     180
cagcctccag gtcctctcct ttggggctta cggcaccccc atgctacgaa ccgcaggcag     240
ggacggcctc tgtcgcctgt ccacctactt ggaagaactc gaggctgtgg aactgaagaa     300
gttcaagtta tacctgggga ccgcgacaga gctgggagaa ggcaagatcc cctggggaag     360
catggagaag gccggtcccc tggaaatggc ccagctgctc atcacccact tcgggccaga     420
ggaggcctgg aggttggctc tcagcacctt tgagcggata aacaggaagg acctgtggga     480
gagaggacag agagaggacc tggtgaggga taccccacct ggtggcccgt cctcacttgg     540
gaaccagtca acatgccttc tggaagtctc tcttgtcact ccaagaaaag atccccagga     600
aacctacagg gactatgtcc gcaggaaatt ccggctcatg gaagaccgca atgcgcgcct     660
aggggaatgt gtcaacctca gccaccggta cacccggctc ctgctggtga aggagcactc     720
aaaccccatg caggtccagc agcagcttct ggacacaggc cggggacacg cgaggaccgt     780
gggacaccag gctagcccca tcaagataga gaccctcttt gagccagacg aggagcgccc     840
cgagccaccg cgcaccgtgg tcatgcaagg cgcggcaggg ataggcaagt ccatgctggc     900
acacaaggtg atgctggact gggcggacgg gaagctcttc caaggcagat ttgattatct     960
cttctacatc aactgcaggg agatgaacca gagtgccacg gaatgcagca tgcaagacct    1020
catcttcagc tgctggcctg agcccagcgc gcctctccag gagctcatcc gagttcccga    1080
gcgcctcctt ttcatcatcg acggcttcga tgagctcaag ccttctttcc acgatcctca    1140
gggaccctgg tgcctctgct gggaggagaa acggcccacg gagctgcttc ttaacagctt    1200
aattcggaag aagctgctcc ctgagctatc tttgctcatc accacacggc ccacggcttt    1260
ggagaagctc caccgtctgc tggagcaccc caggcatgtg gagatcctgg gcttctctga    1320
ggcagaaagg aaggaatact tctacaagta tttccacaat gcagagcagg cgggccaagt    1380
cttcaattac gtgagggaca acgagcctct cttcaccatg tgcttcgtcc ccctggtgtg    1440
ctgggtggtg tgtacctgcc tccagcagca gctggagggt gggggggctgt tgagacagac   1500
gtccaggacc accactgcag tgtacatgct ctacctgctg agtctgatgc aacccaagcc    1560
gggggccccg cgcctccagc ccccacccaa ccagagaggg ttgtgctcct tggcggcaga    1620
tgggctctgg aatcagaaaa tcctatttga ggagcaggac ctccggaagc acggcctaga    1680
cggggaagac gtctctgcct tcctcaacat gaacatcttc cagaaggaca tcaactgtga    1740
gaggtactac agcttcatcc acttgagttt ccaggaattc tttgcagcta tgtactatat    1800
cctggacgag ggggagggcg gggcaggccc agaccaggac gtgaccaggc tgttgaccga    1860
gtacgcgttt tctgaaagga gcttcctggc actcaccagc cgcttcctgt ttggactcct    1920
gaacgaggag accaggagcc acctggagaa gagtctctgc tggaaggtct cgccgcacat    1980
caagatggac ctgttgcagt ggatccaaag caaagctcag agcgacggct ccaccctgca    2040
```

-continued

```
gcagggctcc ttggagttct tcagctgctt gtacgagatc caggaggagg agtttatcca   2100

gcaggccctg agccacttcc aggtgatcgt ggtcagcaac attgcctcca agatggagca   2160

catggtctcc tcgttctgtc tgaagcgctg caggagcgcc caggtgctgc acttgtatgg   2220

cgccacctac agcgcggacg gggaagaccg cgcgaggtgc tccgcaggag cgcacacgct   2280

gttggtgcag ctcagaccag agaggaccgt tctgctggac gcctacagtg aacatctggc   2340

agcggccctg tgcaccaatc caaacctgat agagctgtct ctgtaccgaa atgccctggg   2400

cagccggggg gtgaagctgc tctgtcaagg actcagacac cccaactgca aacttcagaa   2460

cctgaggctg aagaggtgcc gcatctccag ctcagcctgc gaggacctct ctgcagctct   2520

catagccaat aagaatttga caaggatgga tctcagtggc aacggcgttg gattcccagg   2580

catgatgctg ctttgcgagg gcctgcggca tccccagtgc aggctgcaga tgattcagtt   2640

gaggaagtgt cagctggagt ccggggcttg tcaggagatg gcttctgtgc tcggcaccaa   2700

cccacatctg gttgagttgg acctgacagg aaatgcactg gaggatttgg gcctgaggtt   2760

actatgccag ggactgaggc acccagtctg cagactacgg actttgtggc tgaagatctg   2820

ccgcctcact gctgctgcct gtgacgagct ggcctcaact ctcagtgtga accagagcct   2880

gagagagctg gacctgagcc tgaatgagct gggggacctc ggggtgctgc tgctgtgtga   2940

gggcctcagg catcccacgt gcaagctcca gaccctgcgg ttgggcatct gccggctggg   3000

ctctgccgcc tgtgagggtc tttctgtggt gctccaggcc aaccacaacc tccgggagct   3060

ggacttgagt ttcaacgacc tgggagactg gggcctgtgg ttgctggctg aggggctgca   3120

acatcccgcc tgcagactcc agaaactgtg gctggatagc tgtggcctca cagccaaggc   3180

ttgtgagaat ctttacttca ccctggggat caaccagacc ttgaccgacc tttacctgac   3240

caacaacgcc ctaggggaca caggtgtccg actgctttgc aagcggctga gccatcctgg   3300

ctgcaaactc cgagtcctct ggttatttgg gatggacctg aataaaatga cccacagtag   3360

gttggcagcg cttcgagtaa caaaacctta tttggacatt ggctgctgaa tggtcctatc   3420

tgctggctct cccctgagat ctggacagag gaagatggga gggtgctcat caccccccca   3480

gcataatgat cagcctcctt cctagagaca gactcatgca gattgagatc aaaagtccct   3540

ctgcttggga tcaaattaat gtttgacaga gctggccagg cgtggtggct catgtatgta   3600

atcctagcac ttcgagaggc cgaggcaggt ggatcacgag gtcaggagtt tgagattagc   3660

ctggccaaga tggtgaaacc ctgtctctac taaaaataaa aaaaaattag ccaggaaaaa   3720

aaaaaaaaaa a                                                        3731
```

<210> SEQ ID NO 2
<211> LENGTH: 1062
<212> TYPE: PRT
<213> ORGANISM: Homo sapiens

<400> SEQUENCE: 2

```
Met Leu Arg Thr Ala Gly Arg Asp Gly Leu Cys Arg Leu Ser Thr Tyr
1               5                   10                  15

Leu Glu Glu Leu Glu Ala Val Glu Leu Lys Lys Phe Lys Leu Tyr Leu
            20                  25                  30

Gly Thr Ala Thr Glu Leu Gly Glu Gly Lys Ile Pro Trp Gly Ser Met
        35                  40                  45

Glu Lys Ala Gly Pro Leu Glu Met Ala Gln Leu Leu Ile Thr His Phe
    50                  55                  60
```

-continued

```
Gly Pro Glu Glu Ala Trp Arg Leu Ala Leu Ser Thr Phe Glu Arg Ile
65                  70                  75                  80

Asn Arg Lys Asp Leu Trp Glu Arg Gly Gln Arg Glu Asp Leu Val Arg
                85                  90                  95

Asp Thr Pro Pro Gly Gly Pro Ser Ser Leu Gly Asn Gln Ser Thr Cys
            100                 105                 110

Leu Leu Glu Val Ser Leu Val Thr Pro Arg Lys Asp Pro Gln Glu Thr
        115                 120                 125

Tyr Arg Asp Tyr Val Arg Arg Lys Phe Arg Leu Met Glu Asp Arg Asn
    130                 135                 140

Ala Arg Leu Gly Glu Cys Val Asn Leu Ser His Arg Tyr Thr Arg Leu
145                 150                 155                 160

Leu Leu Val Lys Glu His Ser Asn Pro Met Gln Val Gln Gln Gln Leu
                165                 170                 175

Leu Asp Thr Gly Arg Gly His Ala Arg Thr Val Gly His Gln Ala Ser
            180                 185                 190

Pro Ile Lys Ile Glu Thr Leu Phe Glu Pro Asp Glu Glu Arg Pro Glu
        195                 200                 205

Pro Pro Arg Thr Val Val Met Gln Gly Ala Ala Gly Ile Gly Lys Ser
    210                 215                 220

Met Leu Ala His Lys Val Met Leu Asp Trp Ala Asp Gly Lys Leu Phe
225                 230                 235                 240

Gln Gly Arg Phe Asp Tyr Leu Phe Tyr Ile Asn Cys Arg Glu Met Asn
                245                 250                 255

Gln Ser Ala Thr Glu Cys Ser Met Gln Asp Leu Ile Phe Ser Cys Trp
            260                 265                 270

Pro Glu Pro Ser Ala Pro Leu Gln Glu Leu Ile Arg Val Pro Glu Arg
        275                 280                 285

Leu Leu Phe Ile Ile Asp Gly Phe Asp Glu Leu Lys Pro Ser Phe His
    290                 295                 300

Asp Pro Gln Gly Pro Trp Cys Leu Cys Trp Glu Glu Lys Arg Pro Thr
305                 310                 315                 320

Glu Leu Leu Leu Asn Ser Leu Ile Arg Lys Lys Leu Leu Pro Glu Leu
                325                 330                 335

Ser Leu Leu Ile Thr Thr Arg Pro Thr Ala Leu Glu Lys Leu His Arg
            340                 345                 350

Leu Leu Glu His Pro Arg His Val Glu Ile Leu Gly Phe Ser Glu Ala
        355                 360                 365

Glu Arg Lys Glu Tyr Phe Tyr Lys Tyr Phe His Asn Ala Glu Gln Ala
    370                 375                 380

Gly Gln Val Phe Asn Tyr Val Arg Asp Asn Glu Pro Leu Phe Thr Met
385                 390                 395                 400

Cys Phe Val Pro Leu Val Cys Trp Val Val Cys Thr Cys Leu Gln Gln
                405                 410                 415

Gln Leu Glu Gly Gly Gly Leu Leu Arg Gln Thr Ser Arg Thr Thr Thr
            420                 425                 430

Ala Val Tyr Met Leu Tyr Leu Leu Ser Leu Met Gln Pro Lys Pro Gly
        435                 440                 445

Ala Pro Arg Leu Gln Pro Pro Pro Asn Gln Arg Gly Leu Cys Ser Leu
    450                 455                 460

Ala Ala Asp Gly Leu Trp Asn Gln Lys Ile Leu Phe Glu Glu Gln Asp
465                 470                 475                 480

Leu Arg Lys His Gly Leu Asp Gly Glu Asp Val Ser Ala Phe Leu Asn
```

-continued

```
            485                 490                 495

Met Asn Ile Phe Gln Lys Asp Ile Asn Cys Glu Arg Tyr Tyr Ser Phe
        500                 505                 510

Ile His Leu Ser Phe Gln Glu Phe Phe Ala Ala Met Tyr Tyr Ile Leu
    515                 520                 525

Asp Glu Gly Glu Gly Gly Ala Gly Pro Asp Gln Asp Val Thr Arg Leu
    530                 535                 540

Leu Thr Glu Tyr Ala Phe Ser Glu Arg Ser Phe Leu Ala Leu Thr Ser
545                 550                 555                 560

Arg Phe Leu Phe Gly Leu Leu Asn Glu Glu Thr Arg Ser His Leu Glu
            565                 570                 575

Lys Ser Leu Cys Trp Lys Val Ser Pro His Ile Lys Met Asp Leu Leu
        580                 585                 590

Gln Trp Ile Gln Ser Lys Ala Gln Ser Asp Gly Ser Thr Leu Gln Gln
    595                 600                 605

Gly Ser Leu Glu Phe Phe Ser Cys Leu Tyr Glu Ile Gln Glu Glu Glu
    610                 615                 620

Phe Ile Gln Gln Ala Leu Ser His Phe Gln Val Ile Val Val Ser Asn
625                 630                 635                 640

Ile Ala Ser Lys Met Glu His Met Val Ser Ser Phe Cys Leu Lys Arg
            645                 650                 655

Cys Arg Ser Ala Gln Val Leu His Leu Tyr Gly Ala Thr Tyr Ser Ala
        660                 665                 670

Asp Gly Glu Asp Arg Ala Arg Cys Ser Ala Gly Ala His Thr Leu Leu
    675                 680                 685

Val Gln Leu Arg Pro Glu Arg Thr Val Leu Leu Asp Ala Tyr Ser Glu
    690                 695                 700

His Leu Ala Ala Ala Leu Cys Thr Asn Pro Asn Leu Ile Glu Leu Ser
705                 710                 715                 720

Leu Tyr Arg Asn Ala Leu Gly Ser Arg Gly Val Lys Leu Leu Cys Gln
            725                 730                 735

Gly Leu Arg His Pro Asn Cys Lys Leu Gln Asn Leu Arg Leu Lys Arg
        740                 745                 750

Cys Arg Ile Ser Ser Ser Ala Cys Glu Asp Leu Ser Ala Ala Leu Ile
    755                 760                 765

Ala Asn Lys Asn Leu Thr Arg Met Asp Leu Ser Gly Asn Gly Val Gly
    770                 775                 780

Phe Pro Gly Met Met Leu Leu Cys Glu Gly Leu Arg His Pro Gln Cys
785                 790                 795                 800

Arg Leu Gln Met Ile Gln Leu Arg Lys Cys Gln Leu Glu Ser Gly Ala
            805                 810                 815

Cys Gln Glu Met Ala Ser Val Leu Gly Thr Asn Pro His Leu Val Glu
        820                 825                 830

Leu Asp Leu Thr Gly Asn Ala Leu Glu Asp Leu Gly Leu Arg Leu Leu
    835                 840                 845

Cys Gln Gly Leu Arg His Pro Val Cys Arg Leu Arg Thr Leu Trp Leu
    850                 855                 860

Lys Ile Cys Arg Leu Thr Ala Ala Ala Cys Asp Glu Leu Ala Ser Thr
865                 870                 875                 880

Leu Ser Val Asn Gln Ser Leu Arg Glu Leu Asp Leu Ser Leu Asn Glu
            885                 890                 895

Leu Gly Asp Leu Gly Val Leu Leu Leu Cys Glu Gly Leu Arg His Pro
        900                 905                 910
```

-continued

```
Thr Cys Lys Leu Gln Thr Leu Arg Leu Gly Ile Cys Arg Leu Gly Ser
        915                 920                 925

Ala Ala Cys Glu Gly Leu Ser Val Val Leu Gln Ala Asn His Asn Leu
    930                 935                 940

Arg Glu Leu Asp Leu Ser Phe Asn Asp Leu Gly Asp Trp Gly Leu Trp
945                 950                 955                 960

Leu Leu Ala Glu Gly Leu Gln His Pro Ala Cys Arg Leu Gln Lys Leu
                965                 970                 975

Trp Leu Asp Ser Cys Gly Leu Thr Ala Lys Ala Cys Glu Asn Leu Tyr
            980                 985                 990

Phe Thr Leu Gly Ile Asn Gln Thr  Leu Thr Asp Leu Tyr  Leu Thr Asn
        995                 1000                1005

Asn Ala  Leu Gly Asp Thr Gly  Val Arg Leu Leu Cys  Lys Arg Leu
    1010                1015                1020

Ser His  Pro Gly Cys Lys Leu  Arg Val Leu Trp Leu  Phe Gly Met
    1025                1030                1035

Asp Leu  Asn Lys Met Thr His  Ser Arg Leu Ala Ala  Leu Arg Val
    1040                1045                1050

Thr Lys  Pro Tyr Leu Asp Ile  Gly Cys
    1055                1060


<210> SEQ ID NO 3
<211> LENGTH: 3563
<212> TYPE: DNA
<213> ORGANISM: Homo sapiens

<400> SEQUENCE: 3

attggtgagt ggggcagggc aggagggaac tgaagagtga gaaagcatta tttcagcaaa     60

aggtctttcc tcccttgctc actcctccaa ccactggctc agcctctccg cccgctgcct    120

gtgaatgatg caatggaagg tgtgctgggg tcgccctgtg tcccgtgcat aggagcatct    180

cagcctccag gtcctctcct ttggggctta cggcacccc atgctacgaa ccgcaggcag    240

ggacggcctc tgtcgcctgt ccacctactt ggaagaactc gaggctgtgg aactgaagaa    300

gttcaagtta tacctgggga ccgcgacaga gctgggagaa ggcaagatcc cctggggaag    360

catggagaag gccggtcccc tggaaatggc ccagctgctc atcacccact tcgggccaga    420

ggaggcctgg aggttggctc tcagcacctt tgagcggata aacaggaagg acctgtggga    480

gagaggacag agagaggacc tggtgaggga taccccacct ggtggcccgt cctcacttgg    540

gaaccagtca acatgccttc tggaagtctc tcttgtcact ccaagaaaag atccccagga    600

aacctacagg gactatgtcc gcaggaaatt ccggctcatg gaagaccgca atgcgcgcct    660

aggggaatgt gtcaacctca gccaccggta cacccggctc ctgctggtga aggagcactc    720

aaaccccatg caggtccagc agcagcttct ggacacaggc cggggacacg cgaggaccgt    780

gggacaccag gctagcccca tcaagataga gaccctcttt gagccagacg aggagcgccc    840

cgagccaccg cgcaccgtgg tcatgcaagg cgcggcaggg ataggcaagt ccatgctggc    900

acacaaggtg atgctggact gggcggacgg gaagctcttc caaggcagat ttgattatct    960

cttctacatc aactgcaggg agatgaacca gagtgccacg gaatgcagca tgcaagacct   1020

catcttcagc tgctggcctg agcccagcgc gcctctccag gagctcatcc gagttcccga   1080

gcgcctcctt ttcatcatcg acggcttcga tgagctcaag ccttctttcc acgatcctca   1140

gggaccctgg tgcctctgct gggaggagaa acggcccacg gagctgcttc ttaacagctt   1200
```

-continued

```
aattcggaag aagctgctcc ctgagctatc tttgctcatc accacacggc ccacggcttt   1260
ggagaagctc caccgtctgc tggagcaccc caggcatgtg gagatcctgg gcttctctga   1320
ggcagaaagg aaggaatact tctacaagta tttccacaat gcagagcagg cgggccaagt   1380
cttcaattac gtgagggaca acgagcctct cttcaccatg tgcttcgtcc ccctggtgtg   1440
ctgggtggtg tgtacctgcc tccagcagca gctggagggt ggggggctgt tgagacagac   1500
gtccaggacc accactgcag tgtacatgct ctacctgctg agtctgatgc aacccaagcc   1560
gggggccccg cgcctccagc ccccacccaa ccagagaggg ttgtgctcct tggcggcaga   1620
tgggctctgg aatcagaaaa tcctatttga ggagcaggac ctccggaagc acggcctaga   1680
cggggaagac gtctctgcct tcctcaacat gaacatcttc cagaaggaca tcaactgtga   1740
gaggtactac agcttcatcc acttgagttt ccaggaattc tttgcagcta tgtactatat   1800
cctggacgag gggagggcg gggcaggccc agaccaggac gtgaccaggc tgttgaccga    1860
gtacgcgttt tctgaaagga gcttcctggc actcaccagc cgcttcctgt ttggactcct   1920
gaacgaggag accaggagcc acctggagaa gagtctctgc tggaaggtct cgccgcacat   1980
caagatggac ctgttgcagt ggatccaaag caaagctcag agcgacggct ccaccctgca   2040
gcagggctcc ttggagttct tcagctgctt gtacgagatc caggaggagg agtttatcca   2100
gcaggccctg agccacttcc aggtgatcgt ggtcagcaac attgcctcca agatggagca   2160
catggtctcc tcgttctgtc tgaagcgctg caggagcgcc caggtgctgc acttgtatgg   2220
cgccacctac agcgcggacg gggaagaccg cgcgaggtgc tccgcaggag cgcacacgct   2280
gttggtgcag ctcagaccag agaggaccgt tctgctggac gcctacagtg aacatctggc   2340
agcggccctg tgcaccaatc caaacctgat agagctgtct ctgtaccgaa atgccctggg   2400
cagccggggg gtgaagctgc tctgtcaagg actcagacac cccaactgca aacttcagaa   2460
cctgaggctg aagaggtgcc gcatctccag ctcagcctgc gaggacctct ctgcagctct   2520
catagccaat aagaatttga caaggatgga tctcagtggc aacggcgttg gattcccagg   2580
catgatgctg ctttgcgagg gcctgcggca tccccagtgc aggctgcaga tgattcagtt   2640
gaggaagtgt cagctggagt ccggggcttg tcaggagatg gcttctgtgc tcggcaccaa   2700
cccacatctg gttgagttgg acctgacagg aaatgcactg gaggatttgg gcctgaggtt   2760
actatgccag ggactgaggc acccagtctg cagactacgg actttgtggc tgaagatctg   2820
ccgcctcact gctgctgcct gtgacgagct ggcctcaact ctcagtgtga accagagcct   2880
gagagagctg gacctgagcc tgaatgagct gggggacctc ggggtgctgc tgctgtgtga   2940
gggcctcagg catcccacgt gcaagctcca gaccctgcgg ttgggcatct gccggctggg   3000
ctctgccgcc tgtgagggtc tttctgtggt gctccaggcc aaccacaacc tccgggagct   3060
ggacttgagt ttcaacgacc tgggagactg gggcctgtgg ttgctggctg aggggctgca   3120
acatcccgcc tgcagactcc agaaactgtg gtggttattt gggatggacc tgaataaaat   3180
gacccacagt aggttggcag cgcttcgagt aacaaaacct tatttggaca ttggctgctg   3240
aatggtccta tctgctggct ctcccctgag atctggacag aggaagatgg gagggtgctc   3300
atcacccccc cagcataatg atcagcctcc ttcctagaga cagactcatg cagattgaga   3360
tcaaaagtcc ctctgcttgg gatcaaatta atgtttgaca gagctggcca ggcgtggtgg   3420
ctcatgtatg taatcctagc acttcgagag gccgaggcag gtggatcacg aggtcaggag   3480
tttgagatta gcctggccaa gatggtgaaa ccctgtctct actaaaaata aaaaaaaatt   3540
agccaggaaa aaaaaaaaaa aaa                                          3563
```

<210> SEQ ID NO 4
<211> LENGTH: 1006
<212> TYPE: PRT
<213> ORGANISM: Homo sapiens

<400> SEQUENCE: 4

```
Met Leu Arg Thr Ala Gly Arg Asp Gly Leu Cys Arg Leu Ser Thr Tyr
1               5                   10                  15

Leu Glu Glu Leu Glu Ala Val Glu Leu Lys Lys Phe Lys Leu Tyr Leu
            20                  25                  30

Gly Thr Ala Thr Glu Leu Gly Glu Gly Lys Ile Pro Trp Gly Ser Met
        35                  40                  45

Glu Lys Ala Gly Pro Leu Glu Met Ala Gln Leu Leu Ile Thr His Phe
    50                  55                  60

Gly Pro Glu Glu Ala Trp Arg Leu Ala Leu Ser Thr Phe Glu Arg Ile
65                  70                  75                  80

Asn Arg Lys Asp Leu Trp Glu Arg Gly Gln Arg Glu Asp Leu Val Arg
                85                  90                  95

Asp Thr Pro Pro Gly Gly Pro Ser Ser Leu Gly Asn Gln Ser Thr Cys
            100                 105                 110

Leu Leu Glu Val Ser Leu Val Thr Pro Arg Lys Asp Pro Gln Glu Thr
        115                 120                 125

Tyr Arg Asp Tyr Val Arg Arg Lys Phe Arg Leu Met Glu Asp Arg Asn
    130                 135                 140

Ala Arg Leu Gly Glu Cys Val Asn Leu Ser His Arg Tyr Thr Arg Leu
145                 150                 155                 160

Leu Leu Val Lys Glu His Ser Asn Pro Met Gln Val Gln Gln Gln Leu
                165                 170                 175

Leu Asp Thr Gly Arg Gly His Ala Arg Thr Val Gly His Gln Ala Ser
            180                 185                 190

Pro Ile Lys Ile Glu Thr Leu Phe Glu Pro Asp Glu Glu Arg Pro Glu
        195                 200                 205

Pro Pro Arg Thr Val Val Met Gln Gly Ala Ala Gly Ile Gly Lys Ser
    210                 215                 220

Met Leu Ala His Lys Val Met Leu Asp Trp Ala Asp Gly Lys Leu Phe
225                 230                 235                 240

Gln Gly Arg Phe Asp Tyr Leu Phe Tyr Ile Asn Cys Arg Glu Met Asn
                245                 250                 255

Gln Ser Ala Thr Glu Cys Ser Met Gln Asp Leu Ile Phe Ser Cys Trp
            260                 265                 270

Pro Glu Pro Ser Ala Pro Leu Gln Glu Leu Ile Arg Val Pro Glu Arg
        275                 280                 285

Leu Leu Phe Ile Ile Asp Gly Phe Asp Glu Leu Lys Pro Ser Phe His
    290                 295                 300

Asp Pro Gln Gly Pro Trp Cys Leu Cys Trp Glu Glu Lys Arg Pro Thr
305                 310                 315                 320

Glu Leu Leu Leu Asn Ser Leu Ile Arg Lys Lys Leu Leu Pro Glu Leu
                325                 330                 335

Ser Leu Leu Ile Thr Thr Arg Pro Thr Ala Leu Glu Lys Leu His Arg
            340                 345                 350

Leu Leu Glu His Pro Arg His Val Glu Ile Leu Gly Phe Ser Glu Ala
        355                 360                 365

Glu Arg Lys Glu Tyr Phe Tyr Lys Tyr Phe His Asn Ala Glu Gln Ala
```

-continued

```
    370                 375                 380

Gly Gln Val Phe Asn Tyr Val Arg Asp Asn Glu Pro Leu Phe Thr Met
385                 390                 395                 400

Cys Phe Val Pro Leu Val Cys Trp Val Val Cys Thr Cys Leu Gln Gln
                405                 410                 415

Gln Leu Glu Gly Gly Gly Leu Leu Arg Gln Thr Ser Arg Thr Thr Thr
            420                 425                 430

Ala Val Tyr Met Leu Tyr Leu Leu Ser Leu Met Gln Pro Lys Pro Gly
        435                 440                 445

Ala Pro Arg Leu Gln Pro Pro Pro Asn Gln Arg Gly Leu Cys Ser Leu
    450                 455                 460

Ala Ala Asp Gly Leu Trp Asn Gln Lys Ile Leu Phe Glu Glu Gln Asp
465                 470                 475                 480

Leu Arg Lys His Gly Leu Asp Gly Glu Asp Val Ser Ala Phe Leu Asn
                485                 490                 495

Met Asn Ile Phe Gln Lys Asp Ile Asn Cys Glu Arg Tyr Tyr Ser Phe
            500                 505                 510

Ile His Leu Ser Phe Gln Glu Phe Phe Ala Ala Met Tyr Tyr Ile Leu
        515                 520                 525

Asp Glu Gly Glu Gly Gly Ala Gly Pro Asp Gln Asp Val Thr Arg Leu
    530                 535                 540

Leu Thr Glu Tyr Ala Phe Ser Glu Arg Ser Phe Leu Ala Leu Thr Ser
545                 550                 555                 560

Arg Phe Leu Phe Gly Leu Leu Asn Glu Glu Thr Arg Ser His Leu Glu
                565                 570                 575

Lys Ser Leu Cys Trp Lys Val Ser Pro His Ile Lys Met Asp Leu Leu
            580                 585                 590

Gln Trp Ile Gln Ser Lys Ala Gln Ser Asp Gly Ser Thr Leu Gln Gln
        595                 600                 605

Gly Ser Leu Glu Phe Phe Ser Cys Leu Tyr Glu Ile Gln Glu Glu Glu
    610                 615                 620

Phe Ile Gln Gln Ala Leu Ser His Phe Gln Val Ile Val Val Ser Asn
625                 630                 635                 640

Ile Ala Ser Lys Met Glu His Met Val Ser Ser Phe Cys Leu Lys Arg
                645                 650                 655

Cys Arg Ser Ala Gln Val Leu His Leu Tyr Gly Ala Thr Tyr Ser Ala
            660                 665                 670

Asp Gly Glu Asp Arg Ala Arg Cys Ser Ala Gly Ala His Thr Leu Leu
        675                 680                 685

Val Gln Leu Arg Pro Glu Arg Thr Val Leu Leu Asp Ala Tyr Ser Glu
    690                 695                 700

His Leu Ala Ala Ala Leu Cys Thr Asn Pro Asn Leu Ile Glu Leu Ser
705                 710                 715                 720

Leu Tyr Arg Asn Ala Leu Gly Ser Arg Gly Val Lys Leu Leu Cys Gln
                725                 730                 735

Gly Leu Arg His Pro Asn Cys Lys Leu Gln Asn Leu Arg Leu Lys Arg
            740                 745                 750

Cys Arg Ile Ser Ser Ser Ala Cys Glu Asp Leu Ser Ala Ala Leu Ile
        755                 760                 765

Ala Asn Lys Asn Leu Thr Arg Met Asp Leu Ser Gly Asn Gly Val Gly
    770                 775                 780

Phe Pro Gly Met Met Leu Leu Cys Glu Gly Leu Arg His Pro Gln Cys
785                 790                 795                 800
```

-continued

```
Arg Leu Gln Met Ile Gln Leu Arg Lys Cys Gln Leu Glu Ser Gly Ala
                805                 810                 815

Cys Gln Glu Met Ala Ser Val Leu Gly Thr Asn Pro His Leu Val Glu
            820                 825                 830

Leu Asp Leu Thr Gly Asn Ala Leu Glu Asp Leu Gly Leu Arg Leu Leu
        835                 840                 845

Cys Gln Gly Leu Arg His Pro Val Cys Arg Leu Arg Thr Leu Trp Leu
    850                 855                 860

Lys Ile Cys Arg Leu Thr Ala Ala Ala Cys Asp Glu Leu Ala Ser Thr
865                 870                 875                 880

Leu Ser Val Asn Gln Ser Leu Arg Glu Leu Asp Leu Ser Leu Asn Glu
                885                 890                 895

Leu Gly Asp Leu Gly Val Leu Leu Leu Cys Glu Gly Leu Arg His Pro
            900                 905                 910

Thr Cys Lys Leu Gln Thr Leu Arg Leu Gly Ile Cys Arg Leu Gly Ser
        915                 920                 925

Ala Ala Cys Glu Gly Leu Ser Val Val Leu Gln Ala Asn His Asn Leu
    930                 935                 940

Arg Glu Leu Asp Leu Ser Phe Asn Asp Leu Gly Asp Trp Gly Leu Trp
945                 950                 955                 960

Leu Leu Ala Glu Gly Leu Gln His Pro Ala Cys Arg Leu Gln Lys Leu
                965                 970                 975

Trp Trp Leu Phe Gly Met Asp Leu Asn Lys Met Thr His Ser Arg Leu
            980                 985                 990

Ala Ala Leu Arg Val Thr Lys Pro  Tyr Leu Asp Ile Gly  Cys
        995                 1000                1005


<210> SEQ ID NO 5
<211> LENGTH: 3395
<212> TYPE: DNA
<213> ORGANISM: Homo sapiens

<400> SEQUENCE: 5

attggtgagt ggggcagggc aggagggaac tgaagagtga gaaagcatta tttcagcaaa      60

aggtctttcc tcccttgctc actcctccaa ccactggctc agcctctccg cccgctgcct     120

gtgaatgatg caatggaagg tgtgctgggg tcgccctgtg tcccgtgcat aggagcatct     180

cagcctccag gtcctctcct ttggggctta cggcaccccc atgctacgaa ccgcaggcag     240

ggacggcctc tgtcgcctgt ccacctactt ggaagaactc gaggctgtgg aactgaagaa     300

gttcaagtta tacctgggga ccgcgacaga gctgggagaa ggcaagatcc cctggggaag     360

catggagaag gccggtcccc tggaaatggc ccagctgctc atcacccact tcgggccaga     420

ggaggcctgg aggttggctc tcagcacctt tgagcggata aacaggaagg acctgtggga     480

gagaggacag agagaggacc tggtgaggga taccccacct ggtggcccgt cctcacttgg     540

gaaccagtca acatgccttc tggaagtctc tcttgtcact ccaagaaaag atccccagga     600

aacctacagg gactatgtcc gcaggaaatt ccggctcatg gaagaccgca atgcgcgcct     660

aggggaatgt gtcaacctca gccaccggta cacccggctc ctgctggtga aggagcactc     720

aaaccccatg caggtccagc agcagcttct ggacacaggc cggggacacg cgaggaccgt     780

gggacaccag gctagcccca tcaagataga gaccctcttt gagccagacg aggagcgccc     840

cgagccaccg cgcaccgtgg tcatgcaagg cgcggcaggg ataggcaagt ccatgctggc     900

acacaaggtg atgctggact gggcggacgg gaagctcttc caaggcagat ttgattatct     960
```

-continued cttctacatc aactgcaggg agatgaacca gagtgccacg gaatgcagca tgcaagacct 1020
catcttcagc tgctggcctg agcccagcgc gcctctccag gagctcatcc gagttcccga 1080
gcgcctcctt ttcatcatcg acggcttcga tgagctcaag ccttctttcc acgatcctca 1140
gggaccctgg tgcctctgct gggaggagaa acggcccacg gagctgcttc ttaacagctt 1200
aattcggaag aagctgctcc ctgagctatc tttgctcatc accacacggc ccacggcttt 1260
ggagaagctc caccgtctgc tggagcaccc caggcatgtg gagatcctgg gcttctctga 1320
ggcagaaagg aaggaatact tctacaagta tttccacaat gcagagcagg cgggccaagt 1380
cttcaattac gtgagggaca acgagcctct cttcaccatg tgcttcgtcc ccctggtgtg 1440
ctgggtggtg tgtacctgcc tccagcagca gctggagggt ggggggctgt tgagacagac 1500
gtccaggacc accactgcag tgtacatgct ctacctgctg agtctgatgc aacccaagcc 1560
gggggccccg cgcctccagc ccccacccaa ccagagaggg ttgtgctcct tggcggcaga 1620
tgggctctgg aatcagaaaa tcctatttga ggagcaggac ctccggaagc acggcctaga 1680
cggggaagac gtctctgcct tcctcaacat gaacatcttc cagaaggaca tcaactgtga 1740
gaggtactac agcttcatcc acttgagttt ccaggaattc tttgcagcta tgtactatat 1800
cctggacgag ggggagggcg gggcaggccc agaccaggac gtgaccaggc tgttgaccga 1860
gtacgcgttt tctgaaagga gcttcctggc actcaccagc cgcttcctgt ttggactcct 1920
gaacgaggag accaggagcc acctggagaa gagtctctgc tggaaggtct cgccgcacat 1980
caagatggac ctgttgcagt ggatccaaag caaagctcag agcgacggct ccaccctgca 2040
gcagggctcc ttggagttct tcagctgctt gtacgagatc caggaggagg agtttatcca 2100
gcaggccctg agccacttcc aggtgatcgt ggtcagcaac attgcctcca agatggagca 2160
catggtctcc tcgttctgtc tgaagcgctg caggagcgcc caggtgctgc acttgtatgg 2220
cgccacctac agcgcggacg gggaagaccg cgcgaggtgc tccgcaggag cgcacacgct 2280
gttggtgcag ctcagaccag agaggaccgt tctgctggac gcctacagtg aacatctggc 2340
agcggccctg tgcaccaatc caaacctgat agagctgtct ctgtaccgaa atgccctggg 2400
cagccggggg gtgaagctgc tctgtcaagg actcagacac cccaactgca aacttcagaa 2460
cctgaggctg aagaggtgcc gcatctccag ctcagcctgc gaggacctct ctgcagctct 2520
catagccaat aagaatttga caaggatgga tctcagtggc aacggcgttg gattcccagg 2580
catgatgctg ctttgcgagg gcctgcggca tccccagtgc aggctgcaga tgattcagtt 2640
gaggaagtgt cagctggagt ccggggcttg tcaggagatg gcttctgtgc tcggcaccaa 2700
cccacatctg gttgagttgg acctgacagg aaatgcactg gaggatttgg gcctgaggtt 2760
actatgccag ggactgaggc acccagtctg cagactacgg actttgtggc tgtggctgga 2820
tagctgtggc ctcacagcca aggcttgtga gaatctttac ttcaccctgg ggatcaacca 2880
gaccttgacc gacctttacc tgaccaacaa cgccctaggg gacacaggtg tccgactgct 2940
ttgcaagcgg ctgagccatc ctggctgcaa actccgagtc ctctggttat ttgggatgga 3000
cctgaataaa atgacccaca gtaggttggc agcgcttcga gtaacaaaac cttatttgga 3060
cattggctgc tgaatggtcc tatctgctgg ctctcccctg agatctggac agaggaagat 3120
gggagggtgc tcatcacccc cccagcataa tgatcagcct ccttcctaga gacagactca 3180
tgcagattga gatcaaaagt ccctctgctt gggatcaaat taatgtttga cagagctggc 3240
caggcgtggt ggctcatgta tgtaatccta gcacttcgag aggccgaggc aggtggatca 3300

-continued

```
cgaggtcagg agtttgagat tagcctggcc aagatggtga aaccctgtct ctactaaaaa   3360

taaaaaaaaa ttagccagga aaaaaaaaaa aaaaa                              3395


<210> SEQ ID NO 6
<211> LENGTH: 950
<212> TYPE: PRT
<213> ORGANISM: Homo sapiens

<400> SEQUENCE: 6

Met Leu Arg Thr Ala Gly Arg Asp Gly Leu Cys Arg Leu Ser Thr Tyr
1               5                   10                  15

Leu Glu Glu Leu Glu Ala Val Glu Leu Lys Lys Phe Lys Leu Tyr Leu
            20                  25                  30

Gly Thr Ala Thr Glu Leu Gly Glu Gly Lys Ile Pro Trp Gly Ser Met
        35                  40                  45

Glu Lys Ala Gly Pro Leu Glu Met Ala Gln Leu Leu Ile Thr His Phe
    50                  55                  60

Gly Pro Glu Glu Ala Trp Arg Leu Ala Leu Ser Thr Phe Glu Arg Ile
65                  70                  75                  80

Asn Arg Lys Asp Leu Trp Glu Arg Gly Gln Arg Glu Asp Leu Val Arg
                85                  90                  95

Asp Thr Pro Pro Gly Gly Pro Ser Ser Leu Gly Asn Gln Ser Thr Cys
            100                 105                 110

Leu Leu Glu Val Ser Leu Val Thr Pro Arg Lys Asp Pro Gln Glu Thr
        115                 120                 125

Tyr Arg Asp Tyr Val Arg Arg Lys Phe Arg Leu Met Glu Asp Arg Asn
    130                 135                 140

Ala Arg Leu Gly Glu Cys Val Asn Leu Ser His Arg Tyr Thr Arg Leu
145                 150                 155                 160

Leu Leu Val Lys Glu His Ser Asn Pro Met Gln Val Gln Gln Gln Leu
                165                 170                 175

Leu Asp Thr Gly Arg Gly His Ala Arg Thr Val Gly His Gln Ala Ser
            180                 185                 190

Pro Ile Lys Ile Glu Thr Leu Phe Glu Pro Asp Glu Glu Arg Pro Glu
        195                 200                 205

Pro Pro Arg Thr Val Val Met Gln Gly Ala Ala Gly Ile Gly Lys Ser
    210                 215                 220

Met Leu Ala His Lys Val Met Leu Asp Trp Ala Asp Gly Lys Leu Phe
225                 230                 235                 240

Gln Gly Arg Phe Asp Tyr Leu Phe Tyr Ile Asn Cys Arg Glu Met Asn
                245                 250                 255

Gln Ser Ala Thr Glu Cys Ser Met Gln Asp Leu Ile Phe Ser Cys Trp
            260                 265                 270

Pro Glu Pro Ser Ala Pro Leu Gln Glu Leu Ile Arg Val Pro Glu Arg
        275                 280                 285

Leu Leu Phe Ile Ile Asp Gly Phe Asp Glu Leu Lys Pro Ser Phe His
    290                 295                 300

Asp Pro Gln Gly Pro Trp Cys Leu Cys Trp Glu Glu Lys Arg Pro Thr
305                 310                 315                 320

Glu Leu Leu Leu Asn Ser Leu Ile Arg Lys Lys Leu Leu Pro Glu Leu
                325                 330                 335

Ser Leu Leu Ile Thr Thr Arg Pro Thr Ala Leu Glu Lys Leu His Arg
            340                 345                 350

Leu Leu Glu His Pro Arg His Val Glu Ile Leu Gly Phe Ser Glu Ala
```

-continued

```
        355                 360                 365

Glu Arg Lys Glu Tyr Phe Tyr Lys Tyr Phe His Asn Ala Glu Gln Ala
    370                 375                 380

Gly Gln Val Phe Asn Tyr Val Arg Asp Asn Glu Pro Leu Phe Thr Met
385                 390                 395                 400

Cys Phe Val Pro Leu Val Cys Trp Val Val Cys Thr Cys Leu Gln Gln
                405                 410                 415

Gln Leu Glu Gly Gly Gly Leu Leu Arg Gln Thr Ser Arg Thr Thr Thr
            420                 425                 430

Ala Val Tyr Met Leu Tyr Leu Leu Ser Leu Met Gln Pro Lys Pro Gly
        435                 440                 445

Ala Pro Arg Leu Gln Pro Pro Pro Asn Gln Arg Gly Leu Cys Ser Leu
    450                 455                 460

Ala Ala Asp Gly Leu Trp Asn Gln Lys Ile Leu Phe Glu Glu Gln Asp
465                 470                 475                 480

Leu Arg Lys His Gly Leu Asp Gly Glu Asp Val Ser Ala Phe Leu Asn
                485                 490                 495

Met Asn Ile Phe Gln Lys Asp Ile Asn Cys Glu Arg Tyr Tyr Ser Phe
            500                 505                 510

Ile His Leu Ser Phe Gln Glu Phe Phe Ala Ala Met Tyr Tyr Ile Leu
        515                 520                 525

Asp Glu Gly Glu Gly Gly Ala Gly Pro Asp Gln Asp Val Thr Arg Leu
    530                 535                 540

Leu Thr Glu Tyr Ala Phe Ser Glu Arg Ser Phe Leu Ala Leu Thr Ser
545                 550                 555                 560

Arg Phe Leu Phe Gly Leu Leu Asn Glu Glu Thr Arg Ser His Leu Glu
                565                 570                 575

Lys Ser Leu Cys Trp Lys Val Ser Pro His Ile Lys Met Asp Leu Leu
            580                 585                 590

Gln Trp Ile Gln Ser Lys Ala Gln Ser Asp Gly Ser Thr Leu Gln Gln
        595                 600                 605

Gly Ser Leu Glu Phe Phe Ser Cys Leu Tyr Glu Ile Gln Glu Glu Glu
    610                 615                 620

Phe Ile Gln Gln Ala Leu Ser His Phe Gln Val Ile Val Val Ser Asn
625                 630                 635                 640

Ile Ala Ser Lys Met Glu His Met Val Ser Ser Phe Cys Leu Lys Arg
                645                 650                 655

Cys Arg Ser Ala Gln Val Leu His Leu Tyr Gly Ala Thr Tyr Ser Ala
            660                 665                 670

Asp Gly Glu Asp Arg Ala Arg Cys Ser Ala Gly Ala His Thr Leu Leu
        675                 680                 685

Val Gln Leu Arg Pro Glu Arg Thr Val Leu Leu Asp Ala Tyr Ser Glu
    690                 695                 700

His Leu Ala Ala Ala Leu Cys Thr Asn Pro Asn Leu Ile Glu Leu Ser
705                 710                 715                 720

Leu Tyr Arg Asn Ala Leu Gly Ser Arg Gly Val Lys Leu Leu Cys Gln
                725                 730                 735

Gly Leu Arg His Pro Asn Cys Lys Leu Gln Asn Leu Arg Leu Lys Arg
            740                 745                 750

Cys Arg Ile Ser Ser Ser Ala Cys Glu Asp Leu Ser Ala Ala Leu Ile
        755                 760                 765

Ala Asn Lys Asn Leu Thr Arg Met Asp Leu Ser Gly Asn Gly Val Gly
    770                 775                 780
```

-continued

```
Phe Pro Gly Met Met Leu Leu Cys Glu Gly Leu Arg His Pro Gln Cys
785                 790                 795                 800

Arg Leu Gln Met Ile Gln Leu Arg Lys Cys Gln Leu Glu Ser Gly Ala
                805                 810                 815

Cys Gln Glu Met Ala Ser Val Leu Gly Thr Asn Pro His Leu Val Glu
            820                 825                 830

Leu Asp Leu Thr Gly Asn Ala Leu Glu Asp Leu Gly Leu Arg Leu Leu
        835                 840                 845

Cys Gln Gly Leu Arg His Pro Val Cys Arg Leu Arg Thr Leu Trp Leu
    850                 855                 860

Trp Leu Asp Ser Cys Gly Leu Thr Ala Lys Ala Cys Glu Asn Leu Tyr
865                 870                 875                 880

Phe Thr Leu Gly Ile Asn Gln Thr Leu Thr Asp Leu Tyr Leu Thr Asn
                885                 890                 895

Asn Ala Leu Gly Asp Thr Gly Val Arg Leu Leu Cys Lys Arg Leu Ser
            900                 905                 910

His Pro Gly Cys Lys Leu Arg Val Leu Trp Leu Phe Gly Met Asp Leu
        915                 920                 925

Asn Lys Met Thr His Ser Arg Leu Ala Ala Leu Arg Val Thr Lys Pro
    930                 935                 940

Tyr Leu Asp Ile Gly Cys
945                 950


<210> SEQ ID NO 7
<211> LENGTH: 3221
<212> TYPE: DNA
<213> ORGANISM: Homo sapiens

<400> SEQUENCE: 7

attggtgagt ggggcagggc aggagggaac tgaagagtga gaaagcatta tttcagcaaa     60

aggtctttcc tcccttgctc actcctccaa ccactggctc agcctctccg cccgctgcct    120

gtgaatgatg caatggaagg tgtgctgggg tcgccctgtg tcccgtgcat aggagcatct    180

cagcctccag gtcctctcct ttggggctta cggcaccccc atgctacgaa ccgcaggcag    240

ggacggcctc tgtcgcctgt ccacctactt ggaagaactc gaggctgtgg aactgaagaa    300

gttcaagtta tacctgggga ccgcgacaga gctgggagaa ggcaagatcc cctggggaag    360

catggagaag gccggtcccc tggaaatggc ccagctgctc atcacccact tcgggccaga    420

ggaggcctgg aggttggctc tcagcacctt tgagcggata aacaggaagg acctgtggga    480

gagaggacag agagaggacc tggtgaggga taccccacct ggtggcccgt cctcacttgg    540

gaaccagtca acatgccttc tggaagtctc tcttgtcact ccaagaaaag atccccagga    600

aacctacagg gactatgtcc gcaggaaatt ccggctcatg gaagaccgca atgcgcgcct    660

aggggaatgt gtcaacctca gccaccggta cacccggctc ctgctggtga aggagcactc    720

aaaccccatg caggtccagc agcagcttct ggacacaggc cggggacacg cgaggaccgt    780

gggacaccag gctagcccca tcaagataga gaccctcttt gagccagacg aggagcgccc    840

cgagccaccg cgcaccgtgg tcatgcaagg cgcggcaggg ataggcaagt ccatgctggc    900

acacaaggtg atgctggact gggcggacgg gaagctcttc caaggcagat ttgattatct    960

cttctacatc aactgcaggg agatgaacca gagtgccacg gaatgcagca tgcaagacct   1020

catcttcagc tgctggcctg agcccagcgc gcctctccag gagctcatcc gagttcccga   1080

gcgcctcctt ttcatcatcg acggcttcga tgagctcaag ccttctttcc acgatcctca   1140
```

-continued

```
gggaccctgg tgcctctgct gggaggagaa acggcccacg gagctgcttc ttaacagctt   1200

aattcggaag aagctgctcc ctgagctatc tttgctcatc accacacggc ccacggcttt   1260

ggagaagctc caccgtctgc tggagcaccc caggcatgtg gagatcctgg gcttctctga   1320

ggcagaaagg aaggaatact tctacaagta tttccacaat gcagagcagg cgggccaagt   1380

cttcaattac gtgagggaca acgagcctct cttcaccatg tgcttcgtcc ccctggtgtg   1440

ctgggtggtg tgtacctgcc tccagcagca gctggagggt ggggggctgt tgagacagac   1500

gtccaggacc accactgcag tgtacatgct ctacctgctg agtctgatgc aacccaagcc   1560

gggggccccg cgcctccagc ccccacccaa ccagagaggg ttgtgctcct tggcggcaga   1620

tgggctctgg aatcagaaaa tcctatttga ggagcaggac ctccggaagc acggcctaga   1680

cggggaagac gtctctgcct tcctcaacat gaacatcttc cagaaggaca tcaactgtga   1740

gaggtactac agcttcatcc acttgagttt ccaggaattc tttgcagcta tgtactatat   1800

cctggacgag gggagggcg gggcaggccc agaccaggac gtgaccaggc tgttgaccga    1860

gtacgcgttt tctgaaagga gcttcctggc actcaccagc cgcttcctgt ttggactcct   1920

gaacgaggag accaggagcc acctggagaa gagtctctgc tggaaggtct cgccgcacat   1980

caagatggac ctgttgcagt ggatccaaag caaagctcag agcgacggct ccaccctgca   2040

gcagggctcc ttggagttct tcagctgctt gtacgagatc caggaggagg agtttatcca   2100

gcaggccctg agccacttcc aggtgatcgt ggtcagcaac attgcctcca agatggagca   2160

catggtctcc tcgttctgtc tgaagcgctg caggagcgcc caggtgctgc acttgtatgg   2220

cgccacctac agcgcggacg gggaagaccg cgcgaggtgc tccgcaggag cgcacacgct   2280

gttggtgcag ctcagaccag agaggaccgt tctgctggac gcctacagtg aacatctggc   2340

agcggccctg tgcaccaatc caaacctgat agagctgtct ctgtaccgaa atgccctggg   2400

cagccggggg gtgaagctgc tctgtcaagg actcagacac cccaactgca aacttcagaa   2460

cctgaggctg aagaggtgcc gcatctccag ctcagcctgc gaggacctct ctgcagctct   2520

catagccaat aagaatttga caaggatgga tctcagtggc aacggcgttg gattcccagg   2580

catgatgctg ctttgcgagg gcctgcggca tccccagtgc aggctgcaga tgattcagtt   2640

gaggaagtgt cagctggagt ccggggcttg tcaggagatg gcttctgtgc tcggcaccaa   2700

cccacatctg gttgagttgg acctgacagg aaatgcactg gaggatttgg gcctgaggtt   2760

actatgccag ggactgaggc acccagtctg cagactacgg actttgtggt ggttatttgg   2820

gatggacctg aataaaatga cccacagtag gttggcagcg cttcgagtaa caaaacctta   2880

tttggacatt ggctgctgaa tggtcctatc tgctggctct cccctgagat ctggacagag   2940

gaagatggga gggtgctcat caccccccca gcataatgat cagcctcctt cctagagaca   3000

gactcatgca gattgagatc aaaagtccct ctgcttggga tcaaattaat gtttgacaga   3060

gctggccagg cgtggtggct catgtatgta atcctagcac ttcgagaggc cgaggcaggt   3120

ggatcacgag gtcaggagtt tgagattagc ctggccaaga tggtgaaacc ctgtctctac   3180

taaaaataaa aaaaaattag ccaggaaaaa aaaaaaaaaa a                        3221
```

<210> SEQ ID NO 8
<211> LENGTH: 892
<212> TYPE: PRT
<213> ORGANISM: Homo sapiens

<400> SEQUENCE: 8

-continued

```
Met Leu Arg Thr Ala Gly Arg Asp Gly Leu Cys Arg Leu Ser Thr Tyr
1               5                   10                  15

Leu Glu Glu Leu Glu Ala Val Glu Leu Lys Lys Phe Lys Leu Tyr Leu
            20                  25                  30

Gly Thr Ala Thr Glu Leu Gly Glu Gly Lys Ile Pro Trp Gly Ser Met
        35                  40                  45

Glu Lys Ala Gly Pro Leu Glu Met Ala Gln Leu Leu Ile Thr His Phe
    50                  55                  60

Gly Pro Glu Glu Ala Trp Arg Leu Ala Leu Ser Thr Phe Glu Arg Ile
65                  70                  75                  80

Asn Arg Lys Asp Leu Trp Glu Arg Gly Gln Arg Glu Asp Leu Val Arg
                85                  90                  95

Asp Thr Pro Pro Gly Gly Pro Ser Ser Leu Gly Asn Gln Ser Thr Cys
            100                 105                 110

Leu Leu Glu Val Ser Leu Val Thr Pro Arg Lys Asp Pro Gln Glu Thr
        115                 120                 125

Tyr Arg Asp Tyr Val Arg Arg Lys Phe Arg Leu Met Glu Asp Arg Asn
    130                 135                 140

Ala Arg Leu Gly Glu Cys Val Asn Leu Ser His Arg Tyr Thr Arg Leu
145                 150                 155                 160

Leu Leu Val Lys Glu His Ser Asn Pro Met Gln Val Gln Gln Gln Leu
                165                 170                 175

Leu Asp Thr Gly Arg Gly His Ala Arg Thr Val Gly His Gln Ala Ser
            180                 185                 190

Pro Ile Lys Ile Glu Thr Leu Phe Glu Pro Asp Glu Glu Arg Pro Glu
        195                 200                 205

Pro Pro Arg Thr Val Val Met Gln Gly Ala Ala Gly Ile Gly Lys Ser
    210                 215                 220

Met Leu Ala His Lys Val Met Leu Asp Trp Ala Asp Gly Lys Leu Phe
225                 230                 235                 240

Gln Gly Arg Phe Asp Tyr Leu Phe Tyr Ile Asn Cys Arg Glu Met Asn
                245                 250                 255

Gln Ser Ala Thr Glu Cys Ser Met Gln Asp Leu Ile Phe Ser Cys Trp
            260                 265                 270

Pro Glu Pro Ser Ala Pro Leu Gln Glu Leu Ile Arg Val Pro Glu Arg
        275                 280                 285

Leu Leu Phe Ile Ile Asp Gly Phe Asp Glu Leu Lys Pro Ser Phe His
    290                 295                 300

Asp Pro Gln Gly Pro Trp Cys Leu Cys Trp Glu Glu Lys Arg Pro Thr
305                 310                 315                 320

Glu Leu Leu Leu Asn Ser Leu Ile Arg Lys Lys Leu Leu Pro Glu Leu
                325                 330                 335

Ser Leu Leu Ile Thr Thr Arg Pro Thr Ala Leu Glu Lys Leu His Arg
            340                 345                 350

Leu Leu Glu His Pro Arg His Val Glu Ile Leu Gly Phe Ser Glu Ala
        355                 360                 365

Glu Arg Lys Glu Tyr Phe Tyr Lys Tyr Phe His Asn Ala Glu Gln Ala
    370                 375                 380

Gly Gln Val Phe Asn Tyr Val Arg Asp Asn Glu Pro Leu Phe Thr Met
385                 390                 395                 400

Cys Phe Val Pro Leu Val Cys Trp Val Val Cys Thr Cys Leu Gln Gln
                405                 410                 415

Gln Leu Glu Gly Gly Gly Leu Leu Arg Gln Thr Ser Arg Thr Thr Thr
```

-continued

```
        420                 425                 430

Ala Val Tyr Met Leu Tyr Leu Leu Ser Leu Met Gln Pro Lys Pro Gly
            435                 440                 445

Ala Pro Arg Leu Gln Pro Pro Pro Asn Gln Arg Gly Leu Cys Ser Leu
    450                 455                 460

Ala Ala Asp Gly Leu Trp Asn Gln Lys Ile Leu Phe Glu Glu Gln Asp
465                 470                 475                 480

Leu Arg Lys His Gly Leu Asp Gly Glu Asp Val Ser Ala Phe Leu Asn
                485                 490                 495

Met Asn Ile Phe Gln Lys Asp Ile Asn Cys Glu Arg Tyr Tyr Ser Phe
            500                 505                 510

Ile His Leu Ser Phe Gln Glu Phe Phe Ala Ala Met Tyr Tyr Ile Leu
        515                 520                 525

Asp Glu Gly Glu Gly Gly Ala Gly Pro Asp Gln Asp Val Thr Arg Leu
    530                 535                 540

Leu Thr Glu Tyr Ala Phe Ser Glu Arg Ser Phe Leu Ala Leu Thr Ser
545                 550                 555                 560

Arg Phe Leu Phe Gly Leu Leu Asn Glu Glu Thr Arg Ser His Leu Glu
                565                 570                 575

Lys Ser Leu Cys Trp Lys Val Ser Pro His Ile Lys Met Asp Leu Leu
            580                 585                 590

Gln Trp Ile Gln Ser Lys Ala Gln Ser Asp Gly Ser Thr Leu Gln Gln
        595                 600                 605

Gly Ser Leu Glu Phe Phe Ser Cys Leu Tyr Glu Ile Gln Glu Glu Glu
    610                 615                 620

Phe Ile Gln Gln Ala Leu Ser His Phe Gln Val Ile Val Val Ser Asn
625                 630                 635                 640

Ile Ala Ser Lys Met Glu His Met Val Ser Ser Phe Cys Leu Lys Arg
                645                 650                 655

Cys Arg Ser Ala Gln Val Leu His Leu Tyr Gly Ala Thr Tyr Ser Ala
            660                 665                 670

Asp Gly Glu Asp Arg Ala Arg Cys Ser Ala Gly Ala His Thr Leu Leu
        675                 680                 685

Val Gln Leu Arg Pro Glu Arg Thr Val Leu Leu Asp Ala Tyr Ser Glu
    690                 695                 700

His Leu Ala Ala Ala Leu Cys Thr Asn Pro Asn Leu Ile Glu Leu Ser
705                 710                 715                 720

Leu Tyr Arg Asn Ala Leu Gly Ser Arg Gly Val Lys Leu Leu Cys Gln
                725                 730                 735

Gly Leu Arg His Pro Asn Cys Lys Leu Gln Asn Leu Arg Leu Lys Arg
            740                 745                 750

Cys Arg Ile Ser Ser Ser Ala Cys Glu Asp Leu Ser Ala Ala Leu Ile
        755                 760                 765

Ala Asn Lys Asn Leu Thr Arg Met Asp Leu Ser Gly Asn Gly Val Gly
    770                 775                 780

Phe Pro Gly Met Met Leu Leu Cys Glu Gly Leu Arg His Pro Gln Cys
785                 790                 795                 800

Arg Leu Gln Met Ile Gln Leu Arg Lys Cys Gln Leu Glu Ser Gly Ala
                805                 810                 815

Cys Gln Glu Met Ala Ser Val Leu Gly Thr Asn Pro His Leu Val Glu
            820                 825                 830

Leu Asp Leu Thr Gly Asn Ala Leu Glu Asp Leu Gly Leu Arg Leu Leu
        835                 840                 845
```

-continued

```
Cys Gln Gly Leu Arg His Pro Val Cys Arg Leu Arg Thr Leu Trp Trp
    850                 855                 860

Leu Phe Gly Met Asp Leu Asn Lys Met Thr His Ser Arg Leu Ala Ala
865                 870                 875                 880

Leu Arg Val Thr Lys Pro Tyr Leu Asp Ile Gly Cys
                885                 890


<210> SEQ ID NO 9
<211> LENGTH: 3102
<212> TYPE: DNA
<213> ORGANISM: Mus musculus

<400> SEQUENCE: 9

atgttgccgt ctacagccag ggatggcctc tatcgactgt ctacctacct ggaagaactc     60

gaggctgggg aactgaagaa attcaaatta ttcctgggga ttgcagagga cctgagccag    120

gacaaaattc cctggggacg aatggagaag gctggtcctc tggaaatggc tcagctgatg    180

gtggcccaca tggggacaag ggaggcttgg cttctggctc tcagcacctt tcagaggatt    240

cacaggaagg acctgtggga gcgaggacag ggagaagacc tggtgagggg taaggagggc    300

aagggagatc tacagacaac ctacaaagac tatgtccgaa ggaaattcca gctaatggaa    360

gaccgcaatg cacgattagg cgaatgtgtg aacctgagca atcgttacac tcggcttctc    420

ctagtaaaag aacactcaaa tcctatctgg acacagcaga aatttgtaga tgtagagtgg    480

gaacgctcca gaaccaggcg tcaccagact agtcctatcc aaatggagac cctctttgag    540

ccagacgaag aacgccccga gccaccacac acagtggtat tacaaggggc agcggggatg    600

gggaagtcca tgctggccca caaagtgatg ttggactggg ccgatgggag gctcttccaa    660

ggccggtttg attatgtctt ctatatcagc tgcagggagt tgaatagaag ccacacccag    720

tgcagtgtac aagacctcat ctccagctgc tggccggagc gtggtatatc cctcgaagac    780

ctcatgcagg ctcctgaccg tctcctattc atcattgatg gcttcgataa actccatcct    840

tctttccatg atgctcaggg tccctggtgc ctctgctggg aggagaaaca acctactgaa    900

gtcctcctcg gaagtctgat tcggaggttg cttctgcccc aggtctctct gctcatcacc    960

acacgaccct gtgcactgga gaagctgcac ggcttgctag aacaccccag gcacgtggag   1020

atcctgggct tctccgagga agctaggaag gaatatttct acagatattt ccacaacact   1080

ggacaagcaa gccgggtgtt aagcttcttg atggactatg agcccctctt taccatgtgt   1140

tttgttccca tggtgtcctg ggtggtctgc acctgcctaa agcagcagct ggaaagtggg   1200

gagcttttaa gacaaacacc taggaccacc acagctgttt atatgttcta ccttctgagc   1260

ctgatgcagc ccaagccagg gactccaacc ttcaaagtcc cagccaacca gagaggcctg   1320

gtctctctgg ctgcagaggg cctctggaat cagaagattc tatttgatga acaggatctt   1380

gggaaacacg gcctagatgg agcagatgtg tccactttcc tcaacgtgaa catattccag   1440

aagggtatca aatgtgagaa attctacagc ttcatccacc tgagtttcca ggaattcttc   1500

gcagccatgt actgtgcact gaatggcaga gaggcggtga ggagagcgct ggctgagtat   1560

ggtttttcgg aaaggaactt cttggccctc acggtccact ttctgtttgg cctcctcaac   1620

gaagagatga gatgctacct tgagaggaat ctcggctgga gcatctcccc tcaggtgaag   1680

gaggaagtgt tggcatggat ccaaaacaag gctgggagtg aaggctccac cctgcagcat   1740

ggctccctgg agctactcag ctgcttgtat gaggtccagg aggaggactt catccagcag   1800

gccctgagcc actttcaagt ggttgtagtc agaagcatct caacaaagat ggagcacatg   1860
```

-continued

```
gtctgctcgt tttgtgcgag gtattgcaga agtacagaag tgcttcactt gcatgggagt   1920
gcttatagta caggcatgga ggacgaccca ccagaacctt caggagtcca gactcagtcc   1980
acatacttac aggaaaggaa catgctgcct gatgtctaca gtgcatacct ttcagcagct   2040
gtctgtacca actccaacct gatcgagctg gccttatacc gaaatgcctt gggcagccag   2100
ggtgtaaggc tgctctgtca aggcctccga catgccagct gcaagctgca gaacctgagg   2160
ctgaagaggt gtcagatctc cggatcagcc tgccaggacc tcgcagccgc tgtcatcgcc   2220
aacaggaatt taatcaggct ggacctcagt gacaacagca ttggggtgcc aggcctggag   2280
ctgctctgtg aggggctgca gcaccccagg tgtaggctgc agatgatcca gctgaggaag   2340
tgtctgttgg aggctgcagc tggccgatcc ctggcttctg ttctcagcaa caactcatat   2400
ctggtagaac tggatctgac aggaaacccc ttggaagatt cggggctgaa gttactgtgt   2460
caagggctaa ggcaccctgt ctgcaggctg cgtaccctgt ggctgaagat ctgccacctt   2520
ggacaagctt cctgcgaaga tctggcctct actctcaaaa tgaaccagag cctgctggag   2580
ctggacctgg gtctgaatga tcttggagat tctggggtgc ttctgctgtg tgaaggcctc   2640
agtcatccag attgcaaact ccagaccctt cggttgggca tttgccgact gggctcagtc   2700
gcgtgtgtgg ggatcgccag tgtgctccag gtcaacacat gcctccaaga gctggacctg   2760
agcttcaatg acttgggaga caggggcctg cagctgctgg gggaaggcct gaggcaccag   2820
acctgcagac tccagaagct gtggctggac aactgcggac tcacctccaa agcatgtgag   2880
gacctttctt ctatcctggg aatcagccag accctgcatg agctttattt gaccaataat   2940
gctctggggg acacaggtgt ctgtctgctg tgcaagaggc tgaggcatcc aggctgcaag   3000
cttcgagtcc tgtggctgtt tgggatggac ctgaataaaa agactcacag gaggatggca   3060
gcacttcgag tcacaaaacc gtacctggat attgggtgtt ga                      3102
```

```
<210> SEQ ID NO 10
<211> LENGTH: 1033
<212> TYPE: PRT
<213> ORGANISM: Mus musculus

<400> SEQUENCE: 10

Met Leu Pro Ser Thr Ala Arg Asp Gly Leu Tyr Arg Leu Ser Thr Tyr
1               5                   10                  15

Leu Glu Glu Leu Glu Ala Gly Glu Leu Lys Lys Phe Lys Leu Phe Leu
            20                  25                  30

Gly Ile Ala Glu Asp Leu Ser Gln Asp Lys Ile Pro Trp Gly Arg Met
        35                  40                  45

Glu Lys Ala Gly Pro Leu Glu Met Ala Gln Leu Met Val Ala His Met
    50                  55                  60

Gly Thr Arg Glu Ala Trp Leu Leu Ala Leu Ser Thr Phe Gln Arg Ile
65                  70                  75                  80

His Arg Lys Asp Leu Trp Glu Arg Gly Gln Gly Glu Asp Leu Val Arg
                85                  90                  95

Gly Lys Glu Gly Lys Gly Asp Leu Gln Thr Thr Tyr Lys Asp Tyr Val
            100                 105                 110

Arg Arg Lys Phe Gln Leu Met Glu Asp Arg Asn Ala Arg Leu Gly Glu
        115                 120                 125

Cys Val Asn Leu Ser Asn Arg Tyr Thr Arg Leu Leu Leu Val Lys Glu
    130                 135                 140

His Ser Asn Pro Ile Trp Thr Gln Gln Lys Phe Val Asp Val Glu Trp
```

-continued 145 150 155 160

Glu Arg Ser Arg Thr Arg Arg His Gln Thr Ser Pro Ile Gln Met Glu
165 170 175

Thr Leu Phe Glu Pro Asp Glu Glu Arg Pro Glu Pro Pro His Thr Val
180 185 190

Val Leu Gln Gly Ala Ala Gly Met Gly Lys Ser Met Leu Ala His Lys
195 200 205

Val Met Leu Asp Trp Ala Asp Gly Arg Leu Phe Gln Gly Arg Phe Asp
210 215 220

Tyr Val Phe Tyr Ile Ser Cys Arg Glu Leu Asn Arg Ser His Thr Gln
225 230 235 240

Cys Ser Val Gln Asp Leu Ile Ser Ser Cys Trp Pro Glu Arg Gly Ile
245 250 255

Ser Leu Glu Asp Leu Met Gln Ala Pro Asp Arg Leu Leu Phe Ile Ile
260 265 270

Asp Gly Phe Asp Lys Leu His Pro Ser Phe His Asp Ala Gln Gly Pro
275 280 285

Trp Cys Leu Cys Trp Glu Glu Lys Gln Pro Thr Glu Val Leu Leu Gly
290 295 300

Ser Leu Ile Arg Arg Leu Leu Leu Pro Gln Val Ser Leu Leu Ile Thr
305 310 315 320

Thr Arg Pro Cys Ala Leu Glu Lys Leu His Gly Leu Leu Glu His Pro
325 330 335

Arg His Val Glu Ile Leu Gly Phe Ser Glu Glu Ala Arg Lys Glu Tyr
340 345 350

Phe Tyr Arg Tyr Phe His Asn Thr Gly Gln Ala Ser Arg Val Leu Ser
355 360 365

Phe Leu Met Asp Tyr Glu Pro Leu Phe Thr Met Cys Phe Val Pro Met
370 375 380

Val Ser Trp Val Val Cys Thr Cys Leu Lys Gln Gln Leu Glu Ser Gly
385 390 395 400

Glu Leu Leu Arg Gln Thr Pro Arg Thr Thr Thr Ala Val Tyr Met Phe
405 410 415

Tyr Leu Leu Ser Leu Met Gln Pro Lys Pro Gly Thr Pro Thr Phe Lys
420 425 430

Val Pro Ala Asn Gln Arg Gly Leu Val Ser Leu Ala Ala Glu Gly Leu
435 440 445

Trp Asn Gln Lys Ile Leu Phe Asp Glu Gln Asp Leu Gly Lys His Gly
450 455 460

Leu Asp Gly Ala Asp Val Ser Thr Phe Leu Asn Val Asn Ile Phe Gln
465 470 475 480

Lys Gly Ile Lys Cys Glu Lys Phe Tyr Ser Phe Ile His Leu Ser Phe
485 490 495

Gln Glu Phe Phe Ala Ala Met Tyr Cys Ala Leu Asn Gly Arg Glu Ala
500 505 510

Val Arg Arg Ala Leu Ala Glu Tyr Gly Phe Ser Glu Arg Asn Phe Leu
515 520 525

Ala Leu Thr Val His Phe Leu Phe Gly Leu Leu Asn Glu Glu Met Arg
530 535 540

Cys Tyr Leu Glu Arg Asn Leu Gly Trp Ser Ile Ser Pro Gln Val Lys
545 550 555 560

Glu Glu Val Leu Ala Trp Ile Gln Asn Lys Ala Gly Ser Glu Gly Ser
565 570 575

-continued

```
Thr Leu Gln His Gly Ser Leu Glu Leu Leu Ser Cys Leu Tyr Glu Val
            580                 585                 590

Gln Glu Glu Asp Phe Ile Gln Gln Ala Leu Ser His Phe Gln Val Val
        595                 600                 605

Val Val Arg Ser Ile Ser Thr Lys Met Glu His Met Val Cys Ser Phe
    610                 615                 620

Cys Ala Arg Tyr Cys Arg Ser Thr Glu Val Leu His Leu His Gly Ser
625                 630                 635                 640

Ala Tyr Ser Thr Gly Met Glu Asp Asp Pro Pro Glu Pro Ser Gly Val
                645                 650                 655

Gln Thr Gln Ser Thr Tyr Leu Gln Glu Arg Asn Met Leu Pro Asp Val
            660                 665                 670

Tyr Ser Ala Tyr Leu Ser Ala Ala Val Cys Thr Asn Ser Asn Leu Ile
        675                 680                 685

Glu Leu Ala Leu Tyr Arg Asn Ala Leu Gly Ser Gln Gly Val Arg Leu
    690                 695                 700

Leu Cys Gln Gly Leu Arg His Ala Ser Cys Lys Leu Gln Asn Leu Arg
705                 710                 715                 720

Leu Lys Arg Cys Gln Ile Ser Gly Ser Ala Cys Gln Asp Leu Ala Ala
                725                 730                 735

Ala Val Ile Ala Asn Arg Asn Leu Ile Arg Leu Asp Leu Ser Asp Asn
            740                 745                 750

Ser Ile Gly Val Pro Gly Leu Glu Leu Leu Cys Glu Gly Leu Gln His
        755                 760                 765

Pro Arg Cys Arg Leu Gln Met Ile Gln Leu Arg Lys Cys Leu Leu Glu
    770                 775                 780

Ala Ala Ala Gly Arg Ser Leu Ala Ser Val Leu Ser Asn Asn Ser Tyr
785                 790                 795                 800

Leu Val Glu Leu Asp Leu Thr Gly Asn Pro Leu Glu Asp Ser Gly Leu
                805                 810                 815

Lys Leu Leu Cys Gln Gly Leu Arg His Pro Val Cys Arg Leu Arg Thr
            820                 825                 830

Leu Trp Leu Lys Ile Cys His Leu Gly Gln Ala Ser Cys Glu Asp Leu
        835                 840                 845

Ala Ser Thr Leu Lys Met Asn Gln Ser Leu Leu Glu Leu Asp Leu Gly
    850                 855                 860

Leu Asn Asp Leu Gly Asp Ser Gly Val Leu Leu Leu Cys Glu Gly Leu
865                 870                 875                 880

Ser His Pro Asp Cys Lys Leu Gln Thr Leu Arg Leu Gly Ile Cys Arg
                885                 890                 895

Leu Gly Ser Val Ala Cys Val Gly Ile Ala Ser Val Leu Gln Val Asn
            900                 905                 910

Thr Cys Leu Gln Glu Leu Asp Leu Ser Phe Asn Asp Leu Gly Asp Arg
        915                 920                 925

Gly Leu Gln Leu Leu Gly Glu Gly Leu Arg His Gln Thr Cys Arg Leu
    930                 935                 940

Gln Lys Leu Trp Leu Asp Asn Cys Gly Leu Thr Ser Lys Ala Cys Glu
945                 950                 955                 960

Asp Leu Ser Ser Ile Leu Gly Ile Ser Gln Thr Leu His Glu Leu Tyr
                965                 970                 975

Leu Thr Asn Asn Ala Leu Gly Asp Thr Gly Val Cys Leu Leu Cys Lys
            980                 985                 990
```

-continued

```
Arg Leu Arg His Pro Gly Cys Lys  Leu Arg Val Leu Trp  Leu Phe Gly
        995                 1000                1005

Met Asp  Leu Asn Lys Lys Thr  His Arg Arg Met Ala  Ala Leu Arg
    1010                1015                1020

Val Thr  Lys Pro Tyr Leu Asp  Ile Gly Cys
    1025                1030


<210> SEQ ID NO 11
<211> LENGTH: 3039
<212> TYPE: DNA
<213> ORGANISM: Homo sapiens

<400> SEQUENCE: 11

atggcagatt catcatcatc ttctttcttt cctgattttg ggctgctatt gtatttggag     60

gagctaaaca aagaggaatt aaatacattc aagttattcc taaaggagac catggaacct    120

gagcatggcc tgacaccctg gaatgaagtg aagaaggcca ggcgggagga cctggccaat    180

ttgatgaaga aatattatcc aggagagaaa gcctggagtg tgtctctcaa aatctttggc    240

aagatgaacc tgaaggatct gtgtgagaga gcgaaagaag agatcaactg gtcggcccag    300

actataggac cagatgatgc caaggctgga gagacacaag aagatcagga ggcagtgctg    360

ggtgatggaa cagaatacag aaatagaata aaggaaaaat tttgcatcac ttgggacaag    420

aagtctttgg ctggaaagcc tgaagatttc catcatggaa ttgcagagaa agatagaaaa    480

ctgttggaac acttgttcga tgtggatgtc aaaaccggtg cacagccaca gatcgtggtg    540

cttcagggag ctgctggagt tgggaaaaca accttggtga gaaaggcaat gttagattgg    600

gcagagggca gtctctacca gcagaggttt aagtatgttt tttatctcaa tgggagagaa    660

attaaccagc tgaaagagag aagctttgct caattgatat caaaggactg gcccagcaca    720

gaaggcccca ttgaagaaat catgtaccag ccaagtagcc tcttgtttat tattgacagt    780

ttcgatgaac tgaactttgc ctttgaagaa cctgagtttg cactgtgcga agactggacc    840

caagaacacc cagtgtcctt cctcatgagt agtttgctga ggaaagtgat gctccctgag    900

gcatccttat tggtgacaac aagactcaca acttctaaga gactaaagca gttgttgaag    960

aatcaccatt atgtagagct actaggaatg tctgaggatg caagagagga gtatatttac   1020

cagtttttg aagataagag gtgggccatg aaagtattca gttcactaaa aagcaatgag   1080

atgctgttta gcatgtgcca agtcccccta gtgtgctggg ccgcttgtac ttgtctgaag   1140

cagcaaatgg agaagggtgg tgatgtcaca ttgacctgcc aaacaaccac agctctgttt   1200

acctgctata tttctagctt gttcacacca gtagatggag gctctcctag tctacccaac   1260

caagcccagc tgagaagact gtgccaagtc gctgccaaag gaatatggac tatgacttac   1320

gtgttttaca gagaaaatct cagaaggctt gggttaactc aatctgatgt ctctagtttt   1380

atggacagca atattattca gaaggacgca gagtatgaaa actgctatgt gttcacccac   1440

cttcatgttc aggagttttt tgcagctatg ttctatatgt tgaaaggcag ttgggaagct   1500

gggaaccctt cctgccagcc ttttgaagat ttgaagtcat tacttcaaag cacaagttat   1560

aaagaccccc atttgacaca gatgaagtgc tttttgtttg gcctttttgaa tgaagatcga   1620

gtaaaacaac tggagaggac ttttaactgt aaaatgtcac tgaagataaa atcaaagtta   1680

cttcagtgta tggaagtatt aggaaacagt gactattctc catcacagct gggatttctg   1740

gagttgtttc actgtctgta tgagactcaa gataaagcgt ttataagcca ggcaatgaga   1800

tgtttcccaa aggttgccat taatatttgt gagaaaatac atttgcttgt atcttctttc   1860
```

-continued

```
tgccttaagc actgccggtg tttgcggacc atcaggctgt ctgtaactgt ggtatttgag   1920

aagaagatat taaaaacaag cctcccaact aacacttggt tgaaatttat cactttccct   1980

gatggttgtc aggatatctc tacttctttg attcataaca agaatctgat gcatcttgac   2040

ctaaaaggga gtgatatagg ggataatgga gtaaagtcat tgtgtgaggc cttgaaacac   2100

ccagagtgta aactacagac tctcaggctg gaatcttgca acctaactgt attttgttgt   2160

ctaaatatat ctaatgctct catcagaagc cagagcctga tatttctgaa tctgtcaacc   2220

aataatctgt tggatgatgg agtgcagctt ttgtgtgagg ccttaagaca tccaaagtgt   2280

tatctagaga gactgtcctt agaaagctgt ggtctcacag aggctggctg tgagtatctt   2340

tctttggctc tcatcagcaa taaaagactg acacatttgt gcttggcaga caatgtcttg   2400

ggtgatggtg gagtaaagct tatgagtgat gccctgcaac atgcacaatg tactctgaag   2460

agccttgtgc tgaggcgttg ccatttcact tcacttagca gtgaatatct gtcaacttct   2520

cttctacaca acaagagcct gacgcatctg gatctaggat caaactggct acaagacaat   2580

ggagtgaagc ttctgtgtga tgtctttcgg catccaagct gtaatcttca ggacttggaa   2640

ttgatgggct gtgttctcac taatgcatgt tgtctggatc tggcttctgt tatttttgaat  2700

aacccaaacc tgaggagcct ggaccttggg aacaacgatt tgcaggatga tggagtgaaa   2760

attctgtgtg atgctttgag atatccaaac tgtaacattc agaggctcgg gttggaatac   2820

tgtggtttga catctctctg ctgtcaagat ctctcctctg ctcttatctg caacaaaaga   2880

ctgataaaaa tgaatctgac acagaatacc ttaggatatg aaggaattgt gaagttatat   2940

aaagtcttga agtctcctaa gtgtaaacta caagttctag gacaacagga tttccaagct   3000

gcccaaggaa aactccaaca aagagctggc tctggatga                          3039
```

```
<210> SEQ ID NO 12
<211> LENGTH: 1012
<212> TYPE: PRT
<213> ORGANISM: Homo sapiens

<400> SEQUENCE: 12

Met Ala Asp Ser Ser Ser Ser Ser Phe Phe Pro Asp Phe Gly Leu Leu
1               5                   10                  15

Leu Tyr Leu Glu Glu Leu Asn Lys Glu Glu Leu Asn Thr Phe Lys Leu
            20                  25                  30

Phe Leu Lys Glu Thr Met Glu Pro Glu His Gly Leu Thr Pro Trp Asn
        35                  40                  45

Glu Val Lys Lys Ala Arg Arg Glu Asp Leu Ala Asn Leu Met Lys Lys
    50                  55                  60

Tyr Tyr Pro Gly Glu Lys Ala Trp Ser Val Ser Leu Lys Ile Phe Gly
65                  70                  75                  80

Lys Met Asn Leu Lys Asp Leu Cys Glu Arg Ala Lys Glu Glu Ile Asn
                85                  90                  95

Trp Ser Ala Gln Thr Ile Gly Pro Asp Asp Ala Lys Ala Gly Glu Thr
            100                 105                 110

Gln Glu Asp Gln Glu Ala Val Leu Gly Asp Gly Thr Glu Tyr Arg Asn
        115                 120                 125

Arg Ile Lys Glu Lys Phe Cys Ile Thr Trp Asp Lys Lys Ser Leu Ala
    130                 135                 140

Gly Lys Pro Glu Asp Phe His His Gly Ile Ala Glu Lys Asp Arg Lys
145                 150                 155                 160

Leu Leu Glu His Leu Phe Asp Val Asp Val Lys Thr Gly Ala Gln Pro
```

-continued

```
                165                 170                 175

Gln Ile Val Val Leu Gln Gly Ala Ala Gly Val Gly Lys Thr Thr Leu
            180                 185                 190

Val Arg Lys Ala Met Leu Asp Trp Ala Glu Gly Ser Leu Tyr Gln Gln
        195                 200                 205

Arg Phe Lys Tyr Val Phe Tyr Leu Asn Gly Arg Glu Ile Asn Gln Leu
    210                 215                 220

Lys Glu Arg Ser Phe Ala Gln Leu Ile Ser Lys Asp Trp Pro Ser Thr
225                 230                 235                 240

Glu Gly Pro Ile Glu Glu Ile Met Tyr Gln Pro Ser Ser Leu Leu Phe
                245                 250                 255

Ile Ile Asp Ser Phe Asp Glu Leu Asn Phe Ala Phe Glu Glu Pro Glu
            260                 265                 270

Phe Ala Leu Cys Glu Asp Trp Thr Gln Glu His Pro Val Ser Phe Leu
        275                 280                 285

Met Ser Ser Leu Leu Arg Lys Val Met Leu Pro Glu Ala Ser Leu Leu
    290                 295                 300

Val Thr Thr Arg Leu Thr Thr Ser Lys Arg Leu Lys Gln Leu Leu Lys
305                 310                 315                 320

Asn His His Tyr Val Glu Leu Leu Gly Met Ser Glu Asp Ala Arg Glu
                325                 330                 335

Glu Tyr Ile Tyr Gln Phe Phe Glu Asp Lys Arg Trp Ala Met Lys Val
            340                 345                 350

Phe Ser Ser Leu Lys Ser Asn Glu Met Leu Phe Ser Met Cys Gln Val
        355                 360                 365

Pro Leu Val Cys Trp Ala Ala Cys Thr Cys Leu Lys Gln Gln Met Glu
    370                 375                 380

Lys Gly Gly Asp Val Thr Leu Thr Cys Gln Thr Thr Thr Ala Leu Phe
385                 390                 395                 400

Thr Cys Tyr Ile Ser Ser Leu Phe Thr Pro Val Asp Gly Gly Ser Pro
                405                 410                 415

Ser Leu Pro Asn Gln Ala Gln Leu Arg Arg Leu Cys Gln Val Ala Ala
            420                 425                 430

Lys Gly Ile Trp Thr Met Thr Tyr Val Phe Tyr Arg Glu Asn Leu Arg
        435                 440                 445

Arg Leu Gly Leu Thr Gln Ser Asp Val Ser Ser Phe Met Asp Ser Asn
    450                 455                 460

Ile Ile Gln Lys Asp Ala Glu Tyr Glu Asn Cys Tyr Val Phe Thr His
465                 470                 475                 480

Leu His Val Gln Glu Phe Phe Ala Ala Met Phe Tyr Met Leu Lys Gly
                485                 490                 495

Ser Trp Glu Ala Gly Asn Pro Ser Cys Gln Pro Phe Glu Asp Leu Lys
            500                 505                 510

Ser Leu Leu Gln Ser Thr Ser Tyr Lys Asp Pro His Leu Thr Gln Met
        515                 520                 525

Lys Cys Phe Leu Phe Gly Leu Leu Asn Glu Asp Arg Val Lys Gln Leu
    530                 535                 540

Glu Arg Thr Phe Asn Cys Lys Met Ser Leu Lys Ile Lys Ser Lys Leu
545                 550                 555                 560

Leu Gln Cys Met Glu Val Leu Gly Asn Ser Asp Tyr Ser Pro Ser Gln
                565                 570                 575

Leu Gly Phe Leu Glu Leu Phe His Cys Leu Tyr Glu Thr Gln Asp Lys
            580                 585                 590
```

-continued

```
Ala Phe Ile Ser Gln Ala Met Arg Cys Phe Pro Lys Val Ala Ile Asn
        595                 600                 605

Ile Cys Glu Lys Ile His Leu Leu Val Ser Ser Phe Cys Leu Lys His
    610                 615                 620

Cys Arg Cys Leu Arg Thr Ile Arg Leu Ser Val Thr Val Val Phe Glu
625                 630                 635                 640

Lys Lys Ile Leu Lys Thr Ser Leu Pro Thr Asn Thr Trp Leu Lys Phe
                645                 650                 655

Ile Thr Phe Pro Asp Gly Cys Gln Asp Ile Ser Thr Ser Leu Ile His
            660                 665                 670

Asn Lys Asn Leu Met His Leu Asp Leu Lys Gly Ser Asp Ile Gly Asp
        675                 680                 685

Asn Gly Val Lys Ser Leu Cys Glu Ala Leu Lys His Pro Glu Cys Lys
    690                 695                 700

Leu Gln Thr Leu Arg Leu Glu Ser Cys Asn Leu Thr Val Phe Cys Cys
705                 710                 715                 720

Leu Asn Ile Ser Asn Ala Leu Ile Arg Ser Gln Ser Leu Ile Phe Leu
                725                 730                 735

Asn Leu Ser Thr Asn Asn Leu Leu Asp Asp Gly Val Gln Leu Leu Cys
            740                 745                 750

Glu Ala Leu Arg His Pro Lys Cys Tyr Leu Glu Arg Leu Ser Leu Glu
        755                 760                 765

Ser Cys Gly Leu Thr Glu Ala Gly Cys Glu Tyr Leu Ser Leu Ala Leu
    770                 775                 780

Ile Ser Asn Lys Arg Leu Thr His Leu Cys Leu Ala Asp Asn Val Leu
785                 790                 795                 800

Gly Asp Gly Gly Val Lys Leu Met Ser Asp Ala Leu Gln His Ala Gln
                805                 810                 815

Cys Thr Leu Lys Ser Leu Val Leu Arg Arg Cys His Phe Thr Ser Leu
            820                 825                 830

Ser Ser Glu Tyr Leu Ser Thr Ser Leu Leu His Asn Lys Ser Leu Thr
        835                 840                 845

His Leu Asp Leu Gly Ser Asn Trp Leu Gln Asp Asn Gly Val Lys Leu
    850                 855                 860

Leu Cys Asp Val Phe Arg His Pro Ser Cys Asn Leu Gln Asp Leu Glu
865                 870                 875                 880

Leu Met Gly Cys Val Leu Thr Asn Ala Cys Cys Leu Asp Leu Ala Ser
                885                 890                 895

Val Ile Leu Asn Asn Pro Asn Leu Arg Ser Leu Asp Leu Gly Asn Asn
            900                 905                 910

Asp Leu Gln Asp Asp Gly Val Lys Ile Leu Cys Asp Ala Leu Arg Tyr
        915                 920                 925

Pro Asn Cys Asn Ile Gln Arg Leu Gly Leu Glu Tyr Cys Gly Leu Thr
    930                 935                 940

Ser Leu Cys Cys Gln Asp Leu Ser Ser Ala Leu Ile Cys Asn Lys Arg
945                 950                 955                 960

Leu Ile Lys Met Asn Leu Thr Gln Asn Thr Leu Gly Tyr Glu Gly Ile
                965                 970                 975

Val Lys Leu Tyr Lys Val Leu Lys Ser Pro Lys Cys Lys Leu Gln Val
            980                 985                 990

Leu Gly Gln Gln Asp Phe Gln Ala  Ala Gln Gly Lys Leu  Gln Gln Arg
        995                 1000                 1005
```

-continued

```
Ala Gly  Ser Gly
    1010


<210> SEQ ID NO 13
<211> LENGTH: 2808
<212> TYPE: DNA
<213> ORGANISM: Homo sapiens

<400> SEQUENCE: 13

atggcagatt catcatcatc ttctttcttt cctgattttg ggctgctatt gtatttggag     60

gagctaaaca aagaggaatt aaatacattc aagttattcc taaaggagac catggaacct    120

gagcatggcc tgacaccctg gaatgaagtg aagaaggcca ggcgggagga cctggccaat    180

ttgatgaaga aatattatcc aggagagaaa gcctggagtg tgtctctcaa aatctttggc    240

aagatgaacc tgaaggatct gtgtgagaga gcgaaagaag agatcaactg gtcggcccag    300

actataggac cagatgatgc caaggctgga gagacacaag aagatcagga ggcagtgctg    360

ggtgatggaa cagaatacag aaatagaata aaggaaaaat tttgcatcac ttgggacaag    420

aagtctttgg ctggaaagcc tgaagatttc catcatggaa ttgcagagaa agatagaaaa    480

ctgttggaac acttgttcga tgtggatgtc aaaaccggtg cacagccaca gatcgtggtg    540

cttcagggag ctgctggagt tgggaaaaca accttggtga gaaaggcaat gttagattgg    600

gcagagggca gtctctacca gcagaggttt aagtatgttt tttatctcaa tgggagagaa    660

attaaccagc tgaaagagag aagctttgct caattgatat caaaggactg gcccaacaca    720

aaagccccca ttgaagaaat catgtaccag ccaagtagcc tcttgtttat tatagacagt    780

ttcgatgaac tgaactttgc ctttgaagaa cctgagtttg cactgtgcga agactggacc    840

caagacaacc cagtgtcctt cctcatgagt agtttgctga ggaaagtgat gctccctgag    900

gcatccttat tggtgacaac aagactcaca acttctaaga gactaaagca gttgttgaag    960

aatcaccatt atgtagagct actaggaatg tctgaggatg caagagagga gtatatttac   1020

cagtttttg aagataagag gtgggccatg aaagtattca gttcactaaa aagcaatgag   1080

atgctgttta gcatgtgcca agtcccccta gtgtgctggg ccgcttgtac ttgtctgaag   1140

cagcaaatgg agaagggtgg tgatgtcaca ttgacctgcc aaacaaccac agctctgttt   1200

acctgctata tttctagctt gttcacacca gtagatggag gctctcctag tctacccaac   1260

caagcccagc tgagaagact gtgccaagtc gctgccaaag gaatatggac tatgacttac   1320

gtgttttaca gagaaaatct cagaaggctt gggttaactc aatctgatgt ctctagtttt   1380

atggacagca atattattca gaaggacgca gagtatgaaa actgctatgt gttcacccac   1440

cttcatgttc aggagttttt tgcagctatg ttctatatgt tgaagggcag ttgggaagct   1500

gggaaccctt cctgccagcc ttttgaagat ttgaagtcat tacttcaaag cacaagttat   1560

aaagaccccc atttgacaca gatgaagtgc tttttgtttg gcctttttgaa tgaagatcga   1620

gtaaaacaac tggagaggac ttttaactgt aaaatgtcac tgaagataaa atcaaagtta   1680

cttcagtgta tggaagtatt aggaaacagt gactattctc catcacagct gggatttctg   1740

gagttgtttc actgtctgta tgagactcaa gataaagcgt ttataagcca ggcaatgaga   1800

tgtttcccaa aggttgccat taatatttgt gagaaaatac attggcttgt atcttctttc   1860

tgccttaagc actgccgatg tttgcagacc atcaggctgt ctgtaactgt gctatttgag   1920

aagaagacat taaaaacaag cctcccaact aacacttggg atggtgatcg cattactcac   1980

tgttggaaag atctctgttc tgtgcttcat acaaatgaac acttgagaga attggacctg   2040
```

-continued

```
taccatagca accttgataa atcagcaatg aatatcctgc atcatgaact aagccaccca   2100

aactgtaaac tacaaaaact actgttgaaa tttatcactt tccctgatgg ttgtcaggat   2160

atctctactt ctttgattca taacaagaat ctgatgcatc ttgacctaaa agggagtgat   2220

ataggggata atggagtaaa gtcattgtgt gaggccttga aacacccaga gtgtaaacta   2280

cagactctca gcttagaaag ctgtggtctc acagaggctg gctgtgagta tctttctttg   2340

gctctcatca gcaataaaag actgacacat ttgtgcttgg cagacaatgt cttgggtgat   2400

ggtggagtaa agcttatgag tgatgccctg caacatgcac aatgtactct gaagagcctt   2460

gtgctgaggc gttgccattt cacttcactt agcagtgaat atctgtcaac ttctcttcta   2520

cacaacaaga gcctgacgca tctggatcta ggatcaaact ggctacaaga caatggagtg   2580

aagcttctgt gtgatgtctt tcggcatcca agctgtaatc ttcaggactt ggaattgatg   2640

ggctgtgttc tcactaatgc atgttgtctg gatctggctt ctgttatttt gaataaccca   2700

aacctgagga gcctggacct tgggaacaac gatttgcagg atgatggagt gaaaattctg   2760

tgtgatgctt tgagatatcc aaactgtaac attcagaggc tcgggtga                2808
```

<210> SEQ ID NO 14
<211> LENGTH: 935
<212> TYPE: PRT
<213> ORGANISM: Homo sapiens

<400> SEQUENCE: 14

```
Met Ala Asp Ser Ser Ser Ser Ser Phe Phe Pro Asp Phe Gly Leu Leu
1               5                   10                  15

Leu Tyr Leu Glu Glu Leu Asn Lys Glu Glu Leu Asn Thr Phe Lys Leu
            20                  25                  30

Phe Leu Lys Glu Thr Met Glu Pro Glu His Gly Leu Thr Pro Trp Asn
        35                  40                  45

Glu Val Lys Lys Ala Arg Arg Glu Asp Leu Ala Asn Leu Met Lys Lys
    50                  55                  60

Tyr Tyr Pro Gly Glu Lys Ala Trp Ser Val Ser Leu Lys Ile Phe Gly
65                  70                  75                  80

Lys Met Asn Leu Lys Asp Leu Cys Glu Arg Ala Lys Glu Glu Ile Asn
                85                  90                  95

Trp Ser Ala Gln Thr Ile Gly Pro Asp Asp Ala Lys Ala Gly Glu Thr
            100                 105                 110

Gln Glu Asp Gln Glu Ala Val Leu Gly Asp Gly Thr Glu Tyr Arg Asn
        115                 120                 125

Arg Ile Lys Glu Lys Phe Cys Ile Thr Trp Asp Lys Lys Ser Leu Ala
    130                 135                 140

Gly Lys Pro Glu Asp Phe His His Gly Ile Ala Glu Lys Asp Arg Lys
145                 150                 155                 160

Leu Leu Glu His Leu Phe Asp Val Asp Val Lys Thr Gly Ala Gln Pro
                165                 170                 175

Gln Ile Val Val Leu Gln Gly Ala Ala Gly Val Gly Lys Thr Thr Leu
            180                 185                 190

Val Arg Lys Ala Met Leu Asp Trp Ala Glu Gly Ser Leu Tyr Gln Gln
        195                 200                 205

Arg Phe Lys Tyr Val Phe Tyr Leu Asn Gly Arg Glu Ile Asn Gln Leu
    210                 215                 220

Lys Glu Arg Ser Phe Ala Gln Leu Ile Ser Lys Asp Trp Pro Asn Thr
225                 230                 235                 240
```

-continued

```
Lys Ala Pro Ile Glu Glu Ile Met Tyr Gln Pro Ser Ser Leu Leu Phe
                245                 250                 255

Ile Ile Asp Ser Phe Asp Glu Leu Asn Phe Ala Phe Glu Glu Pro Glu
            260                 265                 270

Phe Ala Leu Cys Glu Asp Trp Thr Gln Asp Asn Pro Val Ser Phe Leu
        275                 280                 285

Met Ser Ser Leu Leu Arg Lys Val Met Leu Pro Glu Ala Ser Leu Leu
    290                 295                 300

Val Thr Thr Arg Leu Thr Thr Ser Lys Arg Leu Lys Gln Leu Leu Lys
305                 310                 315                 320

Asn His His Tyr Val Glu Leu Leu Gly Met Ser Glu Asp Ala Arg Glu
                325                 330                 335

Glu Tyr Ile Tyr Gln Phe Phe Glu Asp Lys Arg Trp Ala Met Lys Val
            340                 345                 350

Phe Ser Ser Leu Lys Ser Asn Glu Met Leu Phe Ser Met Cys Gln Val
        355                 360                 365

Pro Leu Val Cys Trp Ala Ala Cys Thr Cys Leu Lys Gln Gln Met Glu
    370                 375                 380

Lys Gly Gly Asp Val Thr Leu Thr Cys Gln Thr Thr Thr Ala Leu Phe
385                 390                 395                 400

Thr Cys Tyr Ile Ser Ser Leu Phe Thr Pro Val Asp Gly Gly Ser Pro
                405                 410                 415

Ser Leu Pro Asn Gln Ala Gln Leu Arg Arg Leu Cys Gln Val Ala Ala
            420                 425                 430

Lys Gly Ile Trp Thr Met Thr Tyr Val Phe Tyr Arg Glu Asn Leu Arg
        435                 440                 445

Arg Leu Gly Leu Thr Gln Ser Asp Val Ser Ser Phe Met Asp Ser Asn
    450                 455                 460

Ile Ile Gln Lys Asp Ala Glu Tyr Glu Asn Cys Tyr Val Phe Thr His
465                 470                 475                 480

Leu His Val Gln Glu Phe Phe Ala Ala Met Phe Tyr Met Leu Lys Gly
                485                 490                 495

Ser Trp Glu Ala Gly Asn Pro Ser Cys Gln Pro Phe Glu Asp Leu Lys
            500                 505                 510

Ser Leu Leu Gln Ser Thr Ser Tyr Lys Asp Pro His Leu Thr Gln Met
        515                 520                 525

Lys Cys Phe Leu Phe Gly Leu Leu Asn Glu Asp Arg Val Lys Gln Leu
    530                 535                 540

Glu Arg Thr Phe Asn Cys Lys Met Ser Leu Lys Ile Lys Ser Lys Leu
545                 550                 555                 560

Leu Gln Cys Met Glu Val Leu Gly Asn Ser Asp Tyr Ser Pro Ser Gln
                565                 570                 575

Leu Gly Phe Leu Glu Leu Phe His Cys Leu Tyr Glu Thr Gln Asp Lys
            580                 585                 590

Ala Phe Ile Ser Gln Ala Met Arg Cys Phe Pro Lys Val Ala Ile Asn
        595                 600                 605

Ile Cys Glu Lys Ile His Trp Leu Val Ser Ser Phe Cys Leu Lys His
    610                 615                 620

Cys Arg Cys Leu Gln Thr Ile Arg Leu Ser Val Thr Val Leu Phe Glu
625                 630                 635                 640

Lys Lys Thr Leu Lys Thr Ser Leu Pro Thr Asn Thr Trp Asp Gly Asp
                645                 650                 655

Arg Ile Thr His Cys Trp Lys Asp Leu Cys Ser Val Leu His Thr Asn
```

-continued

```
            660                 665                 670

Glu His Leu Arg Glu Leu Asp Leu Tyr His Ser Asn Leu Asp Lys Ser
        675                 680                 685

Ala Met Asn Ile Leu His His Glu Leu Ser His Pro Asn Cys Lys Leu
    690                 695                 700

Gln Lys Leu Leu Leu Lys Phe Ile Thr Phe Pro Asp Gly Cys Gln Asp
705                 710                 715                 720

Ile Ser Thr Ser Leu Ile His Asn Lys Asn Leu Met His Leu Asp Leu
                725                 730                 735

Lys Gly Ser Asp Ile Gly Asp Asn Gly Val Lys Ser Leu Cys Glu Ala
            740                 745                 750

Leu Lys His Pro Glu Cys Lys Leu Gln Thr Leu Ser Leu Glu Ser Cys
        755                 760                 765

Gly Leu Thr Glu Ala Gly Cys Glu Tyr Leu Ser Leu Ala Leu Ile Ser
    770                 775                 780

Asn Lys Arg Leu Thr His Leu Cys Leu Ala Asp Asn Val Leu Gly Asp
785                 790                 795                 800

Gly Gly Val Lys Leu Met Ser Asp Ala Leu Gln His Ala Gln Cys Thr
                805                 810                 815

Leu Lys Ser Leu Val Leu Arg Arg Cys His Phe Thr Ser Leu Ser Ser
            820                 825                 830

Glu Tyr Leu Ser Thr Ser Leu Leu His Asn Lys Ser Leu Thr His Leu
        835                 840                 845

Asp Leu Gly Ser Asn Trp Leu Gln Asp Asn Gly Val Lys Leu Leu Cys
    850                 855                 860

Asp Val Phe Arg His Pro Ser Cys Asn Leu Gln Asp Leu Glu Leu Met
865                 870                 875                 880

Gly Cys Val Leu Thr Asn Ala Cys Cys Leu Asp Leu Ala Ser Val Ile
                885                 890                 895

Leu Asn Asn Pro Asn Leu Arg Ser Leu Asp Leu Gly Asn Asn Asp Leu
            900                 905                 910

Gln Asp Asp Gly Val Lys Ile Leu Cys Asp Ala Leu Arg Tyr Pro Asn
        915                 920                 925

Cys Asn Ile Gln Arg Leu Gly
    930                 935


<210> SEQ ID NO 15
<211> LENGTH: 2612
<212> TYPE: DNA
<213> ORGANISM: Homo sapiens

<400> SEQUENCE: 15

aagctataca gcggcaccgc cggaacctgg ctgagtggtt cagccggctg cccagggagg      60

agcgccagtt tggcccaacc tttgccctag acacggtcca cgttgaccct gtgatccgcg     120

agagtacccc tgatgagcta cttcgcccac ccgcggagct ggccttggag catcagccac     180

cccaggccgg gctcccccca ctggccttgt ctcagctctt taacccggat gcctgtgggc     240

gccgggtgca gacagtggtg ctgtatggga cagtgggcac aggcaagagc acgctggtgc     300

gcaagatggt tctggactgg tgttatgggc ggctgccggc cttcgagctg ctcatcccct     360

tctcctgtga ggacctgtca tccctgggcc ctgccccagc ctccctgtgc caacttgtgg     420

cccagcgcta cacgcccctg aaggaggttc tgcccctgat ggctgctgct gggtcccacc     480

tcctctttgt gctccatggc ttagagcatc tcaacctcga cttccggctg gcaggcacgg     540
```

-continued

```
gactttgtag tgacccggag gaaccgcagg aaccagctgc tatcatcgtc aacctgctgc    600

gcaaatacat gctgcctcag gccagcattc tggtgaccac tcggccctct gccattggcc    660

gtatccccag caagtacgtg ggccgctatg gtgagatctg cggtttctct gataccaacc    720

tgcagaagct ctacttccag ctccgcctca accagccgta ctgcgggtat gccgttggcg    780

gttcaggtgt ctctgccaca ccagctcagc gtgaccacct ggtgcagatg ctctcccgga    840

acctggaggg gcaccaccag atagccgctg cctgcttcct gccgtcctat tgctggctcg    900

tttgtgccac cttgcacttc ctgcatgccc ccacgcctgc tgggcagacc cttacaagca    960

tctataccag cttcctgcgc ctcaacttca gcggggaaac cctggacagc actgacccct   1020

ccaatttgtc cctgatggcc tatgcagccc gaaccatggg caagttggcc tatgaggggg   1080

tgtcctcccg caagacctac ttctctgaag aggatgtctg tggctgcctg gaggctggca   1140

tcaggacgga ggaggagttt cagctgctgc acatcttccg tcgggatgcc ctgaggtttt   1200

tcctggcccc atgtgtggag ccagggcgtg caggcacctt cgtgttcacc gtgcccgcca   1260

tgcaggaata cctggctgcc ctctacattg tgctgggttt gcgcaagacg accctgcaaa   1320

aggtgggcaa ggaagtggct gagctcgtgg gccgtgttgg ggaggacgtc agcctggtac   1380

tgggcatcat ggccaagctg ctgcctctgc gggctctgcc tctgctcttc aacctgatca   1440

aggtggttcc acgagtgttt gggcgcatgg tgggtaaaag ccgggaggcg gtggctcagg   1500

ccatggtgct ggagatgttt cgagaggagg actactacaa cgatgatgtt ctggaccaga   1560

tgggcgccag tatcctgggc gtggagggcc cccggcgcca cccagatgag ccccctgagg   1620

atgaagtctt cgagctcttc cccatgttca tggggggcgct tctctctgcc cacaaccgag   1680

ctgtgctagc tcagcttggc tgccccatca agaacctgga tgccctggag aatgcccagg   1740

ccatcaagaa gaagctgggc aagctgggcc ggcaggtgct gcccccatca gagctccttg   1800

accacctctt cttccactat gagttccaga accagcgctt ctccgctgag gtgctcagct   1860

ccctgcgtca gctcaacctg gcaggtgtgc gcatgacacc agtcaagtgc acagtggtgg   1920

cagctgtgct gggcagcgga aggcatgccc tggatgaggt gaacttggcc tcctgccagc   1980

tagatcctgc tgggctgcgc acactcctgc ctgtcttcct gcgtgcccgg aagctgggct   2040

tgcaactcaa cagcctgggc cctgaggcct gcaaggacct ccgagacctg ttgctgcatg   2100

accagtgcca aattaccaca ctgcggctgt ccaacaaccc gctgacggcg gcaggcctgg   2160

agctgctggc tgcccagctg gaccgcaacc ggcagctgca ggagctgaac gtggcgtaca   2220

acggtgctgg tgacacagcg gccctggccc tggccagagc tgcccgggag cacccttccc   2280

tggaactgct acaagctcta ctgaatggca tcgactttct ctctcctgcc agcctctact   2340

tcaatgagct gagctcagag ggccgccagg tcttgcgaga cttgggggggt gctgctgaag   2400

gtggtgcccg ggtggtggtg tcactgacag aggggacggc ggtgtcagaa tactggtcag   2460

tgatcctcag tgaagtccag cggaacctca atagctggga tcgggcccgg gttcagcgac   2520

accttgagct cctactgcgg gatctggaag atagccgggg tgccaccctt aatccttggc   2580

gcaaggccca gctgctgcga gtggagggcg ag                                  2612
```

<210> SEQ ID NO 16
<211> LENGTH: 870
<212> TYPE: PRT
<213> ORGANISM: Homo sapiens

<400> SEQUENCE: 16

Ala Ile Gln Arg His Arg Arg Asn Leu Ala Glu Trp Phe Ser Arg Leu

-continued

```
1               5                   10                  15

Pro Arg Glu Glu Arg Gln Phe Gly Pro Thr Phe Ala Leu Asp Thr Val
            20                  25                  30

His Val Asp Pro Val Ile Arg Glu Ser Thr Pro Asp Glu Leu Leu Arg
        35                  40                  45

Pro Pro Ala Glu Leu Ala Leu Glu His Gln Pro Pro Gln Ala Gly Leu
    50                  55                  60

Pro Pro Leu Ala Leu Ser Gln Leu Phe Asn Pro Asp Ala Cys Gly Arg
65                  70                  75                  80

Arg Val Gln Thr Val Val Leu Tyr Gly Thr Val Gly Thr Gly Lys Ser
                85                  90                  95

Thr Leu Val Arg Lys Met Val Leu Asp Trp Cys Tyr Gly Arg Leu Pro
            100                 105                 110

Ala Phe Glu Leu Leu Ile Pro Phe Ser Cys Glu Asp Leu Ser Ser Leu
        115                 120                 125

Gly Pro Ala Pro Ala Ser Leu Cys Gln Leu Val Ala Gln Arg Tyr Thr
    130                 135                 140

Pro Leu Lys Glu Val Leu Pro Leu Met Ala Ala Ala Gly Ser His Leu
145                 150                 155                 160

Leu Phe Val Leu His Gly Leu Glu His Leu Asn Leu Asp Phe Arg Leu
                165                 170                 175

Ala Gly Thr Gly Leu Cys Ser Asp Pro Glu Glu Pro Gln Glu Pro Ala
            180                 185                 190

Ala Ile Ile Val Asn Leu Leu Arg Lys Tyr Met Leu Pro Gln Ala Ser
        195                 200                 205

Ile Leu Val Thr Thr Arg Pro Ser Ala Ile Gly Arg Ile Pro Ser Lys
    210                 215                 220

Tyr Val Gly Arg Tyr Gly Glu Ile Cys Gly Phe Ser Asp Thr Asn Leu
225                 230                 235                 240

Gln Lys Leu Tyr Phe Gln Leu Arg Leu Asn Gln Pro Tyr Cys Gly Tyr
                245                 250                 255

Ala Val Gly Gly Ser Gly Val Ser Ala Thr Pro Ala Gln Arg Asp His
            260                 265                 270

Leu Val Gln Met Leu Ser Arg Asn Leu Glu Gly His His Gln Ile Ala
        275                 280                 285

Ala Ala Cys Phe Leu Pro Ser Tyr Cys Trp Leu Val Cys Ala Thr Leu
    290                 295                 300

His Phe Leu His Ala Pro Thr Pro Ala Gly Gln Thr Leu Thr Ser Ile
305                 310                 315                 320

Tyr Thr Ser Phe Leu Arg Leu Asn Phe Ser Gly Glu Thr Leu Asp Ser
                325                 330                 335

Thr Asp Pro Ser Asn Leu Ser Leu Met Ala Tyr Ala Ala Arg Thr Met
            340                 345                 350

Gly Lys Leu Ala Tyr Glu Gly Val Ser Ser Arg Lys Thr Tyr Phe Ser
        355                 360                 365

Glu Glu Asp Val Cys Gly Cys Leu Glu Ala Gly Ile Arg Thr Glu Glu
    370                 375                 380

Glu Phe Gln Leu Leu His Ile Phe Arg Arg Asp Ala Leu Arg Phe Phe
385                 390                 395                 400

Leu Ala Pro Cys Val Glu Pro Gly Arg Ala Gly Thr Phe Val Phe Thr
                405                 410                 415

Val Pro Ala Met Gln Glu Tyr Leu Ala Ala Leu Tyr Ile Val Leu Gly
            420                 425                 430
```

-continued

```
Leu Arg Lys Thr Thr Leu Gln Lys Val Gly Lys Glu Val Ala Glu Leu
        435                 440                 445

Val Gly Arg Val Gly Glu Asp Val Ser Leu Val Leu Gly Ile Met Ala
    450                 455                 460

Lys Leu Leu Pro Leu Arg Ala Leu Pro Leu Leu Phe Asn Leu Ile Lys
465                 470                 475                 480

Val Val Pro Arg Val Phe Gly Arg Met Val Gly Lys Ser Arg Glu Ala
                485                 490                 495

Val Ala Gln Ala Met Val Leu Glu Met Phe Arg Glu Glu Asp Tyr Tyr
            500                 505                 510

Asn Asp Asp Val Leu Asp Gln Met Gly Ala Ser Ile Leu Gly Val Glu
        515                 520                 525

Gly Pro Arg Arg His Pro Asp Glu Pro Pro Glu Asp Glu Val Phe Glu
    530                 535                 540

Leu Phe Pro Met Phe Met Gly Gly Leu Leu Ser Ala His Asn Arg Ala
545                 550                 555                 560

Val Leu Ala Gln Leu Gly Cys Pro Ile Lys Asn Leu Asp Ala Leu Glu
                565                 570                 575

Asn Ala Gln Ala Ile Lys Lys Lys Leu Gly Lys Leu Gly Arg Gln Val
            580                 585                 590

Leu Pro Pro Ser Glu Leu Leu Asp His Leu Phe Phe His Tyr Glu Phe
        595                 600                 605

Gln Asn Gln Arg Phe Ser Ala Glu Val Leu Ser Ser Leu Arg Gln Leu
    610                 615                 620

Asn Leu Ala Gly Val Arg Met Thr Pro Val Lys Cys Thr Val Val Ala
625                 630                 635                 640

Ala Val Leu Gly Ser Gly Arg His Ala Leu Asp Glu Val Asn Leu Ala
                645                 650                 655

Ser Cys Gln Leu Asp Pro Ala Gly Leu Arg Thr Leu Leu Pro Val Phe
            660                 665                 670

Leu Arg Ala Arg Lys Leu Gly Leu Gln Leu Asn Ser Leu Gly Pro Glu
        675                 680                 685

Ala Cys Lys Asp Leu Arg Asp Leu Leu Leu His Asp Gln Cys Gln Ile
    690                 695                 700

Thr Thr Leu Arg Leu Ser Asn Asn Pro Leu Thr Ala Ala Gly Leu Glu
705                 710                 715                 720

Leu Leu Ala Ala Gln Leu Asp Arg Asn Arg Gln Leu Gln Glu Leu Asn
                725                 730                 735

Val Ala Tyr Asn Gly Ala Gly Asp Thr Ala Ala Leu Ala Leu Ala Arg
            740                 745                 750

Ala Ala Arg Glu His Pro Ser Leu Glu Leu Leu Gln Ala Leu Leu Asn
        755                 760                 765

Gly Ile Asp Phe Leu Ser Pro Ala Ser Leu Tyr Phe Asn Glu Leu Ser
    770                 775                 780

Ser Glu Gly Arg Gln Val Leu Arg Asp Leu Gly Gly Ala Ala Glu Gly
785                 790                 795                 800

Gly Ala Arg Val Val Val Ser Leu Thr Glu Gly Thr Ala Val Ser Glu
                805                 810                 815

Tyr Trp Ser Val Ile Leu Ser Glu Val Gln Arg Asn Leu Asn Ser Trp
            820                 825                 830

Asp Arg Ala Arg Val Gln Arg His Leu Glu Leu Leu Leu Arg Asp Leu
        835                 840                 845
```

-continued

```
Glu Asp Ser Arg Gly Ala Thr Leu Asn Pro Trp Arg Lys Ala Gln Leu
    850                 855                 860

Leu Arg Val Glu Gly Glu
865                 870


<210> SEQ ID NO 17
<211> LENGTH: 3017
<212> TYPE: DNA
<213> ORGANISM: Homo sapiens

<400> SEQUENCE: 17

atgaggtggg gccaccattt gcccagggcc tcttggggct ctggttttag aagagcactc     60

cagcgaccag atgatcgtat ccccttcctg atccactgga gttggcccct tcaaggggag    120

cgtccctttg ggcccccctag ggcctttata cgccaccacg gaagctcggt agatagcgct    180

cccccatccg ggaggcatgg acggctgttc cccagcgcct ctgcaactga agctatacag    240

cggcaccgcc ggaacctggc tgagtggttc agccggctgc ccagggagga gcgccagttt    300

ggcccaacct ttgccctaga cacggtccac gttgaccctg tgatccgcga gagtacccct    360

gatgagctac ttcgcccacc cgcggagctg gccctggagc atcagccacc ccaggccggg    420

ctccccccac tggccttgtc tcagctcttt aacccggatg cctgtgggcg ccgggtgcag    480

acagtggtgc tgtatgggac agtgggcaca ggcaagagca cgctggtgcg caagatggtt    540

ctggactggt gttatgggcg gctgccggcc ttcgagctgc tcatcccctt ctcctgtgag    600

gacctgtcat ccctgggccc tgccccagcc tccctgtgcc aacttgtggc ccagcgctac    660

acgcccctga aggaggttct gcccctgatg gctgctgctg ggtcccacct cctctttgtg    720

ctccatggct tagagcatct caacctcgac ttccggctgg caggcacggg actttgtagt    780

gacccggagg aaccgcagga accagctgct atcatcgtca acctgctgcg caaatacatg    840

ctgcctcagg ccagcattct ggtgaccact cggccctctg ccattggccg tatccccagc    900

aagtacgtgg gccgctatgg tgagatctgc ggtttctctg ataccaacct gcagaagctc    960

tacttccagc tccgcctcaa ccagccgtac tgcgggtatg ccgttggcgg ttcaggtgtc   1020

tctgccacac cagctcagcg tgaccacctg gtgcagatgc tctcccggaa cctggagggg   1080

caccaccaga tagccgctgc ctgcttcctg ccgtcctatt gctggctcgt ttgtgccacc   1140

ttgcacttcc tgcatgcccc cacgcctgct gggcagaccc ttacaagcat ctataccagc   1200

ttcctgcgcc tcaacttcag cggggaaacc ctggacagca ctgaccccctc caatttgtcc   1260

ctgatggcct atgcagcccg aaccatgggc aagttggcct atgagggggt gtcctcccgc   1320

aagacctact tctctgaaga ggatgtctgt ggctgcctgg aggctggcat caggacggag   1380

gaggagtttc agctgctgca catcttccgt cgggatgccc tgaggttttt cctggcccca   1440

tgtgtggagc cagggcgtgc aggcaccttc gtgttcaccg tgcccgccat gcaggaatac   1500

ctggctgccc tctacattgt gctgggtttg cgcaagacga ccctgcaaaa ggtgggcaag   1560

gaagtggctg agctcgtggg ccgtgttggg gaggacgtca gcctggtact gggcatcatg   1620

gccaagctgc tgcctctgcg ggctctgcct ctgctcttca acctgatcaa ggtggttcca   1680

cgagtgtttg ggcgcatggt gggtaaaagc cgggaggcgg tgactcaggc catggtgctg   1740

gagatgtttc gagaggagga ctactacaac gatgatgttc tggaccagat gggcgccagt   1800

atcctgggcg tggagggccc ccggcgccac ccagatgagc cccctgagga tgaagtcttc   1860

gagctcttcc ccatgttcat gggggggctt ctctctgccc acaaccgagc tgtgctagct   1920

cagcttggct gccccatcaa gaacctggat gccctggaga atgcccaggc catcaagaag   1980
```

-continued

```
aagctgggca agctgggccg gcaggtgctg cccccatcag agctccttga ccacctcttc   2040

ttccactatg agttccagaa ccagcgcttc tccgctgagg tgctcagctc cctgcgtcag   2100

ctcaacctgg caggtgtgcg catgacacca gtcaagtgca cagtggtggc agctgtgctg   2160

ggcagcggaa ggcatgccct ggatgaggtg aacttggcct cctgccagct agatcctgct   2220

gggctgcgca cactcctgcc tgtcttcctg cgtgcccgga agctgggctt gcaactcaac   2280

agcctgggcc ctgaggcctg caaggacctc cgagacctgt tgctgcatga ccagtgccaa   2340

attaccacac tgcggctgtc caacaacccg ctgacggagg caggtgttgc cgtgctaatg   2400

gaggggctgg caggaaacac ctcagtgacg cacctgtccc tgctgcacac gggccttggg   2460

gacgaaggcc tggagctgct ggctgcccag ctggaccgca accggcagct gcaggagctg   2520

aacgtggcgt acaacggtgc tggtgacaca gcggccctgg ccctggccag agctgcccgg   2580

gagcaccctt ccctggaact gctacacctc tacttcaatg agctgagctc agagggccgc   2640

caggtcttgc gagacttggg ggtgctgct gaaggtggtg cccgggtggt ggtgtcactg   2700

acagagggga cggcggtgtc agaatactgg tcagtgatcc tcagtgaagt ccagcggaac   2760

ctcaatagct gggatcgggc ccgggttcag cgacaccttg agctcctact gcgggatctg   2820

gaagatagcc ggggtgccac ccttaatcct tgacgcaagg cccagctgct gcgagtggag   2880

ggcgaggtca gggccctcct ggagcagctg ggaagctctg gaagctgaga cactggcggc   2940

aggcacctag ctatgtgacc actggcccta aaccttttcc ctctgtggcc tcctggcttg   3000

cactgctccc tctagaa                                                  3017
```

<210> SEQ ID NO 18
<211> LENGTH: 950
<212> TYPE: PRT
<213> ORGANISM: Homo sapiens

<400> SEQUENCE: 18

```
Met Arg Trp Gly His His Leu Pro Arg Ala Ser Trp Gly Ser Gly Phe
1               5                   10                  15

Arg Arg Ala Leu Gln Arg Pro Asp Asp Arg Ile Pro Phe Leu Ile His
            20                  25                  30

Trp Ser Trp Pro Leu Gln Gly Glu Arg Pro Phe Gly Pro Pro Arg Ala
        35                  40                  45

Phe Ile Arg His His Gly Ser Ser Val Asp Ser Ala Pro Pro Ser Gly
    50                  55                  60

Arg His Gly Arg Leu Phe Pro Ser Ala Ser Ala Thr Glu Ala Ile Gln
65                  70                  75                  80

Arg His Arg Arg Asn Leu Ala Glu Trp Phe Ser Arg Leu Pro Arg Glu
                85                  90                  95

Glu Arg Gln Phe Gly Pro Thr Phe Ala Leu Asp Thr Val His Val Asp
            100                 105                 110

Pro Val Ile Arg Glu Ser Thr Pro Asp Glu Leu Leu Arg Pro Pro Ala
        115                 120                 125

Glu Leu Ala Leu Glu His Gln Pro Pro Gln Ala Gly Leu Pro Pro Leu
    130                 135                 140

Ala Leu Ser Gln Leu Phe Asn Pro Asp Ala Cys Gly Arg Arg Val Gln
145                 150                 155                 160

Thr Val Val Leu Tyr Gly Thr Val Gly Thr Gly Lys Ser Thr Leu Val
                165                 170                 175

Arg Lys Met Val Leu Asp Trp Cys Tyr Gly Arg Leu Pro Ala Phe Glu
```

-continued

```
            180                 185                 190

Leu Leu Ile Pro Phe Ser Cys Glu Asp Leu Ser Ser Leu Gly Pro Ala
        195                 200                 205

Pro Ala Ser Leu Cys Gln Leu Val Ala Gln Arg Tyr Thr Pro Leu Lys
    210                 215                 220

Glu Val Leu Pro Leu Met Ala Ala Ala Gly Ser His Leu Leu Phe Val
225                 230                 235                 240

Leu His Gly Leu Glu His Leu Asn Leu Asp Phe Arg Leu Ala Gly Thr
                245                 250                 255

Gly Leu Cys Ser Asp Pro Glu Glu Pro Gln Glu Pro Ala Ala Ile Ile
            260                 265                 270

Val Asn Leu Leu Arg Lys Tyr Met Leu Pro Gln Ala Ser Ile Leu Val
        275                 280                 285

Thr Thr Arg Pro Ser Ala Ile Gly Arg Ile Pro Ser Lys Tyr Val Gly
    290                 295                 300

Arg Tyr Gly Glu Ile Cys Gly Phe Ser Asp Thr Asn Leu Gln Lys Leu
305                 310                 315                 320

Tyr Phe Gln Leu Arg Leu Asn Gln Pro Tyr Cys Gly Tyr Ala Val Gly
                325                 330                 335

Gly Ser Gly Val Ser Ala Thr Pro Ala Gln Arg Asp His Leu Val Gln
            340                 345                 350

Met Leu Ser Arg Asn Leu Glu Gly His His Gln Ile Ala Ala Ala Cys
        355                 360                 365

Phe Leu Pro Ser Tyr Cys Trp Leu Val Cys Ala Thr Leu His Phe Leu
    370                 375                 380

His Ala Pro Thr Pro Ala Gly Gln Thr Leu Thr Ser Ile Tyr Thr Ser
385                 390                 395                 400

Phe Leu Arg Leu Asn Phe Ser Gly Glu Thr Leu Asp Ser Thr Asp Pro
                405                 410                 415

Ser Asn Leu Ser Leu Met Ala Tyr Ala Ala Arg Thr Met Gly Lys Leu
            420                 425                 430

Ala Tyr Glu Gly Val Ser Ser Arg Lys Thr Tyr Phe Ser Glu Glu Asp
        435                 440                 445

Val Cys Gly Cys Leu Glu Ala Gly Ile Arg Thr Glu Glu Glu Phe Gln
    450                 455                 460

Leu Leu His Ile Phe Arg Arg Asp Ala Leu Arg Phe Phe Leu Ala Pro
465                 470                 475                 480

Cys Val Glu Pro Gly Arg Ala Gly Thr Phe Val Phe Thr Val Pro Ala
                485                 490                 495

Met Gln Glu Tyr Leu Ala Ala Leu Tyr Ile Val Leu Gly Leu Arg Lys
            500                 505                 510

Thr Thr Leu Gln Lys Val Gly Lys Glu Val Ala Glu Leu Val Gly Arg
        515                 520                 525

Val Gly Glu Asp Val Ser Leu Val Leu Gly Ile Met Ala Lys Leu Leu
    530                 535                 540

Pro Leu Arg Ala Leu Pro Leu Leu Phe Asn Leu Ile Lys Val Val Pro
545                 550                 555                 560

Arg Val Phe Gly Arg Met Val Gly Lys Ser Arg Glu Ala Val Thr Gln
                565                 570                 575

Ala Met Val Leu Glu Met Phe Arg Glu Glu Asp Tyr Tyr Asn Asp Asp
            580                 585                 590

Val Leu Asp Gln Met Gly Ala Ser Ile Leu Gly Val Glu Gly Pro Arg
        595                 600                 605
```

-continued

```
Arg His Pro Asp Glu Pro Pro Glu Asp Glu Val Phe Glu Leu Phe Pro
    610                 615                 620

Met Phe Met Gly Gly Leu Leu Ser Ala His Asn Arg Ala Val Leu Ala
625                 630                 635                 640

Gln Leu Gly Cys Pro Ile Lys Asn Leu Asp Ala Leu Glu Asn Ala Gln
                645                 650                 655

Ala Ile Lys Lys Lys Leu Gly Lys Leu Gly Arg Gln Val Leu Pro Pro
            660                 665                 670

Ser Glu Leu Leu Asp His Leu Phe Phe His Tyr Glu Phe Gln Asn Gln
        675                 680                 685

Arg Phe Ser Ala Glu Val Leu Ser Ser Leu Arg Gln Leu Asn Leu Ala
    690                 695                 700

Gly Val Arg Met Thr Pro Val Lys Cys Thr Val Val Ala Ala Val Leu
705                 710                 715                 720

Gly Ser Gly Arg His Ala Leu Asp Glu Val Asn Leu Ala Ser Cys Gln
                725                 730                 735

Leu Asp Pro Ala Gly Leu Arg Thr Leu Leu Pro Val Phe Leu Arg Ala
            740                 745                 750

Arg Lys Leu Gly Leu Gln Leu Asn Ser Leu Gly Pro Glu Ala Cys Lys
        755                 760                 765

Asp Leu Arg Asp Leu Leu Leu His Asp Gln Cys Gln Ile Thr Thr Leu
    770                 775                 780

Arg Leu Ser Asn Asn Pro Leu Thr Glu Ala Gly Val Ala Val Leu Met
785                 790                 795                 800

Glu Gly Leu Ala Gly Asn Thr Ser Val Thr His Leu Ser Leu Leu His
                805                 810                 815

Thr Gly Leu Gly Asp Glu Gly Leu Glu Leu Leu Ala Ala Gln Leu Asp
            820                 825                 830

Arg Asn Arg Gln Leu Gln Glu Leu Asn Val Ala Tyr Asn Gly Ala Gly
        835                 840                 845

Asp Thr Ala Ala Leu Ala Leu Ala Arg Ala Ala Arg Glu His Pro Ser
    850                 855                 860

Leu Glu Leu Leu His Leu Tyr Phe Asn Glu Leu Ser Ser Glu Gly Arg
865                 870                 875                 880

Gln Val Leu Arg Asp Leu Gly Gly Ala Ala Glu Gly Gly Ala Arg Val
                885                 890                 895

Val Val Ser Leu Thr Glu Gly Thr Ala Val Ser Glu Tyr Trp Ser Val
            900                 905                 910

Ile Leu Ser Glu Val Gln Arg Asn Leu Asn Ser Trp Asp Arg Ala Arg
        915                 920                 925

Val Gln Arg His Leu Glu Leu Leu Leu Arg Asp Leu Glu Asp Ser Arg
    930                 935                 940

Gly Ala Thr Leu Asn Pro
945                 950
```

<210> SEQ ID NO 19
<211> LENGTH: 2800
<212> TYPE: DNA
<213> ORGANISM: Homo sapiens

<400> SEQUENCE: 19

```
atgagatggg gccaccattt gcccagggcc tcttggggct ctggttttag aagagcactc      60

cagcgaccag atgatcgtat ccccttcctg atccactgga gttggcccct tcaaggggag     120
```

-continued

```
cgtccctttg ggccccctag ggcctttata cgccaccacg gaagctcggt agatagcgct    180
cccccatccg ggaggcatgg acggctgttc cccagcgcct ctgcaactga agctatacag    240
cggcaccgcc ggaacctggc tgagtggttc agccggctgc ccagggagga gcgccagttt    300
ggcccaacct ttgccctaga cacggtccac gttgaccctg tgatccgcga gagtacccct    360
gatgagctac ttcgcccacc cgcggagctg gccctggagc atcagccacc ccaggccggg    420
ctccccccac tggccttgtc tcagctcttt aacccggatg cctgtgggcg ccgggtgcag    480
acagtggtgc tgtatgggac agtgggcaca ggcaagagca cgctggtgcg caagatggtt    540
ctggactggt gttatgggcg gctgccggcc ttcgagctgc tcatcccctt ctcctgtgag    600
gacctgtcat ccctgggccc tgccccagcc tccctgtgcc aacttgtggc ccagcgctac    660
acgcccctga aggaggttct gcccctgatg gctgctgctg ggtcccacct cctctttgtg    720
ctccatggct tagagcatct caacctcgac ttccggctgg caggcacggg actttgtagt    780
gacccggagg aaccgcagga accagctgct atcatcgtca acctgctgcg caaatacatg    840
ctgcctcagg ccagcattct ggtgaccact cggccctctg ccattggccg tatccccagc    900
aagtacgtgg gccgctatgg tgagatctgc ggtttctctg ataccaacct gcagaagctc    960
tacttccagc tccgcctcaa ccagccgtac tgcgggtatg ccgttggcgg ttcaggtgtc   1020
tctgccacac cagctcagcg tgaccacctg gtgcagatgc tctcccggaa cctggagggg   1080
caccaccaga tagccgctgc ctgcttcctg ccgtcctatt gctggctcgt ttgtgccacc   1140
ttgcacttcc tgcatgcccc cacgcctgct gggcagaccc ttacaagcat ctataccagc   1200
ttcctgcgcc tcaacttcag cggggaaacc ctggacagca ctgacccctc caatttgtcc   1260
ctgatggcct atgcagcccg aaccatgggc aagttggcct atgagggggt gtcctcccgc   1320
aagacctact tctctgaaga ggatgtctgt ggctgcctgg aggctggcat caggacggag   1380
gaggagtttc agctgctgca catcttccgt cgggatgccc tgaggttttt cctggcccca   1440
tgtgtggagc cagggcgtgc aggcaccttc gtgttcaccg tgcccgccat gcaggaatac   1500
ctggctgccc tctacattgt gctgggtttg cgcaagacga ccctgcaaaa ggtgggcaag   1560
gaagtggctg agctcgtggg ccgtgttggg gaggacgtca gcctggtact gggcatcatg   1620
gccaagctgc tgcctctgcg ggctctgcct ctgctcttca acctgatcaa ggtggttcca   1680
cgagtgtttg ggcgcatggt gggtaaaagc cgggaggcgg tgactcaggc catggtgctg   1740
gagatgtttc gagaggagga ctactacaac gatgatgttc tggaccagat gggcgccagt   1800
atcctgggcg tggagggccc ccggcgccac ccagatgagc cccctgagga tgaagtcttc   1860
gagctcttcc ccatgttcat ggggggggctt ctctctgccc acaaccgagc tgtgctagct   1920
cagcttggct gccccatcaa gaacctggat gccctggaga atgcccaggc catcaagaag   1980
aagctgggca agctgggccg gcaggtgctg cccccatcag agctccttga ccacctcttc   2040
ttccactatg agttccagaa ccagcgcttc tccgctgagg tgctcagctc cctgcgtcag   2100
ctcaacctgg caggtgtgcg catgacacca gtcaagtgca cagtggtggc agctgtgctg   2160
ggcagcggaa ggcatgccct ggatgaggtg aacttggcct cctgccagct agatcctgct   2220
gggctgcgca cactcctgcc tgtcttcctg cgtgcccgga agctgggctt gcaactcaac   2280
agcctgggcc ctgaggcctg caaggacctc cgagacctgt tgctgcatga ccagtgccaa   2340
attaccacac tgcggctgtc caacaacccg ctgacggagg caggtgttgc cgtgctaatg   2400
gaggggctgg caggaaacac ctcagtgacg cacctgtccc tgctgcacac gggccttggg   2460
gacgaaggcc tggagctgct ggctgcccag ctggaccgca accggcagct gcaggagctg   2520
```

-continued

```
aacgtggcgt acaacggtgc tggtgacaca gcggccctgg ccctggccag agctgcccgg   2580

gagcaccctt ccctggaact gctacagggt gtcgccatcc agatgtgttg gaagcttccc   2640

ctcctgcctt atgctcacct gtggacaccg aggatgccct cacattggtg ctttctcctc   2700

atcctcatgc cccctttgcc acaatggtat gatggcttgg tagcccctcg aggcagatgc   2760

acctgacttg ctgctattaa aaagccgtgt gccttctacc                         2800


<210> SEQ ID NO 20
<211> LENGTH: 932
<212> TYPE: PRT
<213> ORGANISM: Homo sapiens

<400> SEQUENCE: 20

Met Arg Trp Gly His His Leu Pro Arg Ala Ser Trp Gly Ser Gly Phe
1               5                   10                  15

Arg Arg Ala Leu Gln Arg Pro Asp Asp Arg Ile Pro Phe Leu Ile His
            20                  25                  30

Trp Ser Trp Pro Leu Gln Gly Glu Arg Pro Phe Gly Pro Pro Arg Ala
        35                  40                  45

Phe Ile Arg His His Gly Ser Ser Val Asp Ser Ala Pro Pro Ser Gly
    50                  55                  60

Arg His Gly Arg Leu Phe Pro Ser Ala Ser Ala Thr Glu Ala Ile Gln
65                  70                  75                  80

Arg His Arg Arg Asn Leu Ala Glu Trp Phe Ser Arg Leu Pro Arg Glu
                85                  90                  95

Glu Arg Gln Phe Gly Pro Thr Phe Ala Leu Asp Thr Val His Val Asp
            100                 105                 110

Pro Val Ile Arg Glu Ser Thr Pro Asp Glu Leu Leu Arg Pro Pro Ala
        115                 120                 125

Glu Leu Ala Leu Glu His Gln Pro Pro Gln Ala Gly Leu Pro Pro Leu
    130                 135                 140

Ala Leu Ser Gln Leu Phe Asn Pro Asp Ala Cys Gly Arg Arg Val Gln
145                 150                 155                 160

Thr Val Val Leu Tyr Gly Thr Val Gly Thr Gly Lys Ser Thr Leu Val
                165                 170                 175

Arg Lys Met Val Leu Asp Trp Cys Tyr Gly Arg Leu Pro Ala Phe Glu
            180                 185                 190

Leu Leu Ile Pro Phe Ser Cys Glu Asp Leu Ser Ser Leu Gly Pro Ala
        195                 200                 205

Pro Ala Ser Leu Cys Gln Leu Val Ala Gln Arg Tyr Thr Pro Leu Lys
    210                 215                 220

Glu Val Leu Pro Leu Met Ala Ala Ala Gly Ser His Leu Leu Phe Val
225                 230                 235                 240

Leu His Gly Leu Glu His Leu Asn Leu Asp Phe Arg Leu Ala Gly Thr
                245                 250                 255

Gly Leu Cys Ser Asp Pro Glu Glu Pro Gln Glu Pro Ala Ala Ile Ile
            260                 265                 270

Val Asn Leu Leu Arg Lys Tyr Met Leu Pro Gln Ala Ser Ile Leu Val
        275                 280                 285

Thr Thr Arg Pro Ser Ala Ile Gly Arg Ile Pro Ser Lys Tyr Val Gly
    290                 295                 300

Arg Tyr Gly Glu Ile Cys Gly Phe Ser Asp Thr Asn Leu Gln Lys Leu
305                 310                 315                 320
```

-continued

```
Tyr Phe Gln Leu Arg Leu Asn Gln Pro Tyr Cys Gly Tyr Ala Val Gly
                325                 330                 335

Gly Ser Gly Val Ser Ala Thr Pro Ala Gln Arg Asp His Leu Val Gln
            340                 345                 350

Met Leu Ser Arg Asn Leu Glu Gly His His Gln Ile Ala Ala Ala Cys
        355                 360                 365

Phe Leu Pro Ser Tyr Cys Trp Leu Val Cys Ala Thr Leu His Phe Leu
    370                 375                 380

His Ala Pro Thr Pro Ala Gly Gln Thr Leu Thr Ser Ile Tyr Thr Ser
385                 390                 395                 400

Phe Leu Arg Leu Asn Phe Ser Gly Glu Thr Leu Asp Ser Thr Asp Pro
                405                 410                 415

Ser Asn Leu Ser Leu Met Ala Tyr Ala Ala Arg Thr Met Gly Lys Leu
            420                 425                 430

Ala Tyr Glu Gly Val Ser Ser Arg Lys Thr Tyr Phe Ser Glu Glu Asp
        435                 440                 445

Val Cys Gly Cys Leu Glu Ala Gly Ile Arg Thr Glu Glu Glu Phe Gln
    450                 455                 460

Leu Leu His Ile Phe Arg Arg Asp Ala Leu Arg Phe Phe Leu Ala Pro
465                 470                 475                 480

Cys Val Glu Pro Gly Arg Ala Gly Thr Phe Val Phe Thr Val Pro Ala
                485                 490                 495

Met Gln Glu Tyr Leu Ala Ala Leu Tyr Ile Val Leu Gly Leu Arg Lys
            500                 505                 510

Thr Thr Leu Gln Lys Val Gly Lys Glu Val Ala Glu Leu Val Gly Arg
        515                 520                 525

Val Gly Glu Asp Val Ser Leu Val Leu Gly Ile Met Ala Lys Leu Leu
    530                 535                 540

Pro Leu Arg Ala Leu Pro Leu Leu Phe Asn Leu Ile Lys Val Val Pro
545                 550                 555                 560

Arg Val Phe Gly Arg Met Val Gly Lys Ser Arg Glu Ala Val Thr Gln
                565                 570                 575

Ala Met Val Leu Glu Met Phe Arg Glu Glu Asp Tyr Tyr Asn Asp Asp
            580                 585                 590

Val Leu Asp Gln Met Gly Ala Ser Ile Leu Gly Val Glu Gly Pro Arg
        595                 600                 605

Arg His Pro Asp Glu Pro Pro Glu Asp Glu Val Phe Glu Leu Phe Pro
    610                 615                 620

Met Phe Met Gly Gly Leu Leu Ser Ala His Asn Arg Ala Val Leu Ala
625                 630                 635                 640

Gln Leu Gly Cys Pro Ile Lys Asn Leu Asp Ala Leu Glu Asn Ala Gln
                645                 650                 655

Ala Ile Lys Lys Lys Leu Gly Lys Leu Gly Arg Gln Val Leu Pro Pro
            660                 665                 670

Ser Glu Leu Leu Asp His Leu Phe Phe His Tyr Glu Phe Gln Asn Gln
        675                 680                 685

Arg Phe Ser Ala Glu Val Leu Ser Ser Leu Arg Gln Leu Asn Leu Ala
    690                 695                 700

Gly Val Arg Met Thr Pro Val Lys Cys Thr Val Val Ala Ala Val Leu
705                 710                 715                 720

Gly Ser Gly Arg His Ala Leu Asp Glu Val Asn Leu Ala Ser Cys Gln
                725                 730                 735

Leu Asp Pro Ala Gly Leu Arg Thr Leu Leu Pro Val Phe Leu Arg Ala
```

-continued

```
            740                 745                 750

Arg Lys Leu Gly Leu Gln Leu Asn Ser Leu Gly Pro Glu Ala Cys Lys
        755                 760                 765

Asp Leu Arg Asp Leu Leu Leu His Asp Gln Cys Gln Ile Thr Thr Leu
    770                 775                 780

Arg Leu Ser Asn Asn Pro Leu Thr Glu Ala Gly Val Ala Val Leu Met
785                 790                 795                 800

Glu Gly Leu Ala Gly Asn Thr Ser Val Thr His Leu Ser Leu Leu His
                805                 810                 815

Thr Gly Leu Gly Asp Glu Gly Leu Glu Leu Leu Ala Ala Gln Leu Asp
            820                 825                 830

Arg Asn Arg Gln Leu Gln Glu Leu Asn Val Ala Tyr Asn Gly Ala Gly
        835                 840                 845

Asp Thr Ala Ala Leu Ala Leu Ala Arg Ala Ala Arg Glu His Pro Ser
    850                 855                 860

Leu Glu Leu Leu Gln Gly Val Ala Ile Gln Met Cys Trp Lys Leu Pro
865                 870                 875                 880

Leu Leu Pro Tyr Ala His Leu Trp Thr Pro Arg Met Pro Ser His Trp
                885                 890                 895

Cys Phe Leu Leu Ile Leu Met Pro Pro Leu Pro Gln Trp Tyr Asp Gly
            900                 905                 910

Leu Val Ala Pro Arg Gly Arg Cys Thr Leu Ala Ala Ile Lys Lys Pro
        915                 920                 925

Cys Ala Phe Tyr
    930


<210> SEQ ID NO 21
<211> LENGTH: 3464
<212> TYPE: DNA
<213> ORGANISM: Homo sapiens

<400> SEQUENCE: 21

atgctgcaga attttaagta cccaaagttt ctcaacaagt tgattttcaa gcaagctcac      60

cggttcccca gctcatcttc cttccagttc ccctgtcccc cagctcaact gcctgccctc     120

agttcacctg tcccccagtt catcttcctc ctagctcccc tgtcccctag ctcacctgtg     180

ccccagctcc cctgtccccc aggctggctc ctcatggacc ccgttggcct ccagctcggc     240

aacaagaacc tgtggagctg tcttgtgagg ctgctcacca aagacccaga atggctgaac     300

gccaagatga agttcttcct ccccaacacg gacctggatt ccaggaacga gaccttggac     360

cctgaacaga gagtcatcct gcaactcaac aagctgcatg tccagggttc ggacacctgg     420

cagtctttca ttcattgtgt gtgcatgcag ctggaggtgc ctctggacct ggaggtgctg     480

ctgctgagta cttttggcta tgatgatggg ttcaccagcc agctgggagc tgaggggaaa     540

agccaacctg aatctcagct ccaccatggc ctgaagcgcc cacatcagag ctgtgggtcc     600

tcaccccgcc ggaagcagtg caagaagcag cagctagagt tggccaagaa gtacctgcag     660

ctcctgcgga cctctgccca gcagcgctac aggagccaaa tccctgggtc agggcagccc     720

cacgccttcc accaggtcta tgtccctcca atcctgcgcc gggccacagc atccttagac     780

actccggagg gggccattat gggggacgtc aaggtggaag atggtgctga cgtgagcatc     840

tcggacctct tcaacaccag ggttaacaag ggcccgaggg tgaccgtgct tttggggaag     900

gctggcatgg gcaagaccac gctggcccac cggctctgcc agaagtgggc agagggccat     960

ctgaactgtt tccaggccct gttccttttt gaattccgcc agctcaactt gatcacgagg    1020
```

-continued

```
ttcctgacac cgtccgagct cctttttgat ctgtacctga gccctgaatc ggaccacgac   1080
actgtcttcc agtacctgga gaagaacgct gaccaagtcc tgctgatctt tgatgggcta   1140
gatgaggccc tccagcctat gggtcctgat ggcccaggcc cagtcctcac ccttttctcc   1200
catctctgca atgggaccct cctgcctggc tgccgggcag ccatggtcca catgttgggc   1260
tttgatgggc cacgggtgga agaatatgtg aatcacttct tcagcgccca gccatcgcgg   1320
gagggggccc tggtggagtt acagacaaat ggacgtctcc gaagcctgtg tgcggtgccc   1380
gcactgtgcc aagtcgcctg tctctgcctc caccatctgc ttcctgacca cgccccaggc   1440
cagtctgtgg ccctcctgcc caacatgact cagctctata tgcagatggt gctcgccctc   1500
agccccccctg ggcacttgcc cacctcgtcc ctactggacc tgggggaggt ggccctgagg   1560
ggccctggag acagggaagg ccctgggcac cagcagacag gctatgcttt cacccacctc   1620
agcctgcagg agtttcttgc tgccctgcac ctgatggcca gccccaaggt gaacaaagac   1680
acacttaccc agtatgttac cctccattcc cgctgggtac agcggaccaa agctagactg   1740
ggcctctcag accacctccc caccttcctg gcgggcctgg catcctgcac ctgccgcccc   1800
ttccttagcc acctggcgca gggcaatgag gactgtgtgg gtgccaagca ggctgctgta   1860
gtgcaggtgt tgaagaagtt ggccacccgc aagctcacag ggccaaaggt tgtagagctg   1920
tgtcactgtg tggatgagac acaggagcct gagctggcca gtctcaccgc acaaagcctc   1980
ccctatcaac tgcccttcca caatttccca ctgacctgca ccgacctggc caccctgacc   2040
aacatcctag agcacaggga ggcccccatc cacctggatt ttgatggctg tcccctggag   2100
ccccactgcc ctgaggctct ggtaggctgt gggcagatag agaatctcag ctttaagagc   2160
aggaagtgtg gggatgcctt tgcagaagcc ctctccagga gcttgccgac aatggggagg   2220
ctgcagatgc tggggttagc aggaagtaaa atcactgccc gaggcatcag ccacctggtg   2280
aaagctttgc ctctctgtcc acagctgaaa gaagtcagtt ttcgggacaa ccagctcagt   2340
gaccaggtgg tgctgaacat tgtggaggtt ctccctcacc taccacggct ccggaagctt   2400
gacctctcag ggaaccagct ggaagatgaa ggctgtcggc tgatggcaga ggctgcatcc   2460
cagctgcaca tcgccaggaa gctggacctc agtaacaacg ggctttctgt ggccggggtg   2520
cattgtgtgc tgagggccgt gagtgcgtgc tggaccctgg cagagctgca catcaggctg   2580
acacattgtg gcctccaaga aaagcaccta gagcagctct gcaaggctct gggaggaagc   2640
tgccacctcg gtcacctcca cctcgacttc tcaggcaatg ctctgggggga tgaaggtgca   2700
gcccggctgg ctcagctgct cccagggctg ggagctctgc agtccttgaa cctcagtgag   2760
aacggtttgt ccctggatgc cgtgttgggt ttggttcggt gcttctccac tctgcagtgg   2820
ctcttccgct tggacatcag cctcagtgag tgtcctctgg agcccccaag cctcacccgc   2880
ctctgtgcca ctctgaagga ctgcccggga cccctggaac tgcaattgtc ctgtgagttc   2940
ctgagtgacc agagcctgga gactctactg gactgcttac ctcaactccc tcagctgagc   3000
ctgctgcagc tgagccagac gggactgtcc ccgaaaagcc ccttcctgct ggccaacacc   3060
ttaagcctgt gtccacgggt taaaaaggtg gatctcaggt tcacaggctg cagcctcagc   3120
caggagcacg tagagtcact ctgctggttg ctgagcaagt gtaaagacct cagccaggtg   3180
gatctctcag caaacctgct gggcgacagc ggactcagat gccttctgga atgtctgccg   3240
caggtgccca tctccggttt gcttgagagc ttggtcacgg cctgtgggac tgtgtcgccg   3300
atcgcgcccg gcaaccccca atggccaccg aagtgtgcca tccgcgtgcg atgggggaca   3360
```

-continued

```
ccgtgctgcg ggctgtcgtt caggacatct tatgtggggt attgcggcgc caatacccgg   3420

tcacccctat tgcagggggg gatatggcat tctcctctat gtgg                     3464


<210> SEQ ID NO 22
<211> LENGTH: 1154
<212> TYPE: PRT
<213> ORGANISM: Homo sapiens

<400> SEQUENCE: 22

Met Leu Gln Asn Phe Lys Tyr Pro Lys Phe Leu Asn Lys Leu Ile Phe
1               5                   10                  15

Lys Gln Ala His Arg Phe Pro Ser Ser Ser Ser Phe Gln Phe Pro Cys
            20                  25                  30

Pro Pro Ala Gln Leu Pro Ala Leu Ser Ser Pro Val Pro Gln Phe Ile
        35                  40                  45

Phe Leu Leu Ala Pro Leu Ser Pro Ser Ser Pro Val Pro Gln Leu Pro
    50                  55                  60

Cys Pro Pro Gly Trp Leu Leu Met Asp Pro Val Gly Leu Gln Leu Gly
65                  70                  75                  80

Asn Lys Asn Leu Trp Ser Cys Leu Val Arg Leu Leu Thr Lys Asp Pro
                85                  90                  95

Glu Trp Leu Asn Ala Lys Met Lys Phe Phe Leu Pro Asn Thr Asp Leu
            100                 105                 110

Asp Ser Arg Asn Glu Thr Leu Asp Pro Glu Gln Arg Val Ile Leu Gln
        115                 120                 125

Leu Asn Lys Leu His Val Gln Gly Ser Asp Thr Trp Gln Ser Phe Ile
    130                 135                 140

His Cys Val Cys Met Gln Leu Glu Val Pro Leu Asp Leu Glu Val Leu
145                 150                 155                 160

Leu Leu Ser Thr Phe Gly Tyr Asp Asp Gly Phe Thr Ser Gln Leu Gly
                165                 170                 175

Ala Glu Gly Lys Ser Gln Pro Glu Ser Gln Leu His His Gly Leu Lys
            180                 185                 190

Arg Pro His Gln Ser Cys Gly Ser Ser Pro Arg Arg Lys Gln Cys Lys
        195                 200                 205

Lys Gln Gln Leu Glu Leu Ala Lys Lys Tyr Leu Gln Leu Leu Arg Thr
    210                 215                 220

Ser Ala Gln Gln Arg Tyr Arg Ser Gln Ile Pro Gly Ser Gly Gln Pro
225                 230                 235                 240

His Ala Phe His Gln Val Tyr Val Pro Pro Ile Leu Arg Arg Ala Thr
                245                 250                 255

Ala Ser Leu Asp Thr Pro Glu Gly Ala Ile Met Gly Asp Val Lys Val
            260                 265                 270

Glu Asp Gly Ala Asp Val Ser Ile Ser Asp Leu Phe Asn Thr Arg Val
        275                 280                 285

Asn Lys Gly Pro Arg Val Thr Val Leu Leu Gly Lys Ala Gly Met Gly
    290                 295                 300

Lys Thr Thr Leu Ala His Arg Leu Cys Gln Lys Trp Ala Glu Gly His
305                 310                 315                 320

Leu Asn Cys Phe Gln Ala Leu Phe Leu Phe Glu Phe Arg Gln Leu Asn
                325                 330                 335

Leu Ile Thr Arg Phe Leu Thr Pro Ser Glu Leu Leu Phe Asp Leu Tyr
            340                 345                 350

Leu Ser Pro Glu Ser Asp His Asp Thr Val Phe Gln Tyr Leu Glu Lys
```

-continued

```
        355                 360                 365

Asn Ala Asp Gln Val Leu Leu Ile Phe Asp Gly Leu Asp Glu Ala Leu
    370                 375                 380

Gln Pro Met Gly Pro Asp Gly Pro Gly Pro Val Leu Thr Leu Phe Ser
385                 390                 395                 400

His Leu Cys Asn Gly Thr Leu Leu Pro Gly Cys Arg Ala Ala Met Val
                405                 410                 415

His Met Leu Gly Phe Asp Gly Pro Arg Val Glu Glu Tyr Val Asn His
            420                 425                 430

Phe Phe Ser Ala Gln Pro Ser Arg Glu Gly Ala Leu Val Glu Leu Gln
        435                 440                 445

Thr Asn Gly Arg Leu Arg Ser Leu Cys Ala Val Pro Ala Leu Cys Gln
    450                 455                 460

Val Ala Cys Leu Cys Leu His His Leu Leu Pro Asp His Ala Pro Gly
465                 470                 475                 480

Gln Ser Val Ala Leu Leu Pro Asn Met Thr Gln Leu Tyr Met Gln Met
                485                 490                 495

Val Leu Ala Leu Ser Pro Pro Gly His Leu Pro Thr Ser Ser Leu Leu
            500                 505                 510

Asp Leu Gly Glu Val Ala Leu Arg Gly Pro Gly Asp Arg Glu Gly Pro
        515                 520                 525

Gly His Gln Gln Thr Gly Tyr Ala Phe Thr His Leu Ser Leu Gln Glu
    530                 535                 540

Phe Leu Ala Ala Leu His Leu Met Ala Ser Pro Lys Val Asn Lys Asp
545                 550                 555                 560

Thr Leu Thr Gln Tyr Val Thr Leu His Ser Arg Trp Val Gln Arg Thr
                565                 570                 575

Lys Ala Arg Leu Gly Leu Ser Asp His Leu Pro Thr Phe Leu Ala Gly
            580                 585                 590

Leu Ala Ser Cys Thr Cys Arg Pro Phe Leu Ser His Leu Ala Gln Gly
        595                 600                 605

Asn Glu Asp Cys Val Gly Ala Lys Gln Ala Ala Val Val Gln Val Leu
    610                 615                 620

Lys Lys Leu Ala Thr Arg Lys Leu Thr Gly Pro Lys Val Val Glu Leu
625                 630                 635                 640

Cys His Cys Val Asp Glu Thr Gln Glu Pro Glu Leu Ala Ser Leu Thr
                645                 650                 655

Ala Gln Ser Leu Pro Tyr Gln Leu Pro Phe His Asn Phe Pro Leu Thr
            660                 665                 670

Cys Thr Asp Leu Ala Thr Leu Thr Asn Ile Leu Glu His Arg Glu Ala
        675                 680                 685

Pro Ile His Leu Asp Phe Asp Gly Cys Pro Leu Glu Pro His Cys Pro
    690                 695                 700

Glu Ala Leu Val Gly Cys Gly Gln Ile Glu Asn Leu Ser Phe Lys Ser
705                 710                 715                 720

Arg Lys Cys Gly Asp Ala Phe Ala Glu Ala Leu Ser Arg Ser Leu Pro
                725                 730                 735

Thr Met Gly Arg Leu Gln Met Leu Gly Leu Ala Gly Ser Lys Ile Thr
            740                 745                 750

Ala Arg Gly Ile Ser His Leu Val Lys Ala Leu Pro Leu Cys Pro Gln
        755                 760                 765

Leu Lys Glu Val Ser Phe Arg Asp Asn Gln Leu Ser Asp Gln Val Val
    770                 775                 780
```

-continued

```
Leu Asn Ile Val Glu Val Leu Pro His Leu Pro Arg Leu Arg Lys Leu
785                 790                 795                 800

Asp Leu Ser Gly Asn Gln Leu Glu Asp Glu Gly Cys Arg Leu Met Ala
                805                 810                 815

Glu Ala Ala Ser Gln Leu His Ile Ala Arg Lys Leu Asp Leu Ser Asn
            820                 825                 830

Asn Gly Leu Ser Val Ala Gly Val His Cys Val Leu Arg Ala Val Ser
        835                 840                 845

Ala Cys Trp Thr Leu Ala Glu Leu His Ile Arg Leu Thr His Cys Gly
    850                 855                 860

Leu Gln Glu Lys His Leu Glu Gln Leu Cys Lys Ala Leu Gly Gly Ser
865                 870                 875                 880

Cys His Leu Gly His Leu His Leu Asp Phe Ser Gly Asn Ala Leu Gly
                885                 890                 895

Asp Glu Gly Ala Ala Arg Leu Ala Gln Leu Leu Pro Gly Leu Gly Ala
            900                 905                 910

Leu Gln Ser Leu Asn Leu Ser Glu Asn Gly Leu Ser Leu Asp Ala Val
        915                 920                 925

Leu Gly Leu Val Arg Cys Phe Ser Thr Leu Gln Trp Leu Phe Arg Leu
    930                 935                 940

Asp Ile Ser Leu Ser Glu Cys Pro Leu Glu Pro Pro Ser Leu Thr Arg
945                 950                 955                 960

Leu Cys Ala Thr Leu Lys Asp Cys Pro Gly Pro Leu Glu Leu Gln Leu
                965                 970                 975

Ser Cys Glu Phe Leu Ser Asp Gln Ser Leu Glu Thr Leu Leu Asp Cys
            980                 985                 990

Leu Pro Gln Leu Pro Gln Leu Ser  Leu Leu Gln Leu Ser  Gln Thr Gly
        995                 1000                1005

Leu Ser  Pro Lys Ser Pro Phe  Leu Leu Ala Asn Thr  Leu Ser Leu
    1010                1015                1020

Cys Pro  Arg Val Lys Lys Val  Asp Leu Arg Phe Thr  Gly Cys Ser
    1025                1030                1035

Leu Ser  Gln Glu His Val Glu  Ser Leu Cys Trp Leu  Leu Ser Lys
    1040                1045                1050

Cys Lys  Asp Leu Ser Gln Val  Asp Leu Ser Ala Asn  Leu Leu Gly
    1055                1060                1065

Asp Ser  Gly Leu Arg Cys Leu  Leu Glu Cys Leu Pro  Gln Val Pro
    1070                1075                1080

Ile Ser  Gly Leu Leu Glu Ser  Leu Val Thr Ala Cys  Gly Thr Val
    1085                1090                1095

Ser Pro  Ile Ala Pro Gly Asn  Pro Gln Trp Pro Pro  Lys Cys Ala
    1100                1105                1110

Ile Arg  Val Arg Trp Gly Thr  Pro Cys Cys Gly Leu  Ser Phe Arg
    1115                1120                1125

Thr Ser  Tyr Val Gly Tyr Cys  Gly Ala Asn Thr Arg  Ser Pro Leu
    1130                1135                1140

Leu Gln  Gly Gly Ile Trp His  Ser Pro Leu Cys
    1145                1150
```

<210> SEQ ID NO 23
<211> LENGTH: 4464
<212> TYPE: DNA
<213> ORGANISM: Homo sapiens -continued

<400> SEQUENCE: 23

```
ggcccagtcc tcacccttt ctcccatctc tgcaatggga ccctcctgcc tggctgccgg     60
gtgatggcta cctcccgtcc agggaagctg cctgcctgcc tgcctgcaga ggcagccatg    120
gtccacatgt tgggctttga tgggccacgg gtggaagaat atgtgaatca cttcttcagc    180
gcccagccat cgcgggaggg ggccctggtg gagttacaga caaatggacg tctccgaagc    240
ctgtgtgcgg tgcccgcact gtgccaagtc gcctgtctct gcctccacca tctgcttcct    300
gaccacgccc caggccagtc tgtggccctc ctgcccaaca tgactcagct ctatatgcag    360
atggtgctcg ccctcagccc ccctgggcac ttgctcacct cgtccctact ggacctgggg    420
gaggtggccc tgaggggcct ggagacaggg aaggttatct tctatgcaaa agatattgct    480
ccacccttga tagcttttgg ggccactcac agcctgctga cttccttctg cgtccgcaca    540
ggccctgggc accagcagac aggctatgct ttcacccacc tcagcctgca ggagtttctt    600
gctgccctgc acctgatggc cagccccaag gtgaacaaag acacacttac ccagtatgtt    660
accctccatt cccgctgggt acagcggacc aaagctagac tgggcctctc agaccacctc    720
cccaccttcc tggcgggcct ggcatcctgc acctgccgcc ccttccttag ccacctggcg    780
cagggcaatg aggactgtgt gggtgccaag caggctgctg tagtgcaggt gttgaagaag    840
ttggccaccc gcaagctcac agggccaaag gttgtagagc tgtgtcactg tgtggatgag    900
acacaggagc ctgagctggc cagtctcacc gcacaaagcc tcccctatca actgcccttc    960
cacaatttcc cactgacctg caccgacctg gccaccctga ccaacatcct agagcacagg   1020
gaggccccca tccacctgga ttttgatggc tgtcccctgg agccccactg ccctgaggct   1080
ctggtaggct gtgggcagat agagaatctc agctttaaga gcaggaagtg tggggatgcc   1140
tttgcagaag ccctctccag gagcttgccg acaatgggga ggctgcagat gctggggtta   1200
gcaggaagta aaatcactgc ccgaggcatc agccacctgg tgaaagcttt gcctctctgt   1260
ccacagctga aagaagtcag ttttcgggac aaccagctca gtgaccaggt ggtgctgaac   1320
attgtggagg ttctccctca cctaccacgg ctccggaagc ttgacctgag cagcaacagc   1380
atctgcgtgt caaccctact ctgcttggca agggtggcag tcacgtgtcc taccgtcagg   1440
atgcttcagg ccagggagcg gaccatcatc ttccttcttt ccccgcccac agagacaact   1500
gcagagctac aaagagctcc agacctgcag gaaagtgacg gccagaggaa aggggctcag   1560
agcagaagct tgacgctcag gctgcagaag tgtcagctcc aggtccacga tgcggaggcc   1620
ctcatagccc tgctccagga aggccctcac ctggaggaag tggacctctc agggaaccag   1680
ctggaagatg aaggctgtcg gctgatggca gaggctgcat cccagctgca catcgccagg   1740
aagctggacc tcagcgacaa cgggctttct gtggccgggg tgcattgtgt gctgagggcc   1800
gtgagtgcgt gctggaccct ggcagagctg cacatcagcc tgcagcacaa aactgtgatc   1860
ttcatgtttg cccaggagcc agaggagcag aaggggcccc aggagagggc tgcatttctt   1920
gacagcctca tgctccagat gccctctgag ctgcctctga gctcccgaag gatgaggctg   1980
acacattgtg gcctccaaga aaagcaccta gagcagctct gcaaggctct gggaggaagc   2040
tgccacctcg gtcacctcca cctcgacttc tcaggcaatg ctctggggga tgaaggtgca   2100
gcccggctgg ctcagctgct cccagggctg ggagctctgc agtccttgaa cctcagtgag   2160
aacggtttgt ccctggatgc cgtgttgggc ttggttcggt gcttctccac tctgcagtgg   2220
ctcttccgct tggacatcag ctttgaaagc caacacatcc tcctgagagg ggacaagaca   2280
agcagcctca gtgagtgtcc tctggagccc ccaagcctca cccgcctctg tgccactctg   2340
```

-continued

```
aaggactgcc cgggacccct ggaactgcaa ttgtcctgtg agttcctgag tgaccagagc   2400
ctggagactc tactggactg cttacctcaa ctccctcagc tgagcctgct gcagctgagc   2460
cagacgggac tgtccccgaa aagccccttc ctgctggcca acaccttaag cctgtgtcca   2520
cgggttaaaa aggtggatct caggtccctg caccatgcaa ctttgcactt cagatccaac   2580
gaggaggagg aaggcgtgtg ctgtggcagg ttcacaggct gcagcctcag ccaggagcac   2640
gtagagtcac tctgctggtt gctgagcaag tgtaaagacc tcagccaggt ggatctgagt   2700
cacaacagca tttctcagga aagtgccctg tacctgctgg agacactgcc ctcctgccca   2760
cgtgtccggg aggcctcagt gaacctgggc tctgagcaga gcttccggat tcacttctcc   2820
agagaggacc aggctgggaa gacactcagg ctaagtgagt gcagcttccg gccagagcac   2880
gtgtccaggc tggccaccgg cttgagcaag tccctgcagc tgacggagct cacgctgacc   2940
cagtgctgcc tgggccagaa gcagctggcc atcctcctga gcttggtggg gcgacccgca   3000
gggctgttca gcctcagggt gcaggagccg tgggcggaca gagccagggt tctctccctg   3060
ttagaagtct gcgcccaggc ctcaggcagt gtcactgaaa tcagcatctc cgagacccag   3120
cagcagctct gtgtccagct ggaatttcct cgccaggaag agaatccaga agctgtggca   3180
ctcaggttgg ctcactgtga ccttggagcc caccacagcc ttcttgtcgg gcagctgatg   3240
gagacatgtg ccaggctgca gcagctcagc ttgtctcagg ttaacctctg tgaggacgat   3300
gatgccagtt ccctgctgct gcagagcctc ctgctgtccc tctctgagct gaagacattt   3360
cggctgacct ccagctgtgt gagcaccgag ggcctcgccc acctggcatc tggtctgggc   3420
cactgccacc acttggagga gctggacttg tctaacaatc aatttgatga ggagggcacc   3480
aaggcgctga tgagggccct tgaggggaaa tggatgctaa agaggctgga cctcagtcac   3540
cttctgctga acagctccac cttggccttg cttactcaca gactaagcca gatgacctgc   3600
ctgcagagcc tcagactgaa caggaacagt atcggtgatg tcggttgctg ccacctttct   3660
gaggctctca gggctgccac cagcctagag gagctggact tgagccacaa ccagattgga   3720
gacgctggtg tccagcactt agctaccatc ctgcctgggc tgccagagct caggaagata   3780
gacctctcag ggaatagcat cagctcagcc gggggagtgc agttggcaga gtctctcgtt   3840
ctttgcaggc gcctggagga gttgatgctt ggctgcaatg ccctggggga tcccacagcc   3900
ctggggctgg ctcaggagct gccccagcac ctgagggtcc tacacctacc attcagccat   3960
ctgggcccag gtggggccct gagcctggcc caggccctgg atggatcccc ccatttggaa   4020
gagatcagct tggcggaaaa caacctggct ggaggggtcc tgcgtttctg tatggagctc   4080
ccgctgctca gacagataga cctggtttcc tgtaagattg acaaccagac tgccaagctc   4140
ctcacctcca gcttcacgag ctgccctgcc ctggaagtaa tcttgctgtc ctggaatctc   4200
ctcggggatg aggcagctgc cgagctggcc caggtgctgc cgaagatggg ccggctgaag   4260
agagtggacc tggagaagaa tcagatcaca gctttggggg cctggctcct ggctgaagga   4320
ctggcccagg ggtctagcat ccaagtcatc cgcctctgga ataaccccat tccctgcgac   4380
atggcccagc acctgaagag ccaggagccc aggctggact ttgccttctt tgacaaccag   4440
ccccaggccc cttggggtac ttga                                          4464
```

<210> SEQ ID NO 24
<211> LENGTH: 1487
<212> TYPE: PRT
<213> ORGANISM: Homo sapiens -continued

<400> SEQUENCE: 24

```
Gly Pro Val Leu Thr Leu Phe Ser His Leu Cys Asn Gly Thr Leu Leu
1               5                   10                  15

Pro Gly Cys Arg Val Met Ala Thr Ser Arg Pro Gly Lys Leu Pro Ala
            20                  25                  30

Cys Leu Pro Ala Glu Ala Ala Met Val His Met Leu Gly Phe Asp Gly
        35                  40                  45

Pro Arg Val Glu Glu Tyr Val Asn His Phe Phe Ser Ala Gln Pro Ser
    50                  55                  60

Arg Glu Gly Ala Leu Val Glu Leu Gln Thr Asn Gly Arg Leu Arg Ser
65                  70                  75                  80

Leu Cys Ala Val Pro Ala Leu Cys Gln Val Ala Cys Leu Cys Leu His
                85                  90                  95

His Leu Leu Pro Asp His Ala Pro Gly Gln Ser Val Ala Leu Leu Pro
            100                 105                 110

Asn Met Thr Gln Leu Tyr Met Gln Met Val Leu Ala Leu Ser Pro Pro
        115                 120                 125

Gly His Leu Leu Thr Ser Ser Leu Leu Asp Leu Gly Glu Val Ala Leu
    130                 135                 140

Arg Gly Leu Glu Thr Gly Lys Val Ile Phe Tyr Ala Lys Asp Ile Ala
145                 150                 155                 160

Pro Pro Leu Ile Ala Phe Gly Ala Thr His Ser Leu Leu Thr Ser Phe
                165                 170                 175

Arg Val Cys Thr Gly Pro Gly His Gln Gln Thr Gly Tyr Ala Phe Thr
            180                 185                 190

His Leu Ser Leu Gln Glu Phe Leu Ala Ala Leu His Leu Met Ala Ser
        195                 200                 205

Pro Lys Val Asn Lys Asp Thr Leu Thr Gln Tyr Val Thr Leu His Ser
    210                 215                 220

Arg Trp Val Gln Arg Thr Lys Ala Arg Leu Gly Leu Ser Asp His Leu
225                 230                 235                 240

Pro Thr Phe Leu Ala Gly Leu Ala Ser Cys Thr Cys Arg Pro Phe Leu
                245                 250                 255

Ser His Leu Ala Gln Gly Asn Glu Asp Cys Val Gly Ala Lys Gln Ala
            260                 265                 270

Ala Val Val Gln Val Leu Lys Lys Leu Ala Thr Arg Lys Leu Thr Gly
        275                 280                 285

Pro Lys Val Val Glu Leu Cys His Cys Val Asp Glu Thr Gln Glu Pro
    290                 295                 300

Glu Leu Ala Ser Leu Thr Ala Gln Ser Leu Pro Tyr Gln Leu Pro Phe
305                 310                 315                 320

His Asn Phe Pro Leu Thr Cys Thr Asp Leu Ala Thr Leu Thr Asn Ile
                325                 330                 335

Leu Glu His Arg Glu Ala Pro Ile His Leu Asp Phe Asp Gly Cys Pro
            340                 345                 350

Leu Glu Pro His Cys Pro Glu Ala Leu Val Gly Cys Gly Gln Ile Glu
        355                 360                 365

Asn Leu Ser Phe Lys Ser Arg Lys Cys Gly Asp Ala Phe Ala Glu Ala
    370                 375                 380

Leu Ser Arg Ser Leu Pro Thr Met Gly Arg Leu Gln Met Leu Gly Leu
385                 390                 395                 400

Ala Gly Ser Lys Ile Thr Ala Arg Gly Ile Ser His Leu Val Lys Ala
                405                 410                 415
```

-continued

```
Leu Pro Leu Cys Pro Gln Leu Lys Glu Val Ser Phe Arg Asp Asn Gln
            420                 425                 430

Leu Ser Asp Gln Val Val Leu Asn Ile Val Glu Val Leu Pro His Leu
        435                 440                 445

Pro Arg Leu Arg Lys Leu Asp Leu Ser Ser Asn Ser Ile Cys Val Ser
    450                 455                 460

Thr Leu Leu Cys Leu Ala Arg Val Ala Val Thr Cys Pro Thr Val Arg
465                 470                 475                 480

Met Leu Gln Ala Arg Glu Arg Thr Ile Ile Phe Leu Leu Ser Pro Pro
                485                 490                 495

Thr Glu Thr Thr Ala Glu Leu Gln Arg Ala Pro Asp Leu Gln Glu Ser
            500                 505                 510

Asp Gly Gln Arg Lys Gly Ala Gln Ser Arg Ser Leu Thr Leu Arg Leu
        515                 520                 525

Gln Lys Cys Gln Leu Gln Val His Asp Ala Glu Ala Leu Ile Ala Leu
    530                 535                 540

Leu Gln Glu Gly Pro His Leu Glu Glu Val Asp Leu Ser Gly Asn Gln
545                 550                 555                 560

Leu Glu Asp Glu Gly Cys Arg Leu Met Ala Glu Ala Ala Ser Gln Leu
                565                 570                 575

His Ile Ala Arg Lys Leu Asp Leu Ser Asp Asn Gly Leu Ser Val Ala
            580                 585                 590

Gly Val His Cys Val Leu Arg Ala Val Ser Ala Cys Trp Thr Leu Ala
        595                 600                 605

Glu Leu His Ile Ser Leu Gln His Lys Thr Val Ile Phe Met Phe Ala
    610                 615                 620

Gln Glu Pro Glu Glu Gln Lys Gly Pro Gln Glu Arg Ala Ala Phe Leu
625                 630                 635                 640

Asp Ser Leu Met Leu Gln Met Pro Ser Glu Leu Pro Leu Ser Ser Arg
                645                 650                 655

Arg Met Arg Leu Thr His Cys Gly Leu Gln Glu Lys His Leu Glu Gln
            660                 665                 670

Leu Cys Lys Ala Leu Gly Gly Ser Cys His Leu Gly His Leu His Leu
        675                 680                 685

Asp Phe Ser Gly Asn Ala Leu Gly Asp Glu Gly Ala Ala Arg Leu Ala
    690                 695                 700

Gln Leu Leu Pro Gly Leu Gly Ala Leu Gln Ser Leu Asn Leu Ser Glu
705                 710                 715                 720

Asn Gly Leu Ser Leu Asp Ala Val Leu Gly Leu Val Arg Cys Phe Ser
                725                 730                 735

Thr Leu Gln Trp Leu Phe Arg Leu Asp Ile Ser Phe Glu Ser Gln His
            740                 745                 750

Ile Leu Leu Arg Gly Asp Lys Thr Ser Ser Leu Ser Glu Cys Pro Leu
        755                 760                 765

Glu Pro Pro Ser Leu Thr Arg Leu Cys Ala Thr Leu Lys Asp Cys Pro
    770                 775                 780

Gly Pro Leu Glu Leu Gln Leu Ser Cys Glu Phe Leu Ser Asp Gln Ser
785                 790                 795                 800

Leu Glu Thr Leu Leu Asp Cys Leu Pro Gln Leu Pro Gln Leu Ser Leu
                805                 810                 815

Leu Gln Leu Ser Gln Thr Gly Leu Ser Pro Lys Ser Pro Phe Leu Leu
            820                 825                 830
```

-continued

```
Ala Asn Thr Leu Ser Leu Cys Pro Arg Val Lys Lys Val Asp Leu Arg
        835                 840                 845

Ser Leu His His Ala Thr Leu His Phe Arg Ser Asn Glu Glu Glu Glu
    850                 855                 860

Gly Val Cys Cys Gly Arg Phe Thr Gly Cys Ser Leu Ser Gln Glu His
865                 870                 875                 880

Val Glu Ser Leu Cys Trp Leu Leu Ser Lys Cys Lys Asp Leu Ser Gln
                885                 890                 895

Val Asp Leu Ser His Asn Ser Ile Ser Gln Glu Ser Ala Leu Tyr Leu
            900                 905                 910

Leu Glu Thr Leu Pro Ser Cys Pro Arg Val Arg Glu Ala Ser Val Asn
        915                 920                 925

Leu Gly Ser Glu Gln Ser Phe Arg Ile His Phe Ser Arg Glu Asp Gln
    930                 935                 940

Ala Gly Lys Thr Leu Arg Leu Ser Glu Cys Ser Phe Arg Pro Glu His
945                 950                 955                 960

Val Ser Arg Leu Ala Thr Gly Leu Ser Lys Ser Leu Gln Leu Thr Glu
                965                 970                 975

Leu Thr Leu Thr Gln Cys Cys Leu Gly Gln Lys Gln Leu Ala Ile Leu
            980                 985                 990

Leu Ser Leu Val Gly Arg Pro Ala  Gly Leu Phe Ser Leu  Arg Val Gln
        995                 1000                 1005

Glu Pro  Trp Ala Asp Arg Ala  Arg Val Leu Ser Leu  Leu Glu Val
    1010                 1015                 1020

Cys Ala  Gln Ala Ser Gly Ser  Val Thr Glu Ile Ser  Ile Ser Glu
    1025                 1030                 1035

Thr Gln  Gln Gln Leu Cys Val  Gln Leu Glu Phe Pro  Arg Gln Glu
    1040                 1045                 1050

Glu Asn  Pro Glu Ala Val Ala  Leu Arg Leu Ala His  Cys Asp Leu
    1055                 1060                 1065

Gly Ala  His His Ser Leu Leu  Val Gly Gln Leu Met  Glu Thr Cys
    1070                 1075                 1080

Ala Arg  Leu Gln Gln Leu Ser  Leu Ser Gln Val Asn  Leu Cys Glu
    1085                 1090                 1095

Asp Asp  Asp Ala Ser Ser Leu  Leu Leu Gln Ser Leu  Leu Leu Ser
    1100                 1105                 1110

Leu Ser  Glu Leu Lys Thr Phe  Arg Leu Thr Ser Ser  Cys Val Ser
    1115                 1120                 1125

Thr Glu  Gly Leu Ala His Leu  Ala Ser Gly Leu Gly  His Cys His
    1130                 1135                 1140

His Leu  Glu Glu Leu Asp Leu  Ser Asn Asn Gln Phe  Asp Glu Glu
    1145                 1150                 1155

Gly Thr  Lys Ala Leu Met Arg  Ala Leu Glu Gly Lys  Trp Met Leu
    1160                 1165                 1170

Lys Arg  Leu Asp Leu Ser His  Leu Leu Leu Asn Ser  Ser Thr Leu
    1175                 1180                 1185

Ala Leu  Leu Thr His Arg Leu  Ser Gln Met Thr Cys  Leu Gln Ser
    1190                 1195                 1200

Leu Arg  Leu Asn Arg Asn Ser  Ile Gly Asp Val Gly  Cys Cys His
    1205                 1210                 1215

Leu Ser  Glu Ala Leu Arg Ala  Ala Thr Ser Leu Glu  Glu Leu Asp
    1220                 1225                 1230

Leu Ser  His Asn Gln Ile Gly  Asp Ala Gly Val Gln  His Leu Ala
```

-continued

```
    1235                1240                1245

Thr Ile  Leu Pro Gly Leu Pro  Glu Leu Arg Lys Ile  Asp Leu Ser
    1250                1255                1260

Gly Asn  Ser Ile Ser Ser Ala  Gly Gly Val Gln Leu  Ala Glu Ser
    1265                1270                1275

Leu Val  Leu Cys Arg Arg Leu  Glu Glu Leu Met Leu  Gly Cys Asn
    1280                1285                1290

Ala Leu  Gly Asp Pro Thr Ala  Leu Gly Leu Ala Gln  Glu Leu Pro
    1295                1300                1305

Gln His  Leu Arg Val Leu His  Leu Pro Phe Ser His  Leu Gly Pro
    1310                1315                1320

Gly Gly  Ala Leu Ser Leu Ala  Gln Ala Leu Asp Gly  Ser Pro His
    1325                1330                1335

Leu Glu  Glu Ile Ser Leu Ala  Glu Asn Asn Leu Ala  Gly Gly Val
    1340                1345                1350

Leu Arg  Phe Cys Met Glu Leu  Pro Leu Leu Arg Gln  Ile Asp Leu
    1355                1360                1365

Val Ser  Cys Lys Ile Asp Asn  Gln Thr Ala Lys Leu  Leu Thr Ser
    1370                1375                1380

Ser Phe  Thr Ser Cys Pro Ala  Leu Glu Val Ile Leu  Leu Ser Trp
    1385                1390                1395

Asn Leu  Leu Gly Asp Glu Ala  Ala Ala Glu Leu Ala  Gln Val Leu
    1400                1405                1410

Pro Lys  Met Gly Arg Leu Lys  Arg Val Asp Leu Glu  Lys Asn Gln
    1415                1420                1425

Ile Thr  Ala Leu Gly Ala Trp  Leu Leu Ala Glu Gly  Leu Ala Gln
    1430                1435                1440

Gly Ser  Ser Ile Gln Val Ile  Arg Leu Trp Asn Asn  Pro Ile Pro
    1445                1450                1455

Cys Asp  Met Ala Gln His Leu  Lys Ser Gln Glu Pro  Arg Leu Asp
    1460                1465                1470

Phe Ala  Phe Phe Asp Asn Gln  Pro Gln Ala Pro Trp  Gly Thr
    1475                1480                1485
```

```
<210> SEQ ID NO 25
<211> LENGTH: 2230
<212> TYPE: DNA
<213> ORGANISM: Homo sapiens

<400> SEQUENCE: 25

atgaggaagc aagaggtgcg gacgggcagg gaggccggcc agggccacgg tacgggctcc      60

ccagccgagc aggtgaaagc cctcatggat ctgctggctg ggaagggcag tcaaggctcc     120

caggccccgc aggccctgga taggacaccg gatgccccgc tggggccctg cagcaatgac     180

tcaaggatac agaggcaccg caaggccctg ctgagcaagg tgggaggtgg cccggagctg     240

ggcggaccct ggcacaggct ggcctccctc ctgctggtgg agggcctgac ggacctgcag     300

ctgagggaac acgacttcac acaggtggag gccacccgcg ggggcgggca ccccgccagg     360

accgtcgccc tggaccggct cttcctgcct ctctcccggg tgtctgtccc accccgggtc     420

tccatcacta tcggggtggc cggcatgggc aagaccaccc tggtgaggca cttcgtccgc     480

ctctgggccc atgggcaggt cggcaaggac ttctcgctgg tgctgcctct gaccttccgg     540

gatctcaaca cccacgagaa gctgtgtgcc gaccgactca tctgctcggt cttcccgcac     600

gtcggggagc ccagcctggc ggtggcagtc ccagccaggg ccctcctgat cctggacggc     660
```

-continued

```
ttggatgagt gcaggacgcc tctggacttc tccaacaccg tggcctgcac ggacccaaag    720
aaggagatcc cggtggacca cctgatcacc aacatcatcc gtggcaacct ctttccggaa    780
gtttccatct ggatcacctc ccgtcccagt gcatctggcc agatcccagg gggcctggtg    840
gaccggatga cggagatccg gggctttaac gaggaggaga tcaaggtgtg tttggagcag    900
atgttccccg aggaccaggc ccttctgggc tggatgctga gccaagtgca ggctgacagg    960
gccctgtacc tgatgtgcac cgtcccagcc ttctgcaggc tcacggggat ggcgctaggc   1020
cacctgtggc gcagcaggac ggggccccag gatgcagagc tgtggccccc gaggaccctg   1080
tgcgagctct actcatggta ctttaggatg gccctcagcg gggaggggca ggagaagggc   1140
aaggcaagcc ctcgcatcga gcaggtggcc catggtggcc gcaagatggt ggggacattg   1200
ggccgtctgg ccttccatgg gctgctcaag aagaaatacg tgttttacga gcaagacatg   1260
aaggcgtttg gtgtagacct cgctctgctg cagggcgccc cgtgcagctg cttcctgcag   1320
agagaggaga cgttggcatc gtcagtggcc tactgcttca cccacctgtc cctgcaggag   1380
tttgtggcag ccgcgtatta ctatggcgca tccaggaggg ccatcttcga cctcttcact   1440
gagagcggcg tatcctggcc caggctgggc ttcctcacgc atttcaggag cgcagcccag   1500
cgggccatgc aggcagagga cgggaggctg gacgtgttcc tgcgcttcct ctccggcctc   1560
ttgtctccga gggtcaatgc cctcctggcc ggctccctgc tggcccaagg cgagcaccag   1620
gcctaccgga cccaggtggc tgagctcctg cagggctgcc tgcgccccga tgccgcagtc   1680
tgtgcacggg ccatcaacgt gttgcactgc ctgcatgagc tgcagcacac cgagctggcc   1740
cgcagcgtgg aggaggccat ggagagcggg gccctggcca ggctgactgg tcccgcgcac   1800
cgcgctgccc tggcctacct cctgcaggtg tccgacgcct gtgcccagga ggccaacctg   1860
tccctgagcc tcagccaggg cgtccttcag agcctgctgc cccagctgct ctactgccgg   1920
aagctcaggc tgcgttactt cagtctctcc cgtcgcctgg tcatcttctc cctgtgtctg   1980
tctccacatg gtgctgtcct ctcttttttt ttgagatgga gtcttgctct gtcgcccagg   2040
ctggaataca gtggcgcgat ctcagctcac tgcaaacgct gcctcctggg ttcaagcgat   2100
tctcctgcct cagcctccct agtagctggg attacaggtg cccgccatca tgcctggcta   2160
atttttgtgt ttttagtaga gacggggttt caccatgttg gccaggctgc tctcaaactc   2220
ctgacctcag                                                          2230
```

<210> SEQ ID NO 26
<211> LENGTH: 743
<212> TYPE: PRT
<213> ORGANISM: Homo sapiens

<400> SEQUENCE: 26

```
Met Arg Lys Gln Glu Val Arg Thr Gly Arg Glu Ala Gly Gln Gly His
1               5                   10                  15

Gly Thr Gly Ser Pro Ala Glu Gln Val Lys Ala Leu Met Asp Leu Leu
            20                  25                  30

Ala Gly Lys Gly Ser Gln Gly Ser Gln Ala Pro Gln Ala Leu Asp Arg
        35                  40                  45

Thr Pro Asp Ala Pro Leu Gly Pro Cys Ser Asn Asp Ser Arg Ile Gln
    50                  55                  60

Arg His Arg Lys Ala Leu Leu Ser Lys Val Gly Gly Gly Pro Glu Leu
65                  70                  75                  80

Gly Gly Pro Trp His Arg Leu Ala Ser Leu Leu Leu Val Glu Gly Leu
```

-continued

```
                85                  90                  95

Thr Asp Leu Gln Leu Arg Glu His Asp Phe Thr Gln Val Glu Ala Thr
            100                 105                 110

Arg Gly Gly Gly His Pro Ala Arg Thr Val Ala Leu Asp Arg Leu Phe
        115                 120                 125

Leu Pro Leu Ser Arg Val Ser Val Pro Pro Arg Val Ser Ile Thr Ile
    130                 135                 140

Gly Val Ala Gly Met Gly Lys Thr Thr Leu Val Arg His Phe Val Arg
145                 150                 155                 160

Leu Trp Ala His Gly Gln Val Gly Lys Asp Phe Ser Leu Val Leu Pro
                165                 170                 175

Leu Thr Phe Arg Asp Leu Asn Thr His Glu Lys Leu Cys Ala Asp Arg
            180                 185                 190

Leu Ile Cys Ser Val Phe Pro His Val Gly Glu Pro Ser Leu Ala Val
        195                 200                 205

Ala Val Pro Ala Arg Ala Leu Leu Ile Leu Asp Gly Leu Asp Glu Cys
    210                 215                 220

Arg Thr Pro Leu Asp Phe Ser Asn Thr Val Ala Cys Thr Asp Pro Lys
225                 230                 235                 240

Lys Glu Ile Pro Val Asp His Leu Ile Thr Asn Ile Ile Arg Gly Asn
                245                 250                 255

Leu Phe Pro Glu Val Ser Ile Trp Ile Thr Ser Arg Pro Ser Ala Ser
            260                 265                 270

Gly Gln Ile Pro Gly Gly Leu Val Asp Arg Met Thr Glu Ile Arg Gly
        275                 280                 285

Phe Asn Glu Glu Glu Ile Lys Val Cys Leu Glu Gln Met Phe Pro Glu
    290                 295                 300

Asp Gln Ala Leu Leu Gly Trp Met Leu Ser Gln Val Gln Ala Asp Arg
305                 310                 315                 320

Ala Leu Tyr Leu Met Cys Thr Val Pro Ala Phe Cys Arg Leu Thr Gly
                325                 330                 335

Met Ala Leu Gly His Leu Trp Arg Ser Arg Thr Gly Pro Gln Asp Ala
            340                 345                 350

Glu Leu Trp Pro Pro Arg Thr Leu Cys Glu Leu Tyr Ser Trp Tyr Phe
        355                 360                 365

Arg Met Ala Leu Ser Gly Glu Gly Gln Glu Lys Gly Lys Ala Ser Pro
    370                 375                 380

Arg Ile Glu Gln Val Ala His Gly Gly Arg Lys Met Val Gly Thr Leu
385                 390                 395                 400

Gly Arg Leu Ala Phe His Gly Leu Leu Lys Lys Lys Tyr Val Phe Tyr
                405                 410                 415

Glu Gln Asp Met Lys Ala Phe Gly Val Asp Leu Ala Leu Leu Gln Gly
            420                 425                 430

Ala Pro Cys Ser Cys Phe Leu Gln Arg Glu Glu Thr Leu Ala Ser Ser
        435                 440                 445

Val Ala Tyr Cys Phe Thr His Leu Ser Leu Gln Glu Phe Val Ala Ala
    450                 455                 460

Ala Tyr Tyr Tyr Gly Ala Ser Arg Arg Ala Ile Phe Asp Leu Phe Thr
465                 470                 475                 480

Glu Ser Gly Val Ser Trp Pro Arg Leu Gly Phe Leu Thr His Phe Arg
                485                 490                 495

Ser Ala Ala Gln Arg Ala Met Gln Ala Glu Asp Gly Arg Leu Asp Val
            500                 505                 510
```

-continued

```
Phe Leu Arg Phe Leu Ser Gly Leu Leu Ser Pro Arg Val Asn Ala Leu
        515                 520                 525

Leu Ala Gly Ser Leu Leu Ala Gln Gly Glu His Gln Ala Tyr Arg Thr
    530                 535                 540

Gln Val Ala Glu Leu Leu Gln Gly Cys Leu Arg Pro Asp Ala Ala Val
545                 550                 555                 560

Cys Ala Arg Ala Ile Asn Val Leu His Cys Leu His Glu Leu Gln His
                565                 570                 575

Thr Glu Leu Ala Arg Ser Val Glu Glu Ala Met Glu Ser Gly Ala Leu
            580                 585                 590

Ala Arg Leu Thr Gly Pro Ala His Arg Ala Ala Leu Ala Tyr Leu Leu
        595                 600                 605

Gln Val Ser Asp Ala Cys Ala Gln Glu Ala Asn Leu Ser Leu Ser Leu
    610                 615                 620

Ser Gln Gly Val Leu Gln Ser Leu Leu Pro Gln Leu Leu Tyr Cys Arg
625                 630                 635                 640

Lys Leu Arg Leu Arg Tyr Phe Ser Leu Ser Arg Arg Leu Val Ile Phe
                645                 650                 655

Ser Leu Cys Leu Ser Pro His Gly Ala Val Leu Ser Phe Phe Leu Arg
            660                 665                 670

Trp Ser Leu Ala Leu Ser Pro Arg Leu Glu Tyr Ser Gly Ala Ile Ser
        675                 680                 685

Ala His Cys Lys Arg Cys Leu Leu Gly Ser Ser Asp Ser Pro Ala Ser
    690                 695                 700

Ala Ser Leu Val Ala Gly Ile Thr Gly Ala Arg His His Ala Trp Leu
705                 710                 715                 720

Ile Phe Val Phe Leu Val Glu Thr Gly Phe His His Val Gly Gln Ala
                725                 730                 735

Ala Leu Lys Leu Leu Thr Ser
            740
```

<210> SEQ ID NO 27
<211> LENGTH: 3489
<212> TYPE: DNA
<213> ORGANISM: Homo sapiens

<400> SEQUENCE: 27

```
attcccaggg catctaccac cacgcagctg gagcagggct gagcccagga gcatggagat     60

ggacgccccc aggcccccca gtcttgctgt ccctggagca gcatcgaggc ccgggagaac    120

tgtggacaac ggaaggctga gccccatcca ttgagttcct ggggccccac tggaggggct    180

gctgtggcca gggtgcacgg tcacaaatga agacaccaag gcgcagagag gtgactcagc    240

ctgccctcag tcacctatct gctcctggag gtgatccccg actccatgag gaagcaagag    300

gtgcggacgg gcagggaggc cggccagggc cacggtacgg gctccccagc cgagcaggtg    360

aaagccctca tggatctgct ggctgggaag ggcagtcaag gctcccaggc cccgcaggcc    420

ctggatagga caccggatgc cccgctgggg ccctgcagca atgactcaag gatacagagg    480

caccgcaagg ccctgctgag caaggtggga ggtggcccgg agctgggcgg accctggcac    540

aggctggcct ccctcctgct ggtggagggc ctgacggacc tgcagctgag ggaacacgac    600

ttcacacagg tggaggccac ccgcgggggc gggcaccccg ccaggaccgt cgccctggac    660

cggctcttcc tgcctctctc ccgggtgtct gtcccacccc gggtctccat cactatcggg    720

gtggccggca tgggcaagac caccctggtg aggcacttcg tccgcctctg ggcccatggg    780
```

-continued

```
caggtcggca aggacttctc gctggtgctg cctctgacct tccgggatct caacacccac    840
gagaagctgt gtgccgaccg actcatctgc tcggtcttcc cgcacgtcgg ggagcccagc    900
ctggcggtgg cagtcccagc cagggccctc ctgatcctgg acggcttgga tgagtgcagg    960
acgcctctgg acttctccaa caccgtggcc tgcacggacc caaagaagga gatcccggtg   1020
gaccacctga tcaccaacat catccgtggc aacctctttc cggaagtttc catctggatc   1080
acctcccgtc ccagtgcatc tggccagatc ccagggggcc tggtggaccg gatgacggag   1140
atccggggct ttaacgagga ggagatcaag gtgtgtttgg agcagatgtt ccccgaggac   1200
caggcccttc tgggctggat gctgagccaa gtgcaggctg acagggccct gtacctgatg   1260
tgcaccgtcc cagccttctg caggctcacg ggatggcgc taggccacct gtggcgcagc   1320
aggacggggc cccaggatgc agagctgtgg cccccgagga ccctgtgcga gctctactca   1380
tggtacttta ggatggccct cagcggggag gggcaggaga agggcaaggc aagccctcgc   1440
atcgagcagg tggcccatgg tggccgcaag atggtgggga cattgggccg tctggccttc   1500
catgggctgc tcaagaagaa atacgtgttt tacgagcaag acatgaaggc gtttggtgta   1560
gacctcgctc tgctgcaggg cgccccgtgc agctgcttcc tgcagagaga ggagacgttg   1620
gcatcgtcag tggcctactg cttcacccac ctgtccctgc aggagtttgt ggcagccgcg   1680
tattactatg gcgcatccag gagggccatc ttcgacctct tcactgagag cggcgtatcc   1740
tggcccaggc tgggcttcct cacgcatttc aggagcgcag cccagcgggc catgcaggca   1800
gaggacggga ggctggacgt gttcctgcgc ttcctctccg gcctcttgtc tccgagggtc   1860
aatgccctcc tggccggctc cctgctggcc caaggcgagc accaggccta ccggacccag   1920
gtggctgagc tcctgcaggg ctgcctgcgc cccgatgccg cagtctgtgc acgggccatc   1980
aacgtgttgc actgcctgca tgagctgcag cacaccgagc tggcccgcag cgtggaggag   2040
gccatggaga gcggggccct ggccaggctg accggtcccg cgcaccgcgc tgccctggcc   2100
tacctcctgc aggtgtccga cgcctgtgcc caggaggcca acctgtccct gagcctcagc   2160
cagggcgtcc ttcagagcct gctgccccag ctgctctact gccggaagct caggctggac   2220
accaaccagt tccaggaccc cgtgatggag ctgctgggca gcgtgctgag tgggaaggac   2280
tgtcgcattc agaagatcag cttggcggag aaccagatca gtaacaaagg ggccaaagct   2340
ctggccagat ccctcttggt caacagaagt ctgacctctc tggacctccg cggtaactcc   2400
attggaccac aaggggccaa ggcgctggca gacgctttga agatcaaccg caccctgacc   2460
tccctgagcc tccagggcaa caccgttagg gatgatggtg ccaggtccat ggctgaggcc   2520
ttggcctcca accggaccct ctccatgctg cacctgcaga agaacagcat cgggcccatg   2580
ggagcccagc ggatggcaga tgccttgaag cagaacagga gtctgaaaga gctcatgttc   2640
tccagtaata gtattggtga tggaggtgcc aaggccctgg ctgaggccct gaaggtgaac   2700
cagggcctgg agagcctgga cctgcagagc aattccatca gtgacgcagg agtggcagca   2760
ctgatggggg ccctctgcac caaccagacc ctcctcagcc tcagccttcg agaaaactcc   2820
atcagtcccg agggagccca ggccatcgct catgccctct gcgccaacag caccctgaag   2880
aacctggacc tgacagccaa cctcctccac gaccagggtg cccgggccat cgcagtggca   2940
gtgagagaaa accgcaccct cacctccctt cacctgcagt ggaacttcat ccaggccggc   3000
gctgcccagg ccctgggaca agcactacag ctcaacagga gcctcaccag cttagattta   3060
caggagaacg ccatcgggga tgacggagcg tgtgcggtgg cccgtgcact gaaggtcaac   3120
```

-continued

```
acagccctca ctgctctcta tctccaggtg gcctcaattg gtgcttcagg cgcccaggtg   3180

ctaggggaag ccttggctgt gaacagaacc ttggagattc tcgacttaag aggaaatgcc   3240

attggggtgg ctggagccaa agccctggca aatgctctga aggtaaactc aagtctccgg   3300

agactcaatc ttcaagagaa ttctctgggg atggacgggg cgatatgcat tgccacagca   3360

ctgtctggaa accacaggct ccagcatatc aatctccagg gaaaccacat tggggactcc   3420

ggggccagga tgatctcaga ggccatcaag acaaatgctc ccacgtgcac tgttgaaatg   3480

tgatcctgg                                                           3489
```

<210> SEQ ID NO 28
<211> LENGTH: 1065
<212> TYPE: PRT
<213> ORGANISM: Homo sapiens

<400> SEQUENCE: 28

```
Met Arg Lys Gln Glu Val Arg Thr Gly Arg Glu Ala Gly Gln Gly His
1               5                   10                  15

Gly Thr Gly Ser Pro Ala Glu Gln Val Lys Ala Leu Met Asp Leu Leu
            20                  25                  30

Ala Gly Lys Gly Ser Gln Gly Ser Gln Ala Pro Gln Ala Leu Asp Arg
        35                  40                  45

Thr Pro Asp Ala Pro Leu Gly Pro Cys Ser Asn Asp Ser Arg Ile Gln
    50                  55                  60

Arg His Arg Lys Ala Leu Leu Ser Lys Val Gly Gly Gly Pro Glu Leu
65                  70                  75                  80

Gly Gly Pro Trp His Arg Leu Ala Ser Leu Leu Leu Val Glu Gly Leu
                85                  90                  95

Thr Asp Leu Gln Leu Arg Glu His Asp Phe Thr Gln Val Glu Ala Thr
            100                 105                 110

Arg Gly Gly Gly His Pro Ala Arg Thr Val Ala Leu Asp Arg Leu Phe
        115                 120                 125

Leu Pro Leu Ser Arg Val Ser Val Pro Pro Arg Val Ser Ile Thr Ile
    130                 135                 140

Gly Val Ala Gly Met Gly Lys Thr Thr Leu Val Arg His Phe Val Arg
145                 150                 155                 160

Leu Trp Ala His Gly Gln Val Gly Lys Asp Phe Ser Leu Val Leu Pro
                165                 170                 175

Leu Thr Phe Arg Asp Leu Asn Thr His Glu Lys Leu Cys Ala Asp Arg
            180                 185                 190

Leu Ile Cys Ser Val Phe Pro His Val Gly Glu Pro Ser Leu Ala Val
        195                 200                 205

Ala Val Pro Ala Arg Ala Leu Leu Ile Leu Asp Gly Leu Asp Glu Cys
    210                 215                 220

Arg Thr Pro Leu Asp Phe Ser Asn Thr Val Ala Cys Thr Asp Pro Lys
225                 230                 235                 240

Lys Glu Ile Pro Val Asp His Leu Ile Thr Asn Ile Ile Arg Gly Asn
                245                 250                 255

Leu Phe Pro Glu Val Ser Ile Trp Ile Thr Ser Arg Pro Ser Ala Ser
            260                 265                 270

Gly Gln Ile Pro Gly Gly Leu Val Asp Arg Met Thr Glu Ile Arg Gly
        275                 280                 285

Phe Asn Glu Glu Glu Ile Lys Val Cys Leu Glu Gln Met Phe Pro Glu
    290                 295                 300
```

-continued

```
Asp Gln Ala Leu Leu Gly Trp Met Leu Ser Gln Val Gln Ala Asp Arg
305                 310                 315                 320

Ala Leu Tyr Leu Met Cys Thr Val Pro Ala Phe Cys Arg Leu Thr Gly
                325                 330                 335

Met Ala Leu Gly His Leu Trp Arg Ser Arg Thr Gly Pro Gln Asp Ala
            340                 345                 350

Glu Leu Trp Pro Pro Arg Thr Leu Cys Glu Leu Tyr Ser Trp Tyr Phe
        355                 360                 365

Arg Met Ala Leu Ser Gly Glu Gly Gln Glu Lys Gly Lys Ala Ser Pro
    370                 375                 380

Arg Ile Glu Gln Val Ala His Gly Gly Arg Lys Met Val Gly Thr Leu
385                 390                 395                 400

Gly Arg Leu Ala Phe His Gly Leu Leu Lys Lys Lys Tyr Val Phe Tyr
                405                 410                 415

Glu Gln Asp Met Lys Ala Phe Gly Val Asp Leu Ala Leu Leu Gln Gly
            420                 425                 430

Ala Pro Cys Ser Cys Phe Leu Gln Arg Glu Glu Thr Leu Ala Ser Ser
        435                 440                 445

Val Ala Tyr Cys Phe Thr His Leu Ser Leu Gln Glu Phe Val Ala Ala
    450                 455                 460

Ala Tyr Tyr Tyr Gly Ala Ser Arg Arg Ala Ile Phe Asp Leu Phe Thr
465                 470                 475                 480

Glu Ser Gly Val Ser Trp Pro Arg Leu Gly Phe Leu Thr His Phe Arg
                485                 490                 495

Ser Ala Ala Gln Arg Ala Met Gln Ala Glu Asp Gly Arg Leu Asp Val
            500                 505                 510

Phe Leu Arg Phe Leu Ser Gly Leu Leu Ser Pro Arg Val Asn Ala Leu
        515                 520                 525

Leu Ala Gly Ser Leu Leu Ala Gln Gly Glu His Gln Ala Tyr Arg Thr
    530                 535                 540

Gln Val Ala Glu Leu Leu Gln Gly Cys Leu Arg Pro Asp Ala Ala Val
545                 550                 555                 560

Cys Ala Arg Ala Ile Asn Val Leu His Cys Leu His Glu Leu Gln His
                565                 570                 575

Thr Glu Leu Ala Arg Ser Val Glu Glu Ala Met Glu Ser Gly Ala Leu
            580                 585                 590

Ala Arg Leu Thr Gly Pro Ala His Arg Ala Ala Leu Ala Tyr Leu Leu
        595                 600                 605

Gln Val Ser Asp Ala Cys Ala Gln Glu Ala Asn Leu Ser Leu Ser Leu
    610                 615                 620

Ser Gln Gly Val Leu Gln Ser Leu Leu Pro Gln Leu Leu Tyr Cys Arg
625                 630                 635                 640

Lys Leu Arg Leu Asp Thr Asn Gln Phe Gln Asp Pro Val Met Glu Leu
                645                 650                 655

Leu Gly Ser Val Leu Ser Gly Lys Asp Cys Arg Ile Gln Lys Ile Ser
            660                 665                 670

Leu Ala Glu Asn Gln Ile Ser Asn Lys Gly Ala Lys Ala Leu Ala Arg
        675                 680                 685

Ser Leu Leu Val Asn Arg Ser Leu Thr Ser Leu Asp Leu Arg Gly Asn
    690                 695                 700

Ser Ile Gly Pro Gln Gly Ala Lys Ala Leu Ala Asp Ala Leu Lys Ile
705                 710                 715                 720

Asn Arg Thr Leu Thr Ser Leu Ser Leu Gln Gly Asn Thr Val Arg Asp
```

-continued

```
                725                 730                 735

Asp Gly Ala Arg Ser Met Ala Glu Ala Leu Ala Ser Asn Arg Thr Leu
            740                 745                 750

Ser Met Leu His Leu Gln Lys Asn Ser Ile Gly Pro Met Gly Ala Gln
        755                 760                 765

Arg Met Ala Asp Ala Leu Lys Gln Asn Arg Ser Leu Lys Glu Leu Met
    770                 775                 780

Phe Ser Ser Asn Ser Ile Gly Asp Gly Gly Ala Lys Ala Leu Ala Glu
785                 790                 795                 800

Ala Leu Lys Val Asn Gln Gly Leu Glu Ser Leu Asp Leu Gln Ser Asn
                805                 810                 815

Ser Ile Ser Asp Ala Gly Val Ala Ala Leu Met Gly Ala Leu Cys Thr
            820                 825                 830

Asn Gln Thr Leu Leu Ser Leu Ser Leu Arg Glu Asn Ser Ile Ser Pro
        835                 840                 845

Glu Gly Ala Gln Ala Ile Ala His Ala Leu Cys Ala Asn Ser Thr Leu
    850                 855                 860

Lys Asn Leu Asp Leu Thr Ala Asn Leu Leu His Asp Gln Gly Ala Arg
865                 870                 875                 880

Ala Ile Ala Val Ala Val Arg Glu Asn Arg Thr Leu Thr Ser Leu His
                885                 890                 895

Leu Gln Trp Asn Phe Ile Gln Ala Gly Ala Ala Gln Ala Leu Gly Gln
            900                 905                 910

Ala Leu Gln Leu Asn Arg Ser Leu Thr Ser Leu Asp Leu Gln Glu Asn
        915                 920                 925

Ala Ile Gly Asp Asp Gly Ala Cys Ala Val Ala Arg Ala Leu Lys Val
    930                 935                 940

Asn Thr Ala Leu Thr Ala Leu Tyr Leu Gln Val Ala Ser Ile Gly Ala
945                 950                 955                 960

Ser Gly Ala Gln Val Leu Gly Glu Ala Leu Ala Val Asn Arg Thr Leu
                965                 970                 975

Glu Ile Leu Asp Leu Arg Gly Asn Ala Ile Gly Val Ala Gly Ala Lys
            980                 985                 990

Ala Leu Ala Asn Ala Leu Lys Val  Asn Ser Ser Leu Arg  Arg Leu Asn
        995                 1000                1005

Leu Gln  Glu Asn Ser Leu Gly  Met Asp Gly Ala Ile  Cys Ile Ala
    1010                1015                1020

Thr Ala  Leu Ser Gly Asn His  Arg Leu Gln His Ile  Asn Leu Gln
    1025                1030                1035

Gly Asn  His Ile Gly Asp Ser  Gly Ala Arg Met Ile  Ser Glu Ala
    1040                1045                1050

Ile Lys  Thr Asn Ala Pro Thr  Cys Thr Val Glu Met
    1055                1060                1065


<210> SEQ ID NO 29
<211> LENGTH: 282
<212> TYPE: DNA
<213> ORGANISM: Homo sapiens

<400> SEQUENCE: 29

atggcaagca cccgctgcaa gctggccagg tacctggagg acctggagga tgtggacttg      60

aagaaattta agatgcactt agaggactat cctccccaga agggctgcat ccccctcccg     120

aggggtcaga cagagaaggc agaccatgtg gatctagcca cgctaatgat cgacttcaat     180
```

-continued

```
ggggaggaga aggcgtgggc catggccgtg tggatcttcg ctgcgatcaa caggagagac    240

ctttatgaga aagcaaaaag agatgagccg aagtggggtt ag                       282


<210> SEQ ID NO 30
<211> LENGTH: 93
<212> TYPE: PRT
<213> ORGANISM: Homo sapiens

<400> SEQUENCE: 30

Met Ala Ser Thr Arg Cys Lys Leu Ala Arg Tyr Leu Glu Asp Leu Glu
1               5                   10                  15

Asp Val Asp Leu Lys Lys Phe Lys Met His Leu Glu Asp Tyr Pro Pro
            20                  25                  30

Gln Lys Gly Cys Ile Pro Leu Pro Arg Gly Gln Thr Glu Lys Ala Asp
        35                  40                  45

His Val Asp Leu Ala Thr Leu Met Ile Asp Phe Asn Gly Glu Glu Lys
    50                  55                  60

Ala Trp Ala Met Ala Val Trp Ile Phe Ala Ala Ile Asn Arg Arg Asp
65                  70                  75                  80

Leu Tyr Glu Lys Ala Lys Arg Asp Glu Pro Lys Trp Gly
                85                  90


<210> SEQ ID NO 31
<211> LENGTH: 2154
<212> TYPE: DNA
<213> ORGANISM: Homo sapiens

<400> SEQUENCE: 31

atggcaagca cccgctgcaa gctggccagg tacctggagg acctggagga tgtggacttg     60

aagaaattta agatgcactt agaggactat cctccccaga agggctgcat ccccctcccg    120

aggggtcaga cagagaaggc agaccatgtg gatctagcca cgctaatgat cgacttcaat    180

ggggaggaga aggcgtgggc catggccgtg tggatcttcg ctgcgatcaa caggagagac    240

ctttatgaga aagcaaaaag agatgagccg aagtggggtt cagataatgc acgtgtttcg    300

aatcccactg tgatatgcca ggaagacagc attgaagagg agtggatggg tttactggag    360

tacctttcga gaatctctat ttgtaaaatg aagaaagatt accgtaagaa gtacagaaag    420

tacgtgagaa gcagattcca gtgcattgaa gacaggaatg cccgtctggg tgagagtgtg    480

agcctcaaca aacgctacac acgactgcgt ctcatcaagg agcaccggag ccagcaggag    540

agggagcagg agcttctggc catcggcaag accaagacgt gtgagagccc cgtgagtccc    600

attaagatgg agttgctgtt tgaccccgat gatgagcatt ctgagcctgt gcacaccgtg    660

gtgttccagg gggcggcagg gattgggaaa acaatcctgg ccaggaagat gatgttggac    720

tgggcgtcgg ggacactcta ccaagacagg tttgactatc tgttctatat ccactgtcgg    780

gaggtgagcc ttgtgacaca gaggagcctg gggggacctga tcatgagctg ctgccccgac   840

ccaaacccac ccatccacaa gatcgtgaga aaaccctcca gaatcctctt cctcatggac    900

ggcttcgatg agctgcaagg tgcctttgac gagcacatag gaccgctctg cactgactgg    960

cagaaggccg agcggggaga cattctcctg agcagcctca tcagaaagaa gctgcttccc   1020

gaggcctctc tgctcatcac cacgagacct gtggccctgg agaaactgca gcacttgctg   1080

gaccatcctc ggcatgtgga gatcctgggt ttctccgagg ccaaaaggaa agagtacttc   1140

ttcaagtact tctctgatga ggcccaagcc agggcagcct tcagtctgat tcaggagaac   1200

gaggtcctct tcaccatgtg cttcatcccc ctggtctgct ggatcgtgtg cactggactg   1260
```

-continued

```
aaacagcaga tggagagtgg caagagcctt gcccagacat ccaagaccac caccgcggtg   1320
tacgtcttct tcctttccag tttgctgcag ccccggggag ggagccagga gcacggcctc   1380
tgcgcccacc tctgggggct ctgctctttg gctgcagatg gaatctggaa ccagaaaatc   1440
ctgtttgagg agtccgacct caggaatcat ggactgcaga aggcggatgt gtctgctttc   1500
ctgaggatga acctgttcca aaaggaagtg gactgcgaga agttctacag cttcatccac   1560
atgactttcc aggagttctt tgccgccatg tactacctgc tggaagagga aaaggaagga   1620
aggacgaacg ttccagggag tcgtttgaag cttcccagcc gagacgtgac agtccttctg   1680
gaaaactatg gcaaattcga aaaggggtat ttgatttttg ttgtacgttt cctctttggc   1740
ctggtaaacc aggagaggac ctcctacttg gagaagaaat taagttgcaa gatctctcag   1800
caaatcaggc tggagctgct gaaatggatt gaagtgaaag ccaaagctaa aaagctgcag   1860
atccagccca gccagctgga attgttctac tgtttgtacg agatgcagga ggaggacttc   1920
gtgcaaaggg ccatggacta tttccccaag attgagatca atctctccac cagaatggac   1980
cacatggttt cttccttttg cattgagaac tgtcatcggg tggagtcact gtccctgggg   2040
tttctccata acatgcccaa ggaggaagag gaggaggaaa aggaaggccg acaccttgat   2100
atggtgcagt gtgtcctccc aagctcctct catgctgcct gttctcatgg atag         2154
```

<210> SEQ ID NO 32
<211> LENGTH: 717
<212> TYPE: PRT
<213> ORGANISM: Homo sapiens

<400> SEQUENCE: 32

```
Met Ala Ser Thr Arg Cys Lys Leu Ala Arg Tyr Leu Glu Asp Leu Glu
1               5                   10                  15

Asp Val Asp Leu Lys Lys Phe Lys Met His Leu Glu Asp Tyr Pro Pro
            20                  25                  30

Gln Lys Gly Cys Ile Pro Leu Pro Arg Gly Gln Thr Glu Lys Ala Asp
        35                  40                  45

His Val Asp Leu Ala Thr Leu Met Ile Asp Phe Asn Gly Glu Glu Lys
    50                  55                  60

Ala Trp Ala Met Ala Val Trp Ile Phe Ala Ala Ile Asn Arg Arg Asp
65                  70                  75                  80

Leu Tyr Glu Lys Ala Lys Arg Asp Glu Pro Lys Trp Gly Ser Asp Asn
                85                  90                  95

Ala Arg Val Ser Asn Pro Thr Val Ile Cys Gln Glu Asp Ser Ile Glu
            100                 105                 110

Glu Glu Trp Met Gly Leu Leu Glu Tyr Leu Ser Arg Ile Ser Ile Cys
        115                 120                 125

Lys Met Lys Lys Asp Tyr Arg Lys Lys Tyr Arg Lys Tyr Val Arg Ser
    130                 135                 140

Arg Phe Gln Cys Ile Glu Asp Arg Asn Ala Arg Leu Gly Glu Ser Val
145                 150                 155                 160

Ser Leu Asn Lys Arg Tyr Thr Arg Leu Arg Leu Ile Lys Glu His Arg
                165                 170                 175

Ser Gln Gln Glu Arg Glu Gln Glu Leu Leu Ala Ile Gly Lys Thr Lys
            180                 185                 190

Thr Cys Glu Ser Pro Val Ser Pro Ile Lys Met Glu Leu Leu Phe Asp
        195                 200                 205

Pro Asp Asp Glu His Ser Glu Pro Val His Thr Val Val Phe Gln Gly
```

-continued

```
    210                 215                 220

Ala Ala Gly Ile Gly Lys Thr Ile Leu Ala Arg Lys Met Met Leu Asp
225                 230                 235                 240

Trp Ala Ser Gly Thr Leu Tyr Gln Asp Arg Phe Asp Tyr Leu Phe Tyr
                245                 250                 255

Ile His Cys Arg Glu Val Ser Leu Val Thr Gln Arg Ser Leu Gly Asp
            260                 265                 270

Leu Ile Met Ser Cys Cys Pro Asp Pro Asn Pro Pro Ile His Lys Ile
        275                 280                 285

Val Arg Lys Pro Ser Arg Ile Leu Phe Leu Met Asp Gly Phe Asp Glu
    290                 295                 300

Leu Gln Gly Ala Phe Asp Glu His Ile Gly Pro Leu Cys Thr Asp Trp
305                 310                 315                 320

Gln Lys Ala Glu Arg Gly Asp Ile Leu Leu Ser Ser Leu Ile Arg Lys
                325                 330                 335

Lys Leu Leu Pro Glu Ala Ser Leu Leu Ile Thr Thr Arg Pro Val Ala
            340                 345                 350

Leu Glu Lys Leu Gln His Leu Leu Asp His Pro Arg His Val Glu Ile
        355                 360                 365

Leu Gly Phe Ser Glu Ala Lys Arg Lys Glu Tyr Phe Phe Lys Tyr Phe
    370                 375                 380

Ser Asp Glu Ala Gln Ala Arg Ala Ala Phe Ser Leu Ile Gln Glu Asn
385                 390                 395                 400

Glu Val Leu Phe Thr Met Cys Phe Ile Pro Leu Val Cys Trp Ile Val
                405                 410                 415

Cys Thr Gly Leu Lys Gln Gln Met Glu Ser Gly Lys Ser Leu Ala Gln
            420                 425                 430

Thr Ser Lys Thr Thr Thr Ala Val Tyr Val Phe Phe Leu Ser Ser Leu
        435                 440                 445

Leu Gln Pro Arg Gly Gly Ser Gln Glu His Gly Leu Cys Ala His Leu
    450                 455                 460

Trp Gly Leu Cys Ser Leu Ala Ala Asp Gly Ile Trp Asn Gln Lys Ile
465                 470                 475                 480

Leu Phe Glu Glu Ser Asp Leu Arg Asn His Gly Leu Gln Lys Ala Asp
                485                 490                 495

Val Ser Ala Phe Leu Arg Met Asn Leu Phe Gln Lys Glu Val Asp Cys
            500                 505                 510

Glu Lys Phe Tyr Ser Phe Ile His Met Thr Phe Gln Glu Phe Phe Ala
        515                 520                 525

Ala Met Tyr Tyr Leu Leu Glu Glu Glu Lys Glu Gly Arg Thr Asn Val
    530                 535                 540

Pro Gly Ser Arg Leu Lys Leu Pro Ser Arg Asp Val Thr Val Leu Leu
545                 550                 555                 560

Glu Asn Tyr Gly Lys Phe Glu Lys Gly Tyr Leu Ile Phe Val Val Arg
                565                 570                 575

Phe Leu Phe Gly Leu Val Asn Gln Glu Arg Thr Ser Tyr Leu Glu Lys
            580                 585                 590

Lys Leu Ser Cys Lys Ile Ser Gln Gln Ile Arg Leu Glu Leu Leu Lys
        595                 600                 605

Trp Ile Glu Val Lys Ala Lys Ala Lys Lys Leu Gln Ile Gln Pro Ser
    610                 615                 620

Gln Leu Glu Leu Phe Tyr Cys Leu Tyr Glu Met Gln Glu Glu Asp Phe
625                 630                 635                 640
```

-continued

```
Val Gln Arg Ala Met Asp Tyr Phe Pro Lys Ile Glu Ile Asn Leu Ser
                645                 650                 655

Thr Arg Met Asp His Met Val Ser Ser Phe Cys Ile Glu Asn Cys His
            660                 665                 670

Arg Val Glu Ser Leu Ser Leu Gly Phe Leu His Asn Met Pro Lys Glu
        675                 680                 685

Glu Glu Glu Glu Glu Lys Glu Gly Arg His Leu Asp Met Val Gln Cys
    690                 695                 700

Val Leu Pro Ser Ser Ser His Ala Ala Cys Ser His Gly
705                 710                 715


<210> SEQ ID NO 33
<211> LENGTH: 2835
<212> TYPE: DNA
<213> ORGANISM: Homo sapiens

<400> SEQUENCE: 33

atggcaagca cccgctgcaa gctggccagg taccccactg tgatatgcca ggaagacagc     60

attgaagagg agtggatggg tttactggag tacctttcga gaatctctat ttgtaaaatg    120

aagaaagatt accgtaagaa gtacagaaag tacgtgagaa gcagattcca gtgcattgaa    180

gacaggaatg cccgtctggg tgagagtgtg agcctcaaca aacgctacac acgactgcgt    240

ctcatcaagg agcaccggag ccagcaggag agggagcagg agcttctggc catcggcaag    300

accaagacgt gtgagagccc cgtgagtccc attaagatgg agttgctgtt tgaccccgat    360

gatgagcatt ctgagcctgt gcacaccgtg gtgttccagg gggcggcagg gattgggaaa    420

acaatcctgg ccaggaagat gatgttggac tgggcgtcgg ggacactcta ccaagacagg    480

tttgactatc tgttctatat ccactgtcgg gaggtgagcc ttgtgacaca gaggagcctg    540

ggggacctga tcatgagctg ctgccccgac ccaaacccac ccatccacaa gatcgtgaga    600

aaaccctcca gaatcctctt cctcatggac ggcttcgatg agctgcaagg tgcctttgac    660

gagcacatag gaccgctctg cactgactgg cagaaggccg agcggggaga cattctcctg    720

agcagcctca tcagaaagaa gctgcttccc gaggcctctc tgctcatcac cacgagacct    780

gtggccctgg agaaactgca gcacttgctg gaccatcctc ggcatgtgga gatcctgggt    840

ttctccgagg ccaaaaggaa agagtacttc ttcaagtact tctctgatga ggcccaagcc    900

agggcagcct tcagtctgat tcaggagaac gaggtcctct tcaccatgtg cttcatcccc    960

ctggtctgct ggatcgtgtg cactggactg aaacagcaga tggagagtgg caagagcctt   1020

gcccagacat ccaagaccac caccgcggtg tacgtcttct tcctttccag tttgctgcag   1080

ccccggggag ggagccagga gcacggcctc tgcgcccacc tctgggggct ctgctctttg   1140

gctgcagatg gaatctggaa ccagaaaatc ctgtttgagg agtccgacct caggaatcat   1200

ggactgcaga aggcggatgt gtctgctttc ctgaggatga acctgttcca aaaggaagtg   1260

gactgcgaga agttctacag cttcatccac atgactttcc aggagttctt tgccgccatg   1320

tactacctgc tggaagagga aaaggaagga aggacgaacg ttccagggag tcgtttgaag   1380

cttcccagcc gagacgtgac agtccttctg gaaaactatg gcaaattcga aaaggggtat   1440

ttgatttttg ttgtacgttt cctctttggc ctggtaaacc aggagaggac ctcctacttg   1500

gagaagaaat taagttgcaa gatctctcag caaatcaggc tggagctgct gaaatggatt   1560

gaagtgaaag ccaaagctaa aaagctgcag atccagccca gccagctgga attgttctac   1620

tgtttgtacg agatgcagga ggaggacttc gtgcaaaggg ccatggacta tttccccaag   1680
```

-continued

```
attgagatca atctctccac cagaatggac cacatggttt cttccttttg cattgagaac   1740

tgtcatcggg tggagtcact gtccctgggg tttctccata acatgcccaa ggaggaagag   1800

gaggaggaaa aggaaggccg acaccttgat atggtgcagt gtgtcctccc aagctcctct   1860

catgctgcct gttctcatgg attggtgaac agccacctca cttccagttt ttgccggggc   1920

ctcttttcag ttctgagcac cagccagagt ctaactgaat tggacctcag tgacaattct   1980

ctgggggacc cagggatgag agtgttgtgt gaaacgctcc agcatcctgg ctgtaacatt   2040

cggagattgt ggttggggcg ctgtggcctc tcgcatgagt gctgcttcga catctccttg   2100

gtcctcagca gcaaccagaa gctggtggag ctggacctga gtgacaacgc cctcggtgac   2160

ttcggaatca gacttctgtg tgtgggactg aagcacctgt tgtgcaatct gaagaagctc   2220

tggttggtca gctgctgcct cacatcagca tgttgtcagg atcttgcatc agtattgagc   2280

accagccatt ccctgaccag actctatgtg ggggagaatg ccttgggaga ctcaggagtc   2340

gcaattttat gtgaaaaagc caagaatcca cagtgtaacc tgcagaaact ggggttggtg   2400

aattctggcc ttacgtcagt ctgttgttca gctttgtcct cggtactcag cactaatcag   2460

aatctcacgc acctttacct gcgaggcaac actctcggag acaaggggat caaactactc   2520

tgtgagggac tcttgcaccc cgactgcaag cttcaggtgt tggaattaga caactgcaac   2580

ctcacgtcac actgctgctg ggatctttcc acacttctga cctccagcca gagcctgcga   2640

aagctgagcc tgggcaacaa tgacctgggc gacctggggg tcatgatgtt ctgtgaagtg   2700

ctgaaacagc agagctgcct cctgcagaac ctggggttgt ctgaaatgta tttcaattat   2760

gagacaaaaa gtgcgttaga aacacttcaa gaagaaaagc ctgagctgac cgtcgtcttt   2820

gagccttctt ggtag                                                     2835
```

<210> SEQ ID NO 34
<211> LENGTH: 944
<212> TYPE: PRT
<213> ORGANISM: Homo sapiens

<400> SEQUENCE: 34

```
Met Ala Ser Thr Arg Cys Lys Leu Ala Arg Tyr Pro Thr Val Ile Cys
1               5                   10                  15

Gln Glu Asp Ser Ile Glu Glu Glu Trp Met Gly Leu Leu Glu Tyr Leu
            20                  25                  30

Ser Arg Ile Ser Ile Cys Lys Met Lys Lys Asp Tyr Arg Lys Lys Tyr
        35                  40                  45

Arg Lys Tyr Val Arg Ser Arg Phe Gln Cys Ile Glu Asp Arg Asn Ala
    50                  55                  60

Arg Leu Gly Glu Ser Val Ser Leu Asn Lys Arg Tyr Thr Arg Leu Arg
65                  70                  75                  80

Leu Ile Lys Glu His Arg Ser Gln Gln Glu Arg Glu Gln Glu Leu Leu
                85                  90                  95

Ala Ile Gly Lys Thr Lys Thr Cys Glu Ser Pro Val Ser Pro Ile Lys
            100                 105                 110

Met Glu Leu Leu Phe Asp Pro Asp Asp Glu His Ser Glu Pro Val His
        115                 120                 125

Thr Val Val Phe Gln Gly Ala Ala Gly Ile Gly Lys Thr Ile Leu Ala
    130                 135                 140

Arg Lys Met Met Leu Asp Trp Ala Ser Gly Thr Leu Tyr Gln Asp Arg
145                 150                 155                 160
```

-continued

```
Phe Asp Tyr Leu Phe Tyr Ile His Cys Arg Glu Val Ser Leu Val Thr
                165                 170                 175

Gln Arg Ser Leu Gly Asp Leu Ile Met Ser Cys Cys Pro Asp Pro Asn
            180                 185                 190

Pro Pro Ile His Lys Ile Val Arg Lys Pro Ser Arg Ile Leu Phe Leu
        195                 200                 205

Met Asp Gly Phe Asp Glu Leu Gln Gly Ala Phe Asp Glu His Ile Gly
    210                 215                 220

Pro Leu Cys Thr Asp Trp Gln Lys Ala Glu Arg Gly Asp Ile Leu Leu
225                 230                 235                 240

Ser Ser Leu Ile Arg Lys Lys Leu Leu Pro Glu Ala Ser Leu Leu Ile
                245                 250                 255

Thr Thr Arg Pro Val Ala Leu Glu Lys Leu Gln His Leu Leu Asp His
            260                 265                 270

Pro Arg His Val Glu Ile Leu Gly Phe Ser Glu Ala Lys Arg Lys Glu
        275                 280                 285

Tyr Phe Phe Lys Tyr Phe Ser Asp Glu Ala Gln Ala Arg Ala Ala Phe
    290                 295                 300

Ser Leu Ile Gln Glu Asn Glu Val Leu Phe Thr Met Cys Phe Ile Pro
305                 310                 315                 320

Leu Val Cys Trp Ile Val Cys Thr Gly Leu Lys Gln Gln Met Glu Ser
                325                 330                 335

Gly Lys Ser Leu Ala Gln Thr Ser Lys Thr Thr Thr Ala Val Tyr Val
            340                 345                 350

Phe Phe Leu Ser Ser Leu Leu Gln Pro Arg Gly Gly Ser Gln Glu His
        355                 360                 365

Gly Leu Cys Ala His Leu Trp Gly Leu Cys Ser Leu Ala Ala Asp Gly
    370                 375                 380

Ile Trp Asn Gln Lys Ile Leu Phe Glu Glu Ser Asp Leu Arg Asn His
385                 390                 395                 400

Gly Leu Gln Lys Ala Asp Val Ser Ala Phe Leu Arg Met Asn Leu Phe
                405                 410                 415

Gln Lys Glu Val Asp Cys Glu Lys Phe Tyr Ser Phe Ile His Met Thr
            420                 425                 430

Phe Gln Glu Phe Phe Ala Ala Met Tyr Tyr Leu Leu Glu Glu Glu Lys
        435                 440                 445

Glu Gly Arg Thr Asn Val Pro Gly Ser Arg Leu Lys Leu Pro Ser Arg
    450                 455                 460

Asp Val Thr Val Leu Leu Glu Asn Tyr Gly Lys Phe Glu Lys Gly Tyr
465                 470                 475                 480

Leu Ile Phe Val Val Arg Phe Leu Phe Gly Leu Val Asn Gln Glu Arg
                485                 490                 495

Thr Ser Tyr Leu Glu Lys Lys Leu Ser Cys Lys Ile Ser Gln Gln Ile
            500                 505                 510

Arg Leu Glu Leu Leu Lys Trp Ile Glu Val Lys Ala Lys Ala Lys Lys
        515                 520                 525

Leu Gln Ile Gln Pro Ser Gln Leu Glu Leu Phe Tyr Cys Leu Tyr Glu
    530                 535                 540

Met Gln Glu Glu Asp Phe Val Gln Arg Ala Met Asp Tyr Phe Pro Lys
545                 550                 555                 560

Ile Glu Ile Asn Leu Ser Thr Arg Met Asp His Met Val Ser Ser Phe
                565                 570                 575

Cys Ile Glu Asn Cys His Arg Val Glu Ser Leu Ser Leu Gly Phe Leu
```

-continued

```
            580                 585                 590

His Asn Met Pro Lys Glu Glu Glu Glu Glu Glu Lys Glu Gly Arg His
        595                 600                 605

Leu Asp Met Val Gln Cys Val Leu Pro Ser Ser Ser His Ala Ala Cys
    610                 615                 620

Ser His Gly Leu Val Asn Ser His Leu Thr Ser Ser Phe Cys Arg Gly
625                 630                 635                 640

Leu Phe Ser Val Leu Ser Thr Ser Gln Ser Leu Thr Glu Leu Asp Leu
                645                 650                 655

Ser Asp Asn Ser Leu Gly Asp Pro Gly Met Arg Val Leu Cys Glu Thr
            660                 665                 670

Leu Gln His Pro Gly Cys Asn Ile Arg Arg Leu Trp Leu Gly Arg Cys
        675                 680                 685

Gly Leu Ser His Glu Cys Cys Phe Asp Ile Ser Leu Val Leu Ser Ser
    690                 695                 700

Asn Gln Lys Leu Val Glu Leu Asp Leu Ser Asp Asn Ala Leu Gly Asp
705                 710                 715                 720

Phe Gly Ile Arg Leu Leu Cys Val Gly Leu Lys His Leu Leu Cys Asn
                725                 730                 735

Leu Lys Lys Leu Trp Leu Val Ser Cys Cys Leu Thr Ser Ala Cys Cys
            740                 745                 750

Gln Asp Leu Ala Ser Val Leu Ser Thr Ser His Ser Leu Thr Arg Leu
        755                 760                 765

Tyr Val Gly Glu Asn Ala Leu Gly Asp Ser Gly Val Ala Ile Leu Cys
    770                 775                 780

Glu Lys Ala Lys Asn Pro Gln Cys Asn Leu Gln Lys Leu Gly Leu Val
785                 790                 795                 800

Asn Ser Gly Leu Thr Ser Val Cys Cys Ser Ala Leu Ser Ser Val Leu
                805                 810                 815

Ser Thr Asn Gln Asn Leu Thr His Leu Tyr Leu Arg Gly Asn Thr Leu
            820                 825                 830

Gly Asp Lys Gly Ile Lys Leu Leu Cys Glu Gly Leu Leu His Pro Asp
        835                 840                 845

Cys Lys Leu Gln Val Leu Glu Leu Asp Asn Cys Asn Leu Thr Ser His
    850                 855                 860

Cys Cys Trp Asp Leu Ser Thr Leu Leu Thr Ser Ser Gln Ser Leu Arg
865                 870                 875                 880

Lys Leu Ser Leu Gly Asn Asn Asp Leu Gly Asp Leu Gly Val Met Met
                885                 890                 895

Phe Cys Glu Val Leu Lys Gln Gln Ser Cys Leu Leu Gln Asn Leu Gly
            900                 905                 910

Leu Ser Glu Met Tyr Phe Asn Tyr Glu Thr Lys Ser Ala Leu Glu Thr
        915                 920                 925

Leu Gln Glu Glu Lys Pro Glu Leu Thr Val Val Phe Glu Pro Ser Trp
    930                 935                 940


<210> SEQ ID NO 35
<211> LENGTH: 993
<212> TYPE: DNA
<213> ORGANISM: Homo sapiens

<400> SEQUENCE: 35

atggcaagca cccgctgcaa gctggccagg taccatggat tggtgaacag ccacctcact      60

tccagttttt gccggggcct cttttcagtt ctgagcacca gccagagtct aactgaattg     120
```

-continued

```
gacctcagtg acaattctct gggggaccca gggatgagag tgttgtgtga aacgctccag    180

catcctggct gtaacattcg gagattgtgg ttggggcgct gtggcctctc gcatgagtgc    240

tgcttcgaca tctccttggt cctcagcagc aaccagaagc tggtggagct ggacctgagt    300

gacaacgccc tcggtgactt cggaatcaga cttctgtgtg tgggactgaa gcacctgttg    360

tgcaatctga agaagctctg gttggtcagc tgctgcctca catcagcatg ttgtcaggat    420

cttgcatcag tattgagcac cagccattcc ctgaccagac tctatgtggg ggagaatgcc    480

ttgggagact caggagtcgc aattttatgt gaaaaagcca agaatccaca gtgtaacctg    540

cagaaactgg ggttggtgaa ttctggcctt acgtcagtct gttgttcagc tttgtcctcg    600

gtactcagca ctaatcagaa tctcacgcac ctttacctgc gaggcaacac tctcggagac    660

aaggggatca aactactctg tgagggactc ttgcaccccg actgcaagct tcaggtgttg    720

gaattagaca actgcaacct cacgtcacac tgctgctggg atctttccac acttctgacc    780

tccagccaga gcctgcgaaa gctgagcctg ggcaacaatg acctgggcga cctgggggtc    840

atgatgttct gtgaagtgct gaaacagcag agctgcctcc tgcagaacct ggggttgtct    900

gaaatgtatt tcaattatga gacaaaaagt gcgttagaaa cacttcaaga agaaaagcct    960

gagctgaccg tcgtctttga gccttcttgg tag                                 993
```

<210> SEQ ID NO 36
<211> LENGTH: 330
<212> TYPE: PRT
<213> ORGANISM: Homo sapiens

<400> SEQUENCE: 36

```
Met Ala Ser Thr Arg Cys Lys Leu Ala Arg Tyr His Gly Leu Val Asn
1               5                   10                  15

Ser His Leu Thr Ser Ser Phe Cys Arg Gly Leu Phe Ser Val Leu Ser
            20                  25                  30

Thr Ser Gln Ser Leu Thr Glu Leu Asp Leu Ser Asp Asn Ser Leu Gly
        35                  40                  45

Asp Pro Gly Met Arg Val Leu Cys Glu Thr Leu Gln His Pro Gly Cys
    50                  55                  60

Asn Ile Arg Arg Leu Trp Leu Gly Arg Cys Gly Leu Ser His Glu Cys
65                  70                  75                  80

Cys Phe Asp Ile Ser Leu Val Leu Ser Ser Asn Gln Lys Leu Val Glu
                85                  90                  95

Leu Asp Leu Ser Asp Asn Ala Leu Gly Asp Phe Gly Ile Arg Leu Leu
            100                 105                 110

Cys Val Gly Leu Lys His Leu Leu Cys Asn Leu Lys Lys Leu Trp Leu
        115                 120                 125

Val Ser Cys Cys Leu Thr Ser Ala Cys Cys Gln Asp Leu Ala Ser Val
    130                 135                 140

Leu Ser Thr Ser His Ser Leu Thr Arg Leu Tyr Val Gly Glu Asn Ala
145                 150                 155                 160

Leu Gly Asp Ser Gly Val Ala Ile Leu Cys Glu Lys Ala Lys Asn Pro
                165                 170                 175

Gln Cys Asn Leu Gln Lys Leu Gly Leu Val Asn Ser Gly Leu Thr Ser
            180                 185                 190

Val Cys Cys Ser Ala Leu Ser Ser Val Leu Ser Thr Asn Gln Asn Leu
        195                 200                 205

Thr His Leu Tyr Leu Arg Gly Asn Thr Leu Gly Asp Lys Gly Ile Lys
```

-continued

```
    210                 215                 220

Leu Leu Cys Glu Gly Leu Leu His Pro Asp Cys Lys Leu Gln Val Leu
225                 230                 235                 240

Glu Leu Asp Asn Cys Asn Leu Thr Ser His Cys Cys Trp Asp Leu Ser
                245                 250                 255

Thr Leu Leu Thr Ser Ser Gln Ser Leu Arg Lys Leu Ser Leu Gly Asn
            260                 265                 270

Asn Asp Leu Gly Asp Leu Gly Val Met Met Phe Cys Glu Val Leu Lys
        275                 280                 285

Gln Gln Ser Cys Leu Leu Gln Asn Leu Gly Leu Ser Glu Met Tyr Phe
    290                 295                 300

Asn Tyr Glu Thr Lys Ser Ala Leu Glu Thr Leu Gln Glu Glu Lys Pro
305                 310                 315                 320

Glu Leu Thr Val Val Phe Glu Pro Ser Trp
                325                 330


<210> SEQ ID NO 37
<211> LENGTH: 8
<212> TYPE: PRT
<213> ORGANISM: Homo sapiens

<400> SEQUENCE: 37

Gly Ala Ala Gly Ile Gly Lys Thr
1               5


<210> SEQ ID NO 38
<211> LENGTH: 8
<212> TYPE: PRT
<213> ORGANISM: Homo sapiens

<400> SEQUENCE: 38

Gly Asp Ala Gly Val Gly Lys Ser
1               5


<210> SEQ ID NO 39
<211> LENGTH: 8
<212> TYPE: PRT
<213> ORGANISM: Homo sapiens

<400> SEQUENCE: 39

Gly Ser Ala Gly Thr Gly Lys Thr
1               5


<210> SEQ ID NO 40
<211> LENGTH: 8
<212> TYPE: PRT
<213> ORGANISM: Homo sapiens

<400> SEQUENCE: 40

Gly Ala Ala Gly Val Gly Lys Thr
1               5


<210> SEQ ID NO 41
<211> LENGTH: 8
<212> TYPE: PRT
<213> ORGANISM: Homo sapiens

<400> SEQUENCE: 41

Gly Pro Ala Gly Thr Gly Lys Thr
1               5
```

-continued

<210> SEQ ID NO 42
<211> LENGTH: 8
<212> TYPE: PRT
<213> ORGANISM: Homo sapiens

<400> SEQUENCE: 42

Gly Thr Val Gly Thr Gly Lys Ser
1 5

<210> SEQ ID NO 43
<211> LENGTH: 8
<212> TYPE: PRT
<213> ORGANISM: Homo sapiens

<400> SEQUENCE: 43

Gly Lys Ala Gly Gln Gly Lys Ser
1 5

<210> SEQ ID NO 44
<211> LENGTH: 8
<212> TYPE: PRT
<213> ORGANISM: Homo sapiens

<400> SEQUENCE: 44

Gly Glu Ala Gly Ser Gly Lys Ser
1 5

<210> SEQ ID NO 45
<211> LENGTH: 8
<212> TYPE: PRT
<213> ORGANISM: Homo sapiens

<400> SEQUENCE: 45

Gly Lys Ala Gly Met Gly Lys Thr
1 5

<210> SEQ ID NO 46
<211> LENGTH: 8
<212> TYPE: PRT
<213> ORGANISM: Homo sapiens

<400> SEQUENCE: 46

Gly Val Ala Gly Met Gly Lys Thr
1 5

<210> SEQ ID NO 47
<211> LENGTH: 8
<212> TYPE: PRT
<213> ORGANISM: Homo sapiens

<400> SEQUENCE: 47

Gly Ala Ala Gly Ile Gly Lys Ser
1 5

<210> SEQ ID NO 48
<211> LENGTH: 8
<212> TYPE: PRT
<213> ORGANISM: Homo sapiens

<400> SEQUENCE: 48

Gly Pro Ala Gly Leu Gly Lys Thr
1 5

<210> SEQ ID NO 49
<211> LENGTH: 8

-continued

<212> TYPE: PRT
<213> ORGANISM: Homo sapiens

<400> SEQUENCE: 49

Gly Pro Asp Gly Ile Gly Lys Thr
1               5

<210> SEQ ID NO 50
<211> LENGTH: 8
<212> TYPE: PRT
<213> ORGANISM: Homo sapiens

<400> SEQUENCE: 50

Gly Ala Pro Gly Ile Gly Lys Thr
1               5

<210> SEQ ID NO 51
<211> LENGTH: 8
<212> TYPE: PRT
<213> ORGANISM: Homo sapiens

<400> SEQUENCE: 51

Gly Ala Ala Gly Ile Gly Lys Ser
1               5

<210> SEQ ID NO 52
<211> LENGTH: 8
<212> TYPE: PRT
<213> ORGANISM: Homo sapiens

<400> SEQUENCE: 52

Gly Pro Ala Gly Val Gly Lys Thr
1               5

<210> SEQ ID NO 53
<211> LENGTH: 8
<212> TYPE: PRT
<213> ORGANISM: Homo sapiens

<400> SEQUENCE: 53

Gly Pro Gln Gly Ile Gly Lys Thr
1               5

<210> SEQ ID NO 54
<211> LENGTH: 8
<212> TYPE: PRT
<213> ORGANISM: Homo sapiens

<400> SEQUENCE: 54

Gly Glu Arg Ala Ser Gly Lys Thr
1               5

<210> SEQ ID NO 55
<211> LENGTH: 8
<212> TYPE: PRT
<213> ORGANISM: Homo sapiens

<400> SEQUENCE: 55

Gly Arg Ala Gly Val Gly Lys Thr
1               5

<210> SEQ ID NO 56
<211> LENGTH: 8
<212> TYPE: PRT
<213> ORGANISM: Homo sapiens

-continued

<400> SEQUENCE: 56

Gly Lys Ser Gly Ile Gly Lys Ser
1 5

<210> SEQ ID NO 57
<211> LENGTH: 8
<212> TYPE: PRT
<213> ORGANISM: Homo sapiens

<400> SEQUENCE: 57

Ala Cys Ala Gly Thr Gly Lys Thr
1 5

<210> SEQ ID NO 58
<211> LENGTH: 8
<212> TYPE: PRT
<213> ORGANISM: Homo sapiens

<400> SEQUENCE: 58

Gly Met Ala Gly Cys Gly Lys Ser
1 5

<210> SEQ ID NO 59
<211> LENGTH: 8
<212> TYPE: PRT
<213> ORGANISM: Homo sapiens

<400> SEQUENCE: 59

Gly Met Gly Gly Ser Gly Lys Thr
1 5

<210> SEQ ID NO 60
<211> LENGTH: 8
<212> TYPE: PRT
<213> ORGANISM: Homo sapiens

<400> SEQUENCE: 60

Gly Glu Ala Gly Ser Gly Lys Thr
1 5

<210> SEQ ID NO 61
<211> LENGTH: 8
<212> TYPE: PRT
<213> ORGANISM: Homo sapiens

<400> SEQUENCE: 61

Gly Asp Pro Gly Lys Gly Lys Thr
1 5

<210> SEQ ID NO 62
<211> LENGTH: 8
<212> TYPE: PRT
<213> ORGANISM: Homo sapiens

<400> SEQUENCE: 62

Gly Gln Ser Gly Gln Gly Lys Thr
1 5

<210> SEQ ID NO 63
<211> LENGTH: 8
<212> TYPE: PRT
<213> ORGANISM: Homo sapiens

<400> SEQUENCE: 63

-continued

Gly Ala Gly Glu Ser Gly Lys Ser
1               5

<210> SEQ ID NO 64
<211> LENGTH: 4
<212> TYPE: PRT
<213> ORGANISM: Homo sapiens

<400> SEQUENCE: 64

Asp Ala Tyr Gly
1

<210> SEQ ID NO 65
<211> LENGTH: 4
<212> TYPE: PRT
<213> ORGANISM: Homo sapiens

<400> SEQUENCE: 65

Asp Glu Pro Gly
1

<210> SEQ ID NO 66
<211> LENGTH: 4
<212> TYPE: PRT
<213> ORGANISM: Homo sapiens

<400> SEQUENCE: 66

Asp Glu Leu Gly
1

<210> SEQ ID NO 67
<211> LENGTH: 4
<212> TYPE: PRT
<213> ORGANISM: Homo sapiens

<400> SEQUENCE: 67

Asp Ile Cys Gly
1

<210> SEQ ID NO 68
<211> LENGTH: 4
<212> TYPE: PRT
<213> ORGANISM: Homo sapiens

<400> SEQUENCE: 68

Asp Asp Leu Gly
1

<210> SEQ ID NO 69
<211> LENGTH: 4
<212> TYPE: PRT
<213> ORGANISM: Homo sapiens

<400> SEQUENCE: 69

Asp Pro Val Gly
1

<210> SEQ ID NO 70
<211> LENGTH: 4
<212> TYPE: PRT
<213> ORGANISM: Homo sapiens

<400> SEQUENCE: 70

Asp Lys Ser Gly

-continued

1

<210> SEQ ID NO 71
<211> LENGTH: 4
<212> TYPE: PRT
<213> ORGANISM: Homo sapiens

<400> SEQUENCE: 71

Asp His Ala Gly
1

<210> SEQ ID NO 72
<211> LENGTH: 4
<212> TYPE: PRT
<213> ORGANISM: Homo sapiens

<400> SEQUENCE: 72

Asp Gln Asn Gly
1

<210> SEQ ID NO 73
<211> LENGTH: 4
<212> TYPE: PRT
<213> ORGANISM: Homo sapiens

<400> SEQUENCE: 73

Asp Lys Leu Gly
1

<210> SEQ ID NO 74
<211> LENGTH: 5
<212> TYPE: PRT
<213> ORGANISM: Homo sapiens

<400> SEQUENCE: 74

Leu Phe Leu Met Asp
1               5

<210> SEQ ID NO 75
<211> LENGTH: 5
<212> TYPE: PRT
<213> ORGANISM: Homo sapiens

<400> SEQUENCE: 75

Leu Phe Thr Phe Asp
1               5

<210> SEQ ID NO 76
<211> LENGTH: 5
<212> TYPE: PRT
<213> ORGANISM: Homo sapiens

<400> SEQUENCE: 76

Leu Phe Ile Leu Asp
1               5

<210> SEQ ID NO 77
<211> LENGTH: 5
<212> TYPE: PRT
<213> ORGANISM: Homo sapiens

<400> SEQUENCE: 77

Leu Phe Ile Ile Asp
1               5

-continued

<210> SEQ ID NO 78
<211> LENGTH: 5
<212> TYPE: PRT
<213> ORGANISM: Homo sapiens

<400> SEQUENCE: 78

Leu Phe Ile Met Asp
1               5

<210> SEQ ID NO 79
<211> LENGTH: 5
<212> TYPE: PRT
<213> ORGANISM: Homo sapiens

<400> SEQUENCE: 79

Leu Leu Ile Leu Asp
1               5

<210> SEQ ID NO 80
<211> LENGTH: 5
<212> TYPE: PRT
<213> ORGANISM: Homo sapiens

<400> SEQUENCE: 80

Leu Leu Thr Phe Asp
1               5

<210> SEQ ID NO 81
<211> LENGTH: 5
<212> TYPE: PRT
<213> ORGANISM: Homo sapiens

<400> SEQUENCE: 81

Leu Leu Ile Phe Asp
1               5

<210> SEQ ID NO 82
<211> LENGTH: 5
<212> TYPE: PRT
<213> ORGANISM: Homo sapiens

<400> SEQUENCE: 82

Leu Phe Val Ile Asp
1               5

<210> SEQ ID NO 83
<211> LENGTH: 5
<212> TYPE: PRT
<213> ORGANISM: Homo sapiens

<400> SEQUENCE: 83

Leu Leu Leu Leu Asp
1               5

<210> SEQ ID NO 84
<211> LENGTH: 6
<212> TYPE: PRT
<213> ORGANISM: Homo sapiens

<400> SEQUENCE: 84

Leu Phe Ile Leu Glu Asp
1               5

<210> SEQ ID NO 85

-continued

<211> LENGTH: 5
<212> TYPE: PRT
<213> ORGANISM: Homo sapiens

<400> SEQUENCE: 85

Ile Val Val Leu Asp
1 5

<210> SEQ ID NO 86
<211> LENGTH: 5
<212> TYPE: PRT
<213> ORGANISM: Homo sapiens

<400> SEQUENCE: 86

Leu Phe Leu Leu Asp
1 5

<210> SEQ ID NO 87
<211> LENGTH: 5
<212> TYPE: PRT
<213> ORGANISM: Homo sapiens

<400> SEQUENCE: 87

Tyr Leu Ile Ile Asp
1 5

<210> SEQ ID NO 88
<211> LENGTH: 5
<212> TYPE: PRT
<213> ORGANISM: Homo sapiens

<400> SEQUENCE: 88

Val Leu Ile Ile Asp
1 5

<210> SEQ ID NO 89
<211> LENGTH: 4
<212> TYPE: PRT
<213> ORGANISM: Homo sapiens

<400> SEQUENCE: 89

Ser Lys Ala Asp
1

<210> SEQ ID NO 90
<211> LENGTH: 4
<212> TYPE: PRT
<213> ORGANISM: Homo sapiens

<400> SEQUENCE: 90

Thr Lys His Asp
1

<210> SEQ ID NO 91
<211> LENGTH: 4
<212> TYPE: PRT
<213> ORGANISM: Homo sapiens

<400> SEQUENCE: 91

Ser Lys Gln Asp
1

<210> SEQ ID NO 92
<211> LENGTH: 8
<212> TYPE: PRT

-continued

<213> ORGANISM: Artificial Sequence
<220> FEATURE:
<223> OTHER INFORMATION: Consensus P-Loop Motif
<220> FEATURE:
<221> NAME/KEY: MISC_FEATURE
<222> LOCATION: (2)..(5)
<223> OTHER INFORMATION: "Xaa" denotes any amino acid residue
<220> FEATURE:
<221> NAME/KEY: MISC_FEATURE
<222> LOCATION: (8)..(8)
<223> OTHER INFORMATION: "Xaa" denotes Serine or Threonine.

<400> SEQUENCE: 92

Gly Xaa Xaa Xaa Xaa Gly Lys Xaa
1 5

<210> SEQ ID NO 93
<211> LENGTH: 4
<212> TYPE: PRT
<213> ORGANISM: Artificial Sequence
<220> FEATURE:
<223> OTHER INFORMATION: Consensus Mg+2 Site (G3)
<220> FEATURE:
<221> NAME/KEY: MISC_FEATURE
<222> LOCATION: (2)..(4)
<223> OTHER INFORMATION: "Xaa" denotes any amino acid residue

<400> SEQUENCE: 93

Asp Xaa Xaa Gly
1

<210> SEQ ID NO 94
<211> LENGTH: 5
<212> TYPE: PRT
<213> ORGANISM: Artificial Sequence
<220> FEATURE:
<223> OTHER INFORMATION: Consensus Mg+2 Site (Kinase2)
<220> FEATURE:
<221> NAME/KEY: MISC_FEATURE
<222> LOCATION: (1)..(4)
<223> OTHER INFORMATION: "Xaa" denotes a hydrophobic amino acid residue

<400> SEQUENCE: 94

Xaa Xaa Xaa Xaa Asp
1 5

<210> SEQ ID NO 95
<211> LENGTH: 4
<212> TYPE: PRT
<213> ORGANISM: Artificial Sequence
<220> FEATURE:
<223> OTHER INFORMATION: Consensus Guanine-binding site (G3)
<220> FEATURE:
<221> NAME/KEY: MISC_FEATURE
<222> LOCATION: (1)..(1)
<223> OTHER INFORMATION: "Xaa" denotes Asn, Ser, or Thr
<220> FEATURE:
<221> NAME/KEY: MISC_FEATURE
<222> LOCATION: (3)..(3)
<223> OTHER INFORMATION: "Xaa" denotes any amino acid residue

<400> SEQUENCE: 95

Xaa Lys Xaa Asp
1

<210> SEQ ID NO 96
<211> LENGTH: 20
<212> TYPE: DNA
<213> ORGANISM: Artificial Sequence
<220> FEATURE:
<223> OTHER INFORMATION: Synthetic primer -continued

<400> SEQUENCE: 96
tgctacaagt ccgggacaaa 20

<210> SEQ ID NO 97
<211> LENGTH: 19
<212> TYPE: DNA
<213> ORGANISM: Artificial Sequence
<220> FEATURE:
<223> OTHER INFORMATION: Synthetic primer

<400> SEQUENCE: 97
gcccagttct gggtcattt 19

<210> SEQ ID NO 98
<211> LENGTH: 23
<212> TYPE: DNA
<213> ORGANISM: Artificial Sequence
<220> FEATURE:
<223> OTHER INFORMATION: Synthetic probe

<400> SEQUENCE: 98
cagcagagcc tcagagtgct tcg 23

<210> SEQ ID NO 99
<211> LENGTH: 18
<212> TYPE: DNA
<213> ORGANISM: Artificial Sequence
<220> FEATURE:
<223> OTHER INFORMATION: Synthetic primer

<400> SEQUENCE: 99
gctgctggca ccagactt 18

<210> SEQ ID NO 100
<211> LENGTH: 18
<212> TYPE: DNA
<213> ORGANISM: Artificial Sequence
<220> FEATURE:
<223> OTHER INFORMATION: Synthetic primer

<400> SEQUENCE: 100
cggctaccac atccaagg 18

<210> SEQ ID NO 101
<211> LENGTH: 22
<212> TYPE: DNA
<213> ORGANISM: Artificial Sequence
<220> FEATURE:
<223> OTHER INFORMATION: Synthetic probe

<400> SEQUENCE: 101
caaattaccc actcccgacc cg 22

<210> SEQ ID NO 102
<211> LENGTH: 18
<212> TYPE: DNA
<213> ORGANISM: Artificial Sequence
<220> FEATURE:
<223> OTHER INFORMATION: Synthetic primer

<400> SEQUENCE: 102
agaccctgcc gcgctact 18

<210> SEQ ID NO 103

-continued

<211> LENGTH: 21
<212> TYPE: DNA
<213> ORGANISM: Artificial Sequence
<220> FEATURE:
<223> OTHER INFORMATION: Synthetic primer

<400> SEQUENCE: 103
tccactggag ggtgtgagaa c 21

<210> SEQ ID NO 104
<211> LENGTH: 15
<212> TYPE: DNA
<213> ORGANISM: Artificial Sequence
<220> FEATURE:
<223> OTHER INFORMATION: Synthetic probe

<400> SEQUENCE: 104
aaccagagcg aggcc 15

<210> SEQ ID NO 105
<211> LENGTH: 19
<212> TYPE: DNA
<213> ORGANISM: Artificial Sequence
<220> FEATURE:
<223> OTHER INFORMATION: Synthetic primer

<400> SEQUENCE: 105
gggaccggga gacacagat 19

<210> SEQ ID NO 106
<211> LENGTH: 20
<212> TYPE: DNA
<213> ORGANISM: Artificial Sequence
<220> FEATURE:
<223> OTHER INFORMATION: Synthetic primer

<400> SEQUENCE: 106
gcgcaggttc tctcggtaag 20

<210> SEQ ID NO 107
<211> LENGTH: 16
<212> TYPE: DNA
<213> ORGANISM: Artificial Sequence
<220> FEATURE:
<223> OTHER INFORMATION: Synthetic probe

<400> SEQUENCE: 107
caagaccaac acacag 16

<210> SEQ ID NO 108
<211> LENGTH: 19
<212> TYPE: DNA
<213> ORGANISM: Artificial Sequence
<220> FEATURE:
<223> OTHER INFORMATION: Synthetic primer

<400> SEQUENCE: 108
gccgcagggc tattgctta 19

<210> SEQ ID NO 109
<211> LENGTH: 22
<212> TYPE: DNA
<213> ORGANISM: Artificial Sequence
<220> FEATURE:
<223> OTHER INFORMATION: Synthetic primer

<400> SEQUENCE: 109

-continued catattgaca acgcctccag aa 22

<210> SEQ ID NO 110
<211> LENGTH: 17
<212> TYPE: DNA
<213> ORGANISM: Artificial Sequence
<220> FEATURE:
<223> OTHER INFORMATION: Synthetic probe

<400> SEQUENCE: 110
cactcacaga gacagct 17

<210> SEQ ID NO 111
<211> LENGTH: 20
<212> TYPE: DNA
<213> ORGANISM: Artificial Sequence
<220> FEATURE:
<223> OTHER INFORMATION: Synthetic primer

<400> SEQUENCE: 111
acctcaacta catggtttac 20

<210> SEQ ID NO 112
<211> LENGTH: 20
<212> TYPE: DNA
<213> ORGANISM: Artificial Sequence
<220> FEATURE:
<223> OTHER INFORMATION: Synthetic primer

<400> SEQUENCE: 112
gaagatggtg atgggatttc 20

<210> SEQ ID NO 113
<211> LENGTH: 20
<212> TYPE: DNA
<213> ORGANISM: Artificial Sequence
<220> FEATURE:
<223> OTHER INFORMATION: Synthetic probe

<400> SEQUENCE: 113
caagcttccc gttctcagcc 20

<210> SEQ ID NO 114
<211> LENGTH: 31
<212> TYPE: DNA
<213> ORGANISM: Artificial Sequence
<220> FEATURE:
<223> OTHER INFORMATION: Synthetic primer

<400> SEQUENCE: 114
ggggtaccgc tacgaaccgc aggcagggac g 31

<210> SEQ ID NO 115
<211> LENGTH: 23
<212> TYPE: DNA
<213> ORGANISM: Artificial Sequence
<220> FEATURE:
<223> OTHER INFORMATION: Synthetic primer

<400> SEQUENCE: 115
cagcctggtc acgtcctggt ctg 23

<210> SEQ ID NO 116
<211> LENGTH: 23
<212> TYPE: DNA

-continued

<213> ORGANISM: Artificial Sequence
<220> FEATURE:
<223> OTHER INFORMATION: Synthetic primer

<400> SEQUENCE: 116
cagaaggaca tcaactgtga gag 23

<210> SEQ ID NO 117
<211> LENGTH: 31
<212> TYPE: DNA
<213> ORGANISM: Artificial Sequence
<220> FEATURE:
<223> OTHER INFORMATION: Synthetic primer

<400> SEQUENCE: 117
gctctagaca gcagatagga ccattcagca g 31

<210> SEQ ID NO 118
<211> LENGTH: 23
<212> TYPE: DNA
<213> ORGANISM: Artificial Sequence
<220> FEATURE:
<223> OTHER INFORMATION: Synthetic primer

<400> SEQUENCE: 118
ttgagcggat aaacaggaag gac 23

<210> SEQ ID NO 119
<211> LENGTH: 24
<212> TYPE: DNA
<213> ORGANISM: Artificial Sequence
<220> FEATURE:
<223> OTHER INFORMATION: Synthetic primer

<400> SEQUENCE: 119
atctccctgc agttgatgta gaag 24

<210> SEQ ID NO 120
<211> LENGTH: 26
<212> TYPE: DNA
<213> ORGANISM: Artificial Sequence
<220> FEATURE:
<223> OTHER INFORMATION: Synthetic primer

<400> SEQUENCE: 120
cgtctggctc aaagagggtc tctatc 26

<210> SEQ ID NO 121
<211> LENGTH: 26
<212> TYPE: DNA
<213> ORGANISM: Artificial Sequence
<220> FEATURE:
<223> OTHER INFORMATION: Synthetic primer

<400> SEQUENCE: 121
ctgcggacat agtccctgta ggtttc 26

<210> SEQ ID NO 122
<211> LENGTH: 19
<212> TYPE: DNA
<213> ORGANISM: Homo sapiens

<400> SEQUENCE: 122
gtccatgctg gcacacaag 19

-continued

<210> SEQ ID NO 123
<211> LENGTH: 19
<212> TYPE: DNA
<213> ORGANISM: Artificial Sequence
<220> FEATURE:
<223> OTHER INFORMATION: Synthetic oligonucleotide

<400> SEQUENCE: 123
gtccatgcta acacacaag 19

<210> SEQ ID NO 124
<211> LENGTH: 21
<212> TYPE: DNA
<213> ORGANISM: Artificial Sequence
<220> FEATURE:
<223> OTHER INFORMATION: Synthetic primer

<400> SEQUENCE: 124
agaggacctg gtgagggata c 21

<210> SEQ ID NO 125
<211> LENGTH: 20
<212> TYPE: DNA
<213> ORGANISM: Artificial Sequence
<220> FEATURE:
<223> OTHER INFORMATION: Synthetic primer

<400> SEQUENCE: 125
cttccagaag gcatgttgac 20

<210> SEQ ID NO 126
<211> LENGTH: 21
<212> TYPE: DNA
<213> ORGANISM: Artificial Sequence
<220> FEATURE:
<223> OTHER INFORMATION: Synthetic probe

<400> SEQUENCE: 126
cccgtcctca cttgggaacc a 21

<210> SEQ ID NO 127
<211> LENGTH: 23
<212> TYPE: DNA
<213> ORGANISM: Artificial Sequence
<220> FEATURE:
<223> OTHER INFORMATION: Synthetic primer

<400> SEQUENCE: 127
cagaaggaca tcaactgtga gag 23

<210> SEQ ID NO 128
<211> LENGTH: 31
<212> TYPE: DNA
<213> ORGANISM: Artificial Sequence
<220> FEATURE:
<223> OTHER INFORMATION: Synthetic primer

<400> SEQUENCE: 128
gctctagaca gcagatagga ccattcagca g 31

<210> SEQ ID NO 129
<211> LENGTH: 24
<212> TYPE: DNA
<213> ORGANISM: Artificial Sequence
<220> FEATURE:
<223> OTHER INFORMATION: Synthetic primer -continued

<400> SEQUENCE: 129
aactttgcct ttgaagaacc tgag 24

<210> SEQ ID NO 130
<211> LENGTH: 24
<212> TYPE: DNA
<213> ORGANISM: Artificial Sequence
<220> FEATURE:
<223> OTHER INFORMATION: Synthetic primer

<400> SEQUENCE: 130
acatgaaggt gggygaacac atag 24

<210> SEQ ID NO 131
<211> LENGTH: 26
<212> TYPE: DNA
<213> ORGANISM: Artificial Sequence
<220> FEATURE:
<223> OTHER INFORMATION: Synthetic primer

<400> SEQUENCE: 131
atggcagatt catcatcatc atcttc 26

<210> SEQ ID NO 132
<211> LENGTH: 25
<212> TYPE: DNA
<213> ORGANISM: Artificial Sequence
<220> FEATURE:
<223> OTHER INFORMATION: Synthetic primer

<400> SEQUENCE: 132
tcacccgagc ctctgaatgt tacag 25

<210> SEQ ID NO 133
<211> LENGTH: 128
<212> TYPE: DNA
<213> ORGANISM: Artificial Sequence
<220> FEATURE:
<223> OTHER INFORMATION: Synthetic oligonucleotide

<400> SEQUENCE: 133
gatccccgaa gagatcaact ggtcggttca agagaccgac cagttgatct cttctttttg 60
gaaagggctt ctctagttga ccagccacgt tctctggctg gtcaactaga gaagaaaaac 120
ctttagct 128

<210> SEQ ID NO 134
<211> LENGTH: 57
<212> TYPE: DNA
<213> ORGANISM: Artificial Sequence
<220> FEATURE:
<223> OTHER INFORMATION: Synthetic primer

<400> SEQUENCE: 134
ccgggtacca tggactacaa agacgatgac gataaaggtg gcaggtgggg gcaccat 57

<210> SEQ ID NO 135
<211> LENGTH: 24
<212> TYPE: DNA
<213> ORGANISM: Artificial Sequence
<220> FEATURE:
<223> OTHER INFORMATION: Synthetic primer

<400> SEQUENCE: 135
atcttctgaa tgcgacagtc cttc 24

-continued

<210> SEQ ID NO 136
<211> LENGTH: 24
<212> TYPE: DNA
<213> ORGANISM: Artificial Sequence
<220> FEATURE:
<223> OTHER INFORMATION: Synthetic primer

<400> SEQUENCE: 136
aaggactgtc gcattcagaa gatc 24

<210> SEQ ID NO 137
<211> LENGTH: 31
<212> TYPE: DNA
<213> ORGANISM: Artificial Sequence
<220> FEATURE:
<223> OTHER INFORMATION: Synthetic primer

<400> SEQUENCE: 137
ataggatccc caggatcaca tttcaacagt g 31

<210> SEQ ID NO 138
<211> LENGTH: 18
<212> TYPE: DNA
<213> ORGANISM: Artificial Sequence
<220> FEATURE:
<223> OTHER INFORMATION: Synthetic primer

<400> SEQUENCE: 138
ctgggaaggg cagtcaag 18

<210> SEQ ID NO 139
<211> LENGTH: 20
<212> TYPE: DNA
<213> ORGANISM: Artificial Sequence
<220> FEATURE:
<223> OTHER INFORMATION: Synthetic primer

<400> SEQUENCE: 139
tgcctctgta tccttgagtc 20

<210> SEQ ID NO 140
<211> LENGTH: 24
<212> TYPE: DNA
<213> ORGANISM: Artificial Sequence
<220> FEATURE:
<223> OTHER INFORMATION: Synthetic probe

<400> SEQUENCE: 140
cccgcaggcc ctggatagga cacc 24

<210> SEQ ID NO 141
<211> LENGTH: 20
<212> TYPE: DNA
<213> ORGANISM: Artificial Sequence
<220> FEATURE:
<223> OTHER INFORMATION: Synthetic primer

<400> SEQUENCE: 141
tgctacaagt ccgggacaaa 20

<210> SEQ ID NO 142
<211> LENGTH: 19
<212> TYPE: DNA
<213> ORGANISM: Artificial Sequence
<220> FEATURE:

-continued

<223> OTHER INFORMATION: Synthetic primer

<400> SEQUENCE: 142
gcccagttct gggtcattt 19

<210> SEQ ID NO 143
<211> LENGTH: 23
<212> TYPE: DNA
<213> ORGANISM: Artificial Sequence
<220> FEATURE:
<223> OTHER INFORMATION: Synthetic probe

<400> SEQUENCE: 143
cagcagagcc tcagagtgct tcg 23

<210> SEQ ID NO 144
<211> LENGTH: 19
<212> TYPE: DNA
<213> ORGANISM: Homo sapiens

<400> SEQUENCE: 144
ggagatcccg gtggaccac 19

<210> SEQ ID NO 145
<211> LENGTH: 19
<212> TYPE: DNA
<213> ORGANISM: Artificial Sequence
<220> FEATURE:
<223> OTHER INFORMATION: Synthetic oligonucleotide

<400> SEQUENCE: 145
ggagatcctg gtggaccac 19

<210> SEQ ID NO 146
<211> LENGTH: 20
<212> TYPE: DNA
<213> ORGANISM: Artificial Sequence
<220> FEATURE:
<223> OTHER INFORMATION: Synthetic primer

<400> SEQUENCE: 146
ggcatatcac agtgggattc 20

<210> SEQ ID NO 147
<211> LENGTH: 19
<212> TYPE: DNA
<213> ORGANISM: Artificial Sequence
<220> FEATURE:
<223> OTHER INFORMATION: Synthetic primer

<400> SEQUENCE: 147
gatcttcgct gcgatcaac 19

<210> SEQ ID NO 148
<211> LENGTH: 2934
<212> TYPE: DNA
<213> ORGANISM: Mus musculus

<400> SEQUENCE: 148
atggcaagca cccgctgcaa gctggccagg tacctggagg acctggagga tgtggacttg 60
aagaaattta agatgcactt agaggactat cctccccaga agggctgcat ccccctcccg 120
aggggtcaga cagagaaggc agaccatgtg gatctagcca cgctaatgat cgacttcaat 180
ggggaggaga aggcgtgggc catggccgtg tggatcttcg ctgcgatcaa caggagagac 240

-continued

```
ctttatgaga aagcaaaaag agatgagccg aagtggggtt cagataatgc acgtgtttcg    300
aatcccactg tgatatgcca ggaagacagc attgaagagg agtggatggg tttactggag    360
tacctttcga gaatctctat ttgtaaaatg aagaaagatt accgtaagaa gtacagaaag    420
tacgtgagaa gcagattcca gtgcattgaa gacaggaatg cccgtctggg tgagagtgtg    480
agcctcaaca aacgctacac acgactgcgt ctcatcaagg agcaccggag ccagcaggag    540
agggagcagg agcttctggc catcggcaag accaagacgt gtgagagccc cgtgagtccc    600
attaagatgg agttgctgtt tgaccccgat gatgagcatt ctgagcctgt gcacaccgtg    660
gtgttccagg gggcggcagg gattgggaaa acaatcctgg ccaggaagat gatgttggac    720
tgggcgtcgg ggacactcta ccaagacagg tttgactatc tgttctatat ccactgtcgg    780
gaggtgagcc ttgtgacaca gaggagcctg ggggacctga tcatgagctg ctgccccgac    840
ccaaacccac ccatccacaa gatcgtgaga aaaccctcca gaatcctctt cctcatggac    900
ggcttcgatg agctgcaagg tgcctttgac gagcacatag gaccgctctg cactgactgg    960
cagaaggccg agcggggaga cattctcctg agcagcctca tcagaaagaa gctgcttccc   1020
gaggcctctc tgctcatcac cacgagacct gtggccctgg agaaactgca gcacttgctg   1080
gaccatcctc ggcatgtgga gatcctgggt ttctccgagg ccaaaaggaa agagtacttc   1140
ttcaagtact tctctgatga ggcccaagcc agggcagcct tcagtctgat tcaggagaac   1200
gaggtcctct tcaccatgtg cttcatcccc ctggtctgct ggatcgtgtg cactggactg   1260
aaacagcaga tggagagtgg caagagcctt gcccagacat ccaagaccac caccgcggtg   1320
tacgtcttct tcctttccag tttgctgcag ccccggggag ggagccagga gcacggcctc   1380
tgcgcccacc tctgggggct ctgctctttg gctgcagatg gaatctggaa ccagaaaatc   1440
ctgtttgagg agtccgacct caggaatcat ggactgcaga aggcggatgt gtctgctttc   1500
ctgaggatga acctgttcca aaaggaagtg gactgcgaga agttctacag cttcatccac   1560
atgactttcc aggagttctt tgccgccatg tactacctgc tggaagagga aaaggaagga   1620
aggacgaacg ttccagggag tcgtttgaag cttcccagcc gagacgtgac agtccttctg   1680
gaaaactatg gcaaattcga aaaggggtat ttgatttttg ttgtacgttt cctctttggc   1740
ctggtaaacc aggagaggac ctcctacttg gagaagaaat taagttgcaa gatctctcag   1800
caaatcaggc tggagctgct gaaatggatt gaagtgaaag ccaaagctaa aaagctgcag   1860
atccagccca gccagctgga attgttctac tgtttgtacg agatgcagga ggaggacttc   1920
gtgcaaaggg ccatggacta tttccccaag attgagatca atctctccac cagaatggac   1980
cacatggttt cttccttttg cattgagaac tgtcatcggg tggagtcact gtccctgggg   2040
tttctccata acatgcccaa ggaggaagag gaggaggaaa aggaaggccg acaccttgat   2100
atggtgcagt gtgtcctccc aagctcctct catgctgcct gttctcatgg gttggggcgc   2160
tgtggcctct cgcatgagtg ctgcttcgac atctccttgg tcctcagcag caaccagaag   2220
ctggtggagc tggacctgag tgacaacgcc ctcggtgact tcggaatcag acttctgtgt   2280
gtgggactga agcacctgtt gtgcaatctg aagaagctct ggttggtcag ctgctgcctc   2340
acatcagcat gttgtcagga tcttgcatca gtattgagca ccagccattc cctgaccaga   2400
ctctatgtgg gggagaatgc cttgggagac tcaggagtcg caattttatg tgaaaaagcc   2460
aagaatccac agtgtaacct gcagaaactg gggttggtga attctggcct tacgtcagtc   2520
tgttgttcag ctttgtcctc ggtactcagc actaatcaga atctcacgca cctttacctg   2580
```

-continued

```
cgaggcaaca ctctcggaga caaggggatc aaactactct gtgagggact cttgcacccc   2640

gactgcaagc ttcaggtgtt ggaattagac aactgcaacc tcacgtcaca ctgctgctgg   2700

gatctttcca cacttctgac ctccagccag agcctgcgaa agctgagcct gggcaacaat   2760

gacctgggcg acctgggggt catgatgttc tgtgaagtgc tgaaacagca gagctgcctc   2820

ctgcagaacc tggggttgtc tgaaatgtat ttcaattatg agacaaaaag tgcgttagaa   2880

acacttcaag aagaaaagcc tgagctgacc gtcgtctttg agccttcttg gtag         2934
```

```
<210> SEQ ID NO 149
<211> LENGTH: 977
<212> TYPE: PRT
<213> ORGANISM: Mus musculus

<400> SEQUENCE: 149

Met Ala Ser Thr Arg Cys Lys Leu Ala Arg Tyr Leu Glu Asp Leu Glu
1               5                   10                  15

Asp Val Asp Leu Lys Lys Phe Lys Met His Leu Glu Asp Tyr Pro Pro
            20                  25                  30

Gln Lys Gly Cys Ile Pro Leu Pro Arg Gly Gln Thr Glu Lys Ala Asp
        35                  40                  45

His Val Asp Leu Ala Thr Leu Met Ile Asp Phe Asn Gly Glu Glu Lys
    50                  55                  60

Ala Trp Ala Met Ala Val Trp Ile Phe Ala Ala Ile Asn Arg Arg Asp
65                  70                  75                  80

Leu Tyr Glu Lys Ala Lys Arg Asp Glu Pro Lys Trp Gly Ser Asp Asn
                85                  90                  95

Ala Arg Val Ser Asn Pro Thr Val Ile Cys Gln Glu Asp Ser Ile Glu
            100                 105                 110

Glu Glu Trp Met Gly Leu Leu Glu Tyr Leu Ser Arg Ile Ser Ile Cys
        115                 120                 125

Lys Met Lys Lys Asp Tyr Arg Lys Lys Tyr Arg Lys Tyr Val Arg Ser
    130                 135                 140

Arg Phe Gln Cys Ile Glu Asp Arg Asn Ala Arg Leu Gly Glu Ser Val
145                 150                 155                 160

Ser Leu Asn Lys Arg Tyr Thr Arg Leu Arg Leu Ile Lys Glu His Arg
                165                 170                 175

Ser Gln Gln Glu Arg Glu Gln Glu Leu Leu Ala Ile Gly Lys Thr Lys
            180                 185                 190

Thr Cys Glu Ser Pro Val Ser Pro Ile Lys Met Glu Leu Leu Phe Asp
        195                 200                 205

Pro Asp Asp Glu His Ser Glu Pro Val His Thr Val Val Phe Gln Gly
    210                 215                 220

Ala Ala Gly Ile Gly Lys Thr Ile Leu Ala Arg Lys Met Met Leu Asp
225                 230                 235                 240

Trp Ala Ser Gly Thr Leu Tyr Gln Asp Arg Phe Asp Tyr Leu Phe Tyr
                245                 250                 255

Ile His Cys Arg Glu Val Ser Leu Val Thr Gln Arg Ser Leu Gly Asp
            260                 265                 270

Leu Ile Met Ser Cys Cys Pro Asp Pro Asn Pro Pro Ile His Lys Ile
        275                 280                 285

Val Arg Lys Pro Ser Arg Ile Leu Phe Leu Met Asp Gly Phe Asp Glu
    290                 295                 300

Leu Gln Gly Ala Phe Asp Glu His Ile Gly Pro Leu Cys Thr Asp Trp
305                 310                 315                 320
```

-continued

```
Gln Lys Ala Glu Arg Gly Asp Ile Leu Leu Ser Ser Leu Ile Arg Lys
                325                 330                 335

Lys Leu Leu Pro Glu Ala Ser Leu Leu Ile Thr Thr Arg Pro Val Ala
            340                 345                 350

Leu Glu Lys Leu Gln His Leu Leu Asp His Pro Arg His Val Glu Ile
        355                 360                 365

Leu Gly Phe Ser Glu Ala Lys Arg Lys Glu Tyr Phe Phe Lys Tyr Phe
    370                 375                 380

Ser Asp Glu Ala Gln Ala Arg Ala Ala Phe Ser Leu Ile Gln Glu Asn
385                 390                 395                 400

Glu Val Leu Phe Thr Met Cys Phe Ile Pro Leu Val Cys Trp Ile Val
                405                 410                 415

Cys Thr Gly Leu Lys Gln Gln Met Glu Ser Gly Lys Ser Leu Ala Gln
            420                 425                 430

Thr Ser Lys Thr Thr Thr Ala Val Tyr Val Phe Phe Leu Ser Ser Leu
        435                 440                 445

Leu Gln Pro Arg Gly Gly Ser Gln Glu His Gly Leu Cys Ala His Leu
    450                 455                 460

Trp Gly Leu Cys Ser Leu Ala Ala Asp Gly Ile Trp Asn Gln Lys Ile
465                 470                 475                 480

Leu Phe Glu Glu Ser Asp Leu Arg Asn His Gly Leu Gln Lys Ala Asp
                485                 490                 495

Val Ser Ala Phe Leu Arg Met Asn Leu Phe Gln Lys Glu Val Asp Cys
            500                 505                 510

Glu Lys Phe Tyr Ser Phe Ile His Met Thr Phe Gln Glu Phe Phe Ala
        515                 520                 525

Ala Met Tyr Tyr Leu Leu Glu Glu Glu Lys Glu Gly Arg Thr Asn Val
    530                 535                 540

Pro Gly Ser Arg Leu Lys Leu Pro Ser Arg Asp Val Thr Val Leu Leu
545                 550                 555                 560

Glu Asn Tyr Gly Lys Phe Glu Lys Gly Tyr Leu Ile Phe Val Val Arg
                565                 570                 575

Phe Leu Phe Gly Leu Val Asn Gln Glu Arg Thr Ser Tyr Leu Glu Lys
            580                 585                 590

Lys Leu Ser Cys Lys Ile Ser Gln Gln Ile Arg Leu Glu Leu Leu Lys
        595                 600                 605

Trp Ile Glu Val Lys Ala Lys Ala Lys Lys Leu Gln Ile Gln Pro Ser
    610                 615                 620

Gln Leu Glu Leu Phe Tyr Cys Leu Tyr Glu Met Gln Glu Glu Asp Phe
625                 630                 635                 640

Val Gln Arg Ala Met Asp Tyr Phe Pro Lys Ile Glu Ile Asn Leu Ser
                645                 650                 655

Thr Arg Met Asp His Met Val Ser Ser Phe Cys Ile Glu Asn Cys His
            660                 665                 670

Arg Val Glu Ser Leu Ser Leu Gly Phe Leu His Asn Met Pro Lys Glu
        675                 680                 685

Glu Glu Glu Glu Glu Lys Glu Gly Arg His Leu Asp Met Val Gln Cys
    690                 695                 700

Val Leu Pro Ser Ser Ser His Ala Ala Cys Ser His Gly Leu Gly Arg
705                 710                 715                 720

Cys Gly Leu Ser His Glu Cys Cys Phe Asp Ile Ser Leu Val Leu Ser
                725                 730                 735
```

-continued

```
Ser Asn Gln Lys Leu Val Glu Leu Asp Leu Ser Asp Asn Ala Leu Gly
            740                 745                 750

Asp Phe Gly Ile Arg Leu Leu Cys Val Gly Leu Lys His Leu Leu Cys
        755                 760                 765

Asn Leu Lys Lys Leu Trp Leu Val Ser Cys Cys Leu Thr Ser Ala Cys
    770                 775                 780

Cys Gln Asp Leu Ala Ser Val Leu Ser Thr Ser His Ser Leu Thr Arg
785                 790                 795                 800

Leu Tyr Val Gly Glu Asn Ala Leu Gly Asp Ser Gly Val Ala Ile Leu
                805                 810                 815

Cys Glu Lys Ala Lys Asn Pro Gln Cys Asn Leu Gln Lys Leu Gly Leu
            820                 825                 830

Val Asn Ser Gly Leu Thr Ser Val Cys Cys Ser Ala Leu Ser Ser Val
        835                 840                 845

Leu Ser Thr Asn Gln Asn Leu Thr His Leu Tyr Leu Arg Gly Asn Thr
    850                 855                 860

Leu Gly Asp Lys Gly Ile Lys Leu Leu Cys Glu Gly Leu Leu His Pro
865                 870                 875                 880

Asp Cys Lys Leu Gln Val Leu Glu Leu Asp Asn Cys Asn Leu Thr Ser
                885                 890                 895

His Cys Cys Trp Asp Leu Ser Thr Leu Leu Thr Ser Ser Gln Ser Leu
            900                 905                 910

Arg Lys Leu Ser Leu Gly Asn Asn Asp Leu Gly Asp Leu Gly Val Met
        915                 920                 925

Met Phe Cys Glu Val Leu Lys Gln Gln Ser Cys Leu Leu Gln Asn Leu
    930                 935                 940

Gly Leu Ser Glu Met Tyr Phe Asn Tyr Glu Thr Lys Ser Ala Leu Glu
945                 950                 955                 960

Thr Leu Gln Glu Glu Lys Pro Glu Leu Thr Val Val Phe Glu Pro Ser
                965                 970                 975

Trp


<210> SEQ ID NO 150
<211> LENGTH: 30
<212> TYPE: PRT
<213> ORGANISM: Artificial Sequence
<220> FEATURE:
<223> OTHER INFORMATION: Consensus  Motif I
<220> FEATURE:
<221> NAME/KEY: MISC_FEATURE
<222> LOCATION: (1)..(1)
<223> OTHER INFORMATION: "Xaa" denotes any amino acid residue.
<220> FEATURE:
<221> NAME/KEY: MISC_FEATURE
<222> LOCATION: (6)..(6)
<223> OTHER INFORMATION: "Xaa" denotes any amino acid residue.
<220> FEATURE:
<221> NAME/KEY: MISC_FEATURE
<222> LOCATION: (8)..(8)
<223> OTHER INFORMATION: "Xaa" denotes any amino acid residue.
<220> FEATURE:
<221> NAME/KEY: MISC_FEATURE
<222> LOCATION: (11)..(11)
<223> OTHER INFORMATION: "Xaa" denotes a hydrophobic amino acid residue.
<220> FEATURE:
<221> NAME/KEY: MISC_FEATURE
<222> LOCATION: (18)..(19)
<223> OTHER INFORMATION: "Xaa" denotes a basic amino acid residue.
<220> FEATURE:
<221> NAME/KEY: MISC_FEATURE
<222> LOCATION: (20)..(21)
<223> OTHER INFORMATION: "Xaa" denotes a hydrophobic amino acid residue.
<220> FEATURE:
```

-continued

```
<221> NAME/KEY: MISC_FEATURE
<222> LOCATION: (23)..(23)
<223> OTHER INFORMATION: “Xaa” denotes any amino acid residue.
<220> FEATURE:
<221> NAME/KEY: MISC_FEATURE
<222> LOCATION: (26)..(26)
<223> OTHER INFORMATION: “Xaa” denotes any amino acid residue.
<220> FEATURE:
<221> NAME/KEY: MISC_FEATURE
<222> LOCATION: (28)..(28)
<223> OTHER INFORMATION: “Xaa” denotes any amino acid residue.
<220> FEATURE:
<221> NAME/KEY: MISC_FEATURE
<222> LOCATION: (30)..(30)
<223> OTHER INFORMATION: “Xaa” denotes an aromatic amino acid residue.

<400> SEQUENCE: 150

Xaa Thr Val Val Leu Xaa Gly Xaa Ala Gly Xaa Gly Lys Thr Thr Leu
1               5                   10                  15

Ala Xaa Xaa Xaa Xaa Leu Xaa Trp Ala Xaa Gly Xaa Leu Xaa
            20                  25                  30


<210> SEQ ID NO 151
<211> LENGTH: 29
<212> TYPE: PRT
<213> ORGANISM: Artificial Sequence
<220> FEATURE:
<223> OTHER INFORMATION: Consensus Motif II
<220> FEATURE:
<221> NAME/KEY: MISC_FEATURE
<222> LOCATION: (2)..(2)
<223> OTHER INFORMATION: “Xaa” denotes any amino acid residue.
<220> FEATURE:
<221> NAME/KEY: MISC_FEATURE
<222> LOCATION: (3)..(3)
<223> OTHER INFORMATION: “Xaa” denotes an aromatic amino acid residue.
<220> FEATURE:
<221> NAME/KEY: MISC_FEATURE
<222> LOCATION: (4)..(4)
<223> OTHER INFORMATION: “Xaa” denotes a hydrophobic amino acid residue.
<220> FEATURE:
<221> NAME/KEY: MISC_FEATURE
<222> LOCATION: (6)..(6)
<223> OTHER INFORMATION: “Xaa” denotes an aromatic amino acid residue.
<220> FEATURE:
<221> NAME/KEY: MISC_FEATURE
<222> LOCATION: (7)..(7)
<223> OTHER INFORMATION: “Xaa” denotes a hydrophobic amino acid residue.
<220> FEATURE:
<221> NAME/KEY: MISC_FEATURE
<222> LOCATION: (8)..(8)
<223> OTHER INFORMATION: “Xaa” denotes any amino acid residue.
<220> FEATURE:
<221> NAME/KEY: MISC_FEATURE
<222> LOCATION: (10)..(10)
<223> OTHER INFORMATION: “Xaa” denotes a basic amino acid residue.
<220> FEATURE:
<221> NAME/KEY: MISC_FEATURE
<222> LOCATION: (12)..(12)
<223> OTHER INFORMATION: “Xaa” denotes a hydrophobic amino acid residue.
<220> FEATURE:
<221> NAME/KEY: MISC_FEATURE
<222> LOCATION: (13)..(18)
<223> OTHER INFORMATION: “Xaa” denotes any amino acid residue.
<220> FEATURE:
<221> NAME/KEY: MISC_FEATURE
<222> LOCATION: (20)..(20)
<223> OTHER INFORMATION: “Xaa” denotes a hydrophobic amino acid residue.
<220> FEATURE:
<221> NAME/KEY: MISC_FEATURE
<222> LOCATION: (21)..(21)
<223> OTHER INFORMATION: “Xaa” denotes any amino acid residue.
<220> FEATURE:
<221> NAME/KEY: MISC_FEATURE
<222> LOCATION: (22)..(22)
<223> OTHER INFORMATION: “Xaa” denotes an acidic amino acid residue.
```

-continued

<220> FEATURE:
<221> NAME/KEY: MISC_FEATURE
<222> LOCATION: (25)..(27)
<223> OTHER INFORMATION: "Xaa" denotes any amino acid residue.
<220> FEATURE:
<221> NAME/KEY: MISC_FEATURE
<222> LOCATION: (28)..(28)
<223> OTHER INFORMATION: "Xaa" denotes an aromatic amino acid residue.

<400> SEQUENCE: 151

Phe Xaa Xaa Xaa Phe Xaa Xaa Xaa Cys Xaa Glu Xaa Xaa Xaa Xaa Xaa
1 5 10 15

Xaa Xaa Ser Xaa Xaa Xaa Leu Leu Xaa Xaa Xaa Xaa Pro
20 25

<210> SEQ ID NO 152
<211> LENGTH: 19
<212> TYPE: PRT
<213> ORGANISM: Artificial Sequence
<220> FEATURE:
<223> OTHER INFORMATION: Consensus Motif III
<220> FEATURE:
<221> NAME/KEY: MISC_FEATURE
<222> LOCATION: (1)..(1)
<223> OTHER INFORMATION: "Xaa" denotes any amino acid residue.
<220> FEATURE:
<221> NAME/KEY: MISC_FEATURE
<222> LOCATION: (3)..(3)
<223> OTHER INFORMATION: "Xaa" denotes a hydrophobic amino acid residue.
<220> FEATURE:
<221> NAME/KEY: MISC_FEATURE
<222> LOCATION: (4)..(5)
<223> OTHER INFORMATION: "Xaa" denotes any amino acid residue.
<220> FEATURE:
<221> NAME/KEY: MISC_FEATURE
<222> LOCATION: (7)..(7)
<223> OTHER INFORMATION: "Xaa" denotes an acidic amino acid residue.
<220> FEATURE:
<221> NAME/KEY: MISC_FEATURE
<222> LOCATION: (13)..(13)
<223> OTHER INFORMATION: "Xaa" denotes a hydrophobic amino acid residue.

<400> SEQUENCE: 152

Xaa Leu Xaa Xaa Xaa Pro Xaa Arg Leu Leu Phe Leu Xaa Asp Gly Phe
1 5 10 15

Asp Glu Leu

<210> SEQ ID NO 153
<211> LENGTH: 25
<212> TYPE: PRT
<213> ORGANISM: Artificial Sequence
<220> FEATURE:
<223> OTHER INFORMATION: Consensus Motif IV
<220> FEATURE:
<221> NAME/KEY: MISC_FEATURE
<222> LOCATION: (3)..(3)
<223> OTHER INFORMATION: "Xaa" denotes any amino acid residue.
<220> FEATURE:
<221> NAME/KEY: MISC_FEATURE
<222> LOCATION: (7)..(7)
<223> OTHER INFORMATION: "Xaa" denotes a basic amino acid residue.
<220> FEATURE:
<221> NAME/KEY: MISC_FEATURE
<222> LOCATION: (9)..(9)
<223> OTHER INFORMATION: "Xaa" denotes any amino acid residue.
<220> FEATURE:
<221> NAME/KEY: MISC_FEATURE
<222> LOCATION: (20)..(20)
<223> OTHER INFORMATION: "Xaa" denotes serine or threonine.
<220> FEATURE:
<221> NAME/KEY: MISC_FEATURE
<222> LOCATION: (23)..(23)
<223> OTHER INFORMATION: "Xaa" denotes any amino acid residue.

-continued

<220> FEATURE:
<221> NAME/KEY: MISC_FEATURE
<222> LOCATION: (25)..(25)
<223> OTHER INFORMATION: "Xaa" denotes a hydrophobic amino acid residue.

<400> SEQUENCE: 153

Leu Leu Xaa Ser Leu Leu Xaa Lys Xaa Leu Leu Pro Glu Ala Ser Leu
1 5 10 15

Leu Leu Thr Xaa Arg Pro Xaa Ala Xaa
20 25

<210> SEQ ID NO 154
<211> LENGTH: 31
<212> TYPE: PRT
<213> ORGANISM: Artificial Sequence
<220> FEATURE:
<223> OTHER INFORMATION: Consensus Motif V
<220> FEATURE:
<221> NAME/KEY: MISC_FEATURE
<222> LOCATION: (2)..(3)
<223> OTHER INFORMATION: "Xaa" denotes any amino acid residue.
<220> FEATURE:
<221> NAME/KEY: MISC_FEATURE
<222> LOCATION: (4)..(4)
<223> OTHER INFORMATION: "Xaa" denotes a hydrophobic amino acid residue.
<220> FEATURE:
<221> NAME/KEY: MISC_FEATURE
<222> LOCATION: (6)..(8)
<223> OTHER INFORMATION: "Xaa" denotes any amino acid residue.
<220> FEATURE:
<221> NAME/KEY: MISC_FEATURE
<222> LOCATION: (9)..(9)
<223> OTHER INFORMATION: "Xaa" denotes a basic amino acid residue.
<220> FEATURE:
<221> NAME/KEY: MISC_FEATURE
<222> LOCATION: (10)..(10)
<223> OTHER INFORMATION: "Xaa" denotes any amino acid residue.
<220> FEATURE:
<221> NAME/KEY: MISC_FEATURE
<222> LOCATION: (11)..(11)
<223> OTHER INFORMATION: "Xaa" denotes a hydrophobic amino acid residue.
<220> FEATURE:
<221> NAME/KEY: MISC_FEATURE
<222> LOCATION: (12)..(12)
<223> OTHER INFORMATION: "Xaa" denotes any amino acid residue.
<220> FEATURE:
<221> NAME/KEY: MISC_FEATURE
<222> LOCATION: (13)..(13)
<223> OTHER INFORMATION: "Xaa" denotes a hydrophobic amino acid residue.
<220> FEATURE:
<221> NAME/KEY: MISC_FEATURE
<222> LOCATION: (14)..(14)
<223> OTHER INFORMATION: "Xaa" denotes any amino acid residue.
<220> FEATURE:
<221> NAME/KEY: MISC_FEATURE
<222> LOCATION: (19)..(19)
<223> OTHER INFORMATION: "Xaa" denotes any amino acid residue.
<220> FEATURE:
<221> NAME/KEY: MISC_FEATURE
<222> LOCATION: (20)..(20)
<223> OTHER INFORMATION: "Xaa" denotes an acidic amino acid residue.
<220> FEATURE:
<221> NAME/KEY: MISC_FEATURE
<222> LOCATION: (21)..(22)
<223> OTHER INFORMATION: "Xaa" denotes a basic amino acid residue.
<220> FEATURE:
<221> NAME/KEY: MISC_FEATURE
<222> LOCATION: (23)..(24)
<223> OTHER INFORMATION: "Xaa" denotes any amino acid residue.
<220> FEATURE:
<221> NAME/KEY: MISC_FEATURE
<222> LOCATION: (27)..(28)
<223> OTHER INFORMATION: "Xaa" denotes any amino acid residue.
<220> FEATURE:
<221> NAME/KEY: MISC_FEATURE
<222> LOCATION: (29)..(29)

-continued

<223> OTHER INFORMATION: "Xaa" denotes an aromatic amino acid residue.
<220> FEATURE:
<221> NAME/KEY: MISC_FEATURE
<222> LOCATION: (30)..(30)
<223> OTHER INFORMATION: "Xaa" denotes any amino acid residue.
<220> FEATURE:
<221> NAME/KEY: MISC_FEATURE
<222> LOCATION: (31)..(31)
<223> OTHER INFORMATION: "Xaa" denotes an acidic amino acid residue.

<400> SEQUENCE: 154

```
Leu Xaa Xaa Xaa Leu Xaa Xaa Xaa Xaa Xaa Xaa Xaa Xaa Xaa Gly Phe
1               5                   10                  15

Ser Glu Xaa Xaa Xaa Xaa Xaa Xaa Tyr Phe Xaa Xaa Xaa Xaa Xaa
            20                  25                  30
```

<210> SEQ ID NO 155
<211> LENGTH: 38
<212> TYPE: PRT
<213> ORGANISM: Artificial Sequence
<220> FEATURE:
<223> OTHER INFORMATION: Consensus Motif VI
<220> FEATURE:
<221> NAME/KEY: MISC_FEATURE
<222> LOCATION: (2)..(2)
<223> OTHER INFORMATION: "Xaa" denotes any amino acid residue.
<220> FEATURE:
<221> NAME/KEY: MISC_FEATURE
<222> LOCATION: (3)..(3)
<223> OTHER INFORMATION: "Xaa" denotes a basic amino acid residue.
<220> FEATURE:
<221> NAME/KEY: MISC_FEATURE
<222> LOCATION: (5)..(5)
<223> OTHER INFORMATION: "Xaa" denotes a hydrophobic amino acid residue.
<220> FEATURE:
<221> NAME/KEY: MISC_FEATURE
<222> LOCATION: (6)..(7)
<223> OTHER INFORMATION: "Xaa" denotes any amino acid residue.
<220> FEATURE:
<221> NAME/KEY: MISC_FEATURE
<222> LOCATION: (8)..(8)
<223> OTHER INFORMATION: "Xaa" denotes a hydrophobic amino acid residue.
<220> FEATURE:
<221> NAME/KEY: MISC_FEATURE
<222> LOCATION: (9)..(9)
<223> OTHER INFORMATION: "Xaa" denotes a basic amino acid residue.
<220> FEATURE:
<221> NAME/KEY: MISC_FEATURE
<222> LOCATION: (10)..(10)
<223> OTHER INFORMATION: "Xaa" denotes any amino acid residue.
<220> FEATURE:
<221> NAME/KEY: MISC_FEATURE
<222> LOCATION: (12)..(13)
<223> OTHER INFORMATION: "Xaa" denotes any amino acid residue.
<220> FEATURE:
<221> NAME/KEY: MISC_FEATURE
<222> LOCATION: (15)..(15)
<223> OTHER INFORMATION: "Xaa" denotes an aromatic amino acid residue.
<220> FEATURE:
<221> NAME/KEY: MISC_FEATURE
<222> LOCATION: (16)..(16)
<223> OTHER INFORMATION: "Xaa" denotes any amino acid residue.
<220> FEATURE:
<221> NAME/KEY: MISC_FEATURE
<222> LOCATION: (17)..(17)
<223> OTHER INFORMATION: "Xaa" denotes a hydrophobic amino acid residue.
<220> FEATURE:
<221> NAME/KEY: MISC_FEATURE
<222> LOCATION: (19)..(19)
<223> OTHER INFORMATION: "Xaa" denotes any amino acid residue.
<220> FEATURE:
<221> NAME/KEY: MISC_FEATURE
<222> LOCATION: (22)..(22)
<223> OTHER INFORMATION: "Xaa" denotes any amino acid residue.
<220> FEATURE:
<221> NAME/KEY: MISC_FEATURE -continued
<222> LOCATION: (23)..(23)
<223> OTHER INFORMATION: “Xaa” denotes a hydrophobic amino acid residue.
<220> FEATURE:
<221> NAME/KEY: MISC_FEATURE
<222> LOCATION: (26)..(26)
<223> OTHER INFORMATION: “Xaa” denotes a hydrophobic amino acid residue.
<220> FEATURE:
<221> NAME/KEY: MISC_FEATURE
<222> LOCATION: (29)..(29)
<223> OTHER INFORMATION: “Xaa” denotes serine or threonine.
<220> FEATURE:
<221> NAME/KEY: MISC_FEATURE
<222> LOCATION: (30)..(30)
<223> OTHER INFORMATION: “Xaa” denotes any amino acid residue.
<220> FEATURE:
<221> NAME/KEY: MISC_FEATURE
<222> LOCATION: (32)..(32)
<223> OTHER INFORMATION: “Xaa” denotes a basic amino acid residue.
<220> FEATURE:
<221> NAME/KEY: MISC_FEATURE
<222> LOCATION: (33)..(33)
<223> OTHER INFORMATION: “Xaa” denotes any amino acid residue.
<220> FEATURE:
<221> NAME/KEY: MISC_FEATURE
<222> LOCATION: (35)..(35)
<223> OTHER INFORMATION: “Xaa” denotes a hydrophobic amino acid residue.
<220> FEATURE:
<221> NAME/KEY: MISC_FEATURE
<222> LOCATION: (36)..(36)
<223> OTHER INFORMATION: “Xaa” denotes an acidic amino acid residue.
<220> FEATURE:
<221> NAME/KEY: MISC_FEATURE
<222> LOCATION: (37)..(37)
<223> OTHER INFORMATION: “Xaa” denotes any amino acid residue.

<400> SEQUENCE: 155

```
Ala Xaa Xaa Ser Xaa Xaa Xaa Xaa Xaa Xaa Asn Xaa Xaa Leu Xaa Xaa
1               5                   10                  15

Xaa Cys Xaa Val Pro Xaa Xaa Cys Trp Xaa Val Cys Xaa Xaa Leu Xaa
            20                  25                  30

Xaa Gln Xaa Xaa Xaa Gly
        35
```

<210> SEQ ID NO 156
<211> LENGTH: 14
<212> TYPE: PRT
<213> ORGANISM: Artificial Sequence
<220> FEATURE:
<223> OTHER INFORMATION: Consensus Motif VII
<220> FEATURE:
<221> NAME/KEY: MISC_FEATURE
<222> LOCATION: (2)..(2)
<223> OTHER INFORMATION: “Xaa” denotes any amino acid residue.
<220> FEATURE:
<221> NAME/KEY: MISC_FEATURE
<222> LOCATION: (4)..(4)
<223> OTHER INFORMATION: “Xaa” denotes any amino acid residue.
<220> FEATURE:
<221> NAME/KEY: MISC_FEATURE
<222> LOCATION: (5)..(5)
<223> OTHER INFORMATION: “Xaa” denotes a hydrophobic amino acid residue.
<220> FEATURE:
<221> NAME/KEY: MISC_FEATURE
<222> LOCATION: (6)..(6)
<223> OTHER INFORMATION: “Xaa” denotes an aromatic amino acid residue.
<220> FEATURE:
<221> NAME/KEY: MISC_FEATURE
<222> LOCATION: (7)..(8)
<223> OTHER INFORMATION: “Xaa” denotes any amino acid residue.
<220> FEATURE:
<221> NAME/KEY: MISC_FEATURE
<222> LOCATION: (9)..(9)
<223> OTHER INFORMATION: “Xaa” denotes an aromatic amino acid residue.
<220> FEATURE:
<221> NAME/KEY: MISC_FEATURE -continued
<222> LOCATION: (10)..(10)
<223> OTHER INFORMATION: "Xaa" denotes a hydrophobic amino acid residue.
<220> FEATURE:
<221> NAME/KEY: MISC_FEATURE
<222> LOCATION: (11)..(13)
<223> OTHER INFORMATION: "Xaa" denotes any amino acid residue.
<220> FEATURE:
<221> NAME/KEY: MISC_FEATURE
<222> LOCATION: (14)..(14)
<223> OTHER INFORMATION: "Xaa" denotes a hydrophobic acid residue.

<400> SEQUENCE: 156

Thr Xaa Thr Xaa Xaa Xaa Xaa Xaa Xaa Xaa Xaa Xaa Xaa Xaa
1               5                   10

<210> SEQ ID NO 157
<211> LENGTH: 43
<212> TYPE: PRT
<213> ORGANISM: Artificial Sequence
<220> FEATURE:
<223> OTHER INFORMATION: Consensus Motif VIII
<220> FEATURE:
<221> NAME/KEY: MISC_FEATURE
<222> LOCATION: (2)..(2)
<223> OTHER INFORMATION: "Xaa" denotes a basic amino acid residue.
<220> FEATURE:
<221> NAME/KEY: MISC_FEATURE
<222> LOCATION: (3)..(3)
<223> OTHER INFORMATION: "Xaa" denotes any amino acid residue.
<220> FEATURE:
<221> NAME/KEY: MISC_FEATURE
<222> LOCATION: (6)..(6)
<223> OTHER INFORMATION: "Xaa" denotes any amino acid residue.
<220> FEATURE:
<221> NAME/KEY: MISC_FEATURE
<222> LOCATION: (12)..(12)
<223> OTHER INFORMATION: "Xaa" denotes a hydrophobic amino acid residue.
<220> FEATURE:
<221> NAME/KEY: MISC_FEATURE
<222> LOCATION: (14)..(17)
<223> OTHER INFORMATION: "Xaa" denotes any amino acid residue.
<220> FEATURE:
<221> NAME/KEY: MISC_FEATURE
<222> LOCATION: (18)..(18)
<223> OTHER INFORMATION: "Xaa" denotes a hydrophobic amino acid residue.
<220> FEATURE:
<221> NAME/KEY: MISC_FEATURE
<222> LOCATION: (20)..(21)
<223> OTHER INFORMATION: "Xaa" denotes any amino acid residue.
<220> FEATURE:
<221> NAME/KEY: MISC_FEATURE
<222> LOCATION: (22)..(22)
<223> OTHER INFORMATION: "Xaa" denotes an acidic amino acid residue.
<220> FEATURE:
<221> NAME/KEY: MISC_FEATURE
<222> LOCATION: (25)..(27)
<223> OTHER INFORMATION: "Xaa" denotes any amino acid residue.
<220> FEATURE:
<221> NAME/KEY: MISC_FEATURE
<222> LOCATION: (30)..(33)
<223> OTHER INFORMATION: "Xaa" denotes any amino acid residue.
<220> FEATURE:
<221> NAME/KEY: MISC_FEATURE
<222> LOCATION: (34)..(34)
<223> OTHER INFORMATION: "Xaa" denotes a hydrophobic amino acid residue.
<220> FEATURE:
<221> NAME/KEY: MISC_FEATURE
<222> LOCATION: (35)..(36)
<223> OTHER INFORMATION: "Xaa" denotes any amino acid residue.
<220> FEATURE:
<221> NAME/KEY: MISC_FEATURE
<222> LOCATION: (39)..(41)
<223> OTHER INFORMATION: "Xaa" denotes any amino acid residue.
<220> FEATURE:
<221> NAME/KEY: MISC_FEATURE
<222> LOCATION: (42)..(43)
<223> OTHER INFORMATION: "Xaa" denotes a hydrophobic amino acid residue.

-continued

<400> SEQUENCE: 157

```
Leu Xaa Xaa Leu Cys Xaa Leu Ala Ala Glu Gly Xaa Trp Xaa Xaa Xaa
1               5                   10                  15

Xaa Xaa Phe Xaa Xaa Xaa Asp Leu Xaa Xaa Xaa Gly Leu Xaa Xaa Xaa
            20                  25                  30

Xaa Xaa Xaa Xaa Phe Leu Xaa Xaa Xaa Xaa Xaa
        35                  40
```

<210> SEQ ID NO 158
<211> LENGTH: 19
<212> TYPE: PRT
<213> ORGANISM: Artificial Sequence
<220> FEATURE:
<223> OTHER INFORMATION: Consensus Motif IX
<220> FEATURE:
<221> NAME/KEY: MISC_FEATURE
<222> LOCATION: (2)..(2)
<223> OTHER INFORMATION: "Xaa" denotes any amino acid residue.
<220> FEATURE:
<221> NAME/KEY: MISC_FEATURE
<222> LOCATION: (4)..(4)
<223> OTHER INFORMATION: "Xaa" denotes a hydrophobic amino acid residue.
<220> FEATURE:
<221> NAME/KEY: MISC_FEATURE
<222> LOCATION: (7)..(7)
<223> OTHER INFORMATION: "Xaa" denotes serine or threonine.
<220> FEATURE:
<221> NAME/KEY: MISC_FEATURE
<222> LOCATION: (8)..(8)
<223> OTHER INFORMATION: "Xaa" denotes a hydrophobic amino acid residue.
<220> FEATURE:
<221> NAME/KEY: MISC_FEATURE
<222> LOCATION: (12)..(12)
<223> OTHER INFORMATION: "Xaa" denotes any amino acid residue.
<220> FEATURE:
<221> NAME/KEY: MISC_FEATURE
<222> LOCATION: (15)..(15)
<223> OTHER INFORMATION: "Xaa" denotes a hydrophobic amino acid residue.
<220> FEATURE:
<221> NAME/KEY: MISC_FEATURE
<222> LOCATION: (16)..(16)
<223> OTHER INFORMATION: "Xaa" denotes an aromatic acid residue.
<220> FEATURE:
<221> NAME/KEY: MISC_FEATURE
<222> LOCATION: (18)..(18)
<223> OTHER INFORMATION: "Xaa" denotes a hydrophobic acid residue.

<400> SEQUENCE: 158

```
Tyr Xaa Phe Xaa His Leu Xaa Xaa Gln Glu Phe Xaa Ala Ala Xaa Xaa
1               5                   10                  15

Tyr Xaa Leu
```

<210> SEQ ID NO 159
<211> LENGTH: 26
<212> TYPE: PRT
<213> ORGANISM: Artificial Sequence
<220> FEATURE:
<223> OTHER INFORMATION: Consensus Motif X
<220> FEATURE:
<221> NAME/KEY: MISC_FEATURE
<222> LOCATION: (7)..(7)
<223> OTHER INFORMATION: "Xaa" denotes any amino acid residue.
<220> FEATURE:
<221> NAME/KEY: MISC_FEATURE
<222> LOCATION: (8)..(8)
<223> OTHER INFORMATION: "Xaa" denotes any amino acid residue and is varialble in length.
<220> FEATURE:
<221> NAME/KEY: MISC_FEATURE
<222> LOCATION: (10)..(10)
<223> OTHER INFORMATION: "Xaa" denotes any amino acid residue.

-continued

```
<220> FEATURE:
<221> NAME/KEY: MISC_FEATURE
<222> LOCATION: (11)..(11)
<223> OTHER INFORMATION: "Xaa" denotes a basic amino acid residue.
<220> FEATURE:
<221> NAME/KEY: MISC_FEATURE
<222> LOCATION: (12)..(12)
<223> OTHER INFORMATION: "Xaa" denotes any amino acid residue.
<220> FEATURE:
<221> NAME/KEY: MISC_FEATURE
<222> LOCATION: (15)..(16)
<223> OTHER INFORMATION: "Xaa" denotes any amino acid residue.
<220> FEATURE:
<221> NAME/KEY: MISC_FEATURE
<222> LOCATION: (19)..(20)
<223> OTHER INFORMATION: "Xaa" denotes any amino acid residue.
<220> FEATURE:
<221> NAME/KEY: MISC_FEATURE
<222> LOCATION: (21)..(21)
<223> OTHER INFORMATION: "Xaa" denotes a hydrophobic amino acid residue.
<220> FEATURE:
<221> NAME/KEY: MISC_FEATURE
<222> LOCATION: (23)..(24)
<223> OTHER INFORMATION: "Xaa" denotes any amino acid residue.
<220> FEATURE:
<221> NAME/KEY: MISC_FEATURE
<222> LOCATION: (25)..(25)
<223> OTHER INFORMATION: "Xaa" denotes a hydrophobic amino acid residue.
<220> FEATURE:
<221> NAME/KEY: MISC_FEATURE
<222> LOCATION: (26)..(26)
<223> OTHER INFORMATION: "Xaa" denotes a basic amino acid residue.

<400> SEQUENCE: 159

Phe Leu Phe Gly Leu Leu Xaa Xaa Asn Xaa Xaa Xaa Leu Glu Xaa Xaa
1               5                   10                  15

Phe Ser Xaa Xaa Xaa Ser Xaa Xaa Xaa Xaa
            20                  25


<210> SEQ ID NO 160
<211> LENGTH: 28
<212> TYPE: PRT
<213> ORGANISM: Artificial Sequence
<220> FEATURE:
<223> OTHER INFORMATION: Consensus Motif XI
<220> FEATURE:
<221> NAME/KEY: MISC_FEATURE
<222> LOCATION: (1)..(1)
<223> OTHER INFORMATION: "Xaa" denotes a hydrophobic amino acid residue.
<220> FEATURE:
<221> NAME/KEY: MISC_FEATURE
<222> LOCATION: (2)..(2)
<223> OTHER INFORMATION: "Xaa" denotes an acidic amino acid residue.
<220> FEATURE:
<221> NAME/KEY: MISC_FEATURE
<222> LOCATION: (5)..(5)
<223> OTHER INFORMATION: "Xaa" denotes any amino acid residue.
<220> FEATURE:
<221> NAME/KEY: MISC_FEATURE
<222> LOCATION: (8)..(8)
<223> OTHER INFORMATION: "Xaa" denotes an aromatic amino acid residue.
<220> FEATURE:
<221> NAME/KEY: MISC_FEATURE
<222> LOCATION: (9)..(9)
<223> OTHER INFORMATION: "Xaa" denotes an acidic amino acid residue.
<220> FEATURE:
<221> NAME/KEY: MISC_FEATURE
<222> LOCATION: (10)..(10)
<223> OTHER INFORMATION: "Xaa" denotes any amino acid residue.
<220> FEATURE:
<221> NAME/KEY: MISC_FEATURE
<222> LOCATION: (13)..(13)
<223> OTHER INFORMATION: "Xaa" denotes any amino acid residue.
<220> FEATURE:
<221> NAME/KEY: MISC_FEATURE
<222> LOCATION: (14)..(14)
```

-continued

<223> OTHER INFORMATION: "Xaa" denotes an acidic amino acid residue.
<220> FEATURE:
<221> NAME/KEY: MISC_FEATURE
<222> LOCATION: (16)..(16)
<223> OTHER INFORMATION: "Xaa" denotes a hydrophobic amino acid residue.
<220> FEATURE:
<221> NAME/KEY: MISC_FEATURE
<222> LOCATION: (17)..(19)
<223> OTHER INFORMATION: "Xaa" denotes any amino acid residue.
<220> FEATURE:
<221> NAME/KEY: MISC_FEATURE
<222> LOCATION: (20)..(20)
<223> OTHER INFORMATION: "Xaa" denotes a hydrophobic amino acid residue.
<220> FEATURE:
<221> NAME/KEY: MISC_FEATURE
<222> LOCATION: (21)..(25)
<223> OTHER INFORMATION: "Xaa" denotes any amino acid residue.
<220> FEATURE:
<221> NAME/KEY: MISC_FEATURE
<222> LOCATION: (26)..(26)
<223> OTHER INFORMATION: "Xaa" denotes a hydrophobic amino acid residue.
<220> FEATURE:
<221> NAME/KEY: MISC_FEATURE
<222> LOCATION: (27)..(27)
<223> OTHER INFORMATION: "Xaa" denotes any amino acid residue.
<220> FEATURE:
<221> NAME/KEY: MISC_FEATURE
<222> LOCATION: (28)..(28)
<223> OTHER INFORMATION: "Xaa" denotes a hydrophobic amino acid residue.

<400> SEQUENCE: 160

```
Xaa Xaa Leu Phe Xaa Cys Leu Arg Ala Xaa Gln Glu Xaa Ala Phe His
1               5                   10                  15

Xaa Xaa Xaa His Xaa Xaa Xaa Xaa Xaa His Xaa His
            20                  25
```

<210> SEQ ID NO 161
<211> LENGTH: 20
<212> TYPE: PRT
<213> ORGANISM: Artificial Sequence
<220> FEATURE:
<223> OTHER INFORMATION: Consensus Motif XII
<220> FEATURE:
<221> NAME/KEY: MISC_FEATURE
<222> LOCATION: (1)..(1)
<223> OTHER INFORMATION: "Xaa" denotes an acidic amino acid residue.
<220> FEATURE:
<221> NAME/KEY: MISC_FEATURE
<222> LOCATION: (2)..(3)
<223> OTHER INFORMATION: "Xaa" denotes a hydrophobic amino acid residue.
<220> FEATURE:
<221> NAME/KEY: MISC_FEATURE
<222> LOCATION: (5)..(5)
<223> OTHER INFORMATION: "Xaa" denotes any amino acid residue.
<220> FEATURE:
<221> NAME/KEY: MISC_FEATURE
<222> LOCATION: (6)..(6)
<223> OTHER INFORMATION: "Xaa" denotes serine or threonine.
<220> FEATURE:
<221> NAME/KEY: MISC_FEATURE
<222> LOCATION: (10)..(11)
<223> OTHER INFORMATION: "Xaa" denotes a basic amino acid residue.
<220> FEATURE:
<221> NAME/KEY: MISC_FEATURE
<222> LOCATION: (13)..(14)
<223> OTHER INFORMATION: "Xaa" denotes any amino acid residue.
<220> FEATURE:
<221> NAME/KEY: MISC_FEATURE
<222> LOCATION: (15)..(15)
<223> OTHER INFORMATION: "Xaa" denotes a hydrophobic amino acid residue.
<220> FEATURE:
<221> NAME/KEY: MISC_FEATURE
<222> LOCATION: (16)..(17)
<223> OTHER INFORMATION: "Xaa" denotes any amino acid residue.
<220> FEATURE:
<221> NAME/KEY: MISC_FEATURE -continued
<222> LOCATION: (19)..(19)
<223> OTHER INFORMATION: "Xaa" denotes any amino acid residue.

<400> SEQUENCE: 161

Xaa Xaa Xaa Val Xaa Xaa Phe Cys Leu Xaa Xaa Cys Xaa Xaa Xaa Xaa
1 5 10 15

Xaa Leu Xaa Leu
20

<210> SEQ ID NO 162
<211> LENGTH: 479
<212> TYPE: PRT
<213> ORGANISM: Homo sapiens

<400> SEQUENCE: 162

Met Glu Leu Leu Phe Asp Pro Asp Asp Glu His Ser Glu Pro Val His
1 5 10 15

Thr Val Val Phe Gln Gly Ala Ala Gly Ile Gly Lys Thr Ile Leu Ala
20 25 30

Arg Lys Met Met Leu Asp Trp Ala Ser Gly Thr Leu Tyr Gln Asp Arg
35 40 45

Phe Asp Tyr Leu Phe Tyr Ile His Cys Arg Glu Val Ser Leu Val Thr
50 55 60

Gln Arg Ser Leu Gly Asp Leu Ile Met Ser Cys Cys Pro Asp Pro Asn
65 70 75 80

Pro Pro Ile His Lys Ile Val Arg Lys Pro Ser Arg Ile Leu Phe Leu
85 90 95

Met Asp Gly Phe Asp Glu Leu Gln Gly Ala Phe Asp Glu His Ile Gly
100 105 110

Pro Leu Cys Thr Asp Trp Gln Lys Ala Glu Arg Gly Asp Ile Leu Leu
115 120 125

Ser Ser Leu Ile Arg Lys Lys Leu Leu Pro Glu Ala Ser Leu Leu Ile
130 135 140

Thr Thr Arg Pro Val Ala Leu Glu Lys Leu Gln His Leu Leu Asp His
145 150 155 160

Pro Arg His Val Glu Ile Leu Gly Phe Ser Glu Ala Lys Arg Lys Glu
165 170 175

Tyr Phe Phe Lys Tyr Phe Ser Asp Glu Ala Gln Ala Arg Ala Ala Phe
180 185 190

Ser Leu Ile Gln Glu Asn Glu Val Leu Phe Thr Met Cys Phe Ile Pro
195 200 205

Leu Val Cys Trp Ile Val Cys Thr Gly Leu Lys Gln Gln Met Glu Ser
210 215 220

Gly Lys Ser Leu Ala Gln Thr Ser Lys Thr Ser Thr Ala Val Tyr Val
225 230 235 240

Phe Phe Leu Ser Ser Leu Leu Gln Pro Arg Gly Gly Ser Gln Glu His
245 250 255

Gly Leu Cys Ala His Leu Trp Gly Leu Cys Ser Leu Ala Ala Asp Gly
260 265 270

Ile Trp Asn Gln Lys Ile Leu Phe Glu Glu Ser Asp Leu Arg Asn His
275 280 285

Gly Leu Gln Lys Ala Asp Val Ser Ala Phe Leu Arg Met Asn Leu Phe
290 295 300

Gln Lys Glu Val Asp Cys Glu Lys Phe Tyr Ser Phe Ile His Met Thr
305 310 315 320

-continued

```
Phe Gln Glu Phe Phe Ala Ala Met Tyr Tyr Leu Leu Glu Glu Glu Lys
                325                 330                 335

Glu Gly Arg Thr Asn Val Pro Gly Ser Arg Leu Lys Leu Pro Ser Arg
            340                 345                 350

Asp Val Thr Val Leu Leu Glu Asn Tyr Gly Lys Phe Glu Lys Gly Tyr
        355                 360                 365

Leu Ile Phe Val Val Arg Phe Leu Phe Gly Leu Val Asn Gln Glu Arg
    370                 375                 380

Thr Ser Tyr Leu Glu Lys Lys Leu Ser Cys Met Ile Ser Gln Gln Ile
385                 390                 395                 400

Arg Leu Glu Leu Leu Lys Trp Ile Glu Val Lys Ala Lys Ala Lys Lys
                405                 410                 415

Leu His Asp Gln Pro Ser Gln Leu Glu Leu Phe Tyr Cys Leu Tyr Glu
            420                 425                 430

Met Gln Glu Glu Asp Phe Val Gln Arg Ala Met Asp Tyr Phe Pro Lys
        435                 440                 445

Ile Glu Ile Asn Leu Ser Thr Arg Met Asp His Met Val Ser Ser Phe
    450                 455                 460

Cys Ile Glu Asn Cys His Arg Val Glu Ser Leu Ser Leu Gly Phe
465                 470                 475


<210> SEQ ID NO 163
<211> LENGTH: 472
<212> TYPE: PRT
<213> ORGANISM: Homo sapiens

<400> SEQUENCE: 163

Ile Glu Thr Leu Phe Glu Pro Asp Glu Glu Arg Pro Glu Pro Pro Arg
1               5                   10                  15

Thr Val Val Met Gln Gly Ala Ala Gly Ile Gly Lys Ser Met Leu Ala
            20                  25                  30

His Lys Val Met Leu Asp Trp Ala Asp Gly Lys Leu Phe Gln Gly Arg
        35                  40                  45

Phe Asp Tyr Leu Phe Tyr Ile Asn Cys Arg Glu Met Asn Gln Ser Ala
    50                  55                  60

Thr Glu Cys Ser Met Gln Asp Leu Ile Phe Ser Cys Trp Pro Glu Pro
65                  70                  75                  80

Ser Ala Pro Leu Gln Glu Leu Ile Arg Val Pro Glu Arg Leu Leu Phe
                85                  90                  95

Ile Ile Asp Gly Phe Asp Glu Leu Lys Pro Ser Phe His Asp Pro Gln
            100                 105                 110

Gly Pro Trp Cys Leu Cys Trp Glu Glu Lys Arg Pro Thr Glu Leu Leu
        115                 120                 125

Leu Asn Ser Leu Ile Arg Lys Lys Leu Leu Pro Glu Leu Ser Leu Leu
    130                 135                 140

Ile Thr Thr Arg Pro Thr Ala Leu Glu Lys Leu His Arg Leu Leu Glu
145                 150                 155                 160

His Pro Arg His Val Glu Ile Leu Gly Phe Ser Glu Ala Glu Arg Lys
                165                 170                 175

Glu Tyr Phe Tyr Lys Tyr Phe His Asn Ala Glu Gln Ala Gly Gln Val
            180                 185                 190

Phe Asn Tyr Val Arg Asp Asn Glu Pro Leu Phe Thr Met Cys Phe Val
        195                 200                 205

Pro Leu Val Cys Trp Val Val Cys Thr Cys Leu Gln Gln Gln Leu Glu
    210                 215                 220
```

-continued

```
Gly Gly Gly Leu Leu Arg Gln Thr Ser Arg Thr Thr Thr Ala Val Tyr
225                 230                 235                 240

Met Leu Tyr Leu Leu Ser Leu Met Gln Pro Lys Pro Gly Ala Pro Arg
                245                 250                 255

Leu Gln Pro Pro Pro Asn Gln Arg Gly Leu Cys Ser Leu Ala Ala Asp
            260                 265                 270

Gly Leu Trp Asn Gln Lys Ile Leu Phe Glu Glu Gln Asp Leu Arg Lys
        275                 280                 285

His Gly Leu Asp Gly Glu Asp Val Ser Ala Phe Leu Asn Met Asn Ile
    290                 295                 300

Phe Gln Lys Asp Ile Asn Cys Glu Arg Tyr Tyr Ser Phe Ile His Leu
305                 310                 315                 320

Ser Phe Gln Glu Phe Phe Ala Ala Met Tyr Tyr Ile Leu Asp Glu Gly
                325                 330                 335

Glu Gly Gly Ala Gly Pro Asp Gln Asp Val Thr Arg Leu Leu Thr Glu
            340                 345                 350

Tyr Ala Phe Ser Glu Arg Ser Phe Leu Ala Leu Thr Ser Arg Phe Leu
        355                 360                 365

Phe Gly Leu Leu Asn Glu Glu Thr Arg Ser His Leu Glu Lys Ser Leu
    370                 375                 380

Cys Trp Lys Val Ser Pro His Ile Lys Met Asp Leu Leu Gln Trp Ile
385                 390                 395                 400

Gln Ser Lys Ala Gln Ser Asp Gly Ser Thr Leu Gln Gln Gly Ser Leu
                405                 410                 415

Glu Phe Phe Ser Cys Leu Tyr Glu Ile Gln Glu Glu Glu Phe Ile Gln
            420                 425                 430

Gln Ala Leu Ser His Phe Gln Val Ile Val Val Ser Asn Ile Ala Ser
        435                 440                 445

Lys Met Glu His Met Val Ser Ser Phe Cys Leu Lys Arg Cys Arg Ser
    450                 455                 460

Ala Gln Val Leu His Leu Tyr Gly
465                 470


<210> SEQ ID NO 164
<211> LENGTH: 468
<212> TYPE: PRT
<213> ORGANISM: Homo sapiens

<400> SEQUENCE: 164

Glu Tyr Lys Glu Leu Asn Asp Ala Tyr Thr Ala Ala Ala Arg Arg His
1               5                   10                  15

Thr Val Val Leu Glu Gly Pro Asp Gly Ile Gly Lys Thr Thr Leu Leu
            20                  25                  30

Arg Lys Val Met Leu Asp Trp Ala Glu Gly Asn Leu Trp Lys Asp Arg
        35                  40                  45

Phe Thr Phe Val Phe Phe Leu Asn Val Cys Glu Met Asn Gly Ile Ala
    50                  55                  60

Glu Thr Ser Leu Leu Glu Leu Leu Ser Arg Asp Trp Pro Glu Ser Ser
65                  70                  75                  80

Glu Lys Ile Glu Asp Ile Phe Ser Gln Pro Glu Arg Ile Leu Phe Ile
                85                  90                  95

Met Asp Gly Phe Glu Gln Leu Lys Phe Asn Leu Gln Leu Lys Ala Asp
            100                 105                 110

Leu Ser Asp Asp Trp Arg Gln Arg Gln Pro Met Pro Ile Ile Leu Ser
```

-continued

```
        115                 120                 125

Ser Leu Leu Gln Lys Lys Met Leu Pro Glu Ser Ser Leu Leu Ile Ala
    130                 135                 140

Leu Gly Lys Leu Ala Met Gln Lys His Tyr Phe Met Leu Arg His Pro
145                 150                 155                 160

Lys Leu Ile Lys Leu Leu Gly Phe Ser Glu Ser Glu Lys Lys Ser Tyr
                165                 170                 175

Phe Ser Tyr Phe Phe Gly Glu Lys Ser Lys Ala Leu Lys Val Phe Asn
            180                 185                 190

Phe Val Arg Asp Asn Gly Pro Leu Phe Ile Leu Cys His Asn Pro Phe
        195                 200                 205

Thr Cys Trp Leu Val Cys Thr Cys Val Lys Gln Arg Leu Glu Arg Gly
    210                 215                 220

Glu Asp Leu Glu Ile Asn Ser Gln Asn Thr Thr Tyr Leu Tyr Ala Ser
225                 230                 235                 240

Phe Leu Thr Thr Val Phe Lys Ala Gly Ser Gln Ser Phe Pro Pro Lys
                245                 250                 255

Val Asn Arg Ala Arg Leu Lys Ser Leu Cys Ala Leu Ala Ala Glu Gly
            260                 265                 270

Ile Trp Thr Tyr Thr Phe Val Phe Ser His Gly Asp Leu Arg Arg Asn
        275                 280                 285

Gly Leu Ser Glu Ser Glu Gly Val Met Trp Val Gly Met Arg Leu Leu
    290                 295                 300

Gln Arg Arg Gly Asp Cys Phe Ala Phe Met His Leu Cys Ile Gln Glu
305                 310                 315                 320

Phe Cys Ala Ala Met Phe Tyr Leu Leu Lys Arg Pro Lys Asp Asp Pro
                325                 330                 335

Asn Pro Ala Ile Gly Ser Ile Thr Gln Leu Val Arg Ala Ser Val Val
            340                 345                 350

Gln Pro Gln Thr Leu Leu Thr Gln Val Gly Ile Phe Met Phe Gly Ile
        355                 360                 365

Ser Thr Glu Glu Ile Val Ser Met Leu Glu Thr Ser Phe Gly Phe Pro
    370                 375                 380

Leu Ser Lys Asp Leu Lys Gln Glu Ile Thr Gln Cys Leu Glu Ser Leu
385                 390                 395                 400

Ser Gln Cys Glu Ala Asp Arg Glu Ala Ile Ala Phe Gln Glu Leu Phe
                405                 410                 415

Ile Gly Leu Phe Glu Thr Gln Glu Lys Glu Phe Val Thr Lys Val Met
            420                 425                 430

Asn Phe Phe Glu Glu Val Phe Ile Tyr Ile Gly Asn Ile Glu His Leu
        435                 440                 445

Val Ile Ala Ser Phe Cys Leu Lys His Cys Gln His Leu Thr Thr Leu
    450                 455                 460

Arg Met Cys Val
465
```

<210> SEQ ID NO 165
<211> LENGTH: 297
<212> TYPE: PRT
<213> ORGANISM: Homo sapiens
<220> FEATURE:
<221> NAME/KEY: MISC_FEATURE
<222> LOCATION: (74)..(74)
<223> OTHER INFORMATION: “Xaa” denotes any amino acid residue.
<220> FEATURE:
<221> NAME/KEY: MISC_FEATURE -continued
<222> LOCATION: (136)..(136)
<223> OTHER INFORMATION: "Xaa" denotes any amino acid residue.
<220> FEATURE:
<221> NAME/KEY: MISC_FEATURE
<222> LOCATION: (232)..(232)
<223> OTHER INFORMATION: "Xaa" denotes any amino acid residue.

<400> SEQUENCE: 165

```
His Phe Phe Pro Gln Pro Glu Gln Ile Leu Phe Ile Met Asp Gly Phe
1               5                   10                  15

Glu Gln Leu Lys Phe Asp Leu Glu Leu Lys Ala Asp Leu Cys Asp Asp
            20                  25                  30

Trp Arg Gln Gln Gln Pro Thr Gln Ile Ile Leu Ser Ser Leu Leu Gln
        35                  40                  45

Lys Lys Met Ile Pro Glu Ser Ser Leu Leu Ile Ala Leu Gly Lys Val
    50                  55                  60

Gly Met Gln Lys Asn Tyr Phe Met Leu Xaa His Pro Lys Leu Ile Lys
65                  70                  75                  80

Leu Pro Gly Phe Thr Glu Leu Glu Arg Lys Leu Tyr Phe Ser Tyr Phe
                85                  90                  95

Phe Ser Glu Lys Asn Thr Phe Ile His Leu Leu Lys Met Asn Ala Ser
            100                 105                 110

Phe Leu Thr Asn Val Phe Lys Ala Gly Ser Gln Ser Phe Pro Pro Lys
        115                 120                 125

Gly Met Lys Leu Leu Gln Arg Xaa Gly Glu Cys Phe Thr Phe Ile His
    130                 135                 140

Val Cys Ile Gln Glu Phe Cys Ala Thr Met Phe Tyr Leu Leu Lys Arg
145                 150                 155                 160

Pro Lys Asp Asp Pro Asn Pro Thr Ile Gly Ser Ile Thr Gln Leu Val
                165                 170                 175

Arg Ala Ser Val Ala Gln Pro Gln Thr His Ser Thr Gln Val Gly Val
            180                 185                 190

Phe Val Phe Gly Ile Ser Thr Glu Glu Ile Ile Ser Leu Leu Glu Thr
        195                 200                 205

Ser Phe Gly Phe Pro Leu Leu Lys Asp Leu Lys Lys Glu Ile Thr Gln
    210                 215                 220

Cys Leu Lys Ser Leu Ser Gln Xaa Glu Ala Asp Arg Glu Val Ile Gly
225                 230                 235                 240

Phe Gln Glu Leu Phe His Asp Leu Phe Ala Thr Gln Glu Lys Glu Phe
                245                 250                 255

Val Thr Glu Val Ile Asn Phe Phe Glu Glu Val Phe Ile Cys Thr Gly
            260                 265                 270

Asn Ile Glu His Leu Val Val Ser Ser Phe Cys Arg Lys His Cys Gln
        275                 280                 285

Asn Leu Thr Thr Leu Arg Met Cys Val
    290                 295
```

<210> SEQ ID NO 166
<211> LENGTH: 458
<212> TYPE: PRT
<213> ORGANISM: Homo sapiens

<400> SEQUENCE: 166

```
Ile Arg Asp Leu Phe Gly Pro Gly Leu Asp Thr Gln Glu Pro Arg Ile
1               5                   10                  15

Val Ile Leu Gln Gly Ala Ala Gly Ile Gly Lys Ser Thr Leu Ala Arg
            20                  25                  30
```

-continued

```
Gln Val Lys Glu Ala Trp Gly Arg Gly Gln Leu Tyr Gly Asp Arg Phe
        35                  40                  45

Gln His Val Phe Tyr Phe Ser Cys Arg Glu Leu Ala Gln Ser Lys Val
    50                  55                  60

Val Ser Leu Ala Glu Leu Ile Gly Lys Asp Gly Thr Ala Thr Pro Ala
65                  70                  75                  80

Pro Ile Arg Gln Ile Leu Ser Arg Pro Glu Arg Leu Leu Phe Ile Leu
                85                  90                  95

Asp Gly Val Asp Glu Pro Gly Trp Val Leu Gln Glu Pro Ser Ser Glu
            100                 105                 110

Leu Cys Leu His Trp Ser Gln Pro Gln Pro Ala Asp Ala Leu Leu Gly
        115                 120                 125

Ser Leu Leu Gly Lys Thr Ile Leu Pro Glu Ala Ser Phe Leu Ile Thr
    130                 135                 140

Ala Arg Thr Thr Ala Leu Gln Asn Leu Ile Pro Ser Leu Glu Gln Ala
145                 150                 155                 160

Arg Trp Val Glu Val Leu Gly Phe Ser Glu Ser Ser Arg Lys Glu Tyr
                165                 170                 175

Phe Tyr Arg Tyr Phe Thr Asp Glu Arg Gln Ala Ile Arg Ala Phe Arg
            180                 185                 190

Leu Val Lys Ser Asn Lys Glu Leu Trp Ala Leu Cys Leu Val Pro Trp
        195                 200                 205

Val Ser Trp Leu Ala Cys Thr Cys Leu Met Gln Gln Met Lys Arg Lys
    210                 215                 220

Glu Lys Leu Thr Leu Thr Ser Lys Thr Thr Thr Thr Leu Cys Leu His
225                 230                 235                 240

Tyr Leu Ala Gln Ala Leu Gln Ala Gln Pro Leu Gly Pro Gln Leu Arg
                245                 250                 255

Asp Leu Cys Ser Leu Ala Ala Glu Gly Ile Trp Gln Lys Lys Thr Leu
            260                 265                 270

Phe Ser Pro Asp Asp Leu Arg Lys His Gly Leu Asp Gly Ala Ile Ile
        275                 280                 285

Ser Thr Phe Leu Lys Met Gly Ile Leu Gln Glu His Pro Ile Pro Leu
    290                 295                 300

Ser Tyr Ser Phe Ile His Leu Cys Phe Gln Glu Phe Phe Ala Ala Met
305                 310                 315                 320

Ser Tyr Val Leu Glu Asp Glu Lys Gly Arg Gly Lys His Ser Asn Cys
                325                 330                 335

Ile Ile Asp Leu Glu Lys Thr Leu Glu Ala Tyr Gly Ile His Gly Leu
            340                 345                 350

Phe Gly Ala Ser Thr Thr Arg Phe Leu Leu Gly Leu Leu Ser Asp Glu
        355                 360                 365

Gly Glu Arg Glu Met Glu Asn Ile Phe His Cys Arg Leu Ser Gln Gly
    370                 375                 380

Arg Asn Leu Met Gln Trp Val Pro Ser Leu Gln Leu Leu Leu Gln Pro
385                 390                 395                 400

His Ser Leu Glu Ser Leu His Cys Leu Tyr Glu Thr Arg Asn Lys Thr
                405                 410                 415

Phe Leu Thr Gln Val Met Ala His Phe Glu Glu Met Gly Met Cys Val
            420                 425                 430

Glu Thr Asp Met Glu Leu Leu Val Cys Thr Phe Cys Ile Lys Phe Ser
        435                 440                 445
```

-continued

```
Arg His Val Lys Lys Leu Gln Leu Ile Glu
    450                 455


<210> SEQ ID NO 167
<211> LENGTH: 474
<212> TYPE: PRT
<213> ORGANISM: Homo sapiens

<400> SEQUENCE: 167

Leu Glu His Leu Phe Asp Val Asp Val Lys Thr Gly Ala Gln Pro Gln
1               5                   10                  15

Ile Val Val Leu Gln Gly Ala Ala Gly Val Gly Lys Thr Thr Leu Val
            20                  25                  30

Arg Lys Ala Met Leu Asp Trp Ala Glu Gly Ser Leu Tyr Gln Gln Arg
        35                  40                  45

Phe Lys Tyr Val Phe Tyr Leu Asn Gly Arg Glu Ile Asn Gln Leu Lys
    50                  55                  60

Glu Arg Ser Phe Ala Gln Leu Ile Ser Lys Asp Trp Pro Ser Thr Glu
65                  70                  75                  80

Gly Pro Ile Glu Glu Ile Met Tyr Gln Pro Ser Ser Leu Leu Phe Ile
                85                  90                  95

Ile Asp Ser Phe Asp Glu Leu Asn Phe Ala Phe Glu Glu Pro Glu Phe
            100                 105                 110

Ala Leu Cys Glu Asp Trp Thr Gln Glu His Pro Val Ser Phe Leu Met
        115                 120                 125

Ser Ser Leu Leu Arg Lys Val Met Leu Pro Glu Ala Ser Leu Leu Val
    130                 135                 140

Thr Thr Arg Leu Thr Thr Ser Lys Arg Leu Lys Gln Leu Leu Lys Asn
145                 150                 155                 160

His His Tyr Val Glu Leu Leu Gly Met Ser Glu Asp Ala Arg Glu Glu
                165                 170                 175

Tyr Ile Tyr Gln Phe Phe Glu Asp Lys Arg Trp Ala Met Lys Val Phe
            180                 185                 190

Ser Ser Leu Lys Ser Asn Glu Met Leu Phe Ser Met Cys Gln Val Pro
        195                 200                 205

Leu Val Cys Trp Ala Ala Cys Thr Cys Leu Lys Gln Gln Met Glu Lys
    210                 215                 220

Gly Gly Asp Val Thr Leu Thr Cys Gln Thr Thr Thr Ala Leu Phe Thr
225                 230                 235                 240

Cys Tyr Ile Ser Ser Leu Phe Thr Pro Val Asp Gly Gly Ser Pro Ser
                245                 250                 255

Leu Pro Asn Gln Ala Gln Leu Arg Arg Leu Cys Gln Val Ala Ala Lys
            260                 265                 270

Gly Ile Trp Thr Met Thr Tyr Val Phe Tyr Arg Glu Asn Leu Arg Arg
        275                 280                 285

Leu Gly Leu Thr Gln Ser Asp Val Ser Ser Phe Met Asp Ser Asn Ile
    290                 295                 300

Ile Gln Lys Asp Ala Glu Tyr Glu Asn Cys Tyr Val Phe Thr His Leu
305                 310                 315                 320

His Val Gln Glu Phe Phe Ala Ala Met Phe Tyr Met Leu Lys Gly Ser
                325                 330                 335

Trp Glu Ala Gly Asn Pro Ser Cys Gln Pro Phe Glu Asp Leu Lys Ser
            340                 345                 350

Leu Leu Gln Ser Thr Ser Tyr Lys Asp Pro His Leu Thr Gln Met Lys
        355                 360                 365
```

-continued

```
Cys Phe Leu Phe Gly Leu Leu Asn Glu Asp Arg Val Lys Gln Leu Glu
    370                 375                 380

Arg Thr Phe Asn Cys Lys Met Ser Leu Lys Ile Lys Ser Lys Leu Leu
385                 390                 395                 400

Gln Cys Met Glu Val Leu Gly Asn Ser Asp Tyr Ser Pro Ser Gln Leu
                405                 410                 415

Gly Phe Leu Glu Leu Phe His Cys Leu Tyr Glu Thr Gln Asp Lys Ala
            420                 425                 430

Phe Ile Ser Gln Ala Met Arg Cys Phe Pro Lys Val Ala Ile Asn Ile
        435                 440                 445

Cys Glu Lys Ile His Leu Leu Val Ser Ser Phe Cys Leu Lys His Cys
    450                 455                 460

Arg Cys Leu Arg Thr Ile Arg Leu Ser Val
465                 470


<210> SEQ ID NO 168
<211> LENGTH: 472
<212> TYPE: PRT
<213> ORGANISM: Homo sapiens

<400> SEQUENCE: 168

Leu Asp Arg Leu Phe Ala Pro Lys Glu Thr Gly Lys Gln Pro Arg Thr
1               5                   10                  15

Val Ile Ile Gln Gly Pro Gln Gly Ile Gly Lys Thr Thr Leu Leu Met
            20                  25                  30

Lys Leu Met Met Ala Trp Ser Asp Asn Lys Ile Phe Arg Asp Arg Phe
        35                  40                  45

Leu Tyr Thr Phe Tyr Phe Cys Cys Arg Glu Leu Arg Glu Leu Pro Pro
    50                  55                  60

Thr Ser Leu Ala Asp Leu Ile Ser Arg Glu Trp Pro Asp Pro Ala Ala
65                  70                  75                  80

Pro Ile Thr Glu Ile Val Ser Gln Pro Glu Arg Leu Leu Phe Val Ile
                85                  90                  95

Asp Ser Phe Glu Glu Leu Gln Gly Gly Leu Asn Glu Pro Asp Ser Asp
            100                 105                 110

Leu Cys Gly Asp Leu Met Glu Lys Arg Pro Val Gln Val Leu Leu Ser
        115                 120                 125

Ser Leu Leu Arg Lys Lys Met Leu Pro Glu Ala Ser Leu Leu Ile Ala
    130                 135                 140

Ile Lys Pro Val Cys Pro Lys Glu Leu Arg Asp Gln Val Thr Ile Ser
145                 150                 155                 160

Glu Ile Tyr Gln Pro Arg Gly Phe Asn Glu Ser Asp Arg Leu Val Tyr
                165                 170                 175

Phe Cys Cys Phe Phe Lys Asp Pro Lys Arg Ala Met Glu Ala Phe Asn
            180                 185                 190

Leu Val Arg Glu Ser Glu Gln Leu Phe Ser Ile Cys Gln Ile Pro Leu
        195                 200                 205

Leu Cys Trp Ile Leu Cys Thr Ser Leu Lys Gln Glu Met Gln Lys Gly
    210                 215                 220

Lys Asp Leu Ala Leu Thr Cys Gln Ser Thr Thr Ser Val Tyr Ser Ser
225                 230                 235                 240

Phe Val Phe Asn Leu Phe Thr Pro Glu Gly Ala Glu Gly Pro Thr Pro
                245                 250                 255

Gln Thr Gln His Gln Leu Lys Ala Leu Cys Ser Leu Ala Ala Glu Gly
```

-continued

```
            260                 265                 270

Met Trp Thr Asp Thr Phe Glu Phe Cys Glu Asp Asp Leu Arg Arg Asn
        275                 280                 285

Gly Val Val Asp Ala Asp Ile Pro Ala Leu Leu Gly Thr Lys Ile Leu
    290                 295                 300

Leu Lys Tyr Gly Glu Arg Glu Ser Ser Tyr Val Phe Leu His Val Cys
305                 310                 315                 320

Ile Gln Glu Phe Cys Ala Ala Leu Phe Tyr Leu Leu Lys Ser His Leu
                325                 330                 335

Asp His Pro His Pro Ala Val Arg Cys Val Gln Glu Leu Leu Val Ala
            340                 345                 350

Asn Phe Glu Lys Ala Arg Arg Ala His Trp Ile Phe Leu Gly Cys Phe
        355                 360                 365

Leu Thr Gly Leu Leu Asn Lys Lys Glu Gln Glu Lys Leu Asp Ala Phe
    370                 375                 380

Phe Gly Phe Gln Leu Ser Gln Glu Ile Lys Gln Gln Ile His Gln Cys
385                 390                 395                 400

Leu Lys Ser Leu Gly Glu Arg Gly Asn Pro Gln Gly Gln Val Asp Ser
                405                 410                 415

Leu Ala Ile Phe Tyr Cys Leu Phe Glu Met Gln Asp Pro Ala Phe Val
            420                 425                 430

Lys Gln Ala Val Asn Leu Leu Gln Glu Ala Asn Phe His Ile Ile Asp
        435                 440                 445

Asn Val Asp Leu Val Val Ser Ala Tyr Cys Leu Lys Tyr Cys Ser Ser
    450                 455                 460

Leu Arg Lys Leu Cys Phe Ser Val
465                 470


<210> SEQ ID NO 169
<211> LENGTH: 477
<212> TYPE: PRT
<213> ORGANISM: Homo sapiens

<400> SEQUENCE: 169

Leu Gln Arg Leu Leu Asp Pro Asn Arg Thr Arg Ala Gln Ala Gln Thr
1               5                   10                  15

Ile Val Leu Val Gly Arg Ala Gly Val Gly Lys Thr Thr Leu Ala Met
            20                  25                  30

Arg Ala Met Leu His Trp Ala Asn Gly Val Leu Phe Gln Gln Arg Phe
        35                  40                  45

Ser Tyr Val Phe Tyr Leu Ser Cys His Lys Ile Arg Tyr Met Lys Glu
    50                  55                  60

Thr Thr Phe Ala Glu Leu Ile Ser Leu Asp Trp Pro Asp Phe Asp Ala
65                  70                  75                  80

Pro Ile Glu Glu Phe Met Ser Gln Pro Glu Lys Leu Leu Phe Ile Ile
                85                  90                  95

Asp Gly Phe Glu Glu Ile Ile Ile Ser Glu Ser Arg Ser Glu Ser Leu
            100                 105                 110

Asp Asp Gly Ser Pro Cys Thr Asp Trp Tyr Gln Glu Leu Pro Val Thr
        115                 120                 125

Lys Ile Leu His Ser Leu Leu Lys Lys Glu Leu Val Pro Leu Ala Thr
    130                 135                 140

Leu Leu Ile Thr Ile Lys Thr Trp Phe Val Arg Asp Leu Lys Ala Ser
145                 150                 155                 160
```

-continued

```
Leu Val Asn Pro Cys Phe Val Gln Ile Thr Gly Phe Thr Gly Asp Asp
                165                 170                 175

Leu Arg Val Tyr Phe Met Arg His Phe Asp Asp Ser Ser Glu Val Glu
            180                 185                 190

Lys Ile Leu Gln Gln Leu Arg Lys Asn Glu Thr Leu Phe His Ser Cys
        195                 200                 205

Ser Ala Pro Met Val Cys Trp Thr Val Cys Ser Cys Leu Lys Gln Pro
    210                 215                 220

Lys Val Arg Tyr Tyr Asp Leu Gln Ser Ile Thr Gln Thr Thr Thr Ser
225                 230                 235                 240

Leu Tyr Ala Tyr Phe Phe Ser Asn Leu Phe Ser Thr Ala Glu Val Asp
                245                 250                 255

Leu Ala Asp Asp Ser Trp Pro Gly Gln Trp Arg Ala Leu Cys Ser Leu
            260                 265                 270

Ala Ile Glu Gly Leu Trp Ser Met Asn Phe Thr Phe Asn Lys Glu Asp
        275                 280                 285

Thr Glu Ile Glu Gly Leu Glu Val Pro Phe Ile Asp Ser Leu Tyr Glu
    290                 295                 300

Phe Asn Ile Leu Gln Lys Ile Asn Asp Cys Gly Gly Cys Thr Thr Phe
305                 310                 315                 320

Thr His Leu Ser Phe Gln Glu Phe Phe Ala Ala Met Ser Phe Val Leu
                325                 330                 335

Glu Glu Pro Arg Glu Phe Pro Pro His Ser Thr Lys Pro Gln Glu Met
            340                 345                 350

Lys Met Leu Leu Gln His Val Leu Leu Asp Lys Glu Ala Tyr Trp Thr
        355                 360                 365

Pro Val Val Leu Phe Phe Phe Gly Leu Leu Asn Lys Asn Ile Ala Arg
    370                 375                 380

Glu Leu Glu Asp Thr Leu His Cys Lys Ile Ser Pro Arg Val Met Glu
385                 390                 395                 400

Glu Leu Leu Lys Trp Gly Glu Glu Leu Gly Lys Ala Glu Ser Ala Ser
                405                 410                 415

Leu Gln Phe His Ile Leu Arg Leu Phe His Cys Leu His Glu Ser Gln
            420                 425                 430

Glu Glu Asp Phe Thr Lys Lys Met Leu Gly Arg Ile Phe Glu Val Asp
        435                 440                 445

Leu Asn Ile Leu Glu Asp Glu Glu Leu Gln Ala Ser Ser Phe Cys Leu
    450                 455                 460

Lys His Cys Lys Arg Leu Asn Lys Leu Arg Leu Ser Val
465                 470                 475


<210> SEQ ID NO 170
<211> LENGTH: 473
<212> TYPE: PRT
<213> ORGANISM: Homo sapiens

<400> SEQUENCE: 170

Leu Pro Cys Leu Leu Leu Pro Lys Arg Pro Gln Gly Arg Gln Pro Lys
1               5                   10                  15

Thr Val Ala Ile Gln Gly Ala Pro Gly Ile Gly Lys Thr Ile Leu Ala
            20                  25                  30

Lys Lys Val Met Phe Glu Trp Ala Arg Asn Lys Phe Tyr Ala His Lys
        35                  40                  45

Arg Trp Cys Ala Phe Tyr Phe His Cys Gln Glu Val Asn Gln Thr Thr
    50                  55                  60
```

-continued

```
Asp Gln Ser Phe Ser Glu Leu Ile Glu Gln Lys Trp Pro Gly Ser Gln
65                  70                  75                  80

Asp Leu Val Ser Lys Ile Met Ser Lys Pro Asp Gln Leu Leu Leu Leu
                85                  90                  95

Leu Asp Gly Phe Glu Glu Leu Thr Ser Thr Leu Ile Asp Arg Leu Glu
            100                 105                 110

Asp Leu Ser Glu Asp Trp Arg Gln Lys Leu Pro Gly Ser Val Leu Leu
        115                 120                 125

Ser Ser Leu Leu Ser Lys Thr Met Leu Pro Glu Ala Thr Leu Leu Ile
    130                 135                 140

Met Ile Arg Phe Thr Ser Trp Gln Thr Cys Lys Pro Leu Leu Lys Cys
145                 150                 155                 160

Pro Ser Leu Val Thr Leu Pro Gly Phe Asn Thr Met Glu Lys Ile Lys
                165                 170                 175

Tyr Phe Gln Met Tyr Phe Gly His Thr Glu Glu Gly Asp Gln Val Leu
            180                 185                 190

Ser Phe Ala Met Glu Asn Thr Ile Leu Phe Ser Met Cys Arg Val Pro
        195                 200                 205

Val Val Cys Trp Met Val Cys Ser Gly Leu Lys Gln Gln Met Glu Arg
    210                 215                 220

Gly Asn Asn Leu Thr Gln Ser Cys Pro Asn Ala Thr Ser Val Phe Val
225                 230                 235                 240

Arg Tyr Ile Ser Ser Leu Phe Pro Thr Arg Ala Glu Asn Phe Ser Arg
                245                 250                 255

Lys Ile His Gln Ala Gln Leu Glu Gly Leu Cys His Leu Ala Ala Asp
            260                 265                 270

Ser Met Trp His Arg Lys Trp Val Leu Gly Lys Glu Asp Leu Glu Glu
        275                 280                 285

Ala Lys Leu Asp Gln Thr Gly Val Thr Ala Phe Leu Gly Met Ser Ile
    290                 295                 300

Leu Arg Arg Ile Ala Gly Glu Glu Asp His Tyr Val Phe Thr Leu Val
305                 310                 315                 320

Thr Phe Gln Glu Phe Phe Ala Ala Leu Phe Tyr Val Leu Cys Phe Pro
                325                 330                 335

Gln Arg Leu Lys Asn Phe His Val Leu Ser His Val Asn Ile Gln Arg
            340                 345                 350

Leu Ile Ala Ser Pro Arg Gly Ser Lys Ser Tyr Leu Ser His Met Gly
        355                 360                 365

Leu Phe Leu Phe Gly Phe Leu Asn Glu Ala Cys Ala Ser Ala Val Glu
    370                 375                 380

Gln Ser Phe Gln Cys Lys Val Ser Phe Gly Asn Lys Arg Lys Leu Leu
385                 390                 395                 400

Lys Val Ile Pro Leu Leu His Lys Cys Asp Pro Pro Ser Pro Gly Ser
                405                 410                 415

Gly Val Pro Gln Leu Phe Tyr Cys Leu His Glu Ile Arg Glu Glu Ala
            420                 425                 430

Phe Val Ser Gln Ala Leu Asn Asp Tyr His Lys Val Val Leu Arg Ile
        435                 440                 445

Gly Asn Asn Lys Glu Val Gln Val Ser Ala Phe Cys Leu Lys Arg Cys
    450                 455                 460

Gln Tyr Leu His Glu Val Glu Leu Thr
465                 470
```

-continued

<210> SEQ ID NO 171
<211> LENGTH: 470
<212> TYPE: PRT
<213> ORGANISM: Homo sapiens

<400> SEQUENCE: 171

```
Val Glu Ala Leu Phe Asp Ser Gly Glu Lys Pro Ser Leu Ala Pro Ser
1               5                   10                  15

Leu Val Val Leu Gln Gly Ser Ala Gly Thr Gly Lys Thr Thr Leu Ala
            20                  25                  30

Arg Lys Met Val Leu Asp Trp Ala Thr Gly Thr Leu Tyr Pro Gly Arg
        35                  40                  45

Phe Asp Tyr Val Phe Tyr Val Ser Cys Lys Glu Val Val Leu Leu Leu
    50                  55                  60

Glu Ser Lys Leu Glu Gln Leu Leu Phe Trp Cys Cys Gly Asp Asn Gln
65                  70                  75                  80

Ala Pro Val Thr Glu Ile Leu Arg Gln Pro Glu Arg Leu Leu Phe Ile
                85                  90                  95

Leu Asp Gly Phe Asp Glu Leu Gln Arg Pro Phe Glu Glu Lys Leu Lys
            100                 105                 110

Lys Arg Gly Leu Ser Pro Lys Glu Ser Leu Leu His Leu Leu Ile Arg
        115                 120                 125

Arg His Thr Leu Pro Thr Cys Ser Leu Leu Ile Thr Thr Arg Pro Leu
    130                 135                 140

Ala Leu Arg Asn Leu Glu Pro Leu Leu Lys Gln Ala Arg His Val His
145                 150                 155                 160

Ile Leu Gly Phe Ser Glu Glu Glu Arg Ala Arg Tyr Phe Ser Ser Tyr
                165                 170                 175

Phe Thr Asp Glu Lys Gln Ala Asp Arg Ala Phe Asp Ile Val Gln Lys
            180                 185                 190

Asn Asp Ile Leu Tyr Lys Ala Cys Gln Val Pro Gly Ile Cys Trp Val
        195                 200                 205

Val Cys Ser Trp Leu Gln Gly Gln Met Glu Arg Gly Lys Val Val Leu
    210                 215                 220

Glu Thr Pro Arg Asn Ser Thr Asp Ile Phe Met Ala Tyr Val Ser Thr
225                 230                 235                 240

Phe Leu Pro Pro Asp Asp Asp Gly Gly Cys Ser Glu Leu Ser Arg His
                245                 250                 255

Arg Val Leu Arg Ser Leu Cys Ser Leu Ala Ala Glu Gly Ile Gln His
            260                 265                 270

Gln Arg Phe Leu Phe Glu Glu Ala Glu Leu Arg Lys His Asn Leu Asp
        275                 280                 285

Gly Pro Arg Leu Ala Ala Phe Leu Ser Ser Asn Asp Tyr Gln Leu Gly
    290                 295                 300

Leu Ala Ile Lys Lys Phe Tyr Ser Phe Arg His Ile Ser Phe Gln Asp
305                 310                 315                 320

Phe Phe His Ala Met Ser Tyr Leu Val Lys Glu Asp Gln Ser Arg Leu
                325                 330                 335

Gly Lys Glu Ser Arg Arg Glu Val Gln Arg Leu Leu Glu Val Lys Glu
            340                 345                 350

Gln Glu Gly Asn Asp Glu Met Thr Leu Thr Met Gln Phe Leu Leu Asp
        355                 360                 365

Ile Ser Lys Lys Asp Ser Phe Ser Asn Leu Glu Leu Lys Phe Cys Phe
    370                 375                 380
```

```
Arg Ile Ser Pro Cys Leu Ala Gln Asp Leu Lys His Phe Lys Glu Gln
385                 390                 395                 400

Met Glu Ser Met Lys His Asn Arg Thr Trp Asp Leu Glu Phe Ser Leu
                405                 410                 415

Tyr Glu Ala Lys Ile Lys Asn Leu Val Lys Gly Ile Gln Met Asn Asn
            420                 425                 430

Val Ser Phe Lys Ile Lys His Ser Asn Glu Lys Lys Ser Gln Ser Gln
        435                 440                 445

Asn Leu Phe Ser Val Lys Ser Ser Leu Ser His Gly Pro Lys Glu Glu
    450                 455                 460

Gln Lys Cys Pro Ser Val
465                 470


<210> SEQ ID NO 172
<211> LENGTH: 466
<212> TYPE: PRT
<213> ORGANISM: Homo sapiens

<400> SEQUENCE: 172

Leu Ile Pro Phe Ser Asn Pro Arg Val Leu Pro Gly Pro Phe Ser Tyr
1               5                   10                  15

Thr Val Val Leu Tyr Gly Pro Ala Gly Leu Gly Lys Thr Thr Leu Ala
            20                  25                  30

Gln Lys Leu Met Leu Asp Trp Ala Glu Asp Asn Leu Ile His Lys Phe
        35                  40                  45

Lys Tyr Ala Phe Tyr Leu Ser Cys Arg Glu Leu Ser Arg Leu Gly Pro
    50                  55                  60

Cys Ser Phe Ala Glu Leu Val Phe Arg Asp Trp Pro Glu Leu Gln Asp
65                  70                  75                  80

Asp Ile Pro His Ile Leu Ala Gln Ala Arg Lys Ile Leu Phe Val Ile
                85                  90                  95

Asp Gly Phe Asp Glu Leu Gly Ala Ala Pro Gly Ala Leu Ile Glu Asp
            100                 105                 110

Ile Cys Gly Asp Trp Glu Lys Lys Lys Pro Val Pro Val Leu Leu Gly
        115                 120                 125

Ser Leu Leu Asn Arg Val Met Leu Pro Lys Ala Ala Leu Leu Val Thr
    130                 135                 140

Thr Arg Pro Arg Ala Leu Arg Asp Leu Arg Ile Leu Ala Glu Glu Pro
145                 150                 155                 160

Ile Tyr Ile Arg Val Glu Gly Phe Leu Glu Glu Asp Arg Arg Ala Tyr
                165                 170                 175

Phe Leu Arg His Phe Gly Asp Glu Asp Gln Ala Met Arg Ala Phe Glu
            180                 185                 190

Leu Met Arg Ser Asn Ala Ala Leu Phe Gln Leu Gly Ser Ala Pro Ala
        195                 200                 205

Val Cys Trp Ile Val Cys Thr Thr Leu Lys Leu Gln Met Glu Lys Gly
    210                 215                 220

Glu Asp Pro Val Pro Thr Cys Leu Thr Arg Thr Gly Leu Phe Leu Arg
225                 230                 235                 240

Phe Leu Cys Ser Arg Phe Pro Gln Gly Ala Gln Leu Arg Gly Ala Leu
                245                 250                 255

Arg Thr Leu Ser Leu Leu Ala Ala Gln Gly Leu Trp Ala Gln Thr Ser
            260                 265                 270

Val Leu His Arg Glu Asp Leu Glu Arg Leu Gly Val Gln Glu Ser Asp
```

-continued

```
        275                 280                 285

Leu Arg Leu Phe Leu Asp Gly Asp Ile Leu Arg Gln Asp Arg Val Ser
    290                 295                 300

Lys Gly Cys Tyr Ser Phe Ile His Leu Ser Phe Gln Gln Phe Leu Thr
305                 310                 315                 320

Ala Leu Phe Tyr Thr Leu Glu Lys Glu Glu Glu Glu Asp Arg Asp Gly
                325                 330                 335

His Thr Trp Asp Ile Gly Asp Val Gln Lys Leu Leu Ser Gly Val Glu
            340                 345                 350

Arg Leu Arg Asn Pro Asp Leu Ile Gln Ala Gly Tyr Tyr Ser Phe Gly
        355                 360                 365

Leu Ala Asn Glu Lys Arg Ala Lys Glu Leu Glu Ala Thr Phe Gly Cys
    370                 375                 380

Arg Met Ser Pro Asp Ile Lys Gln Glu Leu Leu Arg Cys Asp Ile Ser
385                 390                 395                 400

Cys Lys Gly Gly His Ser Thr Val Thr Asp Leu Gln Glu Leu Leu Gly
                405                 410                 415

Cys Leu Tyr Glu Ser Gln Glu Glu Glu Leu Val Lys Glu Val Met Ala
            420                 425                 430

Gln Phe Lys Glu Ile Ser Leu His Leu Asn Ala Val Asp Val Val Pro
        435                 440                 445

Ser Ser Phe Cys Val Lys His Cys Arg Asn Leu Gln Lys Met Ser Leu
    450                 455                 460

Gln Val
465


<210> SEQ ID NO 173
<211> LENGTH: 476
<212> TYPE: PRT
<213> ORGANISM: Homo sapiens

<400> SEQUENCE: 173

Thr Leu Ala Gly Ala Phe Asp Ser Asp Arg Trp Gly Phe Arg Pro Arg
1               5                   10                  15

Thr Val Val Leu His Gly Lys Ser Gly Ile Gly Lys Ser Ala Leu Ala
            20                  25                  30

Arg Arg Ile Val Leu Cys Trp Ala Gln Gly Gly Leu Tyr Gln Gly Met
        35                  40                  45

Phe Ser Tyr Val Phe Phe Leu Pro Val Arg Glu Met Gln Arg Lys Lys
    50                  55                  60

Glu Ser Ser Val Thr Glu Phe Ile Ser Arg Glu Trp Pro Asp Ser Gln
65                  70                  75                  80

Ala Pro Val Thr Glu Ile Met Ser Arg Pro Glu Arg Leu Leu Phe Ile
                85                  90                  95

Ile Asp Gly Phe Asp Asp Leu Gly Ser Val Leu Asn Asn Asp Thr Lys
            100                 105                 110

Leu Cys Lys Asp Trp Ala Glu Lys Gln Pro Pro Phe Thr Leu Ile Arg
        115                 120                 125

Ser Leu Leu Arg Lys Val Leu Leu Pro Glu Ser Phe Leu Ile Val Thr
    130                 135                 140

Val Arg Asp Val Gly Thr Glu Lys Leu Lys Ser Glu Val Val Ser Pro
145                 150                 155                 160

Arg Tyr Leu Leu Val Arg Gly Ile Ser Gly Glu Gln Arg Ile His Leu
                165                 170                 175
```

-continued

```
Leu Leu Glu Arg Gly Ile Gly Glu His Gln Lys Thr Gln Gly Leu Arg
            180                 185                 190

Ala Ile Met Asn Asn Arg Glu Leu Leu Asp Gln Cys Gln Val Pro Ala
        195                 200                 205

Val Gly Ser Leu Ile Cys Val Ala Leu Gln Leu Gln Asp Val Val Gly
    210                 215                 220

Glu Ser Val Ala Pro Phe Asn Gln Thr Leu Thr Gly Leu His Ala Ala
225                 230                 235                 240

Phe Val Phe His Gln Leu Thr Pro Arg Gly Val Val Arg Arg Cys Leu
                245                 250                 255

Asn Leu Glu Glu Arg Val Val Leu Lys Arg Phe Cys Arg Met Ala Val
            260                 265                 270

Glu Gly Val Trp Asn Arg Lys Ser Val Phe Asp Gly Asp Asp Leu Met
        275                 280                 285

Val Gln Gly Leu Gly Glu Ser Glu Leu Arg Ala Leu Phe His Met Asn
    290                 295                 300

Ile Leu Leu Pro Asp Ser His Cys Glu Glu Tyr Tyr Thr Phe Phe His
305                 310                 315                 320

Leu Ser Leu Gln Asp Phe Cys Ala Ala Leu Tyr Tyr Val Leu Glu Gly
                325                 330                 335

Leu Glu Ile Glu Pro Ala Leu Cys Pro Leu Tyr Val Glu Lys Thr Lys
            340                 345                 350

Arg Ser Met Glu Leu Lys Gln Ala Gly Phe His Ile His Ser Leu Trp
        355                 360                 365

Met Lys Arg Phe Leu Phe Gly Leu Val Ser Glu Asp Val Arg Arg Pro
    370                 375                 380

Leu Glu Val Leu Leu Gly Cys Pro Val Pro Leu Gly Val Lys Gln Lys
385                 390                 395                 400

Leu Leu His Trp Val Ser Leu Leu Gly Gln Pro Asn Ala Thr Thr
                405                 410                 415

Pro Gly Asp Thr Leu Asp Ala Phe His Cys Leu Phe Glu Thr Gln Asp
            420                 425                 430

Lys Glu Phe Val Arg Leu Ala Leu Asn Ser Phe Gln Glu Val Trp Leu
        435                 440                 445

Pro Ile Asn Gln Asn Leu Asp Leu Ile Ala Ser Ser Phe Cys Leu Gln
    450                 455                 460

His Cys Pro Tyr Leu Arg Lys Ile Arg Val Asp Val
465                 470                 475


<210> SEQ ID NO 174
<211> LENGTH: 496
<212> TYPE: PRT
<213> ORGANISM: Homo sapiens

<400> SEQUENCE: 174

Thr Phe Asn Arg Leu Phe Arg Arg Asp Glu Glu Gly Arg Arg Pro Leu
1               5                   10                  15

Thr Val Val Leu Gln Gly Pro Ala Gly Ile Gly Lys Thr Met Ala Ala
            20                  25                  30

Lys Lys Ile Leu Tyr Asp Trp Ala Ala Gly Lys Leu Tyr Gln Gly Gln
        35                  40                  45

Val Asp Phe Ala Phe Phe Met Pro Cys Gly Glu Leu Leu Glu Arg Pro
    50                  55                  60

Gly Thr Arg Ser Leu Ala Asp Leu Ile Leu Asp Gln Cys Pro Asp Arg
65                  70                  75                  80
```

-continued

```
Gly Ala Pro Val Pro Gln Met Leu Ala Gln Pro Gln Arg Leu Leu Phe
                85                  90                  95

Ile Leu Asp Gly Ala Asp Glu Leu Pro Ala Leu Gly Gly Pro Glu Ala
            100                 105                 110

Ala Pro Cys Thr Asp Pro Phe Glu Ala Ala Ser Gly Ala Arg Val Leu
        115                 120                 125

Gly Gly Leu Leu Ser Lys Ala Leu Leu Pro Thr Ala Leu Leu Leu Val
    130                 135                 140

Thr Thr Arg Ala Ala Ala Pro Gly Arg Leu Gln Gly Arg Leu Cys Ser
145                 150                 155                 160

Pro Gln Cys Ala Glu Val Arg Gly Phe Ser Asp Lys Asp Lys Lys Lys
                165                 170                 175

Tyr Phe Tyr Lys Phe Phe Arg Asp Glu Arg Arg Ala Glu Arg Ala Tyr
            180                 185                 190

Arg Phe Val Lys Glu Asn Glu Thr Leu Phe Ala Leu Cys Phe Val Pro
        195                 200                 205

Phe Val Cys Trp Ile Val Cys Thr Val Leu Arg Gln Gln Leu Glu Leu
    210                 215                 220

Gly Arg Asp Leu Ser Arg Thr Ser Lys Thr Thr Thr Ser Val Tyr Leu
225                 230                 235                 240

Leu Phe Ile Thr Ser Val Leu Ser Ser Ala Pro Val Ala Asp Gly Pro
                245                 250                 255

Arg Leu Gln Gly Asp Leu Arg Asn Leu Cys Arg Leu Ala Arg Glu Gly
            260                 265                 270

Val Leu Gly Arg Arg Ala Gln Phe Ala Glu Lys Glu Leu Glu Gln Leu
        275                 280                 285

Glu Leu Arg Gly Ser Lys Val Gln Thr Leu Phe Leu Ser Lys Lys Glu
    290                 295                 300

Leu Pro Gly Val Leu Glu Thr Glu Val Thr Tyr Gln Phe Ile Asp Gln
305                 310                 315                 320

Ser Phe Gln Glu Phe Leu Ala Ala Leu Ser Tyr Leu Leu Glu Asp Gly
                325                 330                 335

Gly Val Pro Arg Thr Ala Ala Gly Gly Val Gly Thr Leu Leu Arg Gly
            340                 345                 350

Asp Ala Gln Pro His Ser His Leu Val Leu Thr Thr Arg Phe Leu Phe
        355                 360                 365

Gly Leu Leu Ser Ala Glu Arg Met Arg Asp Ile Glu Arg His Phe Gly
    370                 375                 380

Cys Met Val Ser Glu Arg Val Lys Gln Glu Ala Leu Arg Trp Val Gln
385                 390                 395                 400

Gly Gln Gly Gln Gly Cys Pro Gly Val Ala Pro Glu Val Thr Glu Gly
                405                 410                 415

Ala Lys Gly Leu Glu Asp Thr Glu Glu Pro Glu Glu Glu Glu Glu Gly
            420                 425                 430

Glu Glu Pro Asn Tyr Pro Leu Glu Leu Leu Tyr Cys Leu Tyr Glu Thr
        435                 440                 445

Gln Glu Asp Ala Phe Val Arg Gln Ala Leu Cys Arg Phe Pro Glu Leu
    450                 455                 460

Ala Leu Gln Arg Val Arg Phe Cys Arg Met Asp Val Ala Val Leu Ser
465                 470                 475                 480

Tyr Cys Val Arg Cys Cys Pro Ala Gly Gln Ala Leu Arg Leu Ile Ser
                485                 490                 495
```

<210> SEQ ID NO 175
<211> LENGTH: 467
<212> TYPE: PRT
<213> ORGANISM: Homo sapiens

<400> SEQUENCE: 175

```
Leu Gln Leu Ala Tyr Asp Ser Thr Ser Tyr Tyr Ser Ala Asn Asn Leu
1               5                   10                  15

Asn Val Phe Leu Met Gly Glu Arg Ala Ser Gly Lys Thr Ile Val Ile
            20                  25                  30

Asn Leu Ala Val Leu Arg Trp Ile Lys Gly Glu Met Trp Gln Asn Met
        35                  40                  45

Ile Ser Tyr Val Val His Leu Thr Ser His Glu Ile Asn Gln Met Thr
    50                  55                  60

Asn Ser Ser Leu Ala Glu Leu Ile Ala Lys Asp Trp Pro Asp Gly Gln
65                  70                  75                  80

Ala Pro Ile Ala Asp Ile Leu Ser Asp Pro Lys Lys Leu Leu Phe Ile
                85                  90                  95

Leu Glu Asp Leu Asp Asn Ile Arg Phe Glu Leu Asn Val Asn Glu Ser
            100                 105                 110

Ala Leu Cys Ser Asn Ser Thr Gln Lys Val Pro Ile Pro Val Leu Leu
        115                 120                 125

Val Ser Leu Leu Lys Arg Lys Met Ala Pro Gly Cys Trp Phe Leu Ile
    130                 135                 140

Ser Ser Arg Pro Thr Arg Gly Asn Asn Val Lys Thr Phe Leu Lys Glu
145                 150                 155                 160

Val Asp Cys Cys Thr Thr Leu Gln Leu Ser Asn Gly Lys Arg Glu Ile
                165                 170                 175

Tyr Phe Asn Ser Phe Phe Lys Asp Arg Gln Arg Ala Ser Ala Ala Leu
            180                 185                 190

Gln Leu Val His Glu Asp Glu Ile Leu Val Gly Leu Cys Arg Val Ala
        195                 200                 205

Ile Leu Cys Trp Ile Thr Cys Thr Val Leu Lys Arg Gln Met Asp Lys
    210                 215                 220

Gly Arg Asp Phe Gln Leu Cys Cys Gln Thr Pro Thr Asp Leu His Ala
225                 230                 235                 240

His Phe Leu Ala Asp Ala Leu Thr Ser Glu Ala Gly Leu Thr Ala Asn
                245                 250                 255

Gln Tyr His Leu Gly Leu Leu Lys Arg Leu Cys Leu Leu Ala Ala Gly
            260                 265                 270

Gly Leu Phe Leu Ser Thr Leu Asn Phe Ser Gly Glu Asp Leu Arg Cys
        275                 280                 285

Val Gly Phe Thr Glu Ala Asp Val Ser Val Leu Gln Ala Ala Asn Ile
    290                 295                 300

Leu Leu Pro Ser Asn Thr His Lys Asp Arg Tyr Lys Phe Ile His Leu
305                 310                 315                 320

Asn Val Gln Glu Phe Cys Thr Ala Ile Ala Phe Leu Met Ala Val Pro
                325                 330                 335

Asn Tyr Leu Ile Pro Ser Gly Ser Arg Glu Tyr Lys Glu Lys Arg Glu
            340                 345                 350

Gln Tyr Ser Asp Phe Asn Gln Val Phe Thr Phe Ile Phe Gly Leu Leu
        355                 360                 365

Asn Ala Asn Arg Arg Lys Ile Leu Glu Thr Ser Phe Gly Tyr Gln Leu
    370                 375                 380
```

```
Pro Met Val Asp Ser Phe Lys Trp Tyr Ser Val Gly Tyr Met Lys His
385                 390                 395                 400

Leu Asp Arg Asp Pro Glu Lys Leu Thr His His Met Pro Leu Phe Tyr
                405                 410                 415

Cys Leu Tyr Glu Asn Arg Glu Glu Glu Phe Val Lys Thr Ile Val Asp
            420                 425                 430

Ala Leu Met Glu Val Thr Val Tyr Leu Gln Ser Asp Lys Asp Met Met
        435                 440                 445

Val Ser Leu Tyr Cys Leu Asp Tyr Cys Cys His Leu Arg Thr Leu Lys
    450                 455                 460

Leu Ser Val
465


<210> SEQ ID NO 176
<211> LENGTH: 454
<212> TYPE: PRT
<213> ORGANISM: Homo sapiens
<220> FEATURE:
<221> NAME/KEY: MISC_FEATURE
<222> LOCATION: (178)..(178)
<223> OTHER INFORMATION: "Xaa" denotes any amino acid residue.
<220> FEATURE:
<221> NAME/KEY: MISC_FEATURE
<222> LOCATION: (347)..(347)
<223> OTHER INFORMATION: "Xaa" denotes any amino acid residue.

<400> SEQUENCE: 176

Val Val Leu Gln Ala Cys Ala Gly Thr Gly Lys Thr Ala Val Val His
1               5                   10                  15

Lys Phe Met Phe Asp Trp Ala Ala Gly Thr Val Thr Pro Gly Arg Cys
            20                  25                  30

Asp Tyr Leu Ile Tyr Val Asn Cys Ile Glu Ile Ser His Ile Ala Asn
        35                  40                  45

Leu Ser Ser Ala Asp Leu Ile Leu Thr Leu Phe Lys Ile Asn Gly Pro
    50                  55                  60

Ile Leu Asp Thr Ile Leu Ile Tyr Pro Lys Ile Leu Leu Ile Leu Asp
65                  70                  75                  80

Arg Phe Pro Glu Leu Gln Asp Pro Val Gly Asp Gln Glu Glu Asp Leu
                85                  90                  95

Ser Val His Pro Gln Glu Arg Arg Pro Val Glu Ser Leu Leu Cys Ser
            100                 105                 110

Phe Val Arg Lys Lys Leu Phe Pro Glu Ser Ser Leu Leu Ile Thr Ala
        115                 120                 125

Arg Pro Thr Ala Met Lys Lys Leu His Ser Leu Leu Lys Gln Pro Ile
    130                 135                 140

Gln Ala Glu Ile Leu Trp Phe Thr Asp Thr Glu Lys Arg Ala Tyr Leu
145                 150                 155                 160

Leu Ser Gln Phe Ser Gly Ala Asn Thr Thr Met Lys Val Phe Tyr Asp
                165                 170                 175

Leu Xaa Glu Asn Glu Asp Leu Asp Ile Met Ser Ser Leu Pro Ile Val
            180                 185                 190

Ser Trp Met Ile Cys Asn Val Leu Gln Ser Gln Gly Asp Gly Asp Arg
        195                 200                 205

Thr Leu Leu Arg Ser Leu Gln Thr Met Thr Asp Val Tyr Leu Phe Tyr
    210                 215                 220

Phe Ser Lys Cys Leu Lys Thr Leu Thr Gly Ile Ser Val Trp Glu Gly
225                 230                 235                 240
```

-continued

```
Gln Ser Cys Leu Trp Gly Leu Cys Arg Leu Ala Ala Glu Gly Leu Gln
                245                 250                 255

Asn His Gln Val Leu Phe Ala Val Ser Asp Leu Arg Arg His Gly Ile
            260                 265                 270

Gly Val Cys Asp Thr Asn Cys Thr Phe Leu Ser Arg Phe Leu Lys Lys
        275                 280                 285

Ala Glu Gly Ala Val Ser Val Tyr Thr Phe Leu His Phe Ser Phe Gln
    290                 295                 300

Glu Phe Leu Thr Ala Val Phe His Ala Leu Lys Asn Asp Asn Ser Trp
305                 310                 315                 320

Met Phe Phe Tyr Gln Ala Glu Lys Met Trp Gln Glu Met Phe Gln Gln
                325                 330                 335

Tyr Gly Lys Gly Phe Ser Ser Leu Met Ile Xaa Phe Leu Phe Gly Leu
            340                 345                 350

Leu His Lys Gly Lys Gly Lys Ala Val Glu Thr Thr Phe Gly Arg Lys
        355                 360                 365

Val Ser Pro Gly Leu Gln Glu Glu Leu Leu Lys Trp Thr Glu Arg Glu
    370                 375                 380

Ile Lys Asp Lys Ser Ser Arg Leu Gln Ile Glu Pro Val Asp Leu Phe
385                 390                 395                 400

His Cys Leu Tyr Glu Ile Gln Glu Glu Glu Tyr Ala Lys Arg Ile Ile
                405                 410                 415

Asp Asp Leu Gln Ser Ile Ile Leu Leu Gln Pro Thr Tyr Thr Lys Met
            420                 425                 430

Asp Ile Leu Val Met Ser Phe Cys Val Lys Ser Ser His Ser His Leu
        435                 440                 445

Ser Val Ser Leu Lys Cys
    450


<210> SEQ ID NO 177
<211> LENGTH: 588
<212> TYPE: PRT
<213> ORGANISM: Homo sapiens

<400> SEQUENCE: 177

Leu Ser Gln Leu Phe Asn Pro Asp Ala Cys Gly Arg Arg Val Gln Thr
1               5                   10                  15

Val Val Leu Tyr Gly Thr Val Gly Thr Gly Lys Ser Thr Leu Val Arg
            20                  25                  30

Lys Met Val Leu Asp Trp Cys Tyr Gly Arg Leu Pro Ala Phe Glu Leu
        35                  40                  45

Leu Ile Pro Phe Ser Cys Glu Asp Leu Ser Ser Leu Gly Pro Ala Pro
    50                  55                  60

Ala Ser Leu Cys Gln Leu Val Ala Gln Arg Tyr Thr Pro Leu Lys Glu
65                  70                  75                  80

Val Leu Pro Leu Met Ala Ala Ala Gly Ser His Leu Leu Phe Val Leu
                85                  90                  95

His Gly Leu Glu His Leu Asn Leu Asp Phe Arg Leu Ala Gly Thr Gly
            100                 105                 110

Leu Cys Ser Asp Pro Glu Glu Pro Gln Glu Pro Ala Ala Ile Ile Val
        115                 120                 125

Asn Leu Leu Arg Lys Tyr Met Leu Pro Gln Ala Ser Ile Leu Val Thr
    130                 135                 140

Thr Arg Pro Ser Ala Ile Gly Arg Ile Pro Ser Lys Tyr Val Gly Arg
```

-continued

```
145                 150                 155                 160

Tyr Gly Glu Ile Cys Gly Phe Ser Asp Thr Asn Leu Gln Lys Leu Tyr
                165                 170                 175

Phe Gln Leu Arg Leu Asn Gln Pro Tyr Cys Gly Tyr Ala Val Gly Gly
            180                 185                 190

Ser Gly Val Ser Ala Thr Pro Ala Gln Arg Asp His Leu Val Gln Met
        195                 200                 205

Leu Ser Arg Asn Leu Glu Gly His His Gln Ile Ala Ala Ala Cys Phe
    210                 215                 220

Leu Pro Ser Tyr Cys Trp Leu Val Cys Ala Thr Leu His Phe Leu His
225                 230                 235                 240

Ala Pro Thr Pro Ala Gly Gln Thr Leu Thr Ser Ile Tyr Thr Ser Phe
                245                 250                 255

Leu Arg Leu Asn Phe Ser Gly Glu Thr Leu Asp Ser Thr Asp Pro Ser
            260                 265                 270

Asn Leu Ser Leu Met Ala Tyr Ala Ala Arg Thr Met Gly Lys Leu Ala
        275                 280                 285

Tyr Glu Gly Val Ser Ser Arg Lys Thr Tyr Phe Ser Glu Glu Asp Val
    290                 295                 300

Cys Gly Cys Leu Glu Ala Gly Ile Arg Thr Glu Glu Glu Phe Gln Leu
305                 310                 315                 320

Leu His Ile Phe Arg Arg Asp Ala Leu Arg Phe Phe Leu Ala Pro Cys
                325                 330                 335

Val Glu Pro Gly Arg Ala Gly Thr Phe Val Phe Thr Val Pro Ala Met
            340                 345                 350

Gln Glu Tyr Leu Ala Ala Leu Tyr Ile Val Leu Gly Leu Arg Lys Thr
        355                 360                 365

Thr Leu Gln Lys Val Gly Lys Glu Val Ala Glu Leu Val Gly Arg Val
    370                 375                 380

Gly Glu Asp Val Ser Leu Val Leu Gly Ile Met Ala Lys Leu Leu Pro
385                 390                 395                 400

Leu Arg Ala Leu Pro Leu Leu Phe Asn Leu Ile Lys Val Val Pro Arg
                405                 410                 415

Val Phe Gly Arg Met Val Gly Lys Ser Arg Glu Ala Val Ala Gln Ala
            420                 425                 430

Met Val Leu Glu Met Phe Arg Glu Glu Asp Tyr Tyr Asn Asp Asp Val
        435                 440                 445

Leu Asp Gln Met Gly Ala Ser Ile Leu Gly Val Glu Gly Pro Arg Arg
    450                 455                 460

His Pro Asp Glu Pro Pro Glu Asp Glu Val Phe Glu Leu Phe Pro Met
465                 470                 475                 480

Phe Met Gly Gly Leu Leu Ser Ala His Asn Arg Ala Val Leu Ala Gln
                485                 490                 495

Leu Gly Cys Pro Ile Lys Asn Leu Asp Ala Leu Glu Asn Ala Gln Ala
            500                 505                 510

Ile Lys Lys Lys Leu Gly Lys Leu Gly Arg Gln Val Leu Pro Pro Ser
        515                 520                 525

Glu Leu Leu Asp His Leu Phe Phe His Tyr Glu Phe Gln Asn Gln Arg
    530                 535                 540

Phe Ser Ala Glu Val Leu Ser Ser Leu Arg Gln Leu Asn Leu Ala Gly
545                 550                 555                 560

Val Arg Met Thr Pro Val Lys Cys Thr Val Val Ala Ala Val Leu Gly
                565                 570                 575
```

-continued

```
Ser Gly Arg His Ala Leu Asp Glu Val Asn Leu Ala
            580                 585


<210> SEQ ID NO 178
<211> LENGTH: 467
<212> TYPE: PRT
<213> ORGANISM: Homo sapiens

<400> SEQUENCE: 178

Glu Val Leu Leu Ala Ala Lys Glu His Arg Arg Pro Arg Glu Thr Arg
1               5                   10                  15

Val Ile Ala Val Leu Gly Lys Ala Gly Gln Gly Lys Ser Tyr Trp Ala
            20                  25                  30

Gly Ala Val Ser Arg Ala Trp Ala Cys Gly Arg Leu Pro Gln Tyr Asp
        35                  40                  45

Phe Val Phe Ser Val Pro Cys His Cys Leu Asn Arg Pro Gly Asp Ala
    50                  55                  60

Tyr Gly Leu Gln Asp Leu Leu Phe Ser Leu Gly Pro Gln Pro Leu Val
65                  70                  75                  80

Ala Ala Asp Glu Val Phe Ser His Ile Leu Lys Arg Pro Asp Arg Val
                85                  90                  95

Leu Leu Ile Leu Asp Ala Phe Glu Glu Leu Glu Ala Gln Asp Gly Phe
            100                 105                 110

Leu His Ser Thr Cys Gly Pro Ala Pro Ala Glu Pro Cys Ser Leu Arg
        115                 120                 125

Gly Leu Leu Ala Gly Leu Phe Gln Lys Lys Leu Leu Arg Gly Cys Thr
    130                 135                 140

Leu Leu Leu Thr Ala Arg Pro Arg Gly Arg Leu Val Gln Ser Leu Ser
145                 150                 155                 160

Lys Ala Asp Ala Leu Phe Glu Leu Ser Gly Phe Ser Met Glu Gln Ala
                165                 170                 175

Gln Ala Tyr Val Met Arg Tyr Phe Glu Ser Ser Gly Met Thr Glu His
            180                 185                 190

Gln Asp Arg Ala Leu Thr Leu Leu Arg Asp Arg Pro Leu Leu Leu Ser
        195                 200                 205

His Ser His Ser Pro Thr Leu Cys Arg Ala Val Cys Gln Leu Ser Glu
    210                 215                 220

Ala Leu Leu Glu Leu Gly Glu Asp Ala Lys Leu Pro Ser Thr Leu Thr
225                 230                 235                 240

Gly Leu Tyr Val Gly Leu Leu Gly Arg Ala Ala Leu Asp Ser Pro Pro
                245                 250                 255

Gly Ala Leu Ala Glu Leu Ala Lys Leu Ala Trp Glu Leu Gly Arg Arg
            260                 265                 270

His Gln Ser Thr Leu Gln Glu Asp Gln Phe Pro Ser Ala Asp Val Arg
        275                 280                 285

Thr Trp Ala Met Ala Lys Gly Leu Val Gln His Pro Pro Arg Ala Ala
    290                 295                 300

Glu Ser Glu Leu Ala Phe Pro Ser Phe Leu Leu Gln Cys Phe Leu Gly
305                 310                 315                 320

Ala Leu Trp Leu Ala Leu Ser Gly Glu Ile Lys Asp Lys Glu Leu Pro
                325                 330                 335

Gln Tyr Leu Ala Leu Thr Pro Arg Lys Lys Arg Pro Tyr Asp Asn Trp
            340                 345                 350

Leu Glu Gly Val Pro Arg Phe Leu Ala Gly Leu Ile Phe Gln Pro Pro
```

-continued

```
        355                 360                 365

Ala Arg Cys Leu Gly Ala Leu Leu Gly Pro Ser Ala Ala Ala Ser Val
    370                 375                 380

Asp Arg Lys Gln Lys Val Leu Ala Arg Tyr Leu Lys Arg Leu Gln Pro
385                 390                 395                 400

Gly Thr Leu Arg Ala Arg Gln Leu Leu Glu Leu Leu His Cys Ala His
                405                 410                 415

Glu Ala Glu Glu Ala Gly Ile Trp Gln His Val Val Gln Glu Leu Pro
            420                 425                 430

Gly Arg Leu Ser Phe Leu Gly Thr Arg Leu Thr Pro Pro Asp Ala His
        435                 440                 445

Val Leu Gly Lys Ala Leu Glu Ala Ala Gly Gln Asp Phe Ser Leu Asp
    450                 455                 460

Leu Arg Ser
465


<210> SEQ ID NO 179
<211> LENGTH: 465
<212> TYPE: PRT
<213> ORGANISM: Homo sapiens

<400> SEQUENCE: 179

Val Ser Ile Ser Asp Leu Phe Asn Thr Arg Val Asn Lys Gly Pro Arg
1               5                   10                  15

Val Thr Val Leu Leu Gly Lys Ala Gly Met Gly Lys Thr Thr Leu Ala
            20                  25                  30

His Arg Leu Cys Gln Lys Trp Ala Glu Gly His Leu Asn Cys Phe Gln
        35                  40                  45

Ala Leu Phe Leu Phe Glu Phe Arg Gln Leu Asn Leu Ile Thr Arg Phe
    50                  55                  60

Leu Thr Pro Ser Glu Leu Leu Phe Asp Leu Tyr Leu Ser Pro Glu Ser
65                  70                  75                  80

Asp His Asp Thr Val Phe Gln Tyr Leu Glu Lys Asn Ala Asp Gln Val
                85                  90                  95

Leu Leu Ile Phe Asp Gly Leu Asp Glu Ala Leu Gln Pro Met Gly Pro
            100                 105                 110

Asp Gly Pro Gly Pro Val Leu Thr Leu Phe Ser His Leu Cys Asn Gly
        115                 120                 125

Thr Leu Leu Pro Gly Cys Arg Val Met Ala Thr Ser Arg Pro Gly Lys
    130                 135                 140

Leu Pro Ala Cys Leu Pro Ala Glu Ala Ala Met Val His Met Leu Gly
145                 150                 155                 160

Phe Asp Gly Pro Arg Val Glu Glu Tyr Val Asn His Phe Phe Ser Ala
                165                 170                 175

Gln Pro Ser Arg Glu Gly Ala Leu Val Glu Leu Gln Thr Asn Gly Arg
            180                 185                 190

Leu Arg Ser Leu Cys Ala Val Pro Ala Leu Cys Gln Val Ala Cys Leu
        195                 200                 205

Cys Leu His His Leu Leu Pro Asp His Ala Pro Gly Gln Ser Val Ala
    210                 215                 220

Leu Leu Pro Asn Met Thr Gln Leu Tyr Met Gln Met Val Leu Ala Leu
225                 230                 235                 240

Ser Pro Pro Gly His Leu Pro Thr Ser Ser Leu Leu Asp Leu Gly Glu
                245                 250                 255
```

-continued

```
Val Ala Leu Arg Gly Leu Glu Thr Gly Lys Val Ile Phe Tyr Ala Lys
            260                 265                 270

Asp Ile Ala Pro Pro Leu Ile Ala Phe Gly Ala Thr His Ser Leu Leu
        275                 280                 285

Thr Ser Phe Cys Val Cys Thr Gly Pro Gly His Gln Gln Thr Gly Tyr
    290                 295                 300

Ala Phe Thr His Leu Ser Leu Gln Glu Phe Leu Ala Ala Leu His Leu
305                 310                 315                 320

Met Ala Ser Pro Lys Val Asn Lys Asp Thr Leu Thr Gln Tyr Val Thr
                325                 330                 335

Leu His Ser Arg Trp Val Gln Arg Thr Lys Ala Arg Leu Gly Leu Ser
            340                 345                 350

Asp His Leu Pro Thr Phe Leu Ala Gly Leu Ala Ser Cys Thr Cys Arg
        355                 360                 365

Pro Phe Leu Ser His Leu Ala Gln Gly Asn Glu Asp Cys Val Gly Ala
    370                 375                 380

Lys Gln Ala Ala Val Val Gln Val Leu Lys Lys Leu Ala Thr Arg Lys
385                 390                 395                 400

Leu Thr Gly Pro Lys Val Val Glu Leu Cys His Cys Val Asp Glu Thr
                405                 410                 415

Gln Glu Pro Glu Leu Ala Ser Leu Thr Ala Gln Ser Leu Pro Tyr Gln
            420                 425                 430

Leu Pro Phe His Asn Phe Pro Leu Thr Cys Thr Asp Leu Ala Thr Leu
        435                 440                 445

Thr Asn Ile Leu Glu His Arg Glu Ala Pro Ile His Leu Asp Phe Asp
    450                 455                 460

Gly
465


<210> SEQ ID NO 180
<211> LENGTH: 501
<212> TYPE: PRT
<213> ORGANISM: Homo sapiens

<400> SEQUENCE: 180

Leu Asp Arg Leu Phe Leu Pro Leu Ser Arg Val Ser Val Pro Pro Arg
1               5                   10                  15

Val Ser Ile Thr Ile Gly Val Ala Gly Met Gly Lys Thr Thr Leu Val
            20                  25                  30

Arg His Phe Val Arg Leu Trp Ala His Gly Gln Val Gly Lys Asp Phe
        35                  40                  45

Ser Leu Val Leu Pro Leu Thr Phe Arg Asp Leu Asn Thr His Glu Lys
    50                  55                  60

Leu Cys Ala Asp Arg Leu Ile Cys Ser Val Phe Pro His Val Gly Glu
65                  70                  75                  80

Pro Ser Leu Ala Val Ala Val Pro Ala Arg Ala Leu Leu Ile Leu Asp
                85                  90                  95

Gly Leu Asp Glu Cys Arg Thr Pro Leu Asp Phe Ser Asn Thr Val Ala
            100                 105                 110

Cys Thr Asp Pro Lys Lys Glu Ile Pro Val Asp His Leu Ile Thr Asn
        115                 120                 125

Ile Ile Arg Gly Asn Leu Phe Pro Glu Val Ser Ile Trp Ile Thr Ser
    130                 135                 140

Arg Pro Ser Ala Ser Gly Gln Ile Pro Gly Gly Leu Val Asp Arg Met
145                 150                 155                 160
```

-continued

```
Thr Glu Ile Arg Gly Phe Asn Glu Glu Glu Ile Lys Val Cys Leu Glu
                165                 170                 175

Gln Met Phe Pro Glu Asp Gln Ala Leu Leu Gly Trp Met Leu Ser Gln
            180                 185                 190

Val Gln Ala Asp Arg Ala Leu Tyr Leu Met Cys Thr Val Pro Ala Phe
        195                 200                 205

Cys Arg Leu Thr Gly Met Ala Leu Gly His Leu Trp Arg Ser Arg Thr
    210                 215                 220

Gly Pro Gln Asp Ala Glu Leu Trp Pro Pro Arg Thr Leu Cys Glu Leu
225                 230                 235                 240

Tyr Ser Trp Tyr Phe Arg Met Ala Leu Ser Gly Glu Gly Gln Glu Lys
                245                 250                 255

Gly Lys Ala Ser Pro Arg Ile Glu Gln Val Ala His Gly Gly Arg Lys
            260                 265                 270

Met Val Gly Thr Leu Gly Arg Leu Ala Phe His Gly Leu Leu Lys Lys
        275                 280                 285

Lys Tyr Val Phe Tyr Glu Gln Asp Met Lys Ala Phe Gly Val Asp Leu
    290                 295                 300

Ala Leu Leu Gln Gly Ala Pro Cys Ser Cys Phe Leu Gln Arg Glu Glu
305                 310                 315                 320

Thr Leu Ala Ser Ser Val Ala Tyr Cys Phe Thr His Leu Ser Leu Gln
                325                 330                 335

Glu Phe Val Ala Ala Ala Tyr Tyr Tyr Gly Ala Ser Arg Arg Ala Ile
            340                 345                 350

Phe Asp Leu Phe Thr Glu Ser Gly Val Ser Trp Pro Arg Leu Gly Phe
        355                 360                 365

Leu Thr His Phe Arg Ser Ala Ala Gln Arg Ala Met Gln Ala Glu Asp
    370                 375                 380

Gly Arg Leu Asp Val Phe Leu Arg Phe Leu Ser Gly Leu Leu Ser Pro
385                 390                 395                 400

Arg Val Asn Ala Leu Leu Ala Gly Ser Leu Leu Ala Gln Gly Glu His
                405                 410                 415

Gln Ala Tyr Arg Thr Gln Val Ala Glu Leu Leu Gln Gly Cys Leu Arg
            420                 425                 430

Pro Asp Ala Ala Val Cys Ala Arg Ala Ile Asn Val Leu His Cys Leu
        435                 440                 445

His Glu Leu Gln His Thr Glu Leu Ala Arg Ser Val Glu Glu Ala Met
    450                 455                 460

Glu Ser Gly Ala Leu Ala Arg Leu Thr Gly Pro Ala His Arg Ala Ala
465                 470                 475                 480

Leu Ala Tyr Leu Leu Gln Val Ser Asp Ala Cys Ala Gln Glu Ala Asn
                485                 490                 495

Leu Ser Leu Ser Leu
            500


<210> SEQ ID NO 181
<211> LENGTH: 522
<212> TYPE: PRT
<213> ORGANISM: Homo sapiens

<400> SEQUENCE: 181

Leu Glu Glu Leu Phe Ser Thr Pro Gly His Leu Asn Asp Asp Ala Asp
1               5                   10                  15

Thr Val Leu Val Val Gly Glu Ala Gly Ser Gly Lys Ser Thr Leu Leu
```

-continued

```
            20                  25                  30

Gln Arg Leu His Leu Leu Trp Ala Ala Gly Gln Asp Phe Gln Glu Phe
        35                  40                  45

Leu Phe Val Phe Pro Phe Ser Cys Arg Gln Leu Gln Cys Met Ala Lys
    50                  55                  60

Pro Leu Ser Val Arg Thr Leu Leu Phe Glu His Cys Cys Trp Pro Asp
65                  70                  75                  80

Val Gly Gln Glu Asp Ile Phe Gln Leu Leu Leu Asp His Pro Asp Arg
                85                  90                  95

Val Leu Leu Thr Phe Asp Gly Phe Asp Glu Phe Lys Phe Arg Phe Thr
            100                 105                 110

Asp Arg Glu Arg His Cys Ser Pro Thr Asp Pro Thr Ser Val Gln Thr
        115                 120                 125

Leu Leu Phe Asn Leu Leu Gln Gly Asn Leu Leu Lys Asn Ala Arg Lys
    130                 135                 140

Val Val Thr Ser Arg Pro Ala Ala Val Ser Ala Phe Leu Arg Lys Tyr
145                 150                 155                 160

Ile Arg Thr Glu Phe Asn Leu Lys Gly Phe Ser Glu Gln Gly Ile Glu
                165                 170                 175

Leu Tyr Leu Arg Lys Arg His His Glu Pro Gly Val Ala Asp Arg Leu
            180                 185                 190

Ile Arg Leu Leu Gln Glu Thr Ser Ala Leu His Gly Leu Cys His Leu
        195                 200                 205

Pro Val Phe Ser Trp Met Val Ser Lys Cys His Gln Glu Leu Leu Leu
    210                 215                 220

Gln Glu Gly Gly Ser Pro Lys Thr Thr Thr Asp Met Tyr Leu Leu Ile
225                 230                 235                 240

Leu Gln His Phe Leu Leu His Ala Thr Pro Pro Asp Ser Ala Ser Gln
                245                 250                 255

Gly Leu Gly Pro Ser Leu Leu Arg Gly Arg Leu Pro Thr Leu Leu His
            260                 265                 270

Leu Gly Arg Leu Ala Leu Trp Gly Leu Gly Met Cys Cys Tyr Val Phe
        275                 280                 285

Ser Ala Gln Gln Leu Gln Ala Ala Gln Val Ser Pro Asp Asp Ile Ser
    290                 295                 300

Leu Gly Phe Leu Val Arg Ala Lys Gly Val Val Pro Gly Ser Thr Ala
305                 310                 315                 320

Pro Leu Glu Phe Leu His Ile Thr Phe Gln Cys Phe Phe Ala Ala Phe
                325                 330                 335

Tyr Leu Ala Leu Ser Ala Asp Val Pro Pro Ala Leu Leu Arg His Leu
            340                 345                 350

Phe Asn Cys Gly Arg Pro Gly Asn Ser Pro Met Ala Arg Leu Leu Pro
        355                 360                 365

Thr Met Cys Ile Gln Ala Ser Glu Gly Lys Asp Ser Ser Val Ala Ala
    370                 375                 380

Leu Leu Gln Lys Ala Glu Pro His Asn Leu Gln Ile Thr Ala Ala Phe
385                 390                 395                 400

Leu Ala Gly Leu Leu Ser Arg Glu His Trp Gly Leu Leu Ala Glu Cys
                405                 410                 415

Gln Thr Ser Glu Lys Ala Leu Leu Arg Arg Gln Ala Cys Ala Arg Trp
            420                 425                 430

Cys Leu Ala Arg Ser Leu Arg Lys His Phe His Ser Ile Pro Pro Ala
        435                 440                 445
```

-continued

```
Ala Pro Gly Glu Ala Lys Ser Val His Ala Met Pro Gly Phe Ile Trp
    450                 455                 460

Leu Ile Arg Ser Leu Tyr Glu Met Gln Glu Glu Arg Leu Ala Arg Lys
465                 470                 475                 480

Ala Ala Arg Gly Leu Asn Val Gly His Leu Lys Leu Thr Phe Cys Ser
                485                 490                 495

Val Gly Pro Thr Glu Cys Ala Ala Leu Ala Phe Val Leu Gln His Leu
            500                 505                 510

Arg Arg Pro Val Ala Leu Gln Leu Asp Tyr
        515                 520


<210> SEQ ID NO 182
<211> LENGTH: 532
<212> TYPE: PRT
<213> ORGANISM: Homo sapiens

<400> SEQUENCE: 182

Ala Cys Leu Leu Asp His Thr Thr Gly Ile Leu Asn Glu Gln Gly Glu
1               5                   10                  15

Thr Ile Phe Ile Leu Gly Asp Ala Gly Val Gly Lys Ser Met Leu Leu
            20                  25                  30

Gln Arg Leu Gln Ser Leu Trp Ala Thr Gly Arg Leu Asp Ala Gly Val
        35                  40                  45

Lys Phe Phe Phe His Phe Arg Cys Arg Met Phe Ser Cys Phe Lys Glu
    50                  55                  60

Ser Asp Arg Leu Cys Leu Gln Asp Leu Leu Phe Lys His Tyr Cys Tyr
65                  70                  75                  80

Pro Glu Arg Asp Pro Glu Glu Val Phe Ala Phe Leu Leu Arg Phe Pro
                85                  90                  95

His Val Ala Leu Phe Thr Phe Asp Gly Leu Asp Glu Leu His Ser Asp
            100                 105                 110

Leu Asp Leu Ser Arg Val Pro Asp Ser Ser Cys Pro Trp Glu Pro Ala
        115                 120                 125

His Pro Leu Val Leu Leu Ala Asn Leu Leu Ser Gly Lys Leu Leu Lys
    130                 135                 140

Gly Ala Ser Lys Leu Leu Thr Ala Arg Thr Gly Ile Glu Val Pro Arg
145                 150                 155                 160

Gln Phe Leu Arg Lys Lys Val Leu Leu Arg Gly Phe Ser Pro Ser His
                165                 170                 175

Leu Arg Ala Tyr Ala Arg Arg Met Phe Pro Glu Arg Ala Leu Gln Asp
            180                 185                 190

Arg Leu Leu Ser Gln Leu Glu Ala Asn Pro Asn Leu Cys Ser Leu Cys
        195                 200                 205

Ser Val Pro Leu Phe Cys Trp Ile Ile Phe Arg Cys Phe Gln His Phe
    210                 215                 220

Arg Ala Ala Phe Glu Gly Ser Pro Gln Leu Pro Asp Cys Thr Met Thr
225                 230                 235                 240

Leu Thr Asp Val Phe Leu Leu Val Thr Glu Val His Leu Asn Arg Met
                245                 250                 255

Gln Pro Ser Ser Leu Val Gln Arg Asn Thr Arg Ser Pro Val Glu Thr
            260                 265                 270

Leu His Ala Gly Arg Asp Thr Leu Cys Ser Leu Gly Gln Val Ala His
        275                 280                 285

Arg Gly Met Glu Lys Ser Leu Phe Val Phe Thr Gln Glu Glu Val Gln
```

-continued

```
    290                 295                 300

Ala Ser Gly Leu Gln Glu Arg Asp Met Gln Leu Gly Phe Leu Arg Ala
305                 310                 315                 320

Leu Pro Glu Leu Gly Pro Gly Gly Asp Gln Gln Ser Tyr Glu Phe Phe
                325                 330                 335

His Leu Thr Leu Gln Ala Phe Phe Thr Ala Phe Phe Leu Val Leu Asp
            340                 345                 350

Asp Arg Val Gly Thr Gln Glu Leu Leu Arg Phe Phe Gln Glu Trp Met
        355                 360                 365

Pro Pro Ala Gly Ala Ala Thr Thr Ser Cys Tyr Pro Pro Phe Leu Pro
    370                 375                 380

Phe Gln Cys Leu Gln Gly Ser Gly Pro Ala Arg Glu Asp Leu Phe Lys
385                 390                 395                 400

Asn Lys Asp His Phe Gln Phe Thr Asn Leu Phe Leu Cys Gly Leu Leu
                405                 410                 415

Ser Lys Ala Lys Gln Lys Leu Leu Arg His Leu Val Pro Ala Ala Ala
            420                 425                 430

Leu Arg Arg Lys Arg Lys Ala Leu Trp Ala His Leu Phe Ser Ser Leu
        435                 440                 445

Arg Gly Tyr Leu Lys Ser Leu Pro Arg Val Gln Val Glu Ser Phe Asn
    450                 455                 460

Gln Val Gln Ala Met Pro Thr Phe Ile Trp Met Leu Arg Cys Ile Tyr
465                 470                 475                 480

Glu Thr Gln Ser Gln Lys Val Gly Gln Leu Ala Ala Arg Gly Ile Cys
                485                 490                 495

Ala Asn Tyr Leu Lys Leu Thr Tyr Cys Asn Ala Cys Ser Ala Asp Cys
            500                 505                 510

Ser Ala Leu Ser Phe Val Leu His His Phe Pro Lys Arg Leu Ala Leu
        515                 520                 525

Asp Leu Asp Asn
    530


<210> SEQ ID NO 183
<211> LENGTH: 312
<212> TYPE: PRT
<213> ORGANISM: Homo sapiens

<400> SEQUENCE: 183

Arg Val Glu Gln Leu Thr Leu Asn Gly Leu Leu Gln Ala Leu Gln Ser
1               5                   10                  15

Pro Cys Ile Ile Glu Gly Glu Ser Gly Lys Gly Lys Ser Thr Leu Leu
            20                  25                  30

Gln Arg Ile Ala Met Leu Trp Gly Ser Gly Lys Cys Lys Ala Leu Thr
        35                  40                  45

Lys Phe Lys Phe Val Phe Phe Leu Arg Leu Ser Arg Ala Gln Gly Gly
    50                  55                  60

Leu Phe Glu Thr Leu Cys Asp Gln Leu Leu Asp Ile Pro Gly Thr Ile
65                  70                  75                  80

Arg Lys Gln Thr Phe Met Ala Met Leu Leu Lys Leu Arg Gln Arg Val
                85                  90                  95

Leu Phe Leu Leu Asp Gly Tyr Asn Glu Phe Lys Pro Gln Asn Cys Pro
            100                 105                 110

Glu Ile Glu Ala Leu Ile Lys Glu Asn His Arg Phe Lys Asn Met Val
        115                 120                 125
```

-continued

```
Ile Val Thr Thr Thr Thr Glu Cys Leu Arg His Ile Arg Gln Phe Gly
    130                 135                 140

Ala Leu Thr Ala Glu Val Gly Asp Met Thr Glu Asp Ser Ala Gln Ala
145                 150                 155                 160

Leu Ile Arg Glu Val Leu Ile Lys Glu Leu Ala Glu Gly Leu Leu Leu
                165                 170                 175

Gln Ile Gln Lys Ser Arg Cys Leu Arg Asn Leu Met Lys Thr Pro Leu
            180                 185                 190

Phe Val Val Ile Thr Cys Ala Ile Gln Met Gly Glu Ser Glu Phe His
        195                 200                 205

Ser His Thr Gln Thr Thr Leu Phe His Thr Phe Tyr Asp Leu Leu Ile
    210                 215                 220

Gln Lys Asn Lys His Lys His Lys Gly Val Ala Ala Ser Asp Phe Ile
225                 230                 235                 240

Arg Ser Leu Asp His Cys Gly Asp Leu Ala Leu Glu Gly Val Phe Ser
                245                 250                 255

His Lys Phe Asp Phe Glu Leu Gln Asp Val Ser Ser Val Asn Glu Asp
            260                 265                 270

Val Leu Leu Thr Thr Gly Leu Leu Cys Lys Tyr Thr Ala Gln Arg Phe
        275                 280                 285

Lys Pro Lys Tyr Lys Phe Phe His Lys Ser Phe Gln Glu Tyr Thr Ala
    290                 295                 300

Gly Arg Arg Leu Ser Ser Leu Leu
305                 310


<210> SEQ ID NO 184
<211> LENGTH: 312
<212> TYPE: PRT
<213> ORGANISM: Homo sapiens

<400> SEQUENCE: 184

Val Gln Glu Pro Leu Val Leu Pro Glu Val Phe Gly Asn Leu Asn Ser
1               5                   10                  15

Val Met Cys Val Glu Gly Glu Ala Gly Ser Gly Lys Thr Val Leu Leu
            20                  25                  30

Lys Lys Ile Ala Phe Leu Trp Ala Ser Gly Cys Cys Pro Leu Leu Asn
        35                  40                  45

Arg Phe Gln Leu Val Phe Tyr Leu Ser Leu Ser Ser Thr Arg Pro Asp
    50                  55                  60

Glu Gly Leu Ala Ser Ile Ile Cys Asp Gln Leu Leu Glu Lys Glu Gly
65                  70                  75                  80

Ser Val Thr Glu Met Cys Met Arg Asn Ile Ile Gln Gln Leu Lys Asn
                85                  90                  95

Gln Val Leu Phe Leu Leu Asp Asp Tyr Lys Glu Ile Cys Ser Ile Pro
            100                 105                 110

Gln Val Ile Gly Lys Leu Ile Gln Lys Asn His Leu Ser Arg Thr Cys
        115                 120                 125

Leu Leu Ile Ala Val Arg Thr Asn Arg Ala Arg Asp Ile Arg Arg Tyr
    130                 135                 140

Leu Glu Thr Ile Leu Glu Ile Lys Ala Phe Pro Phe Tyr Asn Thr Val
145                 150                 155                 160

Cys Ile Leu Arg Lys Leu Phe Ser His Asn Met Thr Arg Leu Arg Lys
                165                 170                 175

Phe Met Val Tyr Phe Gly Lys Asn Gln Ser Leu Gln Lys Ile Gln Lys
            180                 185                 190
```

-continued

```
Thr Pro Leu Phe Val Ala Ala Ile Cys Ala His Trp Phe Gln Tyr Pro
        195                 200                 205

Phe Asp Pro Ser Phe Asp Asp Val Ala Val Phe Lys Ser Tyr Met Glu
    210                 215                 220

Arg Leu Ser Leu Arg Asn Lys Ala Thr Ala Glu Ile Leu Lys Ala Thr
225                 230                 235                 240

Val Ser Ser Cys Gly Glu Leu Ala Leu Lys Gly Phe Phe Ser Cys Cys
                245                 250                 255

Phe Glu Phe Asn Asp Asp Asp Leu Ala Glu Ala Gly Val Asp Glu Asp
            260                 265                 270

Glu Asp Leu Thr Met Cys Leu Met Ser Lys Phe Thr Ala Gln Arg Leu
        275                 280                 285

Arg Pro Phe Tyr Arg Phe Leu Ser Pro Ala Phe Gln Glu Phe Leu Ala
    290                 295                 300

Gly Met Arg Leu Ile Glu Leu Leu
305                 310


<210> SEQ ID NO 185
<211> LENGTH: 5601
<212> TYPE: DNA
<213> ORGANISM: Homo sapiens

<400> SEQUENCE: 185

atggaccccg ttggcctcca gctcggcaac aagaacctgt ggagctgtct tgtgaggctg     60

ctcaccaaag acccagaatg gctgaacgcc aagatgaagt tcttcctccc caacacggac    120

ctggattcca ggaacgagac cttggaccct gaacagagag tcatcctgca actcaacaag    180

ctgcatgtcc agggttcgga cacctggcag tctttcattc attgcgtgtg catgcagctg    240

gaggtgcctc tggacctgga ggtgcttctg ctaagtactt ttggctatga tgatgggttc    300

accagccagc tgggagctga ggggaaaagc caacctgaat ctcagctcca ccatggcctg    360

aagcgcccac atcagagctg tgggtcctca ccccgccgga agcagtgcaa gaagcagcag    420

ctagagttgg ccaagaagta cctgcagctc ctgcggacct ctgcccagca gcgctacagg    480

agccaaatcc ctgggtcagg gcagccccac gccttccacc aggtctatgt ccctccaatc    540

ctgcgccggg ccacagcatc cttagacact ccggaggggg ccattatggg ggacgtcaag    600

gtggaagatg gtgctgacgt gagcatctcg gacctcttca acaccagggt taacaagggc    660

ccgagggtga ccgtgctttt ggggaaggct ggcatgggca agaccacgct ggcccaccgg    720

ctctgccaga agtgggcaga gggccatctg aactgtttcc aggccctgtt cctttttgaa    780

ttccgccagc tcaacttgat cacgaggttc ctgacaccgt ccgagctcct tttgatctg    840

tacctgagcc ctgaatcgga ccacgacact gtcttccagt acctggagaa gaacgctgac    900

caagtcctgc tgatctttga tggggctagat gaggccctcc agcctatggg tcctgatggc    960

ccaggcccag tcctcaccct tttctcccat ctctgcaatg ggaccctcct gcctggctgc   1020

cgggtgatgg ctacctcccg tccagggaag ctgcctgcct gcctgcctgc agaggcagcc   1080

atggtccaca tgttgggctt tgatgggcca cgggtggaag aatatgtgaa tcacttcttc   1140

agcgcccagc catcgcggga gggggccctg gtggagttac agacaaatgg acgtctccga   1200

agcctgtgtg cggtgcccgc actgtgccaa gtcgcctgtc tctgcctcca ccatctgctt   1260

cctgaccacg ccccaggcca gtctgtggcc ctcctgccca acatgactca gctctatatg   1320

cagatggtgc tcgccctcag cccccctggg cacttgccca cctcgtccct actggacctg   1380
```

-continued

```
ggggaggtgg ccctgagggg cctggagaca gggaaggtta tcttctatgc aaaagatatt   1440
gctccaccct tgatagcttt tggggccact cacagcctgc tgacttcctt ctgcgtctgc   1500
acaggccctg ggcaccagca gacaggctat gctttcaccc acctcagcct gcaggagttt   1560
cttgctgccc tgcacctgat ggccagcccc aaggtgaaca aagacacact tacccagtat   1620
gttaccctcc attcccgctg ggtacagcgg accaaagcta gactgggcct ctcagaccac   1680
ctccccacct tcctggcggg cctggcatcc tgcacctgcc gccccttcct tagccacctg   1740
gcgcagggca atgaggactg tgtgggtgcc aagcaggctg ctgtagtgca ggtgttgaag   1800
aagttggcca cccgcaagct cacagggcca aaggttgtag agctgtgtca ctgtgtggat   1860
gagacacagg agcctgagct ggccagtctc accgcacaaa gcctccccta tcaactgccc   1920
ttccacaatt tcccactgac ctgcaccgac ctggccaccc tgaccaacat cctagagcac   1980
agggaggccc ccatccacct ggattttgat ggctgtcccc tggagcccca ctgccctgag   2040
gctctggtag gctgtgggca gatagagaat ctcagcttta agagcaggaa gtgtggggat   2100
gcctttgcag aagccctctc caggagcttg ccgacaatgg ggaggctgca gatgctgggg   2160
ttagcaggaa gtaaaatcac tgcccgaggc atcagccacc tggtgaaagc tttgcctctc   2220
tgtccacagc tgaaagaagt cagttttcgg gacaaccagc tcagtgacca ggtggtgctg   2280
aacattgtgg aggttctccc tcacctacca cggctccgga agcttgacct gagcagcaac   2340
agcatctgcg tgtcaaccct actctgcttg gcaagggtgg cagtcacgtg tcctaccgtc   2400
aggatgcttc aggccaggga gcggaccatc atcttccttc tttccccgcc cacagagaca   2460
actgcagagc tacaaagagc tccagacctg caggaaagtg acggccagag gaaaggggct   2520
cagagcagaa gcttgacgct caggctgcag aagtgtcagc tccaggtcca cgatgcggag   2580
gccctcatag ccctgctcca ggaaggccct cacctggagg aagtggacct ctcagggaac   2640
cagctggaag atgaaggctg tcggctgatg gcagaggctg catcccagct gcacatcgcc   2700
aggaagctgg acctcagcga caacgggctt tctgtggccg gggtgcattg tgtgctgagg   2760
gccgtgagtg cgtgctggac cctggcagag ctgcacatca gcctgcagca caaaactgtg   2820
atcttcatgt ttgcccagga gccagaggag cagaaggggc cccaggagag ggctgcattt   2880
cttgacagcc tcatgctcca gatgccctct gagctgcctc tgagctcccg aaggatgagg   2940
ctgacacatt gtggcctcca agaaaagcac ctagagcagc tctgcaaggc tctgggagga   3000
agctgccacc tcggtcacct ccacctcgac ttctcaggca atgctctggg ggatgaaggt   3060
gcagcccggc tggctcagct gctcccaggg ctgggagctc tgcagtcctt gaacctcagt   3120
gagaacggtt tgtccctgga tgccgtgttg ggcttggttc ggtgcttctc cactctgcag   3180
tggctcttcc gcttggacat cagctttgaa agccaacaca tcctcctgag aggggacaag   3240
acaagcaggg atatgtgggc cactggatct ttgccagact tcccagctgc agccaagttc   3300
ttagggttcc gtcagcgctg catccccagg agcctctgcc tcagtgagtg tcctctggag   3360
cccccaagcc tcacccgcct ctgtgccact ctgaaggact gcccgggacc cctggaactg   3420
caattgtcct gtgagttcct gagtgaccag agcctggaga ctctactgga ctgcttacct   3480
caactccctc agctgagcct gctgcagctg agccagacgg gactgtcccc gaaaagcccc   3540
ttcctgctgg ccaacacctt aagcctgtgt ccacgggtta aaaaggtgga tctcaggtcc   3600
ctgcaccatg caactttgca cttcagatcc aacgaggagg aggaaggcgt gtgctgtggc   3660
aggttcacag gctgcagcct cagccaggag cacgtagagt cactctgctg gttgctgagc   3720
aagtgtaaag acctcagcca ggtggatctc tcagcaaacc tgctgggcga cagcggactc   3780
```

-continued

```
agatgccttc tggaatgtct gccgcaggtg cccatctccg gtttgcttga tctgagtcac   3840

aacagcattt ctcaggaaag tgccctgtac ctgctggaga cactgccctc ctgcccacgt   3900

gtccgggagg cctcagtgaa cctgggctct gagcagagct tccggattca cttctccaga   3960

gaggaccagg ctgggaagac actcaggcta agtgagtgca gcttccggcc agagcacgtg   4020

tccaggctgg ccaccggctt gagcaagtcc ctgcagctga cggagctcac gctgacccag   4080

tgctgcctgg gccagaagca gctggccatc ctcctgagct tggtggggcg acccgcaggg   4140

ctgttcagcc tcagggtgca ggagccgtgg gcggacagag ccagggttct ctccctgtta   4200

gaagtctgcg cccaggcctc aggcagtgtc actgaaatca gcatctccga gacccagcag   4260

cagctctgtg tccagctgga atttcctcgc caggaagaga atccagaagc tgtggcactc   4320

aggttggctc actgtgacct tggagcccac cacagccttc ttgtcgggca gctgatggag   4380

acatgtgcca ggctgcagca gctcagcttg tctcaggtta acctctgtga ggacgatgat   4440

gccagttccc tgctgctgca gagcctcctg ctgtccctct ctgagctgaa gacatttcgg   4500

ctgacctcca gctgtgtgag caccgagggc ctcgcccacc tggcatctgg tctgggccac   4560

tgccaccact tggaggagct ggacttgtct aacaatcaat ttgatgagga gggcaccaag   4620

gcgctgatga gggcccttga ggggaaatgg atgctaaaga ggctggacct cagtcacctt   4680

ctgctgaaca gctccacctt ggccttgctt actcacagac taagccagat gacctgcctg   4740

cagagcctca gactgaacag gaacagtatc ggtgatgtcg gttgctgcca cctttctgag   4800

gctctcaggg ctgccaccag cctagaggag ctggacttga gccacaacca gattggagac   4860

gctggtgtcc agcacttagc taccatcctg cctgggctgc cagagctcag gaagatagac   4920

ctctcaggga atagcatcag ctcagccggg ggagtgcagt tggcagagtc tctcgttctt   4980

tgcaggcgcc tggaggagtt gatgcttggc tgcaatgccc tgggggatcc cacagccctg   5040

gggctggctc aggagctgcc ccagcacctg agggtcctac acctaccatt cagccatctg   5100

ggcccaggtg gggccctgag cctggcccag gccctggatg gatcccccca tttggaagag   5160

atcagcttgg cggaaaacaa cctggctgga ggggtcctgc gtttctgtat ggagctcccg   5220

ctgctcagac agatagacct ggtttcctgt aagattgaca accagactgc caagctcctc   5280

acctccagct tcacgagctg ccctgccctg gaagtaatct tgctgtcctg gaatctcctc   5340

ggggatgagg cagctgccga gctggcccag gtgctgccga agatgggccg gctgaagaga   5400

gtggacctgg agaagaatca gatcacagct ttgggggcct ggctcctggc tgaaggactg   5460

gcccaggggt ctagcatcca agtcatccgc ctctggaata accccattcc ctgcgacatg   5520

gcccagcacc tgaagagcca ggagcccagg ctggactttg ccttctttga caaccagccc   5580

caggcccctt ggggtacttg a                                             5601
```

<210> SEQ ID NO 186
<211> LENGTH: 1866
<212> TYPE: PRT
<213> ORGANISM: Homo sapiens

<400> SEQUENCE: 186

```
Met Asp Pro Val Gly Leu Gln Leu Gly Asn Lys Asn Leu Trp Ser Cys
1               5                   10                  15

Leu Val Arg Leu Leu Thr Lys Asp Pro Glu Trp Leu Asn Ala Lys Met
            20                  25                  30

Lys Phe Phe Leu Pro Asn Thr Asp Leu Asp Ser Arg Asn Glu Thr Leu
        35                  40                  45
```

-continued

```
Asp Pro Glu Gln Arg Val Ile Leu Gln Leu Asn Lys Leu His Val Gln
    50                  55                  60

Gly Ser Asp Thr Trp Gln Ser Phe Ile His Cys Val Cys Met Gln Leu
65                  70                  75                  80

Glu Val Pro Leu Asp Leu Glu Val Leu Leu Leu Ser Thr Phe Gly Tyr
                85                  90                  95

Asp Asp Gly Phe Thr Ser Gln Leu Gly Ala Glu Gly Lys Ser Gln Pro
            100                 105                 110

Glu Ser Gln Leu His His Gly Leu Lys Arg Pro His Gln Ser Cys Gly
        115                 120                 125

Ser Ser Pro Arg Arg Lys Gln Cys Lys Lys Gln Gln Leu Glu Leu Ala
    130                 135                 140

Lys Lys Tyr Leu Gln Leu Leu Arg Thr Ser Ala Gln Gln Arg Tyr Arg
145                 150                 155                 160

Ser Gln Ile Pro Gly Ser Gly Gln Pro His Ala Phe His Gln Val Tyr
                165                 170                 175

Val Pro Pro Ile Leu Arg Arg Ala Thr Ala Ser Leu Asp Thr Pro Glu
            180                 185                 190

Gly Ala Ile Met Gly Asp Val Lys Val Glu Asp Gly Ala Asp Val Ser
        195                 200                 205

Ile Ser Asp Leu Phe Asn Thr Arg Val Asn Lys Gly Pro Arg Val Thr
    210                 215                 220

Val Leu Leu Gly Lys Ala Gly Met Gly Lys Thr Thr Leu Ala His Arg
225                 230                 235                 240

Leu Cys Gln Lys Trp Ala Glu Gly His Leu Asn Cys Phe Gln Ala Leu
                245                 250                 255

Phe Leu Phe Glu Phe Arg Gln Leu Asn Leu Ile Thr Arg Phe Leu Thr
            260                 265                 270

Pro Ser Glu Leu Leu Phe Asp Leu Tyr Leu Ser Pro Glu Ser Asp His
        275                 280                 285

Asp Thr Val Phe Gln Tyr Leu Glu Lys Asn Ala Asp Gln Val Leu Leu
    290                 295                 300

Ile Phe Asp Gly Leu Asp Glu Ala Leu Gln Pro Met Gly Pro Asp Gly
305                 310                 315                 320

Pro Gly Pro Val Leu Thr Leu Phe Ser His Leu Cys Asn Gly Thr Leu
                325                 330                 335

Leu Pro Gly Cys Arg Val Met Ala Thr Ser Arg Pro Gly Lys Leu Pro
            340                 345                 350

Ala Cys Leu Pro Ala Glu Ala Ala Met Val His Met Leu Gly Phe Asp
        355                 360                 365

Gly Pro Arg Val Glu Glu Tyr Val Asn His Phe Phe Ser Ala Gln Pro
    370                 375                 380

Ser Arg Glu Gly Ala Leu Val Glu Leu Gln Thr Asn Gly Arg Leu Arg
385                 390                 395                 400

Ser Leu Cys Ala Val Pro Ala Leu Cys Gln Val Ala Cys Leu Cys Leu
                405                 410                 415

His His Leu Leu Pro Asp His Ala Pro Gly Gln Ser Val Ala Leu Leu
            420                 425                 430

Pro Asn Met Thr Gln Leu Tyr Met Gln Met Val Leu Ala Leu Ser Pro
        435                 440                 445

Pro Gly His Leu Pro Thr Ser Ser Leu Leu Asp Leu Gly Glu Val Ala
    450                 455                 460
```

-continued

```
Leu Arg Gly Leu Glu Thr Gly Lys Val Ile Phe Tyr Ala Lys Asp Ile
465                 470                 475                 480

Ala Pro Pro Leu Ile Ala Phe Gly Ala Thr His Ser Leu Leu Thr Ser
                485                 490                 495

Phe Cys Val Cys Thr Gly Pro Gly His Gln Gln Thr Gly Tyr Ala Phe
            500                 505                 510

Thr His Leu Ser Leu Gln Glu Phe Leu Ala Ala Leu His Leu Met Ala
        515                 520                 525

Ser Pro Lys Val Asn Lys Asp Thr Leu Thr Gln Tyr Val Thr Leu His
    530                 535                 540

Ser Arg Trp Val Gln Arg Thr Lys Ala Arg Leu Gly Leu Ser Asp His
545                 550                 555                 560

Leu Pro Thr Phe Leu Ala Gly Leu Ala Ser Cys Thr Cys Arg Pro Phe
                565                 570                 575

Leu Ser His Leu Ala Gln Gly Asn Glu Asp Cys Val Gly Ala Lys Gln
            580                 585                 590

Ala Ala Val Val Gln Val Leu Lys Lys Leu Ala Thr Arg Lys Leu Thr
        595                 600                 605

Gly Pro Lys Val Val Glu Leu Cys His Cys Val Asp Glu Thr Gln Glu
    610                 615                 620

Pro Glu Leu Ala Ser Leu Thr Ala Gln Ser Leu Pro Tyr Gln Leu Pro
625                 630                 635                 640

Phe His Asn Phe Pro Leu Thr Cys Thr Asp Leu Ala Thr Leu Thr Asn
                645                 650                 655

Ile Leu Glu His Arg Glu Ala Pro Ile His Leu Asp Phe Asp Gly Cys
            660                 665                 670

Pro Leu Glu Pro His Cys Pro Glu Ala Leu Val Gly Cys Gly Gln Ile
        675                 680                 685

Glu Asn Leu Ser Phe Lys Ser Arg Lys Cys Gly Asp Ala Phe Ala Glu
    690                 695                 700

Ala Leu Ser Arg Ser Leu Pro Thr Met Gly Arg Leu Gln Met Leu Gly
705                 710                 715                 720

Leu Ala Gly Ser Lys Ile Thr Ala Arg Gly Ile Ser His Leu Val Lys
                725                 730                 735

Ala Leu Pro Leu Cys Pro Gln Leu Lys Glu Val Ser Phe Arg Asp Asn
            740                 745                 750

Gln Leu Ser Asp Gln Val Val Leu Asn Ile Val Glu Val Leu Pro His
        755                 760                 765

Leu Pro Arg Leu Arg Lys Leu Asp Leu Ser Ser Asn Ser Ile Cys Val
    770                 775                 780

Ser Thr Leu Leu Cys Leu Ala Arg Val Ala Val Thr Cys Pro Thr Val
785                 790                 795                 800

Arg Met Leu Gln Ala Arg Glu Arg Thr Ile Ile Phe Leu Leu Ser Pro
                805                 810                 815

Pro Thr Glu Thr Thr Ala Glu Leu Gln Arg Ala Pro Asp Leu Gln Glu
            820                 825                 830

Ser Asp Gly Gln Arg Lys Gly Ala Gln Ser Arg Ser Leu Thr Leu Arg
        835                 840                 845

Leu Gln Lys Cys Gln Leu Gln Val His Asp Ala Glu Ala Leu Ile Ala
    850                 855                 860

Leu Leu Gln Glu Gly Pro His Leu Glu Glu Val Asp Leu Ser Gly Asn
865                 870                 875                 880

Gln Leu Glu Asp Glu Gly Cys Arg Leu Met Ala Glu Ala Ala Ser Gln
```

-continued

```
                885                 890                 895

Leu His Ile Ala Arg Lys Leu Asp Leu Ser Asp Asn Gly Leu Ser Val
            900                 905                 910

Ala Gly Val His Cys Val Leu Arg Ala Val Ser Ala Cys Trp Thr Leu
        915                 920                 925

Ala Glu Leu His Ile Ser Leu Gln His Lys Thr Val Ile Phe Met Phe
    930                 935                 940

Ala Gln Glu Pro Glu Glu Gln Lys Gly Pro Gln Glu Arg Ala Ala Phe
945                 950                 955                 960

Leu Asp Ser Leu Met Leu Gln Met Pro Ser Glu Leu Pro Leu Ser Ser
                965                 970                 975

Arg Arg Met Arg Leu Thr His Cys Gly Leu Gln Glu Lys His Leu Glu
            980                 985                 990

Gln Leu Cys Lys Ala Leu Gly Gly  Ser Cys His Leu Gly  His Leu His
        995                 1000                1005

Leu Asp  Phe Ser Gly Asn Ala  Leu Gly Asp Glu Gly  Ala Ala Arg
    1010                1015                1020

Leu Ala  Gln Leu Leu Pro Gly  Leu Gly Ala Leu Gln  Ser Leu Asn
    1025                1030                1035

Leu Ser  Glu Asn Gly Leu Ser  Leu Asp Ala Val Leu  Gly Leu Val
    1040                1045                1050

Arg Cys  Phe Ser Thr Leu Gln  Trp Leu Phe Arg Leu  Asp Ile Ser
    1055                1060                1065

Phe Glu  Ser Gln His Ile Leu  Leu Arg Gly Asp Lys  Thr Ser Arg
    1070                1075                1080

Asp Met  Trp Ala Thr Gly Ser  Leu Pro Asp Phe Pro  Ala Ala Ala
    1085                1090                1095

Lys Phe  Leu Gly Phe Arg Gln  Arg Cys Ile Pro Arg  Ser Leu Cys
    1100                1105                1110

Leu Ser  Glu Cys Pro Leu Glu  Pro Pro Ser Leu Thr  Arg Leu Cys
    1115                1120                1125

Ala Thr  Leu Lys Asp Cys Pro  Gly Pro Leu Glu Leu  Gln Leu Ser
    1130                1135                1140

Cys Glu  Phe Leu Ser Asp Gln  Ser Leu Glu Thr Leu  Leu Asp Cys
    1145                1150                1155

Leu Pro  Gln Leu Pro Gln Leu  Ser Leu Leu Gln Leu  Ser Gln Thr
    1160                1165                1170

Gly Leu  Ser Pro Lys Ser Pro  Phe Leu Leu Ala Asn  Thr Leu Ser
    1175                1180                1185

Leu Cys  Pro Arg Val Lys Lys  Val Asp Leu Arg Ser  Leu His His
    1190                1195                1200

Ala Thr  Leu His Phe Arg Ser  Asn Glu Glu Glu Glu  Gly Val Cys
    1205                1210                1215

Cys Gly  Arg Phe Thr Gly Cys  Ser Leu Ser Gln Glu  His Val Glu
    1220                1225                1230

Ser Leu  Cys Trp Leu Leu Ser  Lys Cys Lys Asp Leu  Ser Gln Val
    1235                1240                1245

Asp Leu  Ser Ala Asn Leu Leu  Gly Asp Ser Gly Leu  Arg Cys Leu
    1250                1255                1260

Leu Glu  Cys Leu Pro Gln Val  Pro Ile Ser Gly Leu  Leu Asp Leu
    1265                1270                1275

Ser His  Asn Ser Ile Ser Gln  Glu Ser Ala Leu Tyr  Leu Leu Glu
    1280                1285                1290
```

-continued

```
Thr Leu  Pro Ser Cys Pro Arg  Val Arg Glu Ala Ser  Val Asn Leu
    1295                 1300                 1305

Gly Ser  Glu Gln Ser Phe Arg  Ile His Phe Ser Arg  Glu Asp Gln
    1310                 1315                 1320

Ala Gly  Lys Thr Leu Arg Leu  Ser Glu Cys Ser Phe  Arg Pro Glu
    1325                 1330                 1335

His Val  Ser Arg Leu Ala Thr  Gly Leu Ser Lys Ser  Leu Gln Leu
    1340                 1345                 1350

Thr Glu  Leu Thr Leu Thr Gln  Cys Cys Leu Gly Gln  Lys Gln Leu
    1355                 1360                 1365

Ala Ile  Leu Leu Ser Leu Val  Gly Arg Pro Ala Gly  Leu Phe Ser
    1370                 1375                 1380

Leu Arg  Val Gln Glu Pro Trp  Ala Asp Arg Ala Arg  Val Leu Ser
    1385                 1390                 1395

Leu Leu  Glu Val Cys Ala Gln  Ala Ser Gly Ser Val  Thr Glu Ile
    1400                 1405                 1410

Ser Ile  Ser Glu Thr Gln Gln  Gln Leu Cys Val Gln  Leu Glu Phe
    1415                 1420                 1425

Pro Arg  Gln Glu Glu Asn Pro  Glu Ala Val Ala Leu  Arg Leu Ala
    1430                 1435                 1440

His Cys  Asp Leu Gly Ala His  His Ser Leu Leu Val  Gly Gln Leu
    1445                 1450                 1455

Met Glu  Thr Cys Ala Arg Leu  Gln Gln Leu Ser Leu  Ser Gln Val
    1460                 1465                 1470

Asn Leu  Cys Glu Asp Asp Asp  Ala Ser Ser Leu Leu  Leu Gln Ser
    1475                 1480                 1485

Leu Leu  Leu Ser Leu Ser Glu  Leu Lys Thr Phe Arg  Leu Thr Ser
    1490                 1495                 1500

Ser Cys  Val Ser Thr Glu Gly  Leu Ala His Leu Ala  Ser Gly Leu
    1505                 1510                 1515

Gly His  Cys His His Leu Glu  Glu Leu Asp Leu Ser  Asn Asn Gln
    1520                 1525                 1530

Phe Asp  Glu Glu Gly Thr Lys  Ala Leu Met Arg Ala  Leu Glu Gly
    1535                 1540                 1545

Lys Trp  Met Leu Lys Arg Leu  Asp Leu Ser His Leu  Leu Leu Asn
    1550                 1555                 1560

Ser Ser  Thr Leu Ala Leu Leu  Thr His Arg Leu Ser  Gln Met Thr
    1565                 1570                 1575

Cys Leu  Gln Ser Leu Arg Leu  Asn Arg Asn Ser Ile  Gly Asp Val
    1580                 1585                 1590

Gly Cys  Cys His Leu Ser Glu  Ala Leu Arg Ala Ala  Thr Ser Leu
    1595                 1600                 1605

Glu Glu  Leu Asp Leu Ser His  Asn Gln Ile Gly Asp  Ala Gly Val
    1610                 1615                 1620

Gln His  Leu Ala Thr Ile Leu  Pro Gly Leu Pro Glu  Leu Arg Lys
    1625                 1630                 1635

Ile Asp  Leu Ser Gly Asn Ser  Ile Ser Ser Ala Gly  Gly Val Gln
    1640                 1645                 1650

Leu Ala  Glu Ser Leu Val Leu  Cys Arg Arg Leu Glu  Glu Leu Met
    1655                 1660                 1665

Leu Gly  Cys Asn Ala Leu Gly  Asp Pro Thr Ala Leu  Gly Leu Ala
    1670                 1675                 1680
```

-continued

```
Gln Glu  Leu Pro Gln His Leu  Arg Val Leu His Leu  Pro Phe Ser
    1685                 1690                 1695

His Leu  Gly Pro Gly Gly Ala  Leu Ser Leu Ala Gln  Ala Leu Asp
    1700                 1705                 1710

Gly Ser  Pro His Leu Glu Glu  Ile Ser Leu Ala Glu  Asn Asn Leu
    1715                 1720                 1725

Ala Gly  Gly Val Leu Arg Phe  Cys Met Glu Leu Pro  Leu Leu Arg
    1730                 1735                 1740

Gln Ile  Asp Leu Val Ser Cys  Lys Ile Asp Asn Gln  Thr Ala Lys
    1745                 1750                 1755

Leu Leu  Thr Ser Ser Phe Thr  Ser Cys Pro Ala Leu  Glu Val Ile
    1760                 1765                 1770

Leu Leu  Ser Trp Asn Leu Leu  Gly Asp Glu Ala Ala  Ala Glu Leu
    1775                 1780                 1785

Ala Gln  Val Leu Pro Lys Met  Gly Arg Leu Lys Arg  Val Asp Leu
    1790                 1795                 1800

Glu Lys  Asn Gln Ile Thr Ala  Leu Gly Ala Trp Leu  Leu Ala Glu
    1805                 1810                 1815

Gly Leu  Ala Gln Gly Ser Ser  Ile Gln Val Ile Arg  Leu Trp Asn
    1820                 1825                 1830

Asn Pro  Ile Pro Cys Asp Met  Ala Gln His Leu Lys  Ser Gln Glu
    1835                 1840                 1845

Pro Arg  Leu Asp Phe Ala Phe  Phe Asp Asn Gln Pro  Gln Ala Pro
    1850                 1855                 1860

Trp Gly  Thr
    1865
```

CATERPILLER GENE FAMILY

RELATED APPLICATION INFORMATION

This application claims the benefit under 35 U.S.C. § 371 from PCT Application No. PCT/US2003/013562 (published under PCT Article 21(2) in English), filed on Apr. 30, 2003, which claims priority from U.S. Provisional Application No. 60/376,626, filed on Apr. 30, 2002, the disclosures of which are incorporated by reference herein in their entireties.

STATEMENT OF FEDERAL SUPPORT

This invention was made, in part, with government support under grant numbers AI29564, AI45580, AI141751, DK38108, T32 CA09156 from the National Institutes of Health. The United States government has certain rights to this invention.

FIELD OF THE INVENTION

The present invention relates to a new family of genes termed CATERPILLER which are characterized by the presence of landmark motifs including nucleotide binding domain (NBD) and leucine rich repeat (LRR) domains.

BACKGROUND OF THE INVENTION

A number of genes with nucleotide-binding domain (NBD) and leucine rich repeat (LRR) domains are rapidly emerging as important in apoptosis, immune and inflammatory disorders. These include CIITA, Nod1/CARD4, Nod2/CARD15, DEFCAP/CARD7/NALP1 and CIAS1/PYPAF1. CIITA, Nod2, and CIAS1 are linked to a number of immunologic disorders. CIITA is the master transcriptional regulator of class II MHC (MHCII). Genetic lesions in CIITA cause an immunodeficiency, Type II Bare Lymphocyte Syndrome (BLS) (Group A) (Steimle et al., (1993) *Cell* 75:135). Recently, mutations in Nod2 and CIAS1 have been linked to four immunologic and inflammatory disorders (Ogura et al., (2001) *Nature* 411:603; Hugot et al., (2001) *Nature* 411:599; Hoffman et al., (2001) *Nat. Genet.* 29:301; Manji et al., (2002) *J. Biol. Chem.* 277:11570).

CIITA was isolated using a complementation cloning strategy to restore MHC II expression to a MHC II deficient cell line (Steimle et al., (1993) *Cell* 75:135). CIITA is a master regulator of transcription, responsible for both interferon-γ and constitutive expression of MHC II and related genes (Harton et al., (2000) *Mol. Cell. Biol.* 20:6185; Reith et al., (2001) *Annu. Rev. Immunol.* 19:331). The N-terminal activation domain of CIITA is necessary for transcriptional activation (Harton et al., (2000) *Mol. Cell. Biol.* 20:6185). The centrally located NBD of CIITA contains a GTP-binding domain required for nuclear import (Harton et al., (2000) *Mol. Cell. Biol.* 20:6185). CIITA undergoes self-association involving sequences in its NBD, C-terminal LRRs, and N-terminus (Ting et al., (2002) *Cell* 109 (Suppl.): S21).

When CIITA was first discovered, initial searches for CIITA-related genes produced no significant matches. Nod1, an activator of caspase-9-mediated apoptosis and NF-κB, also having an NBD and C-terminal LRRs was the first described protein similar to CIITA in domain organization (Bertin et al., (1999) *J. Biol. Chem.* 274:12955; Iohara et al., (1999) *J. Biol. Chem.* 274:14560. Nod2, with functions similar to Nod1, has been strongly implicated in Crohn's disease (Ogura et al., (2001) *Nature* 411:603; Hugot et al., (2001) *Nature* 411:599; Ogura et al., (2001) *J. Biol. Chem.* 276: 4812), and in familial granulomatous synovitis (Blau syndrome) (Miceli-Richard et al., (2001) *Nat. Genet.* 29:19). Most recently, patients with familial cold autoinflammatory syndrome (familial cold urticaria) and Muckle-Wells syndrome were found to have mutations in a new gene called CIAS1, which has a pyrin domain, NBD and LRR (Hoffman et al., (2001) *Nat. Genet.* 29:301). These syndromes are associated with a CIAS1 splice variant called cryopyrin. These proteins may be similar to plant disease resistance proteins (R proteins) which detect pathogens and initiate defense mechanisms including MAP kinase activation, oxygen radical formation, salicylate production, induced transcription of kinases and transcription factors, and rapid cell death (Dangl et al., (2001) *Nature* 411:826). Many of these plant proteins have an NBD and LRRs and may represent the oldest examples of proteins using this CIITA-like domain arrangement.

SUMMARY OF THE INVENTION

The present invention is based, in part, on the discovery of a new family of genes that the inventors have designated the CATERPILLER (CARD, Transcription Enhancer, R(purine)-binding, Pyrin, Lots of Leucine Repeats) gene family. Some members of this family were previously known, but were not recognized as belonging to a large family of structurally and functionally related molecules. The advent of the nearly complete human genome sequence facilitated a search for sequences related to these proteins. The inventors describe the identification of additional CATERPILLER genes encoding mammalian NBD/LRR proteins. This analysis predicts at least twenty-two CATERPILLER genes in the human genome, many of which occur in clusters on individual chromosomes.

The CATERPILLER genes are implicated in inflammatory states, apoptosis, sepsis and infection among other conditions and provide an important new class of therapeutic targets.

Accordingly, as one aspect, the invention provides an isolated nucleic acid encoding a polypeptide selected from the group consisting of: (a) a Monarch-1 polypeptide; (b) a CATERPILLER 11.2 polypeptide; (c) a CATERPILLER 11.3 polypeptide; (d) a CATERPILLER 16.1 polypeptide; (e) a CATERPILLER 16.2 polypeptide; and (f) a functional fragment of any of (a) to (e). Also provided are isolated nucleic acids encoding a functional fragment of CIAS1.

As a further aspect, the invention provides polypeptides encoded by the isolated nucleic acid sequences. Further provided are cells comprising the isolated nucleic acids and polypeptides of the invention.

As yet another aspect, the invention provides an antibody that specifically binds to the polypeptides of the invention.

As still another aspect, the invention provides a method of modulating the cellular activity of a polypeptide selected from the group consisting of Monarch-1, CIAS1, CATERPILLER 11.2, CATERPILLER 11.3, CATERPILLER 16.1, CATERPILLER 16.2, and a functional fragment thereof, comprising introducing into a cell a compound that modulates the activity of the polypeptide in an amount effective to modulate the activity of the polypeptide in the cell. Also provided are methods of modulating cellular inflammatory responses, apoptosis, and a Toll-like receptor pathway activity. In particular embodiments, the compound is an isolated nucleic acid encoding a polypeptide of the invention, an antisense oligonucleotide, an siRNA, or an antibody. In other representative embodiments, the compound is an antisense oligonucleotide or siRNA that is targeted against the CATERPILLER nucleic acid. In other embodiments, the compound is an antibody that binds to the CATERPILLER polypeptide. The methods can be carried out in cultured cells or in vivo.

The present invention further provides screening methods using the nucleic acids and polypeptides of the invention as targets. The screening methods can be carried out in cell-free assays, in cultured cells or in live organisms, such as transgenic non-human animals, plants, fungi or bacteria.

As one particular aspect, the invention provides a method for identifying a compound that binds to a polypeptide selected from the group consisting of Monarch-1, CIAS1, CATERPILLER 11.2, CATERPILLER 11.3, CATERPILLER 16.1, CATERPILLER 16.2, and a functional fragment of any of the foregoing, comprising: contacting the polypeptide with a test compound under conditions whereby binding between the polypeptide and the test compound can be detected; and detecting binding between the polypeptide and the test compound.

As another aspect, the invention provides a method of identifying a compound that modulates the activity of a polypeptide selected from the group consisting of Monarch-1, CIAS1, CATERPILLER 11.2, CATERPILLER 11.3, CATERPILLER 16.1, CATERPILLER 16.2, and a functional fragment of any of the foregoing, comprising: contacting the polypeptide with a test compound under conditions whereby modulation of the activity of the polypeptide can be detected; and detecting modulation of the activity of the polypeptide.

As still a further aspect, the invention provides a method of identifying a compound that can modulate inflammatory responses, comprising: contacting a polypeptide selected from the group consisting of Monarch-1, CIAS1, CATERPILLER 11.2, CATERPILLER 11.3, CATERPILLER 16.1, CATERPILLER 16.2 and a functional fragment of any of the foregoing with a test compound under conditions whereby modulation of the activity of the polypeptide can be detected; and detecting modulation of the activity of the polypeptide, thereby identifying a compound that can modulate inflammatory responses.

As yet another aspect, the invention provides a method of identifying a compound that can modulate apoptosis, comprising: contacting a polypeptide selected from the group consisting of Monarch-1, CIAS1, CATERPILLER 11.2, CATERPILLER 11.3, CATERPILLER 16.1, CATERPILLER 16.2 and a functional fragment of any of the foregoing with a test compound under conditions whereby modulation of the activity of the polypeptide can be detected; and detecting modulation of the activity of the polypeptide, thereby identifying a compound that can modulate apoptosis.

As another aspect, the invention provides a method of identifying a compound that can modulate a Toll-like receptor pathway, comprising: contacting a polypeptide selected from the group consisting of Monarch-1, CIAS1, CATERPILLER 11.2, CATERPILLER 11.3, CATERPILLER 16.1, CATERPILLER 16.2 and a functional fragment of any of the foregoing with a test compound under conditions whereby modulation of the activity of the polypeptide can be detected; and detecting modulation of the activity of the polypeptide, thereby identifying a compound that can modulate the Toll-like receptor pathway.

These and other aspects of the invention are set forth in more detail in the description of the invention below.

BRIEF DESCRIPTION OF THE DRAWINGS

FIG. 2B shows twelve motifs defining the CATERPILLER NBD. Capital letters indicate residues (single letter code) that have a frequency greater than 50% or are invariant. Lower case letters indicate residues with frequency less than 50% but with a predominant characteristic (a=acidic, b=basic, h=hydrophobic, p=serine/threonine, r=aromatic). Asterisks indicate those residues used to define the NACHT family. [1, 2, 3]Indicate NACHT motifs V, VI, and VIII respectively.

FIGS. 3A-3G show the alignment of nucleotide binding domains (NBD) of CATERPILLER family members using Clustal with minor manual adjustments.

FIGS. 6A-C show the nucleotide and deduced amino acid sequences of full-length Monarch-1.

FIGS. 6D-F show the nucleotide and deduced amino acid sequences of Monarch-1 isoform II.

FIGS. 6G-I show the nucleotide and deduced amino acid sequences of Monarch-1 isoform III.

FIGS. 6J-L show the nucleotide and deduced amino acid sequences of Monarch-1 isoform IV.

FIGS. 18A-C show the nucleotide and deduced amino acid sequences of a predicted mouse Monarch-1.

FIGS. 21A-C show the nucleotide and deduced amino acid sequences of predicted CATERPILLER 11.2.

FIGS. 21D-F show the nucleotide and deduced amino acid sequences of cloned CATERPILLER 11.2.

FIGS. 25A-B show the nucleotide and deduced amino acid sequences of predicted CATERPILLER 11.3.

FIGS. 25C-E show the nucleotide and deduced amino acid sequences of cloned CATERPILLER 11.3. Nucleotide sequence includes 5' initiator codon and 3' stop.

FIGS. 25F-G show the nucleotide and deduced amino acid sequences of a splice variant of cloned CATERPILLER 11.3.

FIG. 26 depicts the genomic organization of human CATERPILLER 11.3. Human CATERPILLER 11.3 consists of 9 exons spanning 3561 bp. Exon 4 and 5 both contain a putative nucleotide binding domain. Exons 6 through 9 contain putative leucine-rich repeat regions (LRRs).

FIG. 27 shows that CATERPILLER 11.3 inhibits Myd88-induced NF-κB induction. HEK293T cells were seeded into 96-well plates and transfected on the following day with 50 ng of pNF-κB-luc and pcDNA3HA-MyD88 plasmid together with increasing amounts (1 ng to 400 ng) of pcDNA3HA-11.3. After 24 hrs, cells were harvested, and luciferase activity was determined for each sample. All data are shown as the average of triplicates and expressed in relative light units (RLU). The first bar represents cells transfected with only pcDNA3 and NF-κB-luc reporter. 10 ng/ml human CATERPILLER 11.3 produced an almost 4 fold reduction in Myd88 stimulated NF-κB reporter and was completely abolished at 400 ng/ml CATERPILLER 11.3

FIG. 28 shows that CATERPILLER 11.3 inhibits NIK-induced NF-κB induction. HEK293T cells were seeded into 96-well plates and transfected on the following day with 50 ng of pNF-κB-luc and pcDNA3HA-NIK plasmid together with 100 ng/ml of pcDNA3HA-11.3. After 24 hrs, cells were harvested, and luciferase activity was determined for each sample. All data are shown as the average of triplicates and expressed in relative light units (RLU). The first bar represents cells transfected with only pcDNA3 and NF-κB-luc reporter. 100 ng/ml human CATERPILLER 11.3 produced an almost 2 fold reduction in NIK stimulated NF-κB luciferase reporter.

FIGS. 29A-C show the nucleotide and deduced amino acid sequences predicted CATERPILLER 16.1.

FIGS. 29D-G show the nucleotide and deduced amino acid sequences cloned CATERPILLER 16.1.

FIGS. 30A-D show the nucleotide and deduced amino acid sequence of NOD27. Underlined sequences denote exons not present in cloned CATERPILLER 16.1.

FIG. 31A shows the expression of transcripts of a murine ortholog of CATERPILLER 16.1. CATERPILLER m16.1 transcript levels in murine cell lines were determined by real-time PCR analysis. The average of three analyses is shown. Mouse cell lines include fibroblast (NIH3T3), erythroid leukemia (MEL), melanoma (B16F10), T cell (EL4), B cell (18.81, mature B), monocytic (WEHI3, J774A.1, P388D1), macrophage (RAW264), and primary bone marrow (BM). 18s RNA levels were quantitated and used as an internal standard for each sample.

FIG. 33B shows that CATERPILLER m16.1 expression in transplanted kidney tissues is greatly enhanced. Kidneys transplanted into genetically identical hosts (iso) or MHC-mismatched hosts (allo) were harvested at 7, 15, or 100 days (d) post transplantation and RNA was analyzed by real-time PCR. Multiple samples (n=2-5) for each group were analyzed. Kidney transplant recipients of MHC-mismatched organs surviving for 100 days (100 d allo) have surpassed the critical inflammatory processes that normally result in graft rejection. 18s RNA levels were quantitated and used as an internal standard for each sample.

FIGS. 34A-C show the nucleotide and deduced amino acid sequences predicted CATERPILLER 16.2.

FIGS. 34D-F show the nucleotide and deduced amino acid sequences cloned CATERPILLER 16.2.

FIG. 41B shows the relative activation of NF-κB luciferase in HeLa cells transfected with 1.5 μg/well of pcDNA3 (control) or the indicated construct, followed by transfection with p65, 24 hours post-transfection as described in EXAMPLE 7. Values are means of three experiments ±SEM.

FIGS. 42A-B show the nucleotide and deduced amino acid sequences of a pyrin only containing CIAS1 protein.

FIGS. 42C-E show the nucleotide and deduced amino acid sequences of a pyrin/NBD containing CIAS1 protein.

FIGS. 42F-H show the nucleotide and deduced amino acid sequences of a NBD/LRR containing CIAS1 protein.

FIGS. 42I-J show the nucleotide and deduced amino acid sequences of a LLR containing CIAS1 protein.

FIGS. 42K-M show the nucleotide and deduced amino acid sequences of a FgCIAS1 Del4 isoform.

FIG. 43 shows that CIAS-1 inhibits the ability of overexpressed CIITA to activate DR-Luciferase in HeLa cells.

DETAILED DESCRIPTION OF THE INVENTION

Figure 1:
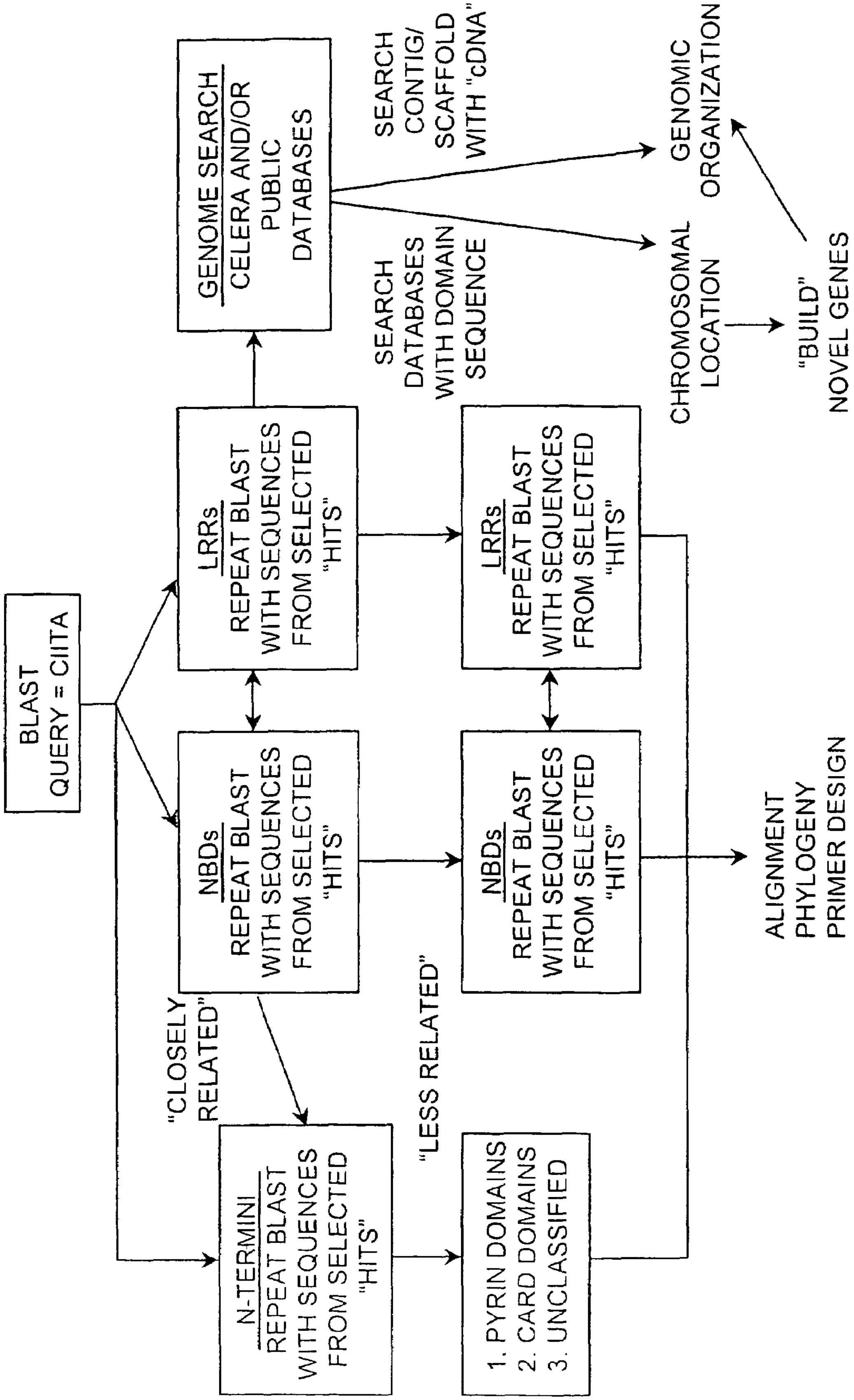
FIG. 1 is a schematic of the database and search strategies used to identify CATERPILLER family members.

The present invention will now be described in more detail with reference to the accompanying drawings, in which preferred embodiments of the invention are shown. This invention may, however, be embodied in different forms and should not be construed as limited to the embodiments set forth herein. Rather, these embodiments are provided so that this disclosure will be thorough and complete, and will fully convey the scope of the invention to those skilled in the art.

Unless otherwise defined, all technical and scientific terms used herein have the same meaning as commonly understood by one of ordinary skill in the art to which this invention belongs. The terminology used in the description of the invention herein is for the purpose of describing particular embodiments only and is not intended to be limiting of the invention. All publications, patent applications, patents, and other references mentioned herein are incorporated by reference in their entirety.

Nucleotide sequences are presented herein by single strand only, in the 5' to 3' direction, from left to right, unless specifically indicated otherwise. Nucleotides and amino acids are represented herein in the manner recommended by the IUPAC-IUB Biochemical Nomenclature Commission, or (for amino acids) by either the one-letter code, or the three letter code, both in accordance with 37 CFR §1.822 and established usage.

Except as otherwise indicated, standard methods known to those skilled in the art may be used for cloning genes, amplifying and detecting nucleic acids, and the like. Such techniques are known to those skilled in the art. See, e.g., SAMBROOK et al., MOLECULAR CLONING: A LABORATORY MANUAL 2nd Ed. (Cold Spring Harbor, N.Y., 1989); F. M. AUSUBEL et al. CURRENT PROTOCOLS IN MOLECULAR BIOLOGY (Green Publishing Associates, Inc. and John Wiley & Sons, Inc., New York).

I. Definitions.

As used in the description of the invention and the appended claims, the singular forms "a," "an" and "the" are intended to include the plural forms as well, unless the context clearly indicates otherwise.

The term "modulate," "modulates" or "modulation" refers to enhancement (e.g., an increase) or inhibition (e.g., a reduction) in the specified activity.

The term "enhance," "enhances," "enhancing" or "enhancement" refers to an increase in the specified parameter (e.g., at least about a 1.25-fold, 1.5-fold, 2-fold, 3-fold, 4-fold, 5-fold, 6-fold, 8-fold, 10-fold, twelve-fold, or even fifteen-fold or more increase).

The term "inhibit" or "reduce" or grammatical variations thereof as used herein refers to a decrease or diminishment in the specified activity of at least about 25%, 35%, 40%, 50%, 60%, 75%, 80%, 90%, 95% or more. In particular embodiments, the inhibition or reduction results in little or essentially no detectible activity (at most, an insignificant amount, e.g., less than about 10% or even 5%).

A "therapeutically effective" amount as used herein is an amount that provides some improvement or benefit to the subject. Alternatively stated, a "therapeutically-effective" amount is an amount that will provide some alleviation, mitigation, or decrease in at least one clinical symptom in the subject (e.g., reduced inflammation, sepsis, or tumor size). Those skilled in the art will appreciate that the therapeutic effects need not be complete or curative, as long as some benefit is provided to the subject.

By the terms "treat," "treating" or "treatment of," it is intended that the severity of the subject's condition is reduced or at least partially improved or modified and that some alleviation, mitigation or decrease in at least one clinical symptom is achieved.

As used herein, a "vector" or "delivery vector" can be a viral or non-viral vector that is used to deliver a nucleic acid to a cell, tissue or subject.

A "recombinant" vector or delivery vector refers to a viral or non-viral vector that comprises one or more heterologous nucleotide sequences (i.e., transgenes), e.g., two, three, four, five or more heterologous nucleotide sequences.

As used herein, the term "polypeptide" encompasses both peptides and proteins, unless indicated otherwise.

A "fusion protein" is a polypeptide produced when two heterologous nucleotide sequences or fragments thereof coding for two (or more) different polypeptides not found fused together in nature are fused together in the correct translational reading frame. Illustrative fusion polypeptides include fusions of a CATERPILLER polypeptide (or a fragment thereof) to all or a portion of glutathione-5-transferase, maltose-binding protein, or a reporter protein (e.g., Green Fluorescent Protein, β-glucuronidase, β-galactosidase, luciferase, etc.), hemagglutinin, c-myc, FLAG epitope, etc.

As used herein, a "functional" polypeptide or "functional fragment" is one that substantially retains at least one biological activity normally associated with that polypeptide. In particular embodiments, the "functional" polypeptide or "functional fragment" substantially retains all of the activities possessed by the unmodified peptide. By "substantially retains" biological activity, it is meant that the polypeptide retains at least about 50%, 60%, 75%, 85%, 90%, 95%, 97%, 98%, 99%, or more, of the biological activity of the native polypeptide (and can even have a higher level of activity than the native polypeptide). A "non-functional" polypeptide is one that exhibits little or essentially no detectable biological activity normally associated with the polypeptide (e.g., at most, only an insignificant amount, e.g., less than about 10% or even 5%).

As used herein, an "isolated" nucleic acid (e.g., an "isolated DNA") means a nucleic acid separated or substantially free from at least some of the other components of the naturally occurring organism or virus, such as for example, the cell or viral structural components or other polypeptides or nucleic acids commonly found associated with the nucleic acid.

Likewise, an "isolated" polypeptide means a polypeptide that is separated or substantially free from at least some of the other components of the naturally occurring organism or virus, for example, the cell or viral structural components or other polypeptides or nucleic acids commonly found associated with the polypeptide. In particular embodiments, the "isolated" polypeptide is at least about 1%, 5%, 10%, 25%, 50%, 60%, 70%, 75%, 80%, 85%, 90%, 95%, 97%, 98%, 99% or more pure (w/w). In other embodiments, an "isolated" polypeptide indicates that at least about a 5-fold, 10-fold, 25-fold, 100-fold, 1000-fold, 10,000-fold, or more enrichment of the protein (w/w) is achieved as compared with the starting material.

By the term "express" or "expression" of a nucleic acid coding sequence, in particular a CATERPILLER coding sequence, it is meant that the sequence is transcribed, and optionally, translated. Typically, according to the present invention, expression of a CATERPILLER coding sequence will result in production of the CATERPILLER polypeptide. The entire expressed polypeptide or fragment can also function in intact cells without purification.

The term "about," as used herein when referring to a measurable value such as an amount of polypeptide, dose, time, temperature, enzymatic activity or other biological activity and the like, is meant to encompass variations of ±20%, ±10%, ±5%, ±1%, ±0.5%, or even ±0.1% of the specified amount.

II. The CATERPILLER Gene Family.

The inventors have discovered and characterized a new family of genes based on the presence of identified protein motifs. The few previously-known genes that belong to this family have roles in inflammation or apoptosis or both, and most are linked to immunologic diseases.

This new gene family comprises at least 22 members. All of the genes classified within this family contain a combination of two or more landmark amino acid stretches. These include a nucleotide-binding domain (NTB) and a leucine-rich repeat (LRR) region. In addition, a majority of the genes have a pyrin domain, a recently described domain associated with Mediterranean Fever. Others have the Caspase recruitment domain (CARD), or an unknown N-terminal domain(s). The inventors have designated this new family as the CATERPILLER (CARD, Transcription Enhancer, R(purine)-binding, Pyrin, Lots of Leucine Repeats) gene family.

The CATERPILLER family is implicated in a variety of disorders. To date, the few known members of the CATERPILLER family have been linked to either apoptosis or autoinflammatory/immune diseases, suggesting that the newly identified genes may also be important for apoptosis and inflammatory diseases. These previously known genes include CIITA (a master regulator of MHCII expression), NOD1 (apoptosis), NOD2 (inflammatory bowel disease and Blau's syndrome), CIAS1/cryopyrin (familial cold autoinflammatory syndrome), and DEFCAP (apoptosis). In fact, the inventors have isolated the nucleic acids, determined the sequences, and characterized several of these newly identified family members and have shown that, in fact, they are also involved in inflammatory processes and cell survival. Further, analysis of one of the known genes, CIAS1/cryopyrin, has indicated a new function in down-regulating important modulators of immune function.

A brief description of several members of the CATERPILLER family (Monarch-1, CIAS1, CATERPILLER 11.2, CATERPILLER 11.3, CATERPILLER 16.1 and CATERPILLER 16.2) is provided below.

Monarch-1 (also known as Caterpiller 19.3): The present investigations have described the entire cDNA sequence (SEQ ID NO:1; Accession No. AY116204) of a Caterpiller family member named Monarch-1, which has pyrin, nucleotide-binding (NBD) and leucine-rich repeat (LRR) domains (amino acid sequence; SEQ ID NO:2). Three naturally occurring isoforms (nucleotide sequences: SEQ ID NO:3, SEQ ID NO:5 and SEQ ID NO:7 and corresponding amino acid sequences: SEQ ID NO:4, SEQ ID NO:6 and SEQ ID NO:8, respectively; see also Accession Nos. AY116205, AY116206 and AY116207) of Monarch-1 have been identified. Monarch-1 is located on human chromosome 19q13, in the multiple sclerosis susceptibility region. A prominent downstream effect of Monarch-1 is induction of both classical and non-classical class I MHC genes and LMP7. The present investigations have further demonstrated that:

(1) Monarch-1 is expressed in monocytic and myeloid cells including granulocytes (neutrophils and eosinophils), monocytes and dendritic cells.

(2) Monarch-1 is reduced by activators of the Toll-like receptor (TLR), that recognize bacterial, fungal and viral products.

(3) All of the Monarch-1 isoforms induce class I MHC genes in cell.

(4) Monarch-1 reduces NF-κB and AP-1 activity, which are important transcription factors involved in both inflammatory responses and cell survival.

(5) A predicted mouse Monarch-1 (GenBank Accession No. XM_142563; the disclosure of which is incorporated herein by reference in its entirety) has been identified, and found to be expressed by immune cells. Mouse Monarch-1 shares about 82% nucleotide sequence similarity with the human sequence.

(6) Human Monarch-1 is part of the endotoxin tolerant pathway and its expression is maintained when cells are tolerant to endotoxin. Endotoxin tolerance is a phenomenon in septic patients, in which tolerance is developed to bacterial products.

(7) Monarch-1 inhibits cellular responses induced by endotoxin from bacteria.

(8) Monarch-1 inhibits IFI16, an interferon responsive protein.

(9) Monarch-1 causes changes in cytokine (IL-6, IL 1β, and IL-10) expression, which are believed to be important for all immune and inflammatory responses. The most dramatic change is in IL-6, which is a strong pro-inflammatory cytokine. IL-1 is also a pro-inflammatory cytokine, while IL-10 typically directs a pro-inflammatory response important in asthma and allergies, among other diseases, and can be immunosuppressive of T cell activation.

(10) Interference RNA has been made which inhibits the function of Monarch-1 and shows its function in the enhancement of class I MHC gene expression and cytokine production.

(11) Monarch-1 interacts with a host of proteins, which can be exploited to interfere or enhance the function of these proteins. These include tubulin, vimentin, hsp-70, TNIK, CARD10, TRAF6, NIK and CIAS1.

Altogether, these data indicate that Monarch-1 is a positive regulator of MHC-I and IL-6/IL-10/IL-1β expression in myeloid monocytic cells, and a target of the TLR pathway. In addition it appears that Monarch-1 represents a new pathway for MHC-I induction separate from the TNF-α and IFN-γ pathway.

CIAS1 (Cold-induced autoinflammatory syndrome1): CIAS1 was first described as the genetic basis for the cold-induced autoinflammatory syndrome and the Muckle-Wells syndrome. The investigations herein describe the activity of CIAS1 in the suppression of NF-κB and CIITA function NF-κB controls inflammatory responses and apoptosis while CIITA controls the expression of major histocompatibility complex (MHC) class II genes, important in the stimulation of T lymphocytes. In addition, the inventors have found that the full length human CIAS1 (Accession No. NM_004895; the disclosure of which is incorporated herein by reference in its entirety) or either of two shorter, naturally occurring isoforms (Accession No. AY092033 [lacking exons 4 and 6], the disclosure of which is incorporated herein by reference in its entirety, and a novel isoform disclosed herein that lacks exon 4 but has exon 6; SEQ ID NO:148 [nucleotide sequence] and SEQ ID NO:149 [amino acid sequence]) dramatically inhibit TNFα-induced activation of NF-κB reporter activity. Transcriptional activity of exogenous NF-κB p65 was also blocked by CIAS1 Studies with a truncated protein (nucleotide sequence, SEQ ID NO:33; amino acid sequence, SEQ ID NO:34) that contains the nucleotide-binding (NTB) and leucine-rich repeat (LRR) regions, but not the pyrin domain, of CIAS1 indicate that the NTB and LRR regions are sufficient for this inhibition. CIAS 1 also suppresses TNFα-induced nuclear translocation of endogenous p65. These data suggest CIAS1 may act as a key negative regulator of inflammation, induced to dampen NF-κB-dependent pro-inflammatory and pro-survival signals. In addition, its suppressive effects on CIITA indicate a function in the downregulation of MHC-II protein, important for T cell stimulation. MHC-II has a variety of roles in autoimmune diseases and transplantation rejection. The inventors have found that ligands recognized by multiple Toll-Like Receptors (TLRs) induce CIAS1 gene expression in primary human monocytes, utilizing the MAPK/p38 but not PI3K signaling pathways.

A mouse homolog of CIAS1 is found at Accession No. NM_145827 (the disclosure of which is incorporated herein by reference in its entirety).

Mutations in CIAS1 have been linked recently to three chronic autoinflammatory disorders. These observations point to an important role for CIAS1 in regulating inflammatory processes. The locus responsible for the chronic, autosomal-dominant autoinflammatory periodic fever syndromes Familial Cold Urticaria (FCU), and Muckle-Wells Syndrome was found on chromosome 1q44 with pathology-associated mutations present in the CIAS1 gene (Hoffman et al., (2001) *Nat. Genet.* 29:301). Common symptoms of these genetic disorders include periodic fever, rash, arthralgia, and conjunctivitis. Mutations of CIAS1 were also found in the chronic infantile neurologic, cutaneous, articular (CINCA) syndrome (Feldmann et al., (2002) *Am. J. Hum. Genet.* 71:198).

CIAS1 contains an amino terminal Pyrin domain, a centrally located predicted NBD, and numerous LRR motifs at its carboxy terminus. The pyrin domain of CIAS1 is highly homologous to its namesake, the Pyrin protein encoded by the MEFV gene. Recent published reports provide evidence that CIAS1 may be involved in the regulation of IL-1 generation and NF-κB activation (Manji et al., (2002) *J. Biol. Chem.* 277:11570; Wang et al., (2002) *J. Biol. Chem.* 277:29874), placing CIAS1 in the inflammatory cascade.

The pro-inflammatory signaling program in myeloid cells leads to activation of the cytokines IL-1, IL-6, IL-8, and TNFα, as well as reactive oxygen species and other molecules through a number of steps culminating in transcriptional activity (reviewed in Suzuki et al., (2002) *Trends Immunol.* 23:503). Initiation of the signaling cascade frequently begins with cell surface-expressed TLRs sensing a variety of pathogenic products, stimulation of the IL-1 receptor, or crosslinking of the TNFα receptor. These diverse signaling pathways initially utilize an assortment of signaling intermediates (Zhang et al., (1999) *J. Biol. Chem.* 274:7611; Suzuki et al., (2002) *Trends Immunol.* 23:503; Chen et al., (2002) *Science* 296:1634) but converge downstream to induce activity of the transcription factors NF-κB, AP-1 and others.

TNFα stimulation leads to phosphorylation, ubiquitination, and degradation of IκBα, liberating the p50 and p65 subunits of NF-κB. The p65 subunit is phosphorylated and enters the nucleus to initiate transcription of various inflammatory genes. The present investigations have evaluated the effects of CIAS1 on TNFα signaling since TNFα is widely regarded as one of the most potent inflammatory stimulants.

The onset of inflammation is a central response to pathogens, autoimmune antigens and injury. Yet the resolution and down-regulatory phase of this response to prevent irrevocable damage is of equal importance. The present inventors have shown that CIAS1 is induced by a number of pathogenic molecules that can activate diverse TLRs, but that it can be a negative regulator of TNFα induced NF-κB activation. This inhibition is concentration-dependent and occurs by disallowing nuclear translocation of the p65 subunit of NF-κB. Previously, CIAS1 has been suggested to play a role in the generation of IL-1 and activation of NF-κB, but only when expressed in concert with the adaptor molecule apoptosis-associated speck-like protein (ASC) (Manji et al., (2002) *J. Biol. Chem.* 277:11570). The data reported herein reveal that CIAS1 alone reduces TNFα and NF-κB responses. Together, these studies suggest that the balance of ASC and CIAS1 determines the extent of inflammatory responses, and that alone, either may serve as an important suppressor molecule. It is interesting to note that NF-κB nuclear translocation is routinely detectable within 10-30 minutes after cell activation while increases in CIAS1 RNA are observed 30-60 minutes after stimulation. One possibility is that CIAS1 is induced to limit the extent of the pro-inflammatory cytokine cascade, preventing hyper-inflammation seen in autoinflammatory syndrome patients. In this scenario, mutations in CIAS1 lead to dysfunctional inhibition and prolonged, exaggerated inflammatory responses.

Other proteins with similar CARD and/or Pyrin domains have been shown to activate NF-κB in-vitro. One example is Nod1, proposed to induce NF-κB activity by bringing the CARD-containing kinase RICK in close proximity with the gamma regulatory subunit of IkappaB kinase (IKK) (Inohara et al., (2000) *J. Biol. Chem.* 275:27823). Another report describes a complex of CARD- and Pyrin-containing proteins assembling to elicit processing of pro-IL-1β, a signaling platform termed the 'inflammasome' (Martinon et al., (2002) *Mol. Cell* 10:417). In contrast, the CARDINAL/TUCAN and PAN2 proteins possess NF-κB suppressor activity (Bouchier-Hayes et al., (2001) *J. Biol. Chem.* 276:44069; Fiorentino et al., (2002) *J. Biol. Chem.* 277:35333). The emerging view is of a complex balance between pro and anti-inflammatory molecules that in the proper context serve to initiate, amplify, or suppress inflammatory processes.

As mentioned above, the NBD and LRR regions of CIAS1 are sufficient for the inhibitory activity of the full-length protein A curious finding is the stimulatory activity of the CIAS1 Pyrin domain alone. Without wishing to be bound by any particular theory of the invention, it appears that the Pyrin domain expressed alone may artificially act as an oligomerization domain bringing NF-κB activating molecules together as has been proposed for Nod 1 On the other hand, positive cooperation of CIAS1 with ASC also involves the pyrin domain (Manji et al., (2002) *J. Biol. Chem.* 277:11570).

CATERPILLER 11.2: The nucleotide (SEQ ID NO:11) and amino acid (SEQ ID NO:12) sequences of another member of the CATERPILLER family, CATERPILLER 11.2, were predicted based on the presence of putative pyrin, nucleotide-binding (NBD) and leucine-rich (LRR) domains. CATERPILLER 11.2 is located on human chromosome 11 The inventors have shown that CATERPILLER 11.2 reduces the function of NF-κB, an important transcription factor involved in both inflammatory responses and cell survival. CATERPILLER 11.2 expression is primarily found in hematopoietic cell lines. The reduction of NF-κB function by CATERPILLER 11.2 suggests that CATERPILLER 11.2 is important in the control of immunity, gene expression and cell survival because NF-κB controls all these processes. In addition, CATERPILLER 11.2 suppresses the expression of the class II Major Histocompatibility Complex (MHC-II) promoter. Proper MHC-II expression is important for immune recognition to elicit T cell responses against all pathogens and antigens.

The inventors have cloned the human CATERPILLER 11.2; the nucleotide and amino acid sequences are shown as SEQ ID NO:13 and SEQ ID NO:14, respectively. The cloned nucleotide sequence differs from the predicted sequence as follows. The cloned sequence contains an additional (non-predicted) exon from approximately nucleotide (nt) 1959 to nt 2123. Further, the cloned sequence lacks a predicted exon from approximately nt 2124 to nt 2292 based on the predicted sequence. The cloned sequence lacks 222 nucleotides from the 3' end relative to the prediction. No evidence has been obtained to date to suggest that the additional 222 nucleotides are present in the coding message.

CATERPILLER 11.3:

The predicted nucleotide (SEQ ID NO:15) and amino acid (SEQ ID NO:16) sequences of another family member, human CATERPILLER 11.3, were determined based on the presence of putative nucleotide-binding (NBD) and leucine-rich (LRR) domains. The inventors have further cloned and characterized the human CATERPILLER 11.3 gene (nucleotide sequence, [SEQ ID NO:17]; amino acid sequence, [SEQ ID NO:18]) and a splice variant (nucleotide sequence, [SEQ ID NO:19]; amino acid sequence, [SEQ ID NO:20]). The CATERPILLER 11.3 gene resides at 11q23 on human chromosome 11 and contains as many as 9 exons based on both bioinformatics predictions as well as sequence data obtained from cloning the CATERPILLER 11.3 gene. Assembly of PCR products from the T cell line Jurkat yielded an approximately 3.6 kilobase pair (kb) insert containing both the initiator codon (ATG) and an in-frame stop codon that precedes a 3'UTR and poly-adenylation site.

CATERPILLER 11.3 is widely expressed and appears to be pro-inflammatory, at least in certain cell types including T-regulatory cells, suggesting that CATERPILLER 11.3 may be important for adaptive immunity (e.g., important for vaccines and transplantation). Expression of CATERPILLER 11.3 is also markedly increased (about 10×) in a mouse model for inflammatory bowel disease.

CATERPILLER 16.1: Another member of the CATERPILLER family, CATERPILLER 16.1, was identified based on the presence of nucleotide binding and leucine rich domains. CATERPILLER 16.1 is located on human chromosome 16q13 and is situated between CTEP and CPNE2. The predicted nucleotide sequence is shown as SEQ ID NO:21 and the predicted amino acid sequence is shown as SEQ ID NO:22. A CATERPILLER 16.1 sequence has been cloned and characterized (nucleotide sequence, [SEQ ID NO:23]; amino acid sequence, [SEQ ID NO:24]).

Expression of CATERPILLER 16.1 is found in cell lines and primary human cells of hematopoietic origin (but not restricted to these cell types), including B and T lymphocytes, monocytes and granulocytes. CATERPILLER 16.1 expression is affected by activation stimuli in Jurkat T cells (a human T lymphocyte cell line) and differentiation stimuli in HL-60 cells (a human promyleocytic cell line). CATERPILLER 16.1 is implicated in both differentiation and activation of certain cell types are implicated in host responses to pathogens or the regulation of autoimmune diseases and/or cancer or precancerous conditions. CATERPILLER 16.1 expression is dramatically increased (about 100-1000×) in the affected tissues of inflammatory disease models of arthritis, transplantation, CNS inflammatory disease, and Crohn's disease. Moreover, CATERPILLER 16.1 maps within the Crohn's susceptibility region.

NOD27, which shares structural similarity with CATERPILLER 16.1, has recently been cloned and identified (GenBank Accession No. AF389420; *Biochem. Biophys. Res. Commun.* 14:302 (2003); the disclosures of which are incorporated by reference in their entireties).

CATERPILLER 16.2: The predicted nucleotide (SEQ ID NO:25) and amino acid (SEQ ID NO:26) sequences of another member of the CATERPILLER family, CATERPILLER 16.2, were predicted based on the presence of putative nucleotide-binding (NBD) and leucine-rich repeat (LRR) domains. This gene is located on human chromosome 16. The inventors have cloned and characterized the entire coding sequence for human CATERPILLER 16.2 (nucleotide sequence, [SEQ ID NO:27]; amino acid sequence, [SEQ ID NO:28]). The cloned sequence of CATERPILLER 16.2 is identical to the predicted sequence from nucleotides 286-2217. Note that nucleotide 286 of the cloned sequences is the position of the initiation methionine in the predicted version. The 3' end of the cloned sequence, nucleotides 2218-3489 differs from the predicted version.

CATERPILLER 16.2 has been shown to reduce the function of two important transcription factors, NF-κB and AP-1, which are involved in both inflammatory responses and cell survival. CATERPILLER 16.2 expression is primarily found in peripheral blood leucocytes, and is reduced by bacterial products that activate the Toll-like receptor (TLR) pathway, the recognition receptors for bacteria, virus, fungus and other pathogens. This observation suggests that 16.2 is part of the TLR pathway.

CATERPILLER Nucleic Acids, Polypeptides, Expression Vectors, Host Cells and Antibodies.

In representative embodiments, the invention provides isolated nucleic acids encoding a CATERPILLER polypeptide (or a functional fragment thereof) as well as the isolated CATERPILLER polypeptides (or a functional fragment thereof). The CATERPILLER nucleic acids and polypeptides of the invention encompass sequences from any species of interest (e.g., mammalian [human, simian, mouse, rat, lagomorph, bovine, ovine, caprine, porcine, equine, feline, canine, etc.], insect, yeast, avian, plants, etc.) as well as allelic variations, isoforms, splice variants and the like (e.g., Monarch-1 encompasses the splice variants and CATERPILLER 11.3 encompasses the splice variant disclosed herein). The CATERPILLER nucleic acids and polypeptides also include modifications that result in functional polypeptides.

Indicia of "functional" CATERPILLER polypeptides include those measures disclosed herein (e.g., in the working Examples) as well as other assays and techniques known in the art for determining inflammatory response, apoptosis, response to pathogens, NF-κB activity, etc. and other activities associated with the function of the specific CATERPILLER polypeptide. Representative assays include NF-κB and AP-1 reporter assays, evaluation of activation and/or production of NF-κB/Ap-1 by inducers such as TNFα, IL-1 or TLR signaling molecules, evaluation of cytokine expression and/or profiles and the like.

Thus, as one aspect, the invention provides an isolated nucleic acid encoding Monarch-1, CIAS1, CATERPILLER 11.2, CATERPILLER 11.3, CATERPILLER 16.1 or CATERPILLER 16.2. In exemplary embodiments, the isolated nucleic acid comprises, consists essentially of, or consists of the nucleotide sequences of SEQ ID NO:1, SEQ ID NO:3, SEQ ID NO:5, SEQ ID NO:7, SEQ ID NO:13, SEQ ID NO:17, SEQ ID NO:19, SEQ ID NO:23, SEQ ID NO:27, SEQ ID NO:33 or SEQ ID NO:148.

Isolated nucleic acids of this invention include RNA, DNA (including cDNAs) and chimeras thereof. The isolated nucleic acids can further comprise modified nucleotides or nucleotide analogs.

In other embodiments, the invention provides a nucleic acid that encodes a functional fragment of a Monarch-1, CIAS1, CATERPILLER 11.2, CATERPILLER 11.3, CATERPILLER 16.1 or CATERPILLER 16.2 polypeptide (e.g., a fragment of SEQ ID NO:1, SEQ ID NO:3, SEQ ID NO:5, SEQ ID NO:7, SEQ ID NO:13, SEQ ID NO:17, SEQ ID NO:19, SEQ ID NO:23, SEQ ID NO:27, SEQ ID NO:33 or SEQ ID NO:148 and other fragments disclosed herein). Such nucleic acids will typically comprise at least about 30, 40, 50, 60, 80, 100, 125, 150, 200, 250 300, 500, 1000 or 1500 contiguous bases of a nucleotide sequence encoding the indicated CATERPILLER polypeptide and encodes a functional fragment thereof.

As yet a further aspect, the invention provides an isolated Monarch-1, CIAS1, CATERPILLER 11.2, CATERPILLER 11.3, CATERPILLER 16.1 or CATERPILLER 16.2 polypeptide. In exemplary embodiments, the polypeptide comprises, consists essentially of, or consists of the amino acid sequence of SEQ ID NO:2, SEQ ID NO:4, SEQ ID NO:6, SEQ ID NO:8, SEQ ID NO:14, SEQ ID NO:18, SEQ ID NO:20, SEQ ID NO:24, SEQ ID NO:28, SEQ ID NO:34 or SEQ ID NO:149.

The CATERPILLER polypeptides of the invention also include functional portions or fragments of a Monarch-1, CIAS1, CATERPILLER 11.2, CATERPILLER 11.3, CATERPILLER 16.1 or CATERPILLER 16.2 polypeptide (e.g., functional fragments of SEQ ID NO:2, SEQ ID NO:4, SEQ ID NO:6, SEQ ID NO:8, SEQ ID NO:14, SEQ ID NO:18, SEQ ID NO:20, SEQ ID NO:24, SEQ ID NO:28, SEQ ID NO:34 or SEQ ID NO:149 and other polypeptide fragments disclosed herein). The length of the fragment is not critical as long as it substantially retains the biological activity of the polypeptide. Illustrative fragments comprise at least about 10, 12, 15, 18, 20, 25, 30, 35, 40, 50, 100, 200, 300, 500 or 1000 contiguous amino acids of a CATERPILLER polypeptide.

The present inventors have discovered that the CATERPILLER family members comprise a nucleotide binding domain (NBD), a leucine rich repeat (LRR) region and, optionally, a pyrin domain. In particular embodiments, the invention provides a functional fragment of a CATERPILLER polypeptide (e.g., Monarch-1, CIAS1, CATERPILLER 11.2, CATERPILLER 11.3, CATERPILLER 16.1 or CATERPILLER 16.2) comprising the NBD or the LRR region, or both (and nucleic acids encoding the same). For those CATERPILLER polypeptides that contain pyrin domains, the functional fragment can further comprise a pyrin domain. As one representative example, the nucleic acid (SEQ ID NO:33) and amino acid (SEQ ID NO:34) sequences of a functional fragment of CIAS1 comprising the NBD and LRR regions are disclosed herein. In other embodiments, the functional fragment of the CATERPILLER polypeptide comprises a pyrin domain, which has been reported to be important in the activity of the FMF (familial Mediterranean fever) protein, see Chae et al., "Targeted disruption of pyrin in the FMF (familial Mediterranean fever) protein caused increased sensitivity to endotoxin and defective macrophage apoptosis," *Mol. Cell.* 11:591 (2003), the disclosure of which is incorporated herein in its entirety). In still other embodiments, the functional fragment of the CATERPILLER polypeptide comprises the CARD domain, which is similar to caspase activation and recruitment domains that can lead to apoptosis (see, Bouchier-Hayes et al., (2002) *EMBO Rep.* 3:616).

With particular respect to Monarch-1, in particular embodiments, a functional fragment of Monarch-1 comprises the N-terminus of the protein (e.g., including the initiator methionine), and the corresponding nucleic acid comprises the 5' end of the coding sequence (e.g., including the initiator codon). In other particular embodiments, the functional fragment comprises at least about 20, 30, 50, 100 or 150 contiguous amino acids from the N-terminal portion of the protein from amino acid 1 to about amino acid 650 or 700 (see, e.g., SEQ ID NO:2).

With respect to CATERPILLER 11.3, in particular embodiments, the functional fragment comprises the amino-terminus of the protein (and the nucleic acid encoding the fragment comprises the 5' coding region and initiation codon). In other embodiments, the functional CATERPILLER 11.3 fragment comprises at least about 20, 30, 50, 100 or 150 contiguous amino acids from the N-terminal region from the initiator Met to about amino acid 300 or 350 (see, e.g., SEQ ID NO:18 and SEQ ID NO:20). With respect to nucleic acids encoding a functional fragment of CATERPILLER 11.3, in particular embodiments, the isolated nucleic acid comprises at least about 20, 40, 50, 100, 150, 200, 250 or 500 or more contiguous bases from nucleotide 1 to about nt 1117 (see, e.g., SEQ ID NO:17 and SEQ ID NO:19). In particular embodiments, the isolated nucleic acid comprises essentially all of nt 1 to nt 1117.

In other embodiments, the full-length or functional fragment of a CATERPILLER 16.1 polypeptide comprises a Leu at amino acid position 132 and/or an Arg at amino acid position 177 (see, e.g., SEQ ID NO:24).

In still other representative embodiments, a functional fragment of a CATERPILLER 16.2 polypeptide comprises the N-terminus of the polypeptide (i.e., the initiator codon). In other embodiments, the nucleic acid encoding the functional fragment of the CATERPILLER 16.2 polypeptide comprises at least about 20, 40, 50, 100, 150, 200, 250, 500 contiguous nucleotides of the 5' 1900 nucleotides of the CATERPILLER 16.2 coding sequence (see, e.g., SEQ ID NO:27). In other embodiments, the nucleic acid encoding the functional fragment of the CATERPILLER 16.2 polypeptide comprises all of nucleotides 1 to 1900 of the 5' coding sequence. Those skilled in the art will understand that according to the foregoing embodiments, the functional fragment of the CATERPILLER 16.2 polypeptide will comprise the corresponding amino acids. In other embodiments, the nucleic acid encoding the functional fragment of CATERPILLER 16.2 comprises nucleotides 509-607 and/or nucleotides 2468-3489. In other particular embodiments, the functional fragment of CATERPILLER 16.2 comprises the C-terminus, e.g., from amino acids 728 to 1065 (see, SEQ ID NO:28). In still other representative embodiments, the functional CATERPILLER 16.2 fragment comprises at least about 20, 30, 50, 100 or 150 contiguous amino acids from the C-terminus from about amino acids 728 to 1065.

Likewise, those skilled in the art will appreciate that the present invention also encompasses fusion proteins (and nucleic acid sequences encoding the same) comprising the CATERPILLER polypeptides of the invention (or a functional fragment thereof). For example, it may be useful to express the CATERPILLER polypeptide (or functional fragment) as a fusion protein that can be recognized by a commercially available antibody (e.g., FLAG motifs) or as a fusion protein that can otherwise be more easily purified (e.g., by addition of a poly-His tail). Additionally, fusion proteins that enhance the stability of the CATERPILLER polypeptide may be produced, e.g., fusion proteins comprising maltose binding protein (MBP) or glutathione-S-transferase. As another alternative, the fusion protein can comprise a reporter molecule.

Likewise, it will be understood that the CATERPILLER polypeptides specifically disclosed herein will typically tolerate substitutions in the amino acid sequence and substantially retain biological activity. To identify polypeptides of the invention other than those specifically disclosed herein, amino acid substitutions may be based on any characteristic known in the art, including the relative similarity or differences of the amino acid side-chain substituents, for example, their hydrophobicity, hydrophilicity, charge, size, and the like.

Amino acid substitutions other than those disclosed herein may be achieved by changing the codons of the DNA sequence (or RNA sequence), according to the following codon table:

TABLE 2

| Amino Acids | | | Codons |
|---|---|---|---|
| Alanine | Ala | A | GCA GCC GCG GCT |
| Cysteine | Cys | C | TGC TGT |
| Aspartic acid | Asp | D | GAC GAT |
| Glutamic acid | Glu | E | GAA GAG |
| Phenylalanine | Phe | F | TTC TTT |
| Glycine | Gly | G | GGA GGC GGG GGT |
| Histidine | His | H | CAC CAT |
| Isoleucine | Ile | I | ATA ATC ATT |
| Lysine | Lys | K | AAA AAG |
| Leucine | Leu | L | TTA TTG CTA CTC CTG CTT |
| Methionine | Met | M | ATG |
| Asparagine | Asn | N | AAC AAT |
| Proline | Pro | P | CCA CCC CCG CCT |
| Glutamine | Gln | Q | CAA CAG |
| Arginine | Arg | R | AGA AGG CGA CGC CGG CGT |
| Serine | Ser | S | AGC ACT TCA TCC TCG TCT |
| Threonine | Thr | T | ACA ACC ACG ACT |
| Valine | Val | V | GTA GTC GTG GTT |
| Tryptophan | Trp | W | TGG |
| Tyrosine | Tyr | Y | TAC TAT |

In identifying amino acid sequences encoding CATERPILLER polypeptides other than those specifically disclosed herein, the hydropathic index of amino acids may be considered. The importance of the hydropathic amino acid index in conferring interactive biologic function on a protein is generally understood in the art (see, Kyte and Doolittle, (1982) *J. Mol. Biol.* 157:105; incorporated herein by reference in its entirety). It is accepted that the relative hydropathic character of the amino acid contributes to the secondary structure of the resultant protein, which in turn defines the interaction of the protein with other molecules, for example, enzymes, substrates, receptors, DNA, antibodies, antigens, and the like.

Each amino acid has been assigned a hydropathic index on the basis of its hydrophobicity and charge characteristics (Kyte and Doolittle, Id.), these are:

isoleucine (+4.5); valine (+4.2); leucine (+3.8); phenylalanine (+2.8); cysteine/cystine (+2.5); methionine (+1.9); alanine (+1.8); glycine (−0.4); threonine (−0.7); serine (−0.8); tryptophan (−0.9); tyrosine (−1.3); proline (−1.6); histidine (−3.2); glutamate (−3.5); glutamine (−3.5); aspartate (−3.5); asparagine (−3.5); lysine (−3.9); and arginine (−4.5).

Accordingly, the hydropathic index of the amino acid (or amino acid sequence) may be considered when modifying the CATERPILLER polypeptides specifically disclosed herein.

It is also understood in the art that the substitution of amino acids can be made on the basis of hydrophilicity. U.S. Pat. No. 4,554,101 (incorporated herein by reference in its entirety) states that the greatest local average hydrophilicity of a protein, as governed by the hydrophilicity of its adjacent amino acids, correlates with a biological property of the protein.

As detailed in U.S. Pat. No. 4,554,101, the following hydrophilicity values have been assigned to amino acid residues: arginine (+3.0); lysine (±3.0); aspartate (+3.0±1); glutamate (+3.0±1); serine (+0.3); asparagine (+0.2); glutamine (+0.2); glycine (0); threonine (−0.4); proline (−0.5±1); alanine (−0.5); histidine (−0.5); cysteine (−1.0); methionine (−1.3); valine (−1.5); leucine (−1.8); isoleucine (−1.8); tyrosine (−2.3); phenylalanine (−2.5); tryptophan (−3.4).

Thus, the hydrophilicity of the amino acid (or amino acid sequence) may be considered when identifying additional CATERPILLER polypeptides beyond those specifically disclosed herein.

In embodiments of the invention, the nucleic acid encoding the CATERPILLER polypeptide (or functional fragment) will hybridize to the nucleic acid sequences specifically disclosed herein or fragments thereof (e.g., SEQ ID NO:1, SEQ ID NO:3, SEQ ID NO:5, SEQ ID NO:7, SEQ ID NO:13, SEQ ID NO:17, SEQ ID NO:19, SEQ ID NO:23, SEQ ID NO:27, SEQ ID NO:33, SEQ ID NO:148) under standard conditions as known by those skilled in the art and encode a functional CATERPILLER polypeptide or functional fragment thereof.

For example, hybridization of such sequences may be carried out under conditions of reduced stringency, medium stringency or even stringent conditions (e.g., conditions represented by a wash stringency of 35-40% Formamide with 5× Denhardt's solution, 0.5% SDS and 1×SSPE at 37° C., conditions represented by a wash stringency of 40-45% Formamide with 5× Denhardt's solution, 0.5% SDS, and 1×SSPE at 42° C.; and conditions represented by a wash stringency of 50% Formamide with 5× Denhardt's solution, 0.5% SDS and 1×SSPE at 42° C., respectively) to the nucleic acid sequences encoding the CATERPILLER polypeptides or functional fragments thereof specifically disclosed herein. See, e.g., Sambrook et al., *Molecular Cloning, A Laboratory Manual* (2d Ed. 1989) (Cold Spring Harbor Laboratory).

In other embodiments, nucleic acid sequences encoding the CATERPILLER polypeptides of the invention have at least about 60%, 70%, 80%, 85%, 90%, 95%, 97% or higher sequence identity with the nucleic acid sequences specifically disclosed herein (or functional fragments thereof, as described above) and encode a functional CATERPILLER polypeptide or functional fragment thereof.

Further, it will be appreciated by those skilled in the art that there can be variability in the polynucleotides that encode the CATERPILLER polypeptides (and fragments thereof) of the present invention due to the degeneracy of the genetic code. The degeneracy of the genetic code, which allows different nucleic acid sequences to code for the same polypeptide, is well known in the literature (See, e.g., Table 2).

Likewise, the CATERPILLER polypeptides (and fragments thereof) of the invention include polypeptides that have at least about 60%, 70%, 80%, 85%, 90%, 95%, 97% or higher amino acid sequence identity with the polypeptide sequences specifically disclosed herein or fragments thereof (as described above).

As is known in the art, a number of different programs can be used to identify whether a nucleic acid or polypeptide has sequence identity or similarity to a known sequence. Sequence identity or similarity may be determined using standard techniques known in the art, including, but not limited to, the local sequence identity algorithm of Smith & Waterman, *Adv. Appl. Math.* 2, 482 (1981), by the sequence identity alignment algorithm of Needleman & Wunsch, *J. Mol. Biol.* 48, 443 (1970), by the search for similarity method of Pearson & Lipman, *Proc. Natl. Acad. Sci. USA* 85, 2444 (1988), by computerized implementations of these algorithms (GAP, BESTFIT, FASTA, and TFASTA in the Wisconsin Genetics Software Package, Genetics Computer Group, 575 Science Drive, Madison, Wis.), the Best Fit sequence program described by Devereux et al., *Nucl. Acid Res.* 12, 387-395 (1984), preferably using the default settings, or by inspection.

An example of a useful algorithm is PILEUP. PILEUP creates a multiple sequence alignment from a group of related sequences using progressive, pairwise alignments. It can also plot a tree showing the clustering relationships used to create the alignment. PILEUP uses a simplification of the progressive alignment method of Feng & Doolittle, *J. Mol. Evol.* 35, 351-360 (1987); the method is similar to that described by Higgins & Sharp, *CABIOS* 5, 151-153 (1989).

Another example of a useful algorithm is the BLAST algorithm, described in Altschul et al., *J. Mol. Biol.* 215, 403-410, (1990) and Karlin et al., *Proc. Natl. Acad. Sci. USA* 90, 5873-5787 (1993). A particularly useful BLAST program is the WU-BLAST-2 program which was obtained from Altschul et al., *Methods in Enzymology,* 266, 460-480 (1996); http://blast.wustl/edu/blast/README.html. WU-BLAST-2 uses several search parameters, which are preferably set to the default values. The parameters are dynamic values and are established by the program itself depending upon the composition of the particular sequence and composition of the particular database against which the sequence of interest is being searched; however, the values may be adjusted to increase sensitivity.

An additional useful algorithm is gapped BLAST as reported by Altschul et al. *Nucleic Acids Res.* 25, 3389-3402.

A percentage amino acid sequence identity value is determined by the number of matching identical residues divided by the total number of residues of the "longer" sequence in the aligned region. The "longer" sequence is the one having the most actual residues in the aligned region (gaps introduced by WU-Blast-2 to maximize the alignment score are ignored).

In a similar manner, percent nucleic acid sequence identity with respect to the coding sequence of the polypeptides disclosed herein is defined as the percentage of nucleotide residues in the candidate sequence that are identical with the nucleotides in the polypeptide specifically disclosed herein.

The alignment may include the introduction of gaps in the sequences to be aligned. In addition, for sequences which contain either more or fewer amino acids than the polypeptides specifically disclosed herein, it is understood that in one embodiment, the percentage of sequence identity will be determined based on the number of identical amino acids in relation to the total number of amino acids. Thus, for example, sequence identity of sequences shorter than a sequence specifically disclosed herein, will be determined using the number of amino acids in the shorter sequence, in one embodiment. In percent identity calculations relative weight is not assigned to various manifestations of sequence variation, such as, insertions, deletions, substitutions, etc.

In one embodiment, only identities are scored positively (+1) and all forms of sequence variation including gaps are assigned a value of "0", which obviates the need for a weighted scale or parameters as described below for sequence similarity calculations. Percent sequence identity can be calculated, for example, by dividing the number of matching identical residues by the total number of residues of the "shorter" sequence in the aligned region and multiplying by 100. The "longer" sequence is the one having the most actual residues in the aligned region.

Those skilled in the art will appreciate that the isolated nucleic acids encoding the CATERPILLER polypeptides of the invention will typically be associated with appropriate expression control sequences, e.g., transcription/translation control signals and polyadenylation signals.

It will further be appreciated that a variety of promoter/enhancer elements can be used depending on the level and tissue-specific expression desired. The promoter can be constitutive or inducible, depending on the pattern of expression desired. The promoter can be native or foreign and can be a natural or a synthetic sequence. By foreign, it is intended that the transcriptional initiation region is not found in the wild-type host into which the transcriptional initiation region is introduced. The promoter is chosen so that it will function in the target cell(s) of interest.

To illustrate, the CATERPILLER coding sequence can be operatively associated with a cytomegalovirus (CMV) major immediate-early promoter, an albumin promoter, an Elongation Factor 1-α (EF1-α) promoter, a PγK promoter, a MFG promoter, or a Rous sarcoma virus promoter.

Inducible promoter/enhancer elements include hormone-inducible and metal-inducible elements, and other promoters regulated by exogenously supplied compounds, including without limitation, the zinc-inducible metalothionein (MT) promoter; the dexamethasone (Dex)-inducible mouse mammary tumor virus (MMTV) promoter; the T7 polymerase promoter system (see WO 98/10088); the ecdysone insect promoter (No et al, (1996) *Proc. Natl. Acad. Sci. USA* 93:3346); the tetracycline-repressible system (Gossen et al., (1992) *Proc. Natl. Acad. Sci. USA* 89:5547); the tetracycline-inducible system (Gossen et al., (1995) *Science* 268:1766; see also Harvey et al., (1998) *Curr. Opin. Chem. Biol.* 2:512); the RU486-inducible system (Wang et al., (1997) *Nat. Biotech.* 15:239; Wang et al., (1997) *Gene Ther.,* 4:432); and the rapamycin-inducible system (Magari et al., (1997) *J. Clin. Invest.* 100:2865).

Other tissue-specific promoters or regulatory promoters include, but are not limited to, promoters that typically confer tissue-specificity in myeloid-monocytic cells or cells of such origin (e.g., granulocytes, macrophages, monocytes, eosinophils, basophils, mast cells, dendritic cells, microglial, Langerhans cells), T cells, and B cells. These include but are not limited to promoters for GM-CSF, CD14, TCR, Ick, B220 and Ig.

Moreover, specific initiation signals are generally required for efficient translation of inserted protein coding sequences. These translational control sequences, which can include the ATG initiation codon and adjacent sequences, can be of a variety of origins, both natural and synthetic.

The present invention further provides cells comprising the isolated nucleic acids and polypeptides of the invention. The cell may be a cultured cell or a cell in vivo, e.g., for use in therapeutic methods, screening methods, methods for studying the biological action of the CATERPILLER polypeptides, in methods of producing CATERPILLER polypeptides, or in methods of maintaining or amplifying the nucleic acids of the invention, etc In particular embodiments, the cell is an untransformed cell or a cell from a cell line representing myeloid-monocytic cells or cells of such origin (e.g., granulocytes, macrophages, monocytes, eosinophils, basophils, mast cells, dendritic cells, microglial, Langerhans cells). In other representative embodiments, the cell is a T cell, B cell, epithelial cell, endothelial cell, or muscle cell.

The isolated nucleic acid can be incorporated into an expression vector. Expression vectors compatible with various host cells are well known in the art and contain suitable elements for transcription and translation of nucleic acids. Typically, an expression vector contains an "expression cassette," which includes, in the 5' to 3' direction, a promoter, a coding sequence encoding a CATERPILLER polypeptide or functional fragment thereof operatively associated with the promoter, and, optionally, a termination sequence including a stop signal for RNA polymerase and a polyadenylation signal for polyadenylase.

Expression vectors can be designed for expression of polypeptides in prokaryotic or eukaryotic cells. For example, polypeptides can be expressed in bacterial cells such as *E. coli*, insect cells (e.g., the baculovirus expression system), yeast cells, plant cells or mammalian cells. Some suitable host cells are discussed further in Goeddel, *Gene Expression Technoloqy*: Methods in Enzymology 185, Academic Press, San Diego, Calif. (1990). Examples of vectors for expression in the yeast *S. cerevisiae* include pYepSecI (Baldari et al., (1987) *EMBO J.* 6:229-234), pMFa (Kurjan and Herskowitz, (1982) *Cell* 30:933-943), pJRY88 (Schultz et al., (1987) *Gene* 54:113-123), and pYES2 (Invitrogen Corporation, San Diego, Calif.). Baculovirus vectors available for expression of nucleic acids to produce proteins in cultured insect cells (e.g., Sf 9 cells) include the pAc series (Smith et al., (1983) *Mol. Cell. Biol.* 3:2156-2165) and the pVL series (Lucklow, V. A., and Summers, M. d. (1989) *Virology* 170:31-39).

Examples of mammalian expression vectors include pCDM8 (Seed, (1987) *Nature* 329:840) and pMT2PC (Kaufman et al. (1987), *EMBO J.* 6:187-195). When used in mammalian cells, the expression vector's control functions are often provided by viral regulatory elements. For example, commonly used promoters are derived from polyoma, adenovirus 2, cytomegalovirus and Simian Virus 40.

In addition to the regulatory control sequences discussed above, the recombinant expression vector can contain additional nucleotide sequences. For example, the recombinant expression vector can encode a selectable marker gene to identify host cells that have incorporated the vector.

Vector DNA can be introduced into prokaryotic or eukaryotic cells via conventional transformation or transfection techniques. As used herein, the terms "transformation" and "transfection" refer to a variety of art-recognized techniques for introducing foreign nucleic acids (e.g., DNA) into a host cell, including calcium phosphate or calcium chloride co-precipitation, DEAE-dextran-mediated transfection, lipofection, electroporation, microinjection, DNA-loaded liposomes, lipofectamine-DNA complexes, cell sonication, gene bombardment using high velocity microprojectiles, and viral-mediated transfection. Suitable methods for transforming or transfecting host cells can be found in Sambrook et al. (Molecular Cloning: A Laboratory Manual, 2nd Edition, Cold Spring Harbor Laboratory press (1989)), and other laboratory manuals.

If stable integration is desired, often only a small fraction of cells (in particular, mammalian cells) integrate the foreign DNA into their genome. In order to identify and select integrants, a nucleic acid that encodes a selectable marker (e.g., resistance to antibiotics) can be introduced into the host cells along with the nucleic acid of interest. Preferred selectable markers include those that confer resistance to drugs, such as G418, hygromycin and methotrexate. Nucleic acids encoding a selectable marker can be introduced into a host cell on the same vector as that comprising the nucleic acid of interest or can be introduced on a separate vector. Cells stably transfected with the introduced nucleic acid can be identified by drug selection (e.g., cells that have incorporated the selectable marker gene will survive, while the other cells die).

The nucleic acid can also be introduced into a plant, plant cell or protoplast and, optionally, the isolated nucleic acid encoding the polypeptide is integrated into the nuclear or plastidic genome. Plant transformation is known as the art. See, in general, *Methods in Enzymology* Vol. 153 ("Recombinant DNA Part D") 1987, Wu and Grossman Eds., Academic Press and European Patent Application EP 693554.

Foreign nucleic acids can be introduced into plant cells or protoplasts by several methods. For example, nucleic acid can be mechanically transferred by microinjection directly into plant cells by use of micropipettes. Foreign nucleic acid can also be transferred into a plant cell by using polyethylene glycol which forms a precipitation complex with the genetic material that is taken up by the cell (Paszkowski et al. (1984) *EMBO J.* 3:2712-22). Foreign nucleic acid can be introduced into a plant cell by electroporation (Fromm et al. (1985) *Proc. Natl. Acad. Sci. USA* 82:5824). In this technique, plant protoplasts are electroporated in the presence of plasmids or nucleic acids containing the relevant genetic construct. Electrical impulses of high field strength reversibly permeabilize biomembranes allowing the introduction of the plasmids. Electroporated plant protoplasts reform the cell wall, divide, and form a plant callus. Selection of the transformed plant cells comprising the foreign nucleic acid can be accomplished using phenotypic markers.

Cauliflower mosaic virus (CaMV) can be used as a vector for introducing foreign nucleic acids into plant cells (Hohn et al. (1982) "Molecular Biology of Plant Tumors," Academic Press, New York, pp. 549-560; Howell, U.S. Pat. No. 4,407,956). The CaMV viral DNA genome is inserted into a parent bacterial plasmid creating a recombinant DNA molecule which can be propagated in bacteria. The recombinant plasmid can be further modified by introduction of the desired DNA sequence. The modified viral portion of the recombinant plasmid is then excised from the parent bacterial plasmid, and used to inoculate the plant cells or plants.

High velocity ballistic penetration by small particles can be used to introduce foreign nucleic acid into plant cells. Nucleic acid is disposed within the matrix of small beads or particles, or on the surface (Klein et al. (1987) *Nature* 327:70-73). Although typically only a single introduction of a new nucleic acid segment is required, this method also provides for multiple introductions.

A nucleic acid can be introduced into a plant cell by infection of a plant cell, an explant, a meristem or a seed with *Agrobacterium tumefaciens* transformed with the nucleic acid. Under appropriate conditions, the transformed plant cells are grown to form shoots, roots, and develop further into plants. The nucleic acids can be introduced into plant cells, for example, by means of the Ti plasmid of *Agrobacterium*

*tumefaciens*. The Ti plasmid is transmitted to plant cells upon infection by *Agrobacterium tumefaciens*, and is stably integrated into the plant genome (Horsch et al (1984) "Inheritance of Functional Foreign Genes in Plants," *Science* 233: 496-498; Fraley et al. (1983) *Proc. Natl. Acad. Sci. USA* 80:4803).

Plants from which protoplasts can be isolated and cultured to give whole regenerated plants can be transformed so that whole plants are recovered which contain the transferred foreign nucleic acid. Some suitable plants include, for example, species from the genera *Fragaria, Lotus, Medicago, Onobrychis, Trifolium, Trigonella, Vigna, Citrus, Linum, Geranium, Manihot, Daucus, Arabidopsis, Brassica, Raphanus, Sinapis, Atropa, Capsicum, Hyoscyamus, Lycopersicon, Nicotiana, Solanum, Petunia, Digitalis, Majorana, Ciohorium, Helianthus, Lactuca, Bromus, Asparagus, Antirrhinum, Hererocallis, Nemesia, Pelargonium, Panicum, Pennisetum, Ranunculus, Senecio, Salpiglossis, Cucumis, Browaalia, Glycine, Lolium, Zea, Triticum, Sorghum*, and *Datura*.

Plant regeneration from cultured protoplasts is described in Evans et al., "Protoplasts Isolation and Culture," Handbook of Plant Cell Cultures 1:124-176 (MacMillan Publishing Co. New York 1983); M. R. Davey, "Recent Developments in the Culture and Regeneration of Plant Protoplasts," Protoplasts (1983)-Lecture Proceedings, pp. 12-29, (Birkhauser, Basal 1983); P. J. Dale, "Protoplast Culture and Plant Regeneration of Cereals and Other Recalcitrant Crops," Protoplasts (1983)-Lecture Proceedings, pp. 31-41, (Birkhauser, Basel 1983); and H. Binding, "Regeneration of Plants," Plant Protoplasts, pp. 21-73, (CRC Press, Boca Raton 1985).

Regeneration from protoplasts varies from species to species of plants, but generally a suspension of transformed protoplasts containing copies of the exogenous sequence is first generated. In certain species, embryo formation can then be induced from the protoplast suspension, to the stage of ripening and germination as natural embryos. The culture medium, can contain various amino acids and hormones, such as auxin and cytokinins. It can also be advantageous to add glutamic acid and proline to the medium, especially for such species as corn and alfalfa. Shoots and roots normally develop simultaneously. Efficient regeneration will depend on the medium, on the genotype, and on the history of the culture. If these three variables are controlled, then regeneration is fully reproducible and repeatable.

Methods for generation of genetically engineered plants are further described in U.S. Pat. Nos. 5,283,184, 5,482,852, and European Patent Application EP 693 554, all of which are hereby incorporated by reference.

As yet a further embodiment, the invention provides antibodies and antibody fragments that specifically bind to Monarch-1, CIAS1, CATERPILLER 11.2, CATERPILLER 11.3, CATERPILLER 16.1 and/or CATERPILLER 16.2.

The term "antibody" or "antibodies" as used herein refers to all types of immunoglobulins, including IgG, IgM, IgA, IgD, and IgE. The antibody can be monoclonal or polyclonal and can be of any species of origin, including (for example) mouse, rat, rabbit, horse, goat, sheep or human, or can be a chimeric antibody. See, e.g., Walker et al., *Molec. Immunol.* 26, 403-11 (1989). The antibodies can be recombinant monoclonal antibodies produced according to the methods disclosed in U.S. Pat. No. 4,474,893 or U.S. Pat. No. 4,816,567. The antibodies can also be chemically constructed according to the method disclosed in U.S. Pat. No. 4,676,980.

Antibody fragments included within the scope of the present invention include, for example, Fab, F(ab')2, and Fc fragments, and the corresponding fragments obtained from antibodies other than IgG. Such fragments can be produced by known techniques. For example, F(ab')2 fragments can be produced by pepsin digestion of the antibody molecule, and Fab fragments can be generated by reducing the disulfide bridges of the F(ab')2 fragments. Alternatively, Fab expression libraries can be constructed to allow rapid and easy identification of monoclonal Fab fragments with the desired specificity (Huse et al., (1989) *Science* 254, 1275-1281).

Polyclonal antibodies used to carry out the present invention can be produced by immunizing a suitable animal (e.g., rabbit, goat, etc.) with an antigen to which a monoclonal antibody to the target binds, collecting immune serum from the animal, and separating the polyclonal antibodies from the immune serum, in accordance with known procedures. The inventors have successfully produced a polyclonal antibody to Monarch-1, which recognizes the protein in ELISA and western blot analysis. The inventors have also produced a polyclonal antibody to CIAS1.

Monoclonal antibodies used to carry out the present invention can be produced in a hybridoma cell line according to the technique of Kohler and Milstein, (1975) *Nature* 265, 495-97. For example, a solution containing the appropriate antigen can be injected into a mouse and, after a sufficient time, the mouse sacrificed and spleen cells obtained. The spleen cells are then immortalized by fusing them with myeloma cells or with lymphoma cells, typically in the presence of polyethylene glycol, to produce hybridoma cells. The hybridoma cells are then grown in a suitable medium and the supernatant screened for monoclonal antibodies having the desired specificity. Monoclonal Fab fragments can be produced in *E. coli* by recombinant techniques known to those skilled in the art. See, e.g., W. Huse, (1989) *Science* 246, 1275-81.

Antibodies specific to the target polypeptide can also be obtained by phage display techniques known in the art.

Various immunoassays can be used for screening to identify antibodies having the desired specificity for the polypeptides of this invention. Numerous protocols for competitive binding or immunoradiometric assays using either polyclonal or monoclonal antibodies with established specificity are well known in the art. Such immunoassays typically involve the measurement of complex formation between an antigen and its specific antibody (e.g., antigen/antibody complex formation). A two-site, monoclonal-based immunoassay utilizing monoclonal antibodies reactive to two non-interfering epitopes on the proteins or peptides of this invention can be used as well as a competitive binding assay.

Antibodies can be conjugated to a solid support (e.g., beads, plates, slides or wells formed from materials such as latex or polystyrene) in accordance with known techniques. Antibodies can likewise be conjugated to detectable groups such as radiolabels (e.g., $^{35}S$, $^{125}I$, $^{131}I$), enzyme labels (e.g., horseradish peroxidase, alkaline phosphatase), and fluorescence labels (e.g., fluorescein) in accordance with known techniques. Determination of the formation of an antibody/antigen complex in the methods of this invention can be by detection of, for example, precipitation, agglutination, flocculation, radioactivity, color development or change, fluorescence, luminescence, etc., as is well known in the art.

III. Applications of the Present Invention.

CATERPILLER nucleic acids, polypeptides, antibodies, cells and other reagents have a wide variety of uses, both in vitro and in vivo. For example, in representative embodiments, these reagents may be used in vitro or in vivo (e.g., in an animal model) to study inflammatory pathways and apoptosis. Further, "knock in" and "knock out" animals can be used as animal models of disease or as screening tools (discussed more below) for compounds that interact with the CATERPILLER genes or polypeptides.

The invention can also be used to achieve therapeutic effects. The CATERPILLER nucleic acids and polypeptides are implicated in the regulation of diseases that are immediately inflammatory in nature, such as viral/bacterial/fungal/parasitic infections, sepsis, arthritis, type I diabetes, allergies, hypersensitivity, systemic lupus, inflammatory bowel diseases (e.g., Crohn's disease), as well as diseases with strong inflammatory components, such as heart diseases, fibrosis, cancer, multiple sclerosis and other CNS disorders with an inflammatory component including Alzheimer's disease, Parkinson's disease, and Huntington's disease. They can also play a role in clinically-induced conditions such as surgery and transplantation. According to the present invention, the activity of one or more CATERPILLER polypeptides can be modulated (e.g., increased or decreased) to treat the above-mentioned inflammatory conditions. The activity of CATERPILLER polypeptides can be directly regulated at the nucleic acid or protein level. Alternatively, or additionally, the activity of CATERPILLER polypeptides can be indirectly modulated by regulating factors that are upstream or downstream in pathways involved in CATERPILLER activity or by regulating any other factor which results in modulation of CATERPILLER activity. Further, interaction domains of CATERPILLER polypeptides with other polypeptides can be used to alter the function of either CATERPILLER or its interaction partner. As an illustration, the Monarch-1 polypeptide interacts with TRAF6 among several other proteins. This interaction site can be defined and used to identify small molecules that can mimic this interaction or block this interaction. In addition, all members of the CATERPILLER family contain a nucleotide-binding domain. Nucleotide analogs may be used to modulate the function of this family. Many nucleotide-binding domains are associated with kinase activity, and such enzyme active sites are ideal targets for drug discovery.

Thus, in representative embodiments, the invention can be practiced to treat inflammatory conditions (including auto-inflammatory conditions) by modulating the activity of one or more CATERPILLER polypeptides. Inflammatory conditions that can be treated according to the present invention include but are not limited to infections, sepsis, arthritis, type I diabetes, allergies, hypersensitivity, systemic lupus, heart diseases, multiple sclerosis, asthma, fibrosis and inflammatory bowel diseases (e.g., Crohn's disease).

Further, CATERPILLER nucleic acids and polypeptides of the invention are involved in the Toll-like receptor (TLR) pathway (which is a group of pattern recognition receptors for bacteria, viruses, fungus, protozoa, parasites and other pathogens). CATERPILLER family members can interfere with some of the TLR signaling molecules. Conversely, CATERPILLER polypeptides are also important for the synthesis of certain cytokines (IL-6, IL-10, IL-1) in response to TLR activation. Thus, the activity of one or more CATERPILLER polypeptides can be modulated to alter TLR pathway activity and/or to alter the response to pathogens, e.g., to decrease the inflammatory response to pathogens.

Moreover, in other embodiments, the CATERPILLER nucleic acids and polypeptides of the invention are involved in cell survival and apoptosis and are thus implicated in the control of abnormal cell proliferation (e.g., cancer and hyperplasia). This is supported by the effect of CATERPILLER polypeptides on NF-κB and AP-1 function. In particular, NF-κB is frequently considered a pro-survival signal, although the opposite effect has been reported as well. Similarly, AP-1 has a dual role in cell death and survival depending on the context. It has increasingly been recognized that apoptosis is a normal process that occurs during phagocytosis, embryonic differentiation, and organ development such as thymic development or brain development. Pathologic changes in apoptosis can lead to hyperplasia and cancer. Thus, the activity of one or more CATERPILLER polypeptides can be modulated to regulate cell survival and/or cell proliferation (e.g., to reduce abnormal cell proliferation and/or to treat cancer).

As used herein, the term "cancer" encompasses tumor-forming cancers. Likewise, the term "cancerous tissue" encompasses tumors.

The term "cancer" has its understood meaning in the art, for example, an uncontrolled growth of tissue that has the potential to spread to distant sites of the body (i.e., metastasize). Exemplary cancers include, but are not limited to, leukemias, lymphomas, colon cancer, renal cancer, liver cancer, breast cancer, lung cancer, prostate cancer, cervical cancer, uterine cancer, ovarian cancer, melanoma, and the like. In embodiments of the invention, the cancer is a brain cancer or other cancer of the CNS.

The term "tumor" is also understood in the art, for example, as an abnormal mass of undifferentiated cells within a multicellular organism. Tumors can be malignant or benign.

By the terms "treating cancer" or "treatment of cancer", it is intended that the severity of the cancer is reduced or the cancer is at least partially eliminated. In particular embodiments, these terms indicate that metastasis of the cancer is reduced or at least partially eliminated. By the terms "prevention of cancer" or "preventing cancer" it is intended that the methods at least partially eliminate or reduce the incidence or onset of cancer. Alternatively stated, the onset of cancer in the subject may be slowed, controlled, decreased in likelihood or probability, or delayed.

It is known in the art that immune responses may be enhanced by immunomodulatory cytokines (e.g., α-interferon, β-interferon, γ-interferon, ω-interferon, τ-interferon, interleukin-1α, interleukin-1β, interleukin-2, interleukin-3, interleukin 4, interleukin 5, interleukin-6, interleukin-7, interleukin-8, interleukin-9, interleukin-10, interleukin-11, interleukin 12, interleukin-13, interleukin-14, interleukin-18, B cell Growth factor, CD40 Ligand, tumor necrosis factor-α, tumor necrosis factor-β, monocyte chemoattractant protein-1, granulocyte-macrophage colony stimulating factor, and lymphotoxin). Accordingly, immunomodulatory cytokines (preferably, CTL inductive cytokines) may be co-administered to a subject.

Cytokines may be administered by any method known in the art. Exogenous cytokines may be administered to the subject, or alternatively, a nucleotide sequence encoding a cytokine may be delivered to the subject using a suitable vector, and the cytokine produced in vivo.

As one particular representative example of how the present invention may be used, Monarch-1 is an immune regulatory factor that upregulates classical and nonclassical class I MHC and its processing molecules (LMP7). It also upregulates a TNF family member, and an IFN-induced DNA-binding protein. Compounds that modulate the expression or function of Monarch-1 can be used to influence these downstream targets. To illustrate, the modulation of MHC is important for transplantation where a downregulation of MHC is preferred. Down-regulation of MHC can also be advantageous for controlling auto-inflammatory and immune conditions. Further, Monarch-1 causes the induction of IL-10, IL-6 and IL-1 in that the elimination of Monarch-1 enhances the level of these cytokines. Enhancement of MHC can be beneficial for combating infections, such as viral, bacterial, protozoan, yeast or fungal infections. Interfering with Monarch-1 can decrease inflammatory response to bacterial and other pathogens.

Furthermore, the inventors have found that Monarch-1 induces the expression of IFI16, a type I and type II interferon induced DNA-binding factor that is known to regulate genes through binding to NF-κB or to down-regulate the function of another DNA-binding protein, AP-1. Monarch-1 down-regulates AP-1 function, and it also decreases AP-1 binding to DNA. Dowregulation of AP-1 is known to modulate inflammatory, growth and differentiation pathways. Interfering with Monarch-1 can be used to interfere with AP-1 function.

In addition, Monarch-1 causes the induction of TNF ligand or CD70. CD70 is known to enhance CD8 T cell responses. Hence, modulation of Monarch-1 can alter T cell responses.

Overall, Monarch-1 is involved in the regulation of cell survival (due to effects on NF-κB and AP-1) and inflammation. Monarch-1 activity can be modulated to treat auto-inflammatory and inflammatory conditions and/or uncontrolled cell growth (cancer, hyperplasia).

As a further illustrative embodiment, it has further been found that another CATERPILLER gene, CIAS1, is activated by all bacterial and viral products evaluated, including LPS, lipoteichoic acid, proteoglycans, and double-stranded RNA. CIAS1 downregulates the NF-κB response and the activation of MHC class II molecules. These two responses are important in innate and adaptive immunity. CIAS1 is increased in a number of models of inflammation. CIAS1 also modulates NF-κB function by preventing its translocation into the nucleus. Domain analysis indicates the importance of the NBD-LRR region in this function. Thus, modulation of CIAS1 expression or function can alter responses to pathogens and can be important in treating sepsis, bacteremia, anti-viral responses, and inflammatory conditions (including auto-inflammatory conditions), in the treatment of uncontrolled cell growth (cancer, hyperplasia) and/or reducing transplant rejection.

Likewise, CATERPILLER 11.2, CATERPILLER 11.3 and CATERPILLER 16.2 reduce the function of NF-κB, which is involved in both inflammatory responses and cell survival. Thus, modulation of NF-κB activity can be used to regulate immunity and cell survival as NF-κB controls these processes. In addition, CATERPILLER 11.2 suppresses the expression of the MHC-II promoter. Proper MHC-II expression is involved in immune recognition to elicit T cell responses against pathogens (viral, bacterial, fungal and parasitic) and antigens and is also implicated in transplant rejection and in autoimmune diseases. CATERPILLER 16.2 expression is reduced by bacterial products that activate the Toll-like receptor pathway, suggesting that CATERPILLER 16.2 is part of the Toll-like receptor pathway. CATERPILLER 11.3 also reduces the function of TLR activated signaling molecules, such as MyD88, and is found to be expressed at high levels in the T regulatory cells. T regulatory cells are typically associated with the suppression of adaptive T 15, cell responses, and are now targets of cancer treatment (e.g., removal of T regulatory cells to enhance anti-cancer immunity), transplantation (e.g., enhancement of T regulatory cells to improve graft acceptance) and other immune responses. CATERPILLER 11.2, CATERPILLER 11.3 and/or CATERPILLER 16.2 activity can be modulated to treat a variety of auto-inflammatory or inflammatory conditions (as described above), in the containment of transplant rejection, regulation of anti-pathogen responses, and/or in the treatment of uncontrolled cell growth (cancer, hyperplasia). Modulation of CATERPILLER polypeptide or nucleic acid activity can also be used to inhibit NF-κB or NF-κB-dependent pathways, which may be pro-survival or pro-apoptotic as well as pro- or anti-inflammatory depending on the context. For example, NF-κB is found to be important in many pro-inflammatory conditions; however, more recent evidence also suggest that it is important in the reparation phase after the initial inflammatory phase.

According to the foregoing methods, one or more CATERPILLER polypeptides (or functional fragment thereof) can be introduced into a cell or administered to a subject. Alternatively, a nucleic acid encoding the polypeptide(s) (or functional fragment) can be delivered so that the polypeptide(s) is produced in the cell or subject. As described in more detail hereinbelow, these polypeptides (or fragments thereof) can be used to screen for small molecules that can interact with them to enhance or block their function. As an example, the nucleotide binding domain is an ideal target that can be associated with kinase activity, and enzyme sites are particularly suited as drug target sites.

It will be apparent to those skilled in the art that any suitable vector can be used to deliver the nucleic acid to a cell or subject. The choice of delivery vector can be made based on a number of factors known in the art, including age and species of the target host, in vitro vs. in vivo delivery, level and persistence of expression desired, intended purpose (e.g., for therapy or screening), the target cell or organ, route of delivery, size of the isolated nucleic acid, safety concerns, and the like.

Suitable vectors include virus vectors (e.g., retrovirus, alphavirus; vaccinia virus; adenovirus, adeno-associated virus and other parvoviruses, retrovirus, lentivirus poxvirus or herpes simplex virus), lipid vectors, poly-lysine vectors, synthetic polyamino polymer vectors, and the like.

Any viral vector that is known in the art can be used in the present invention. Examples of such viral vectors include, but are not limited to vectors derived from: Adenoviridae; Birnaviridae; Bunyaviridae; Caliciviridae, Capillovirus group; Carlavirus group; Carmovirus virus group; Group Caulimovirus; Closterovirus Group; Commelina yellow mottle virus group; Comovirus virus group; Coronaviridae; PM2 phage group; Corcicoviridae; Group Cryptic virus; group Cryptovirus; Cucumovirus virus group Family ([PHgr]6 phage group; Cysioviridae; Group Carnation ringspot; Dianthovirus virus group; Group Broad bean wilt; Fabavirus virus group; Filoviridae; Flaviviridae; Furovirus group; Group Germinivirus; Group Giardiavirus; Hepadnaviridae; Herpesviridae; Hordeivirus virus group; Illarvirus virus group; Inoviridae; Iridoviridae; Leviviridae; Lipothrixviridae; Luteovirus group; Marafivirus virus group; Maize chlorotic dwarf virus group; icroviridae; Myoviridae; Necrovirus group; Nepovirus virus group; Nodaviridae; Orthomyxoviridae; Papovaviridae; Paramyxoviridae; Parsnip yellow fleck virus group; Partitiviridae; Parvoviridae; Pea enation mosaic virus group; Phycodnaviridae; Picornaviridae; Plasmaviridae; Prodoviridae; Polydnaviridae; Potexvirus group; Potyvirus; Poxyiridae; Reoviridae; Retroviridae; Rhabdoviridae; Group Rhizidiovirus; Siphoviridae; Sobemovirus group; SSV 1-Type Phages; Tectiviridae; Tenuivirus; Tetraviridae; Group Tobamovirus; Group Tobravirus; Togaviridae; Group Tombusvirus; Group Torovirus; Totiviridae; Group Tymovirus; and Plant virus satellites.

Protocols for producing recombinant viral vectors and for using viral vectors for nucleic acid delivery can be found in *Current Protocols in Molecular Biology*, Ausubel, F. M. et al. (eds.) Greene Publishing Associates, (1989) and other standard laboratory manuals (e.g., Vectors for Gene Therapy. In: *Current Protocols in Human Genetics*. John Wiley and Sons, Inc.: 1997).

Non-viral transfer methods can also be employed. Many non-viral methods of nucleic acid transfer rely on normal mechanisms used by mammalian cells for the uptake and intracellular transport of macromolecules. In particular embodiments, non-viral nucleic acid delivery systems rely on endocytic pathways for the uptake of the nucleic acid molecule by the targeted cell. Exemplary nucleic acid delivery systems of this type include liposomal derived systems, polylysine conjugates, and artificial viral envelopes.

In particular embodiments, plasmid vectors are used in the practice of the present invention. For example, naked plasmids can be introduced into muscle cells by injection into the tissue. Expression can extend over many months, although the number of positive cells is typically low (Wolff et al., (1989) *Science* 247:247). Cationic lipids have been demonstrated to aid in introduction of nucleic acids into some cells in culture (Felgner and Ringold, (1989) *Nature* 337:387). Injection of cationic lipid plasmid DNA complexes into the circulation of mice has been shown to result in expression of the DNA in lung (Brigham et al., (1989) *Am. J. Med. Sci.* 298:278). One advantage of plasmid DNA is that it can be introduced into non-replicating cells.

In a representative embodiment, a nucleic acid molecule (e.g., a plasmid) can be entrapped in a lipid particle bearing positive charges on its surface and, optionally, tagged with antibodies against cell surface antigens of the target tissue (Mizuno et al., (1992) *No Shinkei Geka* 20:547; PCT publication WO 91/06309; Japanese patent application 1047381; and European patent publication EP-A43075).

Liposomes that consist of amphiphilic cationic molecules are useful as non-viral vectors for nucleic acid delivery in vitro and in vivo (reviewed in Crystal, *Science* 270: 404-410 (1995); Blaese et al., *Cancer Gene Ther.* 2: 291-297 (1995); Behr et al., *Bioconjugate Chem.* 5: 382-389 (1994); Remy et al., *Bioconjugate Chem.* 5: 647-654 (1994); and Gao et al., *Gene Therapy* 2: 710-722 (1995)). The positively charged liposomes are believed to complex with negatively charged nucleic acids via electrostatic interactions to form lipid: nucleic acid complexes. The lipid:nucleic acid complexes have several advantages as nucleic acid transfer vectors. Unlike viral vectors, the lipid:nucleic acid complexes can be used to transfer expression cassettes of essentially unlimited size. Since the complexes lack proteins, they can evoke fewer immunogenic and inflammatory responses. Moreover, they cannot replicate or recombine to form an infectious agent and have low integration frequency. A number of publications have demonstrated that amphiphilic cationic lipids can mediate nucleic acid delivery in vivo and in vitro (Felgner et al., *Proc. Natl. Acad. Sci. USA* 84: 7413-17 (1987); Loeffler et al., *Methods in Enzymology* 217: 599-618 (1993); Felgner et al., *J. Biol. Chem.* 269: 2550-2561 (1994)).

Several groups have reported the use of amphiphilic cationic lipid:nucleic acid complexes for in vivo transfection both in animals and in humans (reviewed in Gao et al., *Gene Therapy* 2: 710-722 (1995); Zhu et al., *Science* 261: 209-211 (1993); and Thierry et al., *Proc. Natl. Acad. Sci. USA* 92: 9742-9746 (1995)) U.S. Pat. No. 6,410,049 describes a method of preparing cationic lipid:nucleic acid complexes that have a prolonged shelf life.

In other embodiments, it is desired to reduce or inhibit the activity of one or more CATERPILLER polypeptides. The activity of CATERPILLER polypeptides can be inhibited at the nucleic acid or protein level. Alternatively, or additionally, the activity of CATERPILLER polypeptides can be indirectly inhibited by regulating factors that are upstream or downstream in pathways involved in CATERPILLER activity or by regulating any other factor which results in inhibition of CATERPILLER activity.

Numerous methods for reducing the activity of one or more CATERPILLER polypeptides in vitro or in vivo are known. For example, the coding and noncoding nucleotide sequences for a number of CATERPILLER genes are disclosed herein or are otherwise known in the art. An antisense nucleotide sequence or nucleic acid encoding an antisense nucleotide sequence can be generated to any portion thereof in accordance with known techniques.

The term "antisense nucleotide sequence" or "antisense oligonucleotide" as used herein, refers to a nucleotide sequence that is complementary to a specified DNA or RNA sequence. Antisense oligonucleotides and nucleic acids that express the same can be made in accordance with conventional techniques. See, e.g., U.S. Pat. No. 5,023,243 to Tullis; U.S. Pat. No. 5,149,797 to Pederson et al.

As illustrative examples of an antisense nucleotide sequence that can be used to carry out the invention is a nucleotide sequence that is complementary to the nucleotide sequences of SEQ ID NO:1, SEQ ID NO:3, SEQ ID NO:5, SEQ ID NO:7, SEQ ID NO:13, SEQ ID NO:17, SEQ ID NO:19, SEQ ID NO:23, SEQ ID NO:27, SEQ ID NO:33 or SEQ ID NO:148 (or a portion thereof of at least 10, 20, 40, 50, 75, 100, 150, 200, 300, 500 or 1000 contiguous bases) and will reduce the level of polypeptide production.

Those skilled in the art will appreciate that it is not necessary that the antisense nucleotide sequence be fully complementary to the target sequence as long as the degree of sequence similarity is sufficient for the antisense nucleotide sequence to hybridize to its target and reduce production of the polypeptide. As is known in the art, a higher degree of sequence similarity is generally required for short antisense nucleotide sequences, whereas a greater degree of mismatched bases will be tolerated by longer antisense nucleotide sequences.

In representative embodiments of the invention, the antisense nucleotide sequence will hybridize to the nucleotide sequences encoding the CATERPILLER polypeptides specifically disclosed herein (e.g., SEQ ID NO:1, SEQ ID NO:3, SEQ ID NO:5, SEQ ID NO:7, SEQ ID NO:13, SEQ ID NO:17, SEQ ID NO:19, SEQ ID NO:23, SEQ ID NO:27, SEQ ID NO:33 or SEQ ID NO:148 or portions thereof) and will reduce the level of polypeptide production.

For example, hybridization of such nucleotide sequences can be carried out under conditions of reduced stringency, medium stringency or even stringent conditions (e.g., conditions represented by a wash stringency of 35-40% Formamide with 5× Denhardt's solution, 0.5% SDS and 1×SSPE at 37° C.; conditions represented by a wash stringency of 40-45% Formamide with 5× Denhardt's solution, 0.5% SDS, and 1×SSPE at 42° C.; and/or conditions represented by a wash stringency of 50% Formamide with 5× Denhardt's solution, 0.5% SDS and 1×SSPE at 42° C., respectively) to the nucleotide sequences specifically disclosed herein. See, e.g., Sambrook et al., *Molecular Cloning, A Laboratory Manual* (2d Ed. 1989) (Cold Spring Harbor Laboratory).

In other embodiments, antisense nucleotide sequences of the invention have at least about 60%, 70%, 80%, 90%, 95%, 97%, 98% or higher sequence similarity with the complement of the coding sequences specifically disclosed herein and will reduce the level of polypeptide production.

In other embodiments, the antisense nucleotide sequence can be directed against any coding sequence, the silencing of which results in a modulation of a CATERPILLER polypeptide.

The length of the antisense nucleotide sequence (i.e., the number of nucleotides therein) is not critical as long as it binds selectively to the intended location and reduces transcription and/or translation of the target sequence, and can be determined in accordance with routine procedures. In general, the antisense nucleotide sequence will be from about eight, ten or twelve nucleotides in length up to about 20, 30, 50, 75 or 100 nucleotides, or longer, in length.

An antisense nucleotide sequence can be constructed using chemical synthesis and enzymatic ligation reactions by procedures known in the art. For example, an antisense nucleotide sequence can be chemically synthesized using naturally occurring nucleotides or various modified nucleotides designed to increase the biological stability of the molecules or to increase the physical stability of the duplex formed between the antisense and sense nucleotide sequences, e.g., phosphorothioate derivatives and acridine substituted nucleotides can be used. Examples of modified nucleotides which can be used to generate the antisense nucleotide sequence include 5-fluorouracil, 5-bromouracil, 5-chlorouracil, 5-iodouracil, hypoxanthine, xanthine, 4-acetylcytosine, 5-(carboxyhydroxylmethyl) uracil, 5-carboxymethylaminomethyl-2-thiouridine, 5-carboxymethylaminomethyluracil, dihydrouracil, beta-D-galactosylqueosine, inosine, N6-isopentenyladenine, 1-methylguanine, 1-methylinosine, 2,2-dimethylguanine, 2-methyladenine, 2-methylguanine, 3-methylcytosine, 5-methylcytosine, N6-adenine, 7-methylguanine, 5-methylaminomethyluracil, 5-methoxyaminomethyl-2-thiouracil, beta-D-mannosylqueosine, 5'-methoxycarboxymethyluracil, 5-methoxyuracil, 2-methylthio-N-6-isopentenyladenine, uracil-5-oxyacetic acid (v), wybutoxosine, pseudouracil, queosine, 2-thiocytosine, 5-methyl-2-thiouracil, 2-thiouracil, 4-thiouracil, 5-methyluracil, uracil-5-oxyacetic acid methylester, uracil-5-oxyacetic acid (v), 5-methyl-2-thiouracil, 3-(3-amino-3-N-2-carboxypropyl) uracil, (acp3)w, and 2,6-diaminopurine. Alternatively, the antisense nucleotide sequence can be produced using an expression vector into which a nucleic acid has been cloned in an antisense orientation (i.e., RNA transcribed from the inserted nucleic acid will be of an antisense orientation to a target nucleic acid of interest).

The antisense nucleotide sequences of the invention further include nucleotide sequences wherein at least one, or all, or the internucleotide bridging phosphate residues are modified phosphates, such as methyl phosphonates, methyl phosphonothioates, phosphoromorpholidates, phosphoropiperazidates and phosphoramidates. For example, every other one of the internucleotide bridging phosphate residues can be modified as described. In another non-limiting example, the antisense nucleotide sequence is a nucleotide sequence in which one, or all, of the nucleotides contain a 2' loweralkyl moiety (e.g., $C_1$-$C_4$, linear or branched, saturated or unsaturated alkyl, such as methyl, ethyl, ethenyl, propyl, 1-propenyl, 2-propenyl, and isopropyl). For example, every other one of the nucleotides can be modified as described. See also, Furdon et al., (1989) *Nucleic Acids Res.* 17, 9193-9204; Agrawal et al., (1990) *Proc. Natl. Acad. Sci. USA* 87, 1401-1405; Baker et al., (1990) *Nucleic Acids Res.* 18, 3537-3543; Sproat et al., (1989) *Nucleic Acids Res.* 17, 3373-3386; Walder and Walder, (1988) *Proc. Natl. Acad. Sci. USA* 85, 5011-5015; incorporated by reference herein in their entireties for their teaching of methods of making antisense molecules, including those containing modified nucleotide bases).

Triple helix base-pairing methods can also be employed to inhibit production of CATERPILLER polypeptides. Triple helix pairing is believed to work by inhibiting the ability of the double helix to open sufficiently for the binding of polymerases, transcription factors, or regulatory molecules. Recent therapeutic advances using triplex DNA have been described in the literature (e.g., Gee et al., (1994) In: Huber et al., Molecular and Immunologic Approaches, Futura Publishing Co., Mt. Kisco, N.Y.).

Small Interference (si) RNA, also known as RNA interference (RNAi) molecules, provides another approach for modulating CATERPILLER polypeptide activity. The siRNA can be directed against the CATERPILLER nucleic acid sequence or any other sequence that results in modulation of CATERPILLER activity.

siRNA is a mechanism of post-transcriptional gene silencing in which double-stranded RNA (dsRNA) corresponding to a coding sequence of interest is introduced into a cell or an organism, resulting in degradation of the corresponding mRNA. The siRNA effect persists for multiple cell divisions before gene expression is regained. siRNA is therefore a powerful method for making targeted knockouts or "knockdowns" at the RNA level. siRNA has proven successful in human cells, including human embryonic kidney and HeLa cells (see, e.g., Elbashir et al., *Nature* (2001) 411:494-8). In one embodiment, silencing can be induced in mammalian cells by enforcing endogenous expression of RNA hairpins (see Paddison et al., (2002), *PNAS USA* 99:1443-1448). In another embodiment, transfection of small (21-23 nt) dsRNA specifically inhibits nucleic acid expression (reviewed in Caplen, (2002) *Trends in Biotechnology* 20:49-51).

The mechanism by which siRNA achieves gene silencing has been reviewed in Sharp et al, (2001) *Genes Dev* 15: 485-490; and Hammond et al., (2001) *Nature Rev Gen* 2:110-119).

siRNA technology utilizes standard molecular biology methods. dsRNA corresponding to all or a part of a target coding sequence to be inactivated can be produced by standard methods, e.g., by simultaneous transcription of both strands of a template DNA (corresponding to the target sequence) with T7 RNA polymerase. Kits for production of dsRNA for use in siRNA are available commercially, e.g., from New England Biolabs, Inc. Methods of transfection of dsRNA or plasmids engineered to make dsRNA are routine in the art.

Silencing effects similar to those produced by siRNA have been reported in mammalian cells with transfection of a mRNA-cDNA hybrid construct (Lin et al., (2001) *Biochem Biophys Res Commun* 281:639-44), providing yet another strategy for silencing a coding sequence of interest.

In particular embodiments, the siRNA molecules comprise SEQ ID NO:122 and/or SEQ ID NO:123 (Monarch-1), SEQ ID NO:133 (CATERPILLER 11.2); SEQ ID NO:187 (CATERPILLER 16.1) or SEQ ID NO:144 and/or SEQ ID NO:145 (CATERPILLER 16.2).

CATERPILLER polypeptide activity can also be inhibited using ribozymes. Ribozymes are RNA-protein complexes that cleave nucleic acids in a site-specific fashion. Ribozymes have specific catalytic domains that possess endonuclease activity (Kim et al., (1987) *Proc. Natl. Acad. Sci. USA* 84:8788; Gerlach et al., (1987) *Nature* 328:802; Forster and Symons, (1987) *Cell* 49:211). For example, a large number of ribozymes accelerate phosphoester transfer reactions with a high degree of specificity, often cleaving only one of several phosphoesters in an oligonucleotide substrate (Michel and Westhof, (1990) *J. Mol. Biol.* 216:585; Reinhold-Hurek and Shub, (1992) *Nature* 357:173). This specificity has been attributed to the requirement that the substrate bind via specific base-pairing interactions to the internal guide sequence ("IGS") of the ribozyme prior to chemical reaction.

Ribozyme catalysis has primarily been observed as part of sequence-specific cleavage/ligation reactions involving nucleic acids (Joyce, (1989) *Nature* 338:217). For example, U.S. Pat. No. 5,354,855 reports that certain ribozymes can act as endonucleases with a sequence specificity greater than that of known ribonucleases and approaching that of the DNA restriction enzymes. Thus, sequence-specific ribozyme-mediated inhibition of gene expression may be particularly suited to therapeutic applications (Scanlon et al., (1991) *Proc. Natl. Acad. Sci. USA* 88:10591; Sarver et al., (1990) *Science* 247:1222; Sioud et al., (1992) *J. Mol. Biol.* 223:831).

CATERPILLER polypeptide activity can further be modulated by interaction with an antibody or antibody fragment. The antibody or antibody fragment can bind to the CATERPILLER polypeptide (e.g., at the nucleotide binding site) or to any other polypeptide of interest (e.g., TRAF6, for example, at the active site), as long as the binding between the antibody or the antibody fragment and the target polypeptide results in modulation of the CATERPILLER polypeptide activity. Antibodies and antibody fragments are as described in more detail hereinabove.

Furthermore, the present invention provides a method of modulating the activity of a CATERPILLER polypeptide (e.g., for therapy or other purposes described above), comprising administering to a cell or to a subject a compound that modulates the activity of a CATERPILLER polypeptide, the compound administered in an amount effective to modulate the activity of the CATERPILLER polypeptide. The compound can enhance or inhibit the activity of the CATERPILLER polypeptide. Further, the compound can interact directly with the CATERPILLER polypeptide (e.g., by binding to the nucleotide binding domain) or at the nucleic acid level to modulate the activity of the polypeptide. Alternatively, the compound can interact with any other polypeptide, nucleic acid or other molecule (e.g., a nucleotide analog that binds to the nucleotide binding domain) if such interaction results in a modulation of the activity of the CATERPILLER polypeptide.

For example, TRAF6 (an enzyme) associates with Monarch-1 and enhances the degradation of Monarch-1. A compound that interferes with this interaction between TRAF6 and Monarch-1 (e.g., by decreasing the production or activity of TRAF6 or by binding to one of the two polypeptides and blocking TRAF6 binding to Monarch-1) can be used to enhance Monarch-1 activity.

The term "compound" as used herein is intended to be interpreted broadly and encompasses organic and inorganic molecules. Organic compounds include, but are not limited to polypeptides, lipids, carbohydrates, coenzymes and nucleic acid molecules (e.g., gene delivery vectors, antisense oligonucleotides, siRNA, all as described above).

Polypeptides include but are not limited to antibodies (described in more detail above) and enzymes. Nucleic acids include but are not limited to DNA, RNA and DNA-RNA chimeric molecules. Suitable RNA molecules include siRNA, antisense RNA molecules and ribozymes (all of which are described in more detail above). The nucleic acid can further encode any polypeptide such that administration of the nucleic acid and production of the polypeptide results in a modulation of the activity of a CATERPILLER polypeptide.

The compound can further be a compound that is identified by any of the screening methods described below.

The compounds of the present invention can optionally be administered in conjunction with other therapeutic agents. The additional therapeutic agents can be administered concurrently with the compounds of the invention. As used herein, the word "concurrently" means sufficiently close in time to produce a combined effect (that is, concurrently can be simultaneously, or it can be two or more events occurring within a short time period before or after each other).

As a further aspect, the invention provides pharmaceutical formulations and methods of administering the same to achieve any of the therapeutic effects (e.g., anti-inflammatory, inhibition of abnormal cell proliferation, etc.) discussed above. The pharmaceutical formulation may comprise any of the reagents discussed above in a pharmaceutically acceptable carrier, e.g., a nucleic acid encoding a CATERPILLER polypeptide or a fragment thereof, a CATERPILLER polypeptide or fragment thereof, an antibody against a CATERPILLER polypeptide, an antisense oligonucleotide, an siRNA molecule, a ribozyme, or any other compound that modulates the activity of a CATERPILLER polypeptide including compounds identified by the screening methods described herein. Small molecules or peptidomimetics that can bind to certain domains of a CATERPILLER polypeptide (e.g., pyrin, CARD, NBC, LRR, etc.) to enhance or block the function of the polypeptide is another pharmaceutical approach. If the polypeptide has an enzyme activity, as is frequently found for NBD sequences, molecules that can block the enzyme activity are well-suited as pharmaceutical compounds as they are exponential in efficiency due to the nature of enzyme reactions.

By "pharmaceutically acceptable" it is meant a material that is not biologically or otherwise undesirable, i.e., the material can be administered to a subject without causing any undesirable biological effects such as toxicity.

The formulations of the invention can optionally comprise medicinal agents, pharmaceutical agents, carriers, adjuvants, dispersing agents, diluents, and the like.

The compounds of the invention can be formulated for administration in a pharmaceutical carrier in accordance with known techniques. See, e.g., Remington, *The Science And Practice of Pharmacy* ($9^{th}$ Ed. 1995). In the manufacture of a pharmaceutical formulation according to the invention, the compound (including the physiologically acceptable salts thereof) is typically admixed with, inter alia, an acceptable carrier. The carrier can be a solid or a liquid, or both, and is preferably formulated with the compound as a unit-dose formulation, for example, a tablet, which can contain from 0.01 or 0.5% to 95% or 99% by weight of the compound. One or more compounds can be incorporated in the formulations of the invention, which can be prepared by any of the well-known techniques of pharmacy.

A further aspect of the invention is a method of treating subjects in vivo, comprising administering to a subject a pharmaceutical composition comprising a compound of the invention in a pharmaceutically acceptable carrier, wherein the pharmaceutical composition is administered in a therapeutically effective amount. Administration of the compounds of the present invention to a human subject or an animal in need thereof can be by any means known in the art for administering compounds.

The formulations of the invention include those suitable for oral, rectal, topical, buccal (e.g., sub-lingual), vaginal, parenteral (e.g., subcutaneous, intramuscular including skeletal muscle, cardiac muscle, diaphragm muscle and smooth muscle, intradermal, intravenous, intraperitoneal), topical (i.e., both skin and mucosal surfaces, including airway surfaces), intranasal, transdermal, intraarticular, intrathecal and inhalation administration, administration to the liver by intraportal delivery, as well as direct organ injection (e.g., into the liver, into the brain for delivery to the central nervous system, into the pancreas). The most suitable route in any given case will depend on the nature and severity of the condition being treated and on the nature of the particular compound which is being used.

For injection, the carrier will typically be a liquid, such as sterile pyrogen-free water, pyrogen-free phosphate-buffered saline solution, bacteriostatic water, or Cremophor EL[R] (BASF, Parsippany, N.J.). For other methods of administration, the carrier can be either solid or liquid.

For oral administration, the compound can be administered in solid dosage forms, such as capsules, tablets, and powders, or in liquid dosage forms, such as elixirs, syrups, and suspensions. Compounds can be encapsulated in gelatin capsules together with inactive ingredients and powdered carriers, such as glucose, lactose, sucrose, mannitol, starch, cellulose or cellulose derivatives, magnesium stearate, stearic acid, sodium saccharin, talcum, magnesium carbonate and the like. Examples of additional inactive ingredients that can be added to provide desirable color, taste, stability, buffering capacity, dispersion or other known desirable features are red iron oxide, silica gel, sodium lauryl sulfate, titanium dioxide, edible white ink and the like. Similar diluents can be used to make compressed tablets. Both tablets and capsules can be manufactured as sustained release products to provide for continuous release of medication over a period of hours. Compressed tablets can be sugar coated or film coated to mask any unpleasant taste and protect the tablet from the atmosphere, or enteric-coated for selective disintegration in the gastrointestinal tract. Liquid dosage forms for oral administration can contain coloring and flavoring to increase patient acceptance.

Formulations suitable for buccal (sub-lingual) administration include lozenges comprising the compound in a flavored base, usually sucrose and acacia or tragacanth; and pastilles comprising the compound in an inert base such as gelatin and glycerin or sucrose and acacia.

Formulations of the present invention suitable for parenteral administration comprise sterile aqueous and non-aqueous injection solutions of the compound, which preparations are preferably isotonic with the blood of the intended recipient. These preparations can contain anti-oxidants, buffers, bacteriostats and solutes which render the formulation isotonic with the blood of the intended recipient. Aqueous and non-aqueous sterile suspensions can include suspending agents and thickening agents. The formulations can be presented in unit\dose or multi-dose containers, for example sealed ampoules and vials, and can be stored in a freeze-dried (lyophilized) condition requiring only the addition of the sterile liquid carrier, for example, saline or water-for-injection immediately prior to use.

Extemporaneous injection solutions and suspensions can be prepared from sterile powders, granules and tablets of the kind previously described. For example, in one aspect of the present invention, there is provided an injectable, stable, sterile composition comprising a compound of the invention, in a unit dosage form in a sealed container. The compound or salt is provided in the form of a lyophilizate which is capable of being reconstituted with a suitable pharmaceutically acceptable carrier to form a liquid composition suitable for injection thereof into a subject. The unit dosage form typically comprises from about 10 mg to about 10 grams of the compound or salt. When the compound or salt is substantially water-insoluble, a sufficient amount of emulsifying agent which is pharmaceutically acceptable can be employed in sufficient quantity to emulsify the compound or salt in an aqueous carrier. One such useful emulsifying agent is phosphatidyl choline.

Formulations suitable for rectal administration are preferably presented as unit dose suppositories. These can be prepared by admixing the compound with one or more conventional solid carriers, for example, cocoa butter, and then shaping the resulting mixture.

Formulations suitable for topical application to the skin preferably take the form of an ointment, cream, lotion, paste, gel, spray, aerosol, or oil. Carriers which can be used include petroleum jelly, lanoline, polyethylene glycols, alcohols, transdermal enhancers, and combinations of two or more thereof.

Formulations suitable for transdermal administration can be presented as discrete patches adapted to remain in intimate contact with the epidermis of the recipient for a prolonged period of time. Formulations suitable for transdermal administration can also be delivered by iontophoresis (see, for example, *Pharmaceutical Research* 3 (6):318 (1986)) and typically take the form of an optionally buffered aqueous solution of the compound. Suitable formulations comprise citrate or bis\tris buffer (pH 6) or ethanol/water and contain from 0.1 to 0.2M of the compound.

The compound can alternatively be formulated for nasal administration or otherwise administered to the lungs of a subject by any suitable means, but is preferably administered by an aerosol suspension of respirable particles comprising the compound, which the subject inhales. The respirable particles can be liquid or solid. The term "aerosol" includes any gas-borne suspended phase, which is capable of being inhaled into the bronchioles or nasal passages. Specifically, aerosol includes a gas-borne suspension of droplets, as can be produced in a metered dose inhaler or nebulizer, or in a mist sprayer. Aerosol also includes a dry powder composition suspended in air or other carrier gas, which can be delivered by insufflation from an inhaler device, for example. See Ganderton & Jones, *Drug Delivery to the Respiratory Tract*, Ellis Horwood (1987); Gonda (1990) *Critical Reviews in Therapeutic Drug Carrier Systems* 6:273-313; and Raeburn et al. (1992) *J. Pharmacol. Toxicol. Methods* 27:143-159. Aerosols of liquid particles comprising the compound can be produced by any suitable means, such as with a pressure-driven aerosol nebulizer or an ultrasonic nebulizer, as is known to those of skill in the art. See, e.g., U.S. Pat. No. 4,501,729. Aerosols of solid particles comprising the compound can likewise be produced with any solid particulate medicament aerosol generator, by techniques known in the pharmaceutical art.

Alternatively, one can administer the compound in a local rather than systemic manner, for example, in a depot or sustained-release formulation.

Further, the present invention provides liposomal formulations of the compounds disclosed herein and salts thereof. The technology for forming liposomal suspensions is well known in the art. When the compound or salt thereof is an aqueous-soluble salt, using conventional liposome technology, the same can be incorporated into lipid vesicles. In such an instance, due to the water solubility of the compound or salt, the compound or salt will be substantially entrained within the hydrophilic center or core of the liposomes. The lipid layer employed can be of any conventional composition and can either contain cholesterol or can be cholesterol-free. When the compound or salt of interest is water-insoluble, again employing conventional liposome formation technology, the salt can be substantially entrained within the hydrophobic lipid bilayer which forms the structure of the liposome. In either instance, the liposomes which are produced can be reduced in size, as through the use of standard sonication and homogenization techniques.

The liposomal formulations containing the compounds disclosed herein or salts thereof, can be lyophilized to produce a lyophilizate which can be reconstituted with a pharmaceutically acceptable carrier, such as water, to regenerate a liposomal suspension.

In the case of water-insoluble compounds, a pharmaceutical composition can be prepared containing the water-insoluble compound, such as for example, in an aqueous base emulsion. In such an instance, the composition will contain a sufficient amount of pharmaceutically acceptable emulsifying agent to emulsify the desired amount of the compound. Particularly useful emulsifying agents include phosphatidyl cholines and lecithin.

In particular embodiments, the compound is administered to the subject in a therapeutically effective amount, as that term is defined above. Dosages of pharmaceutically active compounds can be determined by methods known in the art, see, e.g., *Remington's Pharmaceutical Sciences* (Maack Publishing Co., Easton, Pa.). The therapeutically effective dosage of any specific compound will vary somewhat from compound to compound, and patient to patient, and will depend upon the condition of the patient and the route of delivery. As a general proposition, a dosage from about 0.1 to about 50 mg/kg will have therapeutic efficacy, with all weights being calculated based upon the weight of the compound, including the cases where a salt is employed. Toxicity concerns at the higher level can restrict intravenous dosages to a lower level such as up to about 10 mg/kg, with all weights being calculated based upon the weight of the compound, including the cases where a salt is employed. A dosage from about 10 mg/kg to about 50 mg/kg can be employed for oral administration. Typically, a dosage from about 0.5 mg/kg to 5 mg/kg can be employed for intramuscular injection. Particular dosages are about 1 μmol/kg to 50 μmol/kg, and more particularly to about 22 μmol/kg and to 33 μmol/kg of the compound for intravenous or oral administration, respectively.

In particular embodiments of the invention, more than one administration (e.g., two, three, four, or more administrations) can be employed over a variety of time intervals (e.g., hourly, daily, weekly, monthly, etc.) to achieve therapeutic effects.

The present invention finds use in veterinary and medical applications. Suitable subjects include both avians and mammals, with mammals being preferred. The term "avian" as used herein includes, but is not limited to, chickens, ducks, geese, quail, turkeys and pheasants. The term "mammal" as used herein includes, but is not limited to, humans, bovines, ovines, caprines, equines, felines, canines, lagomorphs, etc. Human subjects include neonates, infants, juveniles, and adults. In other embodiments, the subject is an animal model of inflammatory disease or cancer.

The CATERPILLER nucleic acids may further be used as chromosomal markers, i.e., to map the location of other genes. As another embodiment, the CATERPILLER nucleic acids can be used as genetic markers of diseases, e.g., inflammatory and autoimmune diseases. For example, Monarch-1 maps to the multiple sclerosis susceptibility region and CATERPILLER 16.1 maps within the Crohn's disease susceptibility region. Linkage of these genes with diseases will facilitate gene typing whereby certain allelic variations within a population are linked to a disease, which can be used to identify genetically-susceptible individuals for that disease.

The finding that CATERPILLER gene products are involved in inflammatory responses, cell survival, and pathogen response point to these polypeptides as new drug targets for identifying compounds for treating inflammatory disease, reducing transplant rejection, enhancing immune responses to vaccines, for reducing abnormal cell growth (e.g., for treating cancer or hyperplasia), for regulating responses to pathogens, and other conditions. Accordingly, in one aspect, the present invention provides methods of identifying a compound or compounds that bind to and/or modulate the activity of a CATERPILLER polypeptide. Any desired end-point can be detected, e.g., binding to the CATERPILLER polypeptide, gene or RNA, modulation of the activity of the CATERPILLER polypeptide, modulation of the Toll-like receptor pathway (e.g., in response to pathogens), modulation of NF-κB activity, modulation of MHC-II pathway activity and/or interference with binding by a known regulator of a CATERPILLER gene or polypeptide (e.g., TRAF6 and Monarch-1). Methods of detecting the foregoing activities are known in the art and include the methods disclosed herein.

Any compound of interest can be screened according to the present invention. Suitable test compounds include organic and inorganic molecules. Suitable organic molecules can include but are not limited to polypeptides (including enzymes, antibodies and Fab' fragments), carbohydrates, lipids, coenzymes, and nucleic acid molecules (including DNA, RNA and chimerics and analogs thereof) and nucleotides and nucleotide analogs. In particular embodiments, the compound is an antisense nucleic acid, an siRNA or a ribozyme that inhibits production of CATERPILLER polypeptide.

Further, the methods of the invention can be practiced to screen a compound library, e.g., a combinatorial chemical compound library, a polypeptide library, a cDNA library, a library of antisense nucleic acids, and the like, or an arrayed collection of compounds such as polypeptide and nucleic acid arrays.

In one representative embodiment, the invention provides methods of screening test compounds to identify a test compound that binds to a CATERPILLER polypeptide or functional fragment thereof. Compounds that are identified as binding to the CATERPILLER polypeptide or functional fragment can be subject to further screening (e.g., for modulation of Toll-like receptor pathway activity, for pro- or anti-inflammatory activity, for pro- or anti-apoptosis activity, for modulation of NF-κB and/or for modulation of MHC-II pathways, and the like) using the methods described herein or other suitable techniques.

Also provided are methods of screening compounds to identify those that modulate the activity of a CATERPILLER polypeptide or functional fragment thereof. The term "modulate" is intended to refer to compounds that enhance (e.g., increase) or inhibit (e.g., reduce) the activity of the CATERPILLER polypeptide (or functional fragment). For example, the interaction of the CATERPILLER polypeptide or functional fragment with a binding party can be evaluated. To illustrate, Monarch-1 is known to bind to TNIK, TRAF6, vimentin, and tubulin among other proteins. As another measure of biological activity, nucleotide binding can be measured. As another alternative, physical methods, such as NMR, can be used to assess biological function. Activity of the CATERPILLER polypeptide or functional fragment can be evaluated by any method known in the art, including the methods disclosed herein.

Compounds that are identified as modulators of CATERPILLER activity can optionally be further screened using the methods described herein (e.g., for binding to the CATERPILLER polypeptide or functional fragment thereof, gene or RNA, modulation of Toll-like receptor pathway activity, for pro- or anti-inflammatory activity, for pro- or anti-apoptosis activity, for modulation of NF-κB and/or for modulation of MHC-II pathways, and the like). The compound can directly interact with the CATERPILLER polypeptide or functional fragment, gene or mRNA and thereby modulate its activity. Alternatively, the compound can interact with any other polypeptide, nucleic acid or other molecule as long as the interaction results in a modulation of the activity of the CATERPILLER polypeptide or functional fragment.

As another aspect, the invention provides a method of identifying compounds that modulate inflammatory response (i.e., pro- or anti-inflammatory responses). In one representative embodiment, the method comprises contacting a CATERPILLER polypeptide or functional fragment thereof with a test compound; and detecting whether the test compound binds to the CATERPILLER polypeptide or functional fragment and/or modulates the activity of the CATERPILLER polypeptide (or fragment). In another exemplary embodiment, the method comprises introducing a test compound into a cell that comprises the CATERPILLER polypeptide or functional fragment; and detecting whether the compound binds to the CATERPILLER polypeptide or functional fragment and/or modulates the activity of the CATERPILLER polypeptide or functional fragment in the cell. The CATERPILLER polypeptide can be endogenously produced in the cell. Alternatively or additionally, the cell can be modified to comprise an isolated nucleic acid encoding, and optionally overexpressing, the CATERPILLER polypeptide or functional fragment thereof.

In other representative embodiments, the invention provides a method of identifying a compound that modulates cell survival (both pro- and anti-survival). In one representative embodiment, the method comprises contacting a CATERPILLER polypeptide or functional fragment thereof with a test compound; and detecting whether the test compound binds to the CATERPILLER polypeptide or functional fragment and/or modulates the activity of the CATERPILLER polypeptide/functional fragment. In another exemplary embodiment, the method comprises introducing a test compound into a cell that comprises the CATERPILLER polypeptide or functional fragment thereof; and detecting whether the compound binds to the CATERPILLER polypeptide or functional fragment and/or modulates activity of the CATERPILLER polypeptide/functional fragment in the cell. The CATERPILLER polypeptide can be endogenously produced in the cell. Alternatively or additionally, the cell can be modified to comprise an isolated nucleic acid encoding, and optionally overexpressing, the CATERPILLER polypeptide or functional fragment.

The screening assay can be a cell-based or cell-free assay. Further, the CATERPILLER polypeptide (or functional fragment thereof) or nucleic acid can be free in solution, affixed to a solid support, expressed on a cell surface, or located within a cell.

With respect to cell-free binding assays, test compounds can be synthesized or otherwise affixed to a solid substrate, such as plastic pins, glass slides, plastic wells, and the like. For example, the test compounds can be immobilized utilizing conjugation of biotin and streptavidin by techniques well known in the art. The test compounds are contacted with the CATERPILLER polypeptide or functional fragment thereof and washed. Bound polypeptide can be detected using standard techniques in the art (e.g., by radioactive or fluorescence labeling of the CATERPILLER polypeptide or functional fragment, by ELISA methods, and the like).

Alternatively, the CATERPILLER target can be immobilized to a solid substrate and the test compounds contacted with the bound CATERPILLER polypeptide or functional fragment thereof. Identifying those test compounds that bind to and/or modulate the CATERPILLER polypeptide or functional fragment can be carried out with routine techniques. For example, the test compounds can be immobilized utilizing conjugation of biotin and streptavidin by techniques well known in the art. As another illustrative example, antibodies reactive with the CATERPILLER polypeptide or functional fragment can be bound to the wells of the plate, and the CATERPILLER polypeptide trapped in the wells by antibody conjugation. Preparations of test compounds can be incubated in the CATERPILLER polypeptide (or functional fragments presenting wells and the amount of complex trapped in the well can be quantitated.

In another representative embodiment, a fusion protein can be provided which comprises a domain that facilitates binding of the protein to a matrix. For example, glutathione-5-transferase fusion proteins can be adsorbed onto glutathione sepharose beads (Sigma Chemical, St. Louis, Mo.) or glutathione derivatized microtitre plates, which are then combined with cell lysates (e.g., $^{35}$S-labeled) and the test compound, and the mixture incubated under conditions conducive to complex formation (e.g., at physiological conditions for salt and pH). Following incubation, the beads are washed to remove any unbound label, and the matrix immobilized and radiolabel detected directly, or in the supernatant after the complexes are dissociated. Alternatively, the complexes can be dissociated from the matrix, separated by SDS-PAGE, and the level of CATERPILLER polypeptide or functional fragment thereof found in the bead fraction quantitated from the gel using standard electrophoretic techniques.

Another technique for compound screening provides for high throughput screening of compounds having suitable binding affinity to the polypeptide of interest, as described in published PCT application WO84/03564. In this method, a large number of different small test compounds are synthesized on a solid substrate, such as plastic pins or some other surface. The test compounds are reacted with the CATERPILLER polypeptide or functional fragment thereof and washed. Bound polypeptide is then detected by methods well known in the art. Purified CATERPILLER polypeptide or a functional fragment can also be coated directly onto plates for use in the aforementioned drug screening techniques. Alternatively, non-neutralizing antibodies can be used to capture the peptide and immobilize it on a solid support.

With respect to cell-based assays, any suitable cell can be used including bacteria, yeast, insect cells (e.g., with a baculovirus expression system), avian cells, mammalian cells, or plant cells. In exemplary embodiments, the assay is carried out in a cell line that naturally expresses the CATERPILLER gene or produces the polypeptide. For example, CIAS1 is primarily expressed in monocytic cells, and a monocytic cell line or primary monocytes are suitable for use with CIAS1. Further, in other embodiments, it is desirable to use nontransformed cells (e.g., primary cells) as transformation may alter the function of the polypeptide.

The screening assay can be used to detect compounds that bind to or modulate the activity of the native CATERPILLER polypeptide (e.g., polypeptide that is normally produced by the cell). Alternatively, the cell can be modified to express (e.g., overexpress) a recombinant CATERPILLER polypeptide or functional fragment thereof. According to this embodiment, the cell can be transiently or stably transformed with the nucleic acid encoding the CATERPILLER polypeptide or functional fragment, but is preferably stably transformed, for example, by stable integration into the genome of the organism or by expression from a stably maintained episome (e.g., Epstein Barr Virus derived episomes).

In a cell-based assay, the compound to be screened can interact directly with the CATERPILLER polypeptide or functional fragment thereof (i.e., bind to it) and modulate the activity thereof. Alternatively, the compound can be one that modulates CATERPILLER polypeptide activity (or the activity of a functional fragment) at the nucleic acid level. To illustrate, the compound can modulate transcription of the CATERPILLER gene (or transgene), modulate the accumulation of CATERPILLER mRNA (e.g., by affecting the rate of transcription and/or turnover of the mRNA), and/or modulate the rate and/or amount of translation of the CATERPILLER mRNA transcript.

As a further type of cell-based binding assay, the CATERPILLER polypeptide or functional fragment thereof can be used as a "bait protein" in a two-hybrid or three-hybrid assay (see, e.g., U.S. Pat. No. 5,283,317; Zervos et al., (1993) *Cell* 72:223-232; Madura et al., (1993) *J. Biol. Chem.* 268:12046-12054; Bartel et al., (1993) *Biotechniques* 14:920-924; Iwabuchi et al., (1993) *Oncogene* 8:1693-1696; and PCT publication WO94/10300), to identify other polypeptides that bind to or interact with the CATERPILLER polypeptide or functional fragment thereof.

The two-hybrid system is based on the modular nature of most transcription factors, which consist of separable DNA-binding and activation domains. Briefly, the assay utilizes two different DNA constructs. In one construct, the nucleic acid that encodes the CATERPILLER polypeptide or functional fragment thereof is fused to a nucleic acid encoding the DNA binding domain of a known transcription factor (e.g., GAL-4). In the other construct, a DNA sequence, optionally from a library of DNA sequences, that encodes an unidentified protein ("prey" or "sample") is fused to a nucleic acid that codes for the activation domain of the known transcription factor. If the "bait" and the "prey" proteins are able to interact in vivo, forming a complex, the DNA-binding and activation domains of the transcription factor are brought into close proximity. This proximity allows transcription of a reporter sequence (e.g., LacZ), which is operably linked to a transcriptional regulatory site responsive to the transcription factor. Expression of the reporter can be detected and cell colonies containing the functional transcription factor can be isolated and used to obtain the nucleic acid encoding the polypeptide that exhibited binding to the CATERPILLER polypeptide or functional fragment.

As another cell-based assay, the invention provides a method of screening a compound for modulation of inflammatory response (including pro- and anti-inflammatory responses). As still another cell-based assay, the invention provides a method of screening a compound for modulation of cell apoptosis (including both pro- and anti-apoptosis). In particular embodiments, the cell comprises an isolated nucleic acid encoding the CATERPILLER polypeptide or functional fragment thereof. According to this embodiment, it is preferred that the isolated nucleic acid encoding the CATERPILLER polypeptide or functional fragment is stably incorporated into the cell (i.e., by stable integration into the genome of the organism or by expression from a stably maintained episome such as Epstein Barr Virus derived episomes). In other methods of the invention, compounds are identified that modulate Toll-like receptor activity, NF-κB activity and/or MHC-II pathway activity in the cell.

Methods of measuring these activities in cells are known in the art. For example, to measure inflammatory response, NF-κB, AP-1, JNK and/or p38 activation and/or expression can be measured. The production of products of the inducible nitric oxide synthase (iNOS), e.g., nitric oxide, can also be measured. Cytokine production can also be determined including, but not limited to, production of TNFα, LTα/β, IL-1, IL-4, IL-5, IL-2, IL-6, IL-10, IL-12, IL-18 and IL-23. In addition, phagocytosis of beads, bacteria, other pathogens, and apoptotic or necrotic cells can be used to measure phagocytotic functions Recognition or killing of immune targets such as antigen presentation function or cell-mediated lympholysis can be used to measure either T cell or antigen presenting cell function. Production of cell-specific products, such as immunoglobulin by B cells, is also a measure of immune activation.

Screening assays can also be carried out in vivo in animals. Thus, as still a further aspect, the invention provides a transgenic non-human animal comprising an isolated nucleic acid encoding a CATERPILLER polypeptide or functional fragment thereof, which can be produced according to methods well-known in the art. The transgenic non-human animal can be from any species, including avians and non-human mammals. According to this aspect of the invention, suitable non-human mammals include mice, rats, rabbits, guinea pigs, goats, sheep, pigs and cattle. Suitable avians include chickens, ducks, geese, quail, turkeys and pheasants.

The nucleic acid encoding the CATERPILLER polypeptide or functional fragment can be stably incorporated into cells within the transgenic animal (typically, by stable integration into the genome or by stably maintained episomal constructs). It is not necessary that every cell contain the transgene, and the animal can be a chimera of modified and unmodified cells, as long as a sufficient number of cells comprise and express the nucleic acid encoding the CATERPILLER polypeptide or functional fragment so that the animal is a useful screening tool.

Exemplary methods of using the transgenic non-human animals of the invention for in vivo screening of compounds that modulate inflammatory response (both pro- and anti-inflammatory responses), cell survival (both pro- and anti-survival) and/or the activity of a CATERPILLER polypeptide comprise administering a test compound to a transgenic non-human animal (e.g., a mammal such as a mouse) comprising an isolated nucleic acid encoding a CATERPILLER polypeptide or functional fragment thereof stably incorporated into the genome, administering a test compound to the transgenic non-human animal, and detecting whether the test compound modulates inflammatory response, cell survival and/or CATERPILLER polypeptide activity (or the activity of a functional fragment). Other illustrative methods of the invention can be carried out to identify compounds that modulate MHC-II pathway activity, Toll-like receptor pathway activity, or NF-κB activity in vivo.

It is known in the art how to measure these responses in vivo. Illustrative approaches include observation of changes that can be studied by gross examination (edema, redness, swelling, fever, tenderness), histopathology (cellular infiltrates, cell activation markers, phagocytosis, dead cells), changes in cytokine profiles, and cell surface markers (e.g., changes in TNFα, myeloperoxidase or CD69).

Methods of making transgenic animals are known in the art. DNA constructs can be introduced into the germ line of an avian or mammal to make a transgenic animal. For example, one or several copies of the construct can be incorporated into the genome of an embryo by standard transgenic techniques.

In an exemplary embodiment, a transgenic non-human animal is produced by introducing a transgene into the germ line of the non-human animal. Transgenes can be introduced into embryonal target cells at various developmental stages. Different methods are used depending on the stage of development of the embryonal target cell. The specific line(s) of any animal used should, if possible, be selected for general good health, good embryo yields, good pronuclear visibility in the embryo, and good reproductive fitness.

Introduction of the transgene into the embryo can be accomplished by any of a variety of means known in the art such as microinjection, electroporation, lipofection or a viral vector. For example, the transgene can be introduced into a mammal by microinjection of the construct into the pronuclei of the fertilized mammalian egg(s) to cause one or more copies of the construct to be retained in the cells of the developing mammal(s). Following introduction of the transgene construct into the fertilized egg, the egg can be incubated in vitro for varying amounts of time, or reimplanted into the surrogate host, or both. One common method is to incubate the embryos in vitro for about 1-7 days, depending on the species, and then reimplant them into the surrogate host.

The progeny of the transgenically manipulated embryos can be tested for the presence of the construct by Southern blot analysis of a segment of tissue. An embryo having one or more copies of the exogenous cloned construct stably integrated into the genome can be used to establish a permanent transgenic animal line.

Transgenically altered animals can be assayed after birth for the incorporation of the construct into the genome of the offspring. This can be done by hybridizing a probe corresponding to the DNA sequence coding for the polypeptide or a segment thereof onto chromosomal material from the progeny. Those progeny found to contain at least one copy of the construct in their genome are grown to maturity.

Methods of producing transgenic avians are also known in the art, see, e.g., U.S. Pat. No. 5,162,215.

In particular embodiments, to create an animal model in which the activity or expression of a CATERPILLER polypeptide is decreased, it is desirable to inactivate, replace or knock-out the endogenous CATERPILLER gene by homologous recombination with a transgene using embryonic stem cells. In this context, a transgene is meant to refer to heterologous nucleic acid that upon insertion within or adjacent to the CATERPILLER gene results in a decrease or inactivation of CATERPILLER gene expression or CATERPILLER polypeptide amount or activity.

A knock-out of a CATERPILLER gene means an alteration in the sequence of a CATERPILLER that results in a decrease of function of the CATERPILLER gene, preferably such that the CATERPILLER gene expression or CATERPILLER polypeptide amount or activity is undetectable or insignificant. Knock-outs as used herein also include conditional knock-outs, where alteration of the CATERPILLER gene can occur upon, for example, exposure of the animal to a substance that promotes CATERPILLER gene alteration, introduction of an enzyme that promotes recombination at a CATERPILLER gene site (e.g., Cre in the Cre-lox system), or other method for directing the CATERPILLER gene alteration postnatally. Knock-out animals may be prepared using methods known to those of skill in the art. See, for example, Hogan, et al. (1986) Manipulating the Mouse Embryo: A Laboratory Manual, Cold Spring Harbor Laboratory Press, Cold Spring Harbor, N.Y.

A knock-out construct is a nucleic acid sequence, such as a DNA construct, which, when introduced into a cell, results in suppression (partial or complete) of expression of a polypeptide encoded by endogenous DNA in the cell. A knock-out construct as used herein may include a construct containing a first fragment from the 5' end of the CATERPILLER gene, a second fragment from the 3' end of the CATERPILLER gene and a DNA fragment encoding a selectable marker positioned between the first and second CATERPILLER fragments. It should be understood by the skilled artisan that any suitable 5' and 3' fragments of a CATERPILLER gene may be used as long as the expression of the corresponding CATERPILLER gene is partially or completely suppressed by insertion of the transgene. Suitable selectable markers include, but are not limited to, neomycin, puromycin and hygromycin. In addition, the construct may contain a marker, such as diphtheria toxin A or thymidine kinase, for increasing the frequency of obtaining correctly targeted cells. Suitable vectors include, but are not limited to, pBLUESCRIPT, pBR322, and pGEM7.

Alternatively, a knock-out construct may contain RNA molecules such as antisense RNA, siRNA and the like to decrease the expression of a CATERPILLER gene. In particular embodiments, the siRNA molecules comprise SEQ ID NO:122 and/or SEQ ID NO:123 (Monarch-1), SEQ ID NO:133 (CATERPILLER 11.2) or SEQ ID NO:143 and/or SEQ ID NO:144 (CATERPILLER 16.2). Typically, for stable expression the RNA molecule is placed under the control of a promoter. The promoter may be regulated, if deficiencies in the protein of interest may lead to a lethal phenotype, or the promoter may drive constitutive expression of the RNA molecule such that the gene of interest is silenced under all conditions of growth. While homologous recombination between the knock-out construct and the CATERPILLER gene of interest may not be necessary when using an RNA molecule to decrease CATERPILLER gene expression, it may be advantageous to target the knock-out construct to a particular location in the genome of the host organism so that unintended phenotypes are not generated by random insertion of the knock-out construct.

The knock-out construct may subsequently be incorporated into a viral or nonviral vector for delivery to the host animal or may be introduced into embryonic stem (ES) cells. ES are typically selected for their ability to integrate into and become part of the germ line of a developing embryo so as to create germ line transmission of the knock-out construct. Thus, any ES cell line that can do so is suitable for use herein. Suitable cell lines which may be used include, but are not limited to, the 129J ES cell line or the JI ES cell line. The cells are cultured and prepared for DNA insertion using methods well-known to the skilled artisan (e.g., see Robertson (1987) In: Teratocarcinomas and Embryonic Stem Cells: A Practical Approach, E. J. Robertson, ed. IRL Press, Washington, D.C.; Bradley, et al. (1986) *Curr. Topics Develop. Biol.* 20:357-371; Hogan, et al. (1986) Manipulating the Mouse Embryo: A Laboratory Manual, Cold Spring Harbor Laboratory Press, Cold Spring Harbor, N.Y.).

Insertion of the knock-out construct into the ES cells may be accomplished using a variety of methods well-known in the art, including, for example, electroporation, microinjection, and calcium phosphate treatment. For insertion of the DNA or RNA sequence, the knock-out construct nucleic acids are added to the ES cells under appropriate conditions for the insertion method chosen. If the cells are to be electroporated, the ES cells and construct nucleic acids are exposed to an electric pulse using an electroporation machine (electroporator) and following the manufacturer's guidelines for use. After electroporation, the cells are allowed to recover under suitable incubation conditions. The cells are then screened for the presence of the knockout construct.

Each knock-out construct to be introduced into the cell is first typically linearized if the knock-out construct has been inserted into a vector. Linearization is accomplished by digesting the knock-out construct with a suitable restriction endonuclease selected to cut only within the vector sequence and not within the knock-out construct sequence.

Screening for cells which contain the knock-out construct (homologous recombinants) may be done using a variety of methods. For example, as described herein, cells can be processed as needed to render DNA in them available for hybridization with a nucleic acid probe designed to hybridize only to cells containing the construct. For example, cellular DNA can be probed with $^{32}P$-labelled DNA which locates outside the targeting fragment. This technique can be used to identify those cells with proper integration of the knock-out construct. The DNA can be extracted from the cells using standard methods (e.g., see, Sambrook, et al. (1989) Molecular Cloning: A Laboratory Manual, Second Edition, Cold Spring Harbor Laboratory Press, Cold Spring Harbor, N.Y.). The DNA may then be analyzed by Southern blot with a probe or probes designed to hybridize in a specific pattern to genomic DNA digested with one or more particular restriction enzymes.

Once appropriate ES cells are identified, they are introduced into an embryo using standard methods. They can be introduced using microinjection, for example. Embryos at the proper stage of development for integration of the ES cell to occur are obtained, such as by perfusion of the uterus of pregnant females. For example, mouse embryos at 3-4 days development can be obtained and injected with ES cells using a micropipet. After introduction of the ES cell into the embryo, the embryo is introduced into the uterus of a pseudopregnant female mouse. The stage of the pseudopregnancy is selected to enhance the chance of successful implantation. In mice, 2-3 days pseudopregnant females are appropriate.

Germline transmission of the knockout construct may be determined using standard methods. Offspring resulting from implantation of embryos containing the ES cells described above are screened for the presence of the desired alteration (e.g., CATERPILLER knock-out). This may be done, for example, by obtaining DNA from offspring (e.g., tail DNA) to assess for the knock-out construct, using known methods (e.g., Southern analysis, dot blot analysis, PCR analysis). See, for example, Sambrook, et al. (1989) Molecular Cloning: A Laboratory Manual, Second Edition, Cold Spring Harbor Laboratory Press, Cold Spring Harbor, N.Y.). Offspring identified as chimeras may be crossed with one another to produce homozygous knock-out animals.

Mice are often used as animal models because they are easy to house, relatively inexpensive, and easy to breed. However, other knock-out animals may also be made in accordance with the present invention such as, but not limited to, monkeys, cattle, sheep, pigs, goats, horses, dogs, cats, guinea pigs, rabbits and rats. Accordingly, appropriate vectors and promoters well-known in the art may be selected and used to generate a transgenic animal deficient in CATERPILLAR expression.

Particular embodiments of the present invention are described in greater detail in the following non-limiting examples.

EXAMPLE 1

Identification of Mammalian Genes Containing CARD, Pyrin, Nucleotide Binding, and LRR Domains This example describes the identification of twenty-two known and novel NBD/LRR genes which are spread across 8 human chromosomes, with multi-gene clusters occurring on chromosomes 11, 16, and 19. The N-termini of these proteins vary, but most have a pyrin domain. The genomic organization demonstrates a high degree of conservation in the nucleotide-binding domain (NBD) and C-terminal leucine-rich repeat (LRR) encoding exons. Except for CIITA, all the predicted NBD/LRR proteins appear to contain an ATP-binding domain. Some have broad tissue expression, while others are restricted to immune cells.

Materials and Methods

Databases and Search Strategies. Searches were performed using the published Celera human genome scaffold data (Venter, et al. (2001) *Science* 291:1304); the NCBI "nr" database, containing GENBANK®, EMBL, DDBJ, PDB, and completed phase 3 and 4 high-throughput genomic sequencing (HTGS) sequences; and the NCBI genome database (Lander, et al. (2001) *Nature* 409:860). Initial searches were performed using the B cell form of CIITA protein sequence (Steimle, et al. (1993) *Cell* 75:135) as a query employing the BLAST search algorithms BLASTP and TBLASTN (FIG. 1). BLASTP identifies amino acid sequence similarities through query sequence comparison with database proteins and is more likely to find distant relationships than BLASTN (Pearson (2000) *Methods Mol. Biol.* 132:185). TBLASTN compares the query protein sequence with translations of all six reading frames of available nucleotide sequences and has the same advantages as BLASTP. Analogous domains of the resultant sequences were employed to identify additional sequences and/or confirm initial identities, this is known as DOUBLE-BLAST inspired by the ISS method (Park, et al. (1998) *J. Mol. Biol.* 284:1201; Karplus, et al. (1998) *Bioinformatics* 14:846) and is comparable in homolog detection to Hidden Markov Methods. LRP sequences, the N-terminal pyrin domains of DEFCAP, and the caspase recruitment domains (CARD) of Nod1 and Nod2 were used to perform similar searches. The N-terminal sequences of CIITA yielded no related sequences obviously belonging to an NBD/LRR protein.

Assembly of Putative Novel Genes and Construction of Genomic Maps. Pyrin and LRR sequences identified within contigs containing NBDs were examined for location and orientation to determine the likelihood of residing in the same operon as an identified NBD. Pyrin and LRR domains were considered contiguous with an NBD if they fell upstream and downstream of the NBD, respectively, in the same orientation. CARD domains occur both upstream (Nod 1/2) and downstream (DEFCAP) of the NBD (Hlaing, et al. (2001) *J Biol Chem* 276:9230), but none of the novel sequences contained CARD domains. As sequence data became available for more than a single domain, a putative genomic organization was generated by comparing the "cDNA" sequence to the genome sequence.

Cell Lines, Preparation of RNA, and RT-PCR. HeLa, MCF7, Jurkat, Raji, and RAMOS cell lines were cultured in either Dulbecco's Modified Eagle Medium (DMEM) (high glucose) or RPMI1640 with 10% fetal calf serum, L-glutamine, and penicillin/streptomycin. Peripheral blood leukocytes were obtained as buffy coats from the American Red Cross (Durham, N.C.). Total RNA was prepared using the SV Total RNA Isolation Kit (PROMEGA™, Madison, Wis.). Total RNA was reversed transcribed to cDNA using MMLV reverse transcriptase and amplified in an MJ Thermocycler (MJ Research, San Francisco, Calif.) in a separate reaction with primers specific for each target sequence. Amplification products were electrophoresed on 0.8% agarose and visualized with ethidium bromide.

Experimental Results

Identification of Novel CIITA-Related Sequences. BLAST searches of the published Celera and NCBI genomic databases using the NBD and LRR of CIITA, Nod1, Nod2, DEFCAP and resultant target sequences as queries revealed 22 potential genes and pseudogenes, including the presently known genes, unified by the presence of an NBD and downstream LRRs (Table 1). New genes were assigned a name based on chromosome number and order of discovery (e.g. 19.1, first found on chr. 19). Nod1, Nod2, and DEFCAP contain CARD domains which may be involved in recruiting caspases (Inohara, et al. (1999) *J. Biol. Chem.* 274:14560; Ogura, et al. (2001) *J. Biol. Chem.* 276:4812; Hlaing, et al. (2001) supra). DEFCAP also has an N-terminal Pyrin domain with homology to the familial Mediterranean fever protein (Bertin and DiStefano (2000) *Cell Death Differ.* 7:1273). BLAST searches were also performed for the CARD domains of Nod1/2, the pyrin domain of DEFCAP, and resulting target sequences. CARD domain homologs were not found for any of the novel sequences. The majority of the putative genes had upstream Pyrin domains, but the upstream N-terminal sequences of several remain unknown.

TABLE 1

| | N-terminus | P-loop (Kinase 1/G1)[1] |
|---|---|---|
| 1.1/CIAS1 | Pyrin | GAAGIGKT (SEQ ID NO:37) |
| Nod1 | CARD | GDAGVGKS (SEQ ID NO:38) |
| 11.1 | Pyrin | GSAGTGKT (SEQ ID NO:39) |
| 11.2 | Pyrin | GAAGVGKT (SEQ ID NO:40) |
| 11.4 | Pyrin | GPAGTGKT (SEQ ID NO:41) |
| 11.3 | ? | GTVGTGKS (SEQ ID NO:42) |
| 12 | Pyrin | None |
| CIITA | CARD, Acidic | GKAGQGKS (SEQ ID NO:43) |
| Nod2 | CARD ×2 | GEAGSGKS (SEQ ID NO:44) |
| 16.1 | ? | GKAGMGKT (SEQ ID NO:45) |
| 16.2 | ? | GVAGMGKT (SEQ ID NO:46) |
| NaIp1/DEFCAP | Pyrin | GAAGIGKS (SEQ ID NO:47) |
| NaIp2 | Pyrin | GPAGLGKT (SEQ ID NO:48) |
| 19.1 | ? | GPDGIGKT (SEQ ID NO:49) |
| 19.2 | Pyrin | GAPGIGKT (SEQ ID NO:50) |
| 19.3 | Pyrin | GAAGIGKS (SEQ ID NO:51) |
| 19.4 | Pyrin | GPAGVGKT (SEQ ID NO:52) |
| 19.5 | Pyrin ×2 | GPQGIGKT (SEQ ID NO:53) |
| 19.6 | Pyrin | GERASGKT (SEQ ID NO:54) |
| 19.7 | Pyrin | GRAGVGKT (SEQ ID NO:55) |
| 19.8 | ? | GKSGIGKS (SEQ ID NO:56) |
| *X* | ? | ACAGTGKT (SEQ ID NO:57) |
| Apaf1 | | GMAGCGKS (SEQ ID NO:58) |
| RPM1 | | GMGGSGKT (SEQ ID NO:59) |
| NAIP | | GEAGSGKT (SEQ ID NO:60) |
| HET-E | | GDPGKGKT (SEQ ID NO:61) |
| TP1 | | GQSGQGKT (SEQ ID NO:62) |
| G alpha 12 | | GAGESGKS (SEQ ID NO:63) |

| | GTP-$Mg^{+2}$ (G3)[2] | ATP-$Mg^{+2}$ (Kinase 2)[3] |
|---|---|---|
| 1.1/CIAS1 | — | LFLMD (SEQ ID NO:74) |
| Nod1 | — | LFTFD (SEQ ID NO:75) |
| 11.1 | — | LFILD (SEQ ID NO:76) |
| 11.2 | — | LFIID (SEQ ID NO:77) |
| 11.4 | — | LFILD (SEQ ID NO:76) |
| 11.3 | — | — |
| 12 | — | LFIMD (SEQ ID NO:78) |
| CIITA | DAYG (SEQ ID NO:64) | LLILD (SEQ ID NO:79) |
| Nod2 | — | LLTFD (SEQ ID NO:80) |
| 16.1 | — | LLIFD (SEQ ID NO:81) |
| 16.2 | — | LLILD (SEQ ID NO:79) |
| NaIp1/DEFCAP | DEPG[6] (SEQ ID NO:65) | LFILD (SEQ ID NO:76) |
| NaIp2 | DELG[6] (SEQ ID NO:66) | LFVID (SEQ ID NO:82) |
| 19.1 | — | LFIMD (SEQ ID NO:78) |
| 19.2 | — | LLLLD (SEQ ID NO:83) |
| 19.3 | — | LFIID (SEQ ID NO:77) |
| 19.4 | DICG[6] (SEQ ID NO:67) | LFVID (SEQ ID NO:82) |
| 19.5 | — | LFVID (SEQ ID NO:82) |
| 19.6 | — | LFILED (SEQ ID NO:84) |
| 19.7 | — | LFIID (SEQ ID NO:77) |
| 19.8 | DDLG[6] (SEQ ID NO:68) | LFIID (SEQ ID NO:77) |
| *X* | DPVG[6] (SEQ ID NO:69) | LLILD (SEQ ID NO 79) |
| Apaf1 | DKSG (SEQ ID NO:70) | LLILD (SEQ ID NO:79) |
| RPM1 | — | IVVLD (SEQ ID NO:85) |
| NAIP | — | LFLLD (SEQ ID NO:86) |
| HET-E | DHAG (SEQ ID NO:71) | YLIID (SEQ ID NO:87) |
| TP1 | DQNG[6] (SEQ ID NO:72) | VLIID (SEQ ID NO:88) |
| G alpha 12 | DKLG (SEQ ID NO:73) | — |

TABLE 1-continued

| | Guanine Binding (G4)[4] | Nucleotide Specificity[5] | LRR |
|---|---|---|---|
| 1.1/CIAS1 | — | ATP | Duplex |
| Nod1 | — | ATP | Single |
| 11.1 | — | ATP | Single |
| 11.2 | — | ATP | Duplex |
| 11.4 | — | ATP | Duplex |
| 11.3 | — | — | Non-Uniform |
| 12 | — | — | Single/Duplex |
| CIITA | SKAD (SEQ ID NO:89) | GTP[7] | Single |
| Nod2 | — | ATP | Single |
| 16.1 | — | ATP | Single |
| 16.2 | — | ATP | Single |
| NaIp1/DEFCAP | — | ATP | Single/Duplex |
| NaIp2 | — | ATP | Duplex |
| 19.1 | — | ATP | Duplex |
| 19.2 | — | ATP | Duplex |
| 19.3 | — | ATP | Duplex |
| 19.4 | — | ATP | Duplex |
| 19.5 | — | ATP | Duplex |
| 19.6 | — | ATP | Duplex |
| 19.7 | — | ATP | Duplex |
| 19.8 | — | ATP | Duplex |
| *X* | — | — | Duplex |
| Apaf1 | — | dATP[7]/ATP[7] | WD40 |
| RPM1 | — | ATP | LRR |
| NAIP | — | ATP | LRR |
| HET-E | TKHD (SEQ ID NO:90) | GTP/ATP | WD40 |
| TP1 | — | ATP | WD40 |
| G alpha 12 | SKQD (SEQ ID NO:91) | GTP[7] | — |

[1]Consensus P-loop motif, GXXXXGK(S/T (SEQ ID NO:92));
[2]Consensus Mg+2 site (G3), DXXG (SEQ ID NO:93);
[3]Consensus Mg+2 site (Kinase2), ψψψψD (SEQ ID NO:94), ψ=hydrophobic;
[4]Consensus Guanine-binding site (G4), (N/T/S)KXD (SEQ ID NO:95);
[5]Predicted nucleotide specificity;
[6]G3 motif occurring after kinase2;
[7]Published nucleotide specificity.
NAIP, CIITA, HET-E, and TP1 are the defining members of the NACHT family. Apaf1, RPM1, NAIP, HET-E, TP1, and G alpha 12 are shown for comparison purposes. Pseudogenes and suspected pseudogenes are shown in italics.

Figure 2A:
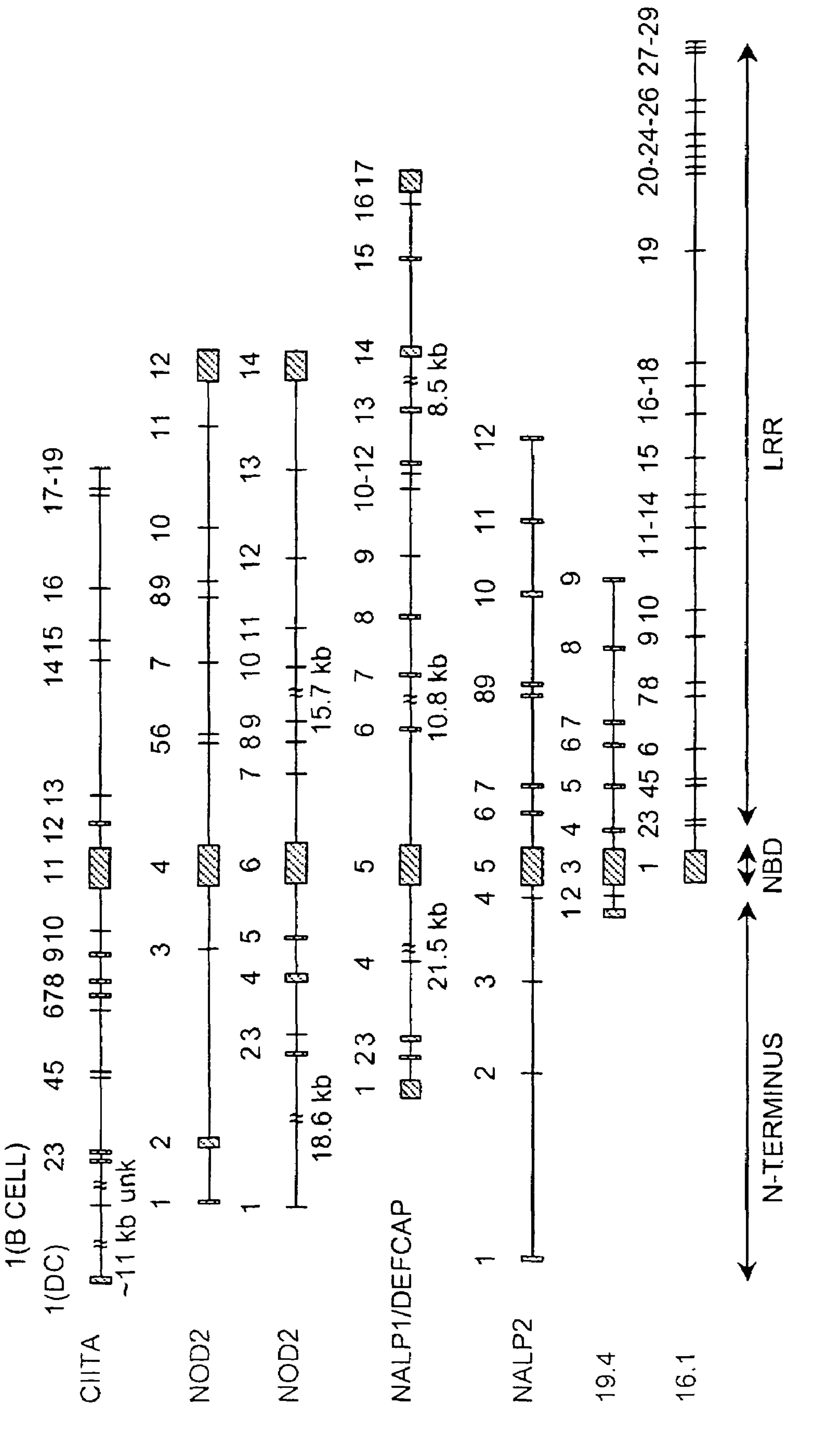
FIG. 2A depicts the genomic organization for known and some predicted members of the CATERPILLER family shown to scale. Black boxes represent exons. Unusually large introns are interrupted and their size indicated below in kilobase pairs. Exons with ambiguous positions are shown as grey boxes. The large 3' exons of Nod1 and Nod2 are 3' untranslated sequences.

Conservation of Intron-Exon Organization. Exon/intron sizes and positions were determined for the known and some predicted NBD/LRR proteins by the location of the sequence corresponding to the mRNA/cDNA, assuming intactness of the contig (FIG. 2A). The genomic organization was complex and remarkably similar for all of the sequences examined, with large NBD exons (~1500 nucleotides) and LRR exons of about 76 nucleotides, 174 nucleotides, or both, depending on the gene. CARD and Pyrin domains were approximately 300 nucleotides long.

CATERPILLER Domains. Distinct domains of each sequence are provided in Table 1. Nod1, Nod2, and CIITA had N-terminal CARD or CARD-like domains. Thirteen had N-terminal Pyrin domains. CIITA was unique in having an N-terminal acidic transactivation domain. Five of these sequences did not have CARD, Pyrin, or CIITA-like activation domains upstream of their NBDs. The diversity of these N-terminal sequences indicates multiple functional modes.

The predicted nucleotide specificity based on motifs found in the CATERPILLER genes is also provided in Table 1. This was compared to another family, containing plant and animal proteins, grouped on the basis of an NTPase domain and C-terminal repeats of either the LRR or WD40 type, called the NACHT family which includes NAIP, CIITA, HET-E and TP1 (Koonin and Aravind (2000) *Trends Biochem. Sci.* 25:223). The majority were predicted to be ATP binding proteins, with the exception of CIITA, which binds GTP, and HET-E. A GTP-binding protein-like magnesium coordination (G3) motif (DXXG; SEQ ID NO:93) occurred in a number of the other sequences, with the exception of the more distantly related Apaf1, it followed the more typical Kinase 2 site found in ATP-binding proteins.

The NBDs of these predicted proteins were aligned, each approximately 500 amino acids in length, and twelve groupings of conserved residues (motifs) were observed (FIG. 2B, FIGS. 3A-G). While the seven NACHT motifs were present, the larger number of compared sequences permitted a refined definition of the NACHT domain that excluded WD40 repeat-containing members thus distinguishing a CATERPILLER NBD from the broader NACHT family. These motif definitions also indicated a divergence between the majority of the NBDs provided herein and those like NAIP. Functionally important motifs may include motif I, which contains the Walker A sequence found in most nucleotide binding proteins (Traut (1994) *Eur. J. Biochem.* 222:9), and Motif III and V that overlap with or are adjacent to leucine-charged domain (LCD) motifs (Heery, et al. (1997) *Nature* 387:733); motifs important for CIITA function (Harton and Ting (2000) *Mol. Cell Biol.* 20:6185). Motif IV contains the Kinase 2 motif which coordinates magnesium ions in ATP binding proteins (Traut (1994) supra).

The presence of LRR sequences downstream of the NBD was required for inclusion as a CATERPILLER family member. The LRR sequences following NBDs had two exon arrangements, a "singlet" (~74 nucleotides) containing one motif iteration or a "duplex" (~180 nucleotides) containing two (Table 1, last column; FIG. 2A; FIGS. 3A-G). The sole requirement for inclusion as an LRR was conservation of the hydrophobic residues "leucines" comprising the motif. It is important to note that BLAST searches for LRRs may miss some sequences due to a greater likelihood of less similarity between non-LRR-motif residues. Thus, without actual cDNA clones it was impossible to be highly confident that all of the LRR exons downstream of the NBD had been identified for each putative gene. Given this caveat, it appears that all of the genes on chromosome 19 had doublet LRR exons while those on chromosome 16 had singlets. DEFCAP and the potential pseudogene 12, had both singlet and doublet exons.

Figure 4:
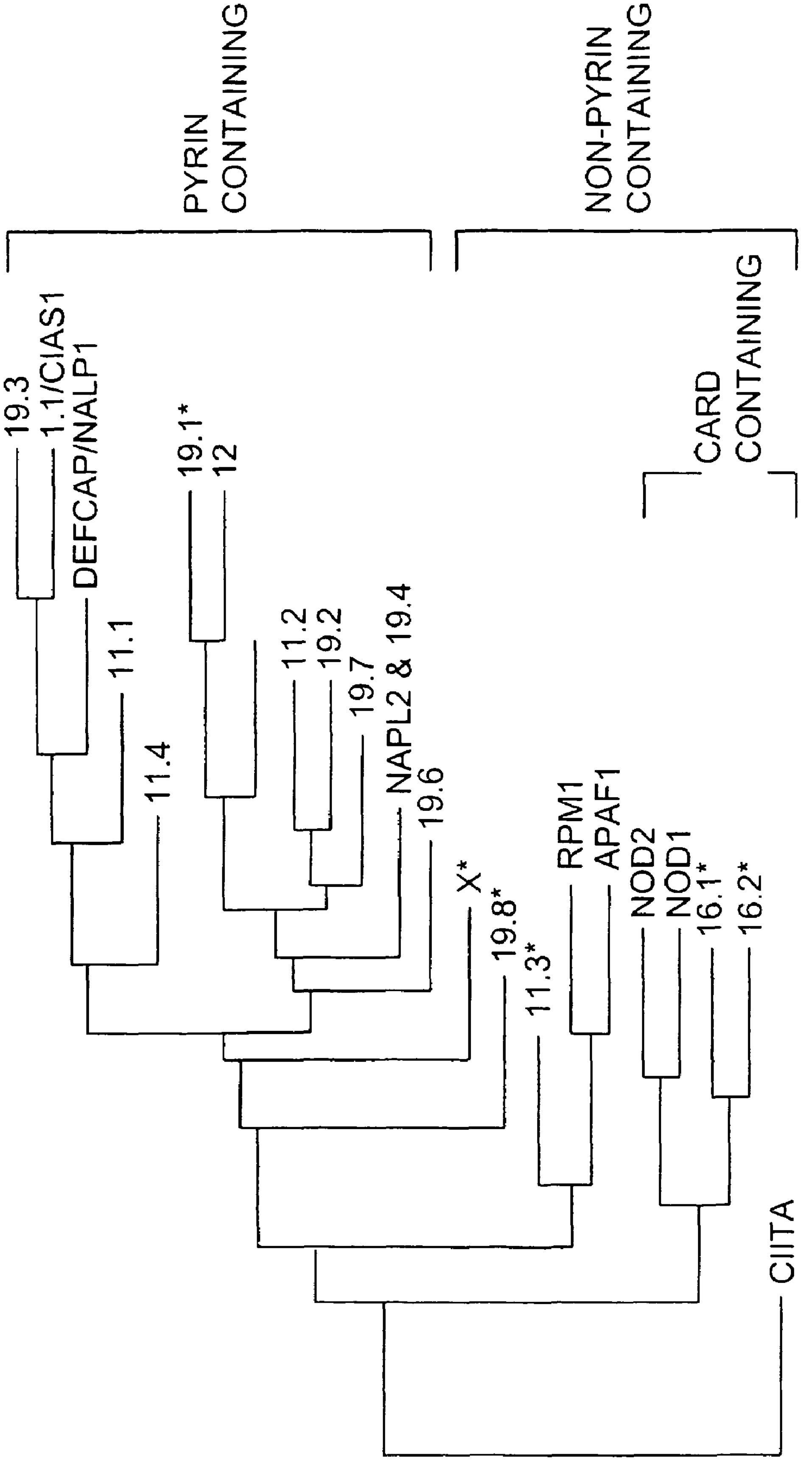
FIG. 4 illustrates a phylogenetic tree for NBDs. Deduced amino acid sequences from NBD exons were compared to one another using alignment and tree generation software in the DAMBE (Data Analysis in Molecular Biology and Evolution) software package. * indicates a predicted gene with unknown N-terminal sequences.

Phylogenetic Analysis of the NBD and Evolutionary Issues. An analysis using protein alignment and tree generation software (Data Analysis in Molecular Biology and Evolution; Xia and Xie (2001) *J. Hered.* 92:371) was performed to examine the potential phylogenetic relationship of the predicted NBD protein sequences (FIG. 4). Apaf1 and RPM1 (Table 1) were included as their NBD regions were similar to this family. Except for 11.3, the newly-identified NBD sequences were more closely related to one another than Apaf1 (FIG. 4), indicating that NBD/WD40-repeat proteins were more distantly related. The NBD of RPM1, an NBD/LRR R protein of *Arabadopsis*, was most closely related to Apaf1. The novel NBD most closely related to RPM1 was 11.3 which has an NBD exon interrupted by an intron. Consistent with divergent evolution, the NBDs of the known and putative proteins with upstream CARD domains were more closely related to each other than to those NBDs with upstream Pyrin domains which form their own grouping phylogenetically.

Figure 5:
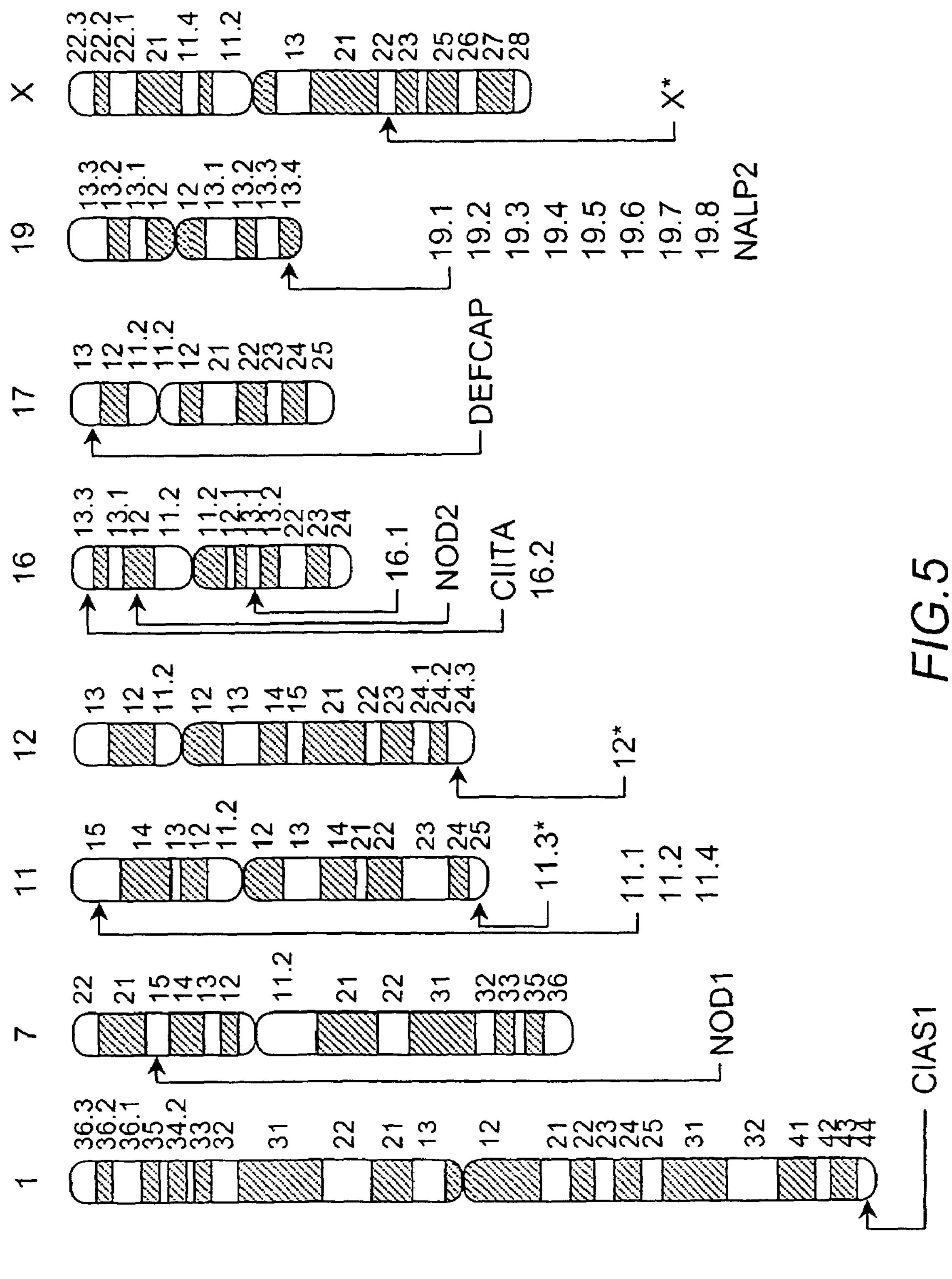
FIG. 5 depicts the chromosomal location of each known or predicted sequence as indicated. For chromosomal locations with multiple sequences, the name order does not correspond to the ordering on the chromosome.

The assignment of the CATERPILLER genes to chromosomal positions is shown in FIG. 5. Most were found in clusters on chromosomes 11, 16, and 19. Three occur at 11p15, three more between 16p12 and 16 pl3, and nine at 19q13. Proximities of the six sequences on a single contig at 19q13.4, indicates that gene duplication had occurred for these sequences. With the exception of four of these sequences, all were near the telomere, indicating that those found singly may have their origins in chromosomal recombination. Among those not at the telomeric end of chromosomes, one (X) may be a pseudogene. In *Saccharomyces*, fermentation gene alleles are thought to have been generated by the duplication of genes close to the telomeric end and subsequent genomic dispersion by recombination (Charron, et al. (1989) *Genetics* 122:307).

The presence of multiple individual exons containing one or two LRR indicates that exon shuffling may occur and that natural selection may favor the maintenance or elimination of a given LRR sequence or pair while simultaneously preserving other aspects of the gene in question. The specificity of plant R proteins is principally dependent upon the LRR and these are targets for diversifying selection (Dangl and Jones (2001) *Nature* 411:826). In Flax, a six amino acid difference in the LRR of P versus P2 determines Rust R protein specificity (Dodds, et al. (2001) *Plant Cell* 13:163). The LRRs of RPS2 contain a small stretch important for cooperation with host factors determining *Arabidopsis* resistance to *Pseudomonas syringae* (Banerjee, et al. (2001) *Genetics* 58:439). Unequal recombination, gene conversion, and accumulated, mutations may generate novel specificities for the NBD/LRR class of R proteins.

Evidence for Expression of the CATERPILLER Genes. Information available on the expression patterns of the known genes was available and reflected their biologic role. CIITA has three different isoforms arising from three different promoters. Nod1 has a wide tissue distribution (Inohara, et al. (1999) supra), while Nod2 and CIAS1 are restricted to monocytes, consistent with inflammatory roles (Hoffman, et al. (2001) *Nat. Genet.* 29:301; Ogura, et al. (2001) supra). The expression of the other sequences was examined by using the NCBI database to search for expressed sequence tags encoding at least part of the sequence (Table 2). UniGene sequence entries existed for CIAS1, Nod1, Nod2, DEFCAP, Nalp2, and 16.1. Fourteen of the genes were represented in the GENBANK® human est database. The gene identified herein as 19.3, also referred to herein as Monarch-1, has been previously described as a partial cDNA encoding a 344 amino acid protein (RNO2) comprised of leucine-rich repeats and is expressed in bone marrow, peripheral blood leukocytes, and nitric oxide treated HL-60 cells (Shami, et al. (2001) *Br. J. Haematol.* 112:138). No est entry was found for 11.2, 12, 19.1, 19.2, 19.5, 19.8, or X. A survey of the expression of these new genes was conduced and is summarized in Table 2. Message was detected for every non-pseudogene except 19.1 and 19.2. Nearly all of the family members were expressed in hematopoeitic cells and are likely restricted as ubiquitous expression was uncommon.

TABLE 2

| Name | UniGene | Genbank EST | Hematopoeitic[1] | Somatic[2] |
|---|---|---|---|---|
| 1.1/ CIAS1 | Hs.159483 | + | + | – |
| Nod1 | Hs.19405 | + | +[3] | +[3] |
| 11.1 | | + | + | + |
| 11.2 | | | + | – |
| 11.3 | | + | + | + |
| 11.4 | | + | + | – |
| 12 | | | NT | NT |
| CIITA | | + | +[3] | +[3,4] |
| Nod2 | Hs.135201 | + | +[3] | –[3] |
| 16.1 | Hs.10888 | + | + | + |
| 16.2 | | + | + | – |
| DEFCAP | Hs.104305 | + | + | + |
| 19.1 | | | – | – |
| 19.2 | | | – | – |
| 19.3 | | + | + | |
| 19.5 | | | + | – |
| 19.6 | | + | + | – |
| 19.7 | | + | + | – |
| 19.8 | | | + | – |
| Nalp2/19.4 | Hs.6844 | + | + | – |
| X | | | NT | NT |

For EST searches, stretches of significant identity to translated EST sequences were considered a positive match.
[1]Primary human hematopoeitic cells or cell lines.
[2]HeLa and MCF7 (non-small cell lung carcinoma).
[3]From published sources.
[4]When induced. Expression was determined by reverse transcriptase-PCR using cDNA derived from the indicated sources.
NT = not tested.

Immunologic Significance. Of the known genes, CIITA, CIAS1, and Nod2 are clearly linked to immune function. CIITA directly controls major histocompatibility complex II (MHC II) gene expression, whereas CIAS1 in familial cold urticaria and Nod2 in Crohn's disease are likely regulating inflammatory responses. DEFCAP and Nod1 both promote apoptosis and activate NF-κB. Activation of NF-κB is also observed for Nod2, and under appropriate conditions for CIAS1. These functions are reminiscent of plant R proteins that promote plant responses similar to innate immune functions (Dangl and Jones (2001) supra).

Innate immune responses mediated by Toll in response to fungal pathogens in *Drosophila* highlight the importance of receptors recognizing specific pathogen-associated molecular patterns (Medzhitov (2001) *Nature Rev. Immunol.* 1:135). LRR-containing proteins in plants and animals serve a similar function which is supported by the threading result with selected LRRs indicating that LRR structural features are conserved in the NBD/LRR family. Toll-like Receptors have extracellular LRRs mediating recognition of a variety of microbial derivatives (Poltorak, et al. (2000) *Proc. Natl. Acad. Sci. USA* 97:2163; Bauer, et al. (2001) *Proc. Natl. Acad. Sci. USA* 98:9237). The LRRs of plant R proteins likewise recognize avirulence proteins from plant pathogens and provide specificity (Van Der Hoorn, et al. (2001) *Plant Cell* 13:273). Recent studies of Nod1 and Nod2 demonstrate that both require their LRRs for responses to various bacterial LPSs (Inohara, et al. (2001) *J. Biol. Chem.* 276:2551). CIITA's LRRs, while not known to interact with any pathogen-specific molecule, are functionally necessary, involved in self-association, interaction with an endogenous protein, and regulation of nuclear import (Linhoff et al. (2001) *MCB* 21:3001; Harton et al., (2002) *Hum. Immunol.* 63:588). Thus, these LRRs may serve as versatile recognition domains with specificity for self-interaction, protein/lipid/sugar recognition, or both. Deletion of the LRRs from Nod1/2, DEFCAP, and CIAS1 enhances their activities indicating that these LRRs are important sites of regulation.

NBD/LRR Genes in Other Organisms. The number of identified mammalian NBD/LRR sequences was significantly smaller than that occurring in some plants (Pan, et al. (2000) *J. Mol. Evol.* 50:203). The mammalian family may be larger than described herein as NAIP and Ipaf (CARD12), despite having NBDs and LRRs, were not detected using the parameters of this study, likely due to the absence of some of the CATERPILLER motifs in their NBDs. Limited BLAST searches of translated nucleotide sequences from *Drosophila* and *C. elegans* genomic databases failed to identify any NBD/LRR genes. A similar search of the *Danio rerio* (zebrafish) database did yield likely NBD/LRR sequences and the mouse genome had at least as many genes in this family as humans. The preponderance of NBD/LRR proteins in plants may be due to reliance upon individual effector molecules for recognizing pathogen-specific products. Higher order eukaryotes have developed a highly complex adaptive immune system driving a staggering array of protein-specific immune responses with a limited number of genes.

N-terminal variation in the known and predicted genes indicates a subdivision of CATERPILLER proteins; Group I, CARD-containing (e.g., Nod1); Group II, Pyrin-containing (e.g., DEFCAP); Group III, transactivation domain (e.g., CIITA); and unknown (e.g., 16.1)(Table 1). However these grouping may be oversimplified. For example, multiple cell-type-specific forms of CIITA are known. The dendritic cell form has a CARD-like N-terminus followed by the activation domain, although no caspase-recruitment activity has been described (Nickerson, et al. (2001) *J. Biol. Chem.* 276:19089). Nod2 and cryopyrin are also expressed as multiple transcripts (Hoffman, et al. (2001) supra; Ogura, et al. (2001) supra). In addition, self-association has been demonstrated for CIITA and Nod1, while heterodimerization of CIAS1 with apoptotic protein ASC may involve CIAS1's pyrin domain (Manji, et al. (2002) *J. Biol. Chem.* 277:11570; Ting and Trowsdale (2002) *Cell* 109 Suppl:S21; Inohara, et al. (1999) supra). Self- and hetero-association may amplify and generate diversity necessary to mediate appropriate responses.

Six of the CATERPILLAR genes predicted herein were cloned and more fully characterized in detail in the following examples.

EXAMPLE 2

Characterization and Functional Analysis of CATERPILLER Monarch-1

This example describes the characterization of nucleic acid sequences encoding murine and human Monarch-1 proteins. Monarch-1 has four different splice forms due to the differential splicing, of LRR motifs. The nucleic acid sequences encoding a full-length human Monarch-1 protein sequence are set forth as SEQ ID NO:1 and SEQ ID NO:2, respectively. The nucleic acid and protein sequences of a human splice isoform II are set forth as SEQ ID NO:3 and SEQ ID NO:4. The nucleic acid and protein sequences of a human splice isoform III are set forth as SEQ ID NO:5 and SEQ ID NO:6. The nucleic acid and protein sequences of a human splice isoform IV are set forth as SEQ ID NO:7 and SEQ ID NO:8. It has now been found that Monarch-1 is expressed by immune cells; is part of the endotoxin tolerant pathway; inhibits cellular responses induced by endotoxin from bacteria; inhibits IFI16, an interferon responsive protein; causes changes in cytokine mRNA (TNF-α and IL-10) expression; functions in the enhancement of class I MHC gene expression; enhances IL-6, IL-10 and IL-1β cytokine production; and interacts with tubulin, vimentin, hsp-70, TNIK, NIK, CARD10, TRAF6 and CIAS1. The results provided herein indicate that Monarch-1 regulates molecules important in the inflammatory response and cell survival.

Materials and Methods

Reagents. [(Z)-1-[2-(2-Aminoethyl)-N-(2-ammonioethyl) amino]diazen-1-um-1,2-diolate] (Deta-NO), an inducer of nitric oxide, was used at 125 μmol/l (Alexis Biochemicals, San Diego, Calif.). IFNγ was used at 1000 U/ml, TGFβ at 1 ng/ml, TNFα at 20 ng/ml (Peprotech, Rocky Hill, N.J.) and phorbol 12-myristate 13-acetate (PMA) (Sigma, St. Louis, Mo.) at 10 ng/ml.

Cell Lines. HeLa cells were transfected with 1 μg of pcDNA3-HA vector or HA-tagged Monarch-1 via FUGENE® (Roche, Indianapolis, Ind.) and selected with 500 μg/ml G418. U937 siRNA clones were selected with 500 μg/ml puromycin.

Cell Preparation and Purification. BMC were isolated from buffy coats (American Red Cross, Durham, N.C.) using Lymphocyte Separation Media (ICN, Costa Mesa, Calif.). T cells, B cells, monocytes and CD15+ granulocytes were individually selected by a magnetic-activated cell sorting (MACS) column (Miltenyi Biotech, Auburn, Calif.). Monocyte-derived dendritic cells were generated by differentiating peripheral blood mononuclear cells (PBMCs) with GM-CSF and IL-4 for 8 days.

TLR Luciferase Reporter Gene Assays. HEK293T cells were plated at $1\times10^4$ cells/well in 96-well plates and transfected the following day using FUGENE™ transfection reagent (Roche, Indianapolis Ind.) in accordance with the manufacturer's recommendations. Cells were transfected with 50 ng of NF-κB-Iuc reporter and 200 ng of vector, MyD88, TRAF6 or IRAK1 expression plasmids to induce NF-κB activity. Cells were cotransfected with either 400 ng of vector or Monarch-1 expression plasmid. Amounts of the relevant expression plasmids were transfected as indicated, maintaining the total amount of DNA constant using pcDNA3 empty vector. Cells were harvested 36 hours after transfection and equal amounts of protein were assayed for luciferase activity following standard procedures. Equal protein amounts were determined using the Bradford protein assay (BIO-RAD®, Hercules, Calif.).

RNA Preparation and Real-Time PCR. Total RNA was isolated using the SV40 Total RNA System (PROMEGA™, Madison, Wis.) with an additional DNase I digestion step. Real-Time PCR was performed with the TAQMAN® sequence detection system (Applied Biosystems, Foster City, Calif.). Primers and probes for mouse Monarch-1 were: forward 5'-TGCTACAAGTCCGGGACAAA-3' (SEQ ID NO:96); reverse 5'-GCCCAGTTCTGGGTCATTT-3' (SEQ ID NO:97); and probe 5'-CAGCAGAGCCTCAGAGTGCTTCG-3' (SEQ ID NO:98). Primers and probe for 18S ribosomal RNA were: forward 5'-GCTGCTGGCACCAGACTT-3' (SEQ ID NO:99); reverse 5'-CGGCTACCACATCCAAGG-3' (SEQ ID NO:100); and probe 5'-CAAATTACCCACTCCCGACCCG-3' (SEQ ID NO:101). Primers and probe for HLA-G were: forward 5'-AGACCCTGCCGCGCTACT-3' (SEQ ID NO:102); reverse 5'-TCCACTGGAGGGTGTGAGAAC-3' (SEQ ID NO:103); and probe 5'-AACCAGAGCGAGGCC-3' (SEQ ID NO:104). Primers and probe for HLA-B were: forward 5'-GGGACCGGGAGACACAGAT-3' (SEQ ID NO:105); reverse 5'-GCGCAGGTTCTCTCGGTAAG-3' (SEQ ID NO:106); and probe 5'-CAAGACCAACACACAG-3' (SEQ ID NO:107). Primers and probe for LMP7b were: forward 5'-GCCGCAGGGCTATTGCTTA-3' (SEQ ID NO:108); reverse 5'-CATATTGACMCGCCTCCAGAA-3' (SEQ ID NO:109); and probe 5'-CACTCACAGAGACAGCT-3' (SEQ ID NO:110). Primers and probe for GAPDH were: forward 5'-ACCTCAACTACATGGTTTAC-3' (SEQ ID NO:111); reverse 5'-GAAGATGGTGATGGGATTTC-3' (SEQ ID NO:112); and probe 5'-CAAGCTTCCCGTTCTCAGCC-3' (SEQ ID NO:113). Results were normalized to the GAPDH mRNA and 18S ribosomal RNA internal controls and were expressed in relative numbers.

Monarch-1 RT-PCR. To clone the N-terminal region of human Monarch-1, the following primers were used: Monarch-1 N-term forward 5'-GGGGTACCGCTACGAACCGCAGGCAGGGACG-3' (SEQ ID NO: 114); Monarch-1 N-term reverse 5'-CAGCCTGGTCACGTCCTGGTCTG-3' (SEQ ID NO:115). To clone the suspected C-terminal region and identify LRR splice forms, the following primers were used: Monarch-1 C-term forward 5'-CAGAAGGACATCAACTGTGAGAG-3' (SEQ ID NO:116); Monarch-1 C-term reverse 5'-GCTCTAGACAGCAGATAGGACCATTCAGCAG-3' (SEQ ID NO:117). The One-Step RT-PCR Kit (QIAGEN®, Valencia, Calif.) was employed following the manufacturer's instructions. For expression analysis, the primers used were Monarch-1 pyr-NBD forward 5'-TTGAGCGGATAAACAGGAAGGAC-3' (SEQ ID NO:118) and Monarch-1 pyr-NBD reverse 5'-ATCTCCCTGCAGTTGATGTAGAAG-3' (SEQ ID NO:119).

5' RACE. 5' RACE was performed using two gene-specific primers following the manufacturer's protocol (Roche, Indianapolis, Ind.). The gene-specific primers were: SP1-5'-CGTCTGGCTCAAAGAGGGTCTCTATC-3' (SEQ ID NO:120) and SP-2-5'-CTGCGGACATAGTCCCTGTAGGTTTC-3' (SEQ ID NO:121). The longest clone was selected as the 5' start of the Monarch-1 mRNA.

Stimulation of Cells with Bacterial Components. Primary human adherent cells, granulocytes or the Thp-1 monocytic cell line were stimulated for the indicated timepoints with lipopolysaccharide (LPS), unextracted LPS, or phenol-extracted LPS at 200 ng/ml as indicated. Lipoteichoic acid (LTA) was used at 1 μg/ml and Pam3Cys at 100 ng/ml. Cells were harvested at the indicated timepoints and analyzed for Monarch-1 expression using real-time PCR. For tolerance studies, Thp-1 cells were initially stimulated at 200 ng/ml for 18 hours, washed and rested for 1 hour, and then restimulated with 1 μg/ml LPS for 6 hours.

AFFYMETRIX® Analysis. Total RNA from pcDNA-HA and HA-Monarch-1 HeLa stable clones was prepared using RNEASY® Mini columns (QIAGEN®, Valencia, Calif.). Ten μg of RNA were reverse-transcribed using Superscript II (STRATAGENE®, La Jolla, Calif.), labeled using the Enzo Bioarray High Yield RNA Transcript Labeling Kit (Enzo Diagnostics, Inc., New York, N.Y.), and analyzed on HG U133A chips according to the AFFYMETRIX® technical manual (http://www.affymetrix.com). Sample quality was assessed by examining 3'-5' intensity ratios of control genes. Arrays were scaled to an average intensity of 2500, and expression data analyzed using GENESPRING® software (Silicon Genetics, Redwood City, Calif.). Altered genes were identified by filtering for increase or decrease in all three Monarch-1-expressing clones compared to their respective control clone of 1.4-fold or more, with a minimum hybridization signal of 500 in the higher expressed sample. P values were determined using AFFYMETRIX® Suite 5.0.

Cytometric Fluorometric Analysis of HLA. Flow cytometry was performed using well-known methods (Martin, et al. (1997) *Immunity* 6:591). FITC-conjugated human pan-reactive HLA antibody (CalTag, Burlingame, Calif.) and control FITC mouse IgG2a κ isotype antibody (Pharmingen, San Diego, Calif.) were utilized.

Small Interference RNA (siRNA) Construction and Transfection. Wild-type and mutant human Monarch-1 short hairpin RNAs were stably expressed in the human U937 or THP-1 monocyte cell line by transfection of plasmids containing short hairpin RNA transcription cassettes followed by clonal selection in puromycin using well-known methods. The target sequence was: GTCCATGCTGGCACACAAG (SEQ ID NO:122) and the mutant sequence was: GTCCATGCTAACACACAAG (SEQ ID NO:123).

Cytometric Bead Assay (QBA). Stable THP-1 clones from wild-type and mutant human Monarch-1 siRNA were stimulated with phenol purified LPS for 48 hours. Supernatants were subjected to an inflammatory cytokine CBA panel following the manufacturer's instructions (BD Pharmingen, San Diego, Calif.). Flow cytometric analysis was performed using standard methodologies.

Cell Culture, Plasmids and Antibodies. 293T cells (Gene Hunter) were maintained in DMEM supplemented with 10% fetal calf serum, 100 mM penicillin, and 100 mM streptomycin and cultured at 37° C. and 5% $CO_2$. cDNA expressing human Monarch-1, TRAF6, MyD88, and IRAK1 were cloned into a pcDNA3-based vector in frame with a double 5' HA tag sequence. FLAG®-tagged Monarch-1 and CIAS1 were amplified by PCR to contain an N-terminal FLAG®-tag and cloned into pcDNA3.1 (INVITROGEN™, Carlsbad, Calif.). The pCMV-Sport6 vector containing NF-κB Inducing Kinase cDNA was obtained from the Mammalian Genome Collection (Image ID#5497185). Anti-Flag M2-agarose was obtained from Sigma (St. Louis, Mo.) and the anti-HA antibody 12C5 was obtained from Roche (Indianapolis, Ind.). The anti-NIK antibody (H-248) was obtained from Santa Cruz Biotechnology, Inc. (Santa Cruz, Calif.).

Transfections and Immunoprecipitations. 2.5 million 293T cells were seeded in 10-cm cell culture plates. Eighteen to twenty-four hours later, 3 μg of each of the indicated plasmids was transfected using FUGENE6™ (Roche, Indianapolis, Ind.) at a 3:1 FUGENE6™ to DNA ratio and the cells were incubated an additional 18 to 24 hours. Cells were lysed in 0.5% NP-40, 150 mM NaCl, 50 mM Tris pH 8.0, 160 mM EDTA, 50 mM NaF, 10 mM sodium phosphate supplemented with protease inhibitor cocktail (Roche, Indianapolis, Ind.). Nuclei were removed and the resulting supernatant was pre-cleared with mouse IgG-conjugated agarose (Sigma, St. Louis) for 1 hour. FLAG®-tagged proteins were subsequently immunoprecipitated overnight with 35 μl M2-agarose equilibrated in lysis buffer. Beads were washed four times in lysis buffer and proteins eluted in sample buffer (20% Glycerol, 4% SDS, 130 mM Tris pH 6.8, 20 mM DTT) for western blot analysis.

Western Blot Analysis. Proteins were separated by polyacrylamide gel electrophoresis and transferred onto nitrocellulose membranes (BIO-RAD®, Hercules, Calif.). Membranes were blocked in 1% BSA in Tris-buffered saline-Tween (TBS-T; 10 mM Tris pH 7.5, 150 mM NaCl, 0.05% Tween-20) for one hour then incubated with the indicated primary antibody overnight. Membranes were washed five times in TBS-T and incubated with the appropriate horseradish peroxidase-conjugated secondary antibody for 30 minutes. Following five additional washes in TBS-T, proteins were visualized by Enhanced Chemiluminescence (Pierce Chemical Co., Rockland,).

Two Dimensional Gel Electrophoresis. Ten 10-cm plates were transfected with FLAG®-tagged Monarch-1 or empty vector as described. Following immunoprecipitation, the beads were combined into one sample and protein complexes were eluted with rehydration buffer (8 M urea, 2 M thiourea, 2% CHAPS, 20 mM DTT, 0.7% immobilized pH gradient (IPG) buffer ampholytes (AMERSHAM™, Piscataway, N.J.). Proteins were separated based on isoelectric point in the first dimension using IPG strips (AMERSHAM™, Piscataway, N.J.) for 57,700 volt hours. The IPG strips were transferred to pre-cast 10% polyacrylamide gels (BIO-RAD®, Hercules, Calif.) and the proteins separated by molecular weight in the second dimension. Protein spots were visualized by silver staining (Blum, et al. (1987) *Electrophoresis* 8:93-99). Protein profiles were compared between empty vector-transfected and FLAG®-Monarch-1-transfected samples and spots unique to FLAG®-Monarch-1-transfected samples were picked for mass spectrometry analysis. Excised protein spots were trypsin digested and processed for MALDI-MS. Protein identities were determined by comparing peptide mass fingerprints to the NCBI, SwissProt, and TrEMBL protein databases using the following software: Mascot (Matrix Sciences, London, UK), Profound (University of California-San Francisco, Calif.), and PeptIdent (EMBL).

RNA Interference Vector for in vivo Knockdown in Mice. An RNA interference vector containing the siRNA provided herein is inserted into a plasmid wherein transcription of the Monarch-1 specific siRNA is under the control of a pol III promoter. Using this plasmid, the siRNA to Monarch-1 is expressed in hematopoietic stem cells. Alternatively, the siRNA is inserted into a targeting vector and ES cells harboring this vector are generated and screened for homologous recombination of the Monarch-1 gene. ES cells with a Monarch-1 gene knockout are used to generate a Monarch-1 knockout mouse.

Experimental Results

Identification of the Human Monarch-1 cDNA. Genes of novel NBD/LRR proteins with structural similarities to CIITA were identified in searches of the published Celera and the NCBI human genome databases (EXAMPLE 1). One predicted gene, Monarch-1 was cloned by RT-PCR using primer pairs specific for nucleic acid sequences encoding both the identified N- and C-terminal regions of the protein. The 5' end of the longest clone was isolated using RACE-PCR of cDNA from U937 cells. The full-length human cDNA, corresponding to accession number AY116204 (SEQ ID NO:1; FIGS. 6A-B), was 3731 bp long with a 220 bp 5'-UTR, a 323 bp 3'-UTR and a 3189 bp open reading frame. Monarch-1 is located on human chromosome 19q13.4. Comparison with known mRNAs in the database revealed the 3' one-third of this gene was previously identified as RNO2 (Shami, et al. (2001) *Br. J. Haematol.* 112:138). The Monarch-1 cDNA, contained in ten exons, encoded a predicted protein of 1063 amino acid residues (SEQ ID NO:2; FIG. 6C) with a predicted molecular mass of 118 kDa. Multiple Monarch-1 splice forms were identified by conducting RT-PCR on PBMC total RNA using primers spanning the end of the NBD through the C-terminal LRR region of Monarch-1. At least four splice forms of the Monarch-1 LRR region were evident. Sequence analysis of the four prominent bands showed that these novel splice forms corresponded to differential splicing of the LRR and were identified as accession number AY116205 (SEQ ID NO:3; FIGS. 6D-E), AY116206 (SEQ ID NO:5; FIGS. 6G-H), and AY116207 (SEQ ID NO:7; FIGS. 6J-K). The full-length Monarch-1 mRNA contains 10 exons and encodes isoform I (SEQ ID NO:2), while nucleic acids encoding isoform II (SEQ ID NO:4; FIG. 6F) lack exon 9, nucleic acids encoding isoform III (SEQ ID NO:6; FIG. 6I) lack exons 7 and 8, and nucleic acids encoding isoform IV (SEQ ID NO:8; FIG. 6L) lack exons 7 through 9. Analysis of Monarch-1 using RT-PCR with primers specific for nucleic acids encoding the N-terminal region indicated that alternative N-terminal splice forms do not exist.

Figure 7A:
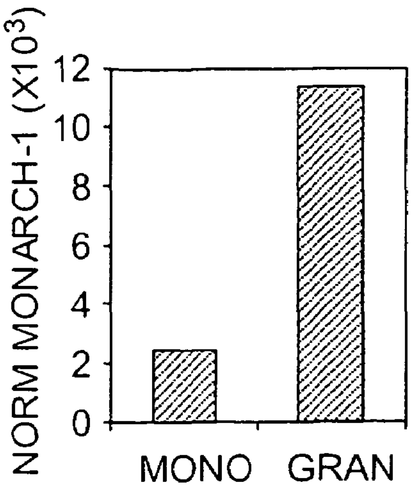
FIG. 7A shows the expression of Monarch-1 in separated human myeloid cell populations as determined by real-time PCR.
Figure 7B:
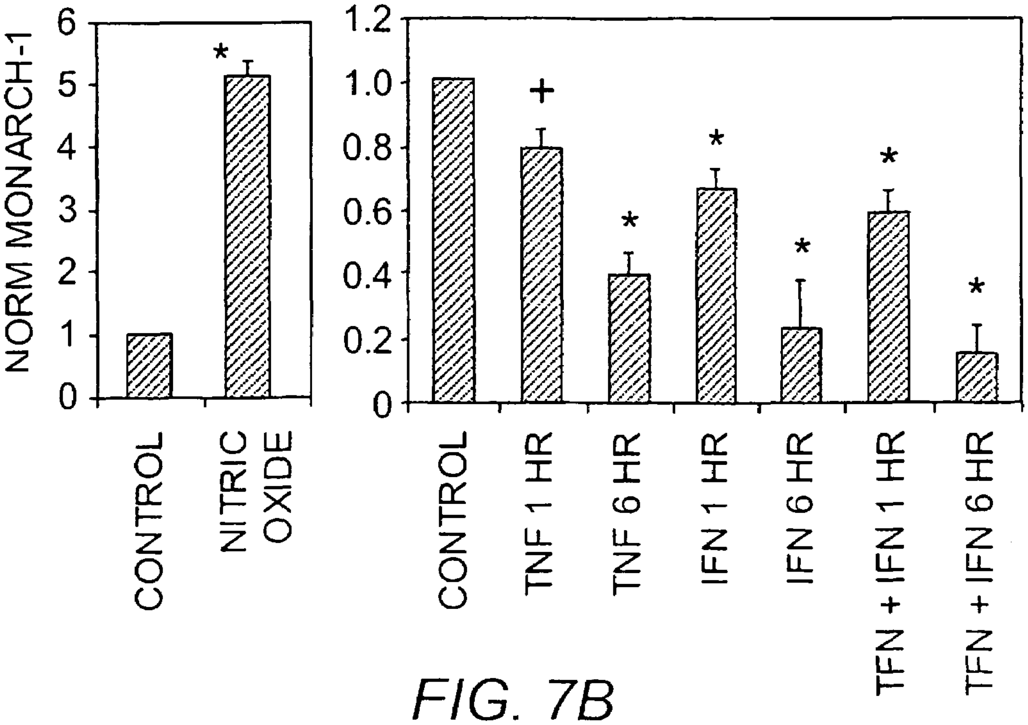
FIG. 7B shows Monarch-1 expression in primary adherent cells after stimulation with DETA-NO, with TNFα or IFNγ alone, or in combination as determined by real-time PCR. Monarch-1 expression was normalized to the expression of 18S rRNA. Student t-test was performed on control compared to treated cells (*=p<0.01, +=p<0.05). Three separate cell preparations were used and tested.

Expression of Monarch-1 is Predominantly in Myeloid-Monocytic Cells. RT-PCR showed expression in U937 and HL-60 cells but not T/B or non-hematopoietic cell lines. Monarch-1 expression was assessed in PBMC subpopulations by RT-PCR and showed expression in dendritic cells, monocytes and granulocytes. A faint band was detected in the lymphocyte preparation, however this may have been due to contamination as these same preparations showed a faint band for the myeloid genes, CD14 and CD15. To more definitively compare Monarch-1 expression among the myeloid-monocytic cells, real-time PCR analysis was employed using forward primer 5'-AGAGGACCTGGTGAGGGATAC-3' (SEQ ID NO:124), reverse primer 5'-CTTCCAGAAGGCATGTTGAC-3' (SEQ ID NO:125) and probe 5'-CCCGTCCTCACTTGGGAACCA-3' (SEQ ID NO:126). High levels of Monarch-1 were detected in granulocytes, with lower expression observed in monocytes (FIG. 7A). An increase in Monarch-1 expression was observed in monocytes in response to DETA-NO (an activator of nitric oxide) consistent with previous findings of nitric oxide induction of RNO2 mRNA expression (Shami, et al. (2001) supra). In contrast, TFN-α, IFNγ, or a combination of the two decreased Monarch-1 expression in a time-dependent fashion (FIG. 7B).

Figure 8:
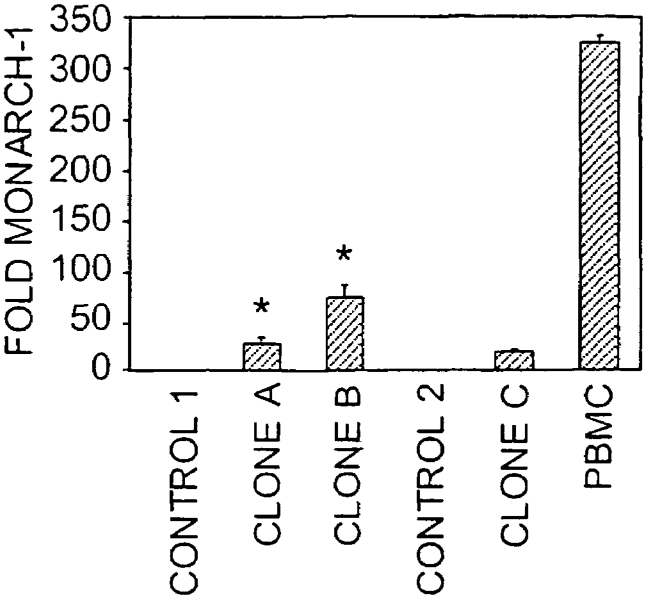
FIG. 8 shows Monarch-1 expression in Hela lines stably transfected with Monarch-1 as determined by real-time PCR. Monarch-1 expression in total PBMCs was included for comparison. The level of Monarch-1 expression was normalized to the expression of GAPDH. Student t-test was performed on controls compared to stably transfected clones (*=p<0.01).

Identification of Monarch-1 Regulated Genes by DNA Microarray Analysis. The downstream effects of increased Monarch-1 were determined using AFFYMETRIX® DNA array analysis to compare gene profiles in the presence or absence of Monarch-1. Stable clones expressing Monarch-1 were made in the HeLa cell line because this cell line does not express Monarch-1 (FIG. 8). Two sets of stable expressing Monarch-1 clones were independently produced on different days by transfection of HeLa cells with either the empty vector control, pcDNA, or with a pcDNA-HA-tagged Monarch-1 expression vector and selected for neomycin resistance. The first experiment resulted in two Monarch-1-containing clones, clone A with lower Monarch-1 expression and clone B with higher expression. The second experiment resulted in one clone, C, with intermediate expression. Analysis of the Monarch-1 expression level in different RNA preparations of these clones relative to total primary human PBMCs indicated that the clones expressed lower levels of Monarch-1 than PBMCs. Thus, changes detected in Monarch-1 expressing lines are relevant and not due to the overexpression of Monarch-1. Clones with a higher Monarch-1 level were not obtained.

DNA microarray analysis was performed for control and Monarch-1 expressing stable clones using AFFYMETRIX® chips comprising approximately 22,000 gene sequences. The most prominent change was a cluster of nine MHC class I-related sequences, including HLA-B (three sequences), HLA-C (two sequences), HLA-F (one sequence), HLA-G (two sequences), and the proteosomal subunit LMP7 required for processing of class I peptides (Table 3, samples with "x"). Multiple appearances of HLA-B, C, and G indicated the validity of these findings. Regulation of MHC-II genes by Monarch-1 was not observed. Expression patterns of all HLA genes was further analyzed to assess if additional MHC-I genes may be modulated by Monarch-1 but were not included due to the stringent cutoff standards used for filtering. All classical MHC-I (HLA-A, B and C) and nonclassical MHC-1 genes (HLA-E, F and G) were upregulated by Monarch-1.

TABLE 3

| Accession # | Clone A | Clone B | Clone C | Gene Name |
|---|---|---|---|---|
| AI923492 | 1.3* | 1.6* | 2.0* | HLA-A |
| AA573862 | 1.4* | 1.8* | 2.4* | HLA-A |
| L07950x | 1.7* | 2.7* | 2.6* | HLA-B |
| D83043x | 1.8* | 2.6* | 4.0* | HLA-B |
| L42024x | 1.5* | 2.3* | 3.1* | HLA-B |
| AK024836x | 1.8* | 2.2* | 3.1* | HLA-C |
| U62824 | 1.3* | 2.0* | 2.1* | HLA-C |
| M12679x | 1.4* | 1.8* | 3.7* | HLA-C |
| BC004489x | 1.5* | 1.9* | 3.9* | HLA-C |
| M31183 | 2.4* | 2.9* | 1.1+ | HLA-E |
| NM_005516 | 1.6* | 2.0* | 1.1* | HLA-E |
| NM_018950 | 1.6* | 2.0* | 1.9* | HLA-F |
| AW514210x | 1.4* | 2.0* | 1.5* | HLA-F |
| AF226990 | 2.0* | 2.8* | 3.8* | HLA-G |
| M90686x | 2.3* | 2.7* | 2.1* | HLA-G |
| M90684x | 1.3* | 1.8* | 2.5* | HLA-G |
| M80469x | 1.1 | 1.6+ | 2.5* | HLA-J |
| U17496x | 1.5* | 2.9* | 4.1* | LMP7 |

Fold induction for each clone was calculated relative to its control clone.
"x" indicate genes identified in the original analysis.
P values were determined using AFFYMETRIX ® Suite 5.0 (*= $p < 0.01$, += $p < 0.05$).

Figures 9A, 9B, 9C:
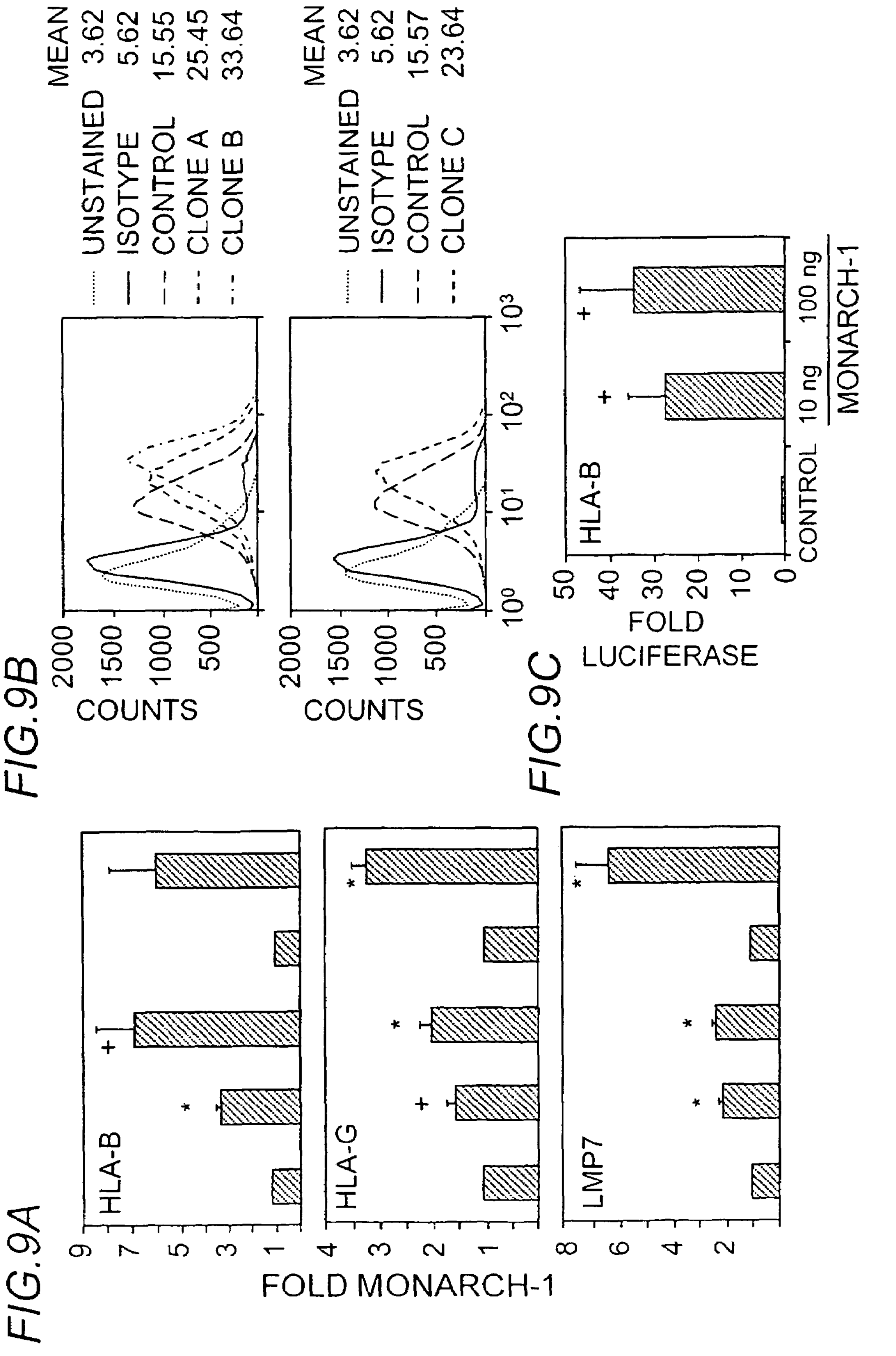
FIG. 9A shows the analysis of selected Monarch-1 regulated genes as determined by real-time PCR. Expression was normalized to the expression of 18S rRNA and shown as an exponential number. Student t-test was performed on controls compared to stable transfected clones (*=p<0.01, +=p<0.05).
FIG. 9B shows human HLA surface expression on each of the Monarch-1 stable HeLa clones as determined by FACS analysis. In each graph expression was compared to unstained (dotted line) and isotype control (solid line). Mean fluorescence intensity is displayed for each sample.
FIG. 9C shows that Monarch-1 activates the HLA-B promoter-luciferase construct. Error bars represent the SEM of five separate experiments. Student t-test was performed on control compared to transfected clones (*=p<0.01, +=p<0.05).

Changes in expression levels were quantified using real-time PCR analysis of total RNA isolated from A, B and C stable clones. The levels of HLA-B, HLA-G and LMP7 mRNA were enhanced in the Monarch-1 stable clones compared to controls (FIG. 9A). FACS analysis further confirmed upregulation of MHC-I antigen (FIG. 9B). To discern the involvement of transcriptional or posttranscriptional mechanisms, a Monarch-1 expression plasmid (or a control plasmid) was transiently co-transfected with a luciferase reporter driven by 220 bp of the HLA-B promoter (Gobin and van den Elsen (1999) *Semin. Cancer Biol.* 9:55) in HeLa cells (FIG. 9C). Monarch-1 enhanced the HLA-B promoter >25-fold. This enhanced activity over that seen for mRNA and protein levels may be due to transient transfection resulting in higher than physiological levels of Monarch-1.

Figure 10B:
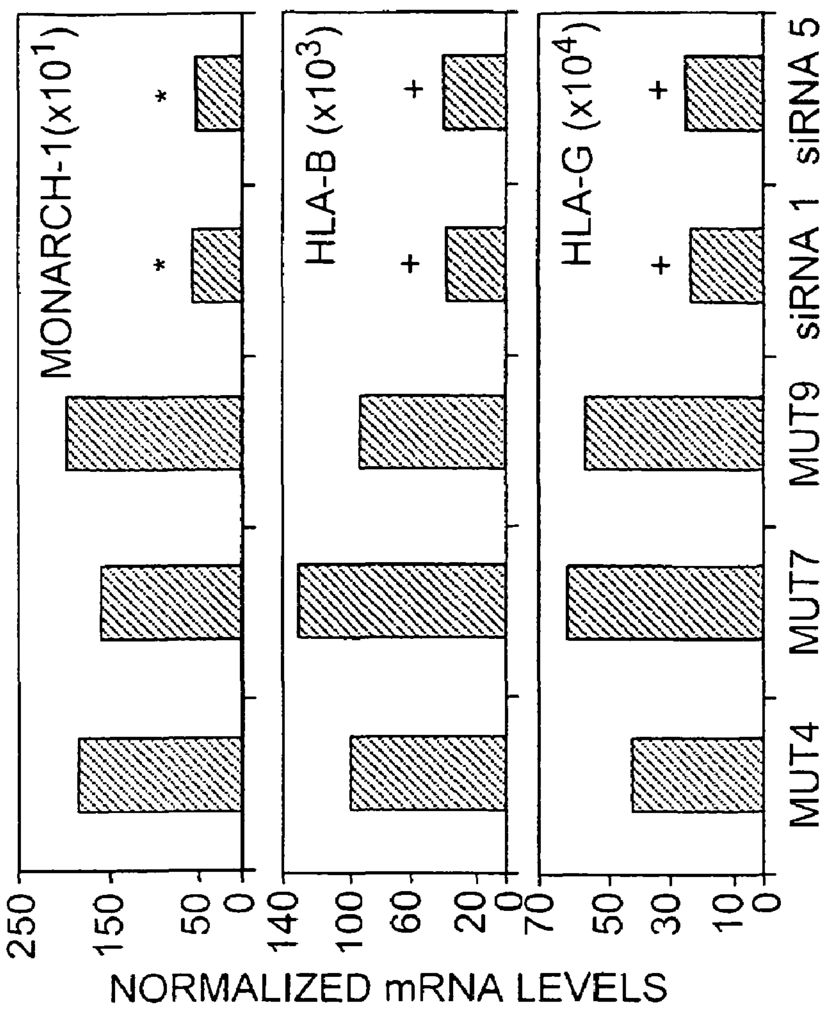
FIG. 10B shows the analysis of Monarch-1, HLA-B and HLA-G expression in Monarch-1 siRNA clones as determined by real-time PCR. Three independent clones generated by stable transfection of the mutant siRNA are shown (represented as mut) and two independent clones generated by stable transfection of WT siRNA are shown (represented as siRNA). Expression was normalized to GAPDH. Data are represented as exponential numbers. Student t-test was performed on the average the control mutant clones compared to siRNA clones (*=p<0.01, +=p<0.05).
Figure 10A:
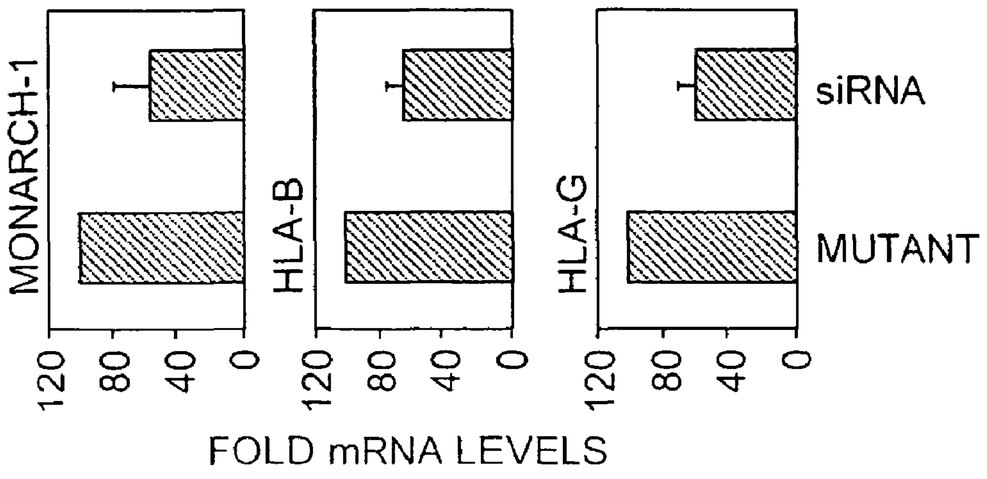
FIG. 10A shows the analysis of Monarch-1, HLA-B and HLA-G expression in Monarch-1 and mutant siRNA bulk cultures determined by real-time PCR. Expression was normalized to the expression of GAPDH mRNA and represented as fold over mutant control.

As the level of expression in the stable clones was less than that in primary blood cells, the regulation of MHC genes was performed in a more relevant system. siRNA technology was used to reduce endogenous Monarch-1 expression levels in U937 cells, which express Monarch-1 and ASC (Masumoto, et al. (1999) *J. Biol. Chem.* 274:33835). A vector containing an siRNA specific for Monarch-1 or a mutant siRNA with two mutated nucleotides was introduced into U937 cells. The bulk culture which should have a mixture of cells containing or lacking Monarch-1 specific siRNA showed a decrease of overall Monarch-1 expression compared to cells with control siRNA (FIG. 10A). Clones were then isolated under selectable conditions. Monarch-1 expression was significantly decreased in Monarch siRNA clones, but not in the controls (FIG. 10B, top panel). The levels of Monarch-1, HLA-B and HLA-G mRNA were correspondingly decreased in the presence of Monarch-1-specific siRNAs but not siRNA controls (FIG. 10B, two lower panels). These data indicate that Monarch-1 controls both classical and nonclassical MHC-I genes in a physiologically relevant cell type and may function as a novel global inducer of MHC-I.

While IFNγ and TFNα, known inducers of class I molecules, decreased Monarch-1 expression, no significant alteration of MHC class I HLA-G gene expression was observed at these timepoints. At later time points, HLA-G expression was enhanced by these two cytokines. This indicates that Monarch-1 may not play a major role in the induction of MHC-I by TNF-α and IFN-γ.

Figure 12:
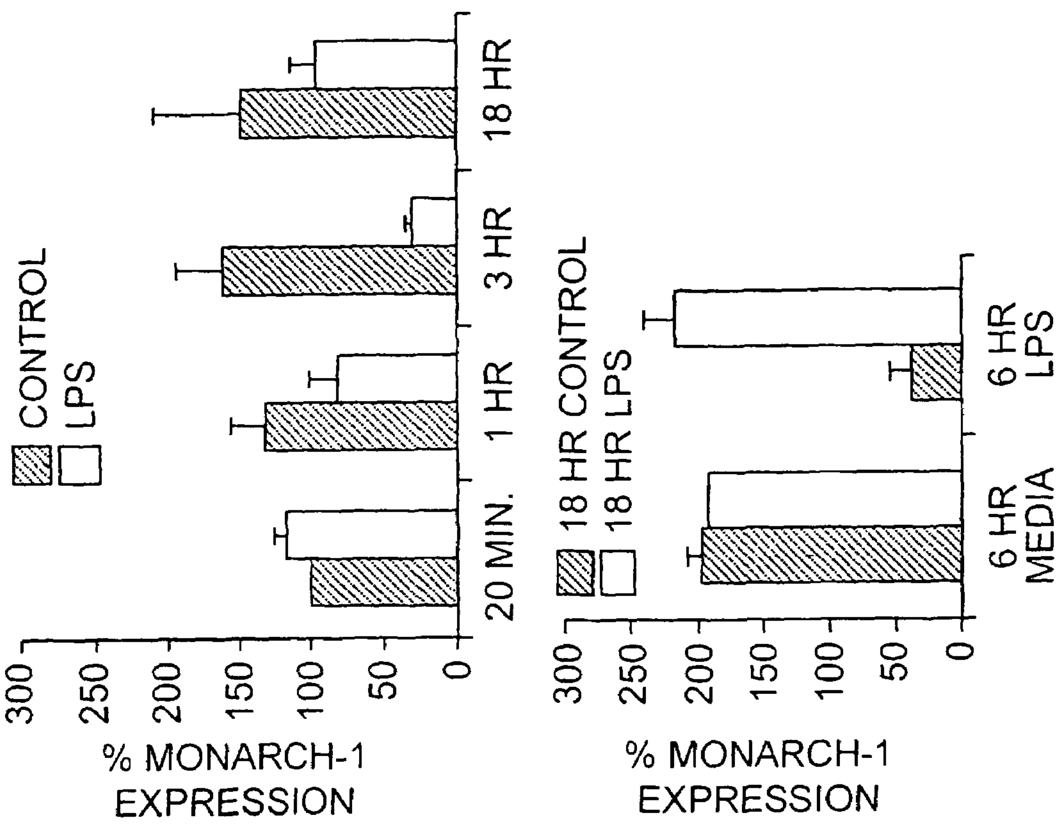
FIG. 12 shows that Monarch-1 is expressed during the LPS tolerant phase. Thp-1 monocytic cells were treated with LPS at the indicated time, and Monarch-1 expression was assessed as described in FIG. 5 (top panel). After 18 hours, cells were washed and treated with media or LPS for 6 hours (bottom panel).
Figure 11:
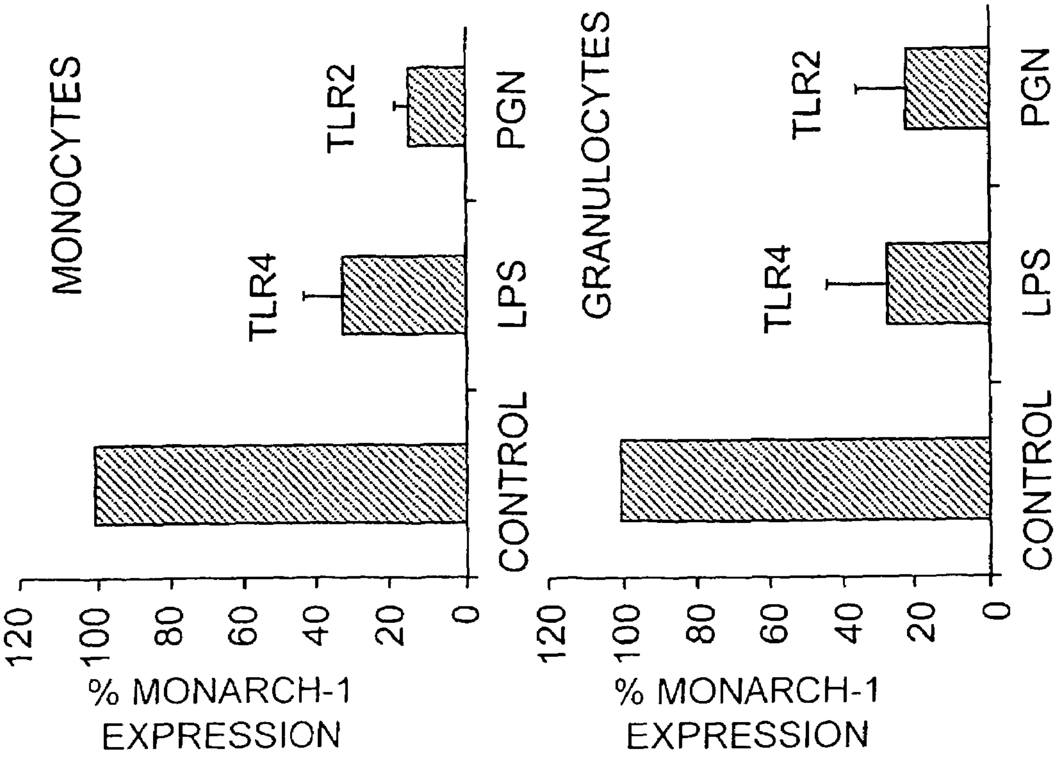
FIG. 11 shows TLR activation reduces Monarch-1 expression. Human peripheral blood monocytes and granulocytes were treated with the different TLR2 and TLR4 activators and Monarch-1 expression was assessed by real-time PCR.

Expression of Human Monarch-1. Human primary adherent cell populations or granulocytes were isolated from human peripheral blood buffy coats using a FICOLL® gradient. The adherent population or granulocytes were subsequently exposed to either LPS or peptidoglycan (PGN) for 1 hour. RNA was harvested followed by real-time PCR analysis for Monarch-1 mRNA expression using primers C-term forward 5'-CAGAAGGACATCAACTGTGAGAG-3'(SEQ ID NO:127) and C-term reverse 5'-GCTCTAGACAGCAGATAGGACCATTCAGCAG-3'(SEQ ID NO:128). A down-regulation of Monarch-1 mRNA expression levels by PGN (TLR2 ligand) and LPS (TLR4 ligand) was observed 1 hour after stimulation in both granulocytes and monocytes (FIG. 11) and the Thp-1 cell line. As some commercially available reagents may be contaminated with endotoxin, granulocytes were stimulated with phenol-purified LPS and the synthetic TLR2 agonist Pam3Cys. The observed down-regulation of Monarch-1 in the phenol-purified LPS and Pam3Cys-treated cells confirmed that Monarch-1 expression was down-regulated by exposure of cells to TLR2 and TLR4 agonists (FIG. 11). Data from at least four experiments indicated that the TLR2 agonist, LTA, did not cause a down-regulation of Monarch-1 expression. It is known that LTA and Pam3Cys signal through slightly different downstream pathways, and these data indicated that Monarch-1 down-regulation may be specific to certain bacterial components. Monarch-1 down-regulated upon exposure of the human Thp-1 cell line to LPS was shown, however, the mRNA for this molecule returns 18 hours after LPS stimulation in Thp-1 cells, and was not further reduced upon a second LPS stimulation (FIG. 12). This second LPS stimulation was typically applied to measure LPS tolerance or endotoxin tolerance, a state of LPS non-responsiveness following an initial LPS stimulation. LPS tolerance may reflect events that occur in septic shock survivors who exhibit suppressed monocytic and inflammatory responses to subsequent LPS. TLR pathway mediators such as IRAK and MyD88 are defective during LPS tolerance. As Monarch-1 expression re-appears during this "LPS"-tolerant phase, the effect of Monarch-1 on TLR-induced downstream signals was examined.

Figure 13:
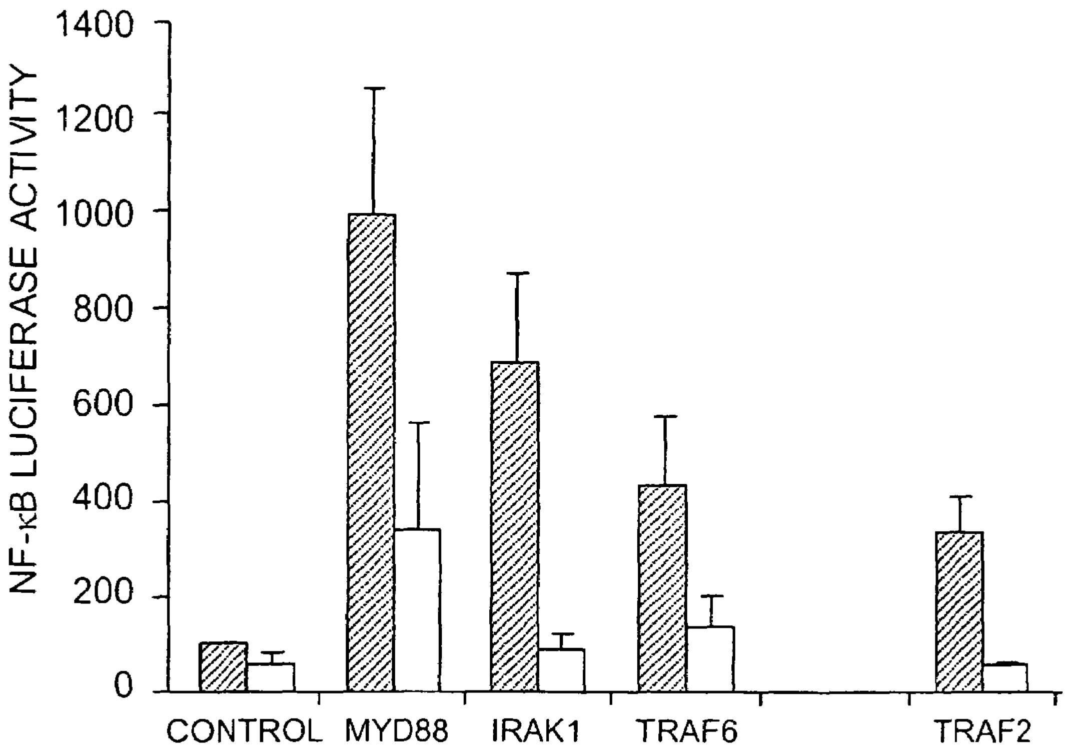
FIG. 13 shows that Monarch-1 suppresses TLR signaling molecule NF-κB activation. 293T cells were co-transfected with Monarch-1, a reporter construct bearing the NF-κB binding site linked to luciferase, and MyD88, IRAK1, TRAF6, or TRAF2 was used to activate an NF-κB reporter construct. Open bars, transfected with a plasmid containing Monarch-1; shaded bars, transfected with an empty vector control.

Regulation of TLR-Induced NF-κB Activity by Monarch-1. Members of the CATERPILLER family of proteins have been found to be critical for apoptosis, immune and inflammatory diseases. Thus, regulation by Monarch-1 of the TLR signaling molecule induced NF-κB activation was examined. HEK293T cells were transiently transfected with a Monarch-1-encoding plasmid together with an NF-κB-dependent luciferase reporter. NF-κB activity was induced by co-transfection with TLR signaling pathway molecules including MyD88, IRAK, TPAF6 and TRAF2. Under these experimental conditions, Monarch-1 appeared to inhibit NF-κB induction by TLR signaling molecules (FIG. 13). These data indicate that Monarch-1 is a negative regulator of NF-κB activity when introduced into epithelial cell lines.

Figure 14:
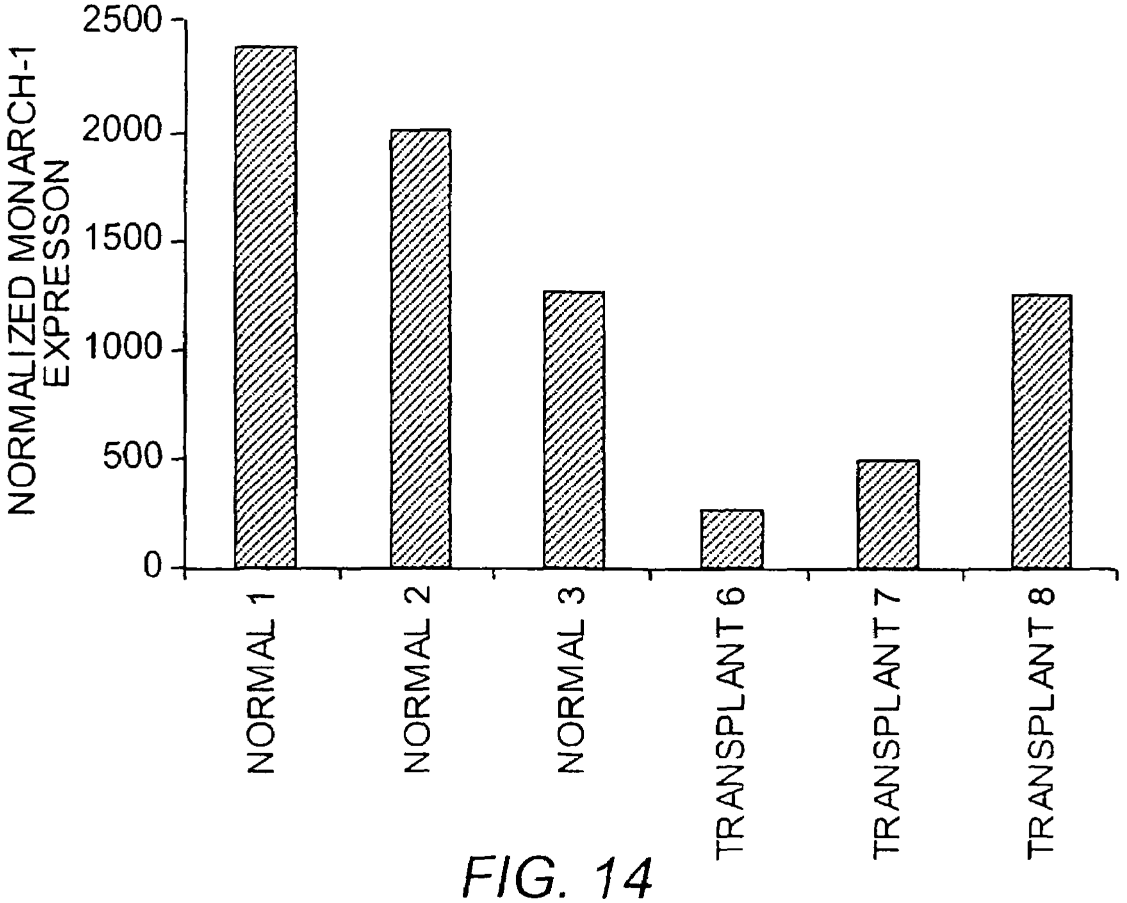
FIG. 14 shows that Monarch-1 is decreased in lung transplant BAL samples. Bronchiolar lavage samples from normal human subjects and lung transplant patients were subjected to real-time PCR analysis for Monarch-1 expression.

Human Monarch-1 Expression in Lung BAL. Bronchiolar lavage samples were obtained from normal human subjects and lung transplant patients. Real-time PCR analysis for Monarch-1 mRNA expression indicated that Monarch-1 expression was down-regulated in BAL samples from transplant patients (FIG. 14).

Figure 15:
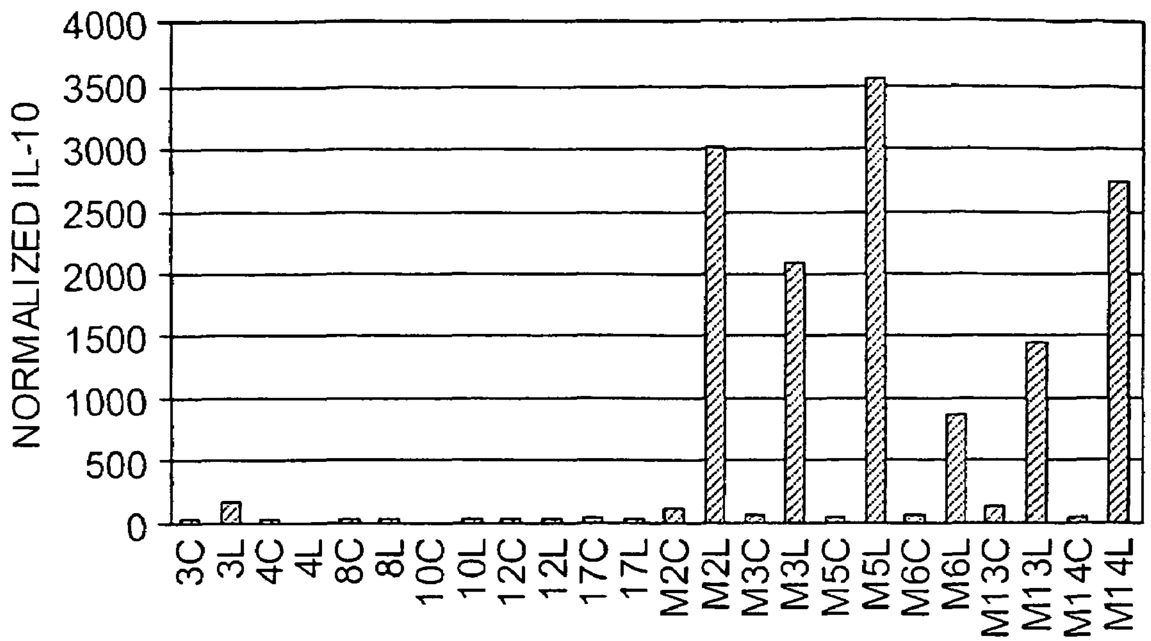
FIG. 15 shows that Monarch-1 enhances IL-10 induction. Stable Thp-1 clones expressing mutant siRNA targeting the Monarch-1 gene (designated by M followed by clone number) and six clones expressing wild-type siRNA (designated by clone number) were left unstimulated (designated by C) or were stimulated with LPS (designated by L) for 24 hours. RNA was harvested and IL-10 expression examined by real-time PCR.
Figure 16:
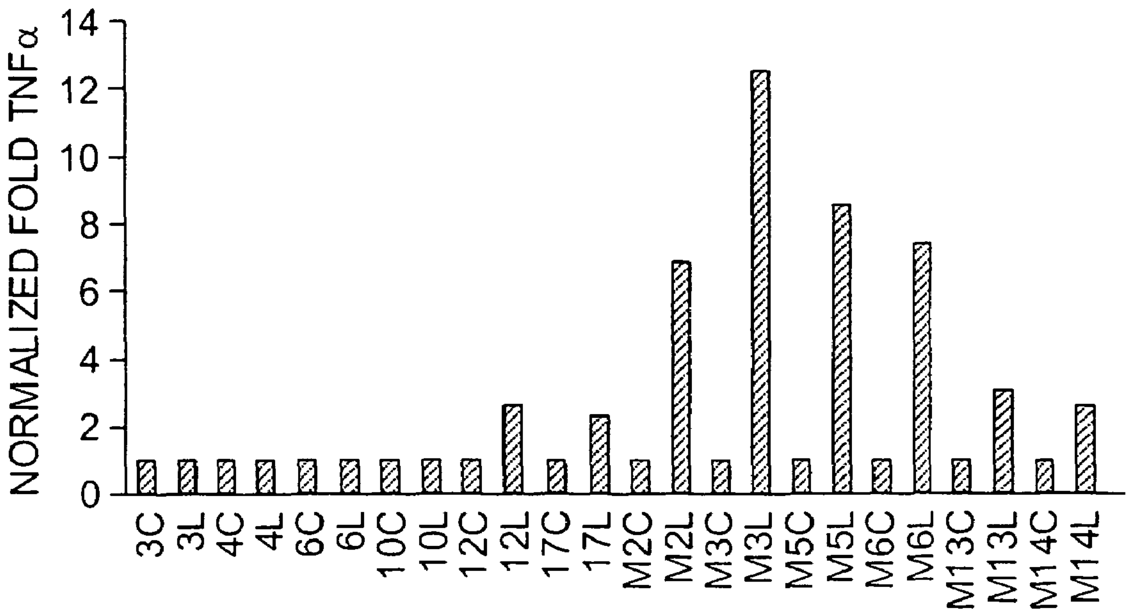
FIG. 16 shows that Monarch-1 enhances TNFα induction. Stable Thp-1 clones expressing mutant siRNA targeting the Monarch-1 gene (designated by M followed by clone number) and six clones expressing wild-type siRNA (designated by clone number) were left unstimulated (designated by C) or were stimulated with LPS (designated by L) for 3 hours. RNA was harvested and TNFα expression examined by real-time PCR.

Human Monarch-1 and Cytokine Expression. Stable Thp-1 clones expressing mutant siRNA Monarch-1 oligo (designated by M followed by clone number in FIG. 15) and six clones expressing wild-type siRNA oligo targeting Monarch-1 expression (designated by clone number) were either unstimulated (designated by C) or stimulated with LPS (designated by L) for 24 hours. RNA was harvested and IL-10 expression was examined by real-time PCR. All clones expressing a Monarch-1 siRNA oligo expressed dramatically lower levels of IL-10 than clones expressing the mutant oligo. As Monarch-1 expression returned to normal levels at 24 hours after LPS stimulation and Monarch-1 was not down-regulated in LPS tolerant cells (FIG. 12), these data indicate that Monarch-1 is a positive regulator of the anti-inflammatory IL-10 cytokine. IL-10 is both an immunosuppressive molecule, as well as a molecule that diverts T cell responses to a T-helper 2 response, leading to an anti-parasitic response, allergic response, asthma response and antibody response. Further, stable Thp-1 clones expressing mutant siRNA Monarch-1 oligo and six clones expressing wild-type siRNA oligo targeting Monarch-1 expression were either unstimulated or stimulated with LPS for 3 hours. RNA was harvested and TNFα expression was examined by real-time PCR. All clones expressing a Monarch-1 siRNA oligo expressed lower levels of TNFα than clones expressing the mutant oligo (FIG. 16).

Figure 17:
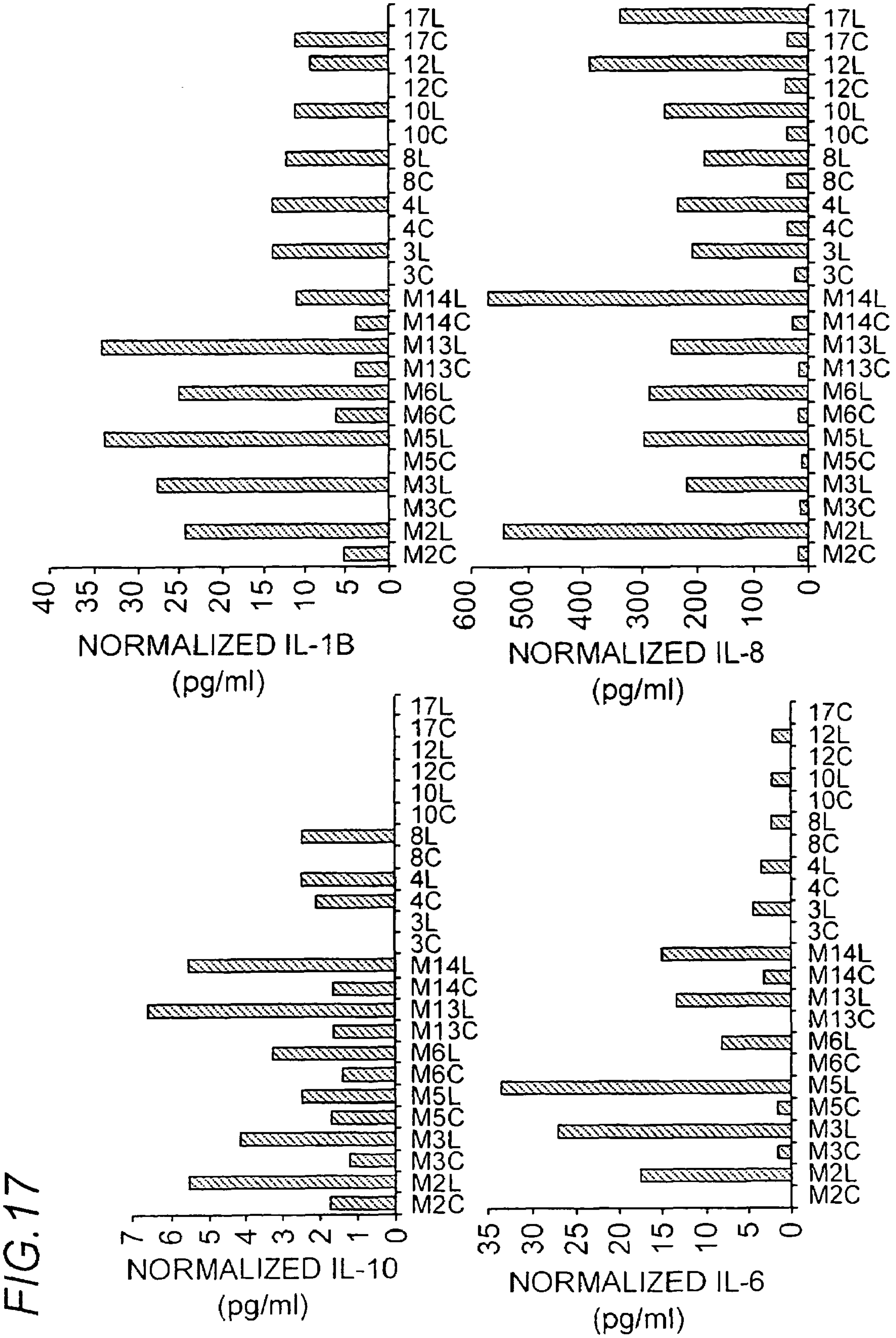
FIG. 17 shows Monarch-1-regulated pro- and anti-inflammatory cytokine induction. Global analysis of cytokine protein expression in stable Thp-1 clones expressing mutant siRNA Monarch-1 oligo (designated by M follows by clone number) and six clones expressing wild-type siRNA oligo targeting Monarch-1 expression (designated by clone number) were left unstimulated (designated by C) or were stimulated with LPS (designated by L) for 48 hours. Supernatants were isolated and a Cytometric Bead Assay (CBA) was performed to assess cytokine production.

A more global analysis of cytokine gene expression was conducted. Stable Thp-1 clones expressing mutant siRNA Monarch-1 oligo (designated by M followed by clone number) and six clones expressing wild-type siRNA oligo targeting Monarch-1 expression (designated by clone number) were either unstimulated (designated by C) or stimulated with LPS (designated by L) for 48 hours. Supernatants were isolated and a Cytometric Bead Assay (CBA) was performed (FIG. 17). All clones expressing a Monarch-1 siRNA oligo expressed lower levels of IL-6, IL-1b, and IL-10 than clones expressing the mutant oligo. In contrast, basal and stimulated levels of IL-8 were similar to the mutant control clones.

Proteomic Analysis of Monarch-1 Interacting Proteins. Interacting partners of Monarch-1 were identified by transfecting 293T cells with FLAG®-tagged Monarch-1 or pcDNA control vector. After 24 hours, the cells were lysed and protein complexes were immunoprecipitated with anti-FLAG® antibodies. Proteins were solubilized and separated by two-dimensional gel electrophoresis. Individual protein spots were visualized by silver staining and those found to be unique to Monarch-1-transfected precipitates were analyzed by matrix-assisted laser desorption/ionization mass spectrometry mass spectrometer (MALDI-MS). Proteins identities were determined by comparing peptide mass fingerprints to the NCBI, SwissProt, and TrEMBL protein databases. Proteins associating with Monarch-1 having the highest significance scores were identified as β and α-tubulin, vimentin, hsp-70 family members. CARD10 and TNIK were also identified with lower significant scores. The interaction between Monarch-1 and vimentin may indicate that Monarch-1 binds to vimentin intracellularly to inhibit the bactericidal activity of secreted vimentin (Mor-Vaknin, et al. (2003) *Nature Cell Biol.* 5:59-63). Further the interaction between Monarch-1 and CARD10 may indicate that Monarch-1 inhibits NF-kB activation by interfering with CARD10.

Monarch-1 Associates with TRAF6 but not MyD88 or IRAK1. In addition to the proteins identified by MALDI-MS, 293T cells were transfected with Monarch-1 cDNA and one of the following: HA-MyD88, HA-TRAF6, or HA-IRAK1. Twenty-four hours later the cells were lysed and Monarch-1-containing protein complexes were immunoprecipitated with anti-FLAG® M2-agarose beads overnight. The beads were washed in lysis buffer and precipitated proteins were separated by polyacrylamide gel electrophoresis. Western blot analysis was performed using the anti-HA antibody 12C5 (Roche, Indianapolis, Ind.) and anti-mouse conjugated to HRP. Of these proteins, only TRAF6 binds Monarch-1.

Monarch-1 Associates with NF-κB Inducing kinase, NIK. To further determine the molecular mechanism by which Monarch-1 may interface with the NF-kB pathway, 293T cells were transfected with plasmids containing Monarch-1 and NIK. After 24 hours, the cells were lysed and Monarch-1-containing protein complexes were immunoprecipitated with anti-FLAG® M2 antibody. Western blot analysis was performed using the anti-NIK antibody H-248 and anti-mouse conjugated to HRP. The results indicate that Monarch-1 also interacts with NIK.

Monarch1 Associates with CIAS1. 293T cells were transfected with plasmids containing the Monarch-1 and CIAS1 genes (also a CATERPILLER family member). After 24 hours, the cells were lysed and CIAS1-containing protein complexes were immunoprecipitated with anti-FLAG® M2 antibody. Western blot analysis was performed using the anti-HA antibody and anti-mouse conjugated to HRP. An association between CIAS1 and Monarch-1 was observed and enhanced in the absence of LRR regions 7-9 of Monarch-1. In contrast, the association was weakened in the absence of the pyrin domain of Monarch-1.

Predicted Mouse Monarch-1 mRNA and Protein Sequence. A predicted mouse Monarch-1 sequence was identified corresponding to NCBI database Accession Number XM_142563 (SEQ ID NO:9; incorporated by reference herein in its entirety). The predicted size of the mouse Monarch-1 mRNA was 3102 bp (FIGS. 18A-B) which encodes a 1035 amino acid residue protein (SEQ ID NO:10; FIG. 18C) The predicted mouse Monarch-1 gene contains 9 exons; however, nucleic acid sequences corresponding to exon 2 of the human Monarch-1 gene were not predicted. Thus, the mouse Monarch-1 gene may contain 10 exons similar to its human homolog. Moreover, the mouse Monarch-1 protein had structural characteristics similar to human Monarch-1, each contained an N-terminal Pyrin domain, a nucleotide-binding domain (NBD) and C-terminal leucine-rich repeats (LRR). The human and mouse Monarch-1 share 82% nucleotide sequence homology.

Figure 19:
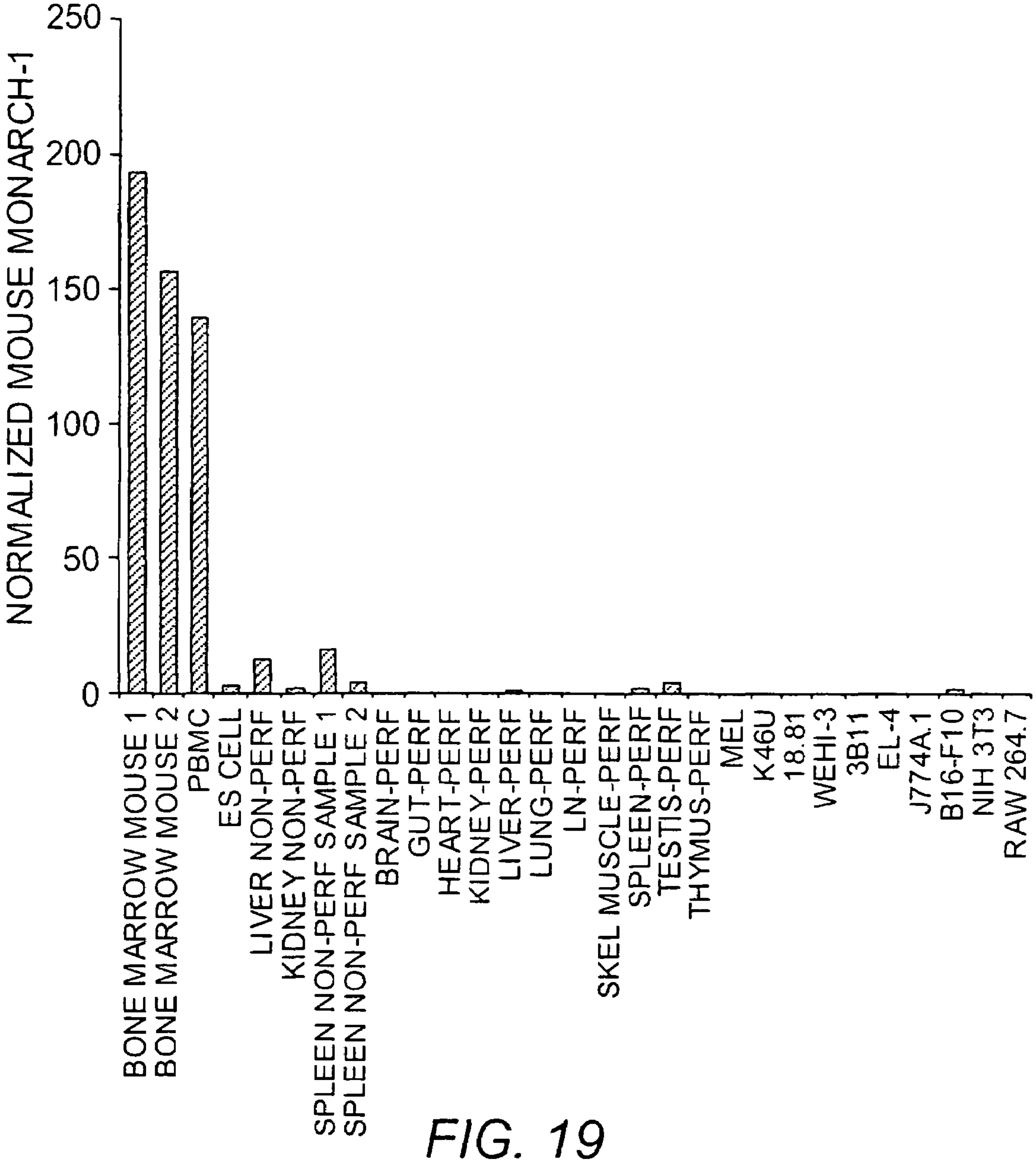
FIG. 19 demonstrates the expression of mouse Monarch-1 in various mouse cell lines as determined by separated real-time PCR and in primary tissues by real-time PCR.
Figure 20:
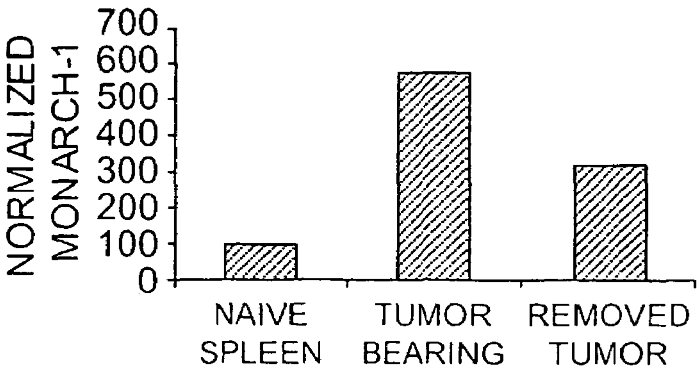
FIG. 20 shows the expression of mouse Monarch-1 in myeloid suppressor cells isolated from BALB/c mice with large primary-mammary carcinomas (tumor bearing) or mice with metastasis wherein primary mammary tumors had been surgically removed (non-tumor bearing). Normal spleen RNA (naïve spleen) was included as a control.

Expression of Mouse Monarch-1. Real-Time PCR analysis showed expression of mouse Monarch-1 in primary PBMCs and bone marrow (FIG. 19). Low levels of Monarch-1 were detected in testis, spleen and liver tissues from a perfused mouse (designated by-perf) but not in other perfused tissues tested. Perfusion was necessary to eliminate contaminating blood cells. Monarch-1 expression was detected in non-perfused tissues at a slightly higher level indicating blood contamination. Monarch-1 expression was not detected in cell lines tested, although a negligible level was detected in B16-F10 fibroblast cells. Mouse Monarch-1 expression was not detected in Brewers Thioglycolate mouse peritoneal macrophages, even upon exposure to LPS. Mouse Monarch-1 expression was detected in CD11b+/Gr-1+ myeloid suppressor cells isolated from BALB/c mice with large primary mammary carcinomas (tumor-bearing) and mice with metastasis wherein primary mammary tumors had been surgically removed (non-tumor-bearing) (FIG. 20). The expression level of Monarch-1 was higher in myeloid suppressor cells from tumor-bearing mice than in non-tumor-bearing mice.

EXAMPLE 3

Cloning, Characterization and Functional Analysis of CATERPILLER 11.2

This example describes the characteristics of the human CATERPILLER 11.2 gene. The cloned human CATERPILLER 11.2 nucleic acid and protein sequences are set forth as SEQ ID NO:13 and SEQ ID NO:14, respectively. It has now been found that CATERPILLER 11.2 reduces the function of NF-κB. CATERPILLER 11.2 expression is primarily found in hematopoietic cell lines. The reduction of NF-κB function by CATERPILLER 11.2 indicates that CATERPILLER 11.2 is important in the control of immunity, gene expression and cell survival. In addition, CATERPILLER 11.2 also suppresses the expression of the class II Major Histocompatibility Complex (MHC-II) promoter. Proper MHC-II expression is important for immune recognition to elicit T cell responses against all pathogens and antigens.

Materials and Methods

Detection of CATERPILLER 11.2 Expression by PCR. RNA samples from various sources, including normal peripheral blood and human cell lines, were prepared using commercially available reagents following the manufacturer's instructions. 50 ng to 1 μg of RNA was reverse transcribed with CATERPILLER 11.2-specific primers using the QIAGEN® One-Step RT-PCR kit (QIAGEN®, Valencia, Calif.).

Cloning of CATERPILLER 11.2. Primers pairs corresponding to the 5' and 3' ends of the predicted gene were used to amplify two fragments of the CATERPILLER 11.2 gene and were as follows. 5'-AAC TTT GCC TTT GAA GAA CCT GAG-3' (SEQ ID NO:129) at nucleotide position 793; 5'-ACA TGA AGG TGG GYG AAC ACA TAG-3' (SEQ ID NO:130) at position 1448; 5'-ATG GCA GAT TCA TCA TCA TCA TCT TC-3' (SEQ ID NO:131) at nucleotide position 1; and 5'-TCA CCC GAG CCT CTG AAT GTT ACA G-3' (SEQ ID NO:132) at nucleotide position 2808. Resulting PCR products were cloned into the TOPO® TA cloning vector and the cloned sequence was verified. Full-length FLAG®-tagged CATERPILLER 11.2 was obtained by transferring the two fragments into pcDNA3 and adding a 5'FLAG® epitope tag sequence.

Transfection and Reporter Assays. HeLa cells were transfected using the FUGENE6™ transfection reagent. $2\times10^5$ cells received 1.0 μg of FLAG®-11.2 or empty vector together with 0.5 μg of reporter plasmid (3×NFκBLuc, AP1 Luc, or DRLuc) and either 100 ng of activator plasmid (NF-κB p65, c-jun, or CIITA) or empty vector. Eighteen hours post-transfection, luciferase assays were performed using standard protocols.

RNA interference. The follow sequence was designed to inhibit expression of CATERPILLER 11.2 in cells:

```
                                        (SEQ ID NO:133)
3'-GAT CCC CGA AGA GAT CAA CTG GTC GGT TCA AGA GAC

CGA CCA GTT GAT CTC TTC TTT TTG GAA AGG GCT TCT

CTA GTT GAC CAG CCA CGT TCT CTG GCT GGT CAA CTA

GAG AAG AAA AAC CTT TAG CT-3'.
```

This sequence is cloned into a plasmid and stably expressed in a human cell line to interfere with the expression of CATERPILLER 11.2 in vivo.

Experimental Results

Figure 22:
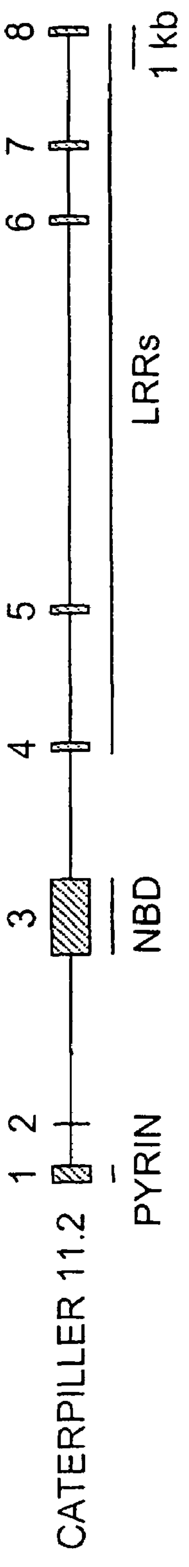
FIG. 22 shows the genomic organization of CATERPILLER 11.2 with boxes representing exons.

Genomic Organization and Sequence of CATERPILLER 11.2. The CATERPILLER 11.2 gene resides at 11p15 on human chromosome 11 and contains as many as 8 exons (FIG. 22) based on both bioinformatics predictions and obtained sequence data. Using the predicted sequence (SEQ ID NO:11; FIGS. 21A-B) encoding the CATERPILLER 11.2 protein (SEQ ID NO:12; FIG. 21C), assembly of PCR products from the B cell line Raji yielded an approximately 2.8 kilobase pair (kb) insert containing both the putative initiator codon (ATG) and an in-frame stop codon that precedes a canonical poly-adenylation site. The DNA sequence of this fragment (SEQ ID NO:13) and the deduced protein sequence (SEQ ID NO:14) are shown in FIGS. 21D-E and FIG. 21F, respectively. This insert was cloned into the pcDNA3 expression vector (INVITROGEN™, Carlsbad, Calif.) and was tagged with the FLAG® epitope for detection with anti-FLAG® monoclonal antibodies.

Expression of CATERPILLER 11.2 CATERPILLER 11.2 was expressed by some common cell lines, but did not appear to be expressed in primary hematopoeitic cells. CATERPILLER 11.2 mRNA transcripts were detected in a number of human B cell lines indicating that CATERPILLER 11.2 may be expressed in later stages of B cell development. While other CATERPILLER genes (e.g., CIAS1) were detected in in vitro matured dendritic cells (DCs), 11.2 mRNA was not detected.

Figure 23A:
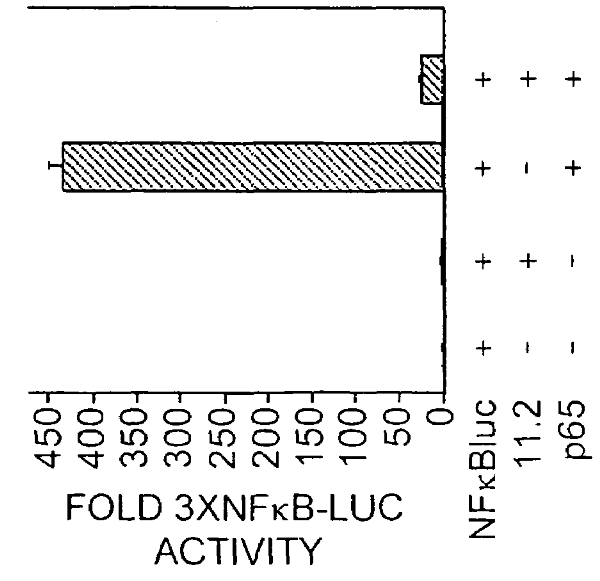
FIG. 23A shows that CATERPILLER 11.2 significantly inhibits NF-κB activity. HeLa cells were transfected with 0.5 μg of 3× NFκBLuc and 1 μg of either empty vector or CATERPILLER 11.2 in the presence or absence of 100 ng of vector or CMV-p65.
Figure 23B:
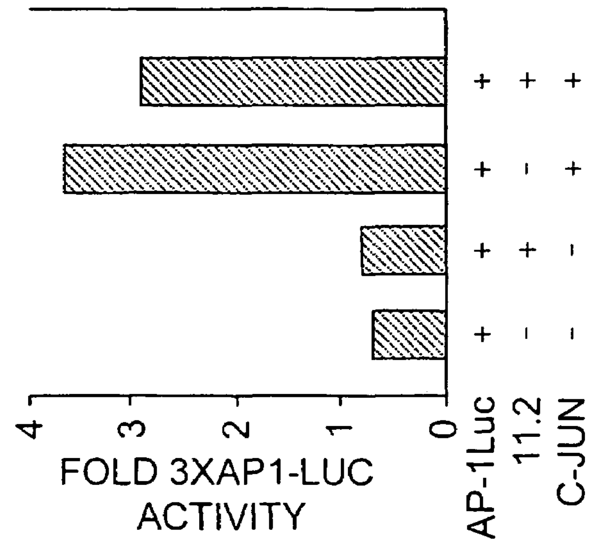
FIG. 23B shows that CATERPILLER 11.2 does not inhibit activation of the AP1 luciferase reporter by transfected c-jun. HeLa cells were transfected with 0.5 μg of AP1 Luc and 1 μg of either empty vector or CATERPILLER 11.2 in the presence or absence of 100 ng of vector or c-jun.
Figure 24:
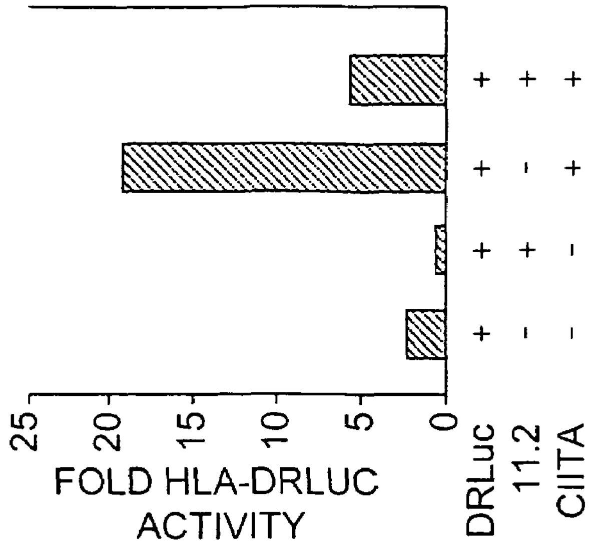
FIG. 24 shows that CATERPILLER 11.2 inhibits basal and CIITA-induced HLA-DR promoter activity. HeLa cells were transfected with 0.5 μg of HLA-DRLuc and 1 μg of either empty vector or CATERPILLER 11.2 in the presence or absence of 100 ng of vector or CIITA.

Transcriptional Inhibition Functions of CATERPILLER 11.2. Expression of CATERPILLER 11.2 inhibited activation of the 3XNFκB luciferase reporter by transfected NF-κB p65 (FIG. 23A), but did not inhibit activation of the AP1 luciferase reporter by transfected c-jun (FIG. 23B). This indicates that CATERPILLER 11.2 acts to inhibit p65 activity either directly, through binding to p65, or indirectly by interfering with the ability of p65 to transit effectively to the nucleus or bind DNA. Alternatively, 11.2 may promote the inactivation of p65 through such mechanisms as p65 degradation or blockade of modifications needed for p65 activity. CATERPILLER 11.2 also inhibited CIITA-mediated HLA-DR transcription as evidenced by its effects on the HLA-DR promoter (FIG. 24). This reporter is not believed to be sensitive to NF-κB, thus other factors may be responsible for the observed effect.

For example, the formation of hetero-oligomers with CIITA itself may be responsible as they are related molecules and CIITA is known to self-associate. Such an interaction may interfere with the ability of CIITA to enter the nucleus or prevent proper association with transcription factors bound to the HLA-DR promoter.

EXAMPLE 4

Cloning and Characterization of CATERPILLER 11.3

This example describes the characteristics of the cloned human CATERPILLER 11.3 gene (SEQ ID NO:17; FIG. 25C-D) and a protein encoded thereby (SEQ ID NO:18; FIG. 25E) as well as a CATERPILLER 11.3 splice variant (SEQ ID NO:19; FIG. 25F) and a protein encoded thereby (SEQ ID NO:20; FIG. 25G).

Materials and Methods

Cloning of Full-Length Human 11.3. Primers designed for detecting expression of CATERPILLER 11.3 were originally developed from the predicted sequence of CATERPILLER 11.3 (see EXAMPLE 1 and FIG. 3; nucleotide sequence [SEQ ID NO:15; FIG. 25A]; amino acid sequence [SEQ ID NO:16; FIG. 15B]). To obtain the full-length open reading frame of human CATERPILLER 11.3, total and polyA$^+$ RNA were isolated from a Jurkat T cell line. PolyA$^+$ mRNA was isolated from the total RNA using the OLIGOTEX® mRNA Mini Kit (QIAGEN® Inc., Valencia, Calif.). The complete 5' sequence of human CATERPILLER 11.3 was cloned using the 5'RACE kit (Roche, Indianapolis, Ind.). Two overlapping sequences were cloned for the remaining portion of human CATERPILLER 11.3 by RT-PCR using PFUTURBO® polymerase (STRATAGENE®, Inc., La Jolla, Calif.). Using these three separate clones, splice overlap extension was performed using Taq polymerase (INVITROGEN™ Life Technologies, Carlsbad, Calif.). The resulting full-length clone and splice variant were ligated into a pcDNA3.1 expression vector containing tandem HA epitopes. In addition, a FLAG® epitope was added to the 5' end of human CATERPILLER 11.3 by RT-PCR and ligated into pcDNA3.1. All cloned products were sequenced for verification.

Human 11.3 Expression. Total RNA was isolated from various sources, including transformed human cell lines and normal peripheral blood, using the SV total RNA isolation system (PROMEGA™, Madison, Wis.). Following RNA isolation, 1 μg RNA was reverse-transcribed and PCR was performed using primers specific for the NBD to determine the expression pattern of CATERPILLER 11.3. In addition, real-time PCR primers were designed for subsequent quantitative expression analysis using the TAQMAN® sequence detection system (Applied Biosystems, Foster City, Calif.)

Luciferase Reporter Gene Assays. HEK293T cells were plated at $1\times10^4$ cells/well in 96-well plates and transfected the following day using FUGENE™ transfection reagent (Roche, Indianapolis, Ind.) following the manufacturer's recommended protocol. For NF-κB or AP-1 reporter assays, cells were transfected with 50 ng of NF-κB-luc and various amounts agonists (MyD88, NIK, Traf6, IRAK1), maintaining the total amount of DNA constant using pcDNA3 empty vector. The p53 reporter assays were performed with 50 ng of p53-luc reporter plasmid, 200 ng of p53 expression vector and 400 ng of CATERPILLER 11.3 expression plasmid. Cells were harvested 24 hours after transfection and assayed for luciferase activity following standard procedures with the equal amounts of protein as determined by the Bradford protein assay (BIO-RAD®, Hercules, Calif.).

Experimental Results

Full-Length Coding Sequence of Human CATERPILLER 11.3. The CATERPILLER 11.3 gene resides at 11q23 on human chromosome 11 and contains as many as 9 exons (FIG. 26) based on both bioinformatics predictions and sequence data obtained from cloning CATERPILLER 11.3. Assembly of PCR products from the T cell line Jurkat yielded an approximately 3.6 kilobase pair (kb) insert containing both the initiator codon (ATG) and an in-frame stop codon that precedes a 3'-UTR and poly-adenylation site. The DNA sequence of this fragment (SEQ ID NO:17) and the deduced protein sequence (SEQ ID NO:18) are shown in FIGS. 25C-D and FIG. 25E, respectively. This insert was cloned into the pcDNA3 expression vector (INVITROGEN™, Carlsbad, Calif.) and was tagged with the FLAG® and HA epitope for detection with monoclonal antibodies. Additionally, a splice variant of CATERPILLER 11.3 was cloned and sequenced with nucleotide (SEQ ID NO:18) and deduced amino acid (SEQ ID NO:19) sequences shown in FIGS. 25F and 25G, respectively.

Expression of Human CATERPILLER 11.3. It has now been shown that human CATERPILLER 11.3 is expressed in a variety of cells. CATERPILLER 11.3 expression was found in T cell, B cell, and myeloid cell lines. In addition, CATERPILLER 11.3 was expressed by primary T-cells with reduced expression in the presence of PHA. Expression in HL-60 cells was also abrogated in response to PMA stimulation. Human CATERPILLER 11.3 did not appear to be expressed by cells of epithelial origin. In addition, mouse CATERPILLER 11.3 was expressed in resting murine CD4+CD25+T regulatory cells at 10-fold higher levels than CD4+CD25−T cells, indicating that CATERPILLER 11.3 may control T regulatory cell function. T regulatory cells are typically associated with a suppressive phenotype. Also, mouse CATERPILLER 11.3 expression in murine T regulatory cells isolated from mice on a B6 background was 10-fold higher than cells harvested from the autoimmune sensitive SLJ background.

Transcriptional Inhibitory Functions of CATERPILLER 11.3. Transfection of CATERPILLER 11.3 inhibited the activation of the NF-κB luciferase reporter by transfected MyD88 (FIG. 27). MyD88 is an important adapter protein that links members of the toll-like receptor (TLR) and interleukin-1 receptor (IL-1R) superfamily to the downstream activation of nuclear factor-κB and mitogen-activated protein kinases. Transfection of CATERPILLER 11.3 abrogated activation of NF-κB luciferase reporter by transfected NIK (NF-κB Inducing Kinase) (FIG. 28). In addition to MyD88, NIK has been shown to be an important molecule for NF-κB signaling. These data indicate that human CATERPILLER 11.3 functions as an inhibitory molecule in the inflammatory signaling pathways leading to activation of NF-κB. This inhibitory effect may be mediated through interactions between CATERPILLER 11.3 and molecules such as MyD88 and NIK.

EXAMPLE 5

Cloning, Characterization, Expression and Functional Analysis of CATERPILLER 16.1

This example describes the characteristics of the cloned human CATERPILLER 16.1 gene (SEQ ID NO:23) and the protein encoded thereby (SEQ ID NO:24). Expression of CATERPILLER 16.1 was found in, but not restricted to, cell lines and primary human cells of hemotapoietic origin, including B and T lymphocytes, monocytes and granulocytes. It was found that CATERPILLER 16.1 expression was affected by activation stimuli in Jurkat T cells (human T lymphocyte cell line) and differentiation stimuli in HL-60 cells (human promyleocytic cell line). These results indicate that CATERPILLER 16.1 is involved in both differentiation and activation of certain cell types that may impact host responses to pathogens or the regulation of autoimmune diseases and/or cancer or precancerous conditions.

Materials and Methods

Human CATERPILLER 16.1 Expression. Total RNA was isolated from various sources, including transformed human cell lines and normal peripheral blood, using the SV total RNA isolation system (PROMEGA™, Madison, Wis.). Following RNA isolation, 1 μg RNA was reverse-transcribed and PCR was performed using primers specific for CATERPILLER 16.1. In addition, real-time PCR primers were designed for subsequent quantitative expression analysis using the TAQMAN® sequence detection system (Applied Biosystems, Foster City, Calif.)

Experimental Results

Genomic Organization and Sequence of CATERPILLER 16.1. CATERPILLAR 16.1 was identified as a predicted novel NBD/LRR protein with structural similarities to CIITA (see EXAMPLE 1). The predicted nucleic acid and protein sequences of CATERPILLER 16.1 are set forth as SEQ ID NO:21 (FIG. 29A-B) and SEQ ID NO:22 (FIG. 29C), respectively. It was found that CATERPILLER 16.1 was located on human chromosome 16q13 and was situated between CTEP and CPNE2. CATERPILLER 16.1 contained as many as 47 exons based on experimental evidence and the transcript was greater than 5500 bp, containing an in-frame stop codon. Two fragments approximately 3000 bp in length with 1500 bp overlap were connected by splice overlap extension to clone the predicted gene. The resulting fragment was approximately 4500 bp in length.

A partial 4500 bp sequence of CATERPILLAR 16.1 was cloned from a Raji B cell line and sequenced (FIGS. 29D-F). The protein sequence of the cloned CATERPILLER 16.1 (FIG. 29G) most closely resembled NOD27. The cloned CATERPILLER 16.1 sequence lacks at least two small exons (underlined in FIGS. 30A-D) present in NOD27 (Accession number AF389420; Dowds, et al. (2003) *Biochem. Biophys. Res. Commun.* 302(3)575-580; the disclosures of which are incorporated by reference herein in their entireties). These exons span nucleotides 3248-3327 and 3745-3828 or 3750-3833 (relative to NOD27). In addition, two nonconservative mutations are predicted, P453L and C500R. The origin of the cDNA for NOD27 has not been described, therefore it further differences between NOD27 and CATERPILLER 16.1 may exist clue to the differences in origin of cDNA.

5' Region of cloned CATERPILLER 16.1. The 5' region of the cloned CATERPILLER 16.1 sequence did not appear to encode a recognizable pyrin domain. Modeling studies indicated that this region did not contain significant homology with any known structure. 5' rapid amplification of the complimentary ends (RACE) is performed to characterize the 5' region of cloned CATERPILLER 16.1.

Expression of CATERPILLER 16.1. CATERPILLER 16.1 was expressed by many cell lines, including transformed B and T lymphocytes (Raji and Jurkat), and pro-monocytic cell lines (U937, THP-1, HL-60). CATERPILLER 16.1 was also expressed in primary hematopoietic cells, including T and B lymphocytes, monocytes, and granulocytes. CATERPILLER 16.1 expression was decreased significantly in HL-60 cells upon differentiation with phorbol esters, and increased with T cell activation.

In vitro Gene Knock Down of CATERPILLER 16.1. RNA interference vectors were constructed to TCTCAGCTTTAAGAGCAGG SEQ ID NO:187) and are useful in examining the function of CATERPILLAR 16.1 in Jurkat T cells, Raji B cells, and HL-60 cells.

Figure 31B:
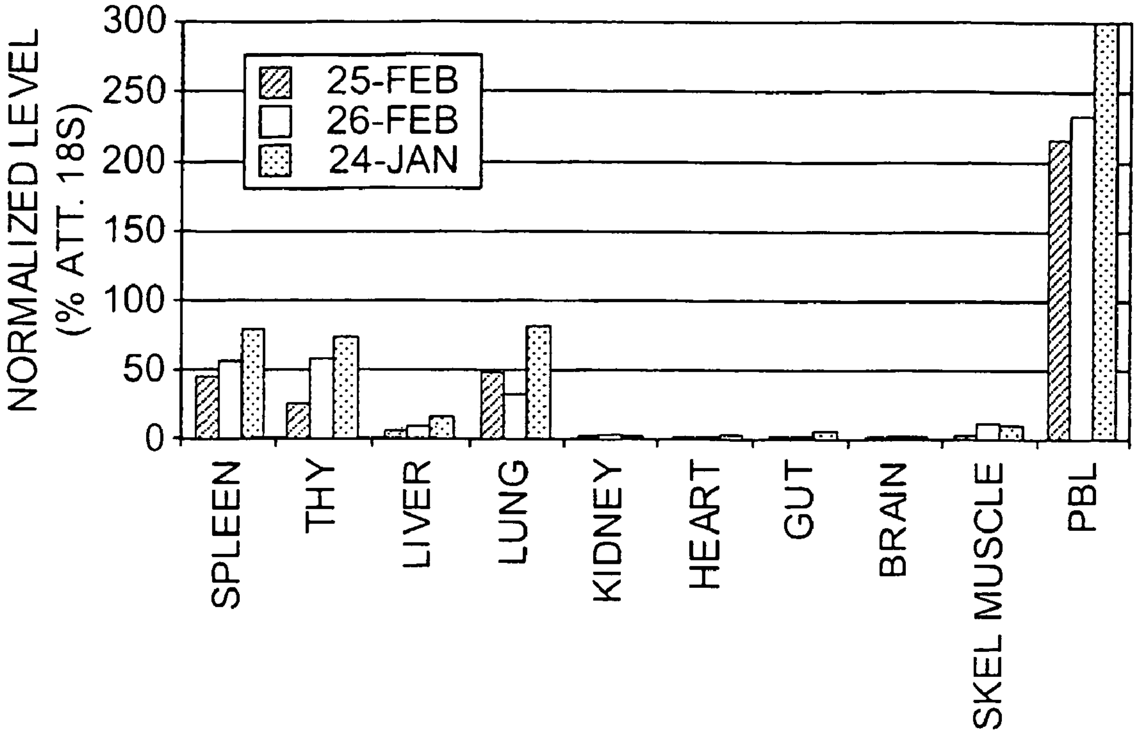
FIG. 31B shows resting levels of CATERPILLER m16.1 transcript in tissues and cells harvested from a saline-perfused mouse as determined by real-time PCR analysis. Data from three analyses are shown. The highest expression is seen in peripheral blood lymphocytes (PBL), spleen, thymus (thy), liver, and lung.
Figure 31C:
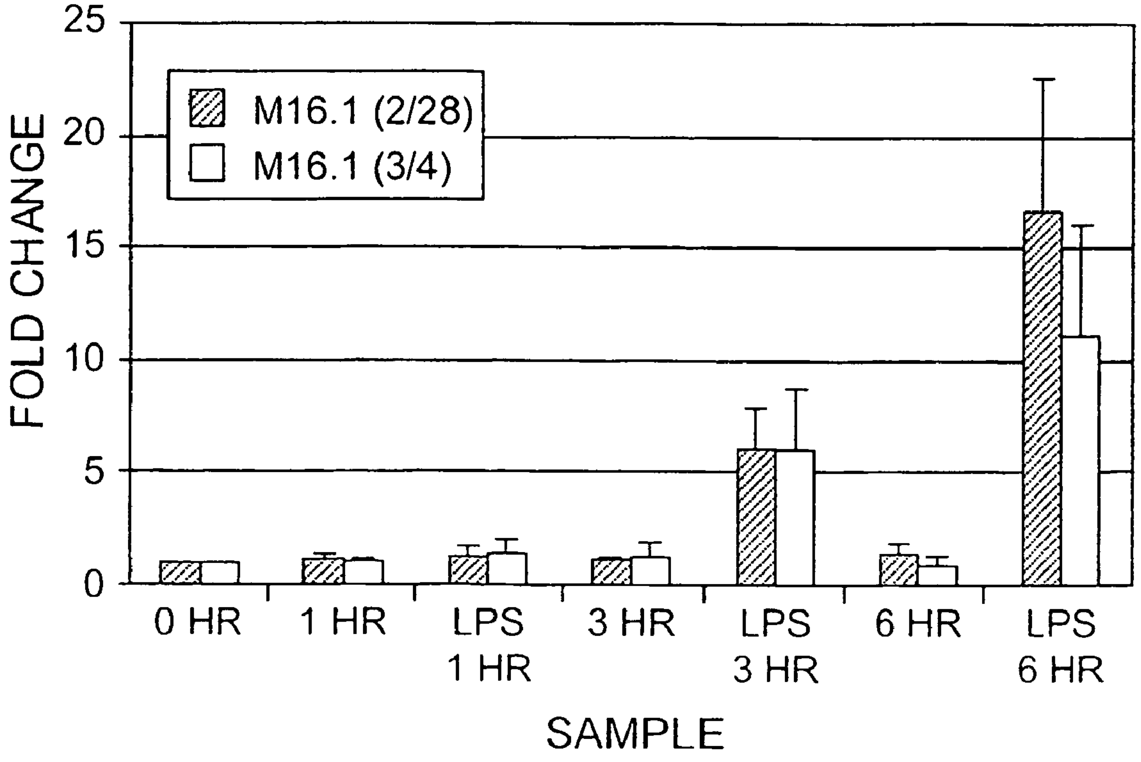
FIG. 31C shows that the expression of CATERPILLER m16.1 in primary macrophage increases with LPS stimulation. Three mice were injected (i.p.) with thioglycolate. Five days after injection, the peritoneal macrophage were isolated and then treated with LPS for 1, 3 or 6 hours in comparison to control macrophages that were untreated for the same time points. An increase in expression of CATERPILLER m16.1 is seen at 3 and 6 hours of LPS stimulation.
Figure 32:
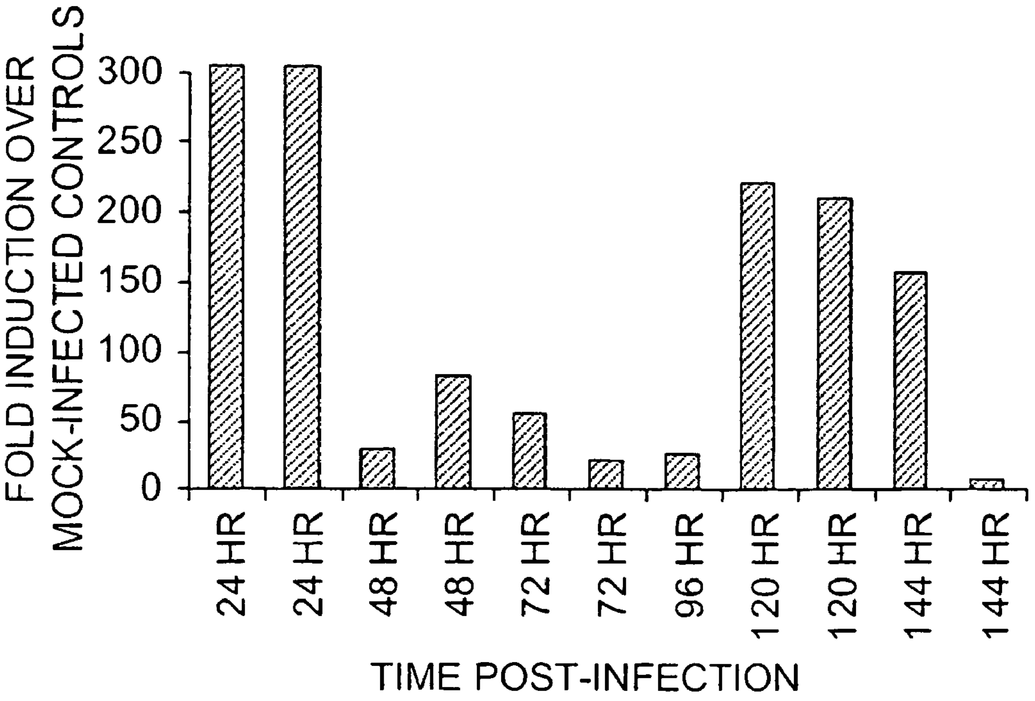
FIG. 32 shows the expression of a murine ortholog of CATERPILLER 16.1 in virally-induced arthritic tissues. RNA was prepared from skeletal muscle samples from arthritic joints of mice injected with Ross River Virus for various times (24-144 hours post-injection). Fold induction of CATERPILLER m16.1 expression in the muscle was determined by real-time PCR analyses through a comparison of viral-infected samples (n=3) to mock-infected samples (n=3) at each time point indicated. Two sets of data at each time point are presented. The expression is greatly induced at 24 hours, while the induction subsides between 48 and 96 hours, and then increases again at 120 and 144 hours.
Figure 33A:
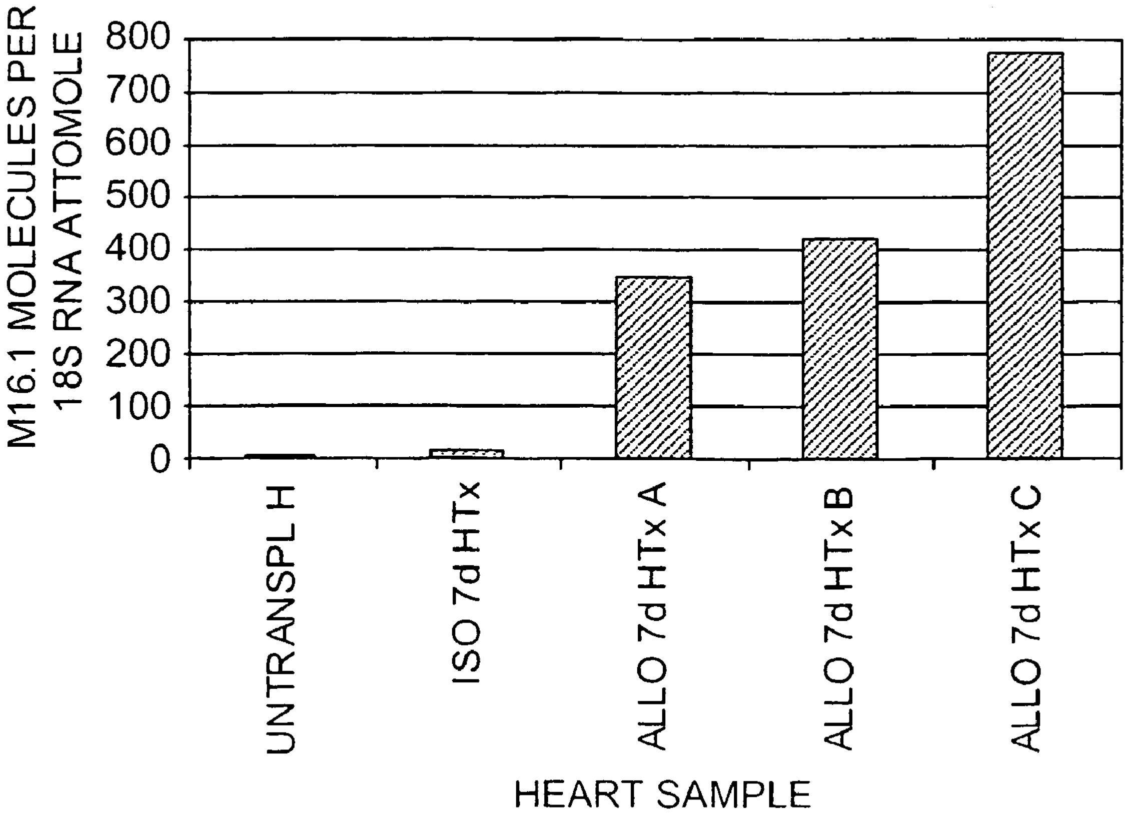
FIG. 33A shows that the expression of a murine ortholog of CATERPILLER 16.1 (m16.1) in transplanted heart tissues is greatly increased. RNA from mismatched heart tissues (allo) vs. genetically identical (iso) tissues harvested 7 days (7d) after transplantation was analyzed by real-time PCR. Samples from three transplanted tissues (A, B, C) are shown. 18s RNA levels were quantitated and used as an internal standard for each sample.

Studies of murine ortholog of CATERPILLER 16.1. Cellular and tissue localization of the murine ortholog of CATERPILLER 16.1, also referred to herein as CATERPILLER m16.1, was determined by real-time PCR. Similar to the human CATERPILLER 16.1, CATERPILLER m16.1 was highly abundant in blood, lymphoid tissues, myeloid and lymphoid cells (see FIGS. 31A and 31B). The expression of CATERPILLER m16.1 was upregulated by treatment of primary peritoneal macrophage with LPS (see FIG. 31C). The expression of m16.1 was correlated with several inflammatory diseases and model systems. The abundance of m16.1 transcript was highly upregulated (150-300-fold) in virally-induced arthritic tissues (see FIG. 32). Dramatic increases in m16.1 expression were evident in heart or kidney organs that were transplanted to MHC mismatched recipients, i.e., greater than 300-fold induction over levels found in genetically matched transplanted tissues (see FIGS. 33A, 33B and 33C).

EXAMPLE 6

Cloning, Characterization and Functional Analysis of CATERPILLER 16.2

This example describes the characteristics of the cloned human CATERPILLER 16.2 gene. The nucleic acid and protein sequences of the cloned CATERPILLER 16.2 are set forth as SEQ ID NO:27 and SEQ ID NO:28, respectively. It has now been found that 16.2 reduces the function of two crucial transcription factors involved in both inflammatory responses and cell survival, namely NF-κB and AP-1. CATERPILLER 16.2 expression is primarily found in peripheral blood leucocytes, and is reduced by bacterial products that activate the Toll-receptor pathway, the recognition receptors for bacteria, virus, fungus and other pathogens. These results indicate that CATERPILLER 16.2 is part of the Toll-receptor pathway and is involved in the regulation of immunity and cell survival.

Materials and Methods

Cloning of Full-Length CATERPILLER 16.2. The majority of the CATERPILLER 16.2 gene sequence was identified as provided in EXAMPLE 1. Total RNA was prepared from the Raji cell line with TRIZOL® reagent (INVITROGEN™, Carlsbad, Calif.). PolyA$^+$ mRNA was isolated from the total RNA using the OLIGOTEX® mRNA Mini Kit (QIAGEN®, Valencia, Calif.). Two gene-specific primer sets were created to clone the 5' and the 3' half of CATERPILLER 16.2, separately. The overlapping pieces of the CATERPILLER 16.2 mRNA were cloned by RT-PCR using Superscript II (INVITROGEN™, Carlsbad, Calif.) and Taq polymerase (INVITROGEN™, Carlsbad, Calif.). The products were ligated into pCR2.1-TOPO® (INVITROGEN™, Carlsbad, Calif.) and sequenced for verification.

Plasmids. To assemble the separately cloned pieces of CATERPILLER 16.2 and to fuse the CATERPILLER 16.2 to a FLAG® epitope, overlap extension PCR was performed with the following primer sets: 5'-CCGGGTACCATGGACTACAAAGACGATGACGATAAAGGTGGCAGGTGGGGGCACCAT-3' (SEQ ID NO:134) and 5'-ATCTTCTGAATGCGACAGTCCTTC-3' (SEQ ID NO:135); 5'-AAGGACTGTCGCATTCAGAAGATC-3' (SEQ ID NO:136) and 5'-AT- AGGATCCCCAGGATCACATTTCAACAGTG-3' (SEQ ID NO:137). The resulting product was digested with XhoI and BamHI and cloned into a similarly cut pcDNA3.1(−) vector (INVITROGEN™, Carlsbad, Calif.) using standard methodologies.

Luciferase Reporter Gene Assays. HEK293T cells were plated at $1\times10^4$ cells/well in 96-well plates and transfected the following day using FUGENE® transfection reagent (Roche, Indianapolis, Ind.) following the manufacturer's recommended protocol. For NF-κB or AP-1 reporter assays, cells were transfected with 50 ng of NF-κB-luc or AP-1-luc reporter and various amounts of the relevant expression plasmids as indicated, maintaining the total amount of DNA constant using pcDNA3 empty vector. The p53 reporter assays were performed in the 50 ng of p53-luc reporter plasmid, 200 ng of p53 expression vector and 400 ng of CATERPILLER 16-2 expression plasmid. 20 ng/ml of TNFα or 5 ng/ml PMA was added to the indicated wells 10 hours post transfection. Cells were harvested 36 hours after transfection and assayed for luciferase activity following standard procedures with the equal amounts of protein as determined by the Bradford protein assay (BIO-RAD®, Hercules, Calif.).

RNA Preparation and Real-Time PCR. Total RNA was isolated according using the SV40 Total RNA System (PROMEGA™, Madison, Wis.) with an additional DNase I digestion step. Real-Time PCR was performed with the TAQMAN® sequence detection system (Applied Biosystems, Foster City, Calif.). Primers and probes for human CATERPILLER 16.2 were: forward 5'-CTGGGAAGGGCAGTCAAG-3' (SEQ ID NO:138); reverse 5'-TGCCTCTGTATCCTTGAGTC-3' (SEQ ID NO:139) and probe 5'-CCCGCAGGCCCTGGATAGGACACC-3' (SEQ ID NO: 140). Primers and probes for mouse CATERPILLER 16.2 were: forward 5'-TGCTACAAGTCCGGGACAAA-3' (SEQ ID NO:141); reverse 5'-GCCCAGTTCTGGGTCATTT-3' (SEQ ID NO:142); and probe 5'-CAGCAGAGCCTCAGAGTGCTTCG-3' (SEQ ID NO:143). Primers and probes for 18S were: forward 5'-GCTGCTGGCACCAGACTT-3' (SEQ ID NO:99); reverse 5'-CGGCTACCACATCCAAGG-3' (SEQ ID NO:100); and probe 5'-CAAATTACCCACTCCCGACCCG-3' (SEQ ID NO:101). Primer-probe sets for 18S ribosomal RNA were used as internal controls. Results were normalized to the internal control and were expressed in normalized numbers.

Small Interference RNA (siRNA) Construction and Transfection. CATERPILLER 16.2 siRNAs were generated and are useful for stably transfecting Raji and Thp-1 cells and discerning the function of CATERPILLER 16.2. The target sequence was: 5'-GGAGATCCCGGTGGACCAC-3' (SEQ ID NO:144) and the mutant sequence was: 5'-GGAGATCCtGGTGGACCAC-3' (SEQ ID NO: 145).

Experimental Results

Full-Length Coding Sequence of CATERPILLER 16.2. The protein coding region of CATERPILLER 16.2 was assembled by searching human genomic sequence for CATERPILLER family genes (see EXAMPLE 1). The predicted nucleic acid and protein sequences are set forth as SEQ ID NO:25 (FIGS. 34A-B) and SEQ ID NO:26 (FIG. 34C), respectively. The cloned sequence of CATERPILLER 16.2 was identical to the predicted CATERPILLER 16.2 sequence from nucleotides 286-2217. Nucleotide 286 of the cloned sequence corresponded to the initiation methionine in the predicted sequence. The 3' end of the cloned sequence, nucleotides 2218-3489, differed completely from the predicted sequence. The CATERPILLER 16.2 genomic sequence (NBCI) and the cloned sequence were compared to correct for any errors introduced by the cloning process. The CATERPILLER 16.2 nucleotide sequence (SEQ ID NO:27, FIGS. 34D-E) included the first ATG after an upstream, in-frame stop codon, the 3198 nucleotide ORF, and translation stop codon. As expected, CATERPILLER 16.2 protein (SEQ ID NO:28; FIG. 34F) contains a nucleotide binding domain (NBD) followed by a number of leucine rich repeats. Additionally, the intron-exon organization conforms to CATERPILLAR gene family; the NBD is encoded by one large exon and each leucine rich repeat is encoded by individual exons of approximately 76 or 174 nucleotides. Unlike many of the CATERPILLER genes, the N-terminus of CATERPILLER 16.2 does not contain a distinguishable Pyrin or CARD domain.

Figure 35A:
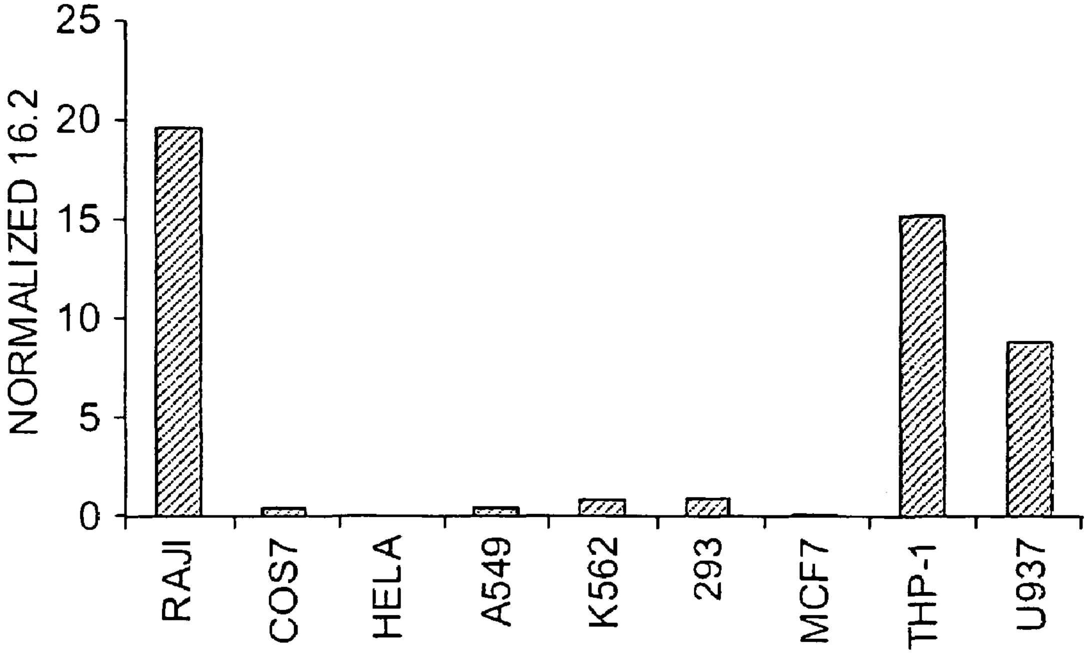
FIG. 35A shows the expression of human CATERPILLER 16.2 mRNA in various human cell lines as determined by separated real-time PCR. Representative of two experiments.
Figure 35B:
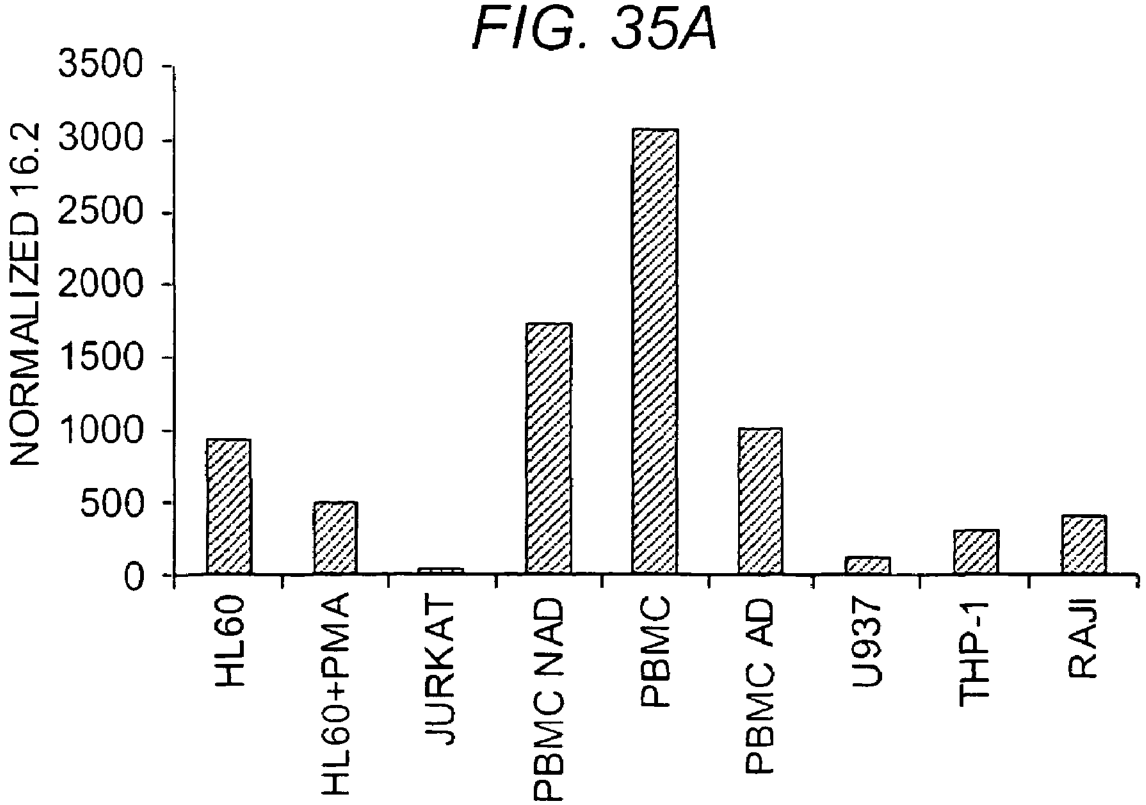
FIG. 35B shows the expression of CATERPILLER 16.2 in human total PBMC populations, PBMCs separated based on adherence, or the indicated human cell lines as determined by real-time PCR. CATERPILLER 16.2 expression was normalized to the expression of 18S rRNA. Representative of two experiments.

Expression of Human CATERPILLER 16.2 is Predominant in Immune Cells. Real-Time PCR showed expression in Raji (B cell line), Thp-1 and U937 (myeloid monocytic cell lines) but not in the non-hematopoietic cell lines examined (FIG. 35A). High levels of CATERPILLER 16.2 were detected in total PBMCs, with lower expression observed in adherent PBMCs relative to the non-adherent population. CATERPILLER 16.2 expression was detected at lower levels in HL-60 cells and was down-regulated by 48 hours after stimulation with PMA. Thp-1 and U937 were included to indicate the relative expression of CATERPILLER 16.2. CATERPILLER 16.2 expression was not observed in the Jurkat T cell line (FIG. 35B).

Figure 36A:
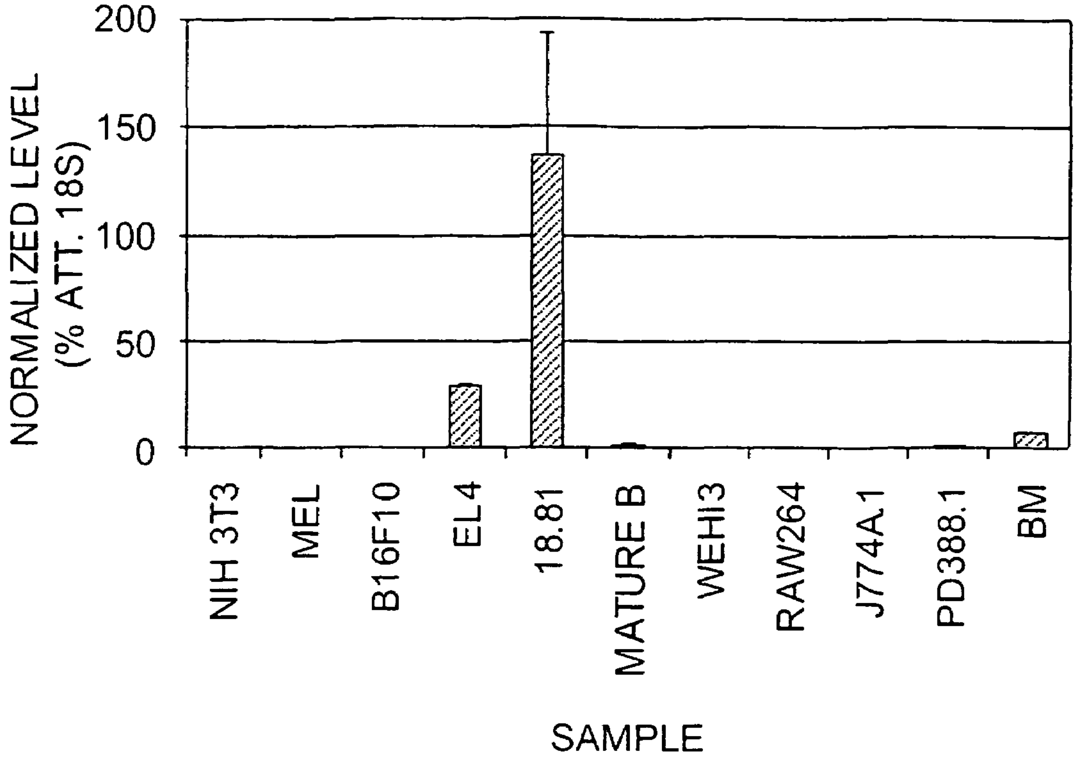
FIG. 36A shows the expression of mouse CATERPILLER 16.2 mRNA in various mouse cell lines as determined by separated real-time PCR. Average of three experiments.
Figure 36B:
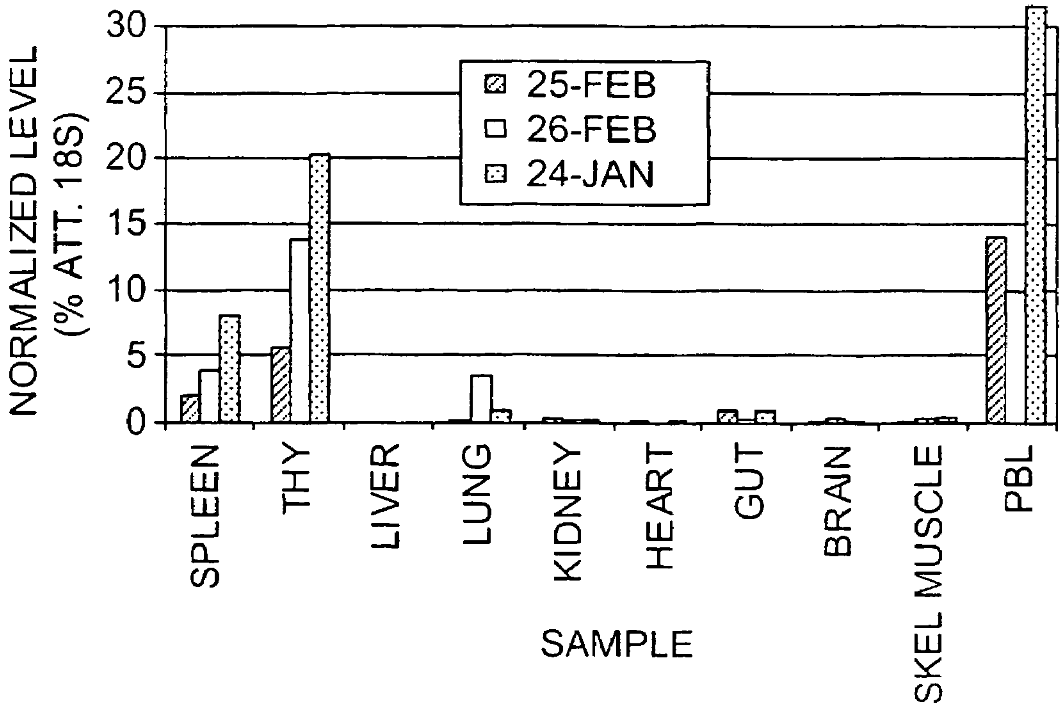
FIG. 36B shows mouse CATERPILLER 16.2 expression in perfused mouse tissues or peripheral blood by real-time PCR. CATERPILLER 16.2 expression was normalized to the expression of 18S rRNA. Three real-time runs were performed and are shown.
Figure 36C:
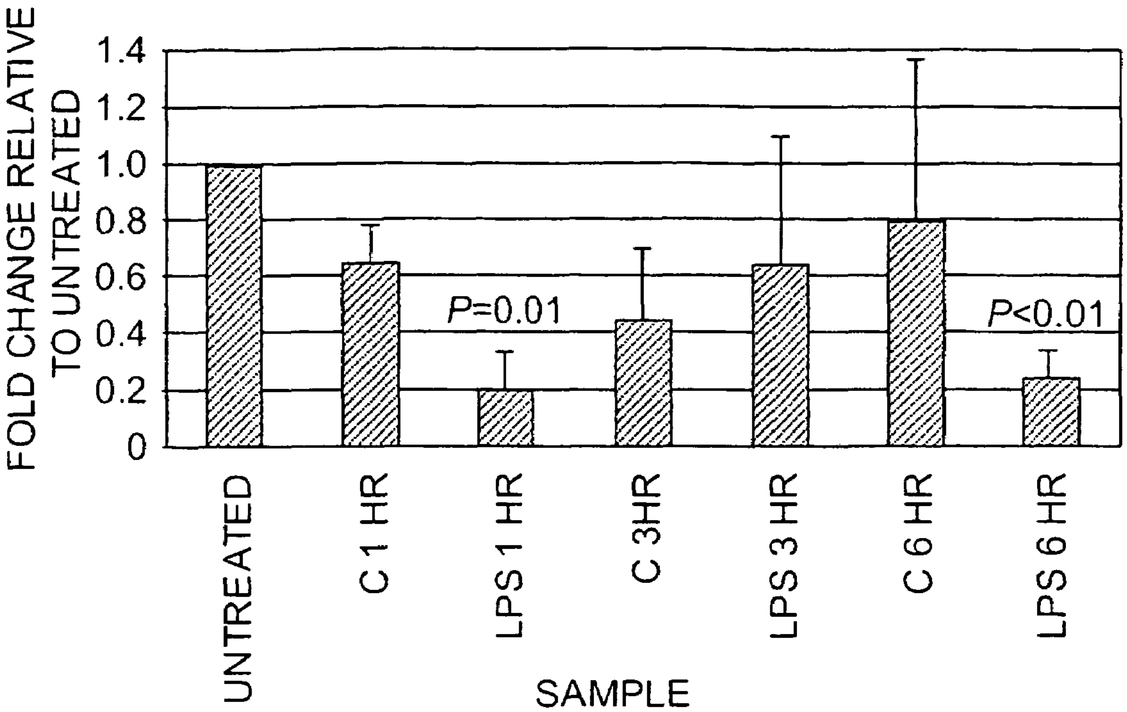
FIG. 36C shows mouse CATERPILLER 16.2 expression in peritoneal macrophage treated with LPS for up to 3 hours compared to control cells (C) not treated with LPS for the same time. Three sets of treated and untreated macrophage were subjected to real-time PCR analysis.

Expression of Mouse 16.2 is Predominant in Immune Cells. Real-Time PCR showed expression of mouse CATERPILLER 16.2 in 18.81 (B cell line), EL4 (T cell line) but not in the non-hematopoietic cell lines examined (FIG. 36A). Unlike human CATERPILLER 16.2, which was found in myeloid cell lines, mouse CATERPILLER 16.2 was not detected in any of the myeloid cell lines examined. Low levels of CATERPILLER 16.2 were detected in primary mouse bone marrow. High levels of mouse CATERPILLER 16.2 were detected in the spleen, thymus and peripheral blood, with a lower level observed in the lung (FIG. 36B). Analysis of CATERPILLER 16.2 expression in Brewers Thioglycolate mouse peritoneal macrophages after treatment with LPS showed that CATERPILLER 16.2 was initially down-regulated at 1 hour after LPS exposure but then returned to near normal levels (FIG. 36C).

Figure 37A:
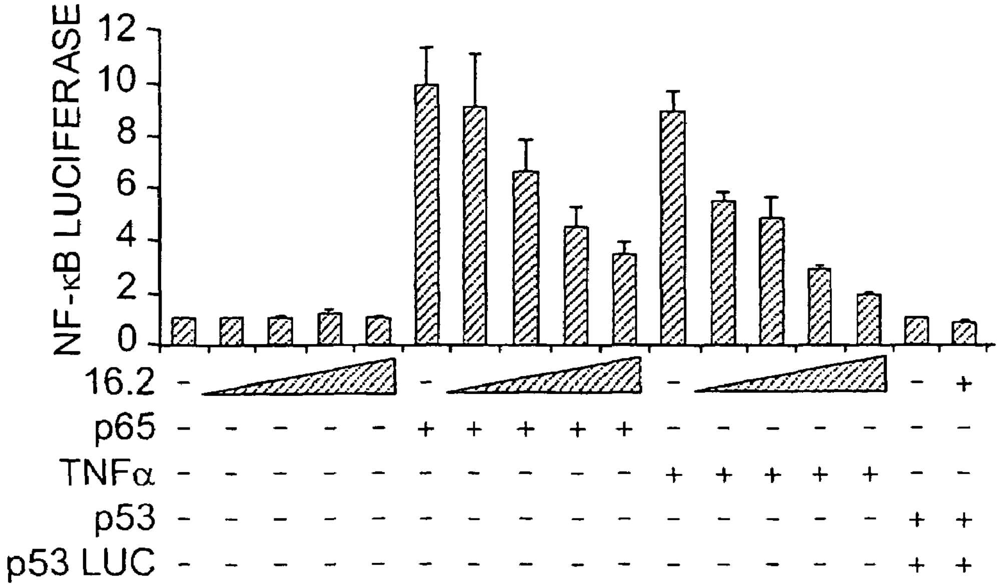
FIG. 37A shows that CATERPILLER 16.2 inhibits NF-κB induction. HEK293T cells were seeded into 96-well plates and transfected on the following day with 50 ng of pNF-κB-luc reporter gene plasmid together with increasing amounts (100 ng to 400 ng) of pcDNA3Fg-16.2 and the indicated wells were stimulated with TNFα. The two last bars represent a control in which 50 ng of p53-luc reporter gene plasmid, 200 ng of p53-encoding plasmid and 400 ng of pcDNA3Fg-16.2 were transfected. After 36 hours, cells were harvested, and luciferase activity was determined for each sample. Numbers indicate fold induction of the NF-κB reporter gene above base-line.
Figure 37B:
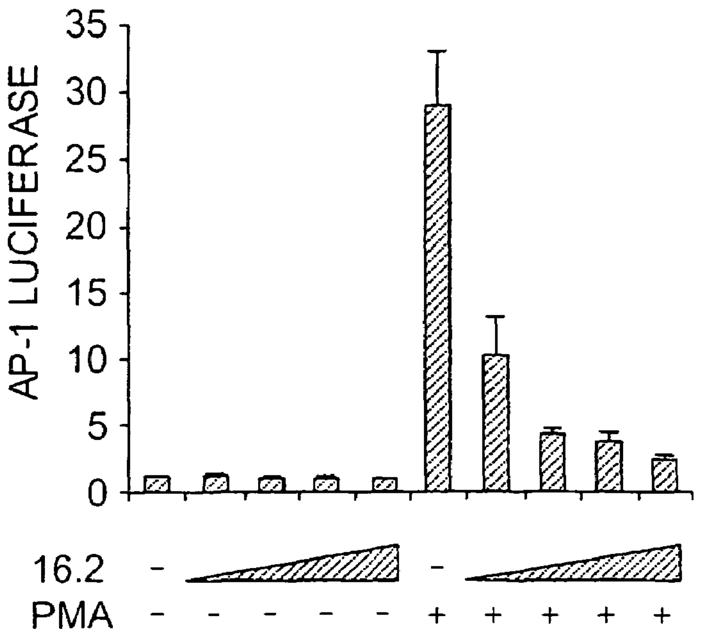
FIG. 37B shows that CATERPILLER 16.2 inhibits AP-1 induction. HEK293T cells were seeded into 96-well plates and transfected on the following day with 50 ng of AP-1-luc reporter gene plasmid together with increasing amounts (100 ng to 400 ng) of pcDNA3Fg-16.2 and the indicated wells were stimulated with PMAβ. After 36 hours, cells were harvested, and luciferase activity was determined for each sample. Numbers indicate fold induction of the AP-1 reporter gene above base-line.

Regulation of NF-κB and AP-1 Activity by CATERPILLER 16.2. HEK293T cells transiently transfected with a CATERPILLER 16.2-encoding plasmid together with NF-κB-dependent or AP-1-dependent luciferase reporters were used to examine the regulation of NF-κB or AP-1 induction by CATERPILLER 16.2. Under the conditions indicated, CATERPILLER 16.2 appeared to inhibit NF-κB induction by TNFα or p65 (FIG. 37A). CATERPILLER 16.2 overexpression also markedly reduced AP-1 activity induced by PMA (FIG. 37B). These effects were specific in that the activity of other transcription factors such as p53 were not suppressed (FIG. 37A).

EXAMPLE 7

Functional Analysis of CIAS1 and Subdomains Thereof

This example describes the characteristics of the full-length CIAS1 protein and two shorter, naturally occurring isoforms. It has now been found that full-length CIAS1 protein and the two shorter isoforms dramatically inhibit TNFα-induced activation of NF-κB reporter activity. Transcriptional activity of exogenous NF-κB p65 is also blocked by CIAS1.

A truncated product, containing the nucleotide-binding and leucine-rich repeat regions but not the pyrin domain of CIAS1, is responsible for this inhibition. CIAS1 suppressed TNFα-induced nuclear translocation of endogenous p65. The results provided herein indicate that CIAS1 may act as a key negative regulator of inflammation, induced to dampen NF-κB-dependent pro-inflammatory and pro-survival signals.

Materials and Methods

Cloning of CIAS1 Isoforms. A number of alternatively spliced isoforms of CIAS1 were identified during the cloning of CIAS1 from human blood cells. All CIAS1 isoforms were cloned in two pieces. Briefly, RT-PCR on total RNA from PBMC was performed with gene-specific primers to amplify the 5' end (pyrin domain up to and including the NBD) and the 3' end (NBD to the last predicted LRR exon), individually. The finished full-length product was subcloned by overlapping extension, and was 3104 bp in total long. The predicted full-length sequence corresponds to accession number NM_004895 (incorporated by reference herein in its entirety). A mouse homolog of CIAS1 was also identified and corresponds to accession number NM_145827 (incorporated by reference herein in its entirety). During the cloning of the 3' end of the human gene, several PCR products were generated, cloned, and sequenced. These products corresponded to naturally-occurring splice variants of CIAS1, missing one or more LRR-containing exons. One such isoform was the originally identified Cryopyrin, with exons 4 and 6 deleted in-frame (accession number AY092033; incorporated by reference herein in its entirety). Also identified, cloned, sequenced, and analyzed was a previously undescribed isoform with exon 4 deleted in-frame. This isoform was designated 'FgCIAS1 Del4' with nucleotide and deduced protein sequences set forth as SEQ ID NO:148 (FIG. 42K-L) and SEQ ID NO:149 (FIG. 42M), respectively.

Monocyte Preparation and Real-Time PCR Analysis. Primary human monocytes were isolated from normal donor buffy coat preparations (American Red Cross, Durham, N.C.). PBMCs were obtained using a standard FICOLL®-centrifugation procedure. The non-adherent fraction was removed and fresh medium was subsequently added alone or with stimulant as indicated. LPS from *E. coli* (026:B6, Sigma Chemicals, St. Louis, Mo.) or *S. enteritidis* (Sigma, St. Louis, Mo.) was added to 200 ng/ml; LTA from *S. aureus* (Sigma, St. Louis, Mo.) or PGN from *S. aureus* (Fluka Biochemika, Buchs, Switzerland) to 1 μg/ml; Poly I:C (Amersham, Piscataway, N.J.) to 10 μg/ml; CpG oligonucleotide (ODN 1668) or control GpC oligonucleotide (ODN 1720, both from TIB MolBiol, Berlin, Germany) to 1 μM. Cells were stimulated for 1 hour at 37° C., except as indicated. In select experiments, freshly isolated monocytes were cultured with signaling pathway inhibitors, DMSO control or medium alone for 20 minutes prior to LPS stimulation. The MAPK inhibitor U0126 (PROMEGA™, Madison, Wis.) and the p38 inhibitor SB203580 (CALBIOCHEM®, San Diego, Calif.) were used at 10 μM final concentration, the PI3K inhibitor Wortmannin at 100 nM. These concentrations have been shown to be effective in inhibiting their intended target (MacKeigan, et al (2000) *J. Biol. Chem.* 275:38953; Yao and Cooper (1995) *Science* 267:2003). RNA was isolated according to the manufacturer's instructions (SV Total RNA Isolation, PROMEGA™, Madison, Wis.) and first strand synthesis was performed using standard methods (MMLV-RT).

Real-Time PCR analyses were performed on the ABI Prism 7700 instrument (ABI, PerkinElmer, Foster City, Calif.) (Wong, et al. (2002) *J. Immunol.* 169:3112). CIAS1 gene expression was determined using the following intron-spanning primers for amplification: forward primer: 5'-GGCATATCACAGTGGGATTC-3' (SEQ ID NO:146) and reverse primer: 5'-GATCTTCGCTGCGATCAAC-3' (SEQ ID NO:147). Amplification of 18S RNA was performed using a standard method (Wong, et al. (2002). *J. Immunol.* 169:3112). CIAS1 expression was quantitated by comparing values obtained to a standard curve generated with plasmid DNA. All CIAS1 values obtained were normalized to 18s RNA (CIAS 1 molecules/Attomole of 18S) and reported as differences in fold induction of CIAS1 over levels of CIAS1 in untreated, resting monocyte cultures.

Cell Transfection and Luciferase Assays. HeLa cells (American Type Tissue Collection, Manassas, Va.) were transfected with the indicated quantities of the following FLAG®-tagged CIAS1 constructs: full-length wild-type (Fg CIAS1), CIAS1 Deletion exon 4 (Fg Del4), CIAS1 Deletion exon 4 and 6 (Fg Del4 Del6), CIAS1 truncation mutants (CIAS1 Pyrin, CIAS1 Pyrin/NBD, CIAS1 NBD/LRR, and CIAS1 LRR), or pcDNA3 together with 100 ng of 3×-NF-κB-Luciferase using FUGENE6™ (Roche, Indianapolis, Ind.). 24 hours post-transfection, cells were stimulated with TNFα (10 ng/ml) or transfected with either empty vector or pCMV4T-p65 (500 ng/well) and incubated at 37° C. for an additional 24 hours. Cells were then lysed and luciferase quantitated using standard methodologies. The p53-luciferase control reporter construct was used at 500 ng/well.

Immunofluorescent Staining and Quantitation. HeLa cells were transfected alone or in combination with 500 ng/well DR-luciferase, 1.5 μg/well FLAG®-CIAS1, or 1.5 μg/well pcDNA3 using FUGENE™ 24 hours after transfection, cells were stimulated with TNFα (10 ng/ml), CIITA (100 ng/well, pcDNA3 (100 ng/well) or medium alone for 30 min at 37° C. as indicated. Twenty-four hours post-stimulation the wells were washed 3×PBS, lysed for 15 minutes at room temperature and Luciferin substrate quantitated as per standard protocol. Other staining was performed using well-known methods. Endogenous p65 was visualized using a rabbit anti-p65 Ab (Santa Cruz Biotechnology, Inc., Santa Cruz, Calif.) and goat anti-rabbit-biotin/Avidin-Texas Red secondary Abs (Vector Laboratories, Burlingame, Calif.). FLAG®-tagged CIAS1 was visualized using the FLAG® antibody M5 (Sigma, St. Louis, Mo.) and goat anti-mouse FITC (BD Pharmingen, San Diego, Calif.). Nuclei were counterstained using DAPI (Vector Laboratories, Burlingame, Calif.). The subcellular localization of p65 was assessed in 100 CIAS1$^{low/neg}$ cells and compared to p65 in 100 CIAS1+ cells in three double-blind studies.

Experimental Results

Figure 38A:
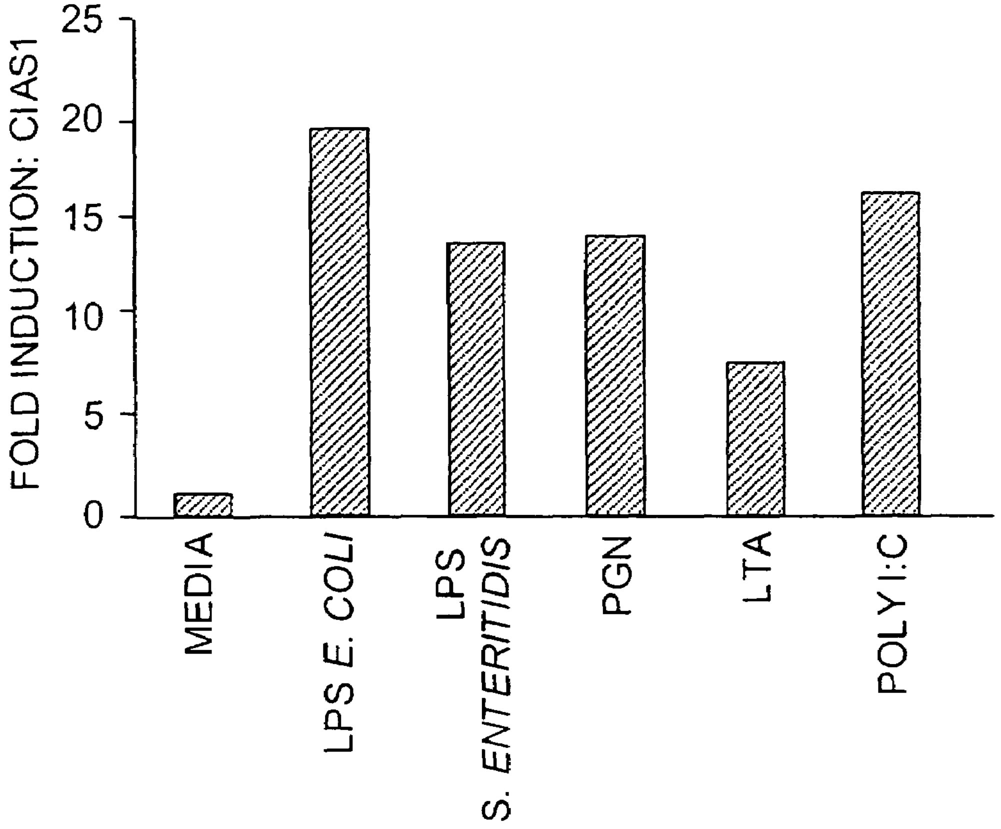
FIG. 38A shows the induction of CIAS1 in primary human monocytes. Adherence-purified human monocytes were stimulated as indicated for 1 hour before lysis, RNA preparation and analysis.

CIAS1 is Induced by Stimulants of Toll-Like Receptor Signaling. Expression of CIAS1 in peripheral blood cells was determined to be primarily restricted to monocytes (Manji, et al. (2002) *J. Biol. Chem.* 277:11570). Real-time PCR analysis was conducted to quantitate levels of CIAS1 RNA in both resting and activated cells to examine the inducibility of CIAS1 in primary human monocytes. LTA, PGN, poly I:C, LPS, and CpG oligonucleotides are well characterized stimulators of TLR-2, -3, -4, and -9, (Schwandner, et al (1999) *J. Biol. Chem.* 274:17406; Alexopoulou, et al. (2001) *Nature* 413:732, Poltorak, et al. (1998) *Science* 282:2085; Hemmi, et al. (2000) *Nature* 408:740). Administration of LTA, LPS, PGN, or Poly I:C to primary human monocytes elicited a robust induction of CIAS1 expression (FIG. 38A). No changes in CIAS1 gene expression were observed with CpG oligonucleotides although this may be due to the restricted expression of TLR9 on human plasmacytoid dendritic cells and B cells whose presence in the preparation was not ascertained.

Figure 38B:
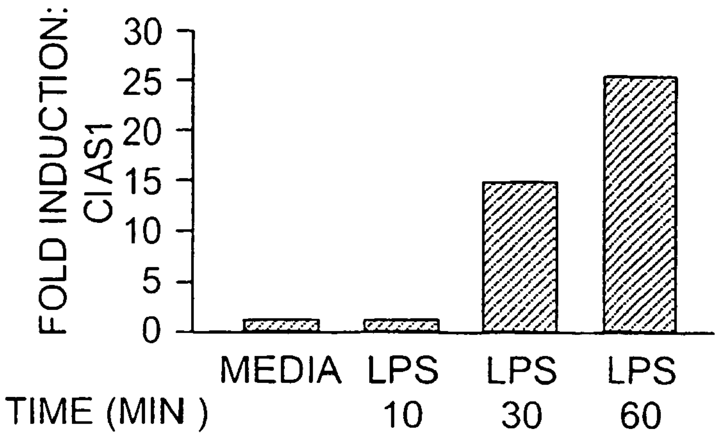
FIG. 38B shows that LPS (200 ng/ml) rapidly induces CIAS1.

*E. coli* LPS acted rapidly to induce an approximate 15-fold Increase in CIAS1 expression within 30 minutes of stimulation, with expression reaching over 20-fold by 1 hour (FIG. 38B). This induction was reproducible within experiments and between multiple donor blood preparations. The expression of CIAS1 may be under tight regulation as CIAS1 RNA was low in resting monocytes, induced strongly within an hour of LPS stimulation, and returning to baseline levels within 12 hours following LPS addition.

Figure 38C:
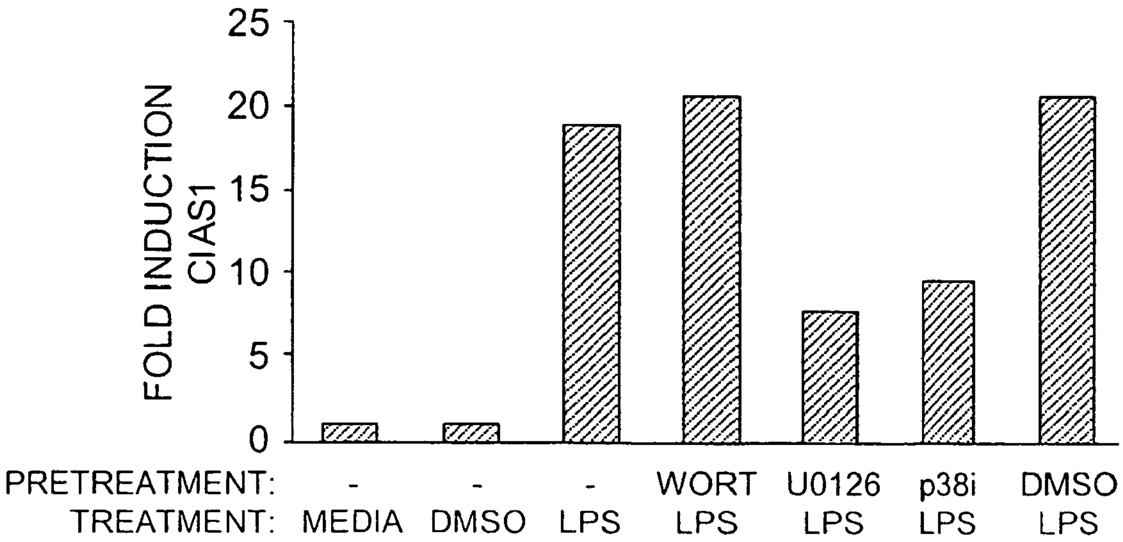
FIG. 38C shows induction of CIAS1 in monocytes pretreated with inhibitors of the MAPK, p38, and PI3K pathways for 20 minutes prior to LPS stimulation.

LPS Induction of CIAS1 Via the MAPK/p38 Pathways. Primary human monocytes were treated with MAPK, p38, or PI3K inhibitors prior to LPS stimulation to determine the pathways involved in CIAS1 expression. Treatment with the MAPK pathway inhibitor U0126 or the p38 pathway inhibitor SB203580 led to a reduction in LPS-induced CIAS1 RNA while the PI3K pathway inhibitor Wortmannin had no effect (FIG. 38C). Thus, LPS induction utilizes the MAPK/p38 but not PI3K signaling pathways to induce CIAS1 expression.

Figures 39A, 39B:
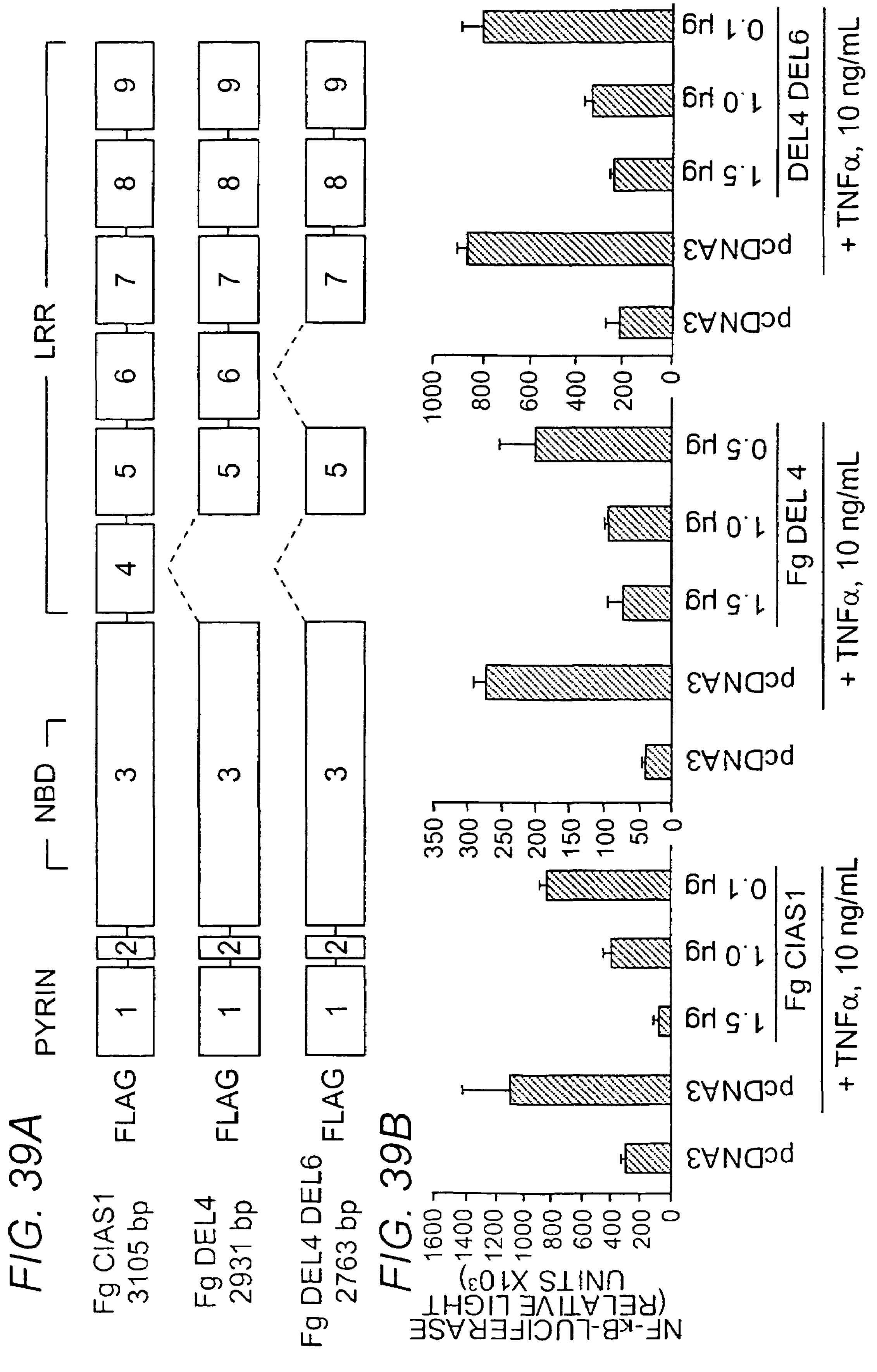
FIG. 39A shows FLAG®-tagged full-length CIAS1 (Fg CIAS1) and the shorter, naturally occurring isoforms missing exon 4 or exons 4 and 6.
FIG. 39B shows that all the CIAS1 constructs inhibited NF-κB-luciferase activation by TNFα in a dose-dependent fashion

Multiple Isoforms of CIAS 1 Inhibit NF-κB Reporter Activity. The rapid induction of CIAS1 by immunostimulatory molecules indicated that CIAS1 plays a role in mediating the inflammatory response. As NF-κB activity has been intimately linked to inflammation (Li and Verma (2002) *Nature Rev. Immunol.* 2:725), NF-κB activity in the presence of transfected CIAS1 was examined. Transfection of full-length CIAS1 or either of two shorter, naturally-occurring splice variants of CIAS1 (FIG. 39A) did not lead to activation of NF-κB-Luciferase. Unexpectedly, relative decreases in basal NF-κB-luciferase activity in the CIAS1 positive lanes was observed. TNFα induces NF-κB, and in the experiments conducted herein, TNFα also elicited NF-κB reporter activity (FIG. 39B, first two lanes). Since the observed decreases in basal activity suggested a possible inhibitory role for CIAS1, we tested the ability of CIAS1 to inhibit TNFα-induced NF-κB-Luciferase. As shown in FIG. 39B, overexpression of all three CIAS1 isoforms led to a strong, dose-dependent inhibition of TNFα-induced NF-κB-luciferase.

Figure 39C:
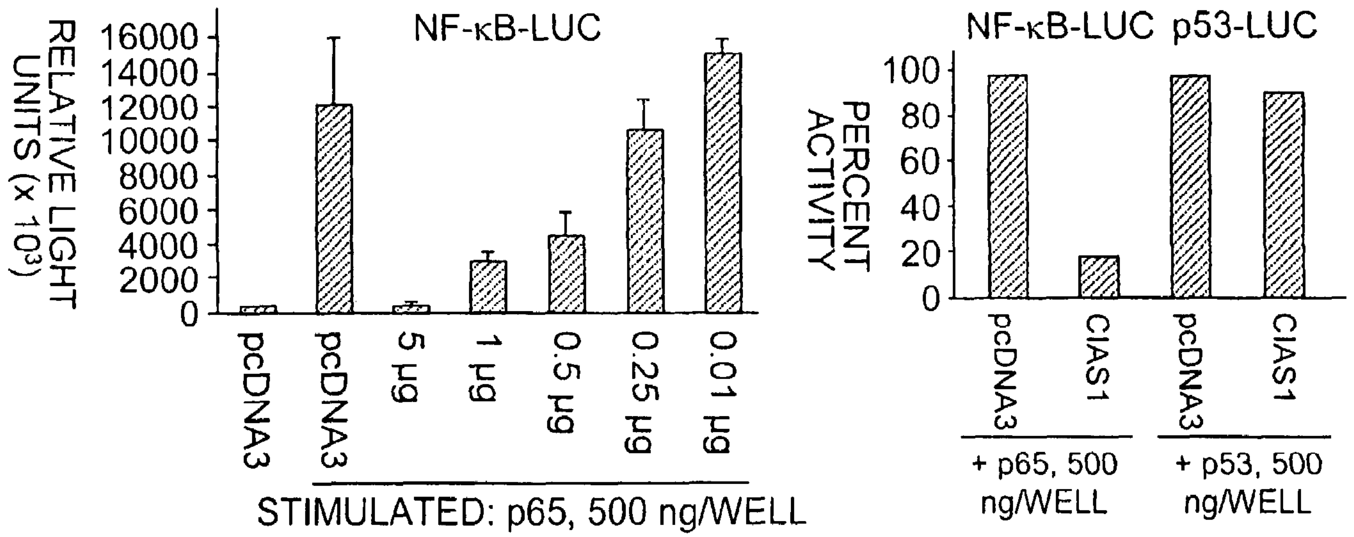
FIG. 39C shows that FgCIAS1 inhibits the ability of transfected p65 to stimulate NF-κB-luciferase in a dose-dependent fashion (left panel). FgCIAS1 does not affect p53 function (right panel). Representative of three or more assays performed in triplicate±SEM.

Many signaling pathways leading to the activation of NF-κB share a common mechanism of action that liberates the p50 and p65 subunits of NF-κB from the IκB complex, allowing them to be phosphorylated and imported into the nucleus. Thus, the effects of CIAS1 on p65-induction of the NF-κB-luciferase construct were analyzed to determine the position CIAS1 occupies in the NF-κB pathway. CIAS1 dramatically inhibited the ability of p65 to activate the NF-κB-luciferase reporter in a dose-dependent fashion (FIG. 39C). This indicates that CIAS1 functions at the distal end of NF-κB signaling by affecting p65 function. p53 induction of a p53-responsive luciferase construct was largely unaffected reflecting the specificity of CIAS1. Additionally, an HA-tagged CIAS1 showed identical results.

CIAS1 Functions in the Cytoplasm. Indirect immunofluorescence studies were performed to visualize the subcellular localization of overexpressed CIAS1. Full-length CIAS1 localizes to the cytoplasm in the absence of any stimulus (Manji, et al. (2002) *J. Biol. Chem.* 277:11570), and the effects of cellular stimulation on the localization of CIAS1 were assessed by transiently transfecting HeLa cells with the concentration of CIAS1 shown to inhibit NF-κB-luciferase and visualizing FLAG®-tagged CIAS1. Twenty minutes of TNFα stimulation potently induced endogenous p65 to enter the nucleus but did not lead to nuclear translocation of FgCIAS1. These results indicate that CIAS1 functions in the cytoplasm to inhibit NF-κB.

Figure 40:
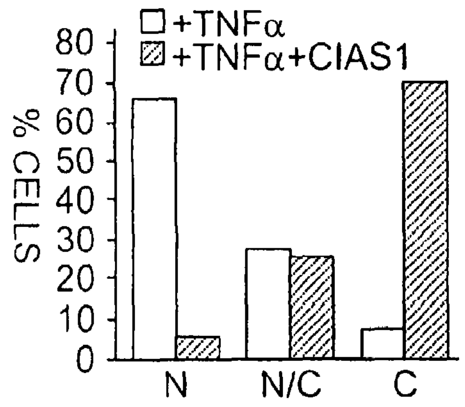
FIG. 40 shows that FgCIAS1 inhibits TNFα-induced nuclear translocation of p65. Localization of p65 in CIAS1-positive cells was scored qualitatively as described in EXAMPLE 7. p65 localization was scored as primarily nuclear (N), evenly nuclear/cytoplasmic (N/C) or primarily cytoplasmic (C) p65. Quantitative data shown are the composite percentages from three individual experiments.

CIAS1 Inhibits Nuclear Translocation of p65. Inhibition of NF-κB may occur at any of several stages in the activation cascade. The observation that CIAS1 inhibits exogenously transfected 'free' p65 indicated that one function of CIAS1 may be to inhibit nuclear translocation of the p65 subunit. Thus, HeLa cells were transiently transfected with CIAS1 and TNFα-induced nuclear translocation of endogenous p65 was analyzed. TNFα stimulation of NF-κB lead to rapid movement of p65 into the nuclear compartment (Beg, et al. (1993) *Mol. Cell. Biol.* 13:3301). In the presence of CIAS1, a significant reduction in the amount of nuclear p65 was observed in response to TNFα. A double-blind numerical analysis of this effect was performed (FIG. 40).

Figure 41A:
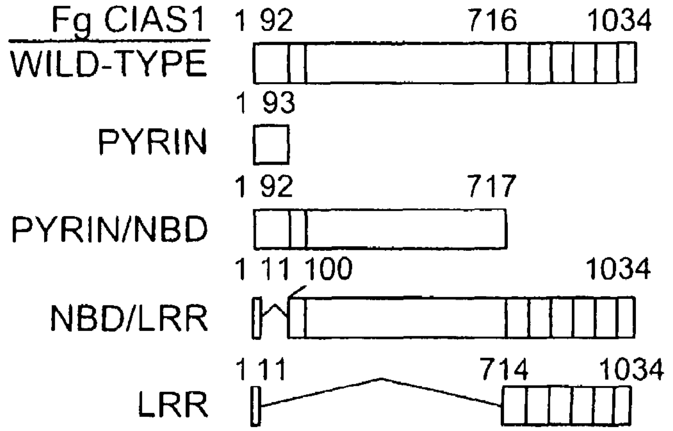
FIG. 41A depicts deletion mutant constructs of CIAS1.

Inhibition of TNFα Signaling is Mediated by the Nucleotide-Binding and Leucine-Rich Repeat Regions of CIAS1. A series of FLAG®-tagged deletion constructs of CIAS1 were generated (FIG. 41A) and tested to determine the inhibitory nature of CIAS1 in TNFα signaling. The pyrin construct contained nucleic acid sequences encoding the pyrin domain, herein set forth as SEQ ID NO:29 (FIG. 42A) and SEQ ID NO:30 (FIG. 42B), respectively. The pyrin/NBD construct contained nucleic acid sequences encoding the pyrin and NBD domains, herein set forth as SEQ ID NO:31 (FIGS. 42C-D) and SEQ ID NO:32 (FIG. 42E), respectively. The NBD/LRR construct contained nucleic acid sequences encoding the NBD/LRR domains, herein set forth as SEQ ID NO:33 (FIG. 42F-G) and SEQ ID NO:34 (FIG. 42H), respectively. The LRR construct contained nucleic acid sequences encoding the LRR domain, herein set forth as SEQ ID NO:35 (FIG. 42I) and SEQ ID NO:36 (FIG. 42J), respectively. The NBD and LRR regions together inhibited TNFα-induced NF-κB activity as did the full-length construct (FIG. 41B). Deletion of the amino-terminal Pyrin domain had no deleterious effect on inhibition and transfection of the Pyrin domain alone served to activate NF-κB-luciferase above and beyond TNFα stimulation.

Regulation of CIITA Activity. The observation that CIAS-1 regulates NF-κB activity indicates that CIAS-1 may play a role in either inflammation or apoptosis, or both. CIAS-1 may be an inflammatory mediator which regulates other molecules involved in the inflammatory process. One arm of the inflammatory response involves antigen presentation through the MHC class I and/or MHC class II pathways. As CIITA is widely regarded as the master regulator of MHC class II gene transcription and to a lesser extent affects MHC class I transcription, the effect of CIAS-1 on CIITA activity was analyzed. Using an MHC class II reporter construct, DR-Luciferase, it was found that CIAS-1 inhibits the ability of overexpressed CIITA to activate DR-LuciFerase in HeLa cells (FIG. 43).

The combination of ASC and CIAS1 causes the induction of NF-κB, but ASC alone has the opposite effect by inhibiting NF-κB activation (Stehlik, et al. (2002) *J. Exp. Med.* 196: 1605). Similarly, the results provided herein revealed that CIAS1 alone, reduced TNFα and NF-κB responses. Together, these results indicate that the balance of ASC and CIAS1 critically determine the extent of inflammatory responses, and that alone, either may serve as an important suppressor molecule. Notably, NF-κB nuclear translocation was routinely detectable within 10-30 minutes after cell activation while increases in CIAS1 RNA were observed 30-60 minutes after stimulation. Thus, CIAS1 may be induced to limit the extent of the pro-inflammatory cytokine cascade, preventing hyper-inflammation seen in autoinflammatory syndrome patients.

The invention is described by the following claims, with equivalents of the claims to be included therein.

The invention claimed is:

1. An isolated nucleic acid encoding a CATERPILLER 11.3 polypeptide comprising a nucleotide sequence selected from the group consisting of:

(a) the nucleotide sequence of SEQ ID NO:17 or SEQ ID NO:19;

(b) a nucleotide sequence that differs from the nucleotide sequences of (a) above due to the degeneracy of the genetic code.

2. An isolated cell comprising the isolated nucleic acid of claim 1.

3. A method of identifying a compound that binds to a CATERPILLER 11.3 polypeptide encoded by the nucleic acid of claim 1 comprising:

contacting the polypeptide with a test compound under conditions whereby binding between the polypeptide and the test compound can be detected; and detecting binding between the polypeptide and the test compound.

4. A method of identifying a compound that modulates the activity of a CATERPILLER 11.3 polypeptide encoded by the nucleic acid of claim 1 comprising:

contacting the polypeptide with a test compound under conditions whereby modulation of the activity of the polypeptide can be detected; and detecting modulation of the activity of the polypeptide, wherein the activity of the polypeptide that is measured is inhibition of Myd88-induced NF-κB induction and/or NIK-induced NF-κB induction.

5. The method of claim 3, wherein the method is carried out in a cell comprising the polypeptide.

6. The method of claim 5, wherein the cell comprises an isolated nucleic acid comprising a nucleotide sequence encoding the polypeptide.

7. The method of claim 6, wherein the cell is stably transformed with the isolated nucleic acid.

8. The method of claim 3, wherein the method is carried out as a cell-free assay.

9. The method of claim 3, wherein the method is carried out in a transgenic non-human mammal comprising an isolated nucleic acid comprising a nucleotide sequence encoding the polypeptide.

10. The isolated nucleic acid of claim 1 encoding the polypeptide of SEQ ID NO:18.

11. The isolated nucleic acid of claim 1 encoding the polypeptide of SEQ ID NO:20.

* * * * *

UNITED STATES PATENT AND TRADEMARK OFFICE

CERTIFICATE OF CORRECTION

PATENT NO. : 7,569,681 B2
APPLICATION NO. : 10/511989
DATED : August 4, 2009
INVENTOR(S) : Ting et al.

It is certified that error appears in the above-identified patent and that said Letters Patent is hereby corrected as shown below:

On the Title Page:

Item 75, Inventors: Jonathan A. Harton's address "Durham NC" should read
-- Tampa, FL --

Item 56, Other Publications, page 3, line 30, right column: Please add "2001." after "Inohara, et al."

In the Patent:

Column 2, Lines 23, 24: Please correct by underlining letters as follows
-- CARD, Transcription Enhancer, R(purine)-binding, Pyrin, Lots of Leucine Repeats) --

Column 59, Line 30: Please add "IL" after "Chemical Co., Rockland,"

Signed and Sealed this

Fifth Day of January, 2010

David J. Kappos
*Director of the United States Patent and Trademark Office*